US012643952B2

(12) United States Patent
Decaillot et al.

(10) Patent No.: US 12,643,952 B2
(45) Date of Patent: Jun. 2, 2026

(54) BCMA/TACI ANTIGEN-BINDING MOLECULES

(71) Applicant: Hummingbird Bioscience Pte. Ltd., Singapore (SG)

(72) Inventors: Fabien Decaillot, Singapore (SG); Jerome Douglas Boyd-Kirkup, Singapore (SG); Dipti Thakkar, Singapore (SG); Piers Ingram, Singapore (SG); Konrad Paszkiewicz, Singapore (SG); Chia-Yi Liu, Singapore (SG)

(73) Assignee: Hummingbird Bioscience Pte. Ltd., Singapore (SG)

( * ) Notice: Subject to any disclaimer, the term of this patent is extended or adjusted under 35 U.S.C. 154(b) by 556 days.

(21) Appl. No.: 18/034,867

(22) PCT Filed: Nov. 2, 2021

(86) PCT No.: PCT/EP2021/080305
§ 371 (c)(1),
(2) Date: May 1, 2023

(87) PCT Pub. No.: WO2022/090556
PCT Pub. Date: May 5, 2022

(65) Prior Publication Data
US 2023/0374147 A1 Nov. 23, 2023

(30) Foreign Application Priority Data

Nov. 2, 2020 (GB) ..................................... 2017319
Apr. 7, 2021 (GB) ..................................... 2104935

(51) Int. Cl.
*A61K 39/395* (2006.01)
*A61P 35/00* (2006.01)
*C07K 16/28* (2006.01)
*A61K 39/00* (2006.01)

(52) U.S. Cl.
CPC ...... *C07K 16/2878* (2013.01); *A61K 39/3955* (2013.01); *A61P 35/00* (2018.01); *C07K 16/2803* (2013.01); *C07K 16/2809* (2013.01); *A61K 2039/505* (2013.01); *C07K 2317/24* (2013.01); *C07K 2317/31* (2013.01); *C07K 2317/33* (2013.01); *C07K 2317/55* (2013.01);

*C07K 2317/622* (2013.01); *C07K 2317/732* (2013.01); *C07K 2317/76* (2013.01); *C07K 2317/92* (2013.01)

(58) Field of Classification Search
CPC ......................... A61K 39/3955; C07K 16/2878
See application file for complete search history.

(56) References Cited

U.S. PATENT DOCUMENTS

| | | |
|---|---|---|
| 2012/0034159 A1 | 2/2012 | Kindsvogel |
| 2014/0161828 A1 | 6/2014 | Armitage et al. |
| 2017/0051068 A1 | 2/2017 | Pillarisetti et al. |
| 2020/0078399 A1 | 3/2020 | Fan et al. |

FOREIGN PATENT DOCUMENTS

| | | |
|---|---|---|
| EP | 3508503 | 7/2019 |
| WO | WO 2002/066516 A2 | 8/2002 |
| WO | WO 2018/201051 A1 | 11/2018 |
| WO | WO 2019/110209 A1 | 6/2019 |
| WO | WO 2019/195017 A1 | 10/2019 |
| WO | WO 2020/014333 A1 | 1/2020 |
| WO | WO 2020/176549 | 9/2020 |

OTHER PUBLICATIONS

Hipp et al., Leukemia, 2017, vol. 31:1743-1751.*
Tai et al., Blood, 2014, vol. 123(20):3128-3138.*
International Search Report and Written Opinion for Application No. PCT/EP2021/080305, mailed Feb. 22, 2022.
International Preliminary Report on Patentability for Application No. PCT/EP2021/080305, mailed May 11, 2023.
Hipp et al., A novel BCMA/CD3 bispecific T-cell engager for the treatment of multiple myeloma induces selective lysis in vitro and in vivo. Leukemia. Aug. 2017;31(8):1743-1751. doi: 10.1038/leu. 2016.388. Epub Dec. 27, 2016.
Schmidts et al., Rational design of a trimeric APRIL-based CAR-binding domain enables efficient targeting of multiple myeloma. Blood Advances. Nov. 12, 2019; 3(21): 3248-3260. https://doi.org/10.1182/bloodadvances.2019000703.

* cited by examiner

*Primary Examiner* — Xiaozhen Xie
(74) *Attorney, Agent, or Firm* — Wolf, Greenfield & Sacks, P.C.

(57) ABSTRACT

BCMA/TACI antigen-binding molecules are disclosed. Also disclosed are nucleic acids and expression vectors encoding, compositions comprising, and methods using, the BCMA/TACI antigen-binding molecules.

18 Claims, 37 Drawing Sheets

Specification includes a Sequence Listing.

539-SP2-H3
539-SP1-C8
539-SP1-C8
539-SP1-C8

552-LN1-F4
552-LN1-F4

552-LN1-F4
552-LN1-F4
J6MO

J6MO

Absorbance 450 nm

Antibody Concentration (ug/ml) log

| Clones | Human BCMA response | Human BCMA $K_D$ | Human BCMA R² Value | Cyno BCMA response | Cyno BCMA $K_D$ | Cyno BCMA R² Value | Mouse BCMA response | Mouse BCMA $K_D$ | Mouse BCMA R² Value |
|---|---|---|---|---|---|---|---|---|---|
| 538-SP5-B10 | 2.3533 | <1.0E-12 | 0.9919 | 0.8951 | 3.14E-08 | 0.9022 | 1.3129 | 4.75E-08 | 0.9686 |
| 539-SP1-C8 | 2.461 | <1.0E-12 | 0.9915 | 0.4563 | 1.47E-08 | 0.9915 | 0.8601 | 2.95E-08 | 0.9403 |
| 539-SP2-H3 | 2.3594 | <1.0E-12 | 0.9908 | 0.2619 | N/A | 0.8611 | 0.29 | 7.25E-09 | 0.2661 |
| 539-SP5-D7 | 2.1359 | <1.0E-12 | 0.9901 | 0.2649 | 1.67E-07 | 0.9501 | 1.0088 | 4.86E-09 | 0.9322 |
| 539-SP7-F4 | 2.6069 | <1.0E-12 | 0.9903 | 1.3553 | 3.41E-08 | 0.9205 | 0.3708 | 8.97E-09 | 0.2621 |
| 552-LN1-E9 | 2.7592 | <1.0E-12 | 0.9933 | 1.7995 | 3.26E-08 | 0.9421 | -0.0875 | N/A | 0 |
| 552-LN1-F4 | 2.3298 | <1.0E-12 | 0.9939 | 0.9182 | 7.10E-08 | 0.9296 | -0.0734 | N/A | 0 |
| 552-LN2-E6 | 2.3672 | <1.0E-12 | 0.9928 | 1.5496 | 3.85E-08 | 0.9552 | -0.107 | N/A | 0 |
| 552-LN2-F8 | 2.3072 | <1.0E-12 | 0.9973 | 1.5816 | 5.98E-08 | 0.9625 | -0.0631 | N/A | 0 |
| IgG1 Isotype Control | -0.0556 | N/A | 0 | -0.1104 | N/A | 0 | -0.0577 | N/A | 0 |
| J6M0 | 2.5264 | <1.0E-12 | 0.9957 | 2.1628 | <1.0E-12 | 0.9963 | 0.0423 | N/A | 0 |

Figure 13

| Clones | BCMA only response | BCMA only $K_D$ | BCMA Only $R^2$ Value | BCMA:APRIL 1:1 response | BCMA:APRIL 1:1 $K_D$ | BCMA:APRIL 1:1 $R^2$ Value |
|---|---|---|---|---|---|---|
| 538-SP5-B10 | 2.3533 | <1.0E-12 | 0.9919 | 0.1509 | N/A | 0.6855 |
| 539-SP1-C8 | 2.461 | <1.0E-12 | 0.9915 | 0.2478 | N/A | 0 |
| 552-LN2-F8 | 2.1359 | <1.0E-12 | 0.9901 | 1.0817 | 6.9E-09 | 0.9932 |
| 539-SP7-F4 | 2.6069 | <1.0E-12 | 0.9903 | 0.0667 | N/A | 0.0554 |
| 552-LN1-E9 | 2.7592 | <1.0E-12 | 0.9933 | 1.32 | 5.49E-09 | 0.9933 |
| 539-SP2-H3 | 2.3594 | <1.0E-12 | 0.9908 | 0.128 | N/A | 0.5793 |
| 552-LN1-F4 | 2.3298 | <1.0E-12 | 0.9939 | 0.7122 | 9.61E-09 | 0.9805 |
| 539-SP5-D7 | 2.1359 | <1.0E-12 | 0.9901 | -0.0214 | N/A | 0 |
| 552-LN2-E6 | 2.3672 | <1.0E-12 | 0.9928 | 0.527 | 1.46E-08 | 0.9889 |
| IgG1 | -0.0556 | N/A | 0 | 0.1209 | N/A | 0 |
| J6M0 | 2.5264 | <1.0E-12 | 0.9957 | 0.18 | N/A | 0.0887 |

Figure 14

| IC50 (nM) | BCMA |
|-----------|------|
| 5B10 | 0.39 |
| 1C8 | 1.17 |
| Anti-BCMA | 0.92 |
| Isotype IgG | n.a. |

| EC50 (nM) | BCMA | TACI | BCMA +TACI |
|---|---|---|---|
| 5B10 | 0.22 | n.a. | 0.032 |
| 1C8 | 0.30 | 8.2 | 0.033 |
| Anti-BCMA | 0.87 | n.a. | 0.045 |
| Isotype IgG | n.a. | n.a. | n.a. |

| EC50 (nM) | BCMA |
|-----------|------|
| 5B10 | 0.085 |
| 1C8 | 0.059 |
| 1E9 | 0.081 |
| Anti-BCMA | 0.044 |
| Isotype IgG | n.a. |

| EC50 (nM) | TACI |
|-----------|------|
| 5B10 | 2.53 |
| 1C8 | 0.083 |
| 1E9 | n.a. |
| Anti-BCMA | n.a. |
| Isotype IgG | n.a. |

| EC50 (nM) | BCMA |
|-----------|------|
| 5B10 | 0.21 |
| 1C8 | 2.56 |
| 1E9 | 0.65 |
| Anti-BCMA | 10.09 |
| Isotype IgG | n.a. |

| EC50 (nM) | TACI |
|-----------|------|
| 5B10 | 24.05 |
| 1C8 | 8.20 |
| 1E9 | n.d. |
| Anti-BCMA | n.d. |
| Isotype IgG | n.a. |

| Test Article | Ani-CD47 | J6M0 | 1-1A1H5 | J6M0 x 1-1A1H5 | 1C8P x 1-1A1H5 | IgG1 |
|---|---|---|---|---|---|---|
| $EC_{50}$ (M) | 3.274e-010 | 1.703e-009 | 1.760e-010 | 1.019e-010 | 6.809e-011 | NA |

| Anti-BCMA Clones | Human BCMA EC50 (nM) | Human TACI EC50 (nM) | Cyno BCMA EC50 (nM) | Cyno TACI EC50 (nM) |
|---|---|---|---|---|
| hu1C8-402 | 0.110 | 0.020 | 0.002 | 0.004 |
| hu1C8-403 | 0.062 | 0.051 | 0.016 | 0.034 |
| hu1C8-507 | 0.087 | 0.021 | 0.038 | 0.011 |
| hu1C8-610 | 0.010 | 0.010 | 0.089 | 0.007 |
| hu1C8 | 0.005 | 1.319 | NA | 0.028 |
| J6M0 | 0.018 | NA | 0.015 | NA |
| IgG isotype | NA | NA | NA | NA |

|  | hu1C8-402 | hu1C8-403 | hu1C8-507 | hu1C8-610 | hu1C8 | J6M0 | IgG1 isotype |
|---|---|---|---|---|---|---|---|
| EC50 (nM) | 0.1278 | 0.1340 | 0.0950 | 0.0677 | 0.1112 | 1.769 | - |

| | hu1C8-402 | hu1C8-403 | hu1C8-507 | hu1C8-610 | hu1C8 | J6M0 | IgG1 isotype |
|---|---|---|---|---|---|---|---|
| EC50 (nM) | 0.1359 | 0.1716 | 0.1362 | 0.1343 | 0.2381 | ~9.614 | - |

| | HuBCMA | | | CyBCMA | | | HuTACI | | | CyTACI | | |
|---|---|---|---|---|---|---|---|---|---|---|---|---|
| | KD (M) | ka(1/Ms) | kd(1/s) | KD (M) | ka(1/Ms) | kd(1/s) | KD (M) | ka(1/Ms) | kd(1/s) | KD (M) | ka(1/Ms) | kd(1/s) |
| hu1C8-402 | 7.91E-10 | 3.95E+06 | 3.12E-03 | 2.40E-09 | 1.13E+06 | 2.72E-03 | 7.02E-08 | 8.21E+05 | 5.76E-02 | 2.59E-09 | 7.18E+05 | 1.86E-03 |
| hu1C8-610 | 6.50E-10 | 4.71E+06 | 3.07E-03 | 2.28E-08 | 1.28E+06 | 2.91E-02 | 2.08E-08 | 9.88E+05 | 2.05E-02 | 1.25E-09 | 6.73E+05 | 8.39E-04 |
| 1C8p-27 | 6.66E-10 | 3.62E+06 | 2.41E-03 | 2.48E-08 | 1.52E+06 | 3.77E-02 | 6.02E-08 | 7.54E+05 | 4.54E-02 | 2.02E-09 | 6.19E+05 | 1.25E-03 |
| 1C8p-25 | 6.19E-10 | 3.76E+06 | 2.33E-03 | 3.91E-08 | 1.46E+06 | 5.73E-02 | 8.70E-08 | 7.59E+05 | 6.61E-02 | 1.80E-09 | 5.70E+05 | 1.03E-03 |
| hu1C8-403 | 5.86E-08 | 4.92E+04 | 2.88E-03 | 6.54E-09 | 1.40E+06 | 9.17E-03 | 1.10E-03 | 1.18E+02 | 1.31E-01 | / | / | / |
| hu1C8-507 | 5.91E-08 | 2.92E+04 | 1.72E-03 | 2.17E-08 | 1.63E+06 | 3.54E-02 | 6.10E-07 | 2.67E+05 | 1.63E-01 | / | / | / |

Figure 27

**BCMA/TACI ANTIGEN-BINDING
MOLECULES**

This application is a national stage filing under
35 U.S.C. § 371 of international PCT application PCT/
EP2021/080305, filed Nov. 2, 2021, which claims priority
from GB 2017319.1 filed Nov. 2, 2020 and GB 2104935.8
filed Apr. 7, 2021, the contents and elements of which are
herein incorporated by reference for all purposes.

This application contains a Sequence Listing which has
been submitted in ASCII format via EFS-Web and is hereby
incorporated by reference in its entirety. Said ASCII copy,
created on Apr. 27, 2023, is named H096970020US00-SEQ-
AZW and is 576,031 bytes in size.

TECHNICAL FIELD

The present disclosure relates to the fields of molecular
biology, more specifically antibody technology.

The present disclosure also relates to methods of medical
treatment and prophylaxis.

BACKGROUND

BCMA is expressed on cells of multiple myeloma, and the
anti-BCMA antibody-drug conjugate J6M0-mcMMAF
(GSK2857916) has been investigated for the treatment of
multiple myeloma (see e.g. Tai et al., Blood. (2014) 123(20):
3128-3138). BCMA is also expressed by cells of B cell
malignancies such as Hodgkin's lymphoma, non-Hodgkin's
lymphoma (e.g. Burkitt lymphoma) and lymphocytic leuke-
mia, and the BCMA/TACI antagonist Atacicept has been
investigated as an agent for use in the treatment of multiple
myeloma, B-cell chronic lymphocytic leukemia, and non-
Hodgkin's lymphoma (Vasiliou, Drugs Fut 2008, 33(11):
921).

Multiple myeloma (MM) is the second most common
hematologic malignancy and the fourteenth leading cause of
cancer deaths in the USA (estimated at over 12,000 deaths
per year). The current treatment landscape for MM patients
includes diverse classes of first and second generation agents
administered as single therapy or in combination, including
alkylating agents, histone deacetylase inhibitors, proteasome
inhibitors, immunomodulatory drugs, monoclonal antibod-
ies, and autologous stem cell transplantation.

Recent therapeutic advances have increased life expec-
tancy of patients from 32 months to 53 months. However,
however 5-year survival is still only 52%, and existing
treatments have important limitations, and. There are serious
side effects associated with such treatment, which can
reduce quality of life. Most patients relapse or become
refractory to existing therapies, and palliative care often
becomes the only option. Response rates decrease with
increasing lines of therapy, and with relapsed and refractory
cases. The recently approved anti-CD38 monoclonal anti-
body daratumumab has shown only a moderate improve-
ment in clinical trials, has its own limitations due to reported
cases of CD38 loss, and can potentially deplete CD38+NK
cells and monocytes.

Emerging therapies such as PD1/PD-L1 antibodies have
shown severe adverse toxicity effects in clinical trials.

There is therefore a large unmet need for novel and more
effective therapies for hematological malignancies, in par-
ticular for patients with relapsed or refractory disease.
BCMA-binding antibodies are disclosed in WO 2002/
066516 A2.

SUMMARY

The present disclosure provides an antigen-binding mol-
ecule, optionally isolated, which is capable of binding to
BCMA. Also provided is an antigen-binding molecule,
optionally isolated, which is capable of binding to TACI.
Also provided is an antigen-binding molecule, optionally
isolated, which is capable of binding (independently) to
BCMA and TACI.

The present disclosure also provides an antigen-binding
molecule, optionally isolated, which displays cross-reactive
binding to BCMA and TACI.

In some embodiments, the antigen-binding molecule
comprises:
(a)
(i) a heavy chain variable (VH) region incorporating
the following CDRs:
HC-CDR1 having the amino acid sequence of SEQ
ID NO:491
HC-CDR2 having the amino acid sequence of SEQ
ID NO:492
HC-CDR3 having the amino acid sequence of SEQ
ID NO:493; and
(ii) a light chain variable (VL) region incorporating the
following CDRs:
LC-CDR1 having the amino acid sequence of SEQ
ID NO:498
LC-CDR2 having the amino acid sequence of SEQ
ID NO:62
LC-CDR3 having the amino acid sequence of SEQ
ID NO:499; or
(b)
(i) a heavy chain variable (VH) region incorporating
the following CDRs:
HC-CDR1 having the amino acid sequence of SEQ
ID NO:53
HC-CDR2 having the amino acid sequence of SEQ
ID NO:54
HC-CDR3 having the amino acid sequence of SEQ
ID NO:456; and
(ii) a light chain variable (VL) region incorporating the
following CDRs:
LC-CDR1 having the amino acid sequence of SEQ
ID NO:61
LC-CDR2 having the amino acid sequence of SEQ
ID NO:62
LC-CDR3 having the amino acid sequence of SEQ
ID NO:460; or
(c)
(i) a heavy chain variable (VH) region incorporating
the following CDRs:
HC-CDR1 having the amino acid sequence of SEQ
ID NO:53
HC-CDR2 having the amino acid sequence of SEQ
ID NO:54
HC-CDR3 having the amino acid sequence of SEQ
ID NO:456; and
(ii) a light chain variable (VL) region incorporating the
following CDRs:
LC-CDR1 having the amino acid sequence of SEQ
ID NO:464
LC-CDR2 having the amino acid sequence of SEQ
ID NO:62
LC-CDR3 having the amino acid sequence of SEQ
ID NO:63; or (d)
  (i) a heavy chain variable (VH) region incorporating the following CDRs:
    HC-CDR1 having the amino acid sequence of SEQ ID NO:466
    HC-CDR2 having the amino acid sequence of SEQ ID NO:54
    HC-CDR3 having the amino acid sequence of SEQ ID NO:55; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:63; or
(e)
  (i) a heavy chain variable (VH) region incorporating the following CDRs:
    HC-CDR1 having the amino acid sequence of SEQ ID NO:53
    HC-CDR2 having the amino acid sequence of SEQ ID NO:472
    HC-CDR3 having the amino acid sequence of SEQ ID NO:55; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:63; or
(f)
  (i) a heavy chain variable (VH) region incorporating the following CDRs:
    HC-CDR1 having the amino acid sequence of SEQ ID NO:53
    HC-CDR2 having the amino acid sequence of SEQ ID NO:54
    HC-CDR3 having the amino acid sequence of SEQ ID NO:55; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:63; or
(g)
  (i) a heavy chain variable (VH) region incorporating the following CDRs:
    HC-CDR1 having the amino acid sequence of SEQ ID NO:53
    HC-CDR2 having the amino acid sequence of SEQ ID NO:54
    HC-CDR3 having the amino acid sequence of SEQ ID NO:456; and
  (ii) a light chain variable (VL) region incorporating the following CDRs:
    LC-CDR1 having the amino acid sequence of SEQ ID NO:484
    LC-CDR2 having the amino acid sequence of SEQ ID NO:62

LC-CDR3 having the amino acid sequence of SEQ ID NO:485; or
(h)
  (i) a heavy chain variable (VH) region incorporating the following CDRs:
    HC-CDR1 having the amino acid sequence of SEQ ID NO:53
    HC-CDR2 having the amino acid sequence of SEQ ID NO:54
    HC-CDR3 having the amino acid sequence of SEQ ID NO:456; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:488; or
(i)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:139; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:63; or
(j)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:139; and
  (ii) a light chain variable (VL) region incorporating the following CDRs:
    LC-CDR1 having the amino acid sequence of SEQ ID NO:31
    LC-CDR2 having the amino acid sequence of SEQ ID NO:32
    LC-CDR3 having the amino acid sequence of SEQ ID NO:33; or
(k)
  (i) a heavy chain variable (VH) region incorporating the following CDRs:
    HC-CDR1 having the amino acid sequence of SEQ ID NO:23
    HC-CDR2 having the amino acid sequence of SEQ ID NO:24
    HC-CDR3 having the amino acid sequence of SEQ ID NO:25; and
  (ii) a light chain variable (VL) region incorporating the following CDRs:
    LC-CDR1 having the amino acid sequence of SEQ ID NO:31

LC-CDR2 having the amino acid sequence of SEQ ID NO:32

LC-CDR3 having the amino acid sequence of SEQ ID NO:33.

In some embodiments, the antigen-binding molecule comprises:

a VH region comprising an amino acid sequence having at least 70% sequence identity to the amino acid sequence of SEQ ID NO:490, 455, 465, 471, 477, 479, 136, 52 or 22; and a VL region comprising an amino acid sequence having at least 70% sequence identity to the amino acid sequence of SEQ ID NO:497, 459, 463, 468, 474, 478, 483, 487, 60 or 30.

In some embodiments, the antigen-binding molecule comprises:

(i) a VH region comprising an amino acid sequence having at least 70% sequence identity to the amino acid sequence of SEQ ID NO:490; and a VL region comprising an amino acid sequence having at least 70% sequence identity to the amino acid sequence of SEQ ID NO:497;

or (ii) a VH region comprising an amino acid sequence having at least 70% sequence identity to the amino acid sequence of SEQ ID NO:455; and a VL region comprising an amino acid sequence having at least 70% sequence identity to the amino acid sequence of SEQ ID NO:459;

or (iii) a VH region comprising an amino acid sequence having at least 70% sequence identity to the amino acid sequence of SEQ ID NO:455; and a VL region comprising an amino acid sequence having at least 70% sequence identity to the amino acid sequence of SEQ ID NO:463;

or (iv) a VH region comprising an amino acid sequence having at least 70% sequence identity to the amino acid sequence of SEQ ID NO:465; and a VL region comprising an amino acid sequence having at least 70% sequence identity to the amino acid sequence of SEQ ID NO:468;

or (v) a VH region comprising an amino acid sequence having at least 70% sequence identity to the amino acid sequence of SEQ ID NO:471; and a VL region comprising an amino acid sequence having at least 70% sequence identity to the amino acid sequence of SEQ ID NO:474;

or (vi) a VH region comprising an amino acid sequence having at least 70% sequence identity to the amino acid sequence of SEQ ID NO:477; and a VL region comprising an amino acid sequence having at least 70% sequence identity to the amino acid sequence of SEQ ID NO:478;

or (vii) a VH region comprising an amino acid sequence having at least 70% sequence identity to the amino acid sequence of SEQ ID NO:479; and a VL region comprising an amino acid sequence having at least 70% sequence identity to the amino acid sequence of SEQ ID NO:483;

or (viii) a VH region comprising an amino acid sequence having at least 70% sequence identity to the amino acid sequence of SEQ ID NO:479; and a VL region comprising an amino acid sequence having at least 70% sequence identity to the amino acid sequence of SEQ ID NO:487;

or (ix) a VH region comprising an amino acid sequence having at least 70% sequence identity to the amino acid sequence of SEQ ID NO:136; and a VL region comprising an amino acid sequence having at least 70% sequence identity to the amino acid sequence of SEQ ID NO:60;

or (x) a VH region comprising an amino acid sequence having at least 70% sequence identity to the amino acid sequence of SEQ ID NO:52; and a VL region comprising an amino acid sequence having at least 70% sequence identity to the amino acid sequence of SEQ ID NO:60;

or (xi) a VH region comprising an amino acid sequence having at least 70% sequence identity to the amino acid sequence of SEQ ID NO:136; and a VL region comprising an amino acid sequence having at least 70% sequence identity to the amino acid sequence of SEQ ID NO:30;

or (xii) a VH region comprising an amino acid sequence having at least 70% sequence identity to the amino acid sequence of SEQ ID NO:22; and a VL region comprising an amino acid sequence having at least 70% sequence identity to the amino acid sequence of SEQ ID NO:30.

In some embodiments, the antigen-binding molecule binds to BCMA via contact with one or more amino acid residues of the region of BCMA corresponding to the region shown in SEQ ID NO:554. In some embodiments, the antigen-binding molecule binds to BCMA via contact with one or more amino acid residues of the region of BCMA corresponding to the region shown in SEQ ID NO:555.

The present disclosure also provides an antigen-binding molecule, optionally isolated, which binds to BCMA, wherein the antigen-binding molecule comprises:

(a)

(i) a heavy chain variable (VH) region incorporating the following CDRs:

HC-CDR1 having the amino acid sequence of SEQ ID NO:491

HC-CDR2 having the amino acid sequence of SEQ ID NO:492

HC-CDR3 having the amino acid sequence of SEQ ID NO:493; and (ii) a light chain variable (VL) region incorporating the following CDRs:

LC-CDR1 having the amino acid sequence of SEQ ID NO:498

LC-CDR2 having the amino acid sequence of SEQ ID NO:62

LC-CDR3 having the amino acid sequence of SEQ ID NO:499; or (b)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:456; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:460; or (c)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:456; and (ii) a light chain variable (VL) region incorporating the following CDRs:

LC-CDR1 having the amino acid sequence of SEQ ID NO:464

LC-CDR2 having the amino acid sequence of SEQ ID NO:62

LC-CDR3 having the amino acid sequence of SEQ ID NO:63; or (d)

(i) a heavy chain variable (VH) region incorporating the following CDRs:

HC-CDR1 having the amino acid sequence of SEQ ID NO:466

HC-CDR2 having the amino acid sequence of SEQ ID NO:54

HC-CDR3 having the amino acid sequence of SEQ ID NO:55; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63; or (e)

(i) a heavy chain variable (VH) region incorporating the following CDRs:

HC-CDR1 having the amino acid sequence of SEQ ID NO:53

HC-CDR2 having the amino acid sequence of SEQ ID NO:472

HC-CDR3 having the amino acid sequence of SEQ ID NO:55; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63; or (f)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:55; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63; or (g)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:456; and (ii) a light chain variable (VL) region incorporating the following CDRs:

LC-CDR1 having the amino acid sequence of SEQ ID NO:484

LC-CDR2 having the amino acid sequence of SEQ ID NO:62

LC-CDR3 having the amino acid sequence of SEQ ID NO:485; or (h)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:456; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:488; or (i)

(i) a heavy chain variable (VH) region incorporating the following CDRs:

HC-CDR1 having the amino acid sequence of SEQ ID NO:137

HC-CDR2 having the amino acid sequence of SEQ ID NO:138

HC-CDR3 having the amino acid sequence of SEQ ID NO:139; and (ii) a light chain variable (VL) region incorporating the following CDRs:

LC-CDR1 having the amino acid sequence of SEQ ID NO:31

LC-CDR2 having the amino acid sequence of SEQ ID NO:32

LC-CDR3 having the amino acid sequence of SEQ ID NO:33; or (j)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:139; and
  (ii) a light chain variable (VL) region incorporating the following CDRs:
    LC-CDR1 having the amino acid sequence of SEQ ID NO:45
    LC-CDR2 having the amino acid sequence of SEQ ID NO:46
    LC-CDR3 having the amino acid sequence of SEQ ID NO:47; or
(k)
  (i) a heavy chain variable (VH) region incorporating the following CDRs:
    HC-CDR1 having the amino acid sequence of SEQ ID NO:137
    HC-CDR2 having the amino acid sequence of SEQ ID NO:138
    HC-CDR3 having the amino acid sequence of SEQ ID NO:139; and
  (ii) a light chain variable (VL) region incorporating the following CDRs:
    LC-CDR1 having the amino acid sequence of SEQ ID NO:61
    LC-CDR2 having the amino acid sequence of SEQ ID NO:62
    LC-CDR3 having the amino acid sequence of SEQ ID NO:63; or
(l)
  (i) a heavy chain variable (VH) region incorporating the following CDRs:
    HC-CDR1 having the amino acid sequence of SEQ ID NO:23
    HC-CDR2 having the amino acid sequence of SEQ ID NO:24
    HC-CDR3 having the amino acid sequence of SEQ ID NO:25; and
  (ii) a light chain variable (VL) region incorporating the following CDRs:
    LC-CDR1 having the amino acid sequence of SEQ ID NO:31
    LC-CDR2 having the amino acid sequence of SEQ ID NO:32
    LC-CDR3 having the amino acid sequence of SEQ ID NO:33; or
(m)
  (i) a heavy chain variable (VH) region incorporating the following CDRs:
    HC-CDR1 having the amino acid sequence of SEQ ID NO:23
    HC-CDR2 having the amino acid sequence of SEQ ID NO:39
    HC-CDR3 having the amino acid sequence of SEQ ID NO:40; and
  (ii) a light chain variable (VL) region incorporating the following CDRs:
    LC-CDR1 having the amino acid sequence of SEQ ID NO:45
    LC-CDR2 having the amino acid sequence of SEQ ID NO:46

LC-CDR3 having the amino acid sequence of SEQ ID NO:47; or
(n)
  (i) a heavy chain variable (VH) region incorporating the following CDRs:
    HC-CDR1 having the amino acid sequence of SEQ ID NO:145
    HC-CDR2 having the amino acid sequence of SEQ ID NO:100
    HC-CDR3 having the amino acid sequence of SEQ ID NO:146; and
  (ii) a light chain variable (VL) region incorporating the following CDRs:
    LC-CDR1 having the amino acid sequence of SEQ ID NO:152
    LC-CDR2 having the amino acid sequence of SEQ ID NO:153
    LC-CDR3 having the amino acid sequence of SEQ ID NO:108; or
(o)
  (i) a heavy chain variable (VH) region incorporating the following CDRs:
    HC-CDR1 having the amino acid sequence of SEQ ID NO:145
    HC-CDR2 having the amino acid sequence of SEQ ID NO:100
    HC-CDR3 having the amino acid sequence of SEQ ID NO:146; and
  (ii) a light chain variable (VL) region incorporating the following CDRs:
    LC-CDR1 having the amino acid sequence of SEQ ID NO:106
    LC-CDR2 having the amino acid sequence of SEQ ID NO:107
    LC-CDR3 having the amino acid sequence of SEQ ID NO:108; or
(p)
  (i) a heavy chain variable (VH) region incorporating the following CDRs:
    HC-CDR1 having the amino acid sequence of SEQ ID NO:145
    HC-CDR2 having the amino acid sequence of SEQ ID NO:100
    HC-CDR3 having the amino acid sequence of SEQ ID NO:146; and
  (ii) a light chain variable (VL) region incorporating the following CDRs:
    LC-CDR1 having the amino acid sequence of SEQ ID NO:119
    LC-CDR2 having the amino acid sequence of SEQ ID NO:120
    LC-CDR3 having the amino acid sequence of SEQ ID NO:108; or
(q)
  (i) a heavy chain variable (VH) region incorporating the following CDRs:
    HC-CDR1 having the amino acid sequence of SEQ ID NO:145
    HC-CDR2 having the amino acid sequence of SEQ ID NO:100
    HC-CDR3 having the amino acid sequence of SEQ ID NO:146; and
  (ii) a light chain variable (VL) region incorporating the following CDRs:
    LC-CDR1 having the amino acid sequence of SEQ ID NO:125

LC-CDR2 having the amino acid sequence of SEQ ID NO:120

LC-CDR3 having the amino acid sequence of SEQ ID NO:108; or (r)
   (i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:101; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (s)
   (i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (t)
   (i) a heavy chain variable (VH) region incorporating the following CDRs:

HC-CDR1 having the amino acid sequence of SEQ ID NO:128

HC-CDR2 having the amino acid sequence of SEQ ID NO:100

HC-CDR3 having the amino acid sequence of SEQ ID NO:129; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (u)
   (i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:101; and (ii) a light chain variable (VL) region incorporating the following CDRs:

LC-CDR1 having the amino acid sequence of SEQ ID NO:106

LC-CDR2 having the amino acid sequence of SEQ ID NO:107

LC-CDR3 having the amino acid sequence of SEQ ID NO:108; or (v)
   (i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:119

LC-CDR2 having the amino acid sequence of SEQ ID NO:120

LC-CDR3 having the amino acid sequence of SEQ ID NO:108; or (w)
   (i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108; or (x)
   (i) a heavy chain variable (VH) region incorporating the following CDRs:

HC-CDR1 having the amino acid sequence of SEQ ID NO:128

HC-CDR2 having the amino acid sequence of SEQ ID NO:100

HC-CDR3 having the amino acid sequence of SEQ ID NO:129; and (ii) a light chain variable (VL) region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108; or (y)
   (i) a heavy chain variable (VH) region incorporating the following CDRs:

HC-CDR1 having the amino acid sequence of SEQ ID NO:68

HC-CDR2 having the amino acid sequence of SEQ ID NO:69

HC-CDR3 having the amino acid sequence of SEQ ID NO:70; and (ii) a light chain variable (VL) region incorporating the following CDRs:
LC-CDR1 having the amino acid sequence of SEQ ID NO:76
LC-CDR2 having the amino acid sequence of SEQ ID NO:77
LC-CDR3 having the amino acid sequence of SEQ ID NO:78; or (z)
(i) a heavy chain variable (VH) region incorporating the following CDRs:
HC-CDR1 having the amino acid sequence of SEQ ID NO:84
HC-CDR2 having the amino acid sequence of SEQ ID NO:85
HC-CDR3 having the amino acid sequence of SEQ ID NO:86; and
(ii) a light chain variable (VL) region incorporating the following CDRs:
LC-CDR1 having the amino acid sequence of SEQ ID NO:91
LC-CDR2 having the amino acid sequence of SEQ ID NO:92
LC-CDR3 having the amino acid sequence of SEQ ID NO:93; or (aa)
(i) a heavy chain variable (VH) region incorporating the following CDRs:
HC-CDR1 having the amino acid sequence of SEQ NO:99
HC-CDR2 having the amino acid sequence of SEQ NO:394
HC-CDR3 having the amino acid sequence of SEQ NO:101; and
(ii) a light chain variable (VL) region incorporating the following CDRs:
LC-CDR1 having the amino acid sequence of SEQ NO:106
LC-CDR2 having the amino acid sequence of SEQ NO:107
LC-CDR3 having the amino acid sequence of SEQ NO:108; or (bb)
(i) a heavy chain variable (VH) region incorporating the following CDRs:
HC-CDR1 having the amino acid sequence of SEQ NO:128
HC-CDR2 having the amino acid sequence of SEQ NO:347
HC-CDR3 having the amino acid sequence of SEQ NO:129; and
(ii) a light chain variable (VL) region incorporating the following CDRs:
LC-CDR1 having the amino acid sequence of SEQ NO:125
LC-CDR2 having the amino acid sequence of SEQ NO:120
LC-CDR3 having the amino acid sequence of SEQ NO:108; or (cc)
(i) a heavy chain variable (VH) region incorporating the following CDRs:
HC-CDR1 having the amino acid sequence of SEQ NO:53
HC-CDR2 having the amino acid sequence of SEQ NO:418

HC-CDR3 having the amino acid sequence of SEQ NO:55; and
(ii) a light chain variable (VL) region incorporating the following CDRs:
LC-CDR1 having the amino acid sequence of SEQ NO:61
LC-CDR2 having the amino acid sequence of SEQ NO:62
LC-CDR3 having the amino acid sequence of SEQ NO:63; or (dd)
(i) a heavy chain variable (VH) region incorporating the following CDRs:
HC-CDR1 having the amino acid sequence of SEQ NO:99
HC-CDR2 having the amino acid sequence of SEQ NO:347
HC-CDR3 having the amino acid sequence of SEQ NO:101; and
(ii) a light chain variable (VL) region incorporating the following CDRs:
LC-CDR1 having the amino acid sequence of SEQ NO:106
LC-CDR2 having the amino acid sequence of SEQ NO:107
LC-CDR3 having the amino acid sequence of SEQ NO:108; or (ee)
(i) a heavy chain variable (VH) region incorporating the following CDRs:
HC-CDR1 having the amino acid sequence of SEQ NO:53
HC-CDR2 having the amino acid sequence of SEQ NO:388
HC-CDR3 having the amino acid sequence of SEQ NO:55; and
(ii) a light chain variable (VL) region incorporating the following CDRs:
LC-CDR1 having the amino acid sequence of SEQ NO:61
LC-CDR2 having the amino acid sequence of SEQ NO:62
LC-CDR3 having the amino acid sequence of SEQ NO:63.

In some embodiments, the antigen-binding molecule comprises:
a VH region comprising an amino acid sequence having at least 70% sequence identity to the amino acid sequence of SEQ ID NO:490, 455, 465, 471, 477, 479, 136, 144, 22, 38, 52, 67, 83, 98, 112, 122, 127, 393, 401, 408, 417, 338, 346, 353, 361, 367, 372, 380 or 387; and
a VL region comprising an amino acid sequence having at least 70% sequence identity to the amino acid sequence of SEQ ID NO:497, 459, 463, 468, 474, 478, 483, 487, 151, 30, 44, 60, 75, 90, 105, 118, 124, 133, 396, 405, 412, 422, 341, 349, 357, 365, 370, 376, 383 or 391.

In some embodiments, the antigen-binding molecule comprises:
(i) a VH region comprising an amino acid sequence having at least 70% sequence identity to the amino acid sequence of SEQ ID NO:490; and
a VL region comprising an amino acid sequence having at least 70% sequence identity to the amino acid sequence of SEQ ID NO:497;

or (ii) a VH region comprising an amino acid sequence having at least 70% sequence identity to the amino acid sequence of SEQ ID NO:455; and
a VL region comprising an amino acid sequence having at least 70% sequence identity to the amino acid sequence of SEQ ID NO:459;

or (iii) a VH region comprising an amino acid sequence having at least 70% sequence identity to the amino acid sequence of SEQ ID NO:455; and
a VL region comprising an amino acid sequence having at least 70% sequence identity to the amino acid sequence of SEQ ID NO:463;

or (iv) a VH region comprising an amino acid sequence having at least 70% sequence identity to the amino acid sequence of SEQ ID NO:465; and
a VL region comprising an amino acid sequence having at least 70% sequence identity to the amino acid sequence of SEQ ID NO:468;

or (v) a VH region comprising an amino acid sequence having at least 70% sequence identity to the amino acid sequence of SEQ ID NO:471; and
a VL region comprising an amino acid sequence having at least 70% sequence identity to the amino acid sequence of SEQ ID NO:474;

or (vi) a VH region comprising an amino acid sequence having at least 70% sequence identity to the amino acid sequence of SEQ ID NO:477; and
a VL region comprising an amino acid sequence having at least 70% sequence identity to the amino acid sequence of SEQ ID NO:478;

or (vii) a VH region comprising an amino acid sequence having at least 70% sequence identity to the amino acid sequence of SEQ ID NO:479; and
a VL region comprising an amino acid sequence having at least 70% sequence identity to the amino acid sequence of SEQ ID NO:483;

or (viii) a VH region comprising an amino acid sequence having at least 70% sequence identity to the amino acid sequence of SEQ ID NO:479; and
a VL region comprising an amino acid sequence having at least 70% sequence identity to the amino acid sequence of SEQ ID NO:487;

or (ix) a VH region comprising an amino acid sequence having at least 70% sequence identity to the amino acid sequence of SEQ ID NO:136; and
a VL region comprising an amino acid sequence having at least 70% sequence identity to the amino acid sequence of SEQ ID NO:30;

or (x) a VH region comprising an amino acid sequence having at least 70% sequence identity to the amino acid sequence of SEQ ID NO:136; and
a VL region comprising an amino acid sequence having at least 70% sequence identity to the amino acid sequence of SEQ ID NO:44;

or (xi) a VH region comprising an amino acid sequence having at least 70% sequence identity to the amino acid sequence of SEQ ID NO:136; and a VL region comprising an amino acid sequence having at least 70% sequence identity to the amino acid sequence of SEQ ID NO:60;

or (xii) a VH region comprising an amino acid sequence having at least 70% sequence identity to the amino acid sequence of SEQ ID NO:22; and
a VL region comprising an amino acid sequence having at least 70% sequence identity to the amino acid sequence of SEQ ID NO:30;

or (xiii) a VH region comprising an amino acid sequence having at least 70% sequence identity to the amino acid sequence of SEQ ID NO:38; and
a VL region comprising an amino acid sequence having at least 70% sequence identity to the amino acid sequence of SEQ ID NO:44;

or (xiv) a VH region comprising an amino acid sequence having at least 70% sequence identity to the amino acid sequence of SEQ ID NO:52; and
a VL region comprising an amino acid sequence having at least 70% sequence identity to the amino acid sequence of SEQ ID NO:60;

or (xv) a VH region comprising an amino acid sequence having at least 70% sequence identity to the amino acid sequence of SEQ ID NO:144; and
a VL region comprising an amino acid sequence having at least 70% sequence identity to the amino acid sequence of SEQ ID NO:151;

or (xvi) a VH region comprising an amino acid sequence having at least 70% sequence identity to the amino acid sequence of SEQ ID NO:144; and
a VL region comprising an amino acid sequence having at least 70% sequence identity to the amino acid sequence of SEQ ID NO:105;

or (xvii) a VH region comprising an amino acid sequence having at least 70% sequence identity to the amino acid sequence of SEQ ID NO:144; and
a VL region comprising an amino acid sequence having at least 70% sequence identity to the amino acid sequence of SEQ ID NO:118;

or (xviii) a VH region comprising an amino acid sequence having at least 70% sequence identity to the amino acid sequence of SEQ ID NO:144; and
a VL region comprising an amino acid sequence having at least 70% sequence identity to the amino acid sequence of SEQ ID NO:124;

or (xix) a VH region comprising an amino acid sequence having at least 70% sequence identity to the amino acid sequence of SEQ ID NO:144; and
a VL region comprising an amino acid sequence having at least 70% sequence identity to the amino acid sequence of SEQ ID NO:133;

or (xx) a VH region comprising an amino acid sequence having at least 70% sequence identity to the amino acid sequence of SEQ ID NO:98; and
a VL region comprising an amino acid sequence having at least 70% sequence identity to the amino acid sequence of SEQ ID NO:151;

or (xxi) a VH region comprising an amino acid sequence having at least 70% sequence identity to the amino acid sequence of SEQ ID NO:112; and a VL region comprising an amino acid sequence having at least 70% sequence identity to the amino acid sequence of SEQ ID NO:151;

or (xxii) a VH region comprising an amino acid sequence having at least 70% sequence identity to the amino acid sequence of SEQ ID NO:122; and a VL region comprising an amino acid sequence having at least 70% sequence identity to the amino acid sequence of SEQ ID NO:151;

or (xxiii) a VH region comprising an amino acid sequence having at least 70% sequence identity to the amino acid sequence of SEQ ID NO:127; and a VL region comprising an amino acid sequence having at least 70% sequence identity to the amino acid sequence of SEQ ID NO:151;

or (xxiv) a VH region comprising an amino acid sequence having at least 70% sequence identity to the amino acid sequence of SEQ ID NO:98; and a VL region comprising an amino acid sequence having at least 70% sequence identity to the amino acid sequence of SEQ ID NO:105;

or (xxv) a VH region comprising an amino acid sequence having at least 70% sequence identity to the amino acid sequence of SEQ ID NO:112; and a VL region comprising an amino acid sequence having at least 70% sequence identity to the amino acid sequence of SEQ ID NO:118;

or (xxvi) a VH region comprising an amino acid sequence having at least 70% sequence identity to the amino acid sequence of SEQ ID NO:122; and a VL region comprising an amino acid sequence having at least 70% sequence identity to the amino acid sequence of SEQ ID NO:124;

or (xxvii) a VH region comprising an amino acid sequence having at least 70% sequence identity to the amino acid sequence of SEQ ID NO:127; and a VL region comprising an amino acid sequence having at least 70% sequence identity to the amino acid sequence of SEQ ID NO:133;

or (xxviii) a VH region comprising an amino acid sequence having at least 70% sequence identity to the amino acid sequence of SEQ ID NO:67; and a VL region comprising an amino acid sequence having at least 70% sequence identity to the amino acid sequence of SEQ ID NO:75;

or (xxix) a VH region comprising an amino acid sequence having at least 70% sequence identity to the amino acid sequence of SEQ ID NO:83; and a VL region comprising an amino acid sequence having at least 70% sequence identity to the amino acid sequence of SEQ ID NO:90.

or (xxx) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:396;

or (xxxi) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:341;

or (xxxii) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:349;

or (xxxiii) a VH region comprising an amino acid sequence having at least 70% sequence identity to the amino acid sequence of SEQ ID NO:338; and a VL region comprising an amino acid sequence having at least 70% sequence identity to the amino acid sequence of SEQ ID NO:396;

or (xxxiv) a VH region comprising an amino acid sequence having at least 70% sequence identity to the amino acid sequence of SEQ ID NO:346; and a VL region comprising an amino acid sequence having at least 70% sequence identity to the amino acid sequence of SEQ ID NO:396;

or (xxxv) a VH region comprising an amino acid sequence having at least 70% sequence identity to the amino acid sequence of SEQ ID NO:338; and a VL region comprising an amino acid sequence having at least 70% sequence identity to the amino acid sequence of SEQ ID NO:341;

or (xxxvi) a VH region comprising an amino acid sequence having at least 70% sequence identity to the amino acid sequence of SEQ ID NO:346; and a VL region comprising an amino acid sequence having at least 70% sequence identity to the amino acid sequence of SEQ ID NO:349;

or (xxxvii) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:405;

or (xxxviii) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:357;

or (xxxix) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:365;

or (xl) a VH region comprising an amino acid sequence having at least 70% sequence identity to the amino acid sequence of SEQ ID NO:353; and
a VL region comprising an amino acid sequence having at least 70% sequence identity to the amino acid sequence of SEQ ID NO:405;

or (xli) a VH region comprising an amino acid sequence having at least 70% sequence identity to the amino acid sequence of SEQ ID NO:361; and
a VL region comprising an amino acid sequence having at least 70% sequence identity to the amino acid sequence of SEQ ID NO:405;

or (xlii) a VH region comprising an amino acid sequence having at least 70% sequence identity to the amino acid sequence of SEQ ID NO:353; and
a VL region comprising an amino acid sequence having at least 70% sequence identity to the amino acid sequence of SEQ ID NO:357;

or (xliii) a VH region comprising an amino acid sequence having at least 70% sequence identity to the amino acid sequence of SEQ ID NO:361; and
a VL region comprising an amino acid sequence having at least 70% sequence identity to the amino acid sequence of SEQ ID NO:365;

or (xliv) a VH region comprising an amino acid sequence having at least 70% sequence identity to the amino acid sequence of SEQ ID NO:408; and
a VL region comprising an amino acid sequence having at least 70% sequence identity to the amino acid sequence of SEQ ID NO:412;

or (xlv) a VH region comprising an amino acid sequence having at least 70% sequence identity to the amino acid sequence of SEQ ID NO:408; and
a VL region comprising an amino acid sequence having at least 70% sequence identity to the amino acid sequence of SEQ ID NO:370;

or (xlvi) a VH region comprising an amino acid sequence having at least 70% sequence identity to the amino acid sequence of SEQ ID NO:408; and
a VL region comprising an amino acid sequence having at least 70% sequence identity to the amino acid sequence of SEQ ID NO:376;

or (xlvii) a VH region comprising an amino acid sequence having at least 70% sequence identity to the amino acid sequence of SEQ ID NO:367; and
a VL region comprising an amino acid sequence having at least 70% sequence identity to the amino acid sequence of SEQ ID NO:412;

or (xlviii) a VH region comprising an amino acid sequence having at least 70% sequence identity to the amino acid sequence of SEQ ID NO:372; and
a VL region comprising an amino acid sequence having at least 70% sequence identity to the amino acid sequence of SEQ ID NO:412;

or (xlix) a VH region comprising an amino acid sequence having at least 70% sequence identity to the amino acid sequence of SEQ ID NO:367; and a VL region comprising an amino acid sequence having at least 70% sequence identity to the amino acid sequence of SEQ ID NO:370;

or (l) a VH region comprising an amino acid sequence having at least 70% sequence identity to the amino acid sequence of SEQ ID NO:372; and
a VL region comprising an amino acid sequence having at least 70% sequence identity to the amino acid sequence of SEQ ID NO:376;

or (li) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:422;

or (lii) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:383;

or (liii) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:391;

or (liv) a VH region comprising an amino acid sequence having at least 70% sequence identity to the amino acid sequence of SEQ ID NO:380; and
a VL region comprising an amino acid sequence having at least 70% sequence identity to the amino acid sequence of SEQ ID NO:422;

or (lv) a VH region comprising an amino acid sequence having at least 70% sequence identity to the amino acid sequence of SEQ ID NO:387; and
a VL region comprising an amino acid sequence having at least 70% sequence identity to the amino acid sequence of SEQ ID NO:422;

or (lvi) a VH region comprising an amino acid sequence having at least 70% sequence identity to the amino acid sequence of SEQ ID NO:380; and
a VL region comprising an amino acid sequence having at least 70% sequence identity to the amino acid sequence of SEQ ID NO:383;

or (lvii) a VH region comprising an amino acid sequence having at least 70% sequence identity to the amino acid sequence of SEQ ID NO:387; and
a VL region comprising an amino acid sequence having at least 70% sequence identity to the amino acid sequence of SEQ ID NO:391

In some embodiments, the antigen-binding molecule binds to TACI.

In some embodiments, the antigen-binding molecule binds to human BCMA and mouse BCMA.

In some embodiments, the antigen-binding molecule is a multispecific antigen-binding molecule, and further comprises an antigen-binding domain which binds to an antigen other than BCMA.

The present disclosure also provides an antigen-binding molecule, optionally isolated, which is a multispecific antigen-binding molecule, wherein the antigen-binding molecule comprises: (i) an antigen-binding domain which binds to BCMA comprising or consisting of an antigen-binding molecule according to the present disclosure, and (ii) an antigen-binding domain which binds to an antigen other than BCMA.

In some embodiments, the antigen other than BCMA is CD47.

In some embodiments, the antigen-binding molecule comprises an antigen-binding domain which binds to CD47 and inhibits interaction between CD47 and SIRPα; optionally wherein the antigen-binding molecule is capable of increasing phagocytosis of BCMA- and/or CD47-expressing cells.

In some embodiments, the antigen other than BCMA is a CD3 polypeptide.

The present disclosure also provides a chimeric antigen receptor (CAR) comprising an antigen-binding molecule according to the present disclosure.

The present disclosure also provides a nucleic acid, or a plurality of nucleic acids, optionally isolated, encoding an antigen-binding molecule according or a CAR according to the present disclosure.

The present disclosure also provides an expression vector, or a plurality of expression vectors, comprising a nucleic acid or a plurality of nucleic acids according to the present disclosure.

The present disclosure also provides a cell comprising an antigen-binding molecule, a CAR, a nucleic acid or plurality of nucleic acids, or an expression vector or plurality of expression vectors according to the present disclosure.

The present disclosure also provides a method comprising culturing a cell according to the present disclosure under conditions suitable for expression of an antigen-binding molecule or CAR by the cell.

The present disclosure also provides a composition comprising an antigen-binding molecule, a CAR, a nucleic acid or plurality of nucleic acids, an expression vector or plurality of expression vectors, or a cell according to the present disclosure, and a pharmaceutically acceptable carrier, diluent, excipient or adjuvant.

The present disclosure also provides an antigen-binding molecule, a CAR, a nucleic acid or plurality of nucleic acids, an expression vector or plurality of expression vectors, a cell, or a composition according to the present disclosure, for use in a method of medical treatment or prophylaxis.

The present disclosure also provides an antigen-binding molecule, a CAR, a nucleic acid or plurality of nucleic acids, an expression vector or plurality of expression vectors, a cell, or a composition according to the present disclosure, for use in a method of treatment or prevention of a cancer.

The present disclosure also provides the use of an antigen-binding molecule, a CAR, a nucleic acid or plurality of nucleic acids, an expression vector or plurality of expression vectors, a cell, or a composition according to the present disclosure, in the manufacture of a medicament for use in a method of treatment or prevention of a cancer.

The present disclosure also provides a method of treating or preventing a cancer, comprising administering to a subject a therapeutically or prophylactically effective amount of an antigen-binding molecule, a CAR, a nucleic acid or plurality of nucleic acids, an expression vector or plurality of expression vectors, a cell, or a composition according to the present disclosure.

In some embodiments, the cancer is selected from: a hematologic malignancy, a myeloid hematologic malignancy, a lymphoblastic hematologic malignancy, a B cell malignancy, multiple myeloma (MM), myelodysplastic syndrome (MDS), acute myeloid leukemia (AML), chronic myeloid leukemia (CML), acute lymphoblastic leukemia (ALL), lymphocytic leukemia, lymphoma, B cell lymphoma, Hodgkin's lymphoma (HL), non-Hodgkin's lymphoma (NHL), follicular lymphoma (FL), mantle cell lymphoma (MCL), Burkitt lymphoma, bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

The present disclosure also provides the use of antigen-binding molecule according to the present disclosure to increase phagocytosis of cells expressing BCMA/TACI.

The present disclosure also provides an in vitro complex, optionally isolated, comprising an antigen-binding molecule according to the present disclosure bound to BCMA/TACI.

The present disclosure also provides a method for detecting BCMA/TACI in a sample, comprising contacting a sample containing, or suspected to contain, BCMA/TACI with an antigen-binding molecule according to the present disclosure, and detecting the formation of a complex of the antigen-binding molecule with BCMA/TACI.

The present disclosure also provides a method of selecting or stratifying a subject for treatment with a BCMA/TACI-targeted agent, the method comprising contacting, in vitro, a sample from the subject with an antigen-binding molecule according to the present disclosure, and detecting the formation of a complex of the antigen-binding molecule with BCMA/TACI.

The present disclosure also provides the use of an antigen-binding molecule according to the present disclosure as an in vitro or in vivo diagnostic or prognostic agent.

The present disclosure also provides the use of an antigen-binding molecule according to the present disclosure in a method for detecting, localizing or imaging a cancer, optionally wherein the cancer is selected from: a hematologic malignancy, a myeloid hematologic malignancy, a lymphoblastic hematologic malignancy, a B cell malignancy, multiple myeloma (MM), myelodysplastic syndrome (MDS), acute myeloid leukemia (AML), chronic myeloid leukemia (CML), acute lymphoblastic leukemia (ALL), lymphocytic leukemia, lymphoma, B cell lymphoma, Hodgkin's lymphoma (HL), non-Hodgkin's lymphoma (NHL), follicular lymphoma (FL), mantle cell lymphoma (MCL), Burkitt lymphoma, bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

Description

The present disclosure provides antigen-binding molecules having combinations of desirable biophysical and/or functional properties as compared to antigen-binding molecules disclosed in the prior art.

Aspects of the present disclosure relate to antigen-binding molecules capable of binding to BCMA. The BCMA-binding molecules described herein are therefore useful for targeting myeloid hematologic malignancies, e.g. multiple myeloma. In aspects described herein antigen-binding molecules are provided which: (i) bind to human BCMA with high affinity, (ii) are cross-reactive with non-human primate BCMA and/or mouse BCMA, (iii) which inhibit interaction between BCMA and APRIL, and/or (iv) are cross-reactive with TACI.

Aspects of the present disclosure relate particularly to antigen-binding molecules capable of binding to BCMA or TACI (i.e. antigen-binding molecules having cross-reactivity for BCMA and TACI). Without wishing to bound by any particular theory, antigen-binding molecules which are demonstrated herein to bind to both BCMA and TACI are thought to recognise regions of BCMA and TACI having high structural homology between the molecules.

BCMA antigen loss is a key challenge to long term clinical benefit, and occurs via cleavage of BCMA from tumor cells by gamma-secretase, and downregulation of expression of BCMA. Targeting additional multiple myeloma antigens such as the commonly co-expressed TACI receptor, might prevent escape via antigen loss. Co-targeting TACI, a co-expressed on MM cells as well as tumor-infiltrating Tregs, can extend anti-BCMA based therapy by overcoming resistance caused by BCMA antigen loss.

Despite the emergence of promising new therapeutic strategies in B cell malignancies such as multiple myeloma (MM), there remains significant unmet need for better approaches. Large populations of tissue resident macrophages in the bone marrow represent an attractive therapeutic target for hematological malignancies. BCMA/TACI and CD47 are highly co-expressed in all characterized MM cell lines and many patient samples, and play functional roles that reduce risk of antigen loss. Their expression levels are prognostic of the progression and outcome of MM.

Overexpression of CD47 is utilized by malignant hematopoietic cells to prevent macrophage clearance and evade immunosurveillance in the bone marrow microenvironment. APRIL secreted by bone marrow osteoclast activates BCMA/TACI receptors in multiple myeloma cells, and induces the upregulation of antiapoptotic, immunosuppressive, and osteoclastogenic genes through the canonical and non-canonical NF-kB pathway.

Aspects of the present disclosure also relate to antigen-binding molecules capable of binding to BCMA/TACI and CD47. The multispecific BCMA/TACI-binding, CD47-binding antigen-binding molecules described herein display preferential binding to cells expressing both BCMA/TACI and CD47, and are therefore useful for targeting myeloid hematologic malignancies, e.g. multiple myeloma. They represent an improved treatment for myeloid hematologic malignancies as compared e.g. to CD47-binding antibodies of the prior art, because the BCMA/TACI-binding arm targets the CD47-binding arm to the cancer cells, minimising off-target effects.

BCMA

Human B cell maturation antigen (BCMA; also known as TNFRSF17) is the protein identified by UniProt Q02223. Alternative splicing of mRNA encoded by the human TNFRSF17 gene yields two isoforms: isoform 1 (UniProt: Q02223-1, v2; SEQ ID NO:1) and isoform 2 (UniProt: Q02223-2; SEQ ID NO:2), in which the amino acid sequence corresponding to positions 44 to 93 of SEQ ID NO:1 are substituted with 'R'.

The structure and function of BCMA is reviewed e.g. in Coquery and Erickson, Crit Rev Immunol. (2012) 32(4): 287-305, which is hereby incorporated by reference in its entirety. BCMA is a cell surface receptor of the TNF receptor superfamily. BCMA comprises an N-terminal extracellular domain (SEQ ID NO:3) having a cysteine-rich TNFR repeat region (SEQ ID NO:4). The extracellular domain is connected by a transmembrane domain (SEQ ID NO:5) to a cytoplasmic domain (SEQ ID NO:6), containing a region which is important for TRAF interaction and activation of NFκB (SEQ ID NO:7; Hatzoglou et al., J Immunol. (2000) 165(3):1322-30).

BCMA is expressed by mature B lymphocytes, and plays an important role in differentiation of B cells into plasma cells (see Tai and Anderson, Immunotherapy (2015) 7(11): 1187-1199, which is hereby incorporated by reference in its entirety). BCMA is expressed by B-cell lineage cells, particularly in the interfollicular region of the germinal center, by plasmablasts and by differentiated plasma cells. BCMA expression is selectively induced during plasma cell differentiation. BCMA may enhance humoral immunity by stimulating the survival of normal plasma cells and plasmablasts, but is absent on naïve and most memory B cells. BCMA is also expressed by CD138$^-$BDCA-4$^+$ plasmacytoid dendritic cells (Chauhan et al., Cancer Cell (2009) 16(4):309-23).

Binding of B cell activation factor (BAFF) and/or a proliferation-inducing ligand (APRIL) to BCMA activates NFκB and MAPK8/JNK intracellular signalling pathways, and thereby promotes the survival and proliferation of BCMA-expressing cells. BCMA is differentially expressed during the differentiation of immature B cells to mature plasma cells, and highly expressed in MM cell lines and CD138+ cells from MM patients. Indeed, BCMA is the most selectively expressed cell surface receptor on MM cell lines and patient MM cells. Serum BCMA levels are also higher in MM patients versus healthy donors.

Expression of BCMA has been observed to be highly variable among multiple myeloma patients (Otero et al., J. Clin. Med. (2020) 9(11): 3577; Cohen et al., J. Clin Invest. (2019) 129(6):2210-2221; Brudno et al., J. Clin. Oncol. (2018) 36(22)). Studies suggest that BCMA is cleaved and shed from cancer cells via the activity of gamma-secretase, which in turn contributes to resistance to BCMA-targeted therapy and relapse in patients treated with such therapy (Otero et al., J. Clin. Med. (2020) 9(11): 3577). Gamma-secretase-mediated cleavage of BCMA moreover yields soluble BCMA (sBCMA), which is able to activate CD4+ T-reg cells. Activated CD4+T-regs express immunomodulatory factors such as IL-10 and TGF-β, and compounding the immunosuppressive BM microenvironment, which is critical for the survival of MM cells and protects them from spontaneous +/- drug-induced apoptosis.

Brudno et al., J. Clin. Oncol. (2018) 36(22) discloses the results of a study in which BCMA expression on MM cells was evaluated prior to and during treatment with BCMA-targeted CAR-T therapy. Prior to CAR-BCMA T-cell infusion, the MM population expressed high levels of BCMA. 56 weeks after CAR-BCMA T-cell infusion, the small number of MM cells that were present lacked BCMA expression, and 68 weeks after CAR-BCMA T-cell infusion, the MM cells displayed mixed BCMA expression, with some cells negative for BCMA expression.

Samur et al., Nature Communications (2021) 12: 868 recently reported that a MM patient treated with 4 prior lines of therapy before being enrolled in a Phase I study with BCMA-targeted CAR T-cell therapy (Idecabtagene Vicleucel) relapsed 9 months after 1st infusion of the CAR-T therapy, and was unresponsive to a higher dose of the therapy at second infusion. The resistant MM cells were found to harbour a deletion in one allele of BCMA, and a translation-aborting mutation in the other allele, resulting in loss of BCMA antigen expression (in turn leading to lack of CAR T-cell activation and proliferation following the second infusion).

In this specification 'BCMA' refers to BCMA from any species and includes BCMA isoforms, fragments, variants or homologues from any species.

A fragment of BCMA may have a minimum length of one of 10, 20, 30, 40, 50, 100, 150 or 175 amino acids, and may have a maximum length of one of 20, 30, 40, 50, 100, 125, 150 or 175 amino acids.

In some embodiments, the BCMA is BCMA from a mammal (e.g. a primate (rhesus, cynomolgous, or human) and/or a rodent (e.g. rat or murine) BCMA). Isoforms, fragments, variants or homologues of BCMA may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature BCMA isoform from a given species, e.g. human.

In some embodiments, the BCMA is human BCMA. In some embodiments, the BCMA is cynomolgous macaque BCMA. In some embodiments, the BCMA is mouse BCMA.

Isoforms, fragments, variants or homologues may optionally be functional isoforms, fragments, variants or homologues, e.g. having a functional property/activity of the reference BCMA (e.g. human BCMA isoform 1), as determined by analysis by a suitable assay for the functional property/activity. For example, an isoform, fragment, variant or homologue of BCMA may display association with e.g. BAFF and/or APRIL.

In some embodiments, the BCMA comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1 or 2.

In some embodiments, a fragment of BCMA comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:3.

Human A proliferation-inducing ligand (APRIL; also known as TNFSF13) is the protein identified by UniProt O75888. APRIL is cleaved in the Golgi between positions 104-105 by a furin convertase to yield the mature, secreted form of the protein (Lopez-Fraga et al. (2001) EMBO Rep. 2: 945-951). APRIL assembles as a homotrimer which establishes contacts with monomeric BCMA and TACI receptors, resulting in receptor trimerisation and activation of the NF-kB pathway. In this specification 'APRIL' refers to APRIL from any species and includes APRIL isoforms, fragments, variants or homologues from any species. In some embodiments, the APRIL is APRIL from a mammal (e.g. a primate (rhesus, cynomolgous, or human) and/or a rodent (e.g. rat or murine) APRIL). Isoforms, fragments, variants or homologues of APRIL may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature APRIL isoform from a given species, e.g. human.

In some embodiments, the APRIL comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:281, 282, 283, 284, 285 or 286.

In some embodiments, a fragment of APRIL comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:287, 288, 289 or 290.

Human B cell activating factor (BAFF; also known as TNFSF13B and BLys) is the protein identified by UniProt Q9Y275. In this specification BAFF' refers to BAFF from any species and includes BAFF isoforms, fragments, variants or homologues from any species. In some embodiments, the BAFF is BAFF from a mammal (e.g. a primate (rhesus, cynomolgous, or human) and/or a rodent (e.g. rat or murine) BAFF). Isoforms, fragments, variants or homologues of BAFF may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature BAFF isoform from a given species, e.g. human.

In some embodiments, the BAFF comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:291, 292 or 293.

In some embodiments, a fragment of BAFF comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:296, 297, 298, 299, 300 or 301.

TACI

Transmembrane activator and CAML interactor (TACI; also known as TNFRSF13B) is the protein identified by UniProt O14836. Alternative splicing of mRNA encoded by the human TNFRSF13B gene yields three isoforms: isoform 1 (UniProt: O14836-1, v1; SEQ ID NO:260), isoform 2 (UniProt: O14836-2; SEQ ID NO:261), in which the amino acid sequence corresponding to positions 21 to 67 of SEQ ID NO:260 are substituted with 'W', and isoform 3 (UniProt: O14836-3; SEQ ID NO:262), in which the amino acid sequence corresponding to positions 150 to 176 of SEQ ID NO:260 are substituted with a 27 amino acid sequence, and lacking the amino acid sequence corresponding to positions 177 to 293 of SEQ ID NO:260.

The structure and function of TACI is reviewed e.g. in Bossen and Schneider, Semin Immunol (2006) 18(5):263-275, which is hereby incorporated by reference in its entirety. TACI is a cell surface receptor of the TNF receptor superfamily, and comprises an N-terminal extracellular domain (SEQ ID NO:333) having two cysteine-rich TNFR repeat regions (SEQ ID NOs:334 and 335). The extracellular domain is connected by a transmembrane domain (SEQ ID NO:336) to a cytoplasmic domain (SEQ ID NO:337).

TACI is expressed by B lymphocytes, and is the receptor for calcium-modulator and cyclophilin ligand (CAML), BAFF and APRIL (Wu et al., Journal of Biological Chemistry (2000) 275 (45):35478-85). BAFF and APRIL signal through TACI, inducing activation of several transcription factors including NFAT, AP-1, and NFκB. TACI is an immune response regulator, inhibiting B cell expansion and promoting the differentiation and survival of plasma cells.

TACI expression is upregulated in B cell malignancies such as multiple myeloma (MM). MM cell lines and fresh tumor samples from patients have been shown to bind soluble BAFF and express BCMA, TACI, and BAFF-R, and BAFF modulates the proliferative capacity of cytokine-stimulated MM cells, likely through its ability to promote survival via signalling through these receptors (Novak et al., Blood (2004) 103:689-694). The expression profile of TACI is highly similar to that of BCMA making it an attractive 'co-target' for BCMA-targeted therapies. In MM, TACI is highly expressed on B cells, and BCMA and TACI are co-expressed in MM patients (Lee et al., Blood. (2018) 131(7): 746-758). TACI is also implicated in other B cell malignancies e.g., Non-Hodgkin's Lymphoma (NHL), Follicular Lymphoma (FL) and Mantle cell lymphoma (MCL) (Xu et al., Cancers (2020) 12(4): 1045; Lee et al., Blood. (2018) 131(7): 746-758; Gupta et al., Blood (2007) 110 (11): 3585; Wada et al. Histopathology (2009) 54: 221-232). In addition to its role as a tumor antigen in MM and other B cell malignancies, TACI is expressed on T-regs in the immunosuppressive tumor microenvironment. APRIL promotes immunosuppression in MM, signaling via TACI and significantly up-regulating proliferation, survival, and immune inhibitory function of T-regs (Tai et al., Leukemia (2019) 33(2): 426-438). T-regs contribute to impairment of anti-tumor immune responses, resulting in immune escape and progression of solid and blood cancers, including MM. APRIL-mediated signaling via TACI expressed on T-regs contributes to the immunosuppressive MM BM milieu. The highest level of expression of the immunosuppressive cytokine IL-10 levels is observed in CD4$^+$CD25$^+$Foxp3$^{high}$ subset, which also expresses the highest levels of TACI.

Importantly, MM cells have been observed to retain TACI expression in the absence of BCMA expression. Therapies targeting both BCMA and TACI merit investigation in MM (particularly relapsed-refractory MM), and other B cell cancers.

Schmidts et al., Blood Adv (2019) 3 (21): 3248-3260 recently described T cells expressing a third-generation, trimeric APRIL-based CAR, which are able to kill target cells expressing either BCMA or TACI. However, few programs employing APRIL-based targeting of BCMA/TACI have progressed to the clinic. APRIL binds BCMA and TACI as a homotrimer which is challenging to express, and APRIL also binds to its targets with affinities which are significantly lower than the levels of affinity typically employed in therapeutic programmes (APRIL binds BCMA with $K_D$=~16 nM, and binds TACI with $K_D$=~11 nM).

In this specification 'TACI' refers to TACI from any species and includes TACI isoforms, fragments, variants or homologues from any species.

A fragment of TACI may have a minimum length of one of 10, 20, 30, 40, 50, 100, 150, 200 or 250 amino acids, and may have a maximum length of one of 20, 30, 40, 50, 100, 125, 150, 200 or 250 amino acids.

In some embodiments, the TACI is TACI from a mammal (e.g. a primate (rhesus, cynomolgous, or human) and/or a rodent (e.g. rat or murine) TACI). Isoforms, fragments, variants or homologues of TACI may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature TACI isoform from a given species, e.g. human.

Isoforms, fragments, variants or homologues may optionally be functional isoforms, fragments, variants or homologues, e.g. having a functional property/activity of the reference TACI (e.g. human TACI isoform 1), as determined by analysis by a suitable assay for the functional property/activity. For example, an isoform, fragment, variant or homologue of TACI may display association with e.g. BAFF and/or APRIL.

In some embodiments, the TACI comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:330, 331 or 332.

In some embodiments, a fragment of TACI comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:333.

BCMA and TACI are attractive therapeutic targets. BCMA and TACI are differentially expressed during the differentiation of immature B cells to mature plasma cells, and are highly expressed in MM cell lines and CD138+ cells from MM patients. Binding of APRIL to BCMA/TACI promotes cell survival, proliferation, and immunosuppression through the canonical and non-canonical NF-kB signalling pathways. Disrupting the interaction between APRIL and BCMA/TACI with competitive antagonists will inhibit downstream BCMA/TACI-mediated signalling.

Herein, reference to BCMA/TACI' encompasses reference to (i) BCMA (only), (i) TACI (only), or (iii) both BCMA and TACI.

Accordingly, molecules which bind to BCMA/TACI' may bind to BCMA, TACI, or may bind to both BCMA and TACI. In some embodiments, molecules which bind to both BCMA and TACI may bind independently to each of BCMA and TACI, and may be described as being cross-reactive for BCMA and TACI.

Reference herein to cells/cancers expressing 'BCMA/TACI' encompasses reference to cells/cancers expressing BCMA, TACI, or both BCMA and TACI.

CD47

Human CD47 (also known as IAP, MER6 and OA3) is the protein identified by UniProt Q08722. Alternative splicing of mRNA encoded by the human CD47 gene yields four isoforms which differ in the sequence of the C-terminal cytoplasmic tail region: isoform OA3-323 (UniProt: Q08722-1, v1; SEQ ID NO:171); isoform OA3-293 (UniProt: Q08722-2; SEQ ID NO:172), which lacks the amino acid sequence corresponding to positions 293 to 323 of SEQ ID NO:171; isoform OA3-305 (UniProt: Q08722-3; SEQ ID NO:173), which comprises the substitutions K304N and A305N relative to SEQ ID NO:171, and which lacks the amino acid sequence corresponding to positions 306 to 323 of SEQ ID NO:171; and isoform OA3-312 (UniProt: Q08722-4; SEQ ID NO:174), which lacks the amino acid sequence corresponding to positions 312 to 323 of SEQ ID NO:171.

The N-terminal 18 amino acids of SEQ ID NOs:171 to 174 constitute a signal peptide, and so the mature form of isoforms OA3-323, OA3-293, OA3-305 and OA3-312 (i.e. after processing to remove the signal peptide) have the amino acid sequences shown in SEQ ID NOs:175 to 178, respectively.

The structure and function of CD47 is reviewed e.g. in Sick et al., Br J Pharmacol. (2012) 167(7): 1415-1430 and Willingham et al. Proc Natl Acad Sci USA. (2012) 109(17): 6662-6667, both of which are hereby incorporated by reference in its entirety. CD47 is a ubiquitously-expressed ~50 kDa multi-pass membrane receptor that belongs to the immunoglobulin superfamily, comprising an N-terminal extracellular region (SEQ ID NO:180) having a V-type Ig-like domain (SEQ ID NO:179), five transmembrane domains (SEQ ID NOs:181, 183, 185, 187 and 189), and a short C-terminal intracellular tail (SEQ ID NO:190).

CD47 is involved in cell-to-cell communication through ligating to the transmembrane signal-regulatory proteins (SIRPs) SIRPα and SIRPγ and integrins (e.g. αvβ3 integrin), and also mediates cell-extracellular matrix interactions through binding to thrombospondin-1 (TSP-1). CD47 is involved in a wide range of cellular processes including adhesion, migration, proliferation and apoptosis, and plays a key role in immune processes and angiogenesis.

CD47 is the ligand for SIRPα, which is expressed on macrophages and dendritic cells. Binding of CD47 to SIRPα on the surface of phagocytic cells, triggers SIRPα ITIM signalling, inhibiting phagocytosis of the CD47 expressing cell. CD47 is a multi-pass transmembrane protein, whereas SIRPα consists of 4 extracellular domains and an intracellular ITIM-domain. The terminal V-set domain of SIRPα interacts with the Ig V-like domain of CD47.

Upon binding CD47, SIRPα initiates a signalling cascade that results in the inhibition of phagocytosis of the CD47-expressing cell. This 'don't eat me' signal is transmitted by phosphorylation by Src kinases of immunoreceptor tyrosine-based inhibitor motifs (ITIMs) in the cytoplasmic domain of SIRPα. Subsequent binding and activation of Src homology-2 (SH2) domain-containing tyrosine phosphatases SHP-1 and SHP-2 blocks phagocytosis, potentially through preventing the accumulation of myosin-IIA at the phagocytic synapse. Disrupting the interaction along the antiparallel beta sheets of CD47 prevents downstream ITIM-mediated signalling, enabling phagocytes to 'eat' and destroy cancer cells.

Aberrant CD47 expression/activity is implicated in the development and progression of many cancers, and accumulating evidence suggests that cell-surface expression of CD47 is a common mechanism by which cancer cells protect themselves from phagocytosis.

In this specification 'CD47' refers to CD47 from any species and includes CD47 isoforms, fragments, variants or homologues from any species.

As used herein, a 'fragment', 'variant' or 'homologue' of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments, fragments, variants, isoforms and homologues of a reference protein may be characterised by their ability to perform a function performed by the reference protein.

A 'fragment' generally refers to a fraction of the reference protein. A 'variant' generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An 'isoform' generally refers to a variant of the reference protein expressed by the same species as the species of the reference protein (e.g. OA3-323, OA3-293, OA3-305 and OA3-312 are all isoforms of one another). A 'homologue' generally refers to a variant of the reference protein produced by a different species as compared to the species of the reference protein. For example, human CD47 isoform OA3-323 (Q08722-1, v1; SEQ ID NO:171) and rhesus macaque CD47 (UniProt: F7F5Y9-1, v2) are homologues of one another. Homologues include orthologues.

A 'fragment' of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of CD47 may have a minimum length of one of 10, 20, 30, 40, 50, 100, 150, 200, 250 or 300 amino acids, and may have a maximum length of one of 20, 30, 40, 50, 100, 150, 200, 250 or 300 amino acids.

In some embodiments, the CD47 is CD47 from a mammal (e.g. a primate (rhesus, cynomolgous, non-human primate or human) and/or a rodent (e.g. rat or murine) CD47). Isoforms, fragments, variants or homologues of CD47 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature CD47 isoform from a given species, e.g. human.

Isoforms, fragments, variants or homologues may optionally be functional isoforms, fragments, variants or homologues, e.g. having a functional property/activity of the reference CD47 (e.g. human CD47 isoform OA3-323), as determined by analysis by a suitable assay for the functional property/activity. For example, an isoform, fragment, variant or homologue of CD47 may display association with one or more of: SIRPα, SIRPγ, TSP-1 and αvβ3 integrin.

In some embodiments, the CD47 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:171 to 178.

In some embodiments, a fragment of CD47 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NO:179 or 180.

CD47 is an attractive therapeutic target. CD47 is usually expressed on the surface of normal healthy cells and migrating hematopoietic stem cells to prevent phagocytosis, and is upregulated in nearly all hematological and solid tumors, including MM cells, to evade immune surveillance and escape phagocytosis. Disrupting the interaction between CD47 and SIRPα enables phagocytes to 'eat' and destroy cancer cells. CD47 blockade repolarises tumor-associated macrophages into a pro-inflammatory, anti-tumor state, and clearance of malignant cells by phagocytic cells offers an additional route for neo-antigen presentation to adaptive immune system.

Antigen-Binding Molecules

The present disclosure provides antigen-binding molecules. In aspects of the present disclosure the antigen-binding molecules are capable of binding to BCMA. In aspects of the present disclosure the antigen-binding molecules are capable of binding to TACI. In aspects of the present disclosure the antigen-binding molecules are capable of binding to BCMA or TACI. In aspects of the present disclosure the antigen-binding molecules are capable of binding to CD47. In aspects of the present disclosure the antigen-binding molecules are capable of binding to BCMA and CD47. In aspects of the present disclosure the antigen-binding molecules are capable of binding to TACI and CD47. In aspects of the present disclosure the antigen-binding molecules are capable of binding to BCMA or TACI and CD47. In aspects of the present disclosure the antigen-binding molecules comprise (i) an antigen-binding domain capable of binding to BCMA and (ii) an antigen-binding domain capable of binding to CD47. In aspects of the present disclosure the antigen-binding molecules comprise (i) an antigen-binding domain capable of binding to TACI and (ii) an antigen-binding domain capable of binding to CD47. In aspects of the present disclosure the antigen-binding molecules comprise (i) an antigen-binding domain capable of binding to BCMA or TACI and (ii) an antigen-binding domain capable of binding to CD47. An antigen-binding molecule that is capable of binding to a given target antigen may also be described as an antigen-binding molecule that binds to the given target antigen.

An 'antigen-binding molecule' refers to a molecule which binds to a target antigen. Antigen-binding molecules include e.g. monoclonal antibodies, polyclonal antibodies, monospecific and multispecific antibodies (e.g., bispecific antibodies), and antibody fragments (e.g. Fv, scFv, Fab, scFab, $F(ab')_2$, $Fab_2$, diabodies, triabodies, scFv-Fc, minibodies, single domain antibodies (e.g. VhH), etc.), as long as they display binding to the relevant target molecule(s).

Antigen-binding molecules according to the present disclosure also include antibody-derived molecules, e.g. molecules comprising an antigen-binding region/domain derived from an antibody. Antibody-derived antigen-binding molecules may comprise an antigen-binding region/domain that comprises, or consists of, the antigen-binding region of an antibody (e.g. an antigen-binding fragment of an antibody). In some embodiments, the antigen-binding region/domain of an antibody-derived antigen-binding molecule may be or comprise the Fv (e.g. provided as an scFv) or the Fab region of an antibody, or the whole antibody. For example, antigen-binding molecules according to the present disclosure include antibody-drug conjugates (ADCs) comprising a (cytotoxic) drug moiety (e.g. as described hereinbelow). Antigen-binding molecules according to the present disclosure also include multispecific antigen-binding molecules such as immune cell engager molecules comprising a domain for recruiting (effector) immune cells (reviewed e.g. in Goebeler and Bargou, Nat. Rev. Clin. Oncol. (2020) 17: 418-434 and Ellerman, Methods (2019) 154:102-117, both of which are hereby incorporated by reference in their entirety), including BiTEs, BiKEs and TriKEs. Antigen-binding molecules according to the present disclosure also include chimeric antigen receptors (CARs), which are recombinant receptors providing both antigen-binding and T cell activating functions (CAR structure, function and engineering is reviewed e.g. in Dotti et al., Immunol Rev (2014) 257(1), which is hereby incorporated by reference in its entirety).

The antigen-binding molecule of the present disclosure comprises a moiety or moieties capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)), affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

As used herein, a 'peptide' refers to a chain of two or more amino acid monomers linked by peptide bonds. A peptide typically has a length in the region of about 2 to 50 amino acids. A 'polypeptide' is a polymer chain of two or more peptides. Polypeptides typically have a length greater than about 50 amino acids.

The antigen-binding molecules of the present disclosure generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments, the polypeptides form part of a larger polypeptide comprising the polypeptides (e.g. in the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present disclosure may be designed and prepared using the sequences of monoclonal antibodies (mAbs) capable of binding to BCMA/TACI and CD47. Antigen-binding regions of antibodies, such as single chain variable fragment (scFv), Fab and $F(ab')_2$ fragments may also be used/provided. An 'antigen-binding region' is any fragment of an antibody which binds to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, MD (1991), Chothia et al., J. Mol. Biol. 196:901-917 (1987), and VBASE2, as described in Retter et al., Nucl. Acids Res. (2005) 33 (suppl 1): D671-D674. The CDRs and FRs of the VH regions and VL regions of the antibody clones described herein were defined according to the international IMGT (ImMunoGeneTics) information system (LeFranc et al., Nucleic Acids Res. (2015) 43 (Database issue):D413-22), which uses the IMGT V-DOMAIN numbering rules as described in Lefranc et al., Dev. Comp. Immunol. (2003) 27:55-77. In preferred embodiments, the CDRs and FRs of antigen-binding molecules referred to herein are defined according to the IMGT information system.

In some embodiments, the antigen-binding molecule comprises the CDRs of an antigen-binding molecule which binds to BCMA/TACI. In some embodiments, the antigen-binding molecule comprises the FRs of an antigen-binding molecule which binds to BCMA/TACI. In some embodiments, the antigen-binding molecule comprises the CDRs and the FRs of an antigen-binding molecule which binds to BCMA/TACI. That is, In some embodiments, the antigen-binding molecule comprises the VH region and the VL region of an antigen-binding molecule which binds to BCMA/TACI.

In some embodiments, the antigen-binding molecule comprises the CDRs, FRs and/or the VH and/or VL regions of a BCMA/TACI-binding antibody clone described herein, or CDRs, FRs and/or VH and/or VL regions which are derived from those of a BCMA/TACI-binding antibody clone described herein. In some embodiments, a BCMA- or TACI-binding antibody clone is selected from: 538-SP5-610, 539-SP2-H3, 539-SP1-C8, 539-SP5-D7, 539-SP7-F4, 552-LN1-E9, 552-LN2-E6, 552-LN1-F4, 552-LN2-F8, 1E9-4H, 1E9-QE, 2F8-2Q, 2F8-5U, 5B10-4Y, 5B10-5I, 1C8-6A, 1C8-EH, 1C8-402, 1C8-403, 1C8-507, 1C8-610, 1C8-6A3, 1C8-25 and 1C8-27.

In some embodiments, the antigen-binding molecule comprises a VH region according to one of (1) to (20) below:

(1) a VH region incorporating the following CDRs:
HC-CDR1 having the amino acid sequence of SEQ ID NO:137
HC-CDR2 having the amino acid sequence of SEQ ID NO:138
HC-CDR3 having the amino acid sequence of SEQ ID NO:139,
or a variant thereof in which one or two or three amino acids in one or more of HC-CDR1, HC-CDR2, or HC-CDR3 are substituted with another amino acid.

(2) a VH region incorporating the following CDRs:
HC-CDR1 having the amino acid sequence of SEQ ID NO:145
HC-CDR2 having the amino acid sequence of SEQ ID NO:100
HC-CDR3 having the amino acid sequence of SEQ ID NO:146,
or a variant thereof in which one or two or three amino acids in one or more of HC-CDR1, HC-CDR2, or HC-CDR3 are substituted with another amino acid.

(3) a VH region incorporating the following CDRs:
HC-CDR1 having the amino acid sequence of SEQ ID NO:23
HC-CDR2 having the amino acid sequence of SEQ ID NO:24
HC-CDR3 having the amino acid sequence of SEQ ID NO:25,
or a variant thereof in which one or two or three amino acids in one or more of HC-CDR1, HC-CDR2, or HC-CDR3 are substituted with another amino acid.

(4) a VH region incorporating the following CDRs:
HC-CDR1 having the amino acid sequence of SEQ ID NO:23
HC-CDR2 having the amino acid sequence of SEQ ID NO:39
HC-CDR3 having the amino acid sequence of SEQ ID NO:40,
or a variant thereof in which one or two or three amino acids in one or more of HC-CDR1, HC-CDR2, or HC-CDR3 are substituted with another amino acid.

(5) a VH region incorporating the following CDRs:
HC-CDR1 having the amino acid sequence of SEQ ID NO:53
HC-CDR2 having the amino acid sequence of SEQ ID NO:54

HC-CDR3 having the amino acid sequence of SEQ ID NO:55,
or a variant thereof in which one or two or three amino acids in one or more of HC-CDR1, HC-CDR2, or HC-CDR3 are substituted with another amino acid.

(6) a VH region incorporating the following CDRs:
HC-CDR1 having the amino acid sequence of SEQ ID NO:68
HC-CDR2 having the amino acid sequence of SEQ ID NO:69
HC-CDR3 having the amino acid sequence of SEQ ID NO:70,
or a variant thereof in which one or two or three amino acids in one or more of HC-CDR1, HC-CDR2, or HC-CDR3 are substituted with another amino acid.

(7) a VH region incorporating the following CDRs:
HC-CDR1 having the amino acid sequence of SEQ ID NO:84
HC-CDR2 having the amino acid sequence of SEQ ID NO:85
HC-CDR3 having the amino acid sequence of SEQ ID NO:86,
or a variant thereof in which one or two or three amino acids in one or more of HC-CDR1, HC-CDR2, or HC-CDR3 are substituted with another amino acid.

(8) a VH region incorporating the following CDRs:
HC-CDR1 having the amino acid sequence of SEQ ID NO:99
HC-CDR2 having the amino acid sequence of SEQ ID NO:100
HC-CDR3 having the amino acid sequence of SEQ ID NO:101,
or a variant thereof in which one or two or three amino acids in one or more of HC-CDR1, HC-CDR2, or HC-CDR3 are substituted with another amino acid.

(9) a VH region incorporating the following CDRs:
HC-CDR1 having the amino acid sequence of SEQ ID NO:99
HC-CDR2 having the amino acid sequence of SEQ ID NO:100
HC-CDR3 having the amino acid sequence of SEQ ID NO:113,
or a variant thereof in which one or two or three amino acids in one or more of HC-CDR1, HC-CDR2, or HC-CDR3 are substituted with another amino acid.

(10) a VH region incorporating the following CDRs:
HC-CDR1 having the amino acid sequence of SEQ ID NO:128
HC-CDR2 having the amino acid sequence of SEQ ID NO:100
HC-CDR3 having the amino acid sequence of SEQ ID NO:129,
or a variant thereof in which one or two or three amino acids in one or more of HC-CDR1, HC-CDR2, or HC-CDR3 are substituted with another amino acid.

(11) a VH region incorporating the following CDRs:
HC-CDR1 having the amino acid sequence of SEQ ID NO:99
HC-CDR2 having the amino acid sequence of SEQ ID NO:394
HC-CDR3 having the amino acid sequence of SEQ ID NO:101,
or a variant thereof in which one or two or three amino acids in one or more of HC-CDR1, HC-CDR2, or HC-CDR3 are substituted with another amino acid.

(12) a VH region incorporating the following CDRs:
  HC-CDR1 having the amino acid sequence of SEQ ID NO:128
  HC-CDR2 having the amino acid sequence of SEQ ID NO:347
  HC-CDR3 having the amino acid sequence of SEQ ID NO:129,
  or a variant thereof in which one or two or three amino acids in one or more of HC-CDR1, HC-CDR2, or HC-CDR3 are substituted with another amino acid.
(13) a VH region incorporating the following CDRs:
  HC-CDR1 having the amino acid sequence of SEQ ID NO:53
  HC-CDR2 having the amino acid sequence of SEQ ID NO:418
  HC-CDR3 having the amino acid sequence of SEQ ID NO:55,
  or a variant thereof in which one or two or three amino acids in one or more of HC-CDR1, HC-CDR2, or HC-CDR3 are substituted with another amino acid.
(14) a VH region incorporating the following CDRs:
  HC-CDR1 having the amino acid sequence of SEQ ID NO:99
  HC-CDR2 having the amino acid sequence of SEQ ID NO:347
  HC-CDR3 having the amino acid sequence of SEQ ID NO:101,
  or a variant thereof in which one or two or three amino acids in one or more of HC-CDR1, HC-CDR2, or HC-CDR3 are substituted with another amino acid.
(15) a VH region incorporating the following CDRs:
  HC-CDR1 having the amino acid sequence of SEQ ID NO:53
  HC-CDR2 having the amino acid sequence of SEQ ID NO:388
  HC-CDR3 having the amino acid sequence of SEQ ID NO:55,
  or a variant thereof in which one or two or three amino acids in one or more of HC-CDR1, HC-CDR2, or HC-CDR3 are substituted with another amino acid.
(16) a VH region incorporating the following CDRs:
  HC-CDR1 having the amino acid sequence of SEQ ID NO:491
  HC-CDR2 having the amino acid sequence of SEQ ID NO:492
  HC-CDR3 having the amino acid sequence of SEQ ID NO:493,
  or a variant thereof in which one or two or three amino acids in one or more of HC-CDR1, HC-CDR2, or HC-CDR3 are substituted with another amino acid.
(17) a VH region incorporating the following CDRs:
  HC-CDR1 having the amino acid sequence of SEQ ID NO:53
  HC-CDR2 having the amino acid sequence of SEQ ID NO:54
  HC-CDR3 having the amino acid sequence of SEQ ID NO:456,
  or a variant thereof in which one or two or three amino acids in one or more of HC-CDR1, HC-CDR2, or HC-CDR3 are substituted with another amino acid.
(18) a VH region incorporating the following CDRs:
  HC-CDR1 having the amino acid sequence of SEQ ID NO:466
  HC-CDR2 having the amino acid sequence of SEQ ID NO:54
  HC-CDR3 having the amino acid sequence of SEQ ID NO:55, or a variant thereof in which one or two or three amino acids in one or more of HC-CDR1, HC-CDR2, or HC-CDR3 are substituted with another amino acid.
(19) a VH region incorporating the following CDRs:
  HC-CDR1 having the amino acid sequence of SEQ ID NO:53
  HC-CDR2 having the amino acid sequence of SEQ ID NO:472
  HC-CDR3 having the amino acid sequence of SEQ ID NO:55,
  or a variant thereof in which one or two or three amino acids in one or more of HC-CDR1, HC-CDR2, or HC-CDR3 are substituted with another amino acid.
In some embodiments, the antigen-binding molecule comprises a VH region according to one of (20) to (47) below:
(20) a VH region incorporating the following FRs:
  HC-FR1 having the amino acid sequence of SEQ ID NO:140
  HC-FR2 having the amino acid sequence of SEQ ID NO:141
  HC-FR3 having the amino acid sequence of SEQ ID NO:142
  HC-FR4 having the amino acid sequence of SEQ ID NO:143,
  or a variant thereof in which one or two or three amino acids in one or more of HC-FR1, HC-FR2, HC-FR3, or HC-FR4 are substituted with another amino acid.
(21) a VH region incorporating the following FRs:
  HC-FR1 having the amino acid sequence of SEQ ID NO:147
  HC-FR2 having the amino acid sequence of SEQ ID NO:148
  HC-FR3 having the amino acid sequence of SEQ ID NO:149
  HC-FR4 having the amino acid sequence of SEQ ID NO:150,
  or a variant thereof in which one or two or three amino acids in one or more of HC-FR1, HC-FR2, HC-FR3, or HC-FR4 are substituted with another amino acid.
(22) a VH region incorporating the following FRs:
  HC-FR1 having the amino acid sequence of SEQ ID NO:26
  HC-FR2 having the amino acid sequence of SEQ ID NO:27
  HC-FR3 having the amino acid sequence of SEQ ID NO:28
  HC-FR4 having the amino acid sequence of SEQ ID NO:29,
  or a variant thereof in which one or two or three amino acids in one or more of HC-FR1, HC-FR2, HC-FR3, or HC-FR4 are substituted with another amino acid.
(23) a VH region incorporating the following FRs:
  HC-FR1 having the amino acid sequence of SEQ ID NO:26
  HC-FR2 having the amino acid sequence of SEQ ID NO:41
  HC-FR3 having the amino acid sequence of SEQ ID NO:42
  HC-FR4 having the amino acid sequence of SEQ ID NO:43,
  or a variant thereof in which one or two or three amino acids in one or more of HC-FR1, HC-FR2, HC-FR3, or HC-FR4 are substituted with another amino acid.
(24) a VH region incorporating the following FRs:
  HC-FR1 having the amino acid sequence of SEQ ID NO:56

HC-FR2 having the amino acid sequence of SEQ ID NO:57

HC-FR3 having the amino acid sequence of SEQ ID NO:58

HC-FR4 having the amino acid sequence of SEQ ID NO:59, or a variant thereof in which one or two or three amino acids in one or more of HC-FR1, HC-FR2, HC-FR3, or HC-FR4 are substituted with another amino acid.

(25) a VH region incorporating the following FRs:

HC-FR1 having the amino acid sequence of SEQ ID NO:71

HC-FR2 having the amino acid sequence of SEQ ID NO:72

HC-FR3 having the amino acid sequence of SEQ ID NO:73

HC-FR4 having the amino acid sequence of SEQ ID NO:74, or a variant thereof in which one or two or three amino acids in one or more of HC-FR1, HC-FR2, HC-FR3, or HC-FR4 are substituted with another amino acid.

(26) a VH region incorporating the following FRs:

HC-FR1 having the amino acid sequence of SEQ ID NO:87

HC-FR2 having the amino acid sequence of SEQ ID NO:88

HC-FR3 having the amino acid sequence of SEQ ID NO:89

HC-FR4 having the amino acid sequence of SEQ ID NO:43, or a variant thereof in which one or two or three amino acids in one or more of HC-FR1, HC-FR2, HC-FR3, or HC-FR4 are substituted with another amino acid.

(27) a VH region incorporating the following FRs:

HC-FR1 having the amino acid sequence of SEQ ID NO:102

HC-FR2 having the amino acid sequence of SEQ ID NO:103

HC-FR3 having the amino acid sequence of SEQ ID NO:104

HC-FR4 having the amino acid sequence of SEQ ID NO:74, or a variant thereof in which one or two or three amino acids in one or more of HC-FR1, HC-FR2, HC-FR3, or HC-FR4 are substituted with another amino acid.

(28) a VH region incorporating the following FRs:

HC-FR1 having the amino acid sequence of SEQ ID NO:114

HC-FR2 having the amino acid sequence of SEQ ID NO:115

HC-FR3 having the amino acid sequence of SEQ ID NO:116

HC-FR4 having the amino acid sequence of SEQ ID NO:117, or a variant thereof in which one or two or three amino acids in one or more of HC-FR1, HC-FR2, HC-FR3, or HC-FR4 are substituted with another amino acid.

(29) a VH region incorporating the following FRs:

HC-FR1 having the amino acid sequence of SEQ ID NO:114

HC-FR2 having the amino acid sequence of SEQ ID NO:115

HC-FR3 having the amino acid sequence of SEQ ID NO:123

HC-FR4 having the amino acid sequence of SEQ ID NO:117, or a variant thereof in which one or two or three amino acids in one or more of HC-FR1, HC-FR2, HC-FR3, or HC-FR4 are substituted with another amino acid.

(30) a VH region incorporating the following FRs:

HC-FR1 having the amino acid sequence of SEQ ID NO:102

HC-FR2 having the amino acid sequence of SEQ ID NO:130

HC-FR3 having the amino acid sequence of SEQ ID NO:131

HC-FR4 having the amino acid sequence of SEQ ID NO:132, or a variant thereof in which one or two or three amino acids in one or more of HC-FR1, HC-FR2, HC-FR3, or HC-FR4 are substituted with another amino acid.

(31) a VH region incorporating the following FRs:

HC-FR1 having the amino acid sequence of SEQ ID NO:227

HC-FR2 having the amino acid sequence of SEQ ID NO:339

HC-FR3 having the amino acid sequence of SEQ ID NO:395

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(32) a VH region incorporating the following FRs:

HC-FR1 having the amino acid sequence of SEQ ID NO:402

HC-FR2 having the amino acid sequence of SEQ ID NO:403

HC-FR3 having the amino acid sequence of SEQ ID NO:404

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(33) a VH region incorporating the following FRs:

HC-FR1 having the amino acid sequence of SEQ ID NO:409

HC-FR2 having the amino acid sequence of SEQ ID NO:410

HC-FR3 having the amino acid sequence of SEQ ID NO:411

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(34) a VH region incorporating the following FRs:

HC-FR1 having the amino acid sequence of SEQ ID NO:419

HC-FR2 having the amino acid sequence of SEQ ID NO:420

HC-FR3 having the amino acid sequence of SEQ ID NO:421

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(35) a VH region incorporating the following FRs:

HC-FR1 having the amino acid sequence of SEQ ID NO:227

HC-FR2 having the amino acid sequence of SEQ ID NO:339

HC-FR3 having the amino acid sequence of SEQ ID NO:340

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(36) a VH region incorporating the following FRs:

HC-FR1 having the amino acid sequence of SEQ ID NO:227

HC-FR2 having the amino acid sequence of SEQ ID NO:339

HC-FR3 having the amino acid sequence of SEQ ID NO:348

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(37) a VH region incorporating the following FRs:

HC-FR1 having the amino acid sequence of SEQ ID NO:354

HC-FR2 having the amino acid sequence of SEQ ID NO:355

HC-FR3 having the amino acid sequence of SEQ ID NO:356

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(38) a VH region incorporating the following FRs:

HC-FR1 having the amino acid sequence of SEQ ID NO:362

HC-FR2 having the amino acid sequence of SEQ ID NO:363

HC-FR3 having the amino acid sequence of SEQ ID NO:364

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(39) a VH region incorporating the following FRs:

HC-FR1 having the amino acid sequence of SEQ ID NO:227

HC-FR2 having the amino acid sequence of SEQ ID NO:368

HC-FR3 having the amino acid sequence of SEQ ID NO:369

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(40) a VH region incorporating the following FRs:

HC-FR1 having the amino acid sequence of SEQ ID NO:373

HC-FR2 having the amino acid sequence of SEQ ID NO:374

HC-FR3 having the amino acid sequence of SEQ ID NO:375

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(41) a VH region incorporating the following FRs:

HC-FR1 having the amino acid sequence of SEQ ID NO:381

HC-FR2 having the amino acid sequence of SEQ ID NO:229

HC-FR3 having the amino acid sequence of SEQ ID NO:382

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(42) a VH region incorporating the following FRs:

HC-FR1 having the amino acid sequence of SEQ ID NO:389

HC-FR2 having the amino acid sequence of SEQ ID NO:374

HC-FR3 having the amino acid sequence of SEQ ID NO:390

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(43) a VH region incorporating the following FRs:

HC-FR1 having the amino acid sequence of SEQ ID NO:227

HC-FR2 having the amino acid sequence of SEQ ID NO:494

HC-FR3 having the amino acid sequence of SEQ ID NO:495

HC-FR4 having the amino acid sequence of SEQ ID NO:496, or a variant thereof in which one or two or three amino acids in one or more of HC-FR1, HC-FR2, HC-FR3, or HC-FR4 are substituted with another amino acid.

(44) a VH region incorporating the following FRs:

HC-FR1 having the amino acid sequence of SEQ ID NO:227

HC-FR2 having the amino acid sequence of SEQ ID NO:457

HC-FR3 having the amino acid sequence of SEQ ID NO:458

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(45) a VH region incorporating the following FRs:

HC-FR1 having the amino acid sequence of SEQ ID NO:227

HC-FR2 having the amino acid sequence of SEQ ID NO:467

HC-FR3 having the amino acid sequence of SEQ ID NO:458

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(46) a VH region incorporating the following FRs:

HC-FR1 having the amino acid sequence of SEQ ID NO:227

HC-FR2 having the amino acid sequence of SEQ ID NO:473

HC-FR3 having the amino acid sequence of SEQ ID NO:458

HC-FR4 having the amino acid sequence of SEQ ID NO:236, or a variant thereof in which one or two or three amino acids in one or more of HC-FR1, HC-FR2, HC-FR3, or HC-FR4 are substituted with another amino acid.

(47) a VH region incorporating the following FRs:

HC-FR1 having the amino acid sequence of SEQ ID NO:227

HC-FR2 having the amino acid sequence of SEQ ID NO:480

HC-FR3 having the amino acid sequence of SEQ ID NO:481

HC-FR4 having the amino acid sequence of SEQ ID NO:482, or a variant thereof in which one or two or three amino acids in one or more of HC-FR1, HC-FR2, HC-FR3, or HC-FR4 are substituted with another amino acid.

In some embodiments, the antigen-binding molecule comprises a VH region comprising the CDRs according to any one of (1) to (19) above, and the FRs according to any one of (20) to (47) above.

In some embodiments, the antigen-binding molecule comprises a VH region according to one of (48) to (76) below:

(48) a VH region comprising the CDRs according to (1) and the FRs according to (20).

(49) a VH region comprising the CDRs according to (2) and the FRs according to (21).

(50) a VH region comprising the CDRs according to (3) and the FRs according to (22).

(51) a VH region comprising the CDRs according to (4) and the FRs according to (23).

(52) a VH region comprising the CDRs according to (5) and the FRs according to (24).

(53) a VH region comprising the CDRs according to (6) and the FRs according to (25).

(54) a VH region comprising the CDRs according to (7) and the FRs according to (26).

(55) a VH region comprising the CDRs according to (8) and the FRs according to (27).

(56) a VH region comprising the CDRs according to (9) and the FRs according to (28).

(57) a VH region comprising the CDRs according to (9) and the FRs according to (29).

(58) a VH region comprising the CDRs according to (10) and the FRs according to (30).

(59) a VH region comprising the CDRs according to (11) and the FRs according to (31).

(60) a VH region comprising the CDRs according to (12) and the FRs according to (32).

(61) a VH region comprising the CDRs according to (3) and the FRs according to (33).

(62) a VH region comprising the CDRs according to (13) and the FRs according to (34).

(63) a VH region comprising the CDRs according to (8) and the FRs according to (35).

(64) a VH region comprising the CDRs according to (14) and the FRs according to (36).

(65) a VH region comprising the CDRs according to (12) and the FRs according to (37).

(66) a VH region comprising the CDRs according to (12) and the FRs according to (38).

(67) a VH region comprising the CDRs according to (3) and the FRs according to (39).

(68) a VH region comprising the CDRs according to (3) and the FRs according to (40).

(69) a VH region comprising the CDRs according to (5) and the FRs according to (41).

(70) a VH region comprising the CDRs according to (15) and the FRs according to (42).

(71) a VH region comprising the CDRs according to (16) and the FRs according to (43).

(72) a VH region comprising the CDRs according to (17) and the FRs according to (44).

(73) a VH region comprising the CDRs according to (18) and the FRs according to (45).

(74) a VH region comprising the CDRs according to (19) and the FRs according to (46).

(75) a VH region comprising the CDRs according to (5) and the FRs according to (44).

(76) a VH region comprising the CDRs according to (17) and the FRs according to (47).

In some embodiments, the antigen-binding molecule comprises a VH region according to one of (77) to (105) below:

(77) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:136.

(78) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:144.

(79) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:22.

(80) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:38.

(81) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:52.

(82) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:67.

(83) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:83.

(84) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:98.

(85) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:112.

(86) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:122.

(87) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:127.

(88) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:393.

(89) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:401.

(90) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:408.

(91) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:417.

(92) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:338.

(93) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:346.

(94) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:353.

(95) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:361.

(96) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:367.

(97) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:372.

(98) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:380.

(99) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:387.

(100) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:490.

(101) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:455.

(102) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:465.

(103) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:471.

(104) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:477.

(105) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:479.

In some embodiments, the antigen-binding molecule comprises a VL region according to one of (106) to (119) below:

(106) a VL region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108, or a variant thereof in which one or two or three amino acids in one or more of LC-CDR1, LC-CDR2, or LC-CDR3 are substituted with another amino acid.

(107) a VL region incorporating the following CDRs:

LC-CDR1 having the amino acid sequence of SEQ ID NO:31

LC-CDR2 having the amino acid sequence of SEQ ID NO:32

LC-CDR3 having the amino acid sequence of SEQ ID NO:33, or a variant thereof in which one or two or three amino acids in one or more of LC-CDR1, LC-CDR2, or LC-CDR3 are substituted with another amino acid.

(108) a VL region incorporating the following CDRs:

LC-CDR1 having the amino acid sequence of SEQ ID NO:45

LC-CDR2 having the amino acid sequence of SEQ ID NO:46

LC-CDR3 having the amino acid sequence of SEQ ID NO:47, or a variant thereof in which one or two or three amino acids in one or more of LC-CDR1, LC-CDR2, or LC-CDR3 are substituted with another amino acid.

(109) a VL region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63, or a variant thereof in which one or two or three amino acids in one or more of LC-CDR1, LC-CDR2, or LC-CDR3 are substituted with another amino acid.

(110) a VL region incorporating the following CDRs:

LC-CDR1 having the amino acid sequence of SEQ ID NO:76

LC-CDR2 having the amino acid sequence of SEQ ID NO:77

LC-CDR3 having the amino acid sequence of SEQ ID NO:78, or a variant thereof in which one or two or three amino acids in one or more of LC-CDR1, LC-CDR2, or LC-CDR3 are substituted with another amino acid.

(111) a VL region incorporating the following CDRs:

LC-CDR1 having the amino acid sequence of SEQ ID NO:91

LC-CDR2 having the amino acid sequence of SEQ ID NO:92

LC-CDR3 having the amino acid sequence of SEQ ID NO:93, or a variant thereof in which one or two or three amino acids in one or more of LC-CDR1, LC-CDR2, or LC-CDR3 are substituted with another amino acid.

(112) a VL region incorporating the following CDRs:

LC-CDR1 having the amino acid sequence of SEQ ID NO:106

LC-CDR2 having the amino acid sequence of SEQ ID NO:107

LC-CDR3 having the amino acid sequence of SEQ ID NO:108, or a variant thereof in which one or two or three amino acids in one or more of LC-CDR1, LC-CDR2, or LC-CDR3 are substituted with another amino acid.

(113) a VL region incorporating the following CDRs:

LC-CDR1 having the amino acid sequence of SEQ ID NO:119

LC-CDR2 having the amino acid sequence of SEQ ID NO:120

LC-CDR3 having the amino acid sequence of SEQ ID NO:108, or a variant thereof in which one or two or three amino acids in one or more of LC-CDR1, LC-CDR2, or LC-CDR3 are substituted with another amino acid.

(114) a VL region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108, or a variant thereof in which one or two or three amino acids in one or more of LC-CDR1, LC-CDR2, or LC-CDR3 are substituted with another amino acid.

(115) a VL region incorporating the following CDRs:

LC-CDR1 having the amino acid sequence of SEQ ID NO:498

LC-CDR2 having the amino acid sequence of SEQ ID NO:62

LC-CDR3 having the amino acid sequence of SEQ ID NO:499, or a variant thereof in which one or two or three amino acids in one or more of LC-CDR1, LC-CDR2, or LC-CDR3 are substituted with another amino acid.

(116) a VL region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:460, or a variant thereof in which one or two or three amino acids in one or more of LC-CDR1, LC-CDR2, or LC-CDR3 are substituted with another amino acid.

(117) a VL region incorporating the following CDRs:

LC-CDR1 having the amino acid sequence of SEQ ID NO:464

LC-CDR2 having the amino acid sequence of SEQ ID NO:62

LC-CDR3 having the amino acid sequence of SEQ ID NO:63, or a variant thereof in which one or two or three amino acids in one or more of LC-CDR1, LC-CDR2, or LC-CDR3 are substituted with another amino acid.

(118) a VL region incorporating the following CDRs:

LC-CDR1 having the amino acid sequence of SEQ ID NO:484

LC-CDR2 having the amino acid sequence of SEQ ID NO:62

LC-CDR3 having the amino acid sequence of SEQ ID NO:485, or a variant thereof in which one or two or three amino acids in one or more of LC-CDR1, LC-CDR2, or LC-CDR3 are substituted with another amino acid.

(119) a VL region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:488, or a variant thereof in which one or two or three amino acids in one or more of LC-CDR1, LC-CDR2, or LC-CDR3 are substituted with another amino acid.

In some embodiments, the antigen-binding molecule comprises a VL region according to one of (120) to (148) below:

(120) a VL region incorporating the following FRs:

LC-FR1 having the amino acid sequence of SEQ ID NO:154

LC-FR2 having the amino acid sequence of SEQ ID NO:155

LC-FR3 having the amino acid sequence of SEQ ID NO:156

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(121) a VL region incorporating the following FRs:

LC-FR1 having the amino acid sequence of SEQ ID NO:34

LC-FR2 having the amino acid sequence of SEQ ID NO:35

LC-FR3 having the amino acid sequence of SEQ ID NO:36

LC-FR4 having the amino acid sequence of SEQ ID NO:37, or a variant thereof in which one or two or three amino acids in one or more of LC-FR1, LC-FR2, LC-FR3, or LC-FR4 are substituted with another amino acid.

(122) a VL region incorporating the following FRs:

LC-FR1 having the amino acid sequence of SEQ ID NO:48

LC-FR2 having the amino acid sequence of SEQ ID NO:49

LC-FR3 having the amino acid sequence of SEQ ID NO:50

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(123) a VL region incorporating the following FRs:

LC-FR1 having the amino acid sequence of SEQ ID NO:64

LC-FR2 having the amino acid sequence of SEQ ID NO:65

LC-FR3 having the amino acid sequence of SEQ ID NO:66

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(124) a VL region incorporating the following FRs:

LC-FR1 having the amino acid sequence of SEQ ID NO:79

LC-FR2 having the amino acid sequence of SEQ ID NO:80

LC-FR3 having the amino acid sequence of SEQ ID NO:81

LC-FR4 having the amino acid sequence of SEQ ID NO:82, or a variant thereof in which one or two or three amino acids in one or more of LC-FR1, LC-FR2, LC-FR3, or LC-FR4 are substituted with another amino acid.

(125) a VL region incorporating the following FRs:

LC-FR1 having the amino acid sequence of SEQ ID NO:94

LC-FR2 having the amino acid sequence of SEQ ID NO:95

LC-FR3 having the amino acid sequence of SEQ ID NO:96

LC-FR4 having the amino acid sequence of SEQ ID NO:97, or a variant thereof in which one or two or three amino acids in one or more of LC-FR1, LC-FR2, LC-FR3, or LC-FR4 are substituted with another amino acid.

(126) a VL region incorporating the following FRs:

LC-FR1 having the amino acid sequence of SEQ ID NO:109

LC-FR2 having the amino acid sequence of SEQ ID NO:110

LC-FR3 having the amino acid sequence of SEQ ID NO:111

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(127) a VL region incorporating the following FRs:

LC-FR1 having the amino acid sequence of SEQ ID NO:121

LC-FR2 having the amino acid sequence of SEQ ID NO:110

LC-FR3 having the amino acid sequence of SEQ ID NO:111

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(128) a VL region incorporating the following FRs:

LC-FR1 having the amino acid sequence of SEQ ID NO:121

LC-FR2 having the amino acid sequence of SEQ ID NO:110

LC-FR3 having the amino acid sequence of SEQ ID NO:126

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(129) a VL region incorporating the following FRs:

LC-FR1 having the amino acid sequence of SEQ ID NO:134

LC-FR2 having the amino acid sequence of SEQ ID NO:135

LC-FR3 having the amino acid sequence of SEQ ID NO:111

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(130) a VL region incorporating the following FRs:

LC-FR1 having the amino acid sequence of SEQ ID NO:397

LC-FR2 having the amino acid sequence of SEQ ID NO:398

LC-FR3 having the amino acid sequence of SEQ ID NO:399

LC-FR4 having the amino acid sequence of SEQ ID NO:400, or a variant thereof in which one or two or three amino acids in one or more of LC-FR1, LC-FR2, LC-FR3, or LC-FR4 are substituted with another amino acid.

(131) a VL region incorporating the following FRs:

LC-FR1 having the amino acid sequence of SEQ ID NO:406

LC-FR2 having the amino acid sequence of SEQ ID NO:407

LC-FR3 having the amino acid sequence of SEQ ID NO:360

LC-FR4 having the amino acid sequence of SEQ ID NO:245, or a variant thereof in which one or two or three amino acids in one or more of LC-FR1, LC-FR2, LC-FR3, or LC-FR4 are substituted with another amino acid.

(132) a VL region incorporating the following FRs:

LC-FR1 having the amino acid sequence of SEQ ID NO:413

LC-FR2 having the amino acid sequence of SEQ ID NO:414

LC-FR3 having the amino acid sequence of SEQ ID NO:415

LC-FR4 having the amino acid sequence of SEQ ID NO:416, or a variant thereof in which one or two or three amino acids in one or more of LC-FR1, LC-FR2, LC-FR3, or LC-FR4 are substituted with another amino acid.

(133) a VL region incorporating the following FRs:

LC-FR1 having the amino acid sequence of SEQ ID NO:384

LC-FR2 having the amino acid sequence of SEQ ID NO:423

LC-FR3 having the amino acid sequence of SEQ ID NO:386

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(134) a VL region incorporating the following FRs:

LC-FR1 having the amino acid sequence of SEQ ID NO:342

LC-FR2 having the amino acid sequence of SEQ ID NO:343

LC-FR3 having the amino acid sequence of SEQ ID NO:344

LC-FR4 having the amino acid sequence of SEQ ID NO:345, or a variant thereof in which one or two or three amino acids in one or more of LC-FR1, LC-FR2, LC-FR3, or LC-FR4 are substituted with another amino acid.

(135) a VL region incorporating the following FRs:

LC-FR1 having the amino acid sequence of SEQ ID NO:350

LC-FR2 having the amino acid sequence of SEQ ID NO:351

LC-FR3 having the amino acid sequence of SEQ ID NO:352

LC-FR4 having the amino acid sequence of SEQ ID NO:170, or a variant thereof in which one or two or three amino acids in one or more of LC-FR1, LC-FR2, LC-FR3, or LC-FR4 are substituted with another amino acid.

(136) a VL region incorporating the following FRs:

LC-FR1 having the amino acid sequence of SEQ ID NO:358

LC-FR2 having the amino acid sequence of SEQ ID NO:359

LC-FR3 having the amino acid sequence of SEQ ID NO:360

LC-FR4 having the amino acid sequence of SEQ ID NO:345, or a variant thereof in which one or two or three amino acids in one or more of LC-FR1, LC-FR2, LC-FR3, or LC-FR4 are substituted with another amino acid.

(137) a VL region incorporating the following FRs:

LC-FR1 having the amino acid sequence of SEQ ID NO:366

LC-FR2 having the amino acid sequence of SEQ ID NO:135

LC-FR3 having the amino acid sequence of SEQ ID NO:360

LC-FR4 having the amino acid sequence of SEQ ID NO:345, or a variant thereof in which one or two or three amino acids in one or more of LC-FR1, LC-FR2, LC-FR3, or LC-FR4 are substituted with another amino acid.

(138) a VL region incorporating the following FRs:

LC-FR1 having the amino acid sequence of SEQ ID NO:342

LC-FR2 having the amino acid sequence of SEQ ID NO:371

LC-FR3 having the amino acid sequence of SEQ ID NO:240

LC-FR4 having the amino acid sequence of SEQ ID NO:170, or a variant thereof in which one or two or three amino acids in one or more of LC-FR1, LC-FR2, LC-FR3, or LC-FR4 are substituted with another amino acid.

(139) a VL region incorporating the following FRs:

LC-FR1 having the amino acid sequence of SEQ ID NO:377

LC-FR2 having the amino acid sequence of SEQ ID NO:378

LC-FR3 having the amino acid sequence of SEQ ID NO:379

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(140) a VL region incorporating the following FRs:

LC-FR1 having the amino acid sequence of SEQ ID NO:384

LC-FR2 having the amino acid sequence of SEQ ID NO:385

LC-FR3 having the amino acid sequence of SEQ ID NO:386

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(141) a VL region incorporating the following FRs:

LC-FR1 having the amino acid sequence of SEQ ID NO:384

LC-FR2 having the amino acid sequence of SEQ ID NO:392

LC-FR3 having the amino acid sequence of SEQ ID NO:386

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(142) a VL region incorporating the following FRs:

LC-FR1 having the amino acid sequence of SEQ ID NO:500

LC-FR2 having the amino acid sequence of SEQ ID NO:501

LC-FR3 having the amino acid sequence of SEQ ID NO:502

LC-FR4 having the amino acid sequence of SEQ ID NO:503, or a variant thereof in which one or two or three amino acids in one or more of LC-FR1, LC-FR2, LC-FR3, or LC-FR4 are substituted with another amino acid.

(143) a VL region incorporating the following FRs:

LC-FR1 having the amino acid sequence of SEQ ID NO:384

LC-FR2 having the amino acid sequence of SEQ ID NO:461

LC-FR3 having the amino acid sequence of SEQ ID NO:462

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(144) a VL region incorporating the following FRs:

LC-FR1 having the amino acid sequence of SEQ ID NO:384

LC-FR2 having the amino acid sequence of SEQ ID NO:385

LC-FR3 having the amino acid sequence of SEQ ID NO:462

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(145) a VL region incorporating the following FRs:

LC-FR1 having the amino acid sequence of SEQ ID NO:384

LC-FR2 having the amino acid sequence of SEQ ID NO:469

LC-FR3 having the amino acid sequence of SEQ ID NO:470

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(146) a VL region incorporating the following FRs:

LC-FR1 having the amino acid sequence of SEQ ID NO:384

LC-FR2 having the amino acid sequence of SEQ ID NO:469

LC-FR3 having the amino acid sequence of SEQ ID NO:475

LC-FR4 having the amino acid sequence of SEQ ID NO:476, or a variant thereof in which one or two or three amino acids in one or more of LC-FR1, LC-FR2, LC-FR3, or LC-FR4 are substituted with another amino acid.

(147) a VL region incorporating the following FRs:

LC-FR1 having the amino acid sequence of SEQ ID NO:384

LC-FR2 having the amino acid sequence of SEQ ID NO:486

LC-FR3 having the amino acid sequence of SEQ ID NO:386

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(148) a VL region incorporating the following FRs:

LC-FR1 having the amino acid sequence of SEQ ID NO:489

LC-FR2 having the amino acid sequence of SEQ ID NO:486

LC-FR3 having the amino acid sequence of SEQ ID NO:386

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

In some embodiments, the antigen-binding molecule comprises a VL region comprising the CDRs according to any one of (106) to (119) above, and the FRs according to any one of (120) to (148) above.

In some embodiments, the antigen-binding molecule comprises a VL region according to one of (149) to (178) below:

(149) a VL region comprising the CDRs according to (106) and the FRs according to (120).

(150) a VL region comprising the CDRs according to (107) and the FRs according to (121).

(151) a VL region comprising the CDRs according to (108) and the FRs according to (122).

(152) a VL region comprising the CDRs according to (109) and the FRs according to (123).

(153) a VL region comprising the CDRs according to (110) and the FRs according to (124).

(154) a VL region comprising the CDRs according to (111) and the FRs according to (125).

(155) a VL region comprising the CDRs according to (112) and the FRs according to (126).

(156) a VL region comprising the CDRs according to (113) and the FRs according to (127).

(157) a VL region comprising the CDRs according to (114) and the FRs according to (128).

(158) a VL region comprising the CDRs according to (114) and the FRs according to (129).

(159) a VL region comprising the CDRs according to (112) and the FRs according to (130).

(160) a VL region comprising the CDRs according to (114) and the FRs according to (131).

(161) a VL region comprising the CDRs according to (107) and the FRs according to (132).

(162) a VL region comprising the CDRs according to (109) and the FRs according to (133).

(163) a VL region comprising the CDRs according to (112) and the FRs according to (134).

(164) a VL region comprising the CDRs according to (112) and the FRs according to (135).

(165) a VL region comprising the CDRs according to (114) and the FRs according to (136).

(166) a VL region comprising the CDRs according to (114) and the FRs according to (137).

(167) a VL region comprising the CDRs according to (107) and the FRs according to (138).

(168) a VL region comprising the CDRs according to (107) and the FRs according to (139).

(169) a VL region comprising the CDRs according to (109) and the FRs according to (140).

(170) a VL region comprising the CDRs according to (109) and the FRs according to (141).

(171) a VL region comprising the CDRs according to (115) and the FRs according to (142).

(172) a VL region comprising the CDRs according to (116) and the FRs according to (143).

(173) a VL region comprising the CDRs according to (117) and the FRs according to (144).

(174) a VL region comprising the CDRs according to (109) and the FRs according to (145).

(175) a VL region comprising the CDRs according to (109) and the FRs according to (146).

(176) a VL region comprising the CDRs according to (109) and the FRs according to (144).

(177) a VL region comprising the CDRs according to (118) and the FRs according to (147).

(178) a VL region comprising the CDRs according to (119) and the FRs according to (148). In some embodiments, the antigen-binding molecule comprises a VL region according to one of (179) to (208) below:

(179) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:151.

(180) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30.

(181) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:44.

(182) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:60.

(183) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:75.

(184) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:90.

(185) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:105.

(186) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:118.

(187) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:124.

(188) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:133.

(189) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:396.

(190) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:405.

(191) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:412.

(192) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:422.

(193) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:341.

(194) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:349.

(195) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:357.

(196) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:365.

(197) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:370.

(198) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:376.

(199) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:383.

(200) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:391.

(201) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:497.

(202) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:459.

(203) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:463.

(204) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:468.

(205) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:474.

(206) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:478.

(207) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:483.

(208) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:487.

In some embodiments, the antigen-binding molecule comprises a VH region according to any one of (1) to (105) above, and a VL region according to any one of (106) to (208) above.

In some embodiments, the antigen-binding molecule comprises the CDRs of an antigen-binding molecule which binds to CD47. In some embodiments, the antigen-binding molecule comprises the FRs of an antigen-binding molecule which binds to CD47. In some embodiments, the antigen-binding molecule comprises the CDRs and the FRs of an antigen-binding molecule which binds to CD47. That is, In some embodiments, the antigen-binding molecule comprises the VH region and the VL region of an antigen-binding molecule which binds to CD47.

In some embodiments, the antigen-binding molecule comprises the CDRs, FRs and/or the VH and/or VL regions of a CD47-binding antibody clone described in WO 2019/086573 A1 (which is hereby incorporated by reference in its entirety), or CDRs, FRs and/or VH and/or VL regions which are derived from those of a CD47-binding antibody clone described in WO 2019/086573 A1.

In some embodiments, the antigen-binding molecule comprises the CDRs, FRs and/or the VH and/or VL regions of a CD47-binding antibody clone described herein, or CDRs, FRs and/or VH and/or VL regions which are derived from those of a CD47-binding antibody clone described herein. In some embodiments, a CD47-binding antibody clone is selected from: 1-1-A1_BM, 1-1-A1, 11A1H1, 11A1H2, 11A1H3, 11A1H4, 11A1H5, 11A1H6, 11A1H7, 11A1H8, 11A1H9, 11A1H10 or 11A1H11.

In some embodiments, the antigen-binding molecule comprises a VH region according to one of (209) to (211) below:

(209) a VH region incorporating the following CDRs:
HC-CDR1 having the amino acid sequence of SEQ ID NO:243
HC-CDR2 having the amino acid sequence of SEQ ID NO:244
HC-CDR3 having the amino acid sequence of SEQ ID NO:194,
or a variant thereof in which one or two or three amino acids in one or more of HC-CDR1, HC-CDR2, or HC-CDR3 are substituted with another amino acid.

(210) a VH region incorporating the following CDRs:
HC-CDR1 having the amino acid sequence of SEQ ID NO:53
HC-CDR2 having the amino acid sequence of SEQ ID NO:193
HC-CDR3 having the amino acid sequence of SEQ ID NO:194,
or a variant thereof in which one or two or three amino acids in one or more of HC-CDR1, HC-CDR2, or HC-CDR3 are substituted with another amino acid.

(211) a VH region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194, or a variant thereof in which one or two or three amino acids in one or more of HC-CDR1, HC-CDR2, or HC-CDR3 are substituted with another amino acid.

In some embodiments, the antigen-binding molecule comprises a VH region according to one of (212) to (220) below:

(212) a VH region incorporating the following FRs:

HC-FR1 having the amino acid sequence of SEQ ID NO:227

HC-FR2 having the amino acid sequence of SEQ ID NO:248

HC-FR3 having the amino acid sequence of SEQ ID NO:249

HC-FR4 having the amino acid sequence of SEQ ID NO:250 or a variant thereof in which one or two or three amino acids in one or more of HC-FR1, HC-FR2, HC-FR3, or HC-FR4 are substituted with another amino acid.

(213) a VH region incorporating the following FRs:

HC-FR1 having the amino acid sequence of SEQ ID NO:195

HC-FR2 having the amino acid sequence of SEQ ID NO:196

HC-FR3 having the amino acid sequence of SEQ ID NO:197

HC-FR4 having the amino acid sequence of SEQ ID NO:74 or a variant thereof in which one or two or three amino acids in one or more of HC-FR1, HC-FR2, HC-FR3, or HC-FR4 are substituted with another amino acid.

(214) a VH region incorporating the following FRs:

HC-FR1 having the amino acid sequence of SEQ ID NO:205

HC-FR2 having the amino acid sequence of SEQ ID NO:41

HC-FR3 having the amino acid sequence of SEQ ID NO:206

HC-FR4 having the amino acid sequence of SEQ ID NO:74 or a variant thereof in which one or two or three amino acids in one or more of HC-FR1, HC-FR2, HC-FR3, or HC-FR4 are substituted with another amino acid.

(215) a VH region incorporating the following FRs:

HC-FR1 having the amino acid sequence of SEQ ID NO:227

HC-FR2 having the amino acid sequence of SEQ ID NO:228

HC-FR3 having the amino acid sequence of SEQ ID NO:231

HC-FR4 having the amino acid sequence of SEQ ID NO:236 or a variant thereof in which one or two or three amino acids in one or more of HC-FR1, HC-FR2, HC-FR3, or HC-FR4 are substituted with another amino acid.

(216) a VH region incorporating the following FRs:

HC-FR1 having the amino acid sequence of SEQ ID NO:227

HC-FR2 having the amino acid sequence of SEQ ID NO:228

HC-FR3 having the amino acid sequence of SEQ ID NO:232

HC-FR4 having the amino acid sequence of SEQ ID NO:236 or a variant thereof in which one or two or three amino acids in one or more of HC-FR1, HC-FR2, HC-FR3, or HC-FR4 are substituted with another amino acid.

(217) a VH region incorporating the following FRs:

HC-FR1 having the amino acid sequence of SEQ ID NO:227

HC-FR2 having the amino acid sequence of SEQ ID NO:229

HC-FR3 having the amino acid sequence of SEQ ID NO:233

HC-FR4 having the amino acid sequence of SEQ ID NO:237 or a variant thereof in which one or two or three amino acids in one or more of HC-FR1, HC-FR2, HC-FR3, or HC-FR4 are substituted with another amino acid.

(218) a VH region incorporating the following FRs:

HC-FR1 having the amino acid sequence of SEQ ID NO:227

HC-FR2 having the amino acid sequence of SEQ ID NO:230

HC-FR3 having the amino acid sequence of SEQ ID NO:234

HC-FR4 having the amino acid sequence of SEQ ID NO:237 or a variant thereof in which one or two or three amino acids in one or more of HC-FR1, HC-FR2, HC-FR3, or HC-FR4 are substituted with another amino acid.

(219) a VH region incorporating the following FRs:

HC-FR1 having the amino acid sequence of SEQ ID NO:227

HC-FR2 having the amino acid sequence of SEQ ID NO:230

HC-FR3 having the amino acid sequence of SEQ ID NO:235

HC-FR4 having the amino acid sequence of SEQ ID NO:236 or a variant thereof in which one or two or three amino acids in one or more of HC-FR1, HC-FR2, HC-FR3, or HC-FR4 are substituted with another amino acid.

(220) a VH region incorporating the following FRs:

HC-FR1 having the amino acid sequence of SEQ ID NO:227

HC-FR2 having the amino acid sequence of SEQ ID NO:230

HC-FR3 having the amino acid sequence of SEQ ID NO:235

HC-FR4 having the amino acid sequence of SEQ ID NO:236 or a variant thereof in which one or two or three amino acids in one or more of HC-FR1, HC-FR2, HC-FR3, or HC-FR4 are substituted with another amino acid.

In some embodiments, the antigen-binding molecule comprises a VH region comprising the CDRs according to one of (209), (210), or (211) above, and the FRs according to one of (212), (213), (214), (215), (216), (217), (218), (219) or (220) above.

In some embodiments, the antigen-binding molecule comprises a VH region according to one of (221) to (180) below:

(221) a VH region comprising the CDRs according to (209) and the FRs according to (212).

(222) a VH region comprising the CDRs according to (210) and the FRs according to (213).

(223) a VH region comprising the CDRs according to (210) and the FRs according to (214).

(224) a VH region comprising the CDRs according to (210) and the FRs according to (215).

(225) a VH region comprising the CDRs according to (210) and the FRs according to (216).

(226) a VH region comprising the CDRs according to (210) and the FRs according to (217).

(227) a VH region comprising the CDRs according to (210) and the FRs according to (218).

(228) a VH region comprising the CDRs according to (1211) and the FRs according to (219).

(229) a VH region comprising the CDRs according to (211) and the FRs according to (220).

In some embodiments, the antigen-binding molecule comprises a VH region according to one of (230) to (237) below:

(230) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:252.

(231) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:192.

(232) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:204.

(233) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:211.

(234) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:213.

(235) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:214.

(236) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:215.

(237) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:216.

In some embodiments, the antigen-binding molecule comprises a VL region according to one of (238) to (243) below:

(238) a VL region incorporating the following CDRs:
LC-CDR1 having the amino acid sequence of SEQ ID NO:245
LC-CDR2 having the amino acid sequence of SEQ ID NO:246
LC-CDR3 having the amino acid sequence of SEQ ID NO:247
or a variant thereof in which one or two or three amino acids in one or more of LC-CDR1, LC-CDR2, or LC-CDR3 are substituted with another amino acid.

(239) a VL region incorporating the following CDRs:
LC-CDR1 having the amino acid sequence of SEQ ID NO:199
LC-CDR2 having the amino acid sequence of SEQ ID NO:200
LC-CDR3 having the amino acid sequence of SEQ ID NO:201
or a variant thereof in which one or two or three amino acids in one or more of LC-CDR1, LC-CDR2, or LC-CDR3 are substituted with another amino acid.

(240) a VL region incorporating the following CDRs:
LC-CDR1 having the amino acid sequence of SEQ ID NO:223
LC-CDR2 having the amino acid sequence of SEQ ID NO:225
LC-CDR3 having the amino acid sequence of SEQ ID NO:201
or a variant thereof in which one or two or three amino acids in one or more of LC-CDR1, LC-CDR2, or LC-CDR3 are substituted with another amino acid.

(241) a VL region incorporating the following CDRs:
LC-CDR1 having the amino acid sequence of SEQ ID NO:224
LC-CDR2 having the amino acid sequence of SEQ ID NO:225
LC-CDR3 having the amino acid sequence of SEQ ID NO:201
or a variant thereof in which one or two or three amino acids in one or more of LC-CDR1, LC-CDR2, or LC-CDR3 are substituted with another amino acid.

(242) a VL region incorporating the following CDRs:
LC-CDR1 having the amino acid sequence of SEQ ID NO:199
LC-CDR2 having the amino acid sequence of SEQ ID NO:225
LC-CDR3 having the amino acid sequence of SEQ ID NO:201
or a variant thereof in which one or two or three amino acids in one or more of LC-CDR1, LC-CDR2, or LC-CDR3 are substituted with another amino acid.

(243) a VL region incorporating the following CDRs:
LC-CDR1 having the amino acid sequence of SEQ ID NO:199
LC-CDR2 having the amino acid sequence of SEQ ID NO:200
LC-CDR3 having the amino acid sequence of SEQ ID NO:226
or a variant thereof in which one or two or three amino acids in one or more of LC-CDR1, LC-CDR2, or LC-CDR3 are substituted with another amino acid.

In some embodiments, the antigen-binding molecule comprises a VL region according to one of (244) to (248) below:

(244) a VL region incorporating the following FRs:

LC-FR1 having the amino acid sequence of SEQ ID NO:238

LC-FR2 having the amino acid sequence of SEQ ID NO:239

LC-FR3 having the amino acid sequence of SEQ ID NO:251

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(245) a VL region incorporating the following FRs:

LC-FR1 having the amino acid sequence of SEQ ID NO:202

LC-FR2 having the amino acid sequence of SEQ ID NO:203

LC-FR3 having the amino acid sequence of SEQ ID NO:50

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(246) a VL region incorporating the following FRs:

LC-FR1 having the amino acid sequence of SEQ ID NO:208

LC-FR2 having the amino acid sequence of SEQ ID NO:209

LC-FR3 having the amino acid sequence of SEQ ID NO:210

LC-FR4 having the amino acid sequence of SEQ ID NO:51, or a variant thereof in which one or two or three amino acids in one or more of LC-FR1, LC-FR2, LC-FR3, or LC-FR4 are substituted with another amino acid.

(247) a VL region incorporating the following FRs:

LC-FR1 having the amino acid sequence of SEQ ID NO:238

LC-FR2 having the amino acid sequence of SEQ ID NO:239

LC-FR3 having the amino acid sequence of SEQ ID NO:240

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

(248) a VL region incorporating the following FRs:

LC-FR1 having the amino acid sequence of SEQ ID NO:238

LC-FR2 having the amino acid sequence of SEQ ID NO:239

LC-FR3 having the amino acid sequence of SEQ ID NO:241

LC-FR4 having the amino acid sequence of SEQ ID NO:242, or a variant thereof in which one or two or three amino acids in one or more of LC-FR1, LC-FR2, LC-FR3, or LC-FR4 are substituted with another amino acid.

In some embodiments, the antigen-binding molecule comprises a VL region comprising the CDRs according to one of (238), (239), (240), (241), (242) or (243) above, and the FRs according to one of (244), (245), (246), (247) or (248) above.

In some embodiments, the antigen-binding molecule comprises a VL region according to one of (249) to (256) below:

(249) a VL region comprising the CDRs according to (238) and the FRs according to (244).

(250) a VL region comprising the CDRs according to (239) and the FRs according to (245).

(251) a VL region comprising the CDRs according to (239) and the FRs according to (246).

(252) a VL region comprising the CDRs according to (239) and the FRs according to (247).

(253) a VL region comprising the CDRs according to (240) and the FRs according to (248).

(254) a VL region comprising the CDRs according to (241) and the FRs according to (248).

(255) a VL region comprising the CDRs according to (242) and the FRs according to (248).

(256) a VL region comprising the CDRs according to (243) and the FRs according to (247).

In some embodiments, the antigen-binding molecule comprises a VL region according to one of (257) to (264) below:

(257) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:253.

(258) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:198.

(259) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:207.

(260) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:212.

(261) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:217.

(262) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:218.

(263) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:219.

(264) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:220.

In some embodiments, the antigen-binding molecule comprises a VH region according to any one of (209) to (237) above, and a VL region according to any one of (238) to (264) above.

In some embodiments, the antigen-binding molecule comprises:

a BCMA/TACI-binding region comprising a VH region according to any one of (1) to (105) above, and a VL region according to any one of (106) to (209) above; and a CD47-binding region comprising a VH region according to any one of (209) to (237) above, and a VL region according to any one of (238) to (264) above.

In embodiments in accordance with the present disclosure in which one or more amino acids are substituted with another amino acid, the substitutions may be conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, In some embodiments, the substitution may not affect (or may not substantially affect) one or more functional properties (e.g. target binding) of the antigen-binding molecule comprising the substitution as compared to the equivalent unsubstituted molecule.

The VH and VL region of an antigen-binding region of an antibody together constitute the Fv region. In some embodiments, the antigen-binding molecule according to the present disclosure comprises, or consists of, an Fv region which binds to BCMA/TACI. In some embodiments, the antigen-binding molecule comprises an Fv region which binds to CD47. In some embodiments, the antigen-binding molecule according to the present disclosure comprises, or consists of, an Fv region which binds to BCMA/TACI and an Fv region which binds to CD47. In some embodiments, the VH and VL regions of the Fv are provided as single polypeptide joined by a linker region, i.e. a single chain Fv (scFv).

The VL and light chain constant (CL) region, and the VH region and heavy chain constant 1 (CH1) region of an antigen-binding region of an antibody together constitute the Fab region. In some embodiments, the antigen-binding molecule comprises a Fab region comprising a VH, a CH1, a VL and a CL (e.g. Cκ or Cλ). In some embodiments, the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments, the Fab region comprises a polypeptide comprising a VH and a CL (e.g. a VH-CL fusion polypeptide) and a polypeptide comprising a VL and a CH (e.g. a VL-CH1 fusion polypeptide); that is, In some embodiments, the Fab region is a CrossFab region. In some embodiments, the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present disclosure comprises, or consists of, a Fab region which binds to BCMA/TACI. In some embodiments, the antigen-binding molecule comprises a Fab region which binds to CD47. In some embodiments, the antigen-binding molecule of the present disclosure comprises, or consists of, a Fab region which binds to BCMA/TACI and a Fab region which binds to CD47.

In some embodiments, the antigen-binding molecule described herein comprises, or consists of, a whole antibody which binds to BCMA/TACI. In some embodiments, the antigen-binding molecule comprises a whole antibody which binds to CD47. In some embodiments, the antigen-binding molecule described herein comprises, or consists of, a whole antibody which binds to BCMA/TACI and a whole antibody which binds to CD47. As used herein, 'whole antibody' refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chains comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to BCMA/TACI. In some embodiments, the antigen-binding molecule described herein comprises an IgG (e.g. IgG1, IgG2, IgG3, IgG4), IgA (e.g. IgA1, IgA2), IgD, IgE, or IgM which binds to CD47.

In some embodiments, the antigen-binding molecule of the present disclosure comprises one or more regions (e.g. CH1, CH2, CH3, etc.) of an immunoglobulin heavy chain constant sequence. In some embodiments, the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM, e.g. a human IgG (e.g. hIgG1, hIgG2, hIgG3, hIgG4), hIgA (e.g. hIgA1, hIgA2), hIgD, hIgE or hIgM. In some embodiments, the immunoglobulin heavy chain constant sequence is, or is derived from, the heavy chain constant sequence of a human IgG1 allotype (e.g. G1m1, G1m2, G1m3 or G1m17).

In some embodiments, the antigen-binding molecule comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:254, 259, 517 or 519.

In some embodiments, the antigen-binding molecule comprises a CH1 region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:255 or 260. In some embodiments, the antigen-binding molecule comprises a hinge region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:256 or 268. In some embodiments, the antigen-binding molecule comprises a CH2 region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:257 or 518. In some embodiments, the antigen-binding molecule comprises a CH3 region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:258 or 261.

It will be appreciated that CH2 and/or CH3 regions may be provided with further substitutions in accordance with modification to an Fc region of the antigen-binding molecule as described herein.

In some embodiments, the antigen-binding molecule of the present disclosure comprises one or more regions of an immunoglobulin light chain constant sequence. In some embodiments, the immunoglobulin light chain constant sequence is human immunoglobulin kappa constant (IGKC; Cκ). In some embodiments, the immunoglobulin light chain constant sequence is a human immunoglobulin lambda constant (IGLC; Cλ), e.g. IGLC1, IGLC2, IGLC3, IGLC6 or IGLC7.

In some embodiments, the antigen-binding molecule comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:262, 263, 264, 265, 266 or 267.

In some embodiments, the antigen-binding molecule is or comprises a fully human antibody/antibody fragment. A fully human antibody/antibody fragment may be encoded by human nucleic acid sequence(s). A fully human antibody/antibody fragment may be devoid of non-human amino acid sequences. Commonly employed techniques for the production of fully human antibodies include (i) phage display, in which human antibody genes are expressed in phage display libraries, and (ii) production of antibodies in transgenic mice engineered to have human antibody genes (described in Park and Smolen, Advances in Protein Chemistry (2001) 56: 369-421). Briefly, in the human antibody gene-phage display technique, genes encoding the VH and VL chains are generated by PCR amplification and cloning from 'naive' human lymphocytes, and assembled into a library from which they can be expressed either as disulfide-linked Fab fragments or as single-chain Fv (scFv) fragments. The Fab- or scFv-encoding genes are fused to a surface coat protein of filamentous bacteriophage and Fab or scFv capable of binding to the target of interest can then be identified by screening the library with antigen.

Molecular evolution or affinity maturation procedures can be employed to enhance the affinity of the Fab/scFv fragment. In the transgenic mouse technique, mice in which the endogenous murine Ig gene loci have been replaced by homologous recombination with their human homologues are immunized with antigen, and monoclonal antibody is prepared by conventional hybridoma technology, to yield a fully human monoclonal antibody.

In some embodiments, the antigen-binding molecule of the present disclosure is a mouse antibody/antibody fragment. In some embodiments, the antibody/antibody fragment is obtained from phage display using a human naïve antibody gene library.

In some embodiments, the antigen-binding molecule is a mouse/human chimeric antibody/antibody fragment (i.e. an antigen-binding molecule comprising mouse antibody variable domains and human antibody constant regions). In some embodiments, the antigen-binding molecule is a humanised antibody/antibody fragment. In some embodiments, the antigen-binding molecule comprises mouse antibody CDRs and human antibody framework and constant regions.

Mouse/human chimeric antigen-binding molecules can be prepared from mouse antibodies by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 8 thereof, in particular section 3 of Chapter 8.

Humanised antigen-binding molecules can be prepared from mouse antibodies by the process of humanisation, e.g. as described in Human Monoclonal Antibodies: Methods and Protocols, Michael Steinitz (Editor), Methods in Molecular Biology 1060, Springer Protocols, Humana Press (2014), in Chapter 7 thereof, in particular section 3.1 of Chapter 7 entitled 'Antibody Humanization'. Techniques for antibody humanisation are also described e.g. in Safdari et al., Biotechnol Genet Eng Rev (2013) 29:175-86.

Aspects of the present disclosure relate to multispecific antigen-binding molecules. By 'multispecific' it is meant that the antigen-binding molecule displays specific binding to more than one target. In some embodiments, the antigen-binding molecule is a bispecific antigen-binding molecule. In some embodiments, the antigen-binding molecule comprises at least two different antigen-binding domains (i.e. at least two antigen-binding domains, e.g. comprising non-identical VHs and VLs).

In some embodiments, the antigen-binding molecule binds to BCMA/TACI and another target (e.g. an antigen other than BCMA/TACI), and so is at least bispecific. The term 'bispecific' means that the antigen-binding molecule is able to bind specifically to at least two distinct antigenic determinants. In some embodiments, the antigen other than BCMA/TACI is CD47. In some embodiments, the antigen-binding molecule binds to CD47 and another target (e.g. an antigen other than CD47). In some embodiments, the antigen other than CD47 is BCMA/TACI.

It will be appreciated that an antigen-binding molecule according to the present disclosure (e.g. a multispecific antigen-binding molecule) may comprise antigen-binding molecules capable of binding to the targets for which the antigen-binding molecule is specific. For example, an antigen-binding molecule which binds to BCMA/TACI and an antigen other than BCMA/TACI (e.g. CD47) may comprise: (i) an antigen-binding molecule which binds to BCMA/TACI, and (ii) an antigen-binding molecule which binds to an antigen other than BCMA/TACI (e.g. CD47). For example, an antigen-binding molecule which binds to CD47 and an antigen other than CD47 (e.g. BCMA/TACI) may comprise: (i) an antigen-binding molecule which binds to CD47, and (ii) an antigen-binding molecule which binds to an antigen other than CD47 (e.g. BCMA/TACI).

It will also be appreciated that an antigen-binding molecule according to the present disclosure (e.g. a multispecific antigen-binding molecule) may comprise antigen-binding polypeptides or antigen-binding polypeptide complexes capable of binding to the targets for which the antigen-binding molecule is specific.

In some embodiments, a component antigen-binding molecule of a larger antigen-binding molecule (e.g. a multispecific antigen-binding molecule) may be referred to e.g. as an 'antigen-binding domain' or 'antigen-binding region' of the larger antigen-binding molecule.

In some embodiments, the antigen other than CD47 or the antigen other than BCMA/TACI in a multispecific antigen-binding molecule is an immune cell surface molecule. In some embodiments, the antigen is a cancer cell antigen. In some embodiments, the antigen is a receptor molecule, e.g. a cell surface receptor. In some embodiments, the antigen is a cell signalling molecule, e.g. a cytokine, chemokine, interferon, interleukin or lymphokine. In some embodiments, the antigen is a growth factor or a hormone.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments, the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present disclosure is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell).

In some embodiments, the antigen is an antigen expressed by cells of a hematologic malignancy, a myeloid hematologic malignancy, a lymphoblastic hematologic malignancy, myelodysplastic syndrome (MDS), acute myeloid leukemia (AML), chronic myeloid leukemia, acute lymphoblastic leukemia (ALL), non-Hodgkin's lymphoma, follicular lymphoma (FL), mantle cell lymphoma (MCL), multiple myeloma, bladder cancer or brain cancer.

In some embodiments, the antigen is an antigen expressed by cells of AML, e.g. as described in Hoseini and Cheung, Blood Cancer J. (2017) 7(2):e522, which is hereby incorporated by reference in its entirety. In some embodiments, the antigen is selected from: TACI, CD33, CD123, Wilms' tumor protein (WT1), CD13, CD15, CD30, CD45, C-type lectin-like molecule 1 (CLL1), Fms-like tyrosine kinase 3 (FLT-3), VEGF and angiopoietin-2 (Ang-2). In some embodiments, the antigen is a CD3 polypeptide (e.g. CD3ε, CD3δ, CD3γ or CD3ζ).

In some embodiments, multispecific antigen-binding molecules described herein display at least monovalent binding with respect to BCMA/TACI, and also display at least monovalent binding with respect to CD47.

In some embodiments, the antigen-binding molecule comprises an antigen-binding region (e.g. a polypeptide, Fv, Fab or antibody) capable of binding to BCMA/TACI, and an antigen-binding region (e.g. a polypeptide, Fv, Fab or antibody) capable of binding to CD47. In some embodiments, the antigen-binding molecule comprises the VH and VL of an antibody capable of binding to BCMA/TACI and the VH and VL of an antibody capable of binding to CD47.

Binding valency refers to the number of binding sites in an antigen-binding molecule for a given antigenic determinant. For example, the bispecific anti-BCMA/TACI, anti-CD47 antibodies described in Example 6 herein display monovalent binding with respect to binding to BCMA/TACI (through the BCMA/TACI-specific Fab), and monovalent binding with respect to binding to CD47 (through the CD47-specific scFv).

Accordingly, In some embodiments, the antigen-binding molecule comprises one binding site for BCMA/TACI and one binding site for CD47.

In some embodiments, multispecific antigen-binding molecules described herein display at least monovalent binding with respect to BCMA/TACI, and also display at least monovalent binding with respect to a CD3 polypeptide (e.g. CD3ε, CD3δ, CD3γ or CD3ζ; preferably CD3ε, CD3δ or CD3γ; or more preferably CD3ε). In some embodiments, the antigen-binding molecule comprises one binding site for BCMA/TACI and one binding site for a CD3 polypeptide.

In some embodiments, the antigen-binding molecule comprises the CDRs of an antigen-binding molecule which binds to a CD3 polypeptide (e.g. CD3ε, CD3δ, CD3γ or CD3ζ; preferably CD3ε, CD3δ or CD3γ; or more preferably CD3ε). In some embodiments, the antigen-binding molecule comprises the FRs of an antigen-binding molecule which binds to a CD3 polypeptide (e.g. CD3ε, CD3δ, CD3γ or CD3ζ; preferably CD3ε, CD3δ or CD3γ; or more preferably CD3ε). In some embodiments, the antigen-binding molecule comprises the CDRs and the FRs of an antigen-binding molecule which binds to a CD3 polypeptide (e.g. CD3ε, CD3δ, CD3γ or CD3ζ; preferably CD3ε, CD3δ or CD3γ; or more preferably CD3ε). That is, In some embodiments, the antigen-binding molecule comprises the VH region and the VL region of an antigen-binding molecule which binds to a CD3 polypeptide (e.g. CD3ε, CD3δ, CD3γ or CD3ζ; preferably CD3ε, CD3δ or CD3γ; or more preferably CD3ε).

In some embodiments, the antigen-binding molecule comprises the CDRs, FRs and/or the VH and/or VL regions of a CD3 polypeptide-binding antibody clone described herein, or CDRs, FRs and/or VH and/or VL regions which are derived from those of a CD3 polypeptide-binding antibody clone described herein. In some embodiments, a CD3 polypeptide-binding antibody clone is selected from: OKT3 (described herein, and also in Kjer-Nielsen et al., PNAS (2004) 101(20):7675-80), SP34 (described e.g. in WO 2014/122143 A1), UCHT1 (described e.g. in WO 2000/041474 A1) HIT3a (Invitrogen Cat #16-0039-85), and clone SK7 (Invitrogen Cat #16-0036-81).

In some embodiments, the antigen-binding molecule comprises the CDRs, FRs and/or the VH and/or VL regions of the Fv formed by SEQ ID NOs:452 and 453. In some embodiments, the antigen-binding molecule comprises the CDRs, FRs and/or the VH and/or VL regions of OKT3. In some embodiments, the antigen-binding molecule comprises: (i) a VH comprising HC-CDR1 shown in SEQ ID NO:525, HC-CDR2 shown in SEQ ID NO:526 and HC-CDR3 shown in SEQ ID NO:527; and (ii) a VL comprising LC-CDR1 shown in SEQ ID NO:531, LC-CDR2 shown in SEQ ID NO:532 and LC-CDR3 shown in SEQ ID NO:533. In some embodiments, the antigen-binding molecule comprises: (i) a VH comprising HC-FR1 shown in SEQ ID NO:528, HC-FR2 shown in SEQ ID NO:529, HC-FR3 shown in SEQ ID NO:530 and HC-FR4 shown in SEQ ID NO:29; and (ii) a VL comprising LC-FR1 shown in SEQ ID NO:534, LC-FR2 shown in SEQ ID NO:535, LC-FR3 shown in SEQ ID NO:536 and LC-FR4 shown in SEQ ID NO:537. In some embodiments, the antigen-binding molecule comprises: (i) a VH having the sequence shown in SEQ ID NO:452; and (ii) a VL having the sequence shown in SEQ ID NO:453.

In some embodiments, the antigen-binding molecule comprises the CDRs, FRs and/or the VH and/or VL regions of the Fv formed by SEQ ID NOs:538 and 545. In some embodiments, the antigen-binding molecule comprises the CDRs, FRs and/or the VH and/or VL regions of SP34. In some embodiments, the antigen-binding molecule comprises: (i) a VH comprising HC-CDR1 shown in SEQ ID NO:539, HC-CDR2 shown in SEQ ID NO:540 and HC-CDR3 shown in SEQ ID NO:541; and (ii) a VL comprising LC-CDR1 shown in SEQ ID NO:546, LC-CDR2 shown in SEQ ID NO:547 and LC-CDR3 shown in SEQ ID NO:548. In some embodiments, the antigen-binding molecule comprises: (i) a VH comprising HC-FR1 shown in SEQ ID NO:542, HC-FR2 shown in SEQ ID NO:543, HC-FR3 shown in SEQ ID NO:544 and HC-FR4 shown in SEQ ID NO:43; and (ii) a VL comprising LC-FR1 shown in SEQ ID NO:549, LC-FR2 shown in SEQ ID NO:550, LC-FR3 shown in SEQ ID NO:551 and LC-FR4 shown in SEQ ID NO:552. In some embodiments, the antigen-binding molecule comprises: (i) a VH having the sequence shown in SEQ ID NO:538; and (ii) a VL having the sequence shown in SEQ ID NO:545.

In some embodiments, the antigen-binding molecule comprises an antigen-binding region (e.g. a polypeptide, Fv, Fab or antibody) capable of binding to BCMA/TACI, and an antigen-binding region (e.g. a polypeptide, Fv, Fab or antibody) capable of binding to a CD3 polypeptide. In some embodiments, the antigen-binding molecule comprises the VH and VL of an antibody capable of binding to BCMA/TACI and the VH and VL of an antibody capable of binding to a CD3 polypeptide.

In some embodiments, the antigen-binding molecule is an immune cell engager. Immune cell engagers are reviewed e.g. in Goebeler and Bargou, Nat. Rev. Clin. Oncol. (2020) 17: 418-434 and Ellerman, Methods (2019) 154:102-117, both of which are hereby incorporated by reference in their entirety.

Immune cell engager molecules comprise an antigen-binding region for a target antigen of interest, and an antigen-binding region for recruiting/engaging an immune cell of interest. Immune cell engagers recruit/engage immune cells through an antigen-binding region specific for an immune cell surface molecule.

The best studied immune cells engagers are bispecific T cell engagers (BiTEs), which comprise a target antigen binding domain, and a CD3 polypeptide (typically CD3ε)-binding domain, through which the BiTE recruits T cells. Binding of the BiTE to its target antigen and to the CD3 polypeptide expressed by the T cell results in activation of the T cell, and ultimately directs T cell effector activity against cells expressing the target antigen. Other kinds of immune cell engagers are well known in the art, and include natural killer cell engagers such as bispecific killer engagers (BiKEs), which recruit and activate NK cells. In some embodiments, the immune cell engaged by the immune cell engager is a T cell or an NK cell. In some embodiments, the immune cell engager is a T cell-engager.

Multispecific antigen-binding molecules according to the present disclosure may be provided in any suitable format, such as those formats described in described in Brinkmann and Kontermann, MAbs (2017) 9(2): 182-212, which is hereby incorporated by reference in its entirety. Suitable formats include those shown in FIG. 2 of Brinkmann and Kontermann, MAbs (2017) 9(2): 182-212: antibody conjugates, e.g. IgG₂, F(ab')₂ or CovX-Body; IgG or IgG-like molecules, e.g. IgG, chimeric IgG, Kλ-body common HC; CH1/CL fusion proteins, e.g. scFv2-CH1/CL, VHH2-CH1/CL; 'variable domain only' bispecific antigen-binding molecules, e.g. tandem scFv (taFV), triplebodies, diabodies (db), dsDb, db(kih), DART, scDB, dsFv-dsFv, tandAbs, triple heads, tandem dAb/VHH, tetravalent dAb.VHH; Non-Ig fusion proteins, e.g. scFv₂-albumin, scDb-albumin, taFv-albumin, taFv-toxin, miniantibody, DNL-Fab₂, DNL-Fab₂-scFv, DNL-Fab₂-IgG-cytokine₂, ImmTAC (TCR-scFv); modified Fc and CH3 fusion proteins, e.g. scFv-Fc (kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc(kih)-scFv, Fab-scFv-Fc(kih), Fab-scFv-Fc(BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, scFv₄-Ig, scFv₂-Fcab; CH3 fusions, e.g. Dia-diabody, scDb-CH3; IgE/IgM CH2 fusions, e.g. scFv-EHD2-scFv, scFvMHD2-scFv; Fab fusion proteins, e.g. Fab-scFv (bi-body), Fab-scFv₂ (tribody), Fab-Fv, Fab-dsFv, Fab-VHH, orthogonal Fab-Fab; non-Ig fusion proteins, e.g. DNL-Fab₃, DNL-Fab₂-scFv, DNL-Fab₂-IgG-cytokine₂; asymmetric IgG or IgG-like molecules, e.g. IgG(kih), IgG(kih) common LC, ZW1 IgG common LC, Biclonics common LC, CrossMab, CrossMab(kih), scFab-IgG(kih), Fab-scFab-IgG (kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-IgG, FcFc*; appended and Fc-modified IgGs, e.g. IgG(kih)-Fv, IgG HA-TF-Fv, IgG(kih)

scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g. Fab-Fc(kih)-scFv, Fab-scFv-Fc(kih), Fab-scFv-Fc(BEAT), Fab-scFv-Fc-SEEDbody, Tri Fab; appended IgGs—HC fusions, e.g. IgG-HC, scFv, IgG-dAb, IgG-taFV, IgG-CrossFab, IgG-orthogonal Fab, IgG-(CaCβ) Fab, scFv-HC-IgG, tandem Fab-IgG (orthogonal Fab), Fab-IgG(CaCβ Fab), Fab-IgG(CR3), Fab-hinge-IgG (CR3); appended IgGs—LC fusions, e.g. IgG-scFv(LC), scFv(LC)-IgG, dAb-IgG; appended IgGs—HC and LC fusions, e.g. DVD-Ig, TVD-Ig, CODV-Ig, scFv$_4$-IgG, Zybody; Fc fusions, e.g. Fab-scFv-Fc, scFv$_4$-Ig; F(ab')2 fusions, e.g. F(ab')$_2$-scFv$_2$; CH$_1$/CL fusion proteins e.g. scFv$_2$-CH1-hinge/CL; modified IgGs, e.g. DAF (two-in one-IgG), DutaMab, Mab$^2$; and non-Ig fusions, e.g. DNL-Fab$_4$-IgG.

The skilled person is able to design and prepare bispecific antigen-binding molecules. Methods for producing bispecific antigen-binding molecules include chemically cross-linking antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers. Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13: 2.13.1-2.13.16.

Bispecific antigen-binding molecules according to the present disclosure can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Färber-Schwarz), or French, How to make bispecific antigen-binding molecules, Methods Mol. Med. 2000; 40:333-339, the entire contents of both of which are hereby incorporated by reference.

For example, a DNA construct encoding the light and heavy chain variable domains for the two antigen-binding fragments (i.e. the light and heavy chain variable domains for the antigen-binding fragment capable of binding BCMA/TACI or CD47, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

In aspects and embodiments of the present disclosure, an antigen-binding molecule capable of binding to BCMA may also be capable of binding to TACI. That is, the antigen-binding molecule may display binding to BCMA or TACI. Such antigen-binding molecules may be described as being 'cross-reactive' for BCMA and TACI. Cross-reactivity refers to the ability of an antigen-binding molecule which displays specific binding to a given antigen (e.g. BCMA) and to another antigen (e.g. TACI). By way of illustration, anti-BCMA-binding clones 538-SP5-610, 539-SP1-C8 and 539-SP2-H3 are shown in Example 3.2 herein to display binding to TACI.

It will be appreciated that the antigen-binding molecule paratope formed by the heavy chain and light chain CDRs of such cross-reactive molecules confers binding to BCMA, and also confers binding to TACI.

Accordingly, throughout the present disclosure, an antigen-binding molecule capable of binding to BCMA may in some aspects and embodiments be an antibody capable of binding to TACI, or an antigen-binding molecule capable of binding to BCMA/TACI.

Fc Regions

In some embodiments, the antigen-binding molecules of the present disclosure comprise an Fc region. An Fc region is composed of CH2 and CH3 regions from one polypeptide, and CH2 and CH3 regions from another polypeptide. The CH2 and CH3 regions from the two polypeptides together form the Fc region.

Fc-mediated functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation. Modifications to antibody Fc regions that influence Fc-mediated functions are known in the art, such as those described e.g. in Wang et al., Protein Cell (2018) 9(1):63-73, which is hereby incorporated by reference in its entirety. Exemplary Fc region modifications known to influence antibody effector function are summarised in Table 1 of Wang et al., Protein Cell (2018) 9(1):63-73. In some embodiments, the antigen-binding molecule of the present disclosure comprises an Fc region comprising modification to increase or reduce an Fc-mediated function as compared to an antigen-binding molecule comprising the corresponding unmodified Fc region.

Where an Fc region/CH2/CH3 is described as comprising modification(s) 'corresponding to' reference substitution(s), equivalent substitution(s) in the homologous Fc/CH2/CH3 are contemplated. By way of illustration, L234A/L235A substitutions in human IgG1 (numbered according to the EU numbering system as described in Kabat et al., Sequences of Proteins of Immunological Interest, 5th Ed. Public Health Service, National Institutes of Health, Bethesda, M D, 1991) correspond to L to A substitutions at positions 117 and 118 of the mouse Ig gamma-2A chain C region (UniProtKB: P01863-1, v1).

Where an Fc region is described as comprising a modification, the modification may be present in one or both of the polypeptide chains which together form the Fc region.

In some embodiments, the antigen-binding molecule of the present disclosure comprises an Fc region comprising modification. In some embodiments, the antigen-binding molecule of the present disclosure comprises an Fc region comprising modification in one or more of the CH2 and/or CH3 regions.

In some embodiments, the Fc region comprises modification to increase an Fc-mediated function. In some embodiments, the Fc region comprises modification to increase ADCC. In some embodiments, the Fc region comprises modification to increase ADCP. In some embodiments, the Fc region comprises modification to increase CDC. An antigen-binding molecule comprising an Fc region comprising modification to increase an Fc-mediated function (e.g. ADCC, ADCP, CDC) induces an increased level of the relevant effector function as compared to an antigen-binding molecule comprising the corresponding unmodified Fc region.

In some embodiments, the Fc region comprises modification to increase binding to an Fc receptor. In some embodiments, the Fc region comprises modification to increase binding to an Fcγ receptor. In some embodiments, the Fc region comprises modification to increase binding to one or more of FcγRI, FcγRIIa, FcγRIIb, FcγRIIc, FcγRIIIa and FcγRIIIb. In some embodiments, the Fc region comprises modification to increase binding to FcγRIIIa. In some embodiments, the Fc region comprises modification to increase binding to FcγRIIa. In some embodiments, the Fc region comprises modification to increase binding to FcγRIIb. In some embodiments, the Fc region comprises modification to increase binding to FcRn. In some embodiments, the Fc region comprises modification to increase binding to a complement protein. In some embodiments, the Fc region comprises modification to increase binding to C1q. In some embodiments, the Fc region comprises modification to promote hexamerisation of the antigen-binding molecule. In some embodiments, the Fc region comprises modification to increase antigen-binding molecule half-life. In some embodiments, the Fc region comprises modification to increase co-engagement.

In some embodiments, the Fc region comprises modification corresponding to the combination of substitutions F243L/R292P/Y300L/V305I/P396L as described in Stavenhagen et al. Cancer Res. (2007) 67:8882-8890. In some embodiments, the Fc region comprises modification corresponding to the combination of substitutions S239D/I332E or S239D/I332E/A330L as described in Lazar et al., Proc Natl Acad Sci USA. (2006) 103:4005-4010. In some embodiments, the Fc region comprises modification corresponding to the combination of substitutions S298A/E333A/K334A as described in Shields et al., J Biol Chem. (2001) 276:6591-6604. In some embodiments, the Fc region comprises modification to one of heavy chain polypeptides corresponding to the combination of substitutions L234Y/L235Q/G236W/S239M/H268D/D270E/S298A, and modification to the other heavy chain polypeptide corresponding to the combination of substitutions D270E/K326D/A330M/K334E, as described in Mimoto et al., MAbs. (2013): 5:229-236. In some embodiments, the Fc region comprises modification corresponding to the combination of substitutions G236A/S239D/I332E as described in Richards et al., Mol Cancer Ther. (2008) 7:2517-2527.

In some embodiments, the Fc region comprises modification corresponding to the combination of substitutions K326W/E333S as described in Idusogie et al. J Immunol. (2001) 166(4):2571-5. In some embodiments, the Fc region comprises modification corresponding to the combination of substitutions S267E/H268F/S324T as described in Moore et al. MAbs. (2010) 2(2):181-9. In some embodiments, the Fc region comprises modification corresponding to the combination of substitutions described in Natsume et al., Cancer Res. (2008) 68(10):3863-72. In some embodiments, the Fc region comprises modification corresponding to the combination of substitutions E345R/E430G/S440Y as described in Diebolder et al. Science (2014) 343(6176):1260-3.

In some embodiments, the Fc region comprises modification corresponding to the combination of substitutions M252Y/S254T/T256E as described in Dall'Acqua et al. J Immunol. (2002) 169:5171-5180. In some embodiments, the Fc region comprises modification corresponding to the combination of substitutions M428L/N434S as described in Zalevsky et al. Nat Biotechnol. (2010) 28:157-159.

In some embodiments, the Fc region comprises modification corresponding to the combination of substitutions S267E/L328F as described in Chu et al., Mol Immunol. (2008) 45:3926-3933. In some embodiments, the Fc region comprises modification corresponding to the combination of substitutions N325S/L328F as described in Shang et al. Biol Chem. (2014) 289:15309-15318.

In some embodiments, the Fc region comprises modification to reduce/prevent an Fc-mediated function. In some embodiments, the Fc region comprises modification to reduce/prevent ADCC. In some embodiments, the Fc region comprises modification to reduce/prevent ADCP. In some embodiments, the Fc region comprises modification to reduce/prevent CDC. An antigen-binding molecule comprising an Fc region comprising modification to reduce/prevent an Fc-mediated function (e.g. ADCC, ADCP, CDC) induces an reduced level of the relevant effector function as compared to an antigen-binding molecule comprising the corresponding unmodified Fc region.

In some embodiments, the Fc region comprises modification to reduce/prevent binding to an Fc receptor. In some embodiments, the Fc region comprises modification to reduce/prevent binding to an Fcγ receptor. In some embodiments, the Fc region comprises modification to reduce/prevent binding to one or more of FcγRI, FcγRIIa, FcγRIIb, FcγRIIc, FcγRIIIa and FcγRIIIb. In some embodiments, the Fc region comprises modification to reduce/prevent binding to FcγRIIIa. In some embodiments, the Fc region comprises modification to reduce/prevent binding to FcγRIIa. In some embodiments, the Fc region comprises modification to reduce/prevent binding to FcγRIIb. In some embodiments, the Fc region comprises modification to reduce/prevent binding to a complement protein. In some embodiments, the Fc region comprises modification to reduce/prevent binding to C1q. In some embodiments, the Fc region comprises modification to reduce/prevent glycosylation of the amino acid residue corresponding to N297.

In some embodiments, the Fc region is not able to induce one or more Fc-mediated functions (i.e. lacks the ability to elicit the relevant Fc-mediated function(s)). Accordingly, antigen-binding molecules comprising such Fc regions also lack the ability to induce the relevant function(s). Such antigen-binding molecules may be described as being devoid of the relevant function(s).

In some embodiments, the Fc region is not able to induce ADCC. In some embodiments, the Fc region is not able to induce ADCP. In some embodiments, the Fc region is not able to induce CDC. In some embodiments, the Fc region is not able to induce ADCC and/or is not able to induce ADCP and/or is not able to induce CDC.

In some embodiments, the Fc region is not able to bind to an Fc receptor. In some embodiments, the Fc region is not able to bind to an Fcγ receptor. In some embodiments, the Fc region is not able to bind to one or more of FcγRI, FcγRIIa, FcγRIIb, FcγRIIc, FcγRIIIa and FcγRIIIb. In some embodiments, the Fc region is not able to bind to FcγRIIIa. In some embodiments, the Fc region is not able to bind to FcγRIIa. In some embodiments, the Fc region is not able to bind to FcγRIIb. In some embodiments, the Fc region is not able to bind to FcRn. In some embodiments, the Fc region is not able to bind to a complement protein. In some embodiments, the Fc region is not able to bind to C1q. In some embodiments, the Fc region is not glycosylated at the amino acid residue corresponding to N297.

In some embodiments, the Fc region comprises modification corresponding to N297A or N297Q or N297G as described in Leabman et al., MAbs. (2013) 5:896-903. In some embodiments, the Fc region comprises modification corresponding to L235E as described in Alegre et al., J Immunol. (1992) 148:3461-3468. In some embodiments, the Fc region comprises modification corresponding to the combination of substitutions L234A/L235A or F234A/L235A as described in Xu et al., Cell Immunol. (2000) 200:16-26. In some embodiments, the Fc region comprises modification corresponding to P329A or P329G as described in Schlothauer et al., Protein Engineering, Design and Selection (2016), 29(10):457-466. In some embodiments, the Fc region comprises modification corresponding to the combination of substitutions L234A/L235A/P329G as described in Lo et al. J. Biol. Chem (2017) 292(9):3900-3908. In some embodiments, the Fc region comprises modification corresponding to the combination of substitutions described in Rother et al., Nat Biotechnol. (2007) 25:1256-1264. In some embodiments, the Fc region comprises modification corresponding to the combination of substitutions S228P/L235E as described in Newman et al., Clin. Immunol. (2001) 98:164-174. In some embodiments, the Fc region comprises modification corresponding to the combination of substitutions H268Q/V309L/A330S/P331S as described in An et al., MAbs. (2009) 1:572-579. In some embodiments, the Fc region comprises modification corresponding to the combination of substitutions V234A/G237A/P238S/H268A/V309L/A330S/P331S as described in Vafa et al., Methods. (2014) 65:114-126. In some embodiments, the Fc region comprises modification corresponding to the combination of substitutions L234A/L235E/G237A/A330S/P331S as described in US 2015/0044231 A1.

The combination of substitutions 'L234A/L235A' and corresponding substitutions (such as e.g. F234A/L235A in human IgG4) are known to disrupt binding of Fc to Fcγ receptors and inhibit ADCC, ADCP, and also to reduce C1q binding and thus CDC (Schlothauer et al., Protein Engineering, Design and Selection (2016), 29(10):457-466, hereby incorporated by reference in entirety). The substitutions 'P329G' and 'P329A' reduce C1q binding (and thereby CDC). Substitution of 'N297' with 'A', 'G' or '0' is known to eliminate glycosylation, and thereby reduce Fc binding to C1q and Fcγ receptors, and thus CDC and ADCC. Lo et al. J. Biol. Chem (2017) 292(9):3900-3908 (hereby incorporated by reference in its entirety) reports that the combination of substitutions L234A/L235A/P329G eliminated complement binding and fixation as well as Fc γ receptor dependent, antibody-dependent, cell-mediated cytotoxicity in both murine IgG2a and human IgG1.

The combination of substitutions L234A/L235E/G237A/A330S/P331S in IgG1 Fc is disclosed in US 2015/0044231 A1 to abolish induction of phagocytosis, ADCC and CDC.

In some embodiments, the Fc region comprises modification corresponding to the substitution S228P as described in Silva et al., J Biol Chem. (2015) 290(9):5462-5469. The substitution S228P in IgG4 Fc reduces Fab-arm exchange (Fab arm exchange can be undesirable).

In some embodiments, the Fc region comprises modification corresponding to corresponding to the combination of substitutions L234A/L235A. In some embodiments, the Fc region comprises modification corresponding to corresponding to the substitution P329G. In some embodiments, the Fc region comprises modification corresponding to corresponding to the substitution N297Q.

In some embodiments, the Fc region comprises modification corresponding to corresponding to the combination of substitutions L234A/L235A/P329G.

In some embodiments, the Fc region comprises modification corresponding to corresponding to the combination of substitutions L234A/L235A/P329G/N297Q.

In some embodiments, the Fc region comprises modification corresponding to corresponding to the combination of substitutions L234A/L235E/G237A/A330S/P331S.

In some embodiments, the Fc region comprises modification corresponding to corresponding to the substitution S228P, e.g. in IgG4.

In some embodiments, the antigen-binding molecule of the present disclosure comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety.

In some embodiments, the antigen antigen-binding molecule of the present disclosure comprises an Fc region comprising paired substitutions in the CH3 regions of the Fc region according to one of the following formats, as shown in Table 1 of Ha et al., Front. Immnol (2016) 7:394: KiH, KiH$_{s-s}$, HA-TF, ZW1, 7.8.60, DD-KK, EW-RVT, EW-RVT$_{s-s}$, SEED or A107.

In some embodiments, the Fc region comprises the 'knob-into-hole' or 'KiH' modification, e.g. as described e.g. in U.S. Pat. No. 7,695,936 and Carter, J Immunol Meth 248, 7-15 (2001). In such embodiments, one of the CH3 regions of the Fc region comprises a 'knob' modification, and the other CH3 region comprises a 'hole' modification. The 'knob' and 'hole' modifications are positioned within the respective CH3 regions so that the 'knob' can be positioned in the 'hole' in order to promote heterodimerisation (and inhibit homodimerisation) of the polypeptides and/or stabilise heterodimers. Knobs are constructed by substituting amino acids having small chains with those having larger side chains (e.g. tyrosine or tryptophan). Holes are created by substituting amino acids having large side chains with those having smaller side chains (e.g. alanine or threonine).

In some embodiments, one of the CH3 regions of the Fc region of the antigen-binding molecule of the present disclosure comprises the substitution (numbering of positions/substitutions in the Fc, CH2 and CH3 regions herein is according to the EU numbering system as described in Kabat et al., Sequences of Proteins of Immunological Interest, 5th Ed. Public Health Service, National Institutes of Health, Bethesda, M D, 1991) T366W, and the other CH3 region of the Fc region comprises the substitution Y407V. In some embodiments, one of the CH3 regions of the Fc region of the antigen-binding molecule comprises the substitution T366W, and the other CH3 region of the Fc region comprises the substitutions T366S and L368A. In some embodiments, one of the CH3 regions of the Fc region of the antigen-binding molecule comprises the substitution T366W, and the other CH3 region of the Fc region comprises the substitutions Y407V, T366S and L368A.

In some embodiments, the Fc region comprises the DD-KK' modification as described e.g. in US 8592562 B2. In some embodiments, one of the CH3 regions comprises the substitutions K392D and K409D, and the other CH3 region of the Fc region comprises the substitutions E356K and D399K. The modifications promote electrostatic interaction between the CH3 regions.

In some embodiments, the antigen-binding molecule of the present disclosure comprises an Fc region modified as described in Labrijn et al., Proc Natl Acad Sci USA. (2013) 110(13):5145-50, referred to as 'Duobody' format. In some embodiments one of the CH3 regions comprises the substitution K409R, and the other CH3 region of the Fc region comprises the substitution F405L.

In some embodiments, the antigen-binding molecule of the present disclosure comprises an Fc region comprising the 'EEE-RRR' modification as described in Strop et al., J Mol Biol. (2012) 420(3):204-19. In some embodiments one of the CH3 regions comprises the substitutions D221E, P228E and L368E, and the other CH3 region of the Fc region comprises the substitutions D221R, P228R and K409R.

In some embodiments, the antigen-binding molecule comprises an Fc region comprising the 'EW-RVT' modification described in Choi et al., Mol Cancer Ther (2013) 12(12):2748-59. In some embodiments one of the CH3 regions comprises the substitutions K360E and K409W, and the other CH3 region of the Fc region comprises the substitutions Q347R, D399V and F405T.

In some embodiments, one of the CH3 regions comprises the substitution S354C, and the other CH3 region of the Fc region comprises the substitution Y349C. Introduction of these cysteine residues results in formation of a disulphide bridge between the two CH3 regions of the Fc region, further stabilizing the heterodimer (Carter (2001), J Immunol Methods 248, 7-15).

In some embodiments, the Fc region comprises the 'KiH$_{s\text{-}s}$' modification. In some embodiments one of the CH3 regions comprises the substitutions T366W and S354C, and the other CH3 region of the Fc region comprises the substitutions T366S, L368A, Y407V and Y349C.

In some embodiments, the antigen-binding molecule of the present disclosure comprises an Fc region comprising the 'SEED' modification as described in Davis et al., Protein Eng Des Sel (2010) 23(4):195-202, in which β-strand segments of human IgG1 CH3 and IgA CH3 are exchanged.

In some embodiments, one of the CH3 regions comprises the substitutions S364H and F405A, and the other CH3 region of the Fc region comprises the substitutions Y349T and T394F (see e.g. Moore et al., MAbs (2011) 3(6):546-57).

In some embodiments, one of the CH3 regions comprises the substitutions T350V, L351Y, F405A and Y407V, and the other CH3 region of the Fc region comprises the substitutions T350V, T366L, K392L and T394W (see e.g. Von Kreudenstein et al., MAbs (2013) 5(5):646-54).

In some embodiments, one of the CH3 regions comprises the substitutions K360D, D399M and Y407A, and the other CH3 region of the Fc region comprises the substitutions E345R, Q347R, T366V and K409V (see e.g. Leaver-Fay et al., Structure (2016) 24(4):641-51).

In some embodiments, one of the CH3 regions comprises the substitutions K370E and K409W, and the other CH3 region of the Fc region comprises the substitutions E357N, D399V and F405T (see e.g. Choi et al., PLoS One (2015) 10(12):e0145349).

In some embodiments an antigen-binding molecule according to the present disclosure comprises a polypeptide comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:269, 270, 271, 272, 273, 274, 275, 276, 278, 279, 280.

Polypeptides and Particular Exemplary Antigen-Binding Molecules

The present disclosure also provides polypeptide constituents of antigen-binding molecules. The polypeptides may be provided in isolated or substantially purified form.

The antigen-binding molecule of the present disclosure may be, or may comprise, a complex of polypeptides.

In the present specification where a polypeptide comprises more than one domain or region, it will be appreciated that the plural domains/regions are preferably present in the same polypeptide chain. That is, the polypeptide comprising more than one domain or region is a fusion polypeptide comprising the domains/regions.

In some embodiments a polypeptide according to the present disclosure comprises, or consists of, a VH as described herein. In some embodiments a polypeptide according to the present disclosure comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments, the polypeptide comprises one or more regions of an immunoglobulin heavy chain constant sequence. In some embodiments, the polypeptide comprises a CH1 region as described herein. In some embodiments, the polypeptide comprises a CH1-CH2 hinge region as described herein. In some embodiments, the polypeptide comprises a CH2 region as described herein. In some embodiments, the polypeptide comprises a CH3 region as described herein.

In some embodiments, the polypeptide comprises a CH3 region comprising any one of the following amino acid substitutions/combinations of amino acid substitutions (shown e.g. in Table 1 of Ha et al., Front. Immnol (2016) 7:394, incorporated by reference hereinabove): T366W; T366S, L368A and Y407V; T366W and S354C; T366S, L368A, Y407V and Y349C; S364H and F405A; Y349T and T394F; T350V, L351Y, F405A and Y407V; T350V, T366L, K392L and T394W; K360D, D399M and Y407A; E345R, Q347R, T366V and K409V; K409D and K392D; D399K and E356K; K360E and K409W; Q347R, D399V and F405T; K360E, K409W and Y349C; Q347R, D399V, F405T and S354C; K370E and K409W; and E357N, D399V and F405T.

In some embodiments, the CH2 and/or CH3 regions of the polypeptide comprise one or more amino acid substitutions for promoting association of the polypeptide with another polypeptide comprising a CH2 and/or CH3 region.

In some embodiments, the polypeptide comprises one or more regions of an immunoglobulin light chain constant sequence. In some embodiments, the polypeptide comprises a CL region as described herein.

In some embodiments, the polypeptide according to the present disclosure comprises a structure from N- to C-terminus according to one of the following:

(i) VH (ii) VL (iii) VH-CH1

(iv) VL-CL (v) VL-CH1

(vi) VH-CL (vii) VH-CH1-CH2-CH3

(viii) VL-CL-CH2-CH3

(ix) VL-CH1-CH2-CH3

(x) VH-CL-CH2-CH3

Also provided by the present disclosure are antigen-binding molecules composed of the polypeptides of the present disclosure. In some embodiments, the antigen-binding molecule of the present disclosure comprises one of the following combinations of polypeptides:

(A) VH+VL (B) VH-CH1+VL-CL (C) VL-CH1+VH-CL (D) VH-CH1-CH2-CH3+VL-CL (E) VH-CL-CH2-CH3+VL-CH1

(F) VL-CH1-CH2-CH3+VH-CL (G) VL-CL-CH2-CH3+VH-CH1

(H) VH-CH1-CH2-CH3+VL-CL-CH2-CH3

(I) VH-CL-CH2-CH3+VL-CH1-CH2-CH3

In some embodiments, the antigen-binding molecule comprises more than one of a polypeptide of the combinations shown in (A) to (I) above. By way of example, with reference to (D) above, In some embodiments, the antigen-binding molecule comprises two polypeptides comprising the structure VH-CH1-CH2-CH3, and two polypeptides comprising the structure VL-CL.

In some embodiments, the antigen-binding molecule of the present disclosure comprises one of the following combinations of polypeptides:

(J) VH (anti-BCMA/TACI)+VL (anti-BCMA/TACI)

(K) VH (anti-BCMA/TACI)-CH1+VL (anti-BCMA/TACI)-CL (L) VL (anti-BCMA/TACI)-CH1+VH (anti-BCMA/TACI)-CL (M) VH (anti-BCMA/TACI)-CH1-CH2-CH3+VL (anti-BCMA/TACI)-CL (N) VH (anti-BCMA/TACI)-CL-CH2-CH3+VL (anti-BCMA/TACI)-CH1

(O) VL (anti-BCMA/TACI)-CH1-CH2-CH3+VH (anti-BCMA/TACI)-CL (P) VL (anti-BCMA/TACI)-CL-CH2-CH3+VH (anti-BCMA/TACI)-CH1

(Q) VH (anti-BCMA/TACI)-CH1-CH2-CH3+VL (anti-BCMA/TACI)-CL-CH2-CH3

(R) VH (anti-BCMA/TACI)-CL-CH2-CH3+VL (anti-BCMA)-CH1-CH2-CH3

(S) VH (anti-BCMA/TACI)+VL (anti-BCMA/TACI)+VH (anti-CD47)+VL (anti-CD47)

(T) VH (anti-BCMA/TACI)-CH1+VL (anti-BCMA/TACI)-CL+VH (anti-CD47)-CH1+VL (anti-CD47)-CL (U) VL (anti-BCMA/TACI)-CH1+VH (anti-BCMA/TACI)-CL+VL (anti-CD47)-CH1+VH (anti-CD47)-CL (V) VH (anti-BCMA/TACI)-CH1-CH2-CH3+VL (anti-BCMA/TACI)-CL+VH (anti-CD47)-CH1-CH2-CH3+VL (anti-CD47)-CL (W) VH (anti-BCMA/TACI)-CL-CH2-CH3+VL (anti-BCMA/TACI)-CH1+VH (anti-CD47)-CL-CH2-CH3+VL (anti-CD47)-CH1

(X) VL (anti-BCMA/TACI)-CH1-CH2-CH3+VH (anti-BCMA/TACI)-CL+VL (anti-CD47)-CH1-CH2-CH3+VH (anti-CD47)-CL (Y) VL (anti-BCMA/TACI)-CL-CH2-CH3+VH (anti-BCMA/TACI)-CH1+VL (anti-CD47)-CL-CH2-CH3+VH (anti-CD47)-CH1

(Z) VH (anti-BCMA/TACI)-CH1-CH2-CH3+VL (anti-BCMA/TACI)-CL-CH2-CH3+VH (anti-CD47)-CH1-CH2-CH3+VL (anti-CD47)-CL-CH2-CH3

(AA) VH (anti-BCMA/TACI)-CL-CH2-CH3+VL (anti-BCMA/TACI)-CH1-CH2-CH3+VH (anti-CD47)-CL-CH2-CH3+VL (anti-CD47)-CH1-CH2-CH3

Wherein: 'VH (anti-BCMA/TACI)' refers to the VH of an antigen-binding molecule capable of binding to BCMA/TACI as described herein, e.g. as defined in one of (1) to (105); 'VL (anti-BCMA/TACI)' refers to the VL of an antigen-binding molecule capable of binding to BCMA/TACI as described herein, e.g. as defined in one of (106) to (209); 'VH (anti-CD47)' refers to the VH of an antigen-binding molecule capable of binding to CD47 as described herein, e.g. as defined in one of (210) to (238); and 'VL (anti-CD47)' refers to the VL of an antigen-binding molecule capable of binding to CD47 as described herein, e.g. as defined in one of (239) to (265).

In some embodiments, the antigen-binding molecule of the present disclosure comprises a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:490, 455, 465, 471, 477, 479, 136, 52, 22, 38, 67, 83, 98, 122, 112, 127, 338, 346, 353, 361, 367, 372, 380 or 387.

In some embodiments, the antigen-binding molecule of the present disclosure comprises a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:497, 459, 463, 468, 474, 478, 483, 487, 60, 30, 44, 75, 90, 105, 124, 118, 133, 341, 349, 357, 365, 370, 376, 383 or 391.

In some embodiments, the antigen-binding molecule of the present disclosure comprises a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:504, 507, 509, 511, 513, 516, 304, 302, 306, 308, 310, 312, 314, 316, 318, 424, 426, 428, 430, 432, 434, 436 or 438.

In some embodiments, the antigen-binding molecule of the present disclosure comprises a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:505, 506, 508, 510, 512, 514, 515, 305, 303, 307, 309, 311, 313, 315, 317, 319, 425, 427, 429, 431, 433, 435, 437 or 439.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:22, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:30.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:52, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:60.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:38, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:44.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:67, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:75.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:83, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:90.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:98, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:105.

In some embodiments, the antigen-binding molecule of the present disclosure comprises: (i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:122, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:124.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:112, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:118.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:127, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:133.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:338, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:341.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:346, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:349.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:353, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:357.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:361, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:365.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:367, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:370.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:372, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:376.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:380, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:383.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:387, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:391.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:490, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:497.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:455, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:459.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:455, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:463.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:465, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:468.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:471, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:474.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:477, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:478.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:479, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:483.

In some embodiments, the antigen-binding molecule of the present disclosure comprises:

(i) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:479, and (ii) a polypeptide which comprises or consists of an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:487.

It will be appreciated that in some embodiments, an antigen-binding molecule may comprise a polypeptide comprising polypeptides according to (i) and (ii) defined in accordance with the preceding paragraphs. For example, in embodiments wherein the antigen-binding molecule comprises or consists of a single-chain Fv, polypeptides according to (i) and (ii) may be provided in tandem in the same polypeptide, e.g. joined by a linker sequence.

Linkers and Additional Sequences

In some embodiments, the antigen-binding molecules and polypeptides of the present disclosure comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments, the linker sequence consists of glycine and serine residues. In some embodiments, the linker sequence comprises one or more copies (e.g. in tandem) of the sequence motif G4S. In some embodiments, the linker sequence has a length of 1-2, 1-3, 1-4, 1-5, 1-10, 1-15, 1-20, 1-25, or 1-30 amino acids.

The antigen-binding molecules and polypeptides of the present disclosure may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His), Myc, GST, MBP, FLAG, HA, E, or Biotin tag, optionally at the N- or C-terminus of the antigen-binding molecule/polypeptide. In some embodiments, the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present disclosure may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Labels and Conjugates

In some embodiments, the antigen-binding molecules of the present disclosure additionally comprise a detectable moiety.

In some embodiments, the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, and Cy5. Radiolabels include radioisotopes such as $Iodine^{123}$, $Iodine^{125}$, $Iodine^{126}$, $Iodine^{131}$, $Iodine^{133}$, $Bromine^{77}$, $Technetium^{99m}$, $Indium^{111}$, $Indium^{113m}$, $Gallium^{67}$, $Gallium^{68}$, $Ruthenium^{95}$, $Ruthenium^{97}$, $Ruthenium^{103}$, $Ruthenium^{105}$, $Mercury^{207}$, $Mercury^{203}$, $Rhenium^{99m}$, $Rhenium^{101}$, $Rhenium^{105}$, $Scandium^{47}$, $Tellurium^{121m}$, $Tellurium^{122m}$, $Tellurium^{125m}$, $Thulium^{165}$, $Thulium^{167}$, $Thulium^{168}$, $Copper^{67}$, $Fluorine^{18}$, $Yttrium^{90}$, $Palladium^{100}$, $Bismuth^{217}$ and $Antimony^{211}$. Luminescent labels include as radioluminescent, chemiluminescent (e.g. acridinium ester, luminol, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments, the antigen-binding molecules of the present disclosure are conjugated to a chemical moiety. The chemical moiety may be a moiety for providing a therapeutic effect. Antibody-drug conjugates are reviewed e.g. in Parslow et al., Biomedicines. 2016 September; 4(3): 14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Functional Properties of the Antigen-Binding Molecules

The antigen-binding molecules described herein may be characterised by reference to certain functional properties. In some embodiments, the antigen-binding molecule described herein may possess one or more of the following properties:

binds to BCMA (e.g. human BCMA, cynomolgus macaque BCMA and/or mouse BCMA);

binds to TACI (e.g. human TACI, cynomolgus macaque TACI and/or mouse TACI);

cross-reactivity for BCMA (e.g. human BCMA, cynomolgus macaque BCMA and/or mouse BCMA) and TACI (e.g. human TACI, cynomolgus macaque TACI and/or mouse TACI);

binds to BCMA in the presence or absence of a ligand for BCMA (e.g. APRIL/BAFF);

binds to a polypeptide complex of BCMA and a ligand for BCMA (e.g. APRIL/BAFF);

inhibits interaction between BCMA and a ligand for BCMA (e.g. APRIL/BAFF);

binds to BCMA-expressing cells;

binds to TACI-expressing cells;

inhibits BCMA-mediated signalling;

increases phagocytosis of BCMA-expressing cells by phagocytic cells (e.g. macrophages);

increases phagocytosis of BCMA/TACI-expressing cells by phagocytic cells (e.g. macrophages);

increases ADCC of BCMA-expressing cells;

increases ADCC of BCMA/TACI-expressing cells;

increases T cell-mediated cytolysis of BCMA-expressing cells;

increases T cell-mediated cytolysis of BCMA/TACI-expressing cells;

binds to CD47 (e.g. human CD47, cynomolgus macaque CD47 and/or mouse CD47);

inhibits interaction between CD47 and a ligand for CD47 (e.g. SIRPα);

binds to CD47-expressing cells;

inhibits SIRPα-mediated signalling;

increases phagocytosis of CD47-expressing cells by phagocytic cells (e.g. macrophages);

increases ADCC of CD47-expressing cells;

binds to BCMA and CD47 (simultaneously);

binds to BCMA/TACI and CD47 (simultaneously);

binds to cells expressing BCMA and CD47;

binds to cells expressing BCMA/TACI and CD47;

binds preferentially to cells expressing BCMA and CD47 over cells expressing BCMA and not expressing CD47, or cells expressing CD47 and not expressing BCMA;

binds preferentially to cells expressing BCMA/TACI and CD47 over cells expressing BCMA/TACI and not expressing CD47, or cells expressing CD47 and not expressing BCMA/TACI;

increases phagocytosis of cells expressing BCMA and CD47 by phagocytic cells (e.g. macrophages);

increases phagocytosis of cells expressing BCMA/TACI and CD47 by phagocytic cells (e.g. macrophages);

increases ADCC of cells expressing BCMA and CD47;

increases ADCC of cells expressing BCMA/TACI and CD47;

increases the number/proportion of cancer antigen-specific immune cells;

does not cause substantial hemagglutination;

causes less hemagglutination as compared to a reference anti-CD47 antibody;

increases killing of cancer cells;

inhibits the development/progression of a cancer.

It will be appreciated that a given antigen-binding molecule may display more than one of the properties recited in the preceding paragraph. A given antigen-binding molecule may be evaluated for the properties recited in the preceding paragraph using suitable assays. For example, the assays may be e.g. in vitro assays, optionally cell-based assays or cell-free assays. In some embodiments, the assays may be e.g. in vivo assays, i.e. performed in non-human animals. In some embodiments, the assays may be e.g. ex vivo assays, i.e. performed using cells/tissue/an organ obtains from a subject.

Where assays are cell-based assays, they may comprise treating cells with a given antigen-binding molecule in order to determine whether the antigen-binding molecule displays one or more of the recited properties. Assays may employ species labelled with detectable entities in order to facilitate their detection. Assays may comprise evaluating the recited properties following treatment of cells separately with a range of quantities/concentrations of a given antigen-binding molecule (e.g. a dilution series). It will be appreciated that the cells preferably express the target antigen for the antigen-binding molecule (e.g. BCMA/TACI).

Analysis of the results of such assays may comprise determining the concentration at which 50% of the maximal level of the relevant activity is attained. The concentration of a given agent at which 50% of the maximal level of the relevant activity is attained may be referred to as the 'half-maximal effective concentration' of the agent in relation to the relevant activity, which may also be referred to as the 'EC$_{50}$'. By way of illustration, the EC$_{50}$ of a given antigen-binding molecule for binding to human BCMA may be the concentration of the antigen-binding molecule at which 50% of the maximal level of binding to human BCMA is achieved.

Depending on the property, the EC$_{50}$ may also be referred to as the 'half-maximal inhibitory concentration' or 'IC$_{50}$', this being the concentration of the agent at which 50% of the maximal level of inhibition of a given property is observed. By way of illustration, the IC$_{50}$ of a given antigen-binding molecule for reducing interaction between BCMA and APRIL may be the concentration of the antigen-binding molecule at which 50% of the maximal level of inhibition of interaction between BCMA and APRIL is achieved.

The antigen-binding molecules described herein bind to BCMA/TACI and/or CD47. The antigen-binding molecules and antigen-binding domains described herein preferably display specific binding to the relevant target antigen(s) (e.g. BCMA/TACI, CD47). As used herein, 'specific binding' refers to binding which is selective for the antigen, and which can be discriminated from non-specific binding to non-target antigen. An antigen-binding molecule/domain that specifically binds to a target molecule preferably binds the target with greater affinity, and/or with greater duration than it binds to other, non-target molecules.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to a non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds with a dissociation constant (KD) that is at least 0.1 order of magnitude (i.e. $0.1 \times 10^n$, where n is an integer representing the order of magnitude) greater than the KD of the antigen-binding molecule towards a non-target molecule. This may optionally be one of at least 0.2, 0.3, 0.4, 0.5, 0.6, 0.7, 0.8, 0.9, 1.0, 1.5, or 2.0.

The affinity of binding to a given target antigen for an antigen-binding molecule described herein may be determined by Bio-Layer Interferometry, e.g. as described in the Examples of the present disclosure.

In some embodiments, the antigen-binding molecule described herein binds to BCMA with an affinity in the micromolar range, i.e. $K_D=9.9\times10^{-4}$ to $1\times10^{-6}$ M. In some embodiments, the antigen-binding molecule described herein binds to BCMA with sub-micromolar affinity, i.e. $K_D<1\times10^{-6}$ M. In some embodiments, the antigen-binding molecule described herein binds to BCMA with an affinity in the nanomolar range, i.e. $K_D=9.9\times10^{-1}$ to $1\times10^{-9}$ M. In some embodiments, the antigen-binding molecule described herein binds to BCMA with sub-nanomolar affinity, i.e. $K_D<1\times10^{-9}$ M. In some embodiments, the antigen-binding molecule described herein binds to BCMA with an affinity in the picomolar range, i.e. $K_D=9.9\times10^{-10}$ to $1\times10^{-12}$ M. In some embodiments, the antigen-binding molecule described herein binds to BCMA with sub-picomolar affinity, i.e. $K_D<1\times10^{-12}$ M.

In some embodiments, the antigen-binding molecule described herein binds to BCMA with a $K_D$ of 10 μM or less, preferably one of ≤5 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM, ≤400 pM, ≤300 pM, ≤200 pM, ≤100 pM, ≤50 pM, ≤40 pM, ≤30 pM, ≤20 pM, ≤10 pM or ≤1 pM (e.g. as determined by analysis as described in Example 3.4).

In some embodiments, the antigen-binding molecule described herein binds to TACI with an affinity in the micromolar range, i.e. $K_D=9.9\times10^{-4}$ to $1\times10^{-6}$ M. In some embodiments, the antigen-binding molecule described herein binds to TACI with sub-micromolar affinity, i.e. $K_D<1\times10^{-6}$ M. In some embodiments, the antigen-binding molecule described herein binds to TACI with an affinity in the nanomolar range, i.e. $K_D=9.9\times10^{-1}$ to $1\times10^{-9}$ M. In some embodiments, the antigen-binding molecule described herein binds to TACI with sub-nanomolar affinity, i.e. $K_D<1\times10^{-9}$ M. In some embodiments, the antigen-binding molecule described herein binds to TACI with an affinity in the picomolar range, i.e. $K_D=9.9\times10^{-10}$ to $1\times10^{-12}$ M. In some embodiments, the antigen-binding molecule described herein binds to TACI with sub-picomolar affinity, i.e. $K_D<1\times10^{-12}$ M.

In some embodiments, the antigen-binding molecule described herein binds to CD47 with an affinity in the micromolar range, i.e. $K_D=9.9\times10^{-4}$ to $1\times10^{-6}$ M. In some embodiments, the antigen-binding molecule described herein binds to CD47 with sub-micromolar affinity, i.e. $K_D<1\times10^{-6}$ M. In some embodiments, the antigen-binding molecule described herein binds to CD47 with an affinity in the nanomolar range, i.e. $K_D=9.9\times10^{-1}$ $1\times10^{-9}$ M. In some embodiments, the antigen-binding molecule described herein binds to CD47 with sub-nanomolar affinity, i.e. $K_D<1\times10^{-9}$ M. In some embodiments, the antigen-binding molecule described herein binds to CD47 with an affinity in the picomolar range, i.e. $K_D=9.9\times10^{-10}$ to $1\times10^{-12}$ M. In some embodiments, the antigen-binding molecule described herein binds to CD47 with sub-picomolar affinity, i.e. $K_D<1\times10^{-12}$ M.

In some embodiments, the antigen-binding molecule described herein binds to CD47 with a $K_D$ of 10 μM or less, preferably one of ≤5 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM or ≤500 pM. In some embodiments, the antigen-binding molecule binds to CD47 with an affinity of $K_D=$ ≤10 nM, ≤9 nM, ≤8 nM, ≤7 nM or ≤6 nM (e.g. as determined by analysis as described in Example 6.2 of WO 2019/086573 A1).

In some embodiments, the antigen-binding molecule described herein binds to human BCMA with a $K_D$ of 100 nM or less, preferably one of ≤75 nM, ≤50 nM, ≤25 nM, ≤10 nM, ≤5 nM, ≤4 nM, ≤3 nM, ≤2 nM, nM, ≤1 nM, ≤900 pM, ≤800 pM, ≤700 pM, ≤600 pM or ≤500 pM (e.g. as determined by analysis as described in Example 13.2).

In some embodiments, the antigen-binding molecule described herein binds to cynomolgous macaque BCMA with a $K_D$ of 100 nM or less, preferably one of ≤75 nM, ≤50 nM, ≤40 nM, ≤30 nM, ≤25 nM, ≤20 nM, ≤15 nM, ≤10 nM, ≤5 nM, ≤2 nM, ≤1.5 nM or ≤1 nM (e.g. as determined by analysis as described in Example 13.2).

In some embodiments, the antigen-binding molecule described herein binds to human TACI with a $K_D$ of 1.5 mM or less, preferably one of ≤1 mM, ≤500 μM, ≤1 μM, ≤900 nM, ≤800 nM, ≤700 nM, ≤600 nM, ≤500 nM, ≤400 nM, ≤300 nM, ≤200 nM, ≤100 nM, ≤50 nM, ≤40 nM, ≤30 nM, ≤25 nM, ≤20 nM, ≤15 nM, ≤10 nM, ≤5 nM, ≤2 nM, ≤1.5 nM or ≤1 nM (e.g. as determined by analysis as described in Example 13.2).

In some embodiments, the antigen-binding molecule described herein binds to human BCMA with an $EC_{50}$ of 1 nM or less, preferably one of ≤500 pM, ≤400 pM, ≤300 pM, ≤200 pM, ≤100 pM, ≤90 pM, ≤80 pM, ≤70 pM, ≤60 pM, ≤50 pM, ≤40 pM, ≤30 pM, ≤20 pM or ≤10 pM (e.g. as determined by analysis as described in Example 13.2).

In some embodiments, the antigen-binding molecule described herein binds to cynomolgous macaque BCMA with an $EC_{50}$ of 1 nM or less, preferably one of ≤500 pM, ≤400 pM, ≤300 pM, ≤200 pM, ≤100 pM, ≤90 pM, ≤80 pM, ≤70 pM, ≤60 pM, ≤50 pM, ≤40 pM, ≤30 pM, ≤20 pM or ≤10 pM (e.g. as determined by analysis as described in Example 13.2).

In some embodiments, the antigen-binding molecule described herein binds to human TACI with an $EC_{50}$ of 5 nM or less, preferably one of ≤2 nM, ≤1.5 nM, ≤1 nM, ≤900 pM, ≤800 pM, ≤700 pM, ≤600 pM, ≤500 pM, ≤400 pM, ≤300 pM, ≤200 pM, ≤100 pM, ≤90 pM, ≤80 pM, ≤70 pM, ≤60 pM, ≤50 pM, ≤40 pM, ≤30 pM, ≤20 pM or ≤10 pM (e.g. as determined by analysis as described in Example 13.2).

In some embodiments, the antigen-binding molecule described herein binds to cynomolgous macaque TACI with an $EC_{50}$ of 1 nM or less, preferably one of ≤500 pM, ≤400 pM, ≤300 pM, ≤200 pM, ≤100 pM, ≤90 pM, ≤80 pM, ≤70 pM, ≤60 pM, ≤50 pM, ≤40 pM, ≤30 pM, ≤20 pM or ≤10 pM (e.g. as determined by analysis as described in Example 13.2).

In some embodiments, the antigen-binding molecules are cross-reactive for one or more homologues of the target antigen (i.e. BCMA/TACI, CD47). In some embodiments, the antigen-binding molecules are cross-reactive for BCMA and TACT. As used herein, a 'cross-reactive' antigen-binding molecule/domain/polypeptide binds to the target antigens for which the antigen-binding molecule/domain is cross-reactive. For example, an antigen-binding molecule/domain/polypeptide which is cross-reactive for human BCMA and mouse BCMA binds to human BCMA, and is also capable of binding to mouse BCMA. Similarly, an antigen-binding molecule/domain/polypeptide which is cross-reactive for BCMA and TACI binds to BCMA, and is also capable of binding to TACT. Cross-reactive antigen-binding molecules/domains/polypeptides may display specific binding to each of the target antigens.

In some embodiments, the antigen-binding molecule binds to human BCMA, cynomolgous macaque BCMA and mouse BCMA. In some embodiments, the antigen-binding molecule binds to human BCMA and cynomolgous macaque BCMA. In some embodiments, the antigen-binding molecule binds to human CD47, cynomolgous macaque CD47 and mouse CD47. In some embodiments, the antigen-binding molecule binds to human CD47 and cynomolgous macaque CD47. In some embodiments, the antigen-binding molecule binds to human TACT, cynomolgous macaque TACI and mouse TACT. In some embodiments, the antigen-binding molecule binds to human TACI and cynomolgous macaque TACT.

In some embodiments, the antigen-binding molecule binds to BCMA (e.g. human BCMA) and TACI (e.g. human TACI).

In some embodiments, the antigen-binding molecule of the present disclosure binds to BCMA and CD47. In some embodiments, the antigen-binding molecule binds simultaneously to BCMA and CD47. In some embodiments, the antigen-binding molecule of the present disclosure binds to BCMA/TACI and CD47. In some embodiments, the antigen-binding molecule binds simultaneously to BCMA/TACI and CD47.

The antigen-binding molecules of the present disclosure may bind to a particular region of interest of the target antigen(s). The antigen-binding region of an antigen-binding molecule according to the present disclosure may bind to linear epitope of a target antigen (e.g. BCMA/TACI, CD47), consisting of a contiguous sequence of amino acids (i.e. an amino acid primary sequence). In some embodiments, the antigen-binding region of an antigen-binding molecule may bind to a conformational epitope of a target antigen, consisting of a discontinuous sequence of amino acids of the amino acid sequence.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety. In preferred embodiments, the region of a peptide/polypeptide to which an antibody binds is determined by hydrogen-deuterium exchange analysis by mass spectrometry, performed essentially as described in Example 14 herein.

In some embodiments, the antigen-binding molecule of the present disclosure binds to the extracellular domain of BCMA. In some embodiments, the antigen-binding molecule binds to the region of BCMA shown in SEQ ID NO:3. In some embodiments, the antigen-binding molecule binds to a polypeptide comprising or consisting of the amino acid sequence shown in SEQ ID NO:3. In some embodiments, the antigen-binding molecule binds to the region of BCMA shown in SEQ ID NO:448. In some embodiments, the antigen-binding molecule contacts the region of BCMA shown in SEQ ID NO:448. In some embodiments, the antigen-binding molecule binds to BCMA via contact with one or more amino acids of the region shown in SEQ ID NO:448. In some embodiments, the epitope of the antigen-binding molecule comprises or consists of the amino acid sequence shown in SEQ ID NO:448. In some embodiments, the antigen-binding molecule binds to a polypeptide comprising or consisting of the amino acid sequence shown in SEQ ID NO:448.

In some embodiments, the antigen-binding molecule binds to the region of BCMA shown in SEQ ID NO:554. In some embodiments, the antigen-binding molecule contacts the region of BCMA shown in SEQ ID NO:554. In some embodiments, the antigen-binding molecule binds to BCMA via contact with one or more amino acids of the region shown in SEQ ID NO:554. In some embodiments, the epitope of the antigen-binding molecule comprises or consists of the amino acid sequence shown in SEQ ID NO:554. In some embodiments, the antigen-binding molecule binds to a polypeptide comprising or consisting of the amino acid sequence shown in SEQ ID NO:554.

In some embodiments, the antigen-binding molecule binds to the region of BCMA shown in SEQ ID NO:555. In some embodiments, the antigen-binding molecule contacts the region of BCMA shown in SEQ ID NO:555. In some embodiments, the antigen-binding molecule binds to BCMA via contact with one or more amino acids of the region shown in SEQ ID NO:555. In some embodiments, the epitope of the antigen-binding molecule comprises or consists of the amino acid sequence shown in SEQ ID NO:555. In some embodiments, the antigen-binding molecule binds to a polypeptide comprising or consisting of the amino acid sequence shown in SEQ ID NO:555.

In some embodiments, the antigen-binding molecule binds to the region of BCMA shown in SEQ ID NO:556. In some embodiments, the antigen-binding molecule contacts the region of BCMA shown in SEQ ID NO:556. In some embodiments, the antigen-binding molecule binds to BCMA via contact with one or more amino acids of the region shown in SEQ ID NO:556. In some embodiments, the epitope of the antigen-binding molecule comprises or consists of the amino acid sequence shown in SEQ ID NO:556. In some embodiments, the antigen-binding molecule binds to a polypeptide comprising or consisting of the amino acid sequence shown in SEQ ID NO:556.

In some embodiments, the antigen-binding molecule binds to the region of BCMA shown in SEQ ID NO:55. In some embodiments, the antigen-binding molecule contacts the region of BCMA shown in SEQ ID NO:557. In some embodiments, the antigen-binding molecule binds to BCMA via contact with one or more amino acids of the region shown in SEQ ID NO:557. In some embodiments, the epitope of the antigen-binding molecule comprises or consists of the amino acid sequence shown in SEQ ID NO:557. In some embodiments, the antigen-binding molecule binds to a polypeptide comprising or consisting of the amino acid sequence shown in SEQ ID NO:557.

In some embodiments, the antigen-binding molecule binds to the region of BCMA shown in SEQ ID NO:558. In some embodiments, the antigen-binding molecule contacts the region of BCMA shown in SEQ ID NO:558. In some embodiments, the antigen-binding molecule binds to BCMA via contact with one or more amino acids of the region shown in SEQ ID NO:558. In some embodiments, the epitope of the antigen-binding molecule comprises or consists of the amino acid sequence shown in SEQ ID NO:558. In some embodiments, the antigen-binding molecule binds to a polypeptide comprising or consisting of the amino acid sequence shown in SEQ ID NO:558.

In some embodiments, the antigen-binding molecule of the present disclosure binds to the extracellular domain of TACT. In some embodiments, the antigen-binding molecule binds to the region of TACI shown in SEQ ID NO:333. In some embodiments, the antigen-binding molecule binds to a polypeptide comprising or consisting of the amino acid sequence shown in SEQ ID NO:333. In some embodiments, the antigen-binding molecule binds to the region of TACI shown in SEQ ID NO:449. In some embodiments, the antigen-binding molecule contacts the region of TACI shown in SEQ ID NO:449. In some embodiments, the antigen-binding molecule binds to TACI via contact with one or more amino acids of the region shown in SEQ ID NO:449. In some embodiments, the epitope of the antigen-binding molecule comprises or consists of the amino acid sequence shown in SEQ ID NO:449. In some embodiments, the antigen-binding molecule binds to a polypeptide comprising or consisting of the amino acid sequence shown in SEQ ID NO:449.

In some embodiments, the antigen-binding molecule binds to the polypeptide consisting of the amino acid sequence shown in SEQ ID NO:1 with greater affinity than the affinity with which the antigen-binding molecule binds to the polypeptide consisting of the amino acid sequence shown in SEQ ID NO:450. In some embodiments, the level of binding of the antigen-binding molecule to the polypeptide consisting of the amino acid sequence shown in SEQ ID NO:450 is less than 50% of the level of binding to the polypeptide consisting of the amino acid sequence shown in SEQ ID NO:1. In some embodiments, the antigen-binding molecule displays substantially no binding to the polypeptide consisting of the amino acid sequence shown in SEQ ID NO:450.

In some embodiments, the antigen-binding molecule binds to the polypeptide consisting of the amino acid sequence shown in SEQ ID NO:330 with greater affinity than the affinity with which the antigen-binding molecule binds to the polypeptide consisting of the amino acid sequence shown in SEQ ID NO:451. In some embodiments, the level of binding of the antigen-binding molecule to the polypeptide consisting of the amino acid sequence shown in SEQ ID NO:451 is less than 50% of the level of binding to the polypeptide consisting of the amino acid sequence shown in SEQ ID NO:330.

In some embodiments, the antigen-binding molecule of the present disclosure binds to an epitope of BCMA which is non-identical to the epitope of BCMA bound by an antibody disclosed in WO 2002/066516 A2 (hereby incorporated by reference in its entirety). In some embodiments, the antigen-binding molecule binds to an epitope of TACI which is non-identical to the epitope of TACI bound by an antibody disclosed in WO 2002/066516 A2.

In some embodiments, the antigen-binding molecule binds to an epitope of BCMA which is non-identical to the epitope of BCMA bound by the antibody clone 255.7 disclosed in WO 2002/066516 A2. In some embodiments, the antigen-binding molecule binds to an epitope of TACI which is non-identical to the epitope of TACI bound by the antibody clone 255.7 disclosed in WO 2002/066516 A2. In some embodiments, the antigen-binding molecule binds to an epitope of BCMA which is non-identical to the epitope of BCMA bound by the antibody clone 255.4 disclosed in WO 2002/066516 A2. In some embodiments, the antigen-binding molecule binds to an epitope of TACI which is non-identical to the epitope of TACI bound by the antibody clone 248.24 disclosed in WO 2002/066516 A2. In some embodiments, the antigen-binding molecule binds to an epitope of TACI which is non-identical to the epitope of TACI bound by the antibody clone 251.10 disclosed in WO 2002/066516 A2. In some embodiments, the antigen-binding molecule binds to an epitope of TACI which is non-identical to the epitope of TACI bound by the antibody clone 250.13 disclosed in WO 2002/066516 A2.

The ability of an antigen-binding molecule to bind to a given peptide/polypeptide can be analysed by methods well known to the skilled person, including analysis by ELISA, immunoblot (e.g. western blot), immunoprecipitation, surface plasmon resonance and biolayer interferometry.

In some embodiments, the antigen-binding molecule of the present disclosure binds to BCMA in a region which is accessible to an antigen-binding molecule (i.e., an extracellular antigen-binding molecule) when BCMA is expressed at the cell surface (i.e. in or at the cell membrane). In some embodiments, the antigen-binding molecule binds to BCMA expressed at the cell surface of a cell expressing BCMA. In some embodiments, the antigen-binding molecule binds to BCMA-expressing cells (e.g. plasma B cells, multiple myeloma cells (e.g. U-266/70 cells, U-266/84 cells, RPMI-8226 cells, MM.1S cells, NCI-H929 cells or Karpas-707 cells), Burkitt lymphoma cells (e.g. Daudi cells, BL36 cells or Raji cells) or lymphocytic leukemia cells (e.g. REH cells)).

In some embodiments, the antigen-binding molecule of the present disclosure binds to TACI in a region which is accessible to an antigen-binding molecule (i.e., an extracellular antigen-binding molecule) when TACI is expressed at the cell surface (i.e. in or at the cell membrane). In some embodiments, the antigen-binding molecule binds to TACI expressed at the cell surface of a cell expressing TACT. In some embodiments, the antigen-binding molecule binds to TACI-expressing cells (e.g. plasma B cells, multiple myeloma cells (e.g. U-266/70 cells, U-266/84 cells, RPMI-8226 cells, MM.1 S cells, NCI-H929 cells), Burkitt lymphoma cells (e.g. Raji cells) or lymphocytic leukemia cells (e.g. REH cells)).

In some embodiments, the antigen-binding molecule of the present disclosure binds to CD47 in a region which is accessible to an antigen-binding molecule (i.e., an extracellular antigen-binding molecule) when CD47 is expressed at the cell surface (i.e. in or at the cell membrane). In some embodiments, the antigen-binding molecule binds to CD47 expressed at the cell surface of a cell expressing CD47. In some embodiments, the antigen-binding molecule binds to CD47-expressing cells (e.g. myeloid cells, myeloid leukemia cells, HL-60 cells, HMC-1 cells, HEL cells or Raji cells).

The ability of an antigen-binding molecule to bind to a given cell type can be analysed by contacting cells with the antigen-binding molecule, and detecting antigen-binding molecule bound to the cells, e.g. after a washing step to remove unbound antigen-binding molecule. The ability of an antigen-binding molecule to bind to immune cell surface molecule-expressing cells and/or cancer cell antigen-expressing cells can be analysed by methods such as flow cytometry and immunofluorescence microscopy.

In some embodiments, the antigen-binding molecule described herein binds to cells expressing BCMA and cells expressing CD47. In some embodiments, the antigen-binding molecule is capable of simultaneously binding to cells expressing BCMA and cells expressing CD47. In some embodiments, the antigen-binding molecule binds to BCMA and CD47 expressed by the same cell. In some embodiments, the antigen-binding molecule binds to BCMA and CD47 expressed by different cells. In some embodiments, the antigen-binding molecule described herein binds to cells expressing BCMA/TACI and cells expressing CD47. In some embodiments, the antigen-binding molecule is capable of simultaneously binding to cells expressing BCMA/TACI and cells expressing CD47. In some embodiments, the antigen-binding molecule binds to BCMA/TACI and CD47 expressed by the same cell. In some embodiments, the antigen-binding molecule binds to BCMA/TACI and CD47 expressed by different cells.

In some embodiments, the antigen-binding molecule preferentially binds to cells expressing BCMA and CD47 (i.e. CD47+BCMA+ cells, e.g. multiple myeloma cells, Raji cells) over cells expressing CD47 and not expressing BCMA (i.e. CD47+BCMA− cells, e.g. HEK293T cells), and/or cells expressing BCMA and not expressing CD47 (i.e. CD47−BCMA+ cells). The ability of an antigen-binding molecule to preferentially bind to CD47+BCMA+ cells over CD47+ BCMA− cells and/or CD47-BCMA+ cells can be determined by analysis of binding of the antigen-binding molecule to CD47+BCMA+ cells and CD47+BCMA− cells and/or CD47−BCMA+ cells, e.g. by flow cytometry. An antigen-binding molecule which preferentially binds to CD47+BCMA+ cells over CD47+BCMA− cells and/or CD47−BCMA+ can be determined by detection of an increased level of staining of CD47+BCMA+ cells by the antigen-binding molecule as compared to the level of staining of CD47+BCMA− cells and/or CD47−BCMA+ cells by the antigen-binding molecule. In some embodiments, the antigen-binding molecule preferentially binds to cells expressing BCMA/TACI and CD47 (i.e. CD47+BCMA/ TACI+ cells, e.g. multiple myeloma cells, Raji cells) over cells expressing CD47 and not expressing BCMA/TACI (i.e. CD47+BCMA/TACI− cells, e.g. HEK293T cells), and/or cells expressing BCMA/TACI and not expressing CD47 (i.e. CD47−BCMA/TACI+ cells). The ability of an antigen-binding molecule to preferentially bind to CD47+BCMA/ TACI+ cells over CD47+BCMA/TACI− cells and/or CD47− BCMA/TACI+ cells can be determined by analysis of binding of the antigen-binding molecule to CD47+BCMA/ TACI+ cells and CD47+BCMA/TACI− cells and/or CD47− BCMA/TACI+ cells, e.g. by flow cytometry. An antigen-binding molecule which preferentially binds to CD47+ BCMA/TACT+ cells over CD47+BCMA/TACI− cells and/ or CD47−BCMA/TACI+ can be determined by detection of an increased level of staining of CD47+BCMA/TACI+ cells by the antigen-binding molecule as compared to the level of staining of CD47+BCMA/TACI− cells and/or CD47− BCMA/TACI+ cells by the antigen-binding molecule.

In some embodiments, the antigen-binding molecule described herein binds to cells expressing human BCMA with an $EC_{50}$ of 10 nM or less, preferably one of ≤5 nM, ≤4 nM, ≤3 nM, ≤2 nM, ≤1 nM, ≤900 pM, ≤800 pM, ≤700 pM, ≤600 pM or ≤500 pM (e.g. as determined by analysis as described in Example 3.2).

In some embodiments, the antigen-binding molecule described herein binds to H929 cells with an $EC_{50}$ of 0.5 nM or less, preferably one of ≤200 pM, ≤150 pM, ≤140 pM, ≤130 pM, ≤120 pM, ≤110 pM, ≤100 pM, ≤90 pM, ≤80 pM, ≤70 pM, ≤60 pM or ≤50 pM (e.g. as determined by analysis as described in Example 13.2).

In some embodiments, the antigen-binding molecule described herein binds to RPMI-8226 cells with an $EC_{50}$ of 0.5 nM or less, preferably one of ≤200 pM, ≤150 pM, ≤140 pM, ≤130 pM, ≤120 pM, ≤110 pM, ≤100 pM, ≤90 pM, ≤80 pM, ≤70 pM, ≤60 pM or ≤50 pM (e.g. as determined by analysis as described in Example 13.2).

In some embodiments, the antigen-binding molecule is capable of binding the same region of BCMA, or an overlapping region of BCMA, to the region of BCMA which is bound by an antibody comprising the VH and VL regions of one of clones 538-SP5-B10, 539-SP2-H3, 539-SP1-C8, 539-SP5-D7, 539-SP7-F4, 552-LN1-E9, 552-LN2-E6, 552-LN1-F4, 552-LN2-F8, 1E9-4H, 1E9-QE, 2F8-2Q, 2F8-5U, 5610-4Y, 5B10 5I, 1C8-6A, 1C8-EH, 1C8-402, 1C8-403, 1C8-507, 1C8-610, 1C8-6A3, 1C8-25 and 1C8-27. In some embodiments, the antigen-binding molecule is capable of binding the same region of TACI, or an overlapping region of TACI, to the region of TACI which is bound by an antibody comprising the VH and VL regions of a TACI-binding clone described herein.

Whether a test antigen-binding molecule binds to the same or an overlapping region of a given target as a reference antigen-binding molecule can be evaluated, for example, by analysis of (i) interaction between the test antigen-binding molecule and the target in the absence of the reference binding molecule, and (ii) interaction between the test antigen-binding molecule in the presence of the reference antigen-binding molecule, or following incubation of the target with the reference antigen-binding molecule. Determination of a reduced level of interaction between the test antigen-binding molecule and the target following analysis according to (ii) as compared to (i) might support an inference that the test and reference antigen-binding molecule bind to the same or an overlapping region of the target. Suitable assays for such analysis include e.g. competition ELISA assays and epitope binning assays.

In some embodiments, the antigen-binding molecule of the present disclosure binds to the extracellular domain of CD47. In some embodiments, the antigen-binding molecule binds to CD47 in extracellular region 1 of CD47 (i.e. the region shown in SEQ ID NO:180). In some embodiments, the antigen-binding molecule binds to the V-type Ig-like domain of CD47 (i.e. the region shown in SEQ ID NO:179). In some embodiments, the antigen-binding molecule binds to a polypeptide comprising or consisting of the amino acid sequence shown in SEQ ID NO:180. In some embodiments, the antigen-binding molecule binds to a polypeptide comprising or consisting of the amino acid sequence shown in SEQ ID NO:179.

In some embodiments, the antigen-binding molecule is capable of binding the same region of CD47, or an overlapping region of CD47, to the region of CD47 which is bound by an antibody comprising a the VH and VL regions of a CD47-binding antibody clone described in WO 2019/086573 A1. In some embodiments, the antigen-binding molecule is capable of binding the same region of CD47, or an overlapping region of CD47, to the region of CD47 which is bound by an antibody comprising the VH and VL regions of a CD47-binding antibody clone selected from: 1-1-A1_BM, 1-1-A1, 11A1H1, 11A1H2, 11A1H3, 11A1H4, 11A1H5, 11A1H6, 11A1H7, 11A1H8, 11A1H9, 11A1H10 or 11A1H11. In some embodiments, the antigen-binding molecule binds to the region of CD47 shown in SEQ ID NO:191. In some embodiments, the antigen-binding molecule binds to a peptide or polypeptide comprising or consisting of the amino acid sequence shown in SEQ ID NO:191.

In some embodiments, the antigen-binding molecule binds to BCMA/TACI in the region which is not bound by a ligand for BCMA/TACI (e.g. APRIL or BAFF). In some embodiments, the antigen-binding molecule does not inhibit interaction between a ligand for BCMA/TACI (e.g. APRIL or BAFF) and BCMA/TACI. In some embodiments, the antigen-binding molecule is not a competitive inhibitor of binding of a ligand for BCMA/TACI (e.g. APRIL or BAFF) to BCMA/TACI. In some embodiments, the antigen-binding molecule is not an allosteric inhibitor of binding of a ligand for BCMA/TACI (e.g. APRIL or BAFF) to BCMA/TACI. In some embodiments, the antigen-binding molecule does not displace a ligand for BCMA/TACI (e.g. APRIL or BAFF) from a polypeptide complex comprising BCMA/TACI and the ligand for BCMA/TACI. In some embodiments, the antigen-binding molecule binds to a polypeptide complex comprising BCMA/TACI and a ligand for BCMA/TACI (e.g. APRIL or BAFF). In some embodiments, the antigen-binding molecule does not bind to the region of BCMA/TACI bound by a polypeptide comprising or consisting of the sequence shown in SEQ ID NO:287, 288, 289 or 290.

In some embodiments, the antigen-binding molecule binds to BCMA/TACI in the region which is bound by a ligand for BCMA/TACI (e.g. APRIL or BAFF). In some embodiments, the antigen-binding molecule inhibits interaction between a ligand for BCMA/TACI (e.g. APRIL or BAFF) and BCMA/TACI. In some embodiments, the antigen-binding molecule is a competitive inhibitor of binding of a ligand for BCMA/TACI (e.g. APRIL or BAFF) to BCMA/TACI. In some embodiments, the antigen-binding molecule is an allosteric inhibitor of binding of a ligand for BCMA/TACI (e.g. APRIL or BAFF) to BCMA/TACI. In some embodiments, the antigen-binding molecule displaces a ligand for BCMA/TACI (e.g. APRIL or BAFF) from a polypeptide complex comprising BCMA/TACI and the ligand for BCMA/TACI. In some embodiments, the antigen-binding molecule does not bind to a polypeptide complex comprising BCMA and a ligand for BCMA/TACI (e.g. APRIL or BAFF). In some embodiments, the antigen-binding molecule binds to BCMA/TACI in the region bound by a polypeptide comprising or consisting of the sequence shown in SEQ ID NO:287, 288, 289 or 290.

The ability of an antigen-binding molecule to inhibit interaction between two factors can be determined for example by analysis of interaction in the presence of, or following incubation of one or both of the interaction partners with, the antibody/fragment. An example of a suitable assay to determine whether a given antigen-binding molecule is capable of inhibiting interaction between two interaction partners is a competition ELISA assay. An antigen-binding molecule which is capable of inhibiting a given interaction (e.g. between BCMA/TACI and APRIL/BAFF, or between CD47 and SIRPα) is identified by the observation of a reduction/decrease in the level of interaction between the interaction partners in the presence of—or following incubation of one or both of the interaction partners with—the antigen-binding molecule, as compared to the level of interaction in the absence of the antigen-binding molecule (or in the presence of an appropriate control antigen-binding molecule). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antigen-binding molecule may be labelled or used in conjunction with a detectable entity for the purposes of detecting and/or measuring the level of interaction.

The ability of an antigen-binding molecule to inhibit interaction between BCMA/TACI and APRIL can be analysed as described in Example 3.3. The ability of an antigen-binding molecule to inhibit interaction between CD47 and SIRPα can be analysed as described in Example 7.5. The ability of an antigen-binding molecule to inhibit interaction between two binding partners can also be determined by analysis of the downstream functional consequences of such interaction.

In some embodiments, the antigen-binding molecule of the present disclosure is capable of inhibiting interaction between BCMA/TACI and a ligand for BCMA/TACI (e.g. APRIL or BAFF) to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, times, ≤0.15 times, ≤0.1 times, ≤0.05 times, or ≤0.01 times the level of interaction between BCMA/TACI and the ligand for BCMA/TACI in the absence of the antigen-binding molecule (or in the presence of an appropriate control antigen-binding molecule).

In some embodiments, the antigen-binding molecule binds to BCMA/TACI in the presence or absence of a ligand for BCMA/TACI (e.g. APRIL or BAFF) (i.e. irrespective of whether BCMA/TACI is provided in the ligand-bound or unbound form).

In some embodiments, the antigen-binding molecule described herein inhibits interaction between human BCMA and human APRIL with an $IC_{50}$ of 5 nM or less, preferably one of ≤2 nM, ≤1.5 nM, ≤1 nM, ≤750 pM, ≤500 pM, ≤200 pM, ≤150 pM, ≤140 pM, ≤130 pM, ≤140 pM, ≤110 pM, ≤100 pM, ≤90 pM, ≤80 pM, ≤70 pM, ≤60 pM, ≤50 pM, ≤40 pM, ≤30 pM, ≤20 pM or ≤10 pM (e.g. as determined by analysis as described in Example 3.3).

In some embodiments, the antigen-binding molecule binds to CD47 in the region which is bound by SIRPα. In some embodiments, the antigen-binding molecule inhibits interaction between SIRPα and CD47. In some embodiments, the antigen-binding molecule is a competitive inhibitor of binding of SIRPα to CD47. In some embodiments, the antigen-binding molecule is not capable of binding to a polypeptide complex comprising CD47 and SIRPα.

In some embodiments, the antigen-binding molecule of the present disclosure is capable of inhibiting interaction between CD47 and SIRPα to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of interaction between CD47 and SIRPα in the absence of the antigen-binding molecule (or in the presence of an appropriate control antigen-binding molecule).

In some embodiments, the antigen-binding molecule is an antagonist of BCMA/TACI. In some embodiments, the antigen-binding molecule is capable of inhibiting a function or process (e.g. interaction, signalling or other activity) mediated by BCMA/TACI or a BCMA/TACI-containing polypeptide complex. Herein, 'inhibition' refers to a reduction, decrease or lessening relative to a control condition.

In some embodiments, the antigen-binding molecule is an antagonist of CD47. In some embodiments, the antigen-binding molecule is capable of inhibiting a function or process mediated by CD47 or a CD47– containing polypeptide complex.

In some embodiments, the antigen-binding molecule inhibits BCMA/TACI-mediated signalling (i.e. signalling mediated by BCMA/TACI or a BCMA/TACI-containing polypeptide complex). BCMA/TACI– mediated signalling can be analysed using BCMA/TACI-expressing cells e.g. using an assay for detecting and/or quantifying BCMA/TACI-mediated signalling.

Suitable assays for investigating BCMA/TACI-mediated signalling include e.g. NFκB reporter assays, and assays for detecting the phosphorylation/activity/expression of factors which are phosphorylated/activated/expressed as a consequence of BCMA/TACI-mediated signalling. Such assays may comprise contacting BCMA/TACI-expressing cells with an antigen-binding molecule according to the present disclosure, e.g. in the presence of APRIL or BAFF.

In some embodiments, the antigen-binding molecule of the present disclosure is capable of inhibiting BCMA/TACI-mediated signalling to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of BCMA/TACI-mediated signalling in the absence of the antigen-binding molecule (or in the presence of an appropriate control antigen-binding molecule).

In some embodiments, the antigen-binding molecule inhibits SIRPα-mediated signalling (i.e. signalling mediated by SIRPα or a SIRPα-containing polypeptide complex). SIRPα-mediated signalling can be analysed using SIRPα-expressing cells e.g. using an assay for detecting and/or quantifying SIRPα ITIM phosphorylation, or using an in vitro assay of phagocytosis of CD47-expressing cells (e.g. Raji cells) by SIRPα-expressing cells (e.g. macrophages). For example, an in vitro assay of phagocytosis of CD47-expressing cells by SIRPα-expressing cells may be performed as described in Feng et al., Proc Natl Acad Sci USA. (2015) 112(7): 2145-2150 (hereby incorporated by reference in its entirety), or as described in the experimental examples herein.

In some embodiments, the antigen-binding molecule of the present disclosure is capable of inhibiting SIRPα-mediated signalling to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of SIRPα-mediated signalling in the absence of the antigen-binding molecule (or in the presence of an appropriate control antigen-binding molecule).

In some embodiments, the antigen-binding molecule of the present disclosure is capable of increasing phagocytosis of CD47-expressing cells. In some embodiments, the antigen-binding molecule of the present disclosure is capable of increasing phagocytosis of cells expressing BCMA/TACI and CD47. In some embodiments, the antigen-binding molecule of the present disclosure is capable of increasing phagocytosis of Raji cells by phagocytic cells, e.g. SIRPα-expressing phagocytic cells (e.g. macrophages).

An antigen-binding molecule which is capable of increasing phagocytosis of a given cell type by phagocytic cells is identified by the observation of an increased level of phagocytosis of the cell type by the phagocytic cells in the presence of, or following incubation of the given cell type with, the antigen-binding molecule, as compared to the level of phagocytosis detected in the absence of the antigen-binding molecule (or in the presence of an appropriate control antigen-binding molecule).

The ability of an antigen-binding molecule to increase phagocytosis of a given cell type by phagocytic cells can be analysed as described in Example 7.6.

In some embodiments, the antigen-binding molecule of the present disclosure is capable of increasing phagocytosis of CD47-expressing cells by phagocytic cells (e.g. macrophages) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level phagocytosis of the CD47-expressing cells by the phagocytic cells in the absence of the antigen-binding molecule (or in the presence of an appropriate control antigen-binding molecule).

In some embodiments, the antigen-binding molecule of the present disclosure is capable of increasing phagocytosis of cells expressing BCMA and CD47 by phagocytic cells (e.g. macrophages) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level phagocytosis of the cells expressing BCMA and CD47 by the phagocytic cells in the absence of the antigen-binding molecule (or in the presence of an appropriate control antigen-binding molecule).

In some embodiments, the antigen-binding molecule of the present disclosure is capable of increasing phagocytosis of cells expressing BCMA/TACI and CD47 by phagocytic cells (e.g. macrophages) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level phagocytosis of the cells expressing BCMA/TACI and CD47 by the phagocytic cells in the absence of the antigen-binding molecule (or in the presence of an appropriate control antigen-binding molecule).

In some embodiments, the antigen-binding molecule described herein potentiates phagocytosis of cells expressing BCMA (e.g. H929 cells) by macrophages with an $EC_{50}$ of 2.5 nM or less, preferably one of ≤2 nM, ≤1.5 nM, ≤1 nM, ≤500 pM, ≤200 pM, ≤150 pM, ≤140 pM, ≤130 pM, ≤140 pM, ≤110 pM, ≤100 pM, ≤90 pM, ≤80 pM, ≤70 pM, ≤60 pM or ≤50 pM (e.g. as determined by analysis as described in Example 7.6). In some embodiments, the antigen-binding molecule of the present disclosure is capable of increasing the number/proportion of cancer antigen-specific immune cells (e.g. CD8+ T cells or CD8+ CTLs) relative to a negative control condition, e.g. in an appropriate in vitro assay, or in vivo. Tseng et al., Proc Natl Acad Sci USA. (2013) 110(27): 11103-11108 (hereby incorporated by reference in its entirety) demonstrated that increased phagocytosis of CD47-expressing cancer cells by macrophages in the presence of an anti-CD47 antibody was associated with increased priming of cancer antigen-specific CD8+ T cells. Antigen-binding molecules capable of causing an increase in the number/proportion of cancer antigen-specific immune cells can be identified using a T cell priming assay e.g. as described in Tseng et al., Proc Natl Acad Sci USA. (2013) 110(27): 11103-11108.

In some embodiments, the antigen-binding molecule of the present disclosure does not cause substantial hemagglutination (e.g. at concentrations of up to 400 pg/ml). Hemagglutination refers to agglutination of red blood cells (erythrocytes). An agent which causes hemagglutination may be referred to as a hemagglutinin. In some embodiments, the antigen-binding molecule of the present disclosure is not a hemagglutinin.

The ability of an antibody to cause hemagglutination can be analysed e.g. using an in vitro hemagglutination assay. A suitable assay of hemagglutination for the purposes of such analysis is described e.g. in Example 5 of WO 2013/119714 A1 (hereby incorporated by reference in its entirety), or the assay of hemagglutination described in Example 7.7 herein. 'Substantial' hemagglutination may be a level of hemagglutination which is more than 2 times, e.g. more than 3, 4, 5, 6, 7, 8, 9 or 10 times the level of hemagglutination detected in the absence of the antigen-binding molecule (or in the presence of an appropriate control antigen-binding molecule which does not cause hemagglutination).

In some embodiments, the antigen-binding molecule of the present disclosure causes less hemagglutination as compared to a reference anti-CD47 antibody (e.g. a prior art anti-CD47 antibody). In some embodiments, the antigen-binding molecule of the present disclosure causes less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of hemagglutination as compared to a reference anti-CD47 antibody (e.g. a prior art anti-CD47 antibody), e.g. as determined using an in vitro assay of hemagglutination.

In some embodiments, an antigen-binding molecule according to the present disclosure may potentiate (i.e. upregulate, enhance) cell killing of cells comprising/expressing BCMA and/or CD47. In some embodiments, an antigen-binding molecule according to the present disclosure may inhibit growth or reduce metastasis of a cancer comprising cells comprising/expressing BCMA and/or CD47. In some embodiments, an antigen-binding molecule according to the present disclosure may potentiate (i.e. upregulate, enhance) cell killing of cells comprising/expressing BCMA/TACI and/or CD47. In some embodiments, an antigen-binding molecule according to the present disclosure may inhibit growth or reduce metastasis of a cancer comprising cells comprising/expressing BCMA/TACI and/or CD47.

In some embodiments an antigen-binding molecule according to the present disclosure is capable of reducing the number/proportion of cells expressing BCMA and/or CD47. In some embodiments an antigen-binding molecule according to the present disclosure is capable of reducing the number/proportion of cells expressing BCMA/TACI and/or CD47. In some embodiments, an antigen-binding molecule according to the present disclosure is capable of depleting/ enhancing depletion of such cells.

Antigen-binding molecules according to the present disclosure may comprise one or more moieties for potentiating a reduction in the number/proportion of cells expressing BCMA/TACI and/or CD47. For example, an antigen-binding molecule according to the present disclosure may e.g. comprise an Fc region and/or a drug moiety.

Fc regions provide for interaction with Fc receptors and other molecules of the immune system to bring about functional effects. IgG Fc-mediated effector functions are reviewed e.g. in Jefferis et al., Immunol Rev 1998 163:59-76 (hereby incorporated by reference in its entirety), and are brought about through Fc-mediated recruitment and activation of immune cells (e.g. macrophages, dendritic cells, neutrophils, basophils, eosinophils, platelets, mast cells, NK cells and T cells) through interaction between the Fc region and Fc receptors expressed by the immune cells, recruitment of complement pathway components through binding of the Fc region to complement protein C1q, and consequent activation of the complement cascade. Fc-mediated functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation.

In some embodiments, an antigen-binding molecule according to the present disclosure comprises an Fc region capable of potentiating/directing one or more of ADCC, ADCP, CDC against, and/or potentiating formation of a MAC on or cell degranulation of, a cell expressing BCMA/ TACI and/or CD47 (e.g. a cell expressing BCMA/TACI and/or CD47, and/or a complex comprising BCMA/TACI and/or a complex comprising CD47 at the cell surface).

In some embodiments, an antigen-binding molecule according to the present disclosure is capable of potentiating/directing ADCC against a cell expressing BCMA. In some embodiments, an antigen-binding molecule is capable of potentiating/directing ADCC against a cell expressing TACT. In some embodiments, an antigen-binding molecule is capable of potentiating/directing ADCC against a cell expressing BCMA and TACT. The ability of an antigen-binding molecule to potentiate/direct ADCC against a cell expressing BCMA and/or TACI can be analysed as described in Example 9.

In some embodiments, the antigen-binding molecule described herein potentiates ADCC against cells expressing BCMA and/or TACI with an EC$_{50}$ of 10 nM or less, preferably one of ≤9 nM, ≤8 nM, ≤7 nM, ≤6 nM, ≤5 nM, ≤4 nM, ≤3 nM, ≤2 nM, ≤1.5 nM, ≤1 nM, ≤0.9 nM, ≤0.8 nM, ≤0.7 nM, ≤0.6 nM, ≤0.5 nM, nM, ≤0.3 nM, ≤0.2 nM, ≤0.1 nM, ≤900 pM, ≤800 pM, ≤700 pM, ≤600 pM, ≤500 pM, ≤400 pM or ≤300 pM (e.g. as determined by analysis as described in Example 9).

In some embodiments, an antigen-binding molecule according to the present disclosure comprises a drug moiety. The antigen-binding molecule may be conjugated to the drug moiety. Antibody-drug conjugates are reviewed e.g. in Parslow et al., Biomedicines. 2016 September; 4 (3):14 (hereby incorporated by reference in its entirety). In some embodiments, the drug moiety is or comprises a cytotoxic agent, such that the antigen-binding molecule displays cytotoxicity to a cell expressing BCMA/TACI and/or CD47 (e.g. a cell expressing BCMA/TACI and/or CD47, and/or a complex comprising BCMA/TACI and/or CD47 at the cell surface). In some embodiments, the drug moiety is or comprises a chemotherapeutic agent.

In some embodiments, an antigen-binding molecule according to the present disclosure comprises an immune cell-engaging moiety. In some embodiments, the antigen-binding molecule comprises a CD3 polypeptide-binding moiety (e.g. an antigen-binding domain capable of binding to a CD3 polypeptide).

In some embodiments, an antigen-binding molecule according to the present disclosure is capable of potentiating/directing T cell-mediated cytolytic activity against a cell expressing BCMA. In some embodiments, an antigen-binding molecule according to the present disclosure is capable of potentiating/directing T cell-mediated cytolytic activity against a cell expressing TACT. In some embodiments, an antigen-binding molecule according to the present disclosure is capable of potentiating/directing T cell-mediated cytolytic activity against a cell expressing BCMA and TACT. The ability of an antigen-binding molecule to potentiate/direct T cell-mediated cytolytic activity against a cell expressing BCMA and/or TACI can be analysed as described in Example 10.

In some embodiments, the antigen-binding molecule of the present disclosure displays anticancer activity. In some embodiments, the antigen-binding molecule of the present disclosure increases killing of cancer cells. In some embodiments, the antigen-binding molecule of the present disclosure causes a reduction in the number of cancer cells in vivo, e.g. as compared to an appropriate control condition. The cancer may be a cancer expressing BCMA. The cancer may be a cancer expressing BCMA and CD47. The cancer may be a cancer expressing BCMA/TACI. The cancer may be a cancer expressing BCMA/TACI and CD47.

The antigen-binding molecule of the present disclosure may be analysed for anticancer activity in an appropriate in vivo model, e.g. multiple myeloma cell line-derived xenograft model or a Burkitt's lymphoma cell line-derived xenograft model (e.g. a Raji, U-266/70, U-266/84, RPMI-8226 or MM.1S cell line-derived xenograft model).

In some embodiments, administration of an antigen-binding molecule according to the present disclosure may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an appropriate cell line-derived xenograft model.

Chimeric Antigen Receptors (CARs)

The present disclosure also provides Chimeric Antigen Receptors (CARs) comprising the antigen-binding polypeptides or polypeptides of the present disclosure.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present disclosure comprises an antigen-binding region which comprises or consists of the antigen-binding molecule of the present disclosure, or which comprises or consists of a polypeptide according to the present disclosure.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1 BB, ICOS and CD27. In some cases CARs are engineered to provide for co-stimulation of different intracellular signalling pathways. For example, signalling associated with CD28 costimulation preferentially activates the phosphatidylinositol 3-kinase (PI3K) pathway, whereas the 4-1BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present disclosure comprises one or more co-stimulatory sequences comprising or consisting of an amino acid sequence which comprises, consists of, or is derived from, the amino acid sequence of the intracellular domain of one or more of CD28, OX40, 4-1 BB, ICOS and CD27.

An optional hinge region may provide separation between the antigen-binding domain and the transmembrane domain, and may act as a flexible linker. Hinge regions may be derived from IgG1. In some embodiments, the CAR of the present disclosure comprises a hinge region comprising or consisting of an amino acid sequence which comprises, consists of, or is derived from, the amino acid sequence of the hinge region of IgG1.

Also provided is a cell comprising a CAR according to the present disclosure. The CAR according to the present disclosure may be used to generate CAR-expressing immune cells, e.g. CAR-T or CAR-NK cells. Engineering of CARs into immune cells may be performed during culture, in vitro.

The antigen-binding region of the CAR of the present disclosure may be provided with any suitable format, e.g. scFv, scFab, etc.

Nucleic Acids and Vectors

The present disclosure provides a nucleic acid, or a plurality of nucleic acids, encoding an antigen-binding molecule, polypeptide or CAR according to the present disclosure. In some embodiments, the nucleic acid(s) comprise or consist of DNA and/or RNA.

The present disclosure also provides a vector, or plurality of vectors, comprising the nucleic acid or plurality of nucleic acids according to the present disclosure.

Nucleic acids and vectors according to the present disclosure may be provided in purified or isolated form, i.e. from other nucleic acid, or naturally-occurring biological material.

The nucleotide sequence may be contained in a vector, e.g. an expression vector. A 'vector' as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the present disclosure.

The term 'operably linked' may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present disclosure may be encoded by different nucleic acids of the plurality of nucleic acids, or by different vectors of the plurality of vectors.

Cells Comprising/Expressing the Antigen-Binding Molecules and Polypeptides

The present disclosure also provides a cell comprising or expressing an antigen-binding molecule, polypeptide or CAR according to the present disclosure. Also provided is a cell comprising or expressing a nucleic acid, a plurality of nucleic acids, a vector or a plurality of vectors according to the present disclosure.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell is, or is derived from, a cell type commonly used for the expression of polypeptides for use in therapy in humans. Exemplary cells are described e.g. in Kunert and Reinhart, Appl Microbiol Biotechnol. (2016) 100:3451-3461 (hereby incorporated by reference in its entirety), and include e.g. CHO, HEK 293, PER.C6, NS0 and BHK cells. In preferred embodiments, the cell is, or is derived from, a CHO cell.

The present disclosure also provides a method for producing a cell comprising a nucleic acid(s) or vector(s) according to the present disclosure, comprising introducing a nucleic acid, a plurality of nucleic acids, a vector or a plurality of vectors according to the present disclosure into a cell. In some embodiments, introducing an isolated nucleic acid(s) or vector(s) according to the present disclosure into a cell comprises transformation, transfection, electroporation or transduction (e.g. retroviral transduction).

The present disclosure also provides a method for producing a cell expressing/comprising an antigen-binding molecule, polypeptide or CAR according to the present disclosure, comprising introducing a nucleic acid, a plurality of nucleic acids, a vector or a plurality of vectors according to the present disclosure in a cell. In some embodiments, the methods additionally comprise culturing the cell under conditions suitable for expression of the nucleic acid(s) or vector(s) by the cell. In some embodiments, the methods are performed in vitro.

The present disclosure also provides cells obtained or obtainable by the methods according to the present disclosure.

Producing the Antigen-Binding Molecules and Polypeptides

Antigen-binding molecules and polypeptides according to the present disclosure may be prepared according to methods for the production of polypeptides known to the skilled person.

Polypeptides may be prepared by chemical synthesis, e.g. liquid or solid phase synthesis. For example, peptides/polypeptides can be synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases, the antigen-binding molecules of the present disclosure are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the present disclosure, any cell suitable for the expression of polypeptides may be used. The cell may be a prokaryote or eukaryote. In some embodiments, the cell is a prokaryotic cell, such as a cell of archaea or bacteria. In some embodiments, the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. a cell described hereinabove.

In some cases, the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according to a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide, it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonication, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

108

Compositions

The present disclosure also provides compositions comprising the antigen-binding molecules, polypeptides, CARs, nucleic acids, expression vectors and cells described herein.

The antigen-binding molecules, polypeptides, CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments, the composition is formulated for injection or infusion, e.g. into a blood vessel, tissue/organ of interest or tumor.

The present disclosure also provides methods for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

For example, a further aspect the present disclosure relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present disclosure provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments, the methods may lead to an improvement in the disease/condition, e.g. a reduction in the symptoms of the disease/condition or reduction in some other correlate of the severity/activity of the disease/condition. In some embodiments, the methods may prevent development of the disease/condition a later stage (e.g. a chronic stage or metastasis).

It will be appreciated that the articles of the present disclosure may be used for the treatment/prevention of any disease/condition that would derive therapeutic or prophylactic benefit from a reduction in the number and/or activity of cells expressing BCMA/TACI and/or CD47. For example, the disease/condition may be a disease/condition in which cells expressing BCMA/TACI and/or CD47 are pathologically implicated, e.g. a disease/condition in which an increased number/proportion of cells expressing BCMA/TACI and/or CD47 is positively associated with the onset, development or progression of the disease/condition, and/or severity of one or more symptoms of the disease/condition, or for which an increased number/proportion of cells expressing BCMA/TACI and/or CD47, is a risk factor for the onset, development or progression of the disease/condition.

In some embodiments, the disease/condition to be treated/prevented in accordance with the present disclosure is a disease/condition characterised by an increase in the number/proportion/activity of cells expressing BCMA/TACI and/or CD47, e.g. as compared to the number/proportion/activity of cells expressing BCMA/TACI and/or CD47 in the absence of the disease/condition.

Treatment in accordance with the methods of the present disclosure may achieve one or more of: a reduction in the number of BCMA/TACI and/or CD47-positive cells (e.g. BCMA/TACI and/or CD47-positive cancer cells) in the subject, a reduction in the size of a BCMA/TACI and/or CD47-positive tumor/lesion in the subject, inhibition of growth of BCMA/TACI and/or CD47-positive cancer cells in the subject, inhibition of growth of a BCMA/TACI and/or CD47-positive tumor/lesion in the subject, inhibition of the development/progression of a BCMA/TACI and/or CD47-positive cancer (e.g. to a later stage, or metastasis), a reduction in the severity of symptoms of a BCMA/TACI and/or CD47-positive cancer in the subject, an increase in survival of the subject (e.g. progression free survival or overall survival), a reduction in a correlate of the number or activity of BCMA/TACI and/or CD47-positive cancer cells in the subject, and/or a reduction in BCMA/TACI and/or CD47-positive cancer burden in the subject.

BCMA is expressed by cells of B cell malignancies such as multiple myeloma, Hodgkin's lymphoma, non-Hodgkin's lymphoma (e.g. Burkitt lymphoma) and lymphocytic leukemia. The anti-BCMA antibody-drug conjugate J6M0-mcM-MAF (GSK2857916) has been investigated for the treatment of multiple myeloma (see e.g. Tai et al., Blood. (2014) 123(20): 3128-3138), and the BCMA/TACI antagonist Atacicept (recombinant fusion protein of the BAFF- and APRIL-binding domains of TACI receptor; see Hartung et al. Ther Adv Neurol Disord. (2010) 3(4): 205-216) has been investigated as an agent for use in the treatment of multiple myeloma, B-cell chronic lymphocytic leukemia, and non-Hodgkin's lymphoma (Vasiliou, Drugs Fut 2008, 33(11): 921). Atacicept has also been investigated as a treatment for systemic lupus erythematosus (SLE), rheumatoid arthritis (RA) optic neuritis and multiple sclerosis (MS)—see e.g. Hartung et al. Ther Adv Neurol Disord. (2010) 3(4): 205-216.

CD47 has been proposed to be a cell-surface marker expressed by all human cancers (Willingham et al., Proc Natl Acad Sci USA. (2012) 109(17): 6662-6667). The role of CD47 in the development and progression of various cancers is reviewed e.g. in Sick et al. Br J Pharmacol. (2012) 167(7): 1415-1430 and Chao et al., Curr Opin Immunol. 2012 April; 24(2): 225-232 (hereby incorporated by reference in its entirety). Elevated CD47 expression is a negative prognostic indicator for several cancers, and may contribute to cancer development/progression by reducing killing of cancer cells and by increasing proliferation, migration and/or invasion of cancer cells. CD47 has been shown to suppress innate macrophage and NK cell-mediated anticancer responses (Soto-Pantoja et al., Expert Opin Ther Targets. (2013) 17(1): 89-103, which is hereby incorporated by reference in its entirety).

CD47 is expressed by acute myeloid leukemia (AML), chronic myeloid leukemia (CML), acute lymphoblastic leukemia (ALL), non-Hodgkin's lymphoma (NHL), multiple myeloma (MM), bladder cancer, brain cancer and ovarian cancer cells. Willingham et al. Proc Natl Acad Sci USA. (2012) 109(17): 6662-6667 reported expression of CD47 on cells of ovarian, breast, colon, bladder, glioblastoma, hepatocellular carcinoma, and prostate tumors, and CD47 has recently been shown to promote tumor invasion and metastasis in Non-small Cell Lung Cancer (NSCLC; Zhao et al., Sci Rep. (2016) 6: 29719) and melanoma (Ngo et al., Cell Reports (2016) 16, 1701-1716).

CD47 is also implicated in the pathogenesis of autoimmune diseases, inflammatory diseases, ischemia-reperfusion injury (IRI) and cardiovascular diseases (see e.g. Soto-Pantoja et al., Expert Opin Ther Targets. (2013) 17(1): 89-103). The CD47-SIRPα axis has been implicated in type I diabetes (Dugas et al., J Autoimmun. (2010) 35(1):23-32). Thrombospondin-1 has been shown to act via CD47 to inhibit nitric oxide signaling throughout the vascular system, and blocking TSP1-CD47 interaction alleviates tissue ischemia (Isenberg et al., Arterioscler Thromb Vasc Biol. (2008) 28(4): 615-621) and reduces ischemia-reperfusion injury (IRI) (Xiao et al., Liver Transpl. (2015) 21(4): 468-477).

Multiple myeloma (MM) is a hematopoietic neoplasia characterized by the clonal proliferation of malignant plasma cells in the bone marrow (see e.g. Ghobrial et al., Nat Rev Clin Oncol (2018) 15(4):219-233). The bone marrow microenvironment plays a crucial role in MM by promoting the proliferation of plasma cells and resistance to conventional therapies. MM cells subvert the bone marrow microenvironment to suppress immune responses and promote their own growth. Overexpression of CD47 by the MM cells prevents their phagocytosis through ligation of SIRPα on tumor-associated and bone marrow-resident macrophages, and overexpression of BCMA/TACI promotes their survival, immune checkpoint suppression, angiogenesis, osteoclast activation, and drug resistance. Secretion of APRIL (the ligand for BCMA) by abnormal osteoclasts enhances the tumorigenic functions of MM cells and promotes remodelling of the bone marrow microenvironment, and overexpression of CD38 by the MM cells promotes the binding and migration through the endothelial cell wall, proliferation, and immune suppression.

BCMA, TACI and CD47 are particularly attractive therapeutics targets for multiple myeloma because they are co-expressed by multiple myeloma cells, and play functional roles which therefore reduce risk of antigen loss. The large population of tissue-resident macrophages in the liver (Kupffer cells) represents an attractive therapeutic mechanism for hematological malignancies, and macrophage-driven clearance of malignant cells offers a further route for neo-antigen presentation to adaptive immune system.

In some embodiments, the disease/disorder to be treated/prevented is a cancer, an autoimmune disease (e.g. type I diabetes), an inflammatory disease, ischemia-reperfusion injury (IRI) or cardiovascular disease.

In some embodiments, the disease/condition to be treated/prevented is a cancer. The cancer may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma.

The treatment/prevention may be aimed at one or more of: delaying/preventing the onset/progression of symptoms of the cancer, reducing the severity of symptoms of the cancer, reducing the survival/growth/invasion/metastasis of cells of the cancer, reducing the number of cells of the cancer and/or increasing survival of the subject.

In some embodiments, the cancer to be treated/prevented comprises cells expressing BCMA/TACI and/or CD47. In some embodiments, the cancer to be treated/prevented is a cancer which is positive for BCMA/TACI and/or CD47. In some embodiments, the cancer over-expresses CD47 and/or BCMA/TACI. Overexpression of BCMA/TACI and/or CD47 can be determined by detection of a level of expression of BCMA/TACI and/or CD47 which is greater than the level of expression by equivalent non-cancerous cells/non-tumor tissue.

BCMA/TACI and/or CD47 expression may be determined by any suitable means. Expression may be gene expression or protein expression. Gene expression can be determined e.g. by detection of mRNA encoding BCMA/

TACI and/or CD47, for example by quantitative real-time PCR (qRT-PCR). Protein expression can be determined e.g. by detection of BCMA/TACI and/or CD47, for example by antibody-based methods, for example by western blot, immunohistochemistry, immunocytochemistry, flow cytometry, or ELISA.

In some embodiments, a patient may be selected for treatment described herein based on the detection of a cancer expressing BCMA/TACI and/or CD47, or overexpressing BCMA/TACI and/or CD47, e.g. in a sample obtained from the subject.

In some embodiments, the cancer to be treated/prevented in accordance with the present disclosure is selected from: a hematologic malignancy, a myeloid hematologic malignancy, a lymphoblastic hematologic malignancy, myelodysplastic syndrome (MDS), acute myeloid leukemia (AML), chronic myeloid leukemia (CML), acute lymphoblastic leukemia (ALL), non-Hodgkin's lymphoma (NHL), follicular lymphoma (FL), mantle cell lymphoma (MCL), multiple myeloma (MM), bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

In some embodiments, the disease/disorder to be treated/prevented is a hematological malignancy, a B cell malignancy, multiple myeloma (MM), lymphoma, B cell lymphoma, Hodgkin's lymphoma (HL), non-Hodgkin's lymphoma (NHL), follicular lymphoma (FL), mantle cell lymphoma (MCL), Burkitt lymphoma, lymphocytic leukemia, an autoimmune disease, systemic lupus erythematosus (SLE), rheumatoid arthritis (RA) optic neuritis or multiple sclerosis (MS).

In some embodiments, the cancer is relapsed with respect to prior treatment with a BCMA-targeted therapy. In some embodiments, the cancer is refractory with respect to prior treatment with a BCMA-targeted therapy. In some embodiments, the cancer harbours a mutation resulting in reduced gene and/or protein expression of BCMA. In some embodiments, the cancer is BCMA-low/negative and TACI-positive.

Administration of the articles of the present disclosure is preferably in a 'therapeutically effective' or 'prophylactically effective' amount, this being sufficient to show therapeutic or prophylactic benefit to the subject. The actual amount administered, and rate and time-course of administration, will depend on the nature and severity of the disease/condition and the particular article administered. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Administration may be alone or in combination with other treatments, either simultaneously or sequentially dependent upon the condition to be treated. The antigen-binding molecule or composition described herein and a therapeutic agent may be administered simultaneously or sequentially.

In some embodiments, the methods comprise additional therapeutic or prophylactic intervention, e.g. for the treatment/prevention of a cancer. In some embodiments, the therapeutic or prophylactic intervention is selected from chemotherapy, immunotherapy, radiotherapy, surgery, vaccination and/or hormone therapy. In some embodiments, the therapeutic or prophylactic intervention comprises leukapheresis. In some embodiments, the therapeutic or prophylactic intervention comprises a stem cell transplant.

The antigen-binding molecules of the present disclosure are particularly suitable for use in conjunction with radiotherapy. Antagonism of CD47 has previously been shown to help maintain the viability of normal tissues after irradiation, while increasing the radiosensitivity of tumors (Maxhimer et al., Science Translational Medicine (2009) 1(3): 3ra7).

Simultaneous administration refers to administration of the antigen-binding molecule, polypeptide, CAR, nucleic acid (or plurality thereof), expression vector (or plurality thereof), cell or composition and therapeutic agent together, for example as a pharmaceutical composition containing both agents (combined preparation), or immediately after each other and optionally via the same route of administration, e.g. to the same artery, vein or other blood vessel. Sequential administration refers to administration of one of the antigen-binding molecule/composition or therapeutic agent followed after a given time interval by separate administration of the other agent. It is not required that the two agents are administered by the same route, although this is the case in some embodiments. The time interval may be any time interval.

Chemotherapy and radiotherapy respectively refer to treatment of a cancer with a drug or with ionising radiation (e.g. radiotherapy using X-rays or y-rays). The drug may be a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment. The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs may be selected from: Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axicabtagene Ciloleucel, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOL-FIRI-BEVACIZUMAB, FOLFIRI-CETUXIMAB, FOL-FIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCIT-ABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Margibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peg interferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib) and Zytiga (Abiraterone Acetate).

In some embodiments, the chemotherapeutic agent is selected from one or more of: Melphalan, Vincristine (Oncovin), Cyclophosphamide (Cytoxan), Etoposide (VP-16), Doxorubicin (Adriamycin), Liposomal doxorubicin (Doxil), Bendamustine (Treanda), Thalidomide (Thalomid), Lenalidomide (Revlimid), Pomalidomide (Pomalyst), Bortezomib (Velcade), Bortezomib (Velcade), Ixazomib (Ninlaro), Panobinostat (Farydak), Daratumumab (Darzalex), Elotuzumab (Empliciti) and Interferon.

In some embodiments, the treatment may comprise administration of a corticosteroid, e.g. dexamethasone and/or prednisone.

Multiple doses of the antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In accordance with various aspects of the present disclosure, a method of treating and/or preventing a disease/condition may comprise one or more of the following: inhibiting interaction between BCMA/TACI and a ligand for BCMA/TACI (e.g. APRIL/BAFF); inhibiting BCMA/TACI-mediated signalling; increasing phagocytosis of BCMA/TACI-expressing cells by phagocytic cells (e.g. macrophages); increasing ADCC of BCMA/TACI-expressing cells; inhibiting interaction between CD47 and a ligand for CD47 (e.g. SIRPα); inhibiting SIRPα-mediated signalling; increasing phagocytosis of CD47-expressing cells by phagocytic cells (e.g. macrophages); increasing ADCC of CD47-expressing cells; increasing phagocytosis of cells expressing BCMA/TACI and CD47 by phagocytic cells (e.g. macrophages); increasing ADCC of cells expressing BCMA/TACI and CD47; increasing the number/proportion of cancer antigen-specific immune cells; increasing killing of cancer cells; inhibiting the development/progression of a cancer.

Methods of Detection

The present disclosure also provides the articles of the present disclosure for use in methods for detecting, localizing or imaging BCMA/TACI and/or CD47, or cells expressing BCMA/TACI and/or CD47.

The antigen-binding molecules described herein may be used in methods that involve detecting binding of the antigen-binding molecule to BCMA/TACI and/or CD47. Such methods may involve detection of the bound complex of the antigen-binding molecule and BCMA/TACI and/or CD47.

As such, a method is provided, comprising contacting a sample containing, or suspected to contain, BCMA/TACI and/or CD47, and detecting the formation of a complex of the antigen-binding molecule and BCMA/TACI and/or CD47. Also provided is a method comprising contacting a sample containing, or suspected to contain, a cell expressing BCMA/TACI and/or CD47, and detecting the formation of a complex of the antigen-binding molecule and a cell expressing BCMA/TACI and/or CD47.

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label as described herein. Detection techniques are well known to those of skill in the art and can be selected to correspond with the labelling agent.

Methods comprising detecting BCMA/TACI and/or CD47 or cells expressing BCMA/TACI and/or CD47 include methods for diagnosing/prognosing cancer, e.g. cancer comprising cells expressing/overexpressing BCMA/TACI and/or CD47.

Methods of this kind may be performed in vitro on a patient sample, or following processing of a patient sample. Once the sample is collected, the patient is not required to be present for the in vitro method to be performed, and therefore the method may be one which is not practised on the human or animal body. In some embodiments, the method is performed in vivo.

Such methods may involve detecting or quantifying one or more of: BCMA, cells expressing BCMA, TACT, cells expressing TACT, CD47, cells expressing CD47, e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

Detection in a sample may be used for the purpose of diagnosis of a disease/condition (e.g. a cancer), predisposition to a disease/condition, or for providing a prognosis (prognosticating) for a disease/condition, e.g. a disease/condition described herein. The diagnosis or prognosis may relate to an existing (previously diagnosed) disease/condition.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/condition (e.g. tissue or tissues in which symptoms of the disease manifest, or which are involved in the pathogenesis of the disease/condition).

A subject may be selected for diagnostic/prognostic evaluation based on the presence of symptoms indicative of a disease/condition described herein, or based on the subject being considered to be at risk of developing a disease/condition described herein.

The present disclosure also provides methods for selecting/stratifying a subject for treatment with a BCMA/TACI and/or CD47-targeted agent. In some embodiments a subject is selected for treatment/prevention in accordance with the methods of the present disclosure, or is identified as a subject which would benefit from such treatment/prevention, based on detection/quantification of BCMA/TACI and/or CD47, or cells expressing BCMA/TACI and/or CD47, e.g. in a sample obtained from the individual.

Subjects

The subject in accordance with aspects of the present disclosure may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present disclosure the subject is preferably a human subject. In some embodiments, the subject to be treated according to a therapeutic or prophylactic method of the present disclosure is a subject having, or at risk of developing, a disease described herein (e.g. a cancer). In embodiments according to the present disclosure, a subject may be selected for treatment according to the methods based on characterisation for certain markers of such disease/condition. The subject may have (e.g. may have been determined to have) a cancer described herein.

Kits

In some aspects of the present disclosure a kit of parts is provided. In some embodiments, the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule, polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments, the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, 'sequence identity' refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780) software. When using such software, the default parameters, e.g. for gap penalty and extension penalty, are preferably used.

Sequences

| SEQ ID NO: | DESCRIPTION | SEQUENCE |
|---|---|---|
| 1 | Human BCMA isoform 1 (UniProt: Q02223-1, v2) | MLQMAGQCSQNEYFDSLLHACIPCQLRCSSNTPPLTCQRYCNASVTNSVKGTNAILWTCLGL SLIISLAVFVLMFLLRKINSEPLKDEFKNTGSGLLGMANIDLEKSRTGDEIILPRGLEYTVEECTC EDCIKSKPKVDSDHCFPLPAMEEGATILVTTKTNDYCKSLPAALSATEIEKSISAR |
| 2 | Human BCMA isoform 2 (UniProt: Q02223-2) | MLQMAGQCSQNEYFDSLLHACIPCQLRCSSNTPPLTCQRYCNARSGLLGMANIDLEKSRTGD EIILPRGLEYTVEECTCEDCIKSKPKVDSDHCFPLPAMEEGATILVTTKTNDYCKSLPAALSATEI EKSISAR |
| 3 | Hu BCMA extracellular region (UniProt: Q02223-1 positions 1-54 | MLQMAGQCSQNEYFDSLLHACIPCQLRCSSNTPPLTCQRYCNASVTNSVKGTNA |
| 4 | Hu BCMA cysteine-rich TNFR repeat (UniProt: Q02223-1 positions 7-41) | QCSQNEYFDSLLHACIPCQLRCSSNTPPLTCQRYC |
| 5 | Hu BCMA transmembrane domain (UniProt: Q02223-1 positions 55-77) | ILWTCLGLSLIISLAVFVLMFLL |
| 6 | Hu BCMA cytoplasmic region (UniProt: Q02223-1 positions 78-184) | RKINSEPLKDEFKNTGSGLLGMANIDLEKSRTGDEIILPRGLEYTVEECTCEDCIKSKPKVDSDH CFPLPAMEEGATILVTTKTNDYCKSLPAALSATEIEKSISAR |

-continued

| | | Sequences |
|---|---|---|

| SEQ ID NO: | DESCRIPTION | SEQUENCE |
|---|---|---|
| 7 | Hu BCMA TRAF interaction region (UniProt: Q02223-1 positions 119-143) | LEYTVEECTCEDCIKSKPKVDSDHC |
| 8 | Cynomolgus macaque BCMA (UniProt: G7Q014-1, v1) | MLQMARQCSQNEYFDSLLHDCKPCQLRCSSTPPLTCQRYCNASMTNSVKGMNAILWTCLGL SLIISLAVFVLTFLLRKMSSEPLKDEFKNTGSGLLGMANIDLEKGRTGDEIVLPRGLEYTVEECT CEDCIKNKPKVDSDHCFPLPAMEEGATILVTTKTNDYCNSLSAALSVTEIEKSISAR |
| 9 | Cy BCMA extracellular region (UniProt: G7Q014-1, v1 positions 1-53) | MLQMARQCSQNEYFDSLLHDCKPCQLRCSSTPPLTCQRYCNASMTNSVKGMNA |
| 10 | Cy BCMA cysteine-rich TNFR repeat (UniProt: G7Q014-1, v1 positions 7-40) | QCSQNEYFDSLLHDCKPCQLRCSSTPPLTCQRYC |
| 11 | Cy BCMA transmembrane domain (UniProt: G7Q014-1, v1 positions 54-76) | ILWTCLGLSLIISLAVFVLTFLL |
| 12 | Cy BCMA cytoplasmic region (UniProt: G7Q014-1, v1 positions 77-183) | RKMSSEPLKDEFKNTGSGLLGMANIDLEKGRTGDEIVLPRGLEYTVEECTCEDCIKNKPKVDS DHCFPLPAMEEGATILVTTKTNDYCNSLSAALSVTEIEKSISAR |
| 13 | Cy BCMA TRAF interaction region (UniProt: UniProt: G7Q014-1, v1 positions 118-142) | LEYTVEECTCEDCIKNKPKVDSDHC |
| 14 | Mouse BCMA isoform 1 (UniProt: O88472-1, v1) | MAQQCFHSEYFDSLLHACKPCHLRCSNPPATCQPYCDPSVTSSVKGTYTVLWIFLGLTLVLSL ALFTISFLLRKMNPEALKDEPQSPGQLDGSAQLDKADTELTRIRAGDDRIFPRSLEYTVEECTC EDCVKSKPKGDSDHFFPLPAMEEGATILVTTKTGDYGKSSVPTALQSVMGMEKPTHTR |
| 15 | Mouse BCMA isoform 2 (UniProt: O88472-2) | MAQQCFHSEYFDSLLHACKPCHLRCSNPPATCQPYCDPSVTSSVKGTYTVLWIFLGLTLVLSL ALFTISFLLRKMNPEALKDEPQSGSAQLDKADTELTRIRAGDDRIFPRSLEYTVEECTCEDCVK SKPKGDSDHFFPLPAMEEGATILVTTKTGDYGKSSVPTALQSVMGMEKPTHTR |
| 16 | Mu BCMA extracellular region (UniProt: O88472-1, v1 positions 1-49) | MAQQCFHSEYFDSLLHACKPCHLRCSNPPATCQPYCDPSVTSSVKGTYT |
| 17 | Cy BCMA cysteine-rich TNFR repeat (UniProt: O88472-1, v1 positions 4-36) | QCFHSEYFDSLLHACKPCHLRCSNPPATCQPYC |
| 18 | Mu BCMA transmembrane domain (UniProt: UniProt: O88472-1, v1 positions 50-70) | VLWIFLGLTLVLSLALFTISF |
| 19 | Mu BCMA isoform 1 cytoplasmic region (UniProt: UniProt: O88472-1, v1 positions 71-185) | LLRKMNPEALKDEPQSPGQLDGSAQLDKADTELTRIRAGDDRIFPRSLEYTVEECTCEDCVKS KPKGDSDHFFPLPAMEEGATILVTTKTGDYGKSSVPTALQSVMGMEKPTHTR |
| 20 | Mu BCMA isoform 2 cytoplasmic region (UniProt: UniProt: O88472-2 positions 71-180) | LLRKMNPEALKDEPQSGSAQLDKADTELTRIRAGDDRIFPRSLEYTVEECTCEDCVKSKPKGD SDHFFPLPAMEEGATILVTTKTGDYGKSSVPTALQSVMGMEKPTHTR |

-continued

| SEQ ID NO: | DESCRIPTION | SEQUENCE |
|---|---|---|
| 21 | Mu BCMA TRAF interaction region (UniProt: UniProt: O88472-1, v1 positions 118 to 142) | LEYTVEECTCEDCVKSKPKGDSDHF |
| 22 | 538-SP5-B10 VH | EVQLQQSGPELVKPGASVKMSCKASGYTFTSYVMHWVKQKPGRGLEWIAYILPFNDVTKYNE KFKGKATLTSDKSSNTAYMELSSLTSEDSAVYYCARWEWDDGYFDYWGQGTTLTVSS |
| 23 | 538-SP5-B10, 539-SP2-H3, 5B10-4Y, 5B10-51 HC-CDR1 | GYTFTSYV |
| 24 | 538-SP5-B10, 5B10-4Y, 5B10-51 HC-CDR2 | ILPFNDVT |
| 25 | 538-SP5-B10, 5B10-4Y, 5B10-51 HC-CDR3 | ARWEWDDGYFDY |
| 26 | 538-SP5-B10, 539-SP2-H3 HC-FR1 | EVQLQQSGPELVKPGASVKMSCKAS |
| 27 | 538-SP5-B10 HC-FR2 | MHWVKQKPGRGLEWIAY |
| 28 | 538-SP5-B10 HC-FR3 | KYNEKFKGKATLTSDKSSNTAYMELSSLTSEDSAVYYC |
| 29 | 538-SP5-B10, OKT3 HC-FR4 | WGQGTTLTVSS |
| 30 | 538-SP5-B10 VL | DAVMTQTPLSLPVSLGDQASISCRSSQSLENSNGNTYLNWYLQKPGQSPQLLIYRVSNRFSG VLDRFSGSGSGTDFTLKISRVEAEDLGVYFCLQVSHVPFTFGAGTKLELK |
| 31 | 538-SP5-B10, 5B10-4Y, 5B10-51 LC-CDR1 | QSLENSNGNTY |
| 32 | 538-SP5-B10, 5B10-4Y, 5B10-51 LC-CDR2 | RVS |
| 33 | 538-SP5-B10, 5B10-4Y, 5B10-51 LC-CDR3 | LQVSHVPFT |
| 34 | 538-SP5-B10 LC-FR1 | DAVMTQTPLSLPVSLGDQASISCRSS |
| 35 | 538-SP5-B10 LC-FR2 | LNWYLQKPGQSPQLLIY |
| 36 | 538-SP5-B10 LC-FR3 | NRFSGVLDRFSGSGSGTDFTLKISRVEAEDLGVYFC |
| 37 | 538-SP5-B10 LC-FR4 | FGAGTKLELK |
| 38 | 539-SP2-H3 VH | EVQLQQSGPELVKPGASVKMSCKASGYTFTSYVIHWVKQKPGQGLEWIGYVLPYNDVIKYNE KFKGKATLTSDKSSSTAYMDLSSLTSEDSAVYYCARWGDFDEGIWFPYWGQGTLVTVSA |
| 39 | 539-SP2-H3 HC-CDR2 | VLPYNDVI |
| 40 | 539-SP2-H3 HC-CDR3 | ARWGDFDEGIWFPY |
| 41 | 539-SP2-H3, 1-1-A1 HC-FR2 | IHWVKQKPGQGLEWIGY |
| 42 | 539-SP2-H3 HC-FR3 | KYNEKFKGKATLTSDKSSSTAYMDLSSLTSEDSAVYYC |
| 43 | 539-SP2-H3, 539-SP7-F4, SP34 HC-FR4 | WGQGTLVTVSA |
| 44 | 539-SP2-H3 VL | DVLMTQTPLSLPVSLGDHASVSCRSSQSIVHTDGNTYLEWYLQKPGQSPKLLIYKVSNRFSGV PDRFSGSGSGTDFTLKISRVEAEDLGVYYCFQGSHVPWTFGGGTKLEIK |
| 45 | 539-SP2-H3 LC-CDR1 | QSIVHTDGNTY |
| 46 | 539-SP2-H3 LC-CDR2 | KVS |
| 47 | 539-SP2-H3 LC-CDR3 | FQGSHVPWT |

-continued

| SEQ ID NO: | DESCRIPTION | SEQUENCE |
|---|---|---|
| 48 | 539-SP2-H3 LC-FR1 | DVLMTQTPLSLPVSLGDHASVSCRSS |
| 49 | 539-SP2-H3 LC-FR2 | LEWYLQKPGQSPKLLIY |
| 50 | 539-SP2-H3, 1-1-A1_BM LC-FR3 | NRFSGVPDRFSGSGSGTDFTLKISRVEAEDLGVYYC |
| 51 | 539-SP2-H3, 539-SP1-C8, 552-LN1-E9, 552-LN2-E6, 552-LN1-F4, 552-LN2-F8, 1-1-A1_BM, 1-1-A1, 1C8-25, 1C8-27 LC-FR4 | FGGGTKLEIK |
| 52 | 539-SP1-C8 VH | EVQLQQSGPELVKPGSSVKMSCKASGYTFTNYVMHWVKQKPGQGLEWIGYILPYNDGTKYN<br>EKFKGKATLTSDKSSSTAYMEFSVLTSEDSAVYYCARYDYEGSFDYWGQGTALTVSS |
| 53 | 539-SP1-C8, 1-1-A1_BM, 1-1-A1, 11A1H1, 11A1H2, 11A1H3, 11A1H4, 11A1H6, 11A1H8, 1C8-6A, 1C8-EH, 1C8-402, 1C8-403, 1C8-610, 1C8-6A3, 1C8-25, 1C8-27 HC-CDR1 | GYTFTNYV |
| 54 | 539-SP1-C8, 1C8-6A, 1C8-402, 1C8-403, 1C8-507, 1C8-6A3, 1C8-25, 1C8-27 HC-CDR2 | ILPYNDGT |
| 55 | 539-SP1-C8, 1C8-6A, 1C8-EH, 1C8-507, 1C8-610, 1C8-6A3 HC-CDR3 | ARYDYEGSFDY |
| 56 | 539-SP1-C8 HC-FR1 | EVQLQQSGPELVKPGSSVKMSCKAS |
| 57 | 539-SP1-C8 HC-FR2 | MHWVKQKPGQGLEWIGY |
| 58 | 539-SP1-C8 HC-FR3 | KYNEKFKGKATLTSDKSSSTAYMEFSVLTSEDSAVYYC |
| 59 | 539-SP1-C8 HC-FR4 | WGQGTALTVSS |
| 60 | 539-SP1-C8 VL | DIQMTQTTSSLSASLGDRVTISCRASQDISNYLNWYQQKPDGTVKLLMCYTSRLHSGVPSRFS<br>GSGSGTDFSLTISNLEQEDIATYFCQQGNTFPPTFGGGTKLEIK |
| 61 | 539-SP1-C8, J6M0, 1C8-6A, 1C8-EH, 1C8-402, 1C8-507, 1C8-610, 1C8-6A3, 1C8-27 LC-CDR1 | QDISNY |
| 62 | 539-SP1-C8, J6M0, 1C8-6A, 1C8-EH, 1C8-402, 1C8-403, 1C8-507, 1C8-610, 1C8-6A3, 1C8-25, 1C8-27, h1C8 CON LC-CDR2 | YTS |
| 63 | 539-SP1-C8, 1C8-6A, 1C8-EH, 1C8-403, 1C8-507, 1C8-610, 1C8-6A3 LC-CDR3 | QQGNTFPPT |
| 64 | 539-SP1-C8 LC-FR1 | DIQMTQTTSSLSASLGDRVTISCRAS |
| 65 | 539-SP1-C8 LC-FR2 | LNWYQQKPDGTVKLLMC |
| 66 | 539-SP1-C8 LC-FR3 | RLHSGVPSRFSGSGSGTDFSLTISNLEQEDIATYFC |

-continued

| SEQ ID NO: | DESCRIPTION | SEQUENCE |
|---|---|---|
| 67 | 539-SP5-D7 VH | EVMLVDSGGNLVKPGGSLKLSCAASGFTFSNYVISWVRQTPEKRLEWVATISTVGTNTYYPD SVRGRFTISRDNAENTLYLQMSSLRSEDTAIYYCSRHKYGYDDPSYAMDYWGQGTSVTVSS |
| 68 | 539-SP5-D7 HC-CDR1 | GFTFSNYV |
| 69 | 539-SP5-D7 HC-CDR2 | ISTVGTNT |
| 70 | 539-SP5-D7 HC-CDR3 | SRHKYGYDDPSYAMDY |
| 71 | 539-SP5-D7 HC-FR1 | EVMLVDSGGNLVKPGGSLKLSCAAS |
| 72 | 539-SP5-D7 HC-FR2 | ISWVRQTPEKRLEWVAT |
| 73 | 539-SP5-D7 HC-FR3 | YYPDSVRGRFTISRDNAENTLYLQMSSLRSEDTAIYYC |
| 74 | 539-SP5-D7, 552-LN1-E9, 1-1-A1_BM, 1-1-A1 HC-FR4 | WGQGTSVTVSS |
| 75 | 539-SP5-D7 VL | QLVLTQSSSASFSLGASAKLTCTLSSQHSTYTIEWYQQQPLKPPKYVMELKKDGSHSTGDGIP DRFSGSSSGADRYLSISNIQAEDEAIYICGVGDTVKEQFVYVFGGGTKVTVL |
| 76 | 539-SP5-D7 LC-CDR1 | SQHSTYT |
| 77 | 539-SP5-D7 LC-CDR2 | LKKDGSH |
| 78 | 539-SP5-D7 LC-CDR3 | GVGDTVKEQFVYV |
| 79 | 539-SP5-D7 LC-FR1 | QLVLTQSSSASFSLGASAKLTCTLS |
| 80 | 539-SP5-D7 LC-FR2 | IEWYQQQPLKPPKYVME |
| 81 | 539-SP5-D7 LC-FR3 | STGDGIPDRFSGSSSGADRYLSISNIQAEDEAIYIC |
| 82 | 539-SP5-D7 LC-FR4 | FGGGTKVTVL |
| 83 | 539-SP7-F4 VH | EVQLQQSGPELVKPGASMKISCKASGYSFTGYIMNWVKQSHGKNLEWIGLINPYNGDSIYNQ KFKGKATLTVDKSSSTAYMELFSLTSEDSTVYYCAAGEEFAYWGQGTLVTVSA |
| 84 | 539-SP7-F4 HC-CDR1 | GYSFTGYI |
| 85 | 539-SP7-F4 HC-CDR2 | INPYNGDS |
| 86 | 539-SP7-F4 HC-CDR3 | AAGEEFAY |
| 87 | 539-SP7-F4 HC-FR1 | EVQLQQSGPELVKPGASMKISCKAS |
| 88 | 539-SP7-F4 HC-FR2 | MNWVKQSHGKNLEWIGL |
| 89 | 539-SP7-F4 HC-FR3 | IYNQKFKGKATLTVDKSSSTAYMELFSLTSEDSTVYYC |
| 90 | 539-SP7-F4 VL | DIQMTQTSSSLSASLGDRVTISCRASQDISIYLNWFQQKPDGTVKLLIYFTSRLHPGVPSRFSA SGSGTDYSLTISHLEHEDIATYFCQQGNTLPRTFGGGTKVELK |
| 91 | 539-SP7-F4 LC-CDR1 | QDISIY |
| 92 | 539-SP7-F4 LC-CDR2 | FTS |
| 93 | 539-SP7-F4 LC-CDR3 | QQGNTLPRT |
| 94 | 539-SP7-F4 LC-FR1 | DIQMTQTSSSLSASLGDRVTISCRAS |
| 95 | 539-SP7-F4 LC-FR2 | LNWFQQKPDGTVKLLIY |
| 96 | 539-SP7-F4 LC-FR3 | RLHPGVPSRFSASGSGTDYSLTISHLEHEDIATYFC |
| 97 | 539-SP7-F4 LC-FR4 | FGGGTKVELK |
| 98 | 552-LN1-E9 VH | QIQLVQSGPELKKPGETVKISCKASGYTFTDYSIYWVKQAPGKGLKWMGWINTETGEPTYAD DFKGRFAFSLETSASSAYLQINTLKNEDTATYFCSISYYYAMDYWGQGTSVTVSS |

-continued

| SEQ ID NO: | DESCRIPTION | SEQUENCE |
|---|---|---|
| 99 | 552-LN1-E9, 552-LN2-E6, 552-LN1-F4, 1E9-4H, 1E9-QE HC-CDR1 | GYTFTDYS |
| 100 | 552-LN1-E9, 552-LN2-E6, 552-LN1-F4, 552-LN2-F8, 1E9-4H HC-CDR2 | INTETGEP |
| 101 | 552-LN1-E9, 1E9-4H, 1E9-QE HC-CDR3 | SISYYYAMDY |
| 102 | 552-LN1-E9, 552-LN2-F8 HC-FR1 | QIQLVQSGPELKKPGETVKISCKAS |
| 103 | 552-LN1-E9 HC-FR2 | IYWVKQAPGKGLKWMGW |
| 104 | 552-LN1-E9 HC-FR3 | TYADDFKGRFAFSLETSASSAYLQINTLKNEDTATYFC |
| 105 | 552-LN1-E9 VL | DIVLTQSPASLAVSLGQRATISCRASKSVSTSGYSFLHWYQQKPGQPPKLLIYFASNLESGVPA RFSGSGSGTDFTLNIHPVEEEDAATYYCQHSRELPRTFGGGTKLEIK |
| 106 | 552-LN1-E9, 1E9-4H 1E9-QE LC-CDR1 | KSVSTSGYSF |
| 107 | 552-LN1-E9, 1E9-4H, 1E9-QE LC-CDR2 | FAS |
| 108 | 552-LN1-E9, 552-LN2-E6, 552-LN1-F4, 552-LN2-F8, 1E9-4H, 1E9-QE, 2F8-2Q, 2F8-5U LC-CDR3 | QHSRELPRT |
| 109 | 552-LN1-E9 LC-FR1 | DIVLTQSPASLAVSLGQRATISCRAS |
| 110 | 552-LN1-E9, 552-LN2-E6, 552-LN1-F4 LC-FR2 | LHWYQQKPGQPPKLLIY |
| 111 | 552-LN1-E9, 552-LN2-E6, 552-LN2-F8 LC-FR3 | NLESGVPARFSGSGSGTDFTLNIHPVEEEDAATYYC |
| 112 | 552-LN2-E6 VH | QIQLVQSGPELKKPGETVKISCMASGYTFTDYSVRWVKQAPGKGLEWMGWINTETGEPTYA DDFKGRFAFSLETSASTAYLQINNLKNEDTATYFCAISYYYALDYWGHGTSVTVSS |
| 113 | 552-LN2-E6, 552-LN1-F4 HC-CDR3 | AISYYYALDY |
| 114 | 552-LN2-E6, 552-LN1-F4 HC-FR1 | QIQLVQSGPELKKPGETVKISCMAS |
| 115 | 552-LN2-E6, 552-LN1-F4 HC-FR2 | VRWVKQAPGKGLEWMGW |
| 116 | 552-LN2-E6 HC-FR3 | TYADDFKGRFAFSLETSASTAYLQINNLKNEDTATYFC |
| 117 | 552-LN2-E6, 552-LN1-F4 HC-FR4 | WGHGTSVTVSS |
| 118 | 552-LN2-E6 VL | DIVLTQSPASLTVSLGQRATISCRASKSVSTSVYSFLHWYQQKPGQPPKLLIYLASNLESGVPA RFSGSGSGTDFTLNIHPVEEEDAATYYCQHSRELPRTFGGGTKLEIK |
| 119 | 552-LN2-E6 LC-CDR1 | KSVSTSVYSF |
| 120 | 552-LN2-E6, 552-LN1-F4, 552-LN2-F8, 2F8-2Q, 2F8-5U LC-CDR2 | LAS |
| 121 | 552-LN2-E6, 552-LN1-F4 LC-FR1 | DIVLTQSPASLTVSLGQRATISCRAS |

-continued

| | Sequences | |
|---|---|---|

| SEQ ID NO: | DESCRIPTION | SEQUENCE |
|---|---|---|
| 122 | 552-LN1-F4 VH | QIQLVQSGPELKKPGETVKISCMASGYTFTDYSVRWVKQAPGKGLEWMGWINTETGEPTYA<br>HDFKGRFAFSLETSASTAYLQINNLKDEDTSTYFCAISYYYALDYWGHGTSVTVSS |
| 123 | 552-LN1-F4 HC-FR3 | TYAHDFKGRFAFSLETSASTAYLQINNLKDEDTSTYFC |
| 124 | 552-LN1-F4 VL | DIVLTQSPASLTVSLGQRATISCRASKSVSTSGYNFLHWYQQKPGQPPKLLIYLASNLESGAPA<br>RFSGSGSGTDFTLNIHPVEEEDAATYYCQHSRELPRTFGGGTKLEIK |
| 125 | 552-LN1-F4, 552-LN2-F8, 2F8-2Q, 2F8-5U LC-CDR1 | KSVSTSGYNF |
| 126 | 552-LN1-F4 LC-FR3 | NLESGAPARFSGSGSGTDFTLNIHPVEEEDAATYYC |
| 127 | 552-LN2-F8 VH | QIQLVQSGPELKKPGETVKISCKASGYTFTDYTMYWVKQAPGKGLKWMGWINTETGEPTYAD<br>DFKGRFVFSLETSANTAYLQINNLKNEDTATYFCAISYYYGMDYWGQGTSVTVTS |
| 128 | 552-LN2-F8, 2F8-2Q, 2F8-5U HC-CDR1 | GYTFTDYT |
| 129 | 552-LN2-F8, 2F8-2Q, 2F8-5U HC-CDR3 | AISYYYGMDY |
| 130 | 552-LN2-F8 HC-FR2 | MYWVKQAPGKGLKWMGW |
| 131 | 552-LN2-F8 HC-FR3 | TYADDFKGRFVFSLETSANTAYLQINNLKNEDTATYFC |
| 132 | 552-LN2-F8 HC-FR4 | WGQGTSVTVTS |
| 133 | 552-LN2-F8 VL | DIILTQSPASLAVSLGQRATITCRASKSVSTSGYNFVYWYQQKPGQPPKLLIYLASNLESGVPA<br>RFSGSGSGTDFTLNIHPVEEEDAATYYCQHSRELPRTFGGGTKLEIK |
| 134 | 552-LN2-F8 LC-FR1 | DIILTQSPASLAVSLGQRATITCRAS |
| 135 | 552-LN2-F8, 2F8-5U LC-FR2 | VYWYQQKPGQPPKLLIY |
| 136 | 538-SP5-B10, 539-SP2-H3, 539-SP1-C8 VH consensus | EVQLQQSGPELVKPGX$_1$SVKMSCKASGYTFTX$_2$YVX$_3$HWVKQKPGX$_4$GLEWIX$_5$YX$_6$LPX$_7$NDX$_8$<br>X$_9$KYNEKFKGKATLTSDKSSX$_{10}$TAYMX$_{11}$X$_{12}$SX$_{13}$LTSEDSAVYYCARX$_{14}$X$_{15}$X$_{16}$X$_{17}$X$_{18}$X$_{19}$X$_{20}$X$_{21}$<br>X$_{22}$FX$_{23}$YWGQGTX$_{24}$X$_{25}$TVSX$_{26}$<br>wherein X$_1$ = A or S, X$_2$ = S or N, X$_3$ = M or I,<br>X$_4$ = Q or R, X$_5$= G or A, X$_6$ = I or V, X$_7$ = Y or F,<br>X$_8$ = V or G, X$_9$= T or I, X$_{10}$ = S or N, X$_{11}$ = E or D,<br>X$_{12}$= L or F, X$_{13}$ = S or V, X$_{14}$ = W or Y, X$_{15}$ =<br>absent or G, X$_{16}$ = D or E, X$_{17}$ = W, F or Y,<br>X$_{18}$ = D or E, X$_{19}$ = D, E or G, X$_{20}$ = G or S, X$_{21}$ =<br>absent or I, X$_{22}$ = Y, W or absent, X$_{23}$ = D<br>or P, X$_{24}$ = T, L or A, X$_{25}$ = L or V, and X$_{26}$ = S or A |
| 137 | 538-SP5-B10, 539-SP2-H3, 539-SP1-C8 consensus HC-CDR1 | GYTFTX$_{27}$YV<br>wherein X$_{27}$ = S or N |
| 138 | 538-SP5-B10, 539-SP2-H3, 539-SP1-C8 consensus HC-CDR2 | X$_{28}$LPX$_{29}$NDX$_{30}$X$_{31}$<br>wherein X$_{28}$ = I or V, X$_{29}$ = Y or F, X$_{30}$ = V or G and X$_{31}$ = T or I |
| 139 | 538-SP5-B10, 539-SP2-H3, 539-SP1-C8 consensus HC-CDR3 | ARX$_{32}$X$_{33}$X$_{34}$X$_{35}$X$_{36}$X$_{37}$X$_{38}$X$_{39}$X$_{40}$FX$_{41}$Y<br>wherein X$_{32}$ = W or Y, X$_{33}$ = absent or G,<br>X$_{34}$ = D or E, X$_{35}$ = W, F or Y, X$_{36}$ = D or E, X$_{37}$ = D, E<br>or G, X$_{38}$ = G or S, X$_{39}$ = absent or I,<br>X$_{40}$ = Y, W or absent, X$_{41}$ = D or P |
| 140 | 538-SP5-B10, 539-SP2-H3, 539-SP1-C8 consensus HC-FR1 | EVQLQQSGPELVKPGX$_{42}$SVKMSCKAS<br>wherein X$_{42}$ = A or S |
| 141 | 538-SP5-B10, 539-SP2-H3, 539-SP1-C8 consensus HC-FR2 | X$_{43}$HWVKQKPGX$_{44}$GLEWIX$_{45}$Y<br>wherein X$_{43}$ = M or I, X$_{44}$ = Q or R and X$_{45}$ = G or A |

Sequences

| SEQ ID NO: | DESCRIPTION | SEQUENCE |
|---|---|---|
| 142 | 538-SP5-B10, 539-SP2-H3, 539-SP1-C8 consensus HC-FR3 | KYNEKFKGATLTSDKSSX$_{46}$TAYMX$_{47}$X$_{48}$SX$_{49}$LTSEDSAVYYC<br>wherein X$_{46}$ = S or N, X$_{47}$ = E or D, X$_{48}$ = L or F and X$_{49}$ = S or V |
| 143 | 538-SP5-B10, 539-SP2-H3, 539-SP1-C8 consensus HC-FR4 | WGQGTX$_{50}$X$_{51}$ TVSX$_{52}$<br>wherein X$_{50}$ = T, L or A, X$_{51}$ = L or V, and X$_{52}$ = S or A |
| 144 | 552-LN1-E9, 552-LN2-E6, 552-LN1-F4, 552-LN2-F8 VH consensus | QIQLVQSGPELKKPGETVKISCX$_{53}$ASGYTFTDYX$_{54}$X$_{55}$X$_{56}$WVKQAPGKGLX$_{57}$WMGWINTETG<br>EPTYAX$_{58}$DFKGRFX$_{59}$FSLETSAX$_{60}$X$_{61}$AYLQINX$_{62}$LKX$_{63}$EDTX$_{64}$TYFCX$_{65}$ISYYYX$_{66}$X$_{67}$DYWG<br>X$_{68}$GTSVTVX$_{69}$S<br>wherein X$_{53}$ = K or M, X$_{54}$ = S or T, X$_{55}$ = V, I or M,<br>X$_{56}$ = Y or R, X$_{57}$ = K or E, X$_{58}$ = D or H, X$_{59}$ = A or V,<br>X$_{60}$ = S or N, X$_{61}$ = T or S, X$_{62}$ = N or T,<br>X$_{63}$ = N or D, X$_{64}$ = A or S, X$_{65}$ = A or S, X$_{66}$ =<br>A or G, X$_{67}$ = L or M, X$_{68}$ = Q or H and X$_{69}$ = S or T |
| 145 | 552-LN1-E9, 552-LN2-E6, 552-LN1-F4, 552-LN2-F8 consensus HC-CDR1 | GYTFTDYX$_{70}$<br>wherein X$_{70}$ = S or T |
| 146 | 552-LN1-E9, 552-LN2-E6, 552-LN1-F4, 552-LN2-F8 consensus HC-CDR3 | X$_{71}$ISYYYX$_{72}$X$_{73}$DY<br>wherein X$_{71}$ = A or S, X$_{72}$ = A or G and X$_{73}$ = L or M |
| 147 | 552-LN1-E9, 552-LN2-E6, 552-LN1-F4, 552-LN2-F8 consensus HC-FR1 | QIQLVQSGPELKKPGETVKISCX$_{74}$AS<br>wherein X$_{74}$ = K or M |
| 148 | 552-LN1-E9, 552-LN2-E6, 552-LN1-F4, 552-LN2-F8 consensus HC-FR2 | X$_{75}$X$_{76}$WVKQAPGKGLX$_{77}$WMGW<br>wherein X$_{75}$ = V, I or M, X$_{76}$ = Y or R and X$_{77}$ = K or E |
| 149 | 552-LN1-E9, 552-LN2-E6, 552-LN1-F4, 552-LN2-F8 consensus HC-FR3 | TYAX$_{78}$DFKGRFX$_{79}$FSLETSAX$_{80}$X$_{81}$AYLQINX$_{82}$LKX$_{83}$EDTX$_{84}$TYFC<br>wherein X$_{78}$ = D or H, X$_{79}$ = A or V, X$_{80}$ = S or N,<br>X$_{81}$ = T or S, X$_{82}$ = N or T, X$_{83}$ = N or D and<br>X$_{84}$ = A or S |
| 150 | 552-LN1-E9, 552-LN2-E6, 552-LN1-F4, 552-LN2-F8 consensus HC-FR4 | WGX$_{85}$GTSVTVX$_{86}$S<br>wherein X$_{85}$ = Q or H and X$_{86}$ = S or T |
| 151 | 552-LN1-E9, 552-LN2-E6, 552-LN1-F4, 552-LN2-F8 VL consensus | DIVLTQSPASLX$_{87}$VSLGQRATIX$_{88}$CRASKSVSTSX$_{89}$YX$_{90}$FX$_{91}$X$_{92}$WYQQKPGQPPKLLIYX$_{93}$AS<br>NLESGX$_{94}$PARFSGSGSGTDFTLNIHPVEEEDAATYYCQHSRELPRTFGGGTKLEIK<br>wherein X$_{87}$ = T or A, X$_{88}$ = S or T, X$_{89}$ = G or V,<br>X$_{90}$ = S or N, X$_{91}$ = L or V, X$_{92}$ = Hor Y, X$_{93}$ =<br>L or F and X$_{94}$ = V or A |
| 152 | 552-LN1-E9, 552-LN2-E6, 552-LN1-F4, 552-LN2-F8 consensus LC-CDR1 | KSVSTSX$_{95}$YX$_{96}$F<br>wherein X$_{95}$ = G or V and X$_{96}$ = S or N |
| 153 | 552-LN1-E9, 552-LN2-E6, 552-LN1-F4, 552-LN2-F8 consensus LC-CDR2 | X$_{97}$AS<br>wherein X$_{97}$ = L or F |
| 154 | 552-LN1-E9, 552-LN2-E6, 552-LN1-F4, 552-LN2-F8 consensus LC-FR1 | DIVLTQSPASLX$_{98}$VSLGQRATIX$_{99}$CRAS<br>wherein X$_{98}$ = T or A and X$_{99}$ = S or T |
| 155 | 552-LN1-E9, 552-LN2-E6, 552-LN1-F4, 552-LN2-F8 consensus LC-FR2 | X$_{100}$X$_{101}$WYQQKPGQPPKLLIY<br>wherein X$_{100}$ = L or V and X$_{101}$ = Hor Y |

-continued

| SEQ ID NO: | DESCRIPTION | SEQUENCE |
|---|---|---|
| 156 | 552-LN1-E9, 552-LN2-E6, 552-LN1-F4, 552-LN2-F8 consensus LC-FR3 | NLESGX$_{102}$PARFSGSGSGTDFTLNIHPVEEEDAATYYC wherein X$_{102}$ = V or A |
| 157 | J6M0 VH | QVQLVQSGAEVKKPGSSVKVSCKASGGTFSNYWMHWVRQAPGQGLEWMGATYRGHSDTY YNQKFKGRVTITADKSTSTAYMELSSLRSEDTAVYYCARGAIYDGYDVLDNWGQGTLVTVSS |
| 158 | J6M0 HC-CDR1 | GGTFSNYW |
| 159 | J6M0 HC-CDR2 | TYRGHSDT |
| 160 | J6M0 HC-CDR3 | ARGAIYDGYDVLDN |
| 161 | J6M0 HC-FR1 | QVQLVQSGAEVKKPGSSVKVSCKAS |
| 162 | J6M0 HC-FR2 | MHWVRQAPGQGLEWMGA |
| 163 | J6M0 HC-FR3 | YYNQKFKGRVTITADKSTSTAYMELSSLRSEDTAVYYC |
| 164 | J6M0 HC-FR4 | WGQGTLVTVSS |
| 165 | J6M0 VL | DIQMTQSPSSLSASVGDRVTITCSASQDISNYLNWYQQKPGKAPKLLIYYTSNLHSGVPSRFS GSGSGTDFTLTISSLQPEDFATYYCQQYRKLPWTFGQGTKLEIK |
| 166 | J6M0 LC-CDR3 | QQYRKLPWT |
| 167 | J6M0 LC-FR1 | DIQMTQSPSSLSASVGDRVTITCSAS |
| 168 | J6M0 LC-FR2 | LNWYQQKPGKAPKLLIY |
| 169 | J6M0 LC-FR3 | NLHSGVPSRFSGSGSGTDFTLTISSLQPEDFATYYC |
| 170 | J6M0, 1E9-QE 5B10-4Y LC-FR4 | FGQGTKLEIK |
| 171 | Human CD47 isoform OA3-323 (UniProt: Q08722-1, v1) | MWPLVAALLLGSACCGSAQLLFNKTKSVEFTFCNDTVVIPCFVTNMEAQNTTEVYVKWKFKG RDIYTFDGALNKSTVPTDFSSAKIEVSQLLKGDASLKMDKSDAVSHTGNYTCEVTELTREGETII ELKYRVVSWFSPNENILIVIFPIFAILLFWGQFGIKTLKYRSGGMDEKTIALLVAGLVITVIVIVGAIL FVPGEYSLKNATGLGLIVTSTGILILLHYYVFSTAIGLTSFVIAILVIQVIAYILAVVGLSLCIAACIPM HGPLLISGLSILALAQLLGLVYMKFVASNQKTIQPPRKAVEEPLNAFKESKGMMNDE |
| 172 | Human CD47 isoform OA3-293 (UniProt: Q08722-2) | MWPLVAALLLGSACCGSAQLLFNKTKSVEFTFCNDTVVIPCFVTNMEAQNTTEVYVKWKFKG RDIYTFDGALNKSTVPTDFSSAKIEVSQLLKGDASLKMDKSDAVSHTGNYTCEVTELTREGETII ELKYRVVSWFSPNENILIVIFPIFAILLFWGQFGIKTLKYRSGGMDEKTIALLVAGLVITVIVIVGAIL FVPGEYSLKNATGLGLIVTSTGILILLHYYVFSTAIGLTSFVIAILVIQVIAYILAVVGLSLCIAACIPM HGPLLISGLSILALAQLLGLVYMKFV |
| 173 | Human CD47 isoform OA3-305 (UniProt: Q08722-3) | MWPLVAALLLGSACCGSAQLLFNKTKSVEFTFCNDTVVIPCFVTNMEAQNTTEVYVKWKFKG RDIYTFDGALNKSTVPTDFSSAKIEVSQLLKGDASLKMDKSDAVSHTGNYTCEVTELTREGETII ELKYRVVSWFSPNENILIVIFPIFAILLFWGQFGIKTLKYRSGGMDEKTIALLVAGLVITVIVIVGAIL FVPGEYSLKNATGLGLIVTSTGILILLHYYVFSTAIGLTSFVIAILVIQVIAYILAVVGLSLCIAACIPM HGPLLISGLSILALAQLLGLVYMKFVASNQKTIQPPRNN |
| 174 | Human CD47 isoform OA3-312 (UniProt: Q08722-4) | MWPLVAALLLGSACCGSAQLLFNKTKSVEFTFCNDTVVIPCFVTNMEAQNTTEVYVKWKFKG RDIYTFDGALNKSTVPTDFSSAKIEVSQLLKGDASLKMDKSDAVSHTGNYTCEVTELTREGETII ELKYRVVSWFSPNENILIVIFPIFAILLFWGQFGIKTLKYRSGGMDEKTIALLVAGLVITVIVIVGAIL FVPGEYSLKNATGLGLIVTSTGILILLHYYVFSTAIGLTSFVIAILVIQVIAYILAVVGLSLCIAACIPM HGPLLISGLSILALAQLLGLVYMKFVASNQKTIQPPRKAVEEPLN |
| 175 | Mature human CD47 isoform OA3-323 (UniProt: Q08722-1, v1 positions 19-323) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETII ELKYRVVSWFSPNENILIV IFPIFAILLFWGQFGIKTLKYRSGGMDEKTIALLVAGLVITVIVIVGAILFVPGEYSLKNATGLGLIV TSTGILILLHYYVFSTAIGLTSFVIAILVIQVIAYILAVVGLSLCIAACIPMHGPLLISGLSILALAQ LLGLVYMKFVASNQKTIQPPRKAVEEPLNAFKESKGMMNDE |
| 176 | Mature human CD47 isoform OA3-293 (UniProt: Q08722-2 positions 19-292) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETII ELKYRVVSWFSPNENILIV IFPIFAILLFWGQFGIKTLKYRSGGMDEKTIALLVAGLVITVIVIVGAILFVPGEYSLKNATGLGLIV TSTGILILLHYYVFSTAIGLTSFVIAILVIQVIAYILAVVGLSLCIAACIPMHGPLLISGLSILALAQ LLGLVYMKFV |

-continued

| SEQ ID NO: | DESCRIPTION | SEQUENCE |
|---|---|---|
| 177 | Mature human CD47 isoform OA3-305 (UniProt: Q08722-3, positions 19-305) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETIIELKYRVVSWFSPNENILIV IFPIFAILLFWGQFGIKTLKYRSGGMDEKTIALLVAGLVITVIVIVGAILFVPGEYSLKNATGLGLIV TSTGILILLHYYVFSTAIGLTSFVIAILVIQVIAYILAVVGLSLCIAACIPMHGPLLISGLSILALAQ LLGLVYMKFVASNQKTIQPPRNN |
| 178 | Mature human CD47 isoform OA3-312 (UniProt: Q08722-4 positions 19-311) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETIIELKYRVVSWFSPNENILIV IFPIFAILLFWGQFGIKTLKYRSGGMDEKTIALLVAGLVITVIVIVGAILFVPGEYSLKNATGLGLIV TSTGILILLHYYVFSTAIGLTSFVIAILVIQVIAYILAVVGLSLCIAACIPMHGPLLISGLSILALAQ LLGLVYMKFVASNQKTIQPPRKAVEEPLN |
| 179 | V-type lg-like domain (UniProt: Q08722-1 positions 19-127) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETII |
| 180 | Human CD47 extracellular region 1 (UniProt: Q08722-1 positions 19-141) | QLLFNKTKSVEFTFCNDTVVIPCFVTNMEAQNTTEVYVKWKFKGRDIYTFDGALNKSTVPTDF SSAKIEVSQLLKGDASLKMDKSDAVSHTGNYTCEVTELTREGETIIELKYRVVSWFSPNE |
| 181 | Human CD47 transmembrane region 1 (UniProt: Q08722-1 positions 142-162) | NILIVIFPIFAILLFWGQFGI |
| 182 | Human CD47 cytoplasmic region 1 (UniProt: Q08722-1 positions 163-176) | KTLKYRSGGMDEKT |
| 183 | Human CD47 transmembrane region 2 (UniProt: Q08722-1 positions 177-197) | IALLVAGLVITVIVIVGAILF |
| 184 | Human CD47 extracellular region 2 (UniProt: Q08722-1 positions 198-207) | VPGEYSLKNA |
| 185 | Human CD47 transmembrane region 3 (UniProt: Q08722-1 positions 208-228) | TGLGLIVTSTGILILLHYYVF |
| 186 | Human CD47 cytoplasmic region 2 (UniProt: Q08722-1 positions 229-235) | STAIGLT |
| 187 | Human CD47 transmembrane region 4 (UniProt: Q08722-1 positions 236-256) | SFVIAILVIQVIAYILAVVGL |
| 188 | Human CD47 extracellular region 3 (UniProt: Q08722-1 positions 257-268) | SLCIAACIPMHG |
| 189 | Human CD47 transmembrane region 5 (UniProt: Q08722-1 positions 269-289) | PLLISGLSILALAQLLGLVYM |
| 190 | Human CD47 cytoplasmic region 3 (UniProt: Q08722-1 positions 290-323) | KFVASNQKTIQPPRKAVEEPLNAFKESKGMMNDE |

-continued

| SEQ ID NO: | DESCRIPTION | SEQUENCE |
|---|---|---|
| 191 | Region of human CD47 targeted by 1-1-A1 and 1-1-A1_BM (UniProt: Q08722-1 positions 56-65) | VKWKFKGRDI |
| 192 | 1-1-A1_BM VH | QVQLQQSGPDLKKPGASVKVSCKVSGYTFTNYVIHWVRQKPGQGLEWMGYINPYNDGTKSN EKFKGKATLTSDKSSTSAYMELSSLTSEDTAVYYCASGGYYTMDYWGQGTSVTVSS |
| 193 | 1-1-A1_BM, 1-1-A1, 11A1H1, 11A1H2, 11A1H3, 11A1H4, 11A1H6, 11A1H8 HC-CDR2 | INPYNDGT |
| 194 | 1-1-A1_BM, 1-1-A1, 11A1H1, 11A1H2, 11A1H3, 11A1H4, 11A1H6, 11A1H8, 11A1H5, 11A1H7, 11A1H9, 11A1H10, 11A1H11 HC-CDR3 | ASGGYYTMDY |
| 195 | 1-1-A1_BM HC-FR1 | QVQLQQSGPDLKKPGASVKVSCKVS |
| 196 | 1-1-A1_BM HC-FR2 | IHWVRQKPGQGLEWMGY |
| 197 | 1-1-A1_BM HC-FR3 | KSNEKFKGKATLTSDKSSTSAYMELSSLTSEDTAVYYC |
| 198 | 1-1-A1_BM VL | DVVMTQTPLSLPVTLGDQASISCRSSQHLEYSNGYSYLHWYQQRPGQSPQLLIYKISNRFSGV PDRFSGSGSGTDFTLKISRVEAEDLGVYYCSQSTHVPYTFGGGTKLEIK |
| 199 | 1-1-A1_BM, 1-1-A1, 11A1H1, 11A1H2, 11A1H3, 11A1H4, 11A1H5, 11A1H10, 11A1H11 LC-CDR1 | QHLEYSNGYSY |
| 200 | 1-1-A1_BM, 1-1-A1, 11A1H1, 11A1H2, 11A1H3, 11A1H4, 11A1H5, 11A1H11 LC-CDR2 | KIS |
| 201 | 1-1-A1_BM, 1-1-A1, 11A1H1, 11A1H2, 11A1H3, 11A1H4, 11A1H5 11A1H6, 11A1H7 11A1H8, 11A1H9 11A1H10 LC-CDR3 | SQSTHVPYT |
| 202 | 1-1-A1_BM LC-FR1 | DVVMTQTPLSLPVTLGDQASISCRSS |
| 203 | 1-1-A1_BM LC-FR2 | LHWYQQRPGQSPQLLIY |
| 204 | 1-1-A1 VH | EVQLQQSGPDLVKPGASVKMSCKASGYTFTNYVIHWVKQKPGQGLEWIGYINPYNDGTKSN EKFKGKATLTSDKSSTSAYMELSSLTSEDSAVYYCASGGYYTMDYWGQGTSVTVSS |
| 205 | 1-1-A1 HC-FR1 | EVQLQQSGPDLVKPGASVKMSCKAS |
| 206 | 1-1-A1 HC-FR3 | KSNEKFKGKATLTSDKSSTSAYMELSSLTSEDSAVYYC |
| 207 | 1-1-A1 VL | DVVMTQTPLSLPVSLGDQASISCRSSQHLEYSNGYSYLHWYLQKPGQSPQLLIYKISNRFSGV PDRFSGSGSGTDFTLKISRVEAEDLGVYFCSQSTHVPYTFGGGTKLEIK |
| 208 | 1-1-A1 LC-FR1 | DVVMTQTPLSLPVSLGDQASISCRSS |
| 209 | 1-1-A1 LC-FR2 | LHWYLQKPGQSPQLLIY |
| 210 | 1-1-A1 LC-FR3 | NRFSGVPDRFSGSGSGTDFTLKISRVEAEDLGVYFC |

-continued

| SEQ ID NO: | DESCRIPTION | SEQUENCE |
|---|---|---|
| 211 | 11A1H1 VH | QVQLVQSGAEVKKPGASVKVSCKASGYTFTNYVIHWVRQAPGKGLEWMGYINPYNDGTKSN EKFKGRVTLTSDKSSTSAYMELSSLRSEDTAVYYCASGGYYTMDYWGQGTLVTVSS |
| 212 | 11A1H1, 11A1H2, 11A1H3, 11A1H4, 11A1H5 VL | DVVMTQSPLSLPVTLGQPASISCRSSQHLEYSNGYSYLHWYQQRPGQSPRLLIYKISNRFSGV PDRFSGSGSGTDFTLKISRVEAEDVGVYYCSQSTHVPYTFGGGTKVEIK |
| 213 | 11A1H2 VH | QVQLVQSGAEVKKPGASVKVSCKASGYTFTNYVIHWVRQAPGKGLEWMGYINPYNDGTKSN EKFKGRVTLTSDTSTTTAYMELSSLRSEDTAVYYCASGGYYTMDYWGQGTLVTVSS |
| 214 | 11A1H3 VH | QVQLVQSGAEVKKPGASVKVSCKASGYTFTNYVMHWVRQAPGQGLEWMGYINPYNDGTKS NEKFQGRVTLTSDTSTSTAYMELSSLRSEDTAVYYCASGGYYTMDYWGQGTLV |
| 215 | 11A1H4, 11A1H6, 11A1H8 VH | QVQLVQSGAEVKKPGASVKVSCKASGYTFTNYVIHWVRQAPGQGLEWMGYINPYNDGTKYN QKFKGRVTLTSDTSTTTAYMELSRLRSDDTAVYYCASGGYYTMDYWGQGTLV |
| 216 | 11A1H5, 11A1H7, 11A1H9, 11A1H10, 11A1H11 VH | QVQLVQSGAEVKKPGASVKVSCKASGYTFTGYVIHWVRQAPGQGLEWMGYINPYNGGTNYA QKFKGRVTLTSDTSTTTAYMELSRLRSEDTAVYYCASGGYYTMDYWGQGTLVTVSS |
| 217 | 11A1H6, 11A1H7 VL | DVVMTQSPLSLPVTLGQPASISCRSSQHLEYSQGYSYLHWYQQRPGQSPRLLIYKVSNRDSG VPDRFSGSGSGTDFTLKISRVEAEDVGVYYCSQSTHVPYTFGGGTKVEIK |
| 218 | 11A1H8, 11A1H9 VL | DVVMTQSPLSLPVTLGQPASISCRSSQHLEYSTGYSYLHWYQQRPGQSPRLLIYKVSNRDSG VPDRFSGSGSGTDFTLKISRVEAEDVGVYYCSQSTHVPYTFGGGTKVEIK |
| 219 | 11A1H10 VL | DVVMTQSPLSLPVTLGQPASISCRSSQHLEYSNGYSYLHWYQQRPGQSPRLLIYKVSNRDSG VPDRFSGSGSGTDFTLKISRVEAEDVGVYYCSQSTHVPYTFGGGTKVEIK |
| 220 | 11A1H11 VL | DVVMTQSPLSLPVTLGQPASISCRSSQHLEYSNGYSYLHWYQQRPGQSPRLLIYKISNRFSGV PDRFSGSGSGTDFTLKISRVEAEDVGVYYCSQGTHVPYTFGGGTKVEIK |
| 221 | 11A1H5, 11A1H7, 11A1H9, 11A1H10, 11A1H11 HC-CDR1 | GYTFTGYV |
| 222 | 11A1H5, 11A1H7, 11A1H9, 11A1H10, 11A1H11 HC-CDR2 | INPYNGGT |
| 223 | 11A1H6, 11A1H7 LC-CDR1 | QHLEYSQGYSY |
| 224 | 11A1H8, 11A1H9 LC-CDR1 | QHLEYSTGYSY |
| 225 | 11A1H6, 11A1H7, 11A1H8, 11A1H9, 11A1H10 LC-CDR2 | KVS |
| 226 | 11A1H11 LC-CDR3 | SQGTHVPYT |
| 227 | 11A1H1, 11A1H2, 11A1H3, 11A1H4, 11A1H5, 11A1H6, 11A1H7, 11A1H8, 11A1H9, 11A1H10, 11A1H11, 1E9-4H, 1E9-QE, 5B10-4Y, 1C8-402, 1C8-403, 1C8-507, 1C8-610, 1C8-6A3, 1C8-25, 1C8-27, h1C8 CON HC-FR1 | QVQLVQSGAEVKKPGASVKVSCKAS |
| 228 | 11A1H1, 11A1H2, HC-FR2 | IHWVRQAPGKGLEWMGY |
| 229 | 11A1H3, 1C8-6A HC-FR2 | MHWVRQAPGQGLEWMGY |

-continued

| | | Sequences |
|---|---|---|

| SEQ ID NO: | DESCRIPTION | SEQUENCE |
|---|---|---|
| 230 | 11A1H4, 11A1H5, 11A1H6, 11A1H7, 11A1H8, 11A1H9, 11A1H10, 11A1H11 HC-FR2 | IHWVRQAPGQGLEWMGY |
| 231 | 11A1H1 HC-FR3 | KSNEKFKGRVTLTSDKSSTSAYMELSSLRSEDTAVYYC |
| 232 | 11A1H2 HC-FR3 | KSNEKFKGRVTLTSDTSTTTAYMELSSLRSEDTAVYYC |
| 233 | 11A1H3 HC-FR3 | KSNEKFQGRVTLTSDTSTSTAYMELSSLRSEDTAVYYC |
| 234 | 11A1H4, 11A1H6, 11A1H8 HC-FR3 | KYNQKFKGRVTLTSDTSTTTAYMELSRLRSDDTAVYYC |
| 235 | 11A1H5, 11A1H7, 11A1H9, 11A1H10, 11A1H11 HC-FR3 | NYAQKFKGRVTLTSDTSTTTAYMELSRLRSEDTAVYYC |
| 236 | 11A1H1, 11A1H2, 11A1H5, 11A1H7, 11A1H9, 11A1H10, 11A1H11, 1E9-4H, 1E9-QE, 2F8-2Q, 2F8-5U, 5B10-4Y, 5B10-51, 1C8-6A, 1C8-EH, 1C8-402, 1C8-403, 1C8-507, 1C8-610, 1C8-6A3 HC-FR4 | WGQGTLVTVSS |
| 237 | 11A1H3, 11A1H4, 11A1H6, 11A1H8 HC-FR4 | WGQGTLV |
| 238 | 11A1H1, 11A1H2, 11A1H3, 11A1H4, 11A1H5, 11A1H6, 11A1H7, 11A1H8, 11A1H9, 11A1H10, 11A1H11 LC-FR1 | DVVMTQSPLSLPVTLGQPASISCRSS |
| 239 | 11A1H1, 11A1H2, 11A1H3, 11A1H4, 11A1H5, 11A1H6, 11A1H7, 11A1H8, 11A1H9, 11A1H10, 11A1H11 LC-FR2 | LHWYQQRPGQSPRLLIY |
| 240 | 11A1H1, 11A1H2, 11A1H3, 11A1H4, 11A1H5, 11A1H11, 5B10-4Y LC-FR3 | NRFSGVPDRFSGSGSGTDFTLKISRVEAEDVGVYYC |
| 241 | 11A1H6, 11A1H7, 11A1H8, 11A1H9, 11A1H10 LC-FR3 | NRDSGVPDRFSGSGSGTDFTLKISRVEAEDVGVYYC |
| 242 | 11A1H1, 11A1H2, 11A1H3, 11A1H4, 11A1H5, 11A1H6, 11A1H7, 11A1H8, 11A1H9, 11A1H10, 11A1H11, 5B10-51, 1C8-6A, 1C8-EH, 1C8-402, 1C8-403, 1C8-507, 1C8-6A3 LC-FR4 | FGGGTKVEIK |
| 243 | 11A1H_C HC-CDR1 | GYTFTX$_{103}$YV wherein X$_{103}$ = N or G |
| 244 | 11A1H_C HC-CDR2 | INPYNX$_{104}$GT wherein X$_{104}$ = D or G |

-continued

| SEQ ID NO: | DESCRIPTION | SEQUENCE |
|---|---|---|
| 245 | 11A1H_C LC-CDR1 | QHLEYSX$_{105}$GYSY<br>wherein X$_{105}$ = N, Q or T |
| 246 | 11A1H_C LC-CDR2 | KX$_{106}$S<br>wherein X$_{106}$ = I or V |
| 247 | 11A1H_C LC-CDR3 | SQX$_{107}$THVPYT<br>wherein X$_{107}$ = S or G |
| 248 | 11A1H_C HC-FR2 | X$_{108}$HWVRQAPGX$_{109}$GLEWMGY<br>wherein X$_{108}$ = I or M and X$_{109}$ = Q or K |
| 249 | 11A1H_C HC-FR3 | X$_{110}$X$_{111}$X$_{112}$X$_{113}$KFX$_{114}$RVTLTSDX$_{115}$SX$_{116}$SX$_{117}$AYMELSX$_{118}$LRSX$_{119}$DTAVYYC<br>wherein X$_{110}$ = K or N, X$_{111}$ = S or Y,<br>X$_{112}$ = N or A, X$_{113}$ = E or Q, X$_{114}$ = K or Q, X$_{115}$ = T or K,<br>X$_{116}$ = T or S, X$_{117}$ = T or S, X$_{118}$ = S or R and X$_{119}$ = E or D |
| 250 | 11A1H_C HC-FR4 | WGQGTLVX$_{120}$X$_{121}$X$_{122}$X$_{123}$<br>wherein X$_{120}$ = T or absent, X$_{121}$ = V or absent,<br>X$_{122}$ = S or absent and X$_{123}$ = S or absent |
| 251 | 11A1H_C LC-FR3 | NRX$_{124}$SGVPDRFSGSGSGTDFTLKISRVEAEDVGVYYC<br>wherein X$_{124}$ = D or F |
| 252 | 11A1H_C VH | QVQLVQSGAEVKKPGASVKVSCKASGYTFTX$_{125}$YVX$_{126}$HWVRQAPGX$_{127}$GLEWMGYINPYNX$_{128}$<br>GTX$_{129}$X$_{130}$X$_{131}$X$_{132}$KFX$_{133}$GRVTLTSDX$_{134}$SX$_{135}$SX$_{136}$AYMELSX$_{137}$LRSX$_{138}$DTAVYYCASGG<br>YYTMDYWGQGTLVX$_{139}$X$_{140}$X$_{141}$X$_{142}$<br>wherein X$_{125}$ = N or G, X$_{126}$ = I or M,<br>X$_{127}$ = Q or K, X$_{128}$ = D or G, X$_{129}$ = K or N, X$_{130}$ = S or Y,<br>X$_{131}$ = N or A, X$_{132}$ = E or Q, X$_{133}$ = K or Q,<br>X$_{134}$ = T or K, X$_{135}$ = T or S, X$_{136}$ = T or S, X$_{137}$ = S<br>or R, X$_{138}$ = E or D, X$_{139}$ = T or absent,<br>X$_{140}$ = V or absent, X$_{141}$ = S or absent and X$_{142}$ = S or<br>absent |
| 253 | 11A1H_C VL | DVVMTQSPLSLPVTLGQPASISCRSSQHLEYSX$_{143}$GYSYLHWYQQRPGQSPRLLIYKX$_{144}$SNR<br>X$_{145}$SGVPDRFSGSGSGTDFTLKISRVEAEDVGVYYCSQX$_{146}$THVPYTFGGGTKVEIK<br>wherein X$_{143}$ = N, Q or T, X$_{144}$ = I or V,<br>X$_{145}$ = D or F and X$_{146}$ = S or G |
| 254 | Human IgG1 constant region (IGHG1; UniProt:P01857-1, v1) | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| 255 | CH1 IgG1 (positions 1-98 of P01857-1, v1) | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKV |
| 256 | Hinge IgG1 (positions 99-110 of P01857-1, v1) | EPKSCDKTHTCP |
| 257 | CH2 IgG1 (positions 111-223 of P01857-1, v1) | PCPAPELLGGPSVFLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKAK |
| 258 | CH3 IgG1 (positions 224-330 of P01857-1, v1) | GQPREPQVYTLPPSRDELTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| 259 | Human IgG1 constant region G1m3 allotype (K214R, D356E and L358M (EU numbering) relative to P01857-1) | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRVEPKSCDKTHTCPPCPAPELLGGPSVFL<br>FPPKPKDTLMISRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| 260 | CH1 IgG1 G1m3 allotype | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRV |

-continued

| SEQ ID NO: | DESCRIPTION | SEQUENCE |
|---|---|---|
| 261 | CH3 IgG1 G1m3 allotype | GQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 262 | Cκ CL (IGKC; UniProt: P01834-1, v2) | RTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 263 | Cλ CL1 (IGLC1; UniProt: P0CG04-1, v1) | GQPKANPTVTLFPPSSEELQANKATLVCLISDFYPGAVTVAWKADGSPVKAGVETTKPSKQS NNKYAASSYLSLTPEQWKSHRSYSCQVTHEGSTVEKTVAPTECS |
| 264 | Cλ CL2 (IGLC2; UniProt: P0DOY2-1, v1) | GQPKAAPSVTLFPPSSEELQANKATLVCLISDFYPGAVTVAWKADSSPVKAGVETTTPSKQSN NKYAASSYLSLTPEQWKSHRSYSCQVTHEGSTVEKTVAPTECS |
| 265 | Cλ CL3 (IGLC3; UniProt: P0DOY3-1, v1) | GQPKAAPSVTLFPPSSEELQANKATLVCLISDFYPGAVTVAWKADSSPVKAGVETTTPSKQSN NKYAASSYLSLTPEQWKSHKSYSCQVTHEGSTVEKTVAPTECS |
| 266 | Cλ CL6 (IGLC6; UniProt: P0CF74-1, v1) | GQPKAAPSVTLFPPSSEELQANKATLVCLISDFYPGAVKVAWKADGSPVNTGVETTTPSKQS NNKYAASSYLSLTPEQWKSHRSYSCQVTHEGSTVEKTVAPAECS |
| 267 | Cλ CL7 (IGLC7; UniProt: A0M8Q6-1, v3) | GQPKAAPSVTLFPPSSEELQANKATLVCLVSDFNPGAVTVAWKADGSPVKVGVETTKPSKQS NNKYAASSYLSLTPEQWKSHRSYSCRVTHEGSTVEKTVAPAECS |
| 268 | C220S Hinge | EPKSSDKTHTCP |
| 269 | CH2-CH3 (T366W, S354C) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLP PCRDELTKNQVSLWCLVKGFYPSDIAVEWESNGQPENNYKTTPPVLDSDGSFFLYSKLTVDK SRWQQGNVFSCSVMHEALHNHYTQKSLSLSPGK |
| 270 | CH2-CH3 (T366S, L368A, Y407V, Y349C) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVCTLP PSRDELTKNQVSLSCAVKGFYPSDIAVEWESNGQPENNYKTTPPVLDSDGSFFLVSKLTVDK SRWQQGNVFSCSVMHEALHNHYTQKSLSLSPGK |
| 271 | CH2-CH3 (K409R) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGSFFLYSRLTVDKS RWQQGNVFSCSVMHEALHNHYTQKSLSLSPGK |
| 272 | Hinge-CH2-CH3 (C220S, T366W, S354C) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVYTLPPCRDELTKNQVSLWCLVKGFYPSDIAVEWESNGQPENNYKTTPPVLDSDG SFFLYSKLTVDKSRWQQGNVFSCSVMHEALHNHYTQKSLSLSPGK |
| 273 | Hinge-CH2-CH3 (C220S, T366S, L368A, Y407V, Y349C) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVCTLPPSRDELTKNQVSLSCAVKGFYPSDIAVEWESNGQPENNYKTTPPVLDSDGS FFLVSKLTVDKSRWQQGNVFSCSVMHEALHNHYTQKSLSLSPGK |
| 274 | Hinge-CH2-CH3 (C220S, K409R) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPVLDSDGS FFLYSRLTVDKSRWQQGNVFSCSVMHEALHNHYTQKSLSLSPGK |
| 275 | CH2-CH3 G1m3 (T366W, S354C) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLP PCREEMTKNQVSLWCLVKGFYPSDIAVEWESNGQPENNYKTTPPVLDSDGSFFLYSKLTVDK SRWQQGNVFSCSVMHEALHNHYTQKSLSLSPGK |
| 276 | CH2-CH3 G1m3 (T366S, L368A, Y407V, Y349C) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVCTLP PSREEMTKNQVSLSCAVKGFYPSDIAVEWESNGQPENNYKTTPPVLDSDGSFFLVSKLTVDK SRWQQGNVFSCSVMHEALHNHYTQKSLSLSPGK |
| 277 | CH2-CH3 G1m3 (K409R) | PCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGSFFLYSRLTVDK SRWQQGNVFSCSVMHEALHNHYTQKSLSLSPGK |

| SEQ ID NO: | DESCRIPTION | SEQUENCE |
|---|---|---|
| 278 | Hinge-CH2-CH3 G1m3 (C220S, T366W, S354C) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVYTLPPCREEMTKNQVSLWCLVKGFYPSDIAVEWESNGQPENNYKTTPPVLDSDG SFFLYSKLTVDKSRWQQGNVFSCSVMHEALHNHYTQKSLSLSPGK |
| 279 | Hinge-CH2-CH3 (C220S, T366S, L368A, Y407V, Y349C) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVCTLPPSREEMTKNQVSLSCAVKGFYPSDIAVEWESNGQPENNYKTTPPVLDSDG SFFLVSKLTVDKSRWQQGNVFSCSVMHEALHNHYTQKSLSLSPGK |
| 280 | Hinge-CH2-CH3 G1m3 (C220S, K409R) | EPKSSDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPVLDSDGS FFLYSRLTVDKSRWQQGNVFSCSVMHEALHNHYTQKSLSLSPGK |
| 281 | Human APRIL isoform alpha (UniProt: O75888-1, v1) | MPASSPFLLAPKGPPGNMGGPVREPALSVALWLSWGAALGAVACAMALLTQQTELQSLRRE VSRLQGTGGPSQNGEGYPWQSLPEQSSDALEAWENGERSRKRRAVLTQKQKKQHSVLHLV PINATSKDDSDVTEVMWQPALRRGRGLQAQGYGVRIQDAGVYLLYSQVLFQDVTFTMGQVV SREGQGRQETLFRCIRSMPSHPDRAYNSCYSAGVFHLHQGDILSVIIPRARAKLNLSPHGTFL GFVKL |
| 282 | Human APRIL isoform beta (UniProt: O75888-2 | MPASSPFLLAPKGPPGNMGGPVREPALSVALWLSWGAALGAVACAMALLTQQTELQSLRRE VSRLQGTGGPSQNGEGYPWQSLPEQSSDALEAWENGERSRKRRAVLTQKQKNDSDVTEVM WQPALRRGRGLQAQGYGVRIQDAGVYLLYSQVLFQDVTFTMGQVVSREGQGRQETLFRCIR SMPSHPDRAYNSCYSAGVFHLHQGDILSVIIPRARAKLNLSPHGTFLGFVKL |
| 283 | Human APRIL isoform gamma (UniProt: O75888-3) | MPASSPFLLAPKGPPGNMGGPVREPALSVALWLSWGAALGAVACAMALLTQQTELQSLRRE VSRLQGTGGPSQNGEGYPWQSLPEQSSDALEAWENGERSRKRRAVLTQKQKKQHSVLHLV PINATSKDDSDVTEVMWQPALRRGRGLQAQGYGVRIQDAGVYLLYSQVLFQDVTFTMGQVV SREGQGRQETLFRCIRSMPSHPDRAYNSCYSAGVFHLHQGDILSVIIPRARAKLNLSPHGTFL GL |
| 284 | Human APRIL isoform 4 (UniProt: O75888-4) | MPASSPFLLAPKGPPGNMGGPVREPALSVALWLSWGAALGAVACAMALLTQQTELQSLRRE VSRLQGTGGPSQNGEGYPWQSLPEQHSVLHLVPINATSKDDSDVTEVMWQPALRRGRGLQ AQGYGVRIQDAGVYLLYSQVLFQDVTFTMGQVVSREGQGRQETLFRCIRSMPSHPDRAYNS CYSAGVFHLHQGDILSVIIPRARAKLNLSPHGTFLGFVKL |
| 285 | Human APRIL isoform TWE-PRIL (UniProt: O43508-2) | MAARRSQRRRGRRGEPGTALLVPLALGLGLALACLGLLLAVVSLGSRASLSAQEPAQEELVA EEDQDPSELNPQTEESQDPAPFLNRLVRPRRSAPKGRKTRARRAIAAHYEVHPRPGQDGAQ AGVDGTVSGWEEARINSSSPLRYNRQIGEFIVTRAGLYYLYCQSSDALEAWENGERSRKRRA VLTQKQKKQHSVLHLVPINATSKDDSDVTEVMWQPALRRGRGLQAQGYGVRIQDAGVYLLYS QVLFQDVTFTMGQVVSREGQGRQETLFRCIRSMPSHPDRAYNSCYSAGVFHLHQGDILSVIIP RARAKLNLSPHGTFLGFVKL |
| 286 | Human APRIL isoform 5 (UniProt: O75888-5) | MGGPVREPALSVALWLSWGAALGAVACAMALLTQQTELQSLRREVSRLQGTGGPSQNGEG YPWQSLPEQHSVLHLVPINATSKDDSDVTEVMWQPALRRGRGLQAQGYGVRIQDAGVYLLY SQVLFQDVTFTMGQVVSREGQGRQETLFRCIRSMPSHPDRAYNSCYSAGVFHLHQGDILSVII PRARAKLNLSPHGTFLGFVKL |
| 287 | Mature human APRIL isoform alpha (UniProt: O75888-1, v1 positions 105 to 250) | AVLTQKQKKQHSVLHLVPINATSKDDSDVTEVMWQPALRRGRGLQAQGYGVRIQDAGVYLLY SQVLFQDVTFTMGQVVSREGQGRQETLFRCIRSMPSHPDRAYNSCYSAGVFHLHQGDILSVII PRARAKLNLSPHGTFLGFVKL |
| 288 | Mature human APRIL isoform beta (UniProt: O75888-2 positions 105 to 234 | AVLTQKQKNDSDVTEVMWQPALRRGRGLQAQGYGVRIQDAGVYLLYSQVLFQDVTFTMGQV VSREGQGRQETLFRCIRSMPSHPDRAYNSCYSAGVFHLHQGDILSVIIPRARAKLNLSPHGTF LGFVKL |
| 289 | Mature human APRIL isoform gamma (UniProt: O75888-3 positions 105 to 247) | AVLTQKQKKQHSVLHLVPINATSKDDSDVTEVMWQPALRRGRGLQAQGYGVRIQDAGVYLLY SQVLFQDVTFTMGQVVSREGQGRQETLFRCIRSMPSHPDRAYNSCYSAGVFHLHQGDILSVII PRARAKLNLSPHGTFLGL |
| 290 | Mature human APRIL isoform TWE-PRIL (UniProt: O43508-2 positions 185 to 330) | AVLTQKQKKQHSVLHLVPINATSKDDSDVTEVMWQPALRRGRGLQAQGYGVRIQDAGVYLLY SQVLFQDVTFTMGQVVSREGQGRQETLFRCIRSMPSHPDRAYNSCYSAGVFHLHQGDILSVII PRARAKLNLSPHGTFLGFVKL |

-continued

| Sequences | | |
|---|---|---|

SEQ
ID
NO: DESCRIPTION    SEQUENCE

291    Human BAFF isoform 1    MDDSTEREQSRLTSCLKKREEMKLKECVSILPRKESPSVRSSKDGKLLAATLLLALLSCCLTVV
       (UniProt: Q9Y275-1,    SFYQVAALQGDLASLRAELQGHHAEKLPAGAGAPKAGLEEAPAVTAGLKIFEPPAPGEGNSS
       v1)                    QNSRNKRAVQGPEETVTQDCLQLIADSETPTIQKGSYTFVPWLLSFKRGSALEEKENKILVKET
                              GYFFIYGQVLYTDKTYAMGHLIQRKKVHVFGDELSLVTLFRCIQNMPETLPNNSCYSAGIAKLE
                              EGDELQLAIPRENAQISLDGDVTFFGALKLL 292    Human BAFF isoform 2    MDDSTEREQSRLTSCLKKREEMKLKECVSILPRKESPSVRSSKDGKLLAATLLLALLSCCLTVV
       (UniProt: Q9Y275-2)    SFYQVAALQGDLASLRAELQGHHAEKLPAGAGAPKAGLEEAPAVTAGLKIFEPPAPGEGNSS
                              QNSRNKRAVQGPEETGSYTFVPWLLSFKRGSALEEKENKILVKETGYFFIYGQVLYTDKTYAM
                              GHLIQRKKVHVFGDELSLVTLFRCIQNMPETLPNNSCYSAGIAKLEEGDELQLAIPRENAQISLD
                              GDVTFFGALKLL 293    Human BAFF isoform 3    MDDSTEREQSRLTSCLKKREEMKLKECVSILPRKESPSVRSSKDGKLLAATLLLALLSCCLTVV
       (UniProt: Q9Y275-3)    SFYQVAALQGDLASLRAELQGHHAEKLPAGAGAPKAGLEEAPAVTAGLKIFEPPAPGEGNSS
                              QNSRNKRAVQGPEETVTQDCLQLIADSETPTIQKGFIY 294    Human BAFF               MDDSTEREQSRLTSCLKKREEMKLKECVSILPRKESPSVRSSKDGK
       cytoplasmic domain
       (UniProt: Q9Y275-1, v1
       positions 1 to 46)

295    Human BAFF               LLAATLLLALLSCCLTVVSFY
       transmembrane domain
       (UniProt: Q9Y275-1, v1
       positions 47 to 67)

296    Human BAFF isoform 1    QVAALQGDLASLRAELQGHHAEKLPAGAGAPKAGLEEAPAVTAGLKIFEPPAPGEGNSSQNS
       extracellular domain    RNKRAVQGPEETVTQDCLQLIADSETPTIQKGSYTFVPWLLSFKRGSALEEKENKILVKETGYF
       (UniProt: Q9Y275-1, v1   FIYGQVLYTDKTYAMGHLIQRKKVHVFGDELSLVTLFRCIQNMPETLPNNSCYSAGIAKLEEGD
       positions 68 to 285)    ELQLAIPRENAQISLDGDVTFFGALKLL 297    Human BAFF isoform 2    QVAALQGDLASLRAELQGHHAEKLPAGAGAPKAGLEEAPAVTAGLKIFEPPAPGEGNSSQNS
       extracellular domain    RNKRAVQGPEETGSYTFVPWLLSFKRGSALEEKENKILVKETGYFFIYGQVLYTDKTYAMGHLI
       (UniProt: Q9Y275-2       QRKKVHVFGDELSLVTLFRCIQNMPETLPNNSCYSAGIAKLEEGDELQLAIPRENAQISLDGDV
       positions 68 to 266)    TFFGALKLL 298    Human BAFF isoform 3    QVAALQGDLASLRAELQGHHAEKLPAGAGAPKAGLEEAPAVTAGLKIFEPPAPGEGNSSQNS
       extracellular domain    RNKRAVQGPEETVTQDCLQLIADSETPTIQKGFIY
       (UniProt: Q9Y275-3
       positions 68 to 164)

299    Human BAFF isoform 1    AVQGPEETVTQDCLQLIADSETPTIQKGSYTFVPWLLSFKRGSALEEKENKILVKETGYFFIYG
       soluble form (UniProt:   QVLYTDKTYAMGHLIQRKKVHVFGDELSLVTLFRCIQNMPETLPNNSCYSAGIAKLEEGDELQL
       Q9Y275-1, v1 positions   AIPRENAQISLDGDVTFFGALKLL
       134 to 285)

300    Human BAFF isoform 2    AVQGPEETGSYTFVPWLLSFKRGSALEEKENKILVKETGYFFIYGQVLYTDKTYAMGHLIQRKK
       soluble form (UniProt:   VHVFGDELSLVTLFRCIQNMPETLPNNSCYSAGIAKLEEGDELQLAIPRENAQISLDGDVTFFG
       Q9Y275-2 positions       ALKLL
       134 to 266)

301    Human BAFF isoform 3    AVQGPEETVTQDCLQLIADSETPTIQKGFIY
       soluble form (UniProt:
       Q9Y275-3 positions
       134 to 164)

302    538-SP5-B10 IgG1 HC     EVQLQQSGPELVKPGASVKMSCKASGYTFTSYVMHWVKQKPGRGLEWIAYILPFNDVTKYNE
                              KFKGKATLTSDKSSNTAYMELSSLTSEDSAVYYCARWEWDDGYFDYWGQGTTLTVSSASTK
                              GPSVFPLAPSSKSTSGGTAALGCLVKDYFPEPVTVSWNSGALTSGVHTFPAVLQSSGLYSLS
                              SVVTVPSSSLGTQTYICNVNHKPSNTKVDKKVEPKSCDKTHTCPPCPAPELLGGPSVFLFPPK
                              PKDTLMISRTPEVTCVVVDVSHEDPEVKFNWYVDGVEVHNAKTKPREEQYNSTYRVVSVLTV
                              LHQDWLNGKEYKCKVSNKALPAPIEKTISKAKGQPREPQVYTLPPSRDELTKNQVSLTCLVKG
                              FYPSDIAVEWESNGQPENNYKTTPPVLDSDGSFFLYSKLTVDKSRWQQGNVFSCSVMHEAL
                              HNHYTQKSLSLSPGK 303    538-SP5-B10 Cκ LC      DAVMTQTPLSLPVSLGDQASISCRSSQSLENSNGNTYLNWYLQKPGQSPQLLIYRVSNRFSG
                              VLDRFSGSGSGTDFTLKISRVEAEDLGVYFCLQVSHVPFTFGAGTKLELKRTVAAPSVFIFPPS
                              DEQLKSGTASVVCLLNNFYPREAKVQWKVDNALQSGNSQESVTEQDSKDSTYSLSSTLTLSK
                              ADYEKHKVYACEVTHQGLSSPVTKSFNRGEC 304    539-SP1-C8 IgG1 HC     EVQLQQSGPELVKPGSSVKMSCKASGYTFTNYVMHWVKQKPGQGLEWIGYILPYNDGTKYN
                              EKFKGKATLTSDKSSSTAYMEFSVLTSEDSAVYYCARYDYEGSFDYWGQGTALTVSSASTKG
                              PSVFPLAPSSKSTSGGTAALGCLVKDYFPEPVTVSWNSGALTSGVHTFPAVLQSSGLYSLSSV

-continued

| | | |
|---|---|---|
| | | Sequences |

| SEQ ID NO: | DESCRIPTION | SEQUENCE |
|---|---|---|
| | | VTVPSSSLGTQTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCSVMHEALHN HYTQKSLSLSPGK |
| 305 | 539-SP1-C8 Cκ LC | DIQMTQTTSSLSASLGDRVTISCRASQDISNYLNWYQQKPDGTVKLLMCYTSRLHSGVPSRFS GSGSGTDFSLTISNLEQEDIATYFCQQGNTFPPTFGGGTKLEIKRTVAAPSVFIFPPSDEQLKS GTASVVCLLNNFYPREAKVQWKVDNALQSGNSQESVTEQDSKDSTYSLSSTLTLSKADYEKH KVYACEVTHQGLSSPVTKSFNRGEC |
| 306 | 539-SP2-H3 IgG1 HC | EVQLQQSGPELVKPGASVKMSCKASGYTFTSYVIHWVKQKPGQGLEWIGYVLPYNDVIKYNE KFKGKATLTSDKSSSTAYMDLSSLTSEDSAVYYCARWGDFDEGIWFPYWGQGTLVTVSAAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEA LHNHYTQKSLSLSPGK |
| 307 | 539-SP2-H3 Cκ LC | DVLMTQTPLSLPVSLGDHASVSCRSSQSIVHTDGNTYLEWYLQKPGQSPKLLIYKVSNRFSGV PDRFSGSGSGTDFTLKISRVEAEDLGVYYCFQGSHVPWTFGGGTKLEIKRTVAAPSVFIFPPS DEQLKSGTASVVCLLNNFYPREAKVQWKVDNALQSGNSQESVTEQDSKDSTYSLSSTLTLSK ADYEKHKVYACEVTHQGLSSPVTKSFNRGEC |
| 308 | 539-SP5-D7 IgG1 HC | EVMLVDSGGNLVKPGGSLKLSCAASGFTFSNYVISWVRQTPEKRLEWVATISTVGTNTYYPD SVRGRFTISRDNAENTLYLQMSSLRSEDTAIYYCSRHKYGYDDPSYAMDYWGQGTSVTVSSA STKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGNVFSCSVMH EALHNHYTQKSLSLSPGK |
| 309 | 539-SP5-D7 Cλ CL1 LC | QLVLTQSSSASFSLGASAKLTCTLSSQHSTYTIEWYQQQPLKPPKYVMELKKDGSHSTGDGIP DRFSGSSSGADRYLSISNIQAEDEAIYICGVGDTVKEQFVYVFGGGTKVTVLGQPKANPTVTLF PPSSEELQANKATLVCLISDFYPGAVTVAWKADGSPVKAGVETTKPSKQSNNKYAASSYLSLT PEQWKSHRSYSCQVTHEGSTVEKTVAPTECS |
| 310 | 539-SP7-F4 IgG1 HC | EVQLQQSGPELVKPGASMKISCKASGYSFTGYIMNWVKQSHGKNLEWIGLINPYNGDSIYNQ KFKGKATLTVDKSSSTAYMELFSLTSEDSTVYYCAAGEEFAYWGQGTLVTVSAASTKGPSVF PLAPSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHEALHNHYTQK SLSLSPGK |
| 311 | 539-SP7-F4 Cκ LC | DIQMTQTSSSLSASLGDRVTISCRASQDISIYLNWFQQKPDGTVKLLIYFTSRLHPGVPSRFSA SGSGTDYSLTISHLEHEDIATYFCQQGNTLPRTFGGGTKVELKRTVAAPSVFIFPPSDEQLKSG TASVVCLLNNFYPREAKVQWKVDNALQSGNSQESVTEQDSKDSTYSLSSTLTLSKADYEKHK VYACEVTHQGLSSPVTKSFNRGEC |
| 312 | 552-LN1-E9 IgG1 HC | QIQLVQSGPELKKPGETVKISCKASGYTFTDYSIYWVKQAPGKGLKWMGWINTETGEPTYAD DFKGRFAFSLETSASSAYLQINTLKNEDTATYFCSISYYYAMDYWGQGTSVTVSSASTKGPSV FPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVMHEALHNHY TQKSLSLSPGK |
| 313 | 552-LN1-E9 Cκ LC | DIVLTQSPASLAVSLGQRATISCRASKSVSTSGYSFLHWYQQKPGQPPKLLIYFASNLESGVPA RFSGSGSGTDFTLNIHPVEEEDAATYYCQHSRELPRTFGGGTKLEIKRTVAAPSVFIFPPSDEQ LKSGTASVVCLLNNFYPREAKVQWKVDNALQSGNSQESVTEQDSKDSTYSLSSTLTLSKADY EKHKVYACEVTHQGLSSPVTKSFNRGEC |
| 314 | 552-LN1-F4 IgG1 HC | QIQLVQSGPELKKPGETVKISCMASGYTFTDYSVRWVKQAPGKGLEWMGWINTETGEPTYA HDFKGRFAFSLETSASTAYLQINNLKDEDTSTYFCAISYYYALDYWGHGTSVTVSSASTKGPS VFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPSRDELTKNQVSLTCLVKGFYPS |

-continued

| SEQ ID NO: | DESCRIPTION | SEQUENCE |
|---|---|---|

DIAVEWESNGQPENNYKTTPPVLDSDGSFFLYSKLTVDKSRWQQGNVFSCSVMHEALHNHY
TQKSLSLSPGK 315 552-LN1-F4 Cκ LC

DIVLTQSPASLTVSLGQRATISCRASKSVSTSGYNFLHWYQQKPGQPPKLLIYLASNLESGAPA
RFSGSGSGTDFTLNIHPVEEEDAATYYCQHSRELPRTFGGGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC 316 552-LN2-E6 IgG1 HC

QIQLVQSGPELKKPGETVKISCMASGYTFTDYSVRWVKQAPGKGLEWMGWINTETGEPTYA
DDFKGRFAFSLETSASTAYLQINNLKNEDTATYFCAISYYYALDYWGHGTSVTVSSASTKGPS
VFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHY
TQKSLSLSPGK 317 552-LN2-E6 Cκ LC

DIVLTQSPASLTVSLGQRATISCRASKSVSTSVYSFLHWYQQKPGQPPKLLIYLASNLESGVPA
RFSGSGSGTDFTLNIHPVEEEDAATYYCQHSRELPRTFGGGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC 318 552-LN2-F8 IgG1 HC

QIQLVQSGPELKKPGETVKISCKASGYTFTDYTMYWVKQAPGKGLKWMGWINTETGEPTYAD
DFKGRFVFSLETSANTAYLQINNLKNEDTATYFCAISYYYALDYWGHGTSVTVTSASTKGPSV
FPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHY
TQKSLSLSPGK 319 552-LN2-F8 Cκ LC

DIILTQSPASLAVSLGQRATITCRASKSVSTSGYNFVYWYQQKPGQPPKLLIYLASNLESGVPA
RFSGSGSGTDFTLNIHPVEEEDAATYYCQHSRELPRTFGGGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC 320 538-SP5-B10 IgG1 CH1-CH2-CH3 (T366W, S354C) HC

EVQLQQSGPELVKPGASVKMSCKASGYTFTSYVMHWVKQKPGRGLEWIAYILPFNDVTKYNE
KFKGKATLTSDKSSNTAYMELSSLTSEDSAVYYCARWEWDDGYFDYWGQGTTLTVSSASTK
GPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPCRDELTKNQVSLWCLVK
GFYPSDIAVEWESNGQPENNYKTTPPVLDSDGSFFLYSKLTVDKSRWQQGNVFSCSVMHEA
LHNHYTQKSLSLSPGK 321 539-SP1-C8 IgG1 CH1-CH2-CH3 (T366W, S354C) HC

EVQLQQSGPELVKPGSSVKMSCKASGYTFTNYVMHWVKQKPGQGLEWIGYILPYNDGTKYN
EKFKGKATLTSDKSSSTAYMEFSVLTSEDSAVYYCARYDYEGSFDYWGQGTALTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPCRDELTKNQVSLWCLVKGF
YPSDIAVEWESNGQPENNYKTTPPVLDSDGSFFLYSKLTVDKSRWQQGNVFSCSVMHEALH
NHYTQKSLSLSPGK 322 539-SP2-H3 IgG1 CH1-CH2-CH3 (T366W, S354C) HC

EVQLQQSGPELVKPGASVKMSCKASGYTFTSYVIHWVKQKPGQGLEWIGYVLPYNDVIKYNE
KFKGKATLTSDKSSSTAYMDLSSLTSEDSAVYYCARWGDFDEGIWFPYWGQGTLVTVSAAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPCRDELTKNQVSLWCLV
KGFYPSDIAVEWESNGQPENNYKTTPPVLDSDGSFFLYSKLTVDKSRWQQGNVFSCSVMHE
ALHNHYTQKSLSLSPGK 323 539-SP5-D7 IgG1 CH1-CH2-CH3 (T366W, S354C) HC

EVMLVDSGGNLVKPGGSLKLSCAASGFTFSNYVISWVRQTPEKRLEWVATISTVGTNTYYPD
SVRGRFTISRDNAENTLYLQMSSLRSEDTAIYYCSRHKYGYDDPSYAMDYWGQGTSVTVSSA
STKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPCRDELTKNQVSLWCL
VKGFYPSDIAVEWESNGQPENNYKTTPPVLDSDGSFFLYSKLTVDKSRWQQGNVFSCSVMH
EALHNHYTQKSLSLSPGK

-continued

| SEQ ID NO: | DESCRIPTION | SEQUENCE |
|---|---|---|
| 324 | 539-SP7-F4 IgG1 CH1-CH2-CH3 (T366W, S354C) HC | EVQLQQSGPELVKPGASMKISCKASGYSFTGYIMNWVKQSHGKNLEWIGLINPYNGDSIYNQ KFKGKATLTVDKSSSTAYMELFSLTSEDSTVYYCAAGEEFAYWGQGTLVTVSAASTKGPSVF PLAPSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVVSVLTVLHQDWL NGKEYKCKVSNKALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVMHEALHNHYTQ KSLSLSPGK |
| 325 | 552-LN1-E9 IgG1 CH1-CH2-CH3 (T366W, S354C) HC | QIQLVQSGPELKKPGETVKISCKASGYTFTDYSIYWVKQAPGKGLKWMGWINTETGEPTYAD DFKGRFAFSLETSASSAYLQINTLKNEDTATYFCSISYYYAMDYWGQGTSVTVSSASTKGPSV FPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPCRDELTKNQVSLWCLVKGFYPS DIAVEWESNGQPENNYKTTPPVLDSDGSFFLYSKLTVDKSRWQQGNVFSCSVMHEALHNHY TQKSLSLSPGK |
| 326 | 552-LN1-F4 IgG1 CH1-CH2-CH3 (T366W, S354C) HC | QIQLVQSGPELKKPGETVKISCMASGYTFTDYSVRWVKQAPGKGLEWMGWINTETGEPTYA HDFKGRFAFSLETSASTAYLQINNLKDEDTSTYFCAISYYYALDYWGHGTSVTVSSASTKGPS VFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPCRDELTKNQVSLWCLVKGFYPS DIAVEWESNGQPENNYKTTPPVLDSDGSFFLYSKLTVDKSRWQQGNVFSCSVMHEALHNHY TQKSLSLSPGK |
| 327 | 552-LN2-E6 IgG1 CH1-CH2-CH3 (T366W, S354C) HC | QIQLVQSGPELKKPGETVKISCMASGYTFTDYSVRWVKQAPGKGLEWMGWINTETGEPTYA DDFKGRFAFSLETSASTAYLQINNLKNEDTATYFCAISYYYALDYWGHGTSVTVSSASTKGPS VFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPCRDELTKNQVSLWCLVKGFYPS DIAVEWESNGQPENNYKTTPPVLDSDGSFFLYSKLTVDKSRWQQGNVFSCSVMHEALHNHY TQKSLSLSPGK |
| 328 | 552-LN2-F8 IgG1 CH1-CH2-CH3 (T366W, S354C) HC | QIQLVQSGPELKKPGETVKISCKASGYTFTDYTMYWVKQAPGKGLKWMGWINTETGEPTYAD DFKGRFVFSLETSANTAYLQINNLKNEDTATYFCASYYYGMDYWGQGTSVTVTSASTKGPSV FPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYRVVSVLTVLHQD WLNGKEYKCKVSNKALPAPIEKTISKAKGQPREPQVYTLPPCRDELTKNQVSLWCLVKGFYPS DIAVEWESNGQPENNYKTTPPVLDSDGSFFLYSKLTVDKSRWQQGNVFSCSVMHEALHNHY TQKSLSLSPGK |
| 329 | 11A1H5 scFv IgG1 CH2-CH3 (T366S, L368A, Y407V, Y349C) | DVVMTQSPLSLPVTLGQPASISCRSSQHLEYSNGYSYLHWYQQRPGQSPRLLIYKISNRFSGV PDRFSGSGSGTDFTLKISRVEAEDVGVYYCSQSTHVPYTFGGGTKVEIKGGGGSGGGGSGG GGSQVQLVQSGAEVKKPGASVKVSCKASGYTFTGYVIHWVRQAPGQGLEWMGYINPYNGG TNYAQKFKGRVTLTSDTSTTTAYMELSRLRSEDTAVYYCASGGYYTMDYWGQGTLVTVSSG GRPKSADKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISK AKGQPREPQVCTLPPSRDELTKNQVSLSCAVKGFYPSDIAVEWESNGQPENNYKTTPPVLDS DGSFFLVSKLTVDKSRWQQGNVFSCSVMHEALHNHYTQKSLSLSPGK |
| 330 | Human TACI isoform 1 (UniProt: O14836-1, v1) | MSGLGRSRRGGRSRVDQEERFPQGLWTGVAMRSCPEEQYWDPLLGTCMSCKTICNHQSQ RTCAAFCRSLSCRKEQGKFYDHLLRDCISCASICGQHPKQCAYFCENKLRSPVNLPPELRRQ RSGEVENNSDNSGRYQGLEHRGSEASPALPGLKLSADQVALVYSTLGLCLCAVLCCFLVAVA CFLKKRGDPCSCQPRSRPRQSPAKSSQDHAMEAGSPVSTSPEPVETCSFCFPECRAPTQES AVTPGTPDPTCAGRWGCHTRTTVLQPCPHIPDSGLGIVCVPAQEGGPGA |
| 331 | Human TACI isoform 2 (UniProt: O14836-2) | MSGLGRSRRGGRSRVDQEERWSLSCRKEQGKFYDHLLRDCISCASICGQHPKQCAYFCENK LRSPVNLPPELRRQRSGEVENNSDNSGRYQGLEHRGSEASPALPGLKLSADQVALVYSTLGL CLCAVLCCFLVAVACFLKKRGDPCSCQPRSRPRQSPAKSSQDHAMEAGSPVSTSPEPVETC SFCFPECRAPTQESAVTPGTPDPTCAGRWGCHTRTTVLQPCPHIPDSGLGIVCVPAQEGGPG A |
| 332 | Human TACI isoform 3 (UniProt: O14836-3) | MSGLGRSRRGGRSRVDQEERFPQGLWTGVAMRSCPEEQYWDPLLGTCMSCKTICNHQSQ RTCAAFCRSLSCRKEQGKFYDHLLRDCISCASICGQHPKQCAYFCENKLRSPVNLPPELRRQ RSGEVENNSDNSGRYQGLEHRGSEASPAPRGCPAPGTRKSFWDKENFQGEGFHLG |

| Sequences | | |
|---|---|---|
| SEQ ID NO: | DESCRIPTION | SEQUENCE |
| 333 | Human TACI Extracellular Domain (UniProt: O14836-1, v1, positions 1 to 165) | MSGLGRSRRGGRSRVDQEERFPQGLWTGVAMRSCPEEQYWDPLLGTCMSCKTICNHQSQ RTCAAFCRSLSCRKEQGKFYDHLLRDCISCASICGQHPKQCAYFCENKLRSPVNLPPELRRQ RSGEVENNSDNSGRYQGLEHRGSEASPALPGLKLSADQVALVYS |
| 334 | Human TACI Cys-rich TNFR repeat 1 (UniProt: O14836-1, v1, positions 33 to 67) | SCPEEQYWDPLLGTCMSCKTICNHQSQRTCAAFCR |
| 335 | Human TACI Cys-rich TNFR repeat 2 (UniProt: O14836-1, v1, positions 70 to 104) | SCRKEQGKFYDHLLRDCISCASICGQHPKQCAYFC |
| 336 | Human TACI transmembrane domain (UniProt: O14836-1, v1, positions 166 to 186) | TLGLCLCAVLCCFLVAVACFL |
| 337 | Human TACI transmembrane domain (UniProt: O14836-1, v1, positions 187 to 293) | KKRGDPCSCQPRSRPRQSPAKSSQDHAMEAGSPVSTSPEPVETCSFCFPECRAPTQESAVT PGTPDPTCAGRWGCHTRTTVLQPCPHIPDSGLGIVCVPAQEGGPGA |
| 338 | 1E9-4H VH | QVQLVQSGAEVKKPGASVKVSCKASGYTFTDYSIYWVRQAPGQGLEWMGWINTETGEPNYA QDVQGRFTMTLDTSTSTAYMELRSLRSDDTAVYYCSISYYYAMDYWGQGTLVTVSS |
| 339 | 1E9-4H, 1E9-QE HC-FR2 | IYWVRQAPGQGLEWMGW |
| 340 | 1E9-4H HC-FR3 | NYAQDVQGRFTMTLDTSTSTAYMELRSLRSDDTAVYYC |
| 341 | 1E9-4H VL | DIVMTQTPLSLSVTPGQPASISCKSSKSVSTSGYSFLHWYLQKPGQPPQLLIYFASNLESGVP DRFSGSGSGTDFTLKISRVEAEDVGVYYCQHSRELPRTFGQGTKVEIK |
| 342 | 1E9-4H, 5B10-4Y LC-FR1 | DIVMTQTPLSLSVTPGQPASISCKSS |
| 343 | 1E9-4H LC-FR2 | LHWYLQKPGQPPQLLI |
| 344 | 1E9-4H LC-FR3 | NLESGVPDRFSGSGSGTDFTLKISRVEAEDVGVYYC |
| 345 | 1E9-4H, 2F8-2Q, 2F8-5U LC-FR4 | FGQGTKVEIK |
| 346 | 1E9-QE VH | QVQLVQSGAEVKKPGASVKVSCKASGYTFTDYSIYWVRQAPGQGLEWMGWINTETGETNYA QDFQGRVTMTTDTETSTAYMELRSLRSDDTAVYYCSISYYYAMDYWGQGTLVTVSS |
| 347 | 1E9-QE, 2F8-2Q, 2F8-5U HC-CDR2 | INTETGET |
| 348 | 1E9-QE HC-FR3 | NYAQDFQGRVTMTTDTETSTAYMELRSLRSDDTAVYYC |
| 349 | 1E9-QE VL | EIVLTQSPATLSLSPGERATLSCRASKSVSTSGYSFLHWYQQKPGQAPRLLIYFASNLETGIPA RFSGSGSGTDFTLTISRLEPEDFAVYYCQHSRELPRTFGQGTKLEIK |
| 350 | 1E9-QE LC-FR1 | EIVLTQSPATLSLSPGERATLSCRAS |
| 351 | 1E9-QE LC-FR2 | LHWYQQKPGQAPRLLIY |
| 352 | 1E9-QE LC-FR3 | NLETGIPARFSGSGSGTDFTLTISRLEPEDFAVYYC |
| 353 | 2F8-2Q VH | EVQLVESGGGLVQPGESLRLSCAASGYTFTDYTMYWVRQAPGKGLEWMGWINTETGETNY ADSVKGRFTISRDNSKNTLYLQMNSLRAEDTAVYYCAISYYYGMDYWGQGTLVTVSS |
| 354 | 2F8-2Q HC-FR1 | EVQLVESGGGLVQPGESLRLSCAAS |
| 355 | 2F8-2Q HC-FR2 | MYWVRQAPGKGLEWMGW |

-continued

| SEQ ID NO: | DESCRIPTION | SEQUENCE |
|---|---|---|
| 356 | 2F8-2Q HC-FR3 | NYADSVKGRFTISRDNSKNTLYLQMNSLRAEDTAVYYC |
| 357 | 2F8-2Q VL | DIQMTQSPSTLSVSVGDRVTITCRASKSVSTSGYNFVYWYQQKPGKAPKLLIYLASNLESGVP SRFSGSGSGTEFTLTISSLQPDDFATYYCQHSRELPRTFGQGTKVEIK |
| 358 | 2F8-2Q LC-FR1 | DIQMTQSPSTLSVSVGDRVTITCRAS |
| 359 | 2F8-2Q LC-FR2 | VYWYQQKPGKAPKLLIY |
| 360 | 2F8-2Q, 2F8-5U LC-FR3 | NLESGVPSRFSGSGSGTEFTLTISSLQPDDFATYYC |
| 361 | 2F8-5U VH | EVQLVESGGGLVQPGGSLRLSCAASGYTFTDYTMYWVRQAPGKGLEWMGDINTETGETTYA DSVKGRFTISRDNSKNTLYLQMNSLRAEDTAVYYCAISYYYGMDYWGQGTLVTVSS |
| 362 | 2F8-5U HC-FR1 | EVQLVESGGGLVQPGGSLRLSCAAS |
| 363 | 2F8-5U HC-FR2 | MYWVRQAPGKGLEWMGD |
| 364 | 2F8-5U HC-FR3 | TYADSVKGRFTISRDNSKNTLYLQMNSLRAEDTAVYYC |
| 365 | 2F8-5U VL | DIQMTQSPSTLSASVGDRVTITCRASKSVSTSGYNFVYWYQQKPGQPPKLLIYLASNLESGVP SRFSGSGSGTEFTLTISSLQPDDFATYYCQHSRELPRTFGQGTKVEIK |
| 366 | 2F8-5U LC-FR1 | DIQMTQSPSTLSASVGDRVTITCRAS |
| 367 | 5B10-4Y VH | QVQLVQSGAEVKKPGASVKVSCKASGYTFTSYVMHWVRQAPGQGLEWMAYILPFNDVTKYN EKFKGRVTMTDKSTSTVYMELSSLRSEDTAVYYCARWEWDDGYFDYWGQGTLVTVSS |
| 368 | 5B10-4Y HC-FR2 | MHWVRQAPGQGLEWMAY |
| 369 | 5B10-4Y HC-FR3 | KYNEKFKGRVTMTDKSTSTVYMELSSLRSEDTAVYYC |
| 370 | 5B10-4Y VL | DIVMTQTPLSLSVTPGQPASISCKSSQSLENSNGNTYLNWYLQKPGQSPKLLIYRVSNRFSGV PDRFSGSGSGTDFTLKISRVEAEDVGVYYCLQVSHVPFTFGQGTKLEIK |
| 371 | 5B10-4Y LC-FR2 | LNWYLQKPGQSPKLLIY |
| 372 | 5B10-51 VH | QVQLVQSGAEVKKPGASVKMSCKASGYTFTSYVMHWVRQAPGQGLEWIAYILPFNDVTNYN QKFQGRVTMTRDTSISTAYMELSRLRSDDTAVYYCARWEWDDGYFDYWGQGTLVTVSS |
| 373 | 5B10-51 HC-FR1 | QVQLVQSGAEVKKPGASVKMSCKAS |
| 374 | 5B10-51, 1C8-EH HC-FR2 | MHWVRQAPGQGLEWIAY |
| 375 | 5B10-5l HC-FR3 | NYNQKFQGRVTMTRDTSISTAYMELSRLRSDDTAVYYC |
| 376 | 5B10-51 VL | DIVMTQSPDSLAVSLGERATINCKSSQSLENSNGNTYLNWYQQKPGQPPKLLIYRVSTRFSGV LDRFSGSGSGTDFTLTISSLQAEDVAVYYCLQVSHVPFTFGGGTKVEIK |
| 377 | 5B10-51 LC-FR1 | DIVMTQSPDSLAVSLGERATINCKSS |
| 378 | 5B10-51 LC-FR2 | LNWYQQKPGQPPKLLIY |
| 379 | 5B10-51 LC-FR3 | TRFSGVLDRFSGSGSGTDFTLTISSLQAEDVAVYYC |
| 380 | 1C8-6A VH | QVQLVQSGAELVKPGSSVKMSCKASGYTFTNYVMHWVRQAPGQGLEWMGYILPYNDGTNY NQKFQGRVTMTDKSTSTAYMELSSLRSEDTAVYYCARYDYEGSFDYWGQGTLVTVSS |
| 381 | 1C8-6A HC-FR1 | QVQLVQSGAELVKPGSSVKMSCKAS |
| 382 | 1C8-6A HC-FR3 | NYNQKFQGRVTMTDKSTSTAYMELSSLRSEDTAVYYC |
| 383 | 1C8-6A VL | DIQMTQSPSSLSASVGDRVTITCRASQDISNYLNWYQQKPGKAPKLLMCYTSRLHSGVPSRF SGSGSGTDFTLTISSLQPEDFATYYCQQGNTFPPTFGGGTKVEIK |
| 384 | 1C8-6A, 1C8-EH, 1C8-402, 1C8-403, 1C8-507, 1C8-610, 1C8-6A3, 1C8-25 LC-FR1 | DIQMTQSPSSLSASVGDRVTITCRAS |

| SEQ ID NO: | DESCRIPTION | SEQUENCE |
|---|---|---|
| 385 | 1C8-6A, 1C8-403, 1C8-6A3 LC-FR2 | LNWYQQKPGKAPKLLMC |
| 386 | 1C8-6A, 1C8-EH, 1C8-25, 1C8-27 LC-FR3 | RLHSGVPSRFSGSGSGTDFTLTISSLQPEDFATYYC |
| 387 | 1C8-EH VH | QVQLVESGGGVVQPGRSLRLSCAASGYTFTNYVMHWVRQAPGQGLEWIAYILPYNDGANYN<br>EKVKGRFTISRDNSKNTLYLQMNSLRAEDTAVYYCARYDYEGSFDYWGQGTLVTVSS |
| 388 | 1C8-EH HC-CDR2 | ILPYNDGA |
| 389 | 1C8-EH HC-FR1 | QVQLVESGGGVVQPGRSLRLSCAAS |
| 390 | 1C8-EH HC-FR3 | NYNEKVKGRFTISRDNSKNTLYLQMNSLRAEDTAVYYC |
| 391 | 1C8-EH VL | DIQMTQSPSSLSASVGDRVTITCRASQDISNYLNWYQQKPGQSVKLLIYYTSRLHSGVPSRFS<br>GSGSGTDFTLTISSLQPEDFATYYCQQGNTFPPTFGGGTKVEIK |
| 392 | 1C8-EH LC-FR2 | LNWYQQKPGQSVKLLIY |
| 393 | 1E9-4H/QE CON VH | QVQLVQSGAEVKKPGASVKVSCKASGYTFTDYSIYWVRQAPGQGLEWMGWINTETGEX$_{147}$N<br>YAQDX$_{148}$QGRX$_{149}$TMTX$_{150}$DTX$_{151}$TSTAYMELRSLRSDDTAVYYCSISYYYAMDYWGQGTLVT<br>VSS<br>wherein X$_{147}$ = P or T, X$_{148}$ = V or F,<br>X$_{149}$ = F or V, X$_{150}$ = L or T and X$_{151}$ = S or E |
| 394 | 1E9-4H/QE CON HC-CDR2 | INTETGEX$_{152}$<br>wherein X$_{152}$ = P or T |
| 395 | 1E9-4H/QE CON HC-FR3 | NYAQDX$_{153}$QGRX$_{154}$TMTX$_{155}$DTX$_{156}$TSTAYMELRSLRSDDTAVYYC<br>wherein X$_{153}$ = V or F, X$_{154}$ = F or V, X$_{155}$ = L or T and X$_{156}$ = S or E |
| 396 | 1E9-4H/QE CON VL | X$_{157}$IVX$_{158}$TQX$_{159}$PX$_{160}$X$_{161}$LSX$_{162}$X$_{163}$PGX$_{164}$X$_{165}$AX$_{166}$X$_{167}$SCX$_{168}$X$_{169}$SKSVSTSGYSFLHWYX$_{170}$<br>QKPGQX$_{171}$PX$_{172}$LLIYFASNLEX$_{173}$GX$_{174}$PX$_{175}$RFSGSGSGTDFTLX$_{176}$ISRX$_{177}$EX$_{178}$EDX$_{179}$X$_{180}$<br>VYYCQHSRELPRTFGQGTKX$_{181}$EIK<br>wherein X$_{157}$ = D or E, X$_{158}$ = M or L,<br>X$_{159}$ T = or S, X$_{160}$ = L or A, X$_{161}$ = S or T, X$_{162}$ = V or L,<br>X$_{163}$ = T or S, X$_{164}$ = Q or E, X$_{165}$ = P or R,<br>X$_{166}$ = S or T, X$_{167}$ = I or L, X$_{168}$ = K or R, X$_{169}$ = S or<br>A, X$_{170}$ = L or Q, X$_{171}$ = P or A, X$_{172}$= Q or R,<br>X$_{173}$ = S or T, X$_{174}$ = V or I, X$_{175}$ = D or A, X$_{176}$ = K<br>or T, X$_{177}$ = V or L, X$_{178}$ = A or P,<br>X$_{179}$ = V or F, X$_{180}$ = G or A and X$_{181}$ = V or L |
| 397 | 1E9-4H/QE CON LC-FR1 | X$_{182}$IVX$_{183}$TQX$_{184}$PX$_{185}$X$_{186}$LSX$_{187}$X$_{188}$PGX$_{189}$X$_{190}$AX$_{191}$X$_{192}$SCX$_{193}$X$_{194}$S<br>wherein X$_{182}$ = D or E, X$_{183}$ = M or L,<br>X$_{184}$ T = or S, X$_{185}$ = L or A, X$_{186}$ = S or T, X$_{187}$ = V or L,<br>X$_{188}$ = T or S, X$_{189}$ = Q or E, X$_{190}$ = P or R,<br>X$_{191}$ = S or T, X$_{192}$ = I or L, X$_{193}$ = K or R and X$_{194}$ =<br>S or A |
| 398 | 1E9-4H/QE CON LC-FR2 | LHWYX$_{195}$QKPGQX$_{196}$PX$_{197}$LLIY<br>wherein X$_{195}$ = L or Q, X$_{196}$ = P or A and X$_{197}$ = Q or R |
| 399 | 1E9-4H/QE CON LC-FR3 | NLEX$_{198}$GX$_{199}$PX$_{200}$RFSGSGSGTDFTLX$_{201}$ISRX$_{202}$EX$_{203}$EDX$_{204}$X$_{205}$VYYC<br>wherein X$_{198}$ = S or T, X$_{199}$ = V or I,<br>X$_{200}$ = D or A, X$_{201}$ = K or T, X$_{202}$ = V or L, X$_{203}$ = A or P,<br>X$_{204}$ = V or F and X$_{205}$ = G or A |
| 400 | 1E9-4H/QE CON LC-FR4 | FGQGTKX$_{206}$EIK<br>wherein X$_{206}$ = V or L |
| 401 | 2F8-2Q/5U CON VH | EVQLVESGGGLVQPGX$_{207}$SLRLSCAASGYTFTDYTMYWVRQAPGKGLEWMGX$_{208}$INTETGET<br>X$_{209}$YADSVKGRFTISRDNSKNTLYLQMNSLRAEDTAVYYCAISYYYGMDYWGQGTLVTVSS<br>wherein X$_{207}$ = G or E, X$_{208}$ = D or W and X$_{209}$ = T or N |
| 402 | 2F8-2Q/5U CON HC-FR1 | EVQLVESGGGLVQPGX$_{210}$SLRLSCAAS<br>wherein X$_{210}$ = G or E |
| 403 | 2F8-2Q/5U CON HC-FR2 | MYWVRQAPGKGLEWMGX$_{211}$<br>wherein X$_{211}$ = D or W |

-continued

| SEQ ID NO: | DESCRIPTION | SEQUENCE |
|---|---|---|
| 404 | 2F8-2Q/5U CON HC-FR3 | $X_{212}$YADSVKGRFTISRDNSKNTLYLQMNSLRAEDTAVYYC<br>wherein $X_{212}$ = T or N |
| 405 | 2F8-2Q/5U CON VL | DIQMTQSPSTLS$X_{213}$SVGDRVTITCRASKSVSTSGYNFVYWYQQKPG$X_{214}$$X_{215}$PKLLIYLASNL<br>ESGVPSRFSGSGSGTEFTLTISSLQPDDFATYYCQHSRELPRTFGQGTKVEIK<br>wherein $X_{213}$ = A or V, $X_{214}$ = Q or K and $X_{215}$ = P or A |
| 406 | 2F8-2Q/5U CON LC-FR1 | DIQMTQSPSTLS$X_{216}$SVGDRVTITCRAS<br>wherein $X_{216}$ = A or V |
| 407 | 2F8-2Q/5U CON LC-FR2 | VYWYQQKPG$X_{217}$$X_{218}$PKLLIY<br>wherein $X_{217}$ = Q or K and $X_{218}$ = P or A |
| 408 | 5B10-4Y/5I CON VH | QVQLVQSGAEVKKPGASVK$X_{219}$SCKASGYTFTSYVMHWVRQAPGQGLEW$X_{220}$AYILPFNDVT<br>$X_{221}$ YN$X_{222}$KF$X_{223}$GRVTMT$X_{224}$D$X_{225}$S$X_{226}$ST$X_{227}$YMELS$X_{228}$LRS$X_{229}$DTAVYYCARWEWDDG<br>YFDYWGQGTLVTVSS<br>wherein $X_{219}$ = V or M, $X_{220}$ = M or I,<br>$X_{221}$ = K or N, $X_{222}$ = E or Q,<br>$X_{223}$ = K or Q, $X_{224}$ = S or R,<br>$X_{225}$ = K or T, $X_{226}$ = T or 1, $X_{227}$ = V or A,<br>$X_{228}$ = S or R and $X_{229}$ = E or D |
| 409 | 5B10-4Y/5I CON HC-FR1 | QVQLVQSGAEVKKPGASVK$X_{230}$SCKAS<br>wherein $X_{230}$ = V or M |
| 410 | 5B10-4Y/5I CON HC-FR2 | MHWVRQAPGQGLEW$X_{231}$AY<br>wherein $X_{231}$ = M or I |
| 411 | 5B10-4Y/5I CON HC-FR3 | $X_{232}$ YN$X_{233}$KF$X_{234}$GRVTMT$X_{235}$D$X_{236}$S$X_{237}$ST$X_{238}$YMELS$X_{239}$LRS$X_{240}$DTAVYYC<br>wherein $X_{232}$ = K or N, $X_{233}$ = E or Q,<br>$X_{234}$ = K or Q, $X_{235}$ = S or R, $X_{236}$ = K or T, $X_{237}$ = T or 1,<br>$X_{238}$ = V or A, $X_{239}$ = S or R and $X_{240}$ = E or D |
| 412 | 5B10-4Y/5I CON VL | DIVMTQ$X_{241}$P$X_{242}$SL$X_{243}$V$X_{244}$$X_{245}$G$X_{246}$$X_{247}$A$X_{248}$I$X_{249}$CKSSQSLENSNGNTYLNWY$X_{250}$QKPG<br>Q$X_{251}$PKLLIYRVS$X_{252}$RFSGV$X_{253}$DRFSGSGSGTDFTLX$X_{254}$ISX$X_{255}$$X_{256}$$X_{257}$AEDVX$X_{258}$VYYCLQV<br>SHVPPTFG$X_{259}$GTK$X_{260}$EIK<br>wherein $X_{241}$ = S or T, $X_{242}$ = D or L, $X_{243}$ = A or S,<br>$X_{244}$ = S or T, $X_{245}$ = L or P, $X_{246}$ = E or Q,<br>$X_{247}$ = R or P, $X_{248}$ = T or S, $X_{249}$ = N or S,<br>$X_{250}$ = Q or L, $X_{251}$ = P or S, $X_{252}$ = T or N, $X_{253}$ = L<br>or P, $X_{254}$ = T or K, $X_{255}$ = S or R, $X_{256}$ = L or V,<br>$X_{257}$ = Q or E, $X_{258}$ = A or G, $X_{259}$ = G or Q and<br>$X_{260}$ = V or L |
| 413 | 5B10-4Y/5I CON LC-FR1 | DIVMTQ$X_{261}$P$X_{262}$SL$X_{263}$V$X_{264}$$X_{265}$G$X_{266}$$X_{267}$A$X_{268}$I$X_{269}$CKSS<br>wherein $X_{261}$ = S or T, $X_{262}$ = D or L, $X_{263}$ = A or S,<br>$X_{264}$ = S or T, $X_{265}$ = L or P, $X_{266}$ = E or Q,<br>$X_{267}$ = R or P, $X_{268}$ = T or S, $X_{269}$ = N or S |
| 414 | 5B10-4Y/5I CON LC-FR2 | LNWY$X_{270}$QKPGQ$X_{271}$PKLLIY<br>wherein $X_{270}$ = Q or L and $X_{271}$ P or S |
| 415 | 5B10-4Y/5I CON LC-FR3 | $X_{272}$RFSGV$X_{273}$DRFSGSGSGTDFTL$X_{274}$IS$X_{275}$$X_{276}$$X_{277}$AEDV$X_{278}$VYYC<br>wherein $X_{272}$ = T or N, $X_{273}$ = L or P, $X_{274}$ = T or K,<br>$X_{275}$ = S or R, $X_{276}$ = L or V, $X_{277}$ = Q or E<br>and $X_{278}$ = A or G |
| 416 | 5B10-4Y/5I CON LC-FR4 | FG$X_{279}$GTK$X_{280}$EIK<br>wherein $X_{279}$ = G or Q and $X_{280}$ V or L |
| 417 | 1C8-6A/EH CON VH | QVQLV$X_{281}$SG$X_{282}$$X_{283}$$X_{284}$V$X_{285}$PG$X_{286}$S$X_{287}$$X_{288}$$X_{289}$SC$X_{290}$ASGYTFTNYVMHWVRQAPGQG<br>LEW$X_{291}$$X_{292}$YILPYNDG$X_{293}$NYN$X_{294}$K$X_{295}$$X_{296}$GR$X_{297}$T$X_{298}$$X_{299}$$X_{300}$D$X_{301}$S$X_{302}$$X_{303}$T$X_{304}$Y$X_{305}$<br>$X_{306}$$X_{307}$$X_{308}$SLR$X_{309}$EDTAVYYCARYDYEGSFDYWGQGTLVTVSS<br>wherein $X_{281}$ = Q or E, $X_{282}$ = A or G, $X_{283}$ = E or G,<br>$X_{284}$ = L or V, $X_{285}$ = K or Q, $X_{286}$ = S or R,<br>$X_{287}$ = V or L, $X_{288}$ = K or R, $X_{289}$ = M or L,<br>$X_{290}$ = K or A, $X_{291}$ = M or I, $X_{292}$ = G or A, $X_{293}$ = T or<br>A, $X_{294}$ = Q or E, $X_{295}$ = F or V, $X_{296}$ = Q or K,<br>$X_{297}$ = V or F, $X_{298}$ = M or I, $X_{299}$ = T or S, $X_{300}$ =<br>S or R, $X_{301}$ = K or N, $X_{302}$ = T or K, $X_{303}$ = S or N,<br>$X_{304}$ = A or L, $X_{305}$ = M or L, $X_{306}$ = E or Q,<br>$X_{307}$ = L or M, $X_{308}$ = S or N and $X_{309}$ = S or A |

-continued

| Sequences | | |
|---|---|---|

| SEQ ID NO: | DESCRIPTION | SEQUENCE |
|---|---|---|
| 418 | 1C8-6A/EH CON HC-CDR2 | ILPYNDGX$_{310}$<br>wherein X$_{310}$ = T or A |
| 419 | 1C8-6A/EH CON HC-FR1 | QVQLVX$_{311}$SGX$_{312}$X$_{313}$X$_{314}$VX$_{315}$PGX$_{316}$SX$_{317}$X$_{318}$X$_{319}$SCX$_{320}$AS<br>wherein X$_{311}$ = Q or E, X$_{312}$ = A or G, X$_{313}$ = E or G,<br>X$_{314}$ = L or V, X$_{315}$ = K or Q, X$_{316}$ = S or R,<br>X$_{317}$ = V or L, X$_{318}$ = K or R, X$_{319}$ = M or Land X$_{320}$ = K or A |
| 420 | 1C8-6A/EH CON HC-FR2 | MHWVRQAPGQGLEWX$_{321}$X$_{322}$Y<br>wherein X$_{321}$ = M or I and X$_{322}$ G or A |
| 421 | 1C8-6A/EH CON HC-FR3 | NYNX$_{323}$KX$_{324}$X$_{325}$GRX$_{326}$TX$_{327}$X$_{328}$X$_{329}$DX$_{330}$SX$_{331}$X$_{332}$TX$_{333}$<br>YX$_{334}$X$_{335}$X$_{336}$X$_{337}$SLRX$_{338}$EDTAVYYC<br>wherein X$_{323}$ = Q or E, X$_{324}$ = F or V, X$_{325}$ = Q or K,<br>X$_{326}$ = V or F, X$_{327}$ = M or I, X$_{328}$ = T or S,<br>X$_{329}$ = S or R, X$_{330}$ = K or N, X$_{331}$ = T or K,<br>X$_{332}$ = S or N, X$_{333}$ = A or L, X$_{334}$ = M or L, X$_{335}$ = E<br>or Q, X$_{336}$ = L or M, X$_{337}$ = S or N and X$_{338}$ = S or A |
| 422 | 1C8-6A/EH CON VL | DIQMTQSPSSLSASVGDRVTITCRASQDISNYLNWYQQKPGX$_{339}$X$_{340}$X$_{341}$KLLX$_{342}$X$_{343}$YTSRLH<br>SGVPSRFSGSGSGTDFTLTISSLQPEDFATYYCQQGNTFPPTFGGGTKVEIK<br>wherein X$_{339}$ = K or Q, X$_{340}$ = A or S, X$_{341}$ = P or V,<br>X$_{342}$ = M or I and X$_{343}$ = C or Y |
| 423 | 1C8-6A/EH CON LC-FR2 | LNWYQQKPGX$_{344}$X$_{345}$X$_{346}$KLLX$_{347}$X$_{348}$<br>wherein X$_{344}$ = K or Q, X$_{345}$ = A or S, X$_{346}$ = P or V,<br>X$_{347}$ = M or I and X$_{348}$ = C or Y |
| 424 | 1E9-4H IgG1 HC | QVQLVQSGAEVKKPGASVKVSCKASGYTFTDYSIYWVRQAPGQGLEWMGWINTETGEPNYA<br>QDVQGRFTMTLDTSTSTAYMELRSLRSDDTAVYYCSISYYYAMDYWGQGTLVTVSSASTKGP<br>SVFPLAPSSKSTSGGTAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLTCLVKGFYP<br>SDIAVEWESNGQPENNYKTTPPVLDSDGSFFLYSKLTVDKSRWQQGNVFSCSVMHEALHNH<br>YTQKSLSLSPGK |
| 425 | 1E9-4H Cκ LC | DIVMTQTPLSLSVTPGQPASISCKSSKSVSTSGYSFLHWYLQKPGQPPQLLIYFASNLESGVP<br>DRFSGSGSGTDFTLKISRVEAEDVGVYYCQHSRELPRTFGGGTKVEIKRTVAAPSVFIFPPSD<br>EQLKSGTASVVCLLNNFYPREAKVQWKVDNALQSGNSQESVTEQDSKDSTYSLSSTLTLSKA<br>DYEKHKVYACEVTHQGLSSPVTKSFNRGEC |
| 426 | 1E9-QE IgG1 HC | QVQLVQSGAEVKKPGASVKVSCKASGYTFTDYSIYWVRQAPGQGLEWMGWINTETGETNYA<br>QDFQGRVTMTTDTETSTAYMELRSLRSDDTAVYYCSISYYYAMDYWGQGTLVTVSSASTKGP<br>SVFPLAPSSKSTSGGTAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLTCLVKGFYP<br>SDIAVEWESNGQPENNYKTTPPVLDSDGSFFLYSKLTVDKSRWQQGNVFSCSVMHEALHNH<br>YTQKSLSLSPGK |
| 427 | 1E9-QE Cκ LC | EIVLTQSPATLSLSPGERATLSCRASKSVSTSGYSFLHWYQQKPGQAPRLLIYFASNLETGIPA<br>RFSGSGSGTDFTLTISRLEPEDFAVYYCQHSRELPRTFGQGTKLEIKRTVAAPSVFIFPPSDEQ<br>LKSGTASVVCLLNNFYPREAKVQWKVDNALQSGNSQESVTEQDSKDSTYSLSSTLTLSKADY<br>EKHKVYACEVTHQGLSSPVTKSFNRGEC |
| 428 | 2F8-2Q IgG1 HC | EVQLVESGGGLVQPGESLRLSCAASGYTFTDYTMYWVRQAPGKGLEWMGWINTETGETNY<br>ADSVKGRFTISRDNSKNTLYLQMNSLRAEDTAVYYCAISYYYGMDYWGQGTLVTVSSASTKG<br>PSVFPLAPSSKSTSGGTAALGCLVKDYFPEPVTVSWNSGALTSGVHTFPAVLQSSGLYSLSS<br>VTVPSSSLGTQTYICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSLTCLVKGFY<br>PSDIAVEWESNGQPENNYKTTPPVLDSDGSFFLYSKLTVDKSRWQQGNVFSCSVMHEALHN<br>HYTQKSLSLSPGK |
| 429 | 2F8-2Q Cκ LC | DIQMTQSPSTLSVSVGDRVTITCRASKSVSTSGYNFVYWYQQKPGKAPKLLIYLASNLESGVP<br>SRFSGSGSGTEFTLTISSLQPDDFATYYCQHSRELPRTFGQGTKVEIKRTVAAPSVFIFPPSDE<br>QLKSGTASVVCLLNNFYPREAKVQWKVDNALQSGNSQESVTEQDSKDSTYSLSSTLTLSKAD<br>YEKHKVYACEVTHQGLSSPVTKSFNRGEC |
| 430 | 2F8-5U IgG1 HC | EVQLVESGGGLVQPGGSLRLSCAASGYTFTDYTMYWVRQAPGKGLEWMGDINTETGETTYA<br>DSVKGRFTISRDNSKNTLYLQMNSLRAEDTAVYYCAISYYYGMDYWGQGTLVTVSSASTKGP<br>SVFPLAPSSKSTSGGTAALGCLVKDYFPEPVTVSWNSGALTSGVHTFPAVLQSSGLYSLSSVV |

| SEQ ID NO: | DESCRIPTION | SEQUENCE |
|---|---|---|
| | | TVPSSSLGTQTYICNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVMHEALHNH YTQKSLSLSPGK |
| 431 | 2F8-5U Cκ LC | DIQMTQSPSTLSASVGDRVTITCRASKSVSTSGYNFVYWYQQKPGQPPKLLIYLASNLESGVP SRFSGSGSGTEFTLTISSLQPDDFATYYCQHSRELPRTFGQGTKVEIKRTVAAPSVFIFPPSDE QLKSGTASVVCLLNNFYPREAKVQWKVDNALQSGNSQESVTEQDSKDSTYSLSSTLTLSKAD YEKHKVYACEVTHQGLSSPVTKSFNRGEC |
| 432 | 5B10-4Y IgG1 HC | QVQLVQSGAEVKKPGASVKVSCKASGYTFTSYVMHWVRQAPGQGLEWMAYILPFNDVTKYN EKFKGRVTMTDKSTSTVYMELSSLRSEDTAVYYCARWEWDDGYFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEA LHNHYTQKSLSLSPGK |
| 433 | 5B10-4Y Cκ LC | DIVMTQTPLSLSVTPGQPASISCKSSQSLENSNGNTYLNWYLQKPGQSPKLLIYRVSNRFSGV PDRFSGSGSGTDFTLKISRVEAEDVGVYYCLQVSHVPFTFGQGTKLEIKRTVAAPSVFIFPPSD EQLKSGTASVVCLLNNFYPREAKVQWKVDNALQSGNSQESVTEQDSKDSTYSLSSTLTLSKA DYEKHKVYACEVTHQGLSSPVTKSFNRGEC |
| 434 | 5B10-51 IgG1 HC | QVQLVQSGAEVKKPGASVKMSCKASGYTFTSYVMHWVRQAPGQGLEWIAYILPFNDVTNYN QKFQGRVTMTRDTSISTAYMELSRLRSDDTAVYYCARWEWDDGYFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEA LHNHYTQKSLSLSPGK |
| 435 | 5B10-51 Cκ LC | DIVMTQSPDSLAVSLGERATINCKSSQSLENSNGNTYLNWYQQKPGQPPKLLIYRVSTRFSGV LDRFSGSGSGTDFTLTISSLQAEDVAVYYCLQVSHVPFTFGGGTKVEIKRTVAAPSVFIFPPSD EQLKSGTASVVCLLNNFYPREAKVQWKVDNALQSGNSQESVTEQDSKDSTYSLSSTLTLSKA DYEKHKVYACEVTHQGLSSPVTKSFNRGEC |
| 436 | 1C8-6A IgG1 HC | QVQLVQSGAELVKPGSSVKMSCKASGYTFTNYVMHWVRQAPGQGLEWMGYILPYNDGTNY NQKFQGRVTMTSDKSTSTAYMELSSLRSEDTAVYYCARYDYEGSFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEA LHNHYTQKSLSLSPGK |
| 437 | 1C8-6A Cκ LC | DIQMTQSPSSLSASVGDRVTITCRASQDISNYLNWYQQKPGKAPKLLMCYTSRLHSGVPSRF SGSGSGTDFTLTISSLQPEDFATYYCQQGNTFPPTFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 438 | 1C8-EH IgG1 HC | QVQLVESGGGVVQPGRSLRLSCAASGYTFTNYVMHWVRQAPGQGLEWIAYILPYNDGANYN EKVKGRFTISRDNSKNTLYLQMNSLRAEDTAVYYCARYDYEGSFDYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCSVMHEALHN HYTQKSLSLSPGK |
| 439 | 1C8-EH Cκ LC | DIQMTQSPSSLSASVGDRVTITCRASQDISNYLNWYQQKPGQSVKLLIYYTSRLHSGVPSRFS GSGSGTDFTLTISSLQPEDFATYYCQQGNTFPPTFGGGTKVEIKRTVAAPSVFIFPPSDEQLKS GTASVVCLLNNFYPREAKVQWKVDNALQSGNSQESVTEQDSKDSTYSLSSTLTLSKADYEKH KVYACEVTHQGLSSPVTKSFNRGEC |
| 440 | 1E9-4H IgG1 CH1-CH2-CH3 (T366W, S354C) HC | QVQLVQSGAEVKKPGASVKVSCKASGYTFTDYSIYWVRQAPGQGLEWMGWINTETGEPNYA QDVQGRFTMTLDTSTSTAYMELRSLRSDDTAVYYCSISYYYAMDYWGQGTLVTVSSASTKGP SVFPLAPSSKSTSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPCRDELTKNQVSLWCLVKGFY |

-continued

| SEQ ID NO: | DESCRIPTION | SEQUENCE |
|---|---|---|
| | | PSDIAVEWESNGQPENNYKTTPPVLDSDGSFFLYSKLTVDKSRWQQGNVFSCSVMHEALHN HYTQKSLSLSPGK |
| 441 | 1E9-QE IgG1 CH1-CH2-CH3 (T366W, S354C) HC | QVQLVQSGAEVKKPGASVKVSCKASGYTFTDYSIYWVRQAPGQGLEWMGWINTETGETNYA QDFQGRVTMTTDTETSTAYMELRSLRSDDTAVYYCSISYYYAMDYWGQGTLVTVSSASTKGP SVFPLAPSSKSTSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPCRDELTKNQVSLWCLVKGFY PSDIAVEWESNGQPENNYKTTPPVLDSDGSFFLYSKLTVDKSRWQQGNVFSCSVMHEALHN HYTQKSLSLSPGK |
| 442 | 2F8-2Q IgG1 CH1-CH2-CH3 (T366W, S354C) HC | EVQLVESGGGLVQPGESLRLSCAASGYTFTDYTMYWVRQAPGKGLEWMGWINTETGETNY ADSVKGRFTISRDNSKNTLYLQMNSLRAEDTAVYYCAISYYYGMDYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPCRDELTKNQVSLWCLVKGF YPSDIAVEWESNGQPENNYKTTPPVLDSDGSFFLYSKLTVDKSRWQQGNVFSCSVMHEALH NHYTQKSLSLSPGK |
| 443 | 2F8-5U IgG1 CH1-CH2-CH3 (T366W, S354C) HC | EVQLVESGGGLVQPGGSLRLSCAASGYTFTDYTMYWVRQAPGKGLEWMGDINTETGETTYA DSVKGRFTISRDNSKNTLYLQMNSLRAEDTAVYYCAISYYYGMDYWGQGTLVTVSSASTKGP SVFPLAPSSKSTSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPCRDELTKNQVSLWCLVKGFY PSDIAVEWESNGQPENNYKTTPPVLDSDGSFFLYSKLTVDKSRWQQGNVFSCSVMHEALHN HYTQKSLSLSPGK |
| 444 | 5B10-4Y IgG1 CH1-CH2-CH3 (T366W, S354C) HC | QVQLVQSGAEVKKPGASVKVSCKASGYTFTSYVMHWVRQAPGQGLEWMAYILPFNDVTKYN EKFKGRVTMTSDKSTSTVYMELSSLRSEDTAVYYCARWEWDDGYFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 445 | 5B10-51 IgG1 CH1-CH2-CH3 (T366W, S354C) HC | QVQLVQSGAEVKKPGASVKMSCKASGYTFTSYVMHWVRQAPGQGLEWIAYILPFNDVTNYN QKFQGRVTMTRDTSISTAYMELSRLRSDDTAVYYCARWEWDDGYFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 446 | 1C8-6A IgG1 CH1-CH2-CH3 (T366W, S354C) HC | QVQLVQSGAELVKPGSSVKMSCKASGYTFTNYVMHWVRQAPGQGLEWMGYILPYNDGTNY NQKFQGRVTMTSDKSTSTAYMELSSLRSEDTAVYYCARYDYEGSFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 447 | 1C8-EH IgG1 CH1-CH2-CH3 (T366W, S354C) HC | QVQLVESGGGVVQPGRSLRLSCAASGYTFTNYVMHWVRQAPGQGLEWIAYILPYNDGANYN EKVKGRFTISRDNSKNTLYLQMNSLRAEDTAVYYCARYDYEGSFDYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPCRDELTKNQVSLWCLVKGF YPSDIAVEWESNGQPENNYKTTPPVLDSDGSFFLYSKLTVDKSRWQQGNVFSCSVMHEALH NHYTQKSLSLSPGK |
| 448 | Region important for binding of 538-SP5-B10 and 539-SP1-C8 to BCMA | YFDSLL |

| | | Sequences |
|---|---|---|
| SEQ ID NO: | DESCRIPTION | SEQUENCE |
| 449 | Region important for binding of 538-SP5-B10 and 539-SP1-C8 to TACI | YWDPLL |
| 450 | BCMA Mut | MLQMAGQCSQNEAFASGGHACIPCQLRCSSNTPPLTCQRYCNASVTNSVKGTNAILWTCLG LSLIISLAVFVLMFLLRKINSEPLKDEFKNTGSGLLGMANIDLEKSRTGDEIILPRGLEYTVEECT CEDCIKSKPKVDSDHCFPLPAMEEGATILVTTKTNDYCKSLPAALSATEIEKSISAR |
| 451 | TACI Mut | MSGLGRSRRGGRSRVDQEERFPQGLWTGVAMRSCPEEQAWAPGGGTCMSCKTICNHQSQ RTCAAFCRSLSCRKEQGKFYDHLLRDCISCASICGQHPKQCAYFCENKLRSPVNLPPELRRQ RSGEVENNSDNSGRYQGLEHRGSEASPALPGLKLSADQVALVYSTLGLCLCAVLCCFLVAVA CFLKKRGDPCSCQPRSRPRQSPAKSSQDHAMEAGSPVSTSPEPVETCSFCFPECRAPTQES AVTPGTPDPTCAGRWGCHTRTTVLQPCPHIPDSGLGIVCVPAQEGGPGA |
| 452 | OKT3 VH | QVQLQQSGAELARPGASVKMSCKASGYTFTRYTMHWVKQRPGQGLEWIGYINPSRGYTNY NQKFKDKATLTTDKSSSTAYMQLSSLTSEDSAVYYCARYYDDHYCLDYWGQGTTLTVSS |
| 453 | OKT3 VL | QIVLTQSPAIMSASPGEKVTMTCSASSSVSYMNWYQQKSGTSPKRWIYDTSKLASGVPAHFR GSGSGTSYSLTISGMEAEDAATYYCQQWSSNPFTFGSGTKLEIN |
| 454 | OKT3 scFv IgG1 CH2-CH3 (T366S, L368A, Y407V, Y349C) | QVQLQQSGAELARPGASVKMSCKASGYTFTRYTMHWVKQRPGQGLEWIGYINPSRGYTNY NQKFKDKATLTTDKSSSTAYMQLSSLTSEDSAVYYCARYYDDHYCLDYWGQGTTLTVSSSG GGGSGGGGSGGGGSQIVLTQSPAIMSASPGEKVTMTCSASSSVSYMNWYQQKSGTSPKRW IYDTSKLASGVPAHFRGSGSGTSYSLTISGMEAEDAATYYCQQWSSNPFTFGSGTKLEINVEP KSCDKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKG QPREPQVCTLPPSRDELTKNQVSLSCAVKGFYPSDIAVEWESNGQPENNYKTTPPVLDSDGS FFLVSKLTVDKSRWQQGNVFSCSVMHEALHNHYTQKSLSLSPGK |
| 455 | 1C8-402, 1C8-403 VH | QVQLVQSGAEVKKPGASVKVSCKASGYTFTNYVMHWVKQKPGQGLEWMGYILPYNDGTKY AQKFQGKVTMTDKSTSTVYMELSSLTSEDTAVYYCARYDWEGSFDYWGQGTLVTVSS |
| 456 | 1C8-402, 1C8-403, 1C8-25, 1C8-27 HC-CDR3 | ARYDWEGSFDY |
| 457 | 1C8-402, 1C8-403, 1C8-6A3 HC-FR2 | MHWVKQKPGQGLEWMGY |
| 458 | 1C8-402, 1C8-403, C8-507, 1C8-610, 1C8-6A3 HC-FR3 | KYAQKFQGKVTMTDKSTSTVYMELSSLTSEDTAVYYC |
| 459 | 1C8-402 VL | DIQMTQSPSSLSASVGDRVTITCRASQDISNYLSWYQQKPGKAPKLLMRYTSRLHSGVPSRF SGSGSGTDFTLTISSLEQEDFATYYCQQGNLFPPTFGGGTKVEIK |
| 460 | 1C8-402 LC-CDR3 | QQGNLFPPT |
| 461 | 1C8-402 LC-FR2 | LSWYQQKPGKAPKLLMR |
| 462 | 1C8-402, 1C8-403, 1C8-6A3 LC-FR3 | RLHSGVPSRFSGSGSGTDFTLTISSLEQEDFATYYC |
| 463 | 1C8-403 VL | DIQMTQSPSSLSASVGDRVTITCRASSDISNYLNWYQQKPGKAPKLLMCYTSRLHSGVPSRFS GSGSGTDFTLTISSLEQEDFATYYCQQGNTFPPTFGGGTKVEIK |
| 464 | 1C8-403 LC-CDR1 | SDISNY |
| 465 | 1C8-507 VH | QVQLVQSGAEVKKPGASVKVSCKASGYTFRNYVMHWVKQKPGQGLEWMGWILPYNDGTKY AQKFQGKVTMTDKSTSTVYMELSSLTSEDTAVYYCARYDYEGSFDYWGQGTLVTVSS |
| 466 | 1C8-507 HC-CDR1 | GYTFRNYV |
| 467 | 1C8-507 HC-FR2 | MHWVKQKPGQGLEWMGW |
| 468 | 1C8-507 VL | DIQMTQSPSSLSASVGDRVTITCRASQDISNYLNWYQQKPGKAPKLLMRYTSLLHSGVPSRFS GSGSGTDFTLTISSLEQEDFATYYCQQGNTFPPTFGGGTKVEIK |
| 469 | 1C8-507, 1C8-610 LC-FR2 | LNWYQQKPGKAPKLLMR |
| 470 | 1C8-507 LC-FR3 | LLHSGVPSRFSGSGSGTDFTLTISSLEQEDFATYYC |

-continued

| SEQ ID NO: | DESCRIPTION | SEQUENCE |
|---|---|---|
| 471 | 1C8-610 VH | QVQLVQSGAEVKKPGASVKVSCKASGYTFTNYVMFWVKQKPGQGLEWMGYITPYNDGTKY AQKFQGKVTMTSDKSTSTVYMELSSLTSEDTAVYYCARYDYEGSFDYWGQGTLVTVSS |
| 472 | 1C8-610 HC-CDR2 | ITPYNDGT |
| 473 | 1C8-610 HC-FR2 | MFWVKQKPGQGLEWMGY |
| 474 | 1C8-610 VL | DIQMTQSPSSLSASVGDRVTITCRASQDISNYLNWYQQKPGKAPKLLMRYTSRFHSGVPSRF SGSGSGTDFTLTISSLEQEDFATYYCQQGNTFPPTSGGGTKVEIK |
| 475 | 1C8-610 LC-FR3 | RFHSGVPSRFSGSGSGTDFTLTISSLEQEDFATYYC |
| 476 | 1C8-610 LC-FR4 | SGGGTKVEIK |
| 477 | 1C8-6A3 VH | QVQLVQSGAEVKKPGASVKVSCKASGYTFTNYVMHWVKQKPGQGLEWMGYILPYNDGTKY AQKFQGKVTMTSDKSTSTVYMELSSLTSEDTAVYYCARYDYEGSFDYWGQGTLVTVSS |
| 478 | 1C8-6A3 VL | DIQMTQSPSSLSASVGDRVTITCRASQDISNYLNWYQQKPGKAPKLLMCYTSRLHSGVPSRF SGSGSGTDFTLTISSLEQEDFATYYCQQGNTFPPTFGGGTKVEIK |
| 479 | 1C8-25, 1C8-27 VH | QVQLVQSGAEVKKPGASVKVSCKASGYTFTNYVMHWVRQAPGQRLEWMGYILPYNDGTKY SQKFQGRVTITRDTSASTAYMELSSLRSEDTAVYYCARYDWEGSFDYWGQGTTVTVSS |
| 480 | 1C8-25, 1C8-27 HC-FR2 | MHWVRQAPGQRLEWMGY |
| 481 | 1C8-25, 1C8-27 HC-FR3 | KYSQKFQGRVTITRDTSASTAYMELSSLRSEDTAVYYC |
| 482 | 1C8-25, 1C8-27 HC-FR4 | WGQGTTVTVSS |
| 483 | 1C8-25 VL | DIQMTQSPSSLSASVGDRVTITCRASQDIGNYLNWYQQKPGKAVKLLMRYTSRLHSGVPSRF SGSGSGTDFTLTISSLQPEDFATYYCQQGFTFPPTFGGGTKLEIK |
| 484 | 1C8-25 LC-CDR1 | QDIGNY |
| 485 | 1C8-25 LC-CDR3 | QQGFTFPPT |
| 486 | 1C8-25, 1C8-27 LC-FR2 | LNWYQQKPGKAVKLLMR |
| 487 | 1C8-27 VL | DIQMTQSPSSLSASVGDRVTITCAASQDISNYLNWYQQKPGKAVKLLMRYTSRLHSGVPSRF SGSGSGTDFTLTISSLQPEDFATYYCQQGNRFPPTFGGGTKLEIK |
| 488 | 1C8-27 LC-CDR3 | QQGNRFPPT |
| 489 | 1C8-27 LC-FR1 | DIQMTQSPSSLSASVGDRVTITCAAS |
| 490 | h1C8 CON VH | QVQLVQSGAEVKKPGASVKVSCKASGYTFX$_{349}$NYVMX$_{350}$WVX$_{351}$QX$_{352}$PGQX$_{353}$LEWMGX$_{3541}$ X$_{355}$PYNDGTKYX$_{356}$QKFQGX$_{357}$VTX$_{358}$TX$_{359}$DX$_{360}$SX$_{361}$STX$_{362}$YMELSSL$_{363}$SEDTAVYYCARY DX$_{364}$EGSFDYWGQGTX$_{365}$VTVSS<br>wherein X$_{349}$ = T or R, X$_{350}$ = H or F, X$_{351}$ = K or R,<br>X$_{352}$ = K or A, X$_{353}$ = G or R, X$_{354}$ = Y or W,<br>X$_{355}$ = L or T, X$_{356}$ = A or S, X$_{357}$ = K or R,<br>X$_{358}$ = M or I, X$_{359}$ = S or R, X$_{360}$ = K or T, X$_{361}$ = T or<br>A, X$_{362}$ = V or A, X$_{363}$ = T or R, X$_{364}$ = Y or W and X$_{365}$ = L or T |
| 491 | h1C8 CON HC-CDR1 | GYTFX$_{366}$NYV<br>wherein X$_{366}$ = T or R |
| 492 | h1C8 CON HC-CDR2 | IX$_{367}$PYNDGT<br>wherein X$_{367}$ = L or T |
| 493 | h1C8 CON HC-CDR3 | ARYDX$_{368}$EGSFDY<br>wherein X$_{368}$ = Y or W |
| 494 | h1C8 CON HC-FR2 | MX$_{369}$WVX$_{370}$QX$_{371}$PGQX$_{372}$LEWMGX$_{373}$<br>wherein X$_{369}$ = H or F, X$_{370}$ = K or R, X$_{371}$ = K or A,<br>X$_{372}$ = G or R and X$_{373}$ = Y or W |

-continued

| | | |
|---|---|---|

Sequences

| SEQ ID NO: | DESCRIPTION | SEQUENCE |
|---|---|---|
| 495 | h1C8 CON HC-FR3 | KYX$_{374}$QKFQGX$_{375}$VTX$_{376}$TX$_{377}$DX$_{378}$SX$_{379}$STX$_{380}$YMELSSL$_{381}$SEDTAVYYC<br>wherein X$_{374}$ = A or S, X$_{375}$ = K or R, X$_{376}$ = M or I,<br>X$_{377}$ = S or R, X$_{378}$ = K or T, X$_{379}$ = T or A,<br>X$_{380}$ = V or A and X$_{381}$ = T or R |
| 496 | h1C8 CON HC-FR4 | WGQGTX$_{382}$VTVSS<br>wherein X$_{382}$ = L or T |
| 497 | h1C8 CON VL | DIQMTQSPSSLSASVGDRVTITCX$_{383}$ASX$_{384}$DIX$_{385}$NYLX$_{386}$WYQQKPGKAX$_{387}$KLLMX$_{388}$YTS<br>X$_{389}$X$_{390}$HSGVPSRFSGSGSGTDFTLTISSLX$_{391}$X$_{392}$EDFATYYCQQGX$_{393}$X$_{394}$FPPTX$_{395}$GGGTK<br>X$_{396}$EIK<br>wherein X$_{383}$ = R or A, X$_{384}$ = Q or S, X$_{385}$ = S or G,<br>X$_{386}$ = N or S, X$_{387}$ = P or V, X$_{388}$ = R or C,<br>X$_{389}$ = R or L, X$_{390}$ = L or F, X$_{391}$ = E or Q,<br>X$_{392}$ = Q or P, X$_{393}$ = N or F, X$_{394}$ = T, L or R, X$_{395}$ =<br>F or S and X$_{396}$ = V or L |
| 498 | h1C8 CON LC-CDR1 | X$_{396}$DIX$_{397}$NY<br>wherein X$_{396}$ = Q or S and X$_{397}$ = S or G |
| 499 | h1C8 CON LC-CDR3 | QQGX$_{398}$X$_{399}$FPPT<br>wherein X$_{398}$ = N or F and X$_{399}$ = T, L or R |
| 500 | h1C8 CON LC-FR1 | DIQMTQSPSSLSASVGDRVTITCX$_{400}$AS<br>wherein X$_{400}$ = R or A |
| 501 | h1C8 CON LC-FR2 | LX$_{401}$WYQQKPGKAX$_{402}$KLLMX$_{403}$<br>wherein X$_{401}$ = N or S, X$_{402}$ = P or V and X$_{403}$ = R or C |
| 502 | h1C8 CON LC-FR3 | X$_{404}$X$_{405}$HSGVPSRFSGSGSGTDFTLTISSLX$_{406}$X$_{407}$EDFATYYC<br>wherein X$_{404}$ = R or L, X$_{405}$ = L or F,<br>X$_{406}$ = E or Q and X$_{407}$ = Q or P |
| 503 | h1C8 CON LC-FR4 | X$_{408}$GGGTKX$_{409}$EIK<br>wherein X$_{408}$ = F or S and X$_{409}$ = V or L |
| 504 | 1C8-402, 1C8-403 IgG1 HC | QVQLVQSGAEVKKPGASVKVSCKASGYTFTNYVMHWVKQKPGQGLEWMGYILPYNDGTKY<br>AQKFQGKVTMTSDKSTSTVYMELSSLTSEDTAVYYCARYDWEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 505 | 1C8-402 Cκ LC | DIQMTQSPSSLSASVGDRVTITCRASQDISNYLSWYQQKPGKAPKLLMRYTSRLHSGVPSRF<br>SGSGSGTDFTLTISSLEQEDFATYYCQQGNLFPPTFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 506 | 1C8-403 Cκ LC | DIQMTQSPSSLSASVGDRVTITCRASSDISNYLNWYQQKPGKAPKLLMCYTSRLHSGVPSRFS<br>GSGSGTDFTLTISSLEQEDFATYYCQQGNTFPPTFGGGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| 507 | 1C8-507 IgG1 HC | QVQLVQSGAEVKKPGASVKVSCKASGYTFRNYVMHWVKQKPGQGLEWMGWILPYNDGTKY<br>AQKFQGKVTMTSDKSTSTVYMELSSLTSEDTAVYYCARYDYEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 508 | 1C8-507 Cκ LC | DIQMTQSPSSLSASVGDRVTITCRASQDISNYLNWYQQKPGKAPKLLMRYTSLLHSGVPSRFS<br>GSGSGTDFTLTISSLEQEDFATYYCQQGNTFPPTFGGGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| 509 | 1C8-610 IgG1 HC | QVQLVQSGAEVKKPGASVKVSCKASGYTFTNYVMFWVKQKPGQGLEWMGYITPYNDGTKY<br>AQKFQGKVTMTSDKSTSTVYMELSSLTSEDTAVYYCARYDYEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP |

-continued

| | | |
|---|---|---|
| | | Sequences |

| SEQ ID NO: | DESCRIPTION | SEQUENCE |
|---|---|---|
| | | KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 510 | 1C8-610 Cκ LC | DIQMTQSPSSLSASVGDRVTITCRASQDISNYLNWYQQKPGKAPKLLMRYTSRFHSGVPSRF<br>SGSGSGTDFTLTISSLEQEDFATYYCQQGNTFPPTSGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 511 | 1C8-6A3 IgG1 HC | QVQLVQSGAEVKKPGASVKVSCKASGYTFTNYVMHWVKQKPGQGLEWMGYILPYNDGTKY<br>AQKFQGKVTMTSDKSTSTVYMELSSLTSEDTAVYYCARYDYEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 512 | 1C8-6A3 Cκ LC | DIQMTQSPSSLSASVGDRVTITCRASQDISNYLNWYQQKPGKAPKLLMCYTSRLHSGVPSRF<br>SGSGSGTDFTLTISSLEQEDFATYYCQQGNTFPPTFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 513 | 1C8-25, 1C8-27 IgG1<br>HC | QVQLVQSGAEVKKPGASVKVSCKASGYTFTNYVMHWVRQAPGQRLEWMGYILPYNDGTKY<br>SQKFQGRVTITRDTSASTAYMELSSLRSEDTAVYYCARYDWEGSFDYWGQGTTVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 514 | 1C8-25 Cκ LC | DIQMTQSPSSLSASVGDRVTITCRASQDIGNYLNWYQQKPGKAVKLLMRYTSRLHSGVPSRF<br>SGSGSGTDFTLTISSLQPEDFATYYCQQGFTFPPTFGGGTKLEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 515 | 1C8-27 Cκ LC | DIQMTQSPSSLSASVGDRVTITCAASQDISNYLNWYQQKPGKAVKLLMRYTSRLHSGVPSRF<br>SGSGSGTDFTLTISSLQPEDFATYYCQQGNRFPPTFGGGTKLEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 516 | 1C8-402, 1C8-403<br>IgG1 LALA HC | QVQLVQSGAEVKKPGASVKVSCKASGYTFTNYVMHWVKQKPGQGLEWMGYILPYNDGTKY<br>AQKFQGKVTMTSDKSTSTVYMELSSLTSEDTAVYYCARYDWEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPEAAGGPSVFLFPP<br>KPKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEA<br>LHNHYTQKSLSLSPGK |
| 517 | Human IgG1 constant<br>region + LALA (L234A<br>and L235A (EU<br>numbering) relative to<br>P01857-1) | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCPAPEAAGGPSVFL<br>FPPKPKDTLMISRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| 518 | CH2 hIgG1 LALA | PCPAPEAAGGPSVFLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKAK |
| 519 | Human IgG1 constant<br>region G1m3 allotype<br>LALA | ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRVEPKSCDKTHTCPPCPAPEAAGGPSVFL<br>FPPKPKDTLMISRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| 520 | 1C8-402, 1C8-403<br>IgG1 CH1-CH2-CH3<br>(T366W, S354C) HC | QVQLVQSGAEVKKPGASVKVSCKASGYTFTNYVMHWVKQKPGQGLEWMGYILPYNDGTKY<br>AQKFQGKVTMTSDKSTSTVYMELSSLTSEDTAVYYCARYDWEGSFDYWGQGTLVTVSSAST<br>KGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPP |

-continued

| Sequences | | |
|---|---|---|

| SEQ ID NO: | DESCRIPTION | SEQUENCE |
|---|---|---|
| | | KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 521 | 1C8-507 IgG1 CH1-CH2-CH3 (T366W, S354C) HC | QVQLVQSGAEVKKPGASVKVSCKASGYTFRNYVMHWVKQKPGQGLEWMGWILPYNDGTKY AQKFQGKVTMTSDKSTSTVYMELSSLTSEDTAVYYCARYDYEGSFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 522 | 1C8-610 IgG1 CH1-CH2-CH3 (T366W, S354C) HC | QVQLVQSGAEVKKPGASVKVSCKASGYTFTNYVMFWVKQKPGQGLEWMGYITPYNDGTKY AQKFQGKVTMTSDKSTSTVYMELSSLTSEDTAVYYCARYDYEGSFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 523 | 1C8-6A3 IgG1 CH1-CH2-CH3 (T366W, S354C) HC | QVQLVQSGAEVKKPGASVKVSCKASGYTFTNYVMHWVKQKPGQGLEWMGYILPYNDGTKY AQKFQGKVTMTSDKSTSTVYMELSSLTSEDTAVYYCARYDYEGSFDYWGQGTLVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 524 | 1C8-25, 1C8-27 IgG1 CH1-CH2-CH3 (T366W, S354C) HC | QVQLVQSGAEVKKPGASVKVSCKASGYTFTNYVMHWVRQAPGQRLEWMGYILPYNDGTKY SQKFQGRVTITRDTSASTAYMELSSLRSEDTAVYYCARYDWEGSFDYWGQGTTVTVSSAST KGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNVFSCSVMHE ALHNHYTQKSLSLSPGK |
| 525 | OKT3 HC-CDR1 | GYTFTRYT |
| 526 | OKT3 HC-CDR2 | INPSRGYT |
| 527 | OKT3 HC-CDR3 | ARYYDDHYCLDY |
| 528 | OKT3 HC-FR1 | QVQLQQSGAELARPGASVKMSCKAS |
| 529 | OKT3 HC-FR2 | MHWVKQRPGQGLEWIGY |
| 530 | OKT3 HC-FR3 | NYNQKFKDKATLTTDKSSSTAYMQLSSLTSEDSAVYYC |
| 531 | OKT3 LC-CDR1 | SSVSY |
| 532 | OKT3 LC-CDR2 | DTS |
| 533 | OKT3 LC-CDR3 | QQWSSNPFT |
| 534 | OKT3 LC-FR1 | QIVLTQSPAIMSASPGEKVTMTCSAS |
| 535 | OKT3 LC-FR2 | MNWYQQKSGTSPKRWIY |
| 536 | OKT3 LC-FR3 | KLASGVPAHFRGSGSGTSYSLTISGMEAEDAATYYC |
| 537 | OKT3 LC-FR4 | FGSGTKLEIN |
| 538 | SP34 VH | EVQLVESGGGLVQPKGSLKLSCAASGFTFNTYAMNWVRQAPGKGLEWVARIRSKYNNYATY YADSVKDRFTISRDDSQSILYLQMNNLKTEDTAMYYCVRHGNFGNSYVSWFAYWGQGTLVT VSA |
| 539 | SP34 HC-CDR1 | GFTFNTYA |

Sequences

| SEQ ID NO: | DESCRIPTION | SEQUENCE |
|---|---|---|
| 540 | SP34 HC-CDR2 | IRSKYNNYAT |
| 541 | SP34 HC-CDR3 | VRHGNFGNSYVSWFAY |
| 542 | SP34 HC-FR1 | EVQLVESGGGLVQPKGSLKLSCAAS |
| 543 | SP34 HC-FR2 | MNWVRQAPGKGLEWVAR |
| 544 | SP34 HC-FR3 | YYADSVKDRFTISRDDSQSILYLQMNNLKTEDTAMYYC |
| 545 | SP34 VL | QAVVTQESALTTSPGETVTLTCRSSTGAVTTSNYANWVQEKPDHLFTGLIGGTNKRAPGVPA<br>RFSGSLIGDKAALTITGAQTEDEAIYFCALWYSNLWVFGGGTKLTVL |
| 546 | SP34 LC-CDR1 | TGAVTTSNY |
| 547 | SP34 LC-CDR2 | GTN |
| 548 | SP34 LC-CDR3 | ALWYSNLWV |
| 549 | SP34 LC-FR1 | QAVVTQESALTTSPGETVTLTCRSS |
| 550 | SP34 LC-FR2 | ANWVQEKPDHLFTGLIG |
| 551 | SP34 LC-FR3 | KRAPGVPARFSGSLIGDKAALTITGAQTEDEAIYFC |
| 552 | SP34 LC-FR4 | FGGGTKLTVL |
| 553 | SP34 scFv IgG1 CH2-CH3 (T366S, L368A, Y407V, Y349C) | EVQLVESGGGLVQPKGSLKLSCAASGFTFNTYAMNWVRQAPGKGLEWVARIRSKYNNYATY<br>YADSVKDRFTISRDDSQSILYLQMNNLKTEDTAMYYCVRHGNFGNSYVSWFAYWGQGTLVT<br>VSASGGGGSGGGGSGGGGSQAVVTQESALTTSPGETVTLTCRSSTGAVTTSNYANWVQEK<br>PDHLFTGLIGGTNKRAPGVPARFSGSLIGDKAALTITGAQTEDEAIYFCALWYSNLWVFGGGT<br>KLTVLVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEK<br>TISKAKGQPREPQVCTLPPSRDELTKNQVSLSCAVKGFYPSDIAVEWESNGQPENNYKTTPP<br>VLDSDGSFFLVSKLTVDKSRWQQGNVFSCSVMHEALHNHYTQKSLSLSPGK |
| 554 | Region of BCMA bound by 539-SP1-C8 and 1C8-derived antibodies 1 | LQMAGQCSQNEYFDSLLHACIPCQL |
| 555 | Region of BCMA bound by 539-SP1-C8 and 1C8-derived antibodies 2 (epitope) | DSLLHACIPCQL |
| 556 | Region of BCMA bound by 539-SP1-C8 and 1C8-derived antibodies 3 (likely primary binding event) | HACIPCQL |
| 557 | Region of BCMA bound by 539-SP1-C8 and 1C8-derived antibodies 4 | LQMAGQCSQNEYFDSLL |
| 558 | Region of BCMA bound by 539-SP1-C8 and 1C8-derived antibodies 5 (likely secondary binding event) | DSLL |

Numbered Paragraphs

The following numbered paragraphs (paras) provide further statements of features and combinations of features which are contemplated in connection with the present invention:

1. An antigen-binding molecule, optionally isolated, which binds to BCMA, wherein the antigen-binding molecule comprises:

(a)

(i) a heavy chain variable (VH) region incorporating the following CDRs:

HC-CDR1 having the amino acid sequence of SEQ ID NO:137

HC-CDR2 having the amino acid sequence of SEQ ID NO:138

HC-CDR3 having the amino acid sequence of SEQ ID NO:139; and (ii) a light chain variable (VL) region incorporating the following CDRs:

LC-CDR1 having the amino acid sequence of SEQ ID NO:31

LC-CDR2 having the amino acid sequence of SEQ ID NO:32

LC-CDR3 having the amino acid sequence of SEQ ID NO:33; or (b)

(i) a heavy chain variable (VH) region incorporating the following CDRs:

HC-CDR1 having the amino acid sequence of SEQ ID NO:137

HC-CDR2 having the amino acid sequence of SEQ ID NO:138

HC-CDR3 having the amino acid sequence of SEQ ID NO:139; and (ii) a light chain variable (VL) region incorporating the following CDRs:

LC-CDR1 having the amino acid sequence of SEQ ID NO:45

LC-CDR2 having the amino acid sequence of SEQ ID NO:46

LC-CDR3 having the amino acid sequence of SEQ ID NO:47; or (c)

(i) a heavy chain variable (VH) region incorporating the following CDRs:

HC-CDR1 having the amino acid sequence of SEQ ID NO:137

HC-CDR2 having the amino acid sequence of SEQ ID NO:138

HC-CDR3 having the amino acid sequence of SEQ ID NO:139; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63; or (d)

(i) a heavy chain variable (VH) region incorporating the following CDRs:

HC-CDR1 having the amino acid sequence of SEQ ID NO:23

HC-CDR2 having the amino acid sequence of SEQ ID NO:24

HC-CDR3 having the amino acid sequence of SEQ ID NO:25; and (ii) a light chain variable (VL) region incorporating the following CDRs:

LC-CDR1 having the amino acid sequence of SEQ ID NO:31

LC-CDR2 having the amino acid sequence of SEQ ID NO:32

LC-CDR3 having the amino acid sequence of SEQ ID NO:33; or (e)

(i) a heavy chain variable (VH) region incorporating the following CDRs:

HC-CDR1 having the amino acid sequence of SEQ ID NO:23

HC-CDR2 having the amino acid sequence of SEQ ID NO:39

HC-CDR3 having the amino acid sequence of SEQ ID NO:40; and (ii) a light chain variable (VL) region incorporating the following CDRs:

LC-CDR1 having the amino acid sequence of SEQ ID NO:45

LC-CDR2 having the amino acid sequence of SEQ ID NO:46

LC-CDR3 having the amino acid sequence of SEQ ID NO:47; or (f)

(i) a heavy chain variable (VH) region incorporating the following CDRs:

HC-CDR1 having the amino acid sequence of SEQ ID NO:53

HC-CDR2 having the amino acid sequence of SEQ ID NO:54

HC-CDR3 having the amino acid sequence of SEQ ID NO:55; and (ii) a light chain variable (VL) region incorporating the following CDRs:

LC-CDR1 having the amino acid sequence of SEQ ID NO:61

LC-CDR2 having the amino acid sequence of SEQ ID NO:62

LC-CDR3 having the amino acid sequence of SEQ ID NO:63; or (g)

(i) a heavy chain variable (VH) region incorporating the following CDRs:

HC-CDR1 having the amino acid sequence of SEQ ID NO:145

HC-CDR2 having the amino acid sequence of SEQ ID NO:100

HC-CDR3 having the amino acid sequence of SEQ ID NO:146; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (h)

(i) a heavy chain variable (VH) region incorporating the following CDRs:

HC-CDR1 having the amino acid sequence of SEQ ID NO:145

HC-CDR2 having the amino acid sequence of SEQ ID NO:100

HC-CDR3 having the amino acid sequence of SEQ ID NO:146; and (ii) a light chain variable (VL) region incorporating the following CDRs:

LC-CDR1 having the amino acid sequence of SEQ ID NO:106

LC-CDR2 having the amino acid sequence of SEQ ID NO:107

LC-CDR3 having the amino acid sequence of SEQ ID NO:108; or (i)

(i) a heavy chain variable (VH) region incorporating the following CDRs:

HC-CDR1 having the amino acid sequence of SEQ ID NO:145

HC-CDR2 having the amino acid sequence of SEQ ID NO:100

HC-CDR3 having the amino acid sequence of SEQ ID NO:146; and (ii) a light chain variable (VL) region incorporating the following CDRs:

LC-CDR1 having the amino acid sequence of SEQ ID NO:119

LC-CDR2 having the amino acid sequence of SEQ ID NO:120

LC-CDR3 having the amino acid sequence of SEQ ID NO:108; or (j)

(i) a heavy chain variable (VH) region incorporating the following CDRs:

HC-CDR1 having the amino acid sequence of SEQ ID NO:145

HC-CDR2 having the amino acid sequence of SEQ ID NO:100

HC-CDR3 having the amino acid sequence of SEQ ID NO:146; and (ii) a light chain variable (VL) region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108; or (k)

(i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:101; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (l)

(i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (m)

(i) a heavy chain variable (VH) region incorporating the following CDRs:

HC-CDR1 having the amino acid sequence of SEQ ID NO:128

HC-CDR2 having the amino acid sequence of SEQ ID NO:100

HC-CDR3 having the amino acid sequence of SEQ ID NO:129; and (ii) a light chain variable (VL) region incorporating the following CDRs:

LC-CDR1 having the amino acid sequence of SEQ ID NO:152

LC-CDR2 having the amino acid sequence of SEQ ID NO:153

LC-CDR3 having the amino acid sequence of SEQ ID NO:108; or (n)

(i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:101; and (ii) a light chain variable (VL) region incorporating the following CDRs:

LC-CDR1 having the amino acid sequence of SEQ ID NO:106

LC-CDR2 having the amino acid sequence of SEQ ID NO:107

LC-CDR3 having the amino acid sequence of SEQ ID NO:108; or (o)

(i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:119

LC-CDR2 having the amino acid sequence of SEQ ID NO:120

LC-CDR3 having the amino acid sequence of SEQ ID NO:108; or (p)

(i) a heavy chain variable (VH) region incorporating the following CDRs:

HC-CDR1 having the amino acid sequence of SEQ ID NO:99

HC-CDR2 having the amino acid sequence of SEQ ID NO:100

HC-CDR3 having the amino acid sequence of SEQ ID NO:113; and (ii) a light chain variable (VL) region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108; or (q)

(i) a heavy chain variable (VH) region incorporating the following CDRs:

HC-CDR1 having the amino acid sequence of SEQ ID NO:128

HC-CDR2 having the amino acid sequence of SEQ ID NO:100

HC-CDR3 having the amino acid sequence of SEQ ID NO:129; and (ii) a light chain variable (VL) region incorporating the following CDRs:

LC-CDR1 having the amino acid sequence of SEQ ID NO:125

LC-CDR2 having the amino acid sequence of SEQ ID NO:120

LC-CDR3 having the amino acid sequence of SEQ ID NO:108; or (r)

(i) a heavy chain variable (VH) region incorporating the following CDRs:

HC-CDR1 having the amino acid sequence of SEQ ID NO:68

HC-CDR2 having the amino acid sequence of SEQ ID NO:69

HC-CDR3 having the amino acid sequence of SEQ ID NO:70; and (ii) a light chain variable (VL) region incorporating the following CDRs:

LC-CDR1 having the amino acid sequence of SEQ ID NO:76

LC-CDR2 having the amino acid sequence of SEQ ID NO:77

LC-CDR3 having the amino acid sequence of SEQ ID NO:78; or (s)

(i) a heavy chain variable (VH) region incorporating the following CDRs:

HC-CDR1 having the amino acid sequence of SEQ ID NO:84

HC-CDR2 having the amino acid sequence of SEQ ID NO:85

HC-CDR3 having the amino acid sequence of SEQ ID NO:86; and (ii) a light chain variable (VL) region incorporating the following CDRs:

LC-CDR1 having the amino acid sequence of SEQ ID NO:91

LC-CDR2 having the amino acid sequence of SEQ ID NO:92

LC-CDR3 having the amino acid sequence of SEQ ID NO:93; or (t)

(i) a heavy chain variable (VH) region incorporating the following CDRs:

HC-CDR1 having the amino acid sequence of SEQ NO:99

HC-CDR2 having the amino acid sequence of SEQ NO:394

HC-CDR3 having the amino acid sequence of SEQ NO:101; and (ii) a light chain variable (VL) region incorporating the following CDRs:

LC-CDR1 having the amino acid sequence of SEQ NO:106

LC-CDR2 having the amino acid sequence of SEQ NO:107

LC-CDR3 having the amino acid sequence of SEQ NO:108; or (u)

(i) a heavy chain variable (VH) region incorporating the following CDRs:

HC-CDR1 having the amino acid sequence of SEQ NO:128

HC-CDR2 having the amino acid sequence of SEQ NO:347

HC-CDR3 having the amino acid sequence of SEQ NO:129; and (ii) a light chain variable (VL) region incorporating the following CDRs:

LC-CDR1 having the amino acid sequence of SEQ NO:125

LC-CDR2 having the amino acid sequence of SEQ NO:120

LC-CDR3 having the amino acid sequence of SEQ NO:108; or (v)

(i) a heavy chain variable (VH) region incorporating the following CDRs:

HC-CDR1 having the amino acid sequence of SEQ NO:53

HC-CDR2 having the amino acid sequence of SEQ NO:418

HC-CDR3 having the amino acid sequence of SEQ NO:55; and (ii) a light chain variable (VL) region incorporating the following CDRs:

LC-CDR1 having the amino acid sequence of SEQ NO:61

LC-CDR2 having the amino acid sequence of SEQ NO:62

LC-CDR3 having the amino acid sequence of SEQ NO:63; or (w)

(i) a heavy chain variable (VH) region incorporating the following CDRs:

HC-CDR1 having the amino acid sequence of SEQ NO:99

HC-CDR2 having the amino acid sequence of SEQ NO:347

HC-CDR3 having the amino acid sequence of SEQ NO:101; and (ii) a light chain variable (VL) region incorporating the following CDRs:

LC-CDR1 having the amino acid sequence of SEQ NO:106

LC-CDR2 having the amino acid sequence of SEQ NO:107

LC-CDR3 having the amino acid sequence of SEQ NO:108; or (x)

(i) a heavy chain variable (VH) region incorporating the following CDRs:

HC-CDR1 having the amino acid sequence of SEQ NO:53

HC-CDR2 having the amino acid sequence of SEQ NO:388

HC-CDR3 having the amino acid sequence of SEQ NO:55; and (ii) a light chain variable (VL) region incorporating the following CDRs:

LC-CDR1 having the amino acid sequence of SEQ NO:61

LC-CDR2 having the amino acid sequence of SEQ
NO:62

LC-CDR3 having the amino acid sequence of SEQ
NO:63.

2. The antigen-binding molecule according to para 1,
wherein the antigen-binding molecule comprises:

a VH region comprising an amino acid sequence having
at least 70% sequence identity to the amino acid
sequence of SEQ ID NO:136, 144, 22, 38, 52, 67, 83,
98, 112, 122, 127, 393, 401, 408, 417, 338, 346, 353,
361, 367, 372, 380 or 387; and a VL region comprising an amino acid sequence having
at least 70% sequence identity to the amino acid
sequence of SEQ ID NO:151, 30, 44, 60, 75, 90, 105,
118, 124, 133, 396, 405, 412, 422, 341, 349, 357,
365, 370, 376, 383 or 391; optionally wherein the
antigen-binding molecule comprises:

(i) a VH region comprising an amino acid sequence
having at least 70% sequence identity to the amino acid
sequence of SEQ ID NO:136; and a VL region comprising an amino acid sequence having
at least 70% sequence identity to the amino acid
sequence of SEQ ID NO:30;

or (ii) a VH region comprising an amino acid sequence
having at least 70% sequence identity to the amino acid
sequence of SEQ ID NO:136; and a VL region comprising an amino acid sequence having
at least 70% sequence identity to the amino acid
sequence of SEQ ID NO:44;

or (iii) a VH region comprising an amino acid sequence
having at least 70% sequence identity to the amino acid
sequence of SEQ ID NO:136; and a VL region comprising an amino acid sequence having
at least 70% sequence identity to the amino acid
sequence of SEQ ID NO:60;

or (iv) a VH region comprising an amino acid sequence
having at least 70% sequence identity to the amino acid
sequence of SEQ ID NO:22; and a VL region comprising an amino acid sequence having
at least 70% sequence identity to the amino acid
sequence of SEQ ID NO:30;

or (v) a VH region comprising an amino acid sequence
having at least 70% sequence identity to the amino acid
sequence of SEQ ID NO:38; and a VL region comprising an amino acid sequence having
at least 70% sequence identity to the amino acid
sequence of SEQ ID NO:44;

or (vi) a VH region comprising an amino acid sequence
having at least 70% sequence identity to the amino acid
sequence of SEQ ID NO:52; and a VL region comprising an amino acid sequence having
at least 70% sequence identity to the amino acid
sequence of SEQ ID NO:60;

or (vii) a VH region comprising an amino acid sequence
having at least 70% sequence identity to the amino acid
sequence of SEQ ID NO:144; and a VL region comprising an amino acid sequence having
at least 70% sequence identity to the amino acid
sequence of SEQ ID NO:151;

or (viii) a VH region comprising an amino acid sequence
having at least 70% sequence identity to the amino acid
sequence of SEQ ID NO:144; and a VL region comprising an amino acid sequence having
at least 70% sequence identity to the amino acid
sequence of SEQ ID NO:105;

or (ix) a VH region comprising an amino acid sequence
having at least 70% sequence identity to the amino acid
sequence of SEQ ID NO:144; and a VL region comprising an amino acid sequence having
at least 70% sequence identity to the amino acid
sequence of SEQ ID NO:118;

or (x) a VH region comprising an amino acid sequence
having at least 70% sequence identity to the amino acid
sequence of SEQ ID NO:144; and a VL region comprising an amino acid sequence having
at least 70% sequence identity to the amino acid
sequence of SEQ ID NO:124;

or (xi) a VH region comprising an amino acid sequence
having at least 70% sequence identity to the amino acid
sequence of SEQ ID NO:144; and a VL region comprising an amino acid sequence having
at least 70% sequence identity to the amino acid
sequence of SEQ ID NO:133;

or (xii) a VH region comprising an amino acid sequence
having at least 70% sequence identity to the amino acid
sequence of SEQ ID NO:98; and a VL region comprising an amino acid sequence having
at least 70% sequence identity to the amino acid
sequence of SEQ ID NO:151;

or (xiii) a VH region comprising an amino acid sequence
having at least 70% sequence identity to the amino acid
sequence of SEQ ID NO:112; and a VL region comprising an amino acid sequence having
at least 70% sequence identity to the amino acid
sequence of SEQ ID NO:151;

or (xiv) a VH region comprising an amino acid sequence
having at least 70% sequence identity to the amino acid
sequence of SEQ ID NO:122; and a VL region comprising an amino acid sequence having
at least 70% sequence identity to the amino acid
sequence of SEQ ID NO:151;

or (xv) a VH region comprising an amino acid sequence
having at least 70% sequence identity to the amino acid
sequence of SEQ ID NO:127; and a VL region comprising an amino acid sequence having
at least 70% sequence identity to the amino acid
sequence of SEQ ID NO:151;

or (xvi) a VH region comprising an amino acid sequence
having at least 70% sequence identity to the amino acid
sequence of SEQ ID NO:98; and a VL region comprising an amino acid sequence having
at least 70% sequence identity to the amino acid
sequence of SEQ ID NO:105;

or (xvii) a VH region comprising an amino acid sequence
having at least 70% sequence identity to the amino acid
sequence of SEQ ID NO:112; and a VL region comprising an amino acid sequence having at least 70% sequence identity to the amino acid sequence of SEQ ID NO:118;

or (xviii) a VH region comprising an amino acid sequence having at least 70% sequence identity to the amino acid sequence of SEQ ID NO:122; and a VL region comprising an amino acid sequence having at least 70% sequence identity to the amino acid sequence of SEQ ID NO:124;

or (xix) a VH region comprising an amino acid sequence having at least 70% sequence identity to the amino acid sequence of SEQ ID NO:127; and a VL region comprising an amino acid sequence having at least 70% sequence identity to the amino acid sequence of SEQ ID NO:133;

or (xx) a VH region comprising an amino acid sequence having at least 70% sequence identity to the amino acid sequence of SEQ ID NO:67; and a VL region comprising an amino acid sequence having at least 70% sequence identity to the amino acid sequence of SEQ ID NO:75;

or (xxi) a VH region comprising an amino acid sequence having at least 70% sequence identity to the amino acid sequence of SEQ ID NO:83; and a VL region comprising an amino acid sequence having at least 70% sequence identity to the amino acid sequence of SEQ ID NO:90.

or (xxii) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:396;

or (xxiii) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:341;

or (xxiv) a VH region comprising an amino acid sequence having at least 70% sequence identity to the amino acid sequence of SEQ ID NO:393; and a VL region comprising an amino acid sequence having at least 70% sequence identity to the amino acid sequence of SEQ ID NO:349;

or (xxv) a VH region comprising an amino acid sequence having at least 70% sequence identity to the amino acid sequence of SEQ ID NO:338; and a VL region comprising an amino acid sequence having at least 70% sequence identity to the amino acid sequence of SEQ ID NO:396;

or (xxvi) a VH region comprising an amino acid sequence having at least 70% sequence identity to the amino acid sequence of SEQ ID NO:346; and a VL region comprising an amino acid sequence having at least 70% sequence identity to the amino acid sequence of SEQ ID NO:396;

or (xxvii) a VH region comprising an amino acid sequence having at least 70% sequence identity to the amino acid sequence of SEQ ID NO:338; and a VL region comprising an amino acid sequence having at least 70% sequence identity to the amino acid sequence of SEQ ID NO:341;

or (xxviii) a VH region comprising an amino acid sequence having at least 70% sequence identity to the amino acid sequence of SEQ ID NO:346; and a VL region comprising an amino acid sequence having at least 70% sequence identity to the amino acid sequence of SEQ ID NO:349;

or (xxix) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:405;

or (xxx) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:357;

or (xxxi) a VH region comprising an amino acid sequence having at least 70% sequence identity to the amino acid sequence of SEQ ID NO:401; and a VL region comprising an amino acid sequence having at least 70% sequence identity to the amino acid sequence of SEQ ID NO:365;

or (xxxii) a VH region comprising an amino acid sequence having at least 70% sequence identity to the amino acid sequence of SEQ ID NO:353; and a VL region comprising an amino acid sequence having at least 70% sequence identity to the amino acid sequence of SEQ ID NO:405;

or (xxxiii) a VH region comprising an amino acid sequence having at least 70% sequence identity to the amino acid sequence of SEQ ID NO:361; and a VL region comprising an amino acid sequence having at least 70% sequence identity to the amino acid sequence of SEQ ID NO:405;

or (xxxiv) a VH region comprising an amino acid sequence having at least 70% sequence identity to the amino acid sequence of SEQ ID NO:353; and a VL region comprising an amino acid sequence having at least 70% sequence identity to the amino acid sequence of SEQ ID NO:357;

or (xxxv) a VH region comprising an amino acid sequence having at least 70% sequence identity to the amino acid sequence of SEQ ID NO:361; and a VL region comprising an amino acid sequence having at least 70% sequence identity to the amino acid sequence of SEQ ID NO:365;

or (xxxvi) a VH region comprising an amino acid sequence having at least 70% sequence identity to the amino acid sequence of SEQ ID NO:408; and

a VL region comprising an amino acid sequence having at least 70% sequence identity to the amino acid sequence of SEQ ID NO:412;

or (xxxvii) a VH region comprising an amino acid sequence having at least 70% sequence identity to the amino acid sequence of SEQ ID NO:408; and
a VL region comprising an amino acid sequence having at least 70% sequence identity to the amino acid sequence of SEQ ID NO:370;

or (xxxviii) a VH region comprising an amino acid sequence having at least 70% sequence identity to the amino acid sequence of SEQ ID NO:408; and
a VL region comprising an amino acid sequence having at least 70% sequence identity to the amino acid sequence of SEQ ID NO:376;

or (xxxix) a VH region comprising an amino acid sequence having at least 70% sequence identity to the amino acid sequence of SEQ ID NO:367; and
a VL region comprising an amino acid sequence having at least 70% sequence identity to the amino acid sequence of SEQ ID NO:412;

or (xl) a VH region comprising an amino acid sequence having at least 70% sequence identity to the amino acid sequence of SEQ ID NO:372; and
a VL region comprising an amino acid sequence having at least 70% sequence identity to the amino acid sequence of SEQ ID NO:412;

(xli) a VH region comprising an amino acid sequence having at least 70% sequence identity to the amino acid sequence of SEQ ID NO:367; and
a VL region comprising an amino acid sequence having at least 70% sequence identity to the amino acid sequence of SEQ ID NO:370;

or (xlii) a VH region comprising an amino acid sequence having at least 70% sequence identity to the amino acid sequence of SEQ ID NO:372; and
a VL region comprising an amino acid sequence having at least 70% sequence identity to the amino acid sequence of SEQ ID NO:376;

or (xliii) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:422;

or (xliv) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:383;

or (xlv) a VH region comprising an amino acid sequence having at least 70% sequence identity to the amino acid sequence of SEQ ID NO:417; and
a VL region comprising an amino acid sequence having at least 70% sequence identity to the amino acid sequence of SEQ ID NO:391;

or (xlvi) a VH region comprising an amino acid sequence having at least 70% sequence identity to the amino acid sequence of SEQ ID NO:380; and
a VL region comprising an amino acid sequence having at least 70% sequence identity to the amino acid sequence of SEQ ID NO:422;

or (xlvii) a VH region comprising an amino acid sequence having at least 70% sequence identity to the amino acid sequence of SEQ ID NO:387; and
a VL region comprising an amino acid sequence having at least 70% sequence identity to the amino acid sequence of SEQ ID NO:422;

or (xlviii) a VH region comprising an amino acid sequence having at least 70% sequence identity to the amino acid sequence of SEQ ID NO:380; and
a VL region comprising an amino acid sequence having at least 70% sequence identity to the amino acid sequence of SEQ ID NO:383;

or (xlix) a VH region comprising an amino acid sequence having at least 70% sequence identity to the amino acid sequence of SEQ ID NO:387; and
a VL region comprising an amino acid sequence having at least 70% sequence identity to the amino acid sequence of SEQ ID NO:391.

3. The antigen-binding molecule according to para 1 or para 2, wherein the antigen-binding molecule binds to human BCMA and mouse BCMA.

4. The antigen-binding molecule according to any one of paras 1 to 3, wherein the antigen-binding molecule binds to TACT.

5. The antigen-binding molecule according to any one of paras 1 to 4, wherein the antigen-binding molecule is a multispecific antigen-binding molecule, and wherein the antigen binding molecule further comprises an antigen-binding domain which binds to an antigen other than BCMA.

6. An antigen-binding molecule, optionally isolated, which is a multispecific antigen-binding molecule, wherein the antigen-binding molecule comprises: (i) an antigen-binding domain which binds to BCMA comprising or consisting of an antigen-binding molecule as defined in any one of paras 1 to 4, and (ii) an antigen-binding domain which binds to an antigen other than BCMA.

7. The antigen-binding molecule according to para 5 or para 6, wherein the antigen other than BCMA is CD47.

8. The antigen-binding molecule according to any one of paras 5 to 7, wherein the antigen-binding molecule comprises an antigen-binding domain which binds to CD47 and inhibits interaction between CD47 and SIRPα; optionally wherein the antigen-binding molecule is capable of increasing phagocytosis of BCMA– and/or CD47-expressing cells.

9. The antigen-binding molecule according to any one of paras 5 to 8, wherein the antigen-binding molecule comprises:

(a)

(i) a heavy chain variable (VH) region incorporating the following CDRs:
HC-CDR1 having the amino acid sequence of SEQ ID NO:243
HC-CDR2 having the amino acid sequence of SEQ ID NO:244
HC-CDR3 having the amino acid sequence of SEQ ID NO:194; and (ii) a light chain variable (VL) region incorporating the following CDRs:

LC-CDR1 having the amino acid sequence of SEQ ID NO:245

LC-CDR2 having the amino acid sequence of SEQ ID NO:246

LC-CDR3 having the amino acid sequence of SEQ ID NO:247; or (b)

(i) a heavy chain variable (VH) region incorporating the following CDRs:

HC-CDR1 having the amino acid sequence of SEQ ID NO:243

HC-CDR2 having the amino acid sequence of SEQ ID NO:244

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:200

LC-CDR3 having the amino acid sequence of SEQ ID NO:201; or (c)

(i) a heavy chain variable (VH) region incorporating the following CDRs:

HC-CDR1 having the amino acid sequence of SEQ ID NO:243

HC-CDR2 having the amino acid sequence of SEQ ID NO:244

HC-CDR3 having the amino acid sequence of SEQ ID NO:194; and (ii) a light chain variable (VL) region incorporating the following CDRs:

LC-CDR1 having the amino acid sequence of SEQ ID NO:223

LC-CDR2 having the amino acid sequence of SEQ ID NO:225

LC-CDR3 having the amino acid sequence of SEQ ID NO:201; or (d)

(i) a heavy chain variable (VH) region incorporating the following CDRs:

HC-CDR1 having the amino acid sequence of SEQ ID NO:243

HC-CDR2 having the amino acid sequence of SEQ ID NO:244

HC-CDR3 having the amino acid sequence of SEQ ID NO:194; and (ii) a light chain variable (VL) region incorporating the following CDRs:

LC-CDR1 having the amino acid sequence of SEQ ID NO:224

LC-CDR2 having the amino acid sequence of SEQ ID NO:225

LC-CDR3 having the amino acid sequence of SEQ ID NO:201; or (e)

(i) a heavy chain variable (VH) region incorporating the following CDRs:

HC-CDR1 having the amino acid sequence of SEQ ID NO:243

HC-CDR2 having the amino acid sequence of SEQ ID NO:244

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:225

LC-CDR3 having the amino acid sequence of SEQ ID NO:201; or (f)

(i) a heavy chain variable (VH) region incorporating the following CDRs:

HC-CDR1 having the amino acid sequence of SEQ ID NO:243

HC-CDR2 having the amino acid sequence of SEQ ID NO:244

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:200

LC-CDR3 having the amino acid sequence of SEQ ID NO:226; or (g)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:245

LC-CDR2 having the amino acid sequence of SEQ ID NO:246

LC-CDR3 having the amino acid sequence of SEQ ID NO:247; or (h)

(i) a heavy chain variable (VH) region incorporating the following CDRs:

HC-CDR1 having the amino acid sequence of SEQ ID NO:53

HC-CDR2 having the amino acid sequence of SEQ ID NO:193

HC-CDR3 having the amino acid sequence of SEQ ID NO:194; and (ii) a light chain variable (VL) region incorporating the following CDRs:

LC-CDR1 having the amino acid sequence of SEQ ID NO:245

LC-CDR2 having the amino acid sequence of SEQ ID NO:246

LC-CDR3 having the amino acid sequence of SEQ ID NO:247; or (i)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:200

LC-CDR3 having the amino acid sequence of SEQ ID NO:201; or (j)

(i) a heavy chain variable (VH) region incorporating the following CDRs:

HC-CDR1 having the amino acid sequence of SEQ ID NO:53

HC-CDR2 having the amino acid sequence of SEQ ID NO:193

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:200

LC-CDR3 having the amino acid sequence of SEQ ID NO:201; or (k)

(i) a heavy chain variable (VH) region incorporating the following CDRs:

HC-CDR1 having the amino acid sequence of SEQ ID NO:53

HC-CDR2 having the amino acid sequence of SEQ ID NO:193

HC-CDR3 having the amino acid sequence of SEQ ID NO:194; and (ii) a light chain variable (VL) region incorporating the following CDRs:

LC-CDR1 having the amino acid sequence of SEQ ID NO:223

LC-CDR2 having the amino acid sequence of SEQ ID NO:225

LC-CDR3 having the amino acid sequence of SEQ ID NO:201; or (l)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:223

LC-CDR2 having the amino acid sequence of SEQ ID NO:225

LC-CDR3 having the amino acid sequence of SEQ ID NO:201; or (m)

(i) a heavy chain variable (VH) region incorporating the following CDRs:

HC-CDR1 having the amino acid sequence of SEQ ID NO:53

HC-CDR2 having the amino acid sequence of SEQ ID NO:193

HC-CDR3 having the amino acid sequence of SEQ ID NO:194; and (ii) a light chain variable (VL) region incorporating the following CDRs:

LC-CDR1 having the amino acid sequence of SEQ ID NO:224

LC-CDR2 having the amino acid sequence of SEQ ID NO:225

LC-CDR3 having the amino acid sequence of SEQ ID NO:201; or (n)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:224

LC-CDR2 having the amino acid sequence of SEQ ID NO:225

LC-CDR3 having the amino acid sequence of SEQ ID NO:201; or (o)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:225

LC-CDR3 having the amino acid sequence of SEQ ID NO:201; or (p)

(i) a heavy chain variable (VH) region incorporating the following CDRs:

HC-CDR1 having the amino acid sequence of SEQ ID NO:221

HC-CDR2 having the amino acid sequence of SEQ ID NO:222

HC-CDR3 having the amino acid sequence of SEQ ID NO:194; and (ii) a light chain variable (VL) region incorporating the following CDRs:

LC-CDR1 having the amino acid sequence of SEQ ID NO:199

LC-CDR2 having the amino acid sequence of SEQ ID NO:200

LC-CDR3 having the amino acid sequence of SEQ ID NO:226.

10. The antigen-binding molecule according to any one of paras 5 to 9, wherein the antigen-binding molecule comprises:

a VH region comprising an amino acid sequence having at least 70% sequence identity to the amino acid sequence of SEQ ID NO:252, 216, 192, 204, 211, 213, 214 or 215; and a VL region comprising an amino acid sequence having at least 70% sequence identity to the amino acid sequence of SEQ ID NO:253, 212, 198, 207, 217, 218, 219 or 220; optionally wherein the antigen-binding molecule comprises:

(i) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:253;
or
(ii) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:212;
or
(iii) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:198;
or
(iv) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:207;
or
(v) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:217;
or
(vi) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:218;
or
(vii) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:219;
or
(viii) a VH region comprising an amino acid sequence having at least 70% sequence identity to the amino acid sequence of SEQ ID NO:252; and
a VL region comprising an amino acid sequence having at least 70% sequence identity to the amino acid sequence of SEQ ID NO:220;

202 or
(ix) a VH region comprising an amino acid sequence having at least 70% sequence identity to the amino acid sequence of SEQ ID NO:216; and
a VL region comprising an amino acid sequence having at least 70% sequence identity to the amino acid sequence of SEQ ID NO:253;
or
(x) a VH region comprising an amino acid sequence having at least 70% sequence identity to the amino acid sequence of SEQ ID NO:192; and
a VL region comprising an amino acid sequence having at least 70% sequence identity to the amino acid sequence of SEQ ID NO:253;
or
(xi) a VH region comprising an amino acid sequence having at least 70% sequence identity to the amino acid sequence of SEQ ID NO:204; and
a VL region comprising an amino acid sequence having at least 70% sequence identity to the amino acid sequence of SEQ ID NO:253;
or
(xii) a VH region comprising an amino acid sequence having at least 70% sequence identity to the amino acid sequence of SEQ ID NO:211; and
a VL region comprising an amino acid sequence having at least 70% sequence identity to the amino acid sequence of SEQ ID NO:253;
or
(xiii) a VH region comprising an amino acid sequence having at least 70% sequence identity to the amino acid sequence of SEQ ID NO:213; and
a VL region comprising an amino acid sequence having at least 70% sequence identity to the amino acid sequence of SEQ ID NO:253;
or
(xiv) a VH region comprising an amino acid sequence having at least 70% sequence identity to the amino acid sequence of SEQ ID NO:214; and
a VL region comprising an amino acid sequence having at least 70% sequence identity to the amino acid sequence of SEQ ID NO:253;
or
(xv) a VH region comprising an amino acid sequence having at least 70% sequence identity to the amino acid sequence of SEQ ID NO:215; and
a VL region comprising an amino acid sequence having at least 70% sequence identity to the amino acid sequence of SEQ ID NO:253;
or
(xvi) a VH region comprising an amino acid sequence having at least 70% sequence identity to the amino acid sequence of SEQ ID NO:216; and
a VL region comprising an amino acid sequence having at least 70% sequence identity to the amino acid sequence of SEQ ID NO:212;
or
(xvii) a VH region comprising an amino acid sequence having at least 70% sequence identity to the amino acid sequence of SEQ ID NO:192; and
a VL region comprising an amino acid sequence having at least 70% sequence identity to the amino acid sequence of SEQ ID NO:198;
or
(xviii) a VH region comprising an amino acid sequence having at least 70% sequence identity to the amino acid sequence of SEQ ID NO:204; and a VL region comprising an amino acid sequence having at least 70% sequence identity to the amino acid sequence of SEQ ID NO:207;

or (xix) a VH region comprising an amino acid sequence having at least 70% sequence identity to the amino acid sequence of SEQ ID NO:211; and a VL region comprising an amino acid sequence having at least 70% sequence identity to the amino acid sequence of SEQ ID NO:212;

or (xx) a VH region comprising an amino acid sequence having at least 70% sequence identity to the amino acid sequence of SEQ ID NO:213; and a VL region comprising an amino acid sequence having at least 70% sequence identity to the amino acid sequence of SEQ ID NO:212;

or (xxi) a VH region comprising an amino acid sequence having at least 70% sequence identity to the amino acid sequence of SEQ ID NO:214; and a VL region comprising an amino acid sequence having at least 70% sequence identity to the amino acid sequence of SEQ ID NO:212;

or (xxii) a VH region comprising an amino acid sequence having at least 70% sequence identity to the amino acid sequence of SEQ ID NO:215; and a VL region comprising an amino acid sequence having at least 70% sequence identity to the amino acid sequence of SEQ ID NO:212;

or (xxiii) a VH region comprising an amino acid sequence having at least 70% sequence identity to the amino acid sequence of SEQ ID NO:215; and a VL region comprising an amino acid sequence having at least 70% sequence identity to the amino acid sequence of SEQ ID NO:217;

or (xxiv) a VH region comprising an amino acid sequence having at least 70% sequence identity to the amino acid sequence of SEQ ID NO:216; and a VL region comprising an amino acid sequence having at least 70% sequence identity to the amino acid sequence of SEQ ID NO:217;

or (xxv) a VH region comprising an amino acid sequence having at least 70% sequence identity to the amino acid sequence of SEQ ID NO:215; and a VL region comprising an amino acid sequence having at least 70% sequence identity to the amino acid sequence of SEQ ID NO:218;

or (xxvi) a VH region comprising an amino acid sequence having at least 70% sequence identity to the amino acid sequence of SEQ ID NO:216; and a VL region comprising an amino acid sequence having at least 70% sequence identity to the amino acid sequence of SEQ ID NO:218;

or (xxvii) a VH region comprising an amino acid sequence having at least 70% sequence identity to the amino acid sequence of SEQ ID NO:216; and a VL region comprising an amino acid sequence having at least 70% sequence identity to the amino acid sequence of SEQ ID NO:219;

or (xxviii) a VH region comprising an amino acid sequence having at least 70% sequence identity to the amino acid sequence of SEQ ID NO:216; and a VL region comprising an amino acid sequence having at least 70% sequence identity to the amino acid sequence of SEQ ID NO:220.

11. A chimeric antigen receptor (CAR) comprising an antigen-binding molecule according to any one of paras 1 to 10.

12. A nucleic acid, or a plurality of nucleic acids, optionally isolated, encoding an antigen-binding molecule according to any one of paras 1 to 10, or a CAR according to para 11.

13. An expression vector, or a plurality of expression vectors, comprising a nucleic acid or a plurality of nucleic acids according to para 12.

14. A cell comprising an antigen-binding molecule according to any one of paras 1 to 10, a CAR according to para 11, a nucleic acid or a plurality of nucleic acids according to para 12, or an expression vector or a plurality of expression vectors according to para 13.

15. A method comprising culturing a cell according to para 14 under conditions suitable for expression of an antigen-binding molecule or CAR by the cell.

16. A composition comprising an antigen-binding molecule according to any one of paras 1 to 10, a CAR according to para 11, a nucleic acid or a plurality of nucleic acids according to para 12, an expression vector or a plurality of expression vectors according to para 13, or a cell according to para 14, and a pharmaceutically acceptable carrier, diluent, excipient or adjuvant.

17. An antigen-binding molecule according to any one of paras 1 to 10, a CAR according to para 11, a nucleic acid or a plurality of nucleic acids according to para 12, an expression vector or a plurality of expression vectors according to para 13, a cell according to para 14, or a composition according to para 16, for use in a method of medical treatment or prophylaxis.

18. An antigen-binding molecule according to any one of paras 1 to 10, a CAR according to para 11, a nucleic acid or a plurality of nucleic acids according to para 12, an expression vector or a plurality of expression vectors according to para 13, a cell according to para 14, or a composition according to para 16, for use in a method of treatment or prevention of a cancer.

19. The antigen-binding molecule, CAR, nucleic acid or plurality of nucleic acids, expression vector or plurality of expression vectors, cell or composition for use according to para 18, wherein the cancer is selected from: a hematologic malignancy, a myeloid hematologic malignancy, a lymphoblastic hematologic malignancy, a B cell malignancy, multiple myeloma (MM), myelodysplastic syndrome (MDS), acute myeloid leukemia (AML), chronic myeloid leukemia (CML), acute lymphoblastic leukemia (ALL), lymphocytic leukemia, lymphoma, B cell lymphoma, Hodgkin's lymphoma (HL), non-Hodgkin's lymphoma (NHL), Burkitt lymphoma, bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

20. Use of antigen-binding molecule according to any one of paras 1 to 10 to increase phagocytosis of cells expressing BCMA and/or CD47.

21. An in vitro complex, optionally isolated, comprising an antigen-binding molecule according to any one of paras 1 to 10 bound to BCMA and/or CD47.

22. A method for detecting BCMA and/or CD47 in a sample, comprising contacting a sample containing, or suspected to contain, BCMA and/or CD47 with an antigen-binding molecule according to any one of paras 1 to 10, and detecting the formation of a complex of the antigen-binding molecule with BCMA and/or CD47.

23. A method of selecting or stratifying a subject for treatment with a BCMA-targeted agent and/or a CD47-targeted agent, the method comprising contacting, in vitro, a sample from the subject with an antigen-binding molecule according to any one of paras 1 to 10 and detecting the formation of a complex of the antigen-binding molecule with BCMA and/or CD47.

24. Use of an antigen-binding molecule according to any one of paras 1 to 10 as an in vitro or in vivo diagnostic or prognostic agent.

25. Use of an antigen-binding molecule according to any one of paras 1 to 10 in a method for detecting, localizing or imaging a cancer, optionally wherein the cancer is selected from: a hematologic malignancy, a myeloid hematologic malignancy, a lymphoblastic hematologic malignancy, a B cell malignancy, multiple myeloma (MM), myelodysplastic syndrome (MDS), acute myeloid leukemia (AML), chronic myeloid leukemia (CML), acute lymphoblastic leukemia (ALL), lymphocytic leukemia, lymphoma, B cell lymphoma, Hodgkin's lymphoma (HL), non-Hodgkin's lymphoma (NHL), Burkitt lymphoma, bladder cancer, brain cancer, glioblastoma, ovarian cancer, breast cancer, colon cancer, liver cancer, hepatocellular carcinoma, prostate cancer, lung cancer, Non-small Cell Lung Cancer (NSCLC), skin cancer and melanoma.

The present disclosure includes the combination of the aspects and preferred features described except where such a combination is clearly impermissible or expressly avoided.

The section headings used herein are for organizational purposes only and are not to be construed as limiting the subject matter described.

Aspects and embodiments of the present disclosure will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word 'comprise,' and variations such as 'comprises' and 'comprising,' will be understood to imply the inclusion of a stated integer or step or group of integers or steps but not the exclusion of any other integer or step or group of integers or steps.

As used herein, an amino acid sequence or a region of a polypeptide which 'corresponds' to a specified reference amino acid sequence or region of a polypeptide has at least 60%, e.g. one of at least 65%, 70%, 75%, 80%, 85%, 90%, 91%, 92%, 93%, 94%, 95%, 96%, 97%, 98%, 99% or 100% sequence identity to the amino acid sequence of the amino acid sequence/polypeptide/region. An amino acid sequence/region of a polypeptide which 'corresponds' to a specified reference amino acid sequence/region of a polypeptide can be identified by sequence alignment of the subject sequence to the reference sequence, e.g. using sequence alignment software such as ClustalOmega (Soding, J. 2005, Bioinformatics 21, 951-960).

It must be noted that, as used in the specification and the appended claims, the singular forms 'a,' 'an,' and 'the' include plural referents unless the context clearly dictates otherwise. Ranges may be expressed herein as from 'about' one particular value, and/or to 'about' another particular value. When such a range is expressed, another embodiment includes from the one particular value and/or to the other particular value. Similarly, when values are expressed as approximations, by the use of the antecedent 'about,' it will be understood that the particular value forms another embodiment.

Where a nucleic acid sequence is disclosed herein, the reverse complement thereof is also expressly contemplated.

Methods described herein may preferably be performed in vitro. The term 'in vitro' is intended to encompass procedures performed with cells in culture whereas the term 'in vivo' is intended to encompass procedures with/on intact multi-cellular organisms.

BRIEF DESCRIPTION OF THE FIGURES

Embodiments and experiments illustrating the principles of the present disclosure will now be discussed with reference to the accompanying figures.

FIG. 13. Table summarising the results of analysis of binding of anti-BMCA antibodies to human BCMA, cynomolgous macaque BCMA and mouse BCMA as determined by biolayer interferometry (BLI) analysis.

FIG. 14. Table summarising the results of analysis of binding of anti-BMCA antibodies to human BCMA following incubation with human APRIL, as determined by biolayer interferometry (BLI) analysis.

FIGS. 26A and 25B. Graphs and tables showing binding of anti-BCMA/TACI antibodies to (25A) H929 cells and (25B) RPM 8226 cells, as determined by flow cytometry. EC50 values for binding to the different cell types are shown.

FIG. 27. Table summarising the results of analysis of binding of anti-BMCA/TACI antibodies to human BCMA (huBCMA), cynomolgous macaque BCMA (CyBCMA), human TACI (huTACI) and cynomolgous macaque TACI (CyTACI), as determined by biolayer interferometry (BLI) analysis.

EXAMPLES

Figure 1A:
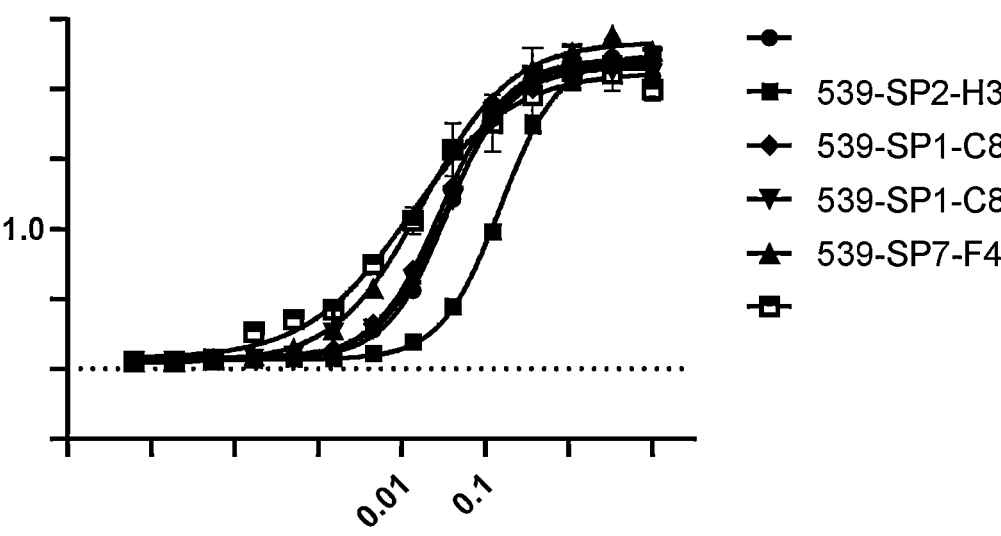
FIGS. 1A and 1B. Graphs showing binding of anti-BCMA antibodies to human BCMA, as determined by ELISA. (1A) shows results for 538-SP5-B10, 539-SP2-H3, 539-SP1-C8, 539-SP5-D7, 539-SP7-F4 and J6M0. (1B) shows results for 552-LN1-E9, 552-LN1-F4, 552-LN2-E6, 552-LN2-F8 and J6M0.
Figure 1B:
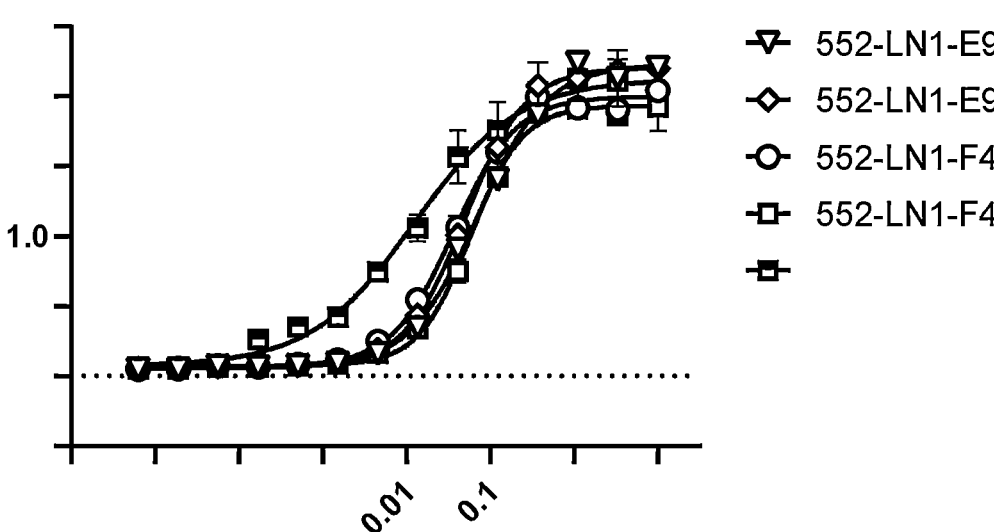

In the following Examples, the inventors describe the generation of novel BCMA-specific antibody clones, and the generation of novel anti-BCMA, anti-CD47 binding molecules, and the biophysical and functional characterisation of these antigen-binding molecules.

Example 1: Anti-BCMA Antibody Hybridoma Production 1.1 Hybridoma Production

Approximately 6 week old female BALB/c mice were obtained from InVivos (Singapore). Animals were housed under specific pathogen-free conditions and were treated in compliance with the Institutional Animal Care and Use Committee (IACUC) guidelines.

For hybridoma production, mice were immunized with proprietary mixtures of antigenic peptide for a total of 4 intraperitoneal injections with a 2 week interval between each injection. Antigen for immunizations included one of the following:

i) Up to 50 µg of synthetic peptide conjugated with KLH (EMC microcollections, Germany)

ii) Up to 50 µg of commercially available recombinant Fc-tagged human BCMA (Sinobiological Inc, China)

48 hours prior to harvesting the spleen for fusion, mice were boosted with antigen. Total splenocytes were isolated and fused with the myeloma cell line P3X63.Ag8.653 (ATCC, USA), by electrofusion according to manufacturer's protocol (Nepagene). Fused cells were allowed to recover in ClonaCell™-HY Medium C (Stemcell Technologies, Canada) overnight at 37° C. in a 5% $CO_2$ incubator. The next day, fused cells were harvested by centrifugation, resuspended in 1 ml of ClonaCell™-HY Medium C and then gently mixed with 90 ml of semisolid methylcellulose-based ClonaCell™-HY Medium D (StemCell Technologies, Canada) containing HAT and 500 µg of FITC-labelled anti-mouse antibody (Jackson Immunoresearch).

The cells were then plated into 8 to 16×6-well plates. Colonies were allowed to grow at 37° C. in a 5% $CO_2$ incubator for 7-9 days. Colonies were then analysed for FITC fluorescence, selected using Clonepix (Fortebio) device and transferred into a 96-well plates containing to ClonaCell™-HY AOF Expansion and Cloning Medium. Picked colonies were allowed to grow for 5 days, after which supernatants were analysed by Enzyme-linked immunosorbent assay (ELISA) to determine binding to human BCMA, and cells of colonies producing BCMA-binding antibodies were harvested by Fluorescence-activated cell sorting (FACs).

1.2 Antibody Variable Region Amplification and Sequencing 1 to $2\times10^6$ cells were collected by centrifugation, resuspended in RNAlater™ solution (Invitrogen) and stored at −80° C. until used. Total RNA was isolated from the hybridoma cells using the RNeasy Plus Micro Kit, in accordance with the manufacturer's instructions. Total RNA was then reverse-transcribed into cDNA using either isotype-specific anti-sense primers or universal primers and using SMARTScribe™ Reverse Transcriptase, in accordance with the manufacturer's instructions. Antibody fragments of heavy chain and light chain variable regions were amplified according GenScript's standard operating procedure (SOP) for rapid amplification of cDNA ends (RACE). Amplified antibody fragments were cloned into a standard cloning vector separately. Colony PCR was performed to screen for clones with inserts of correct sizes. Sequencing analysis was performed and consensus sequences were derived.

Nine monoclonal anti-BCMA antibody clones were selected for further development:

| Antibody clone | VH/VL sequences |
|---|---|
| 538-SP5-B10 | VH = SEQ ID NO: 22 |
| | VL = SEQ ID NO: 30 |
| 539-SP1-C8 | VH = SEQ ID NO: 52 |
| | VL = SEQ ID NO: 60 |
| 539-SP2-H3 | VH = SEQ ID NO: 38 |
| | VL = SEQ ID NO: 44 |
| 539-SP5-D7 | VH = SEQ ID NO: 67 |
| | VL = SEQ ID NO: 75 |
| 539-SP7-F4 | VH = SEQ ID NO: 83 |
| | VL = SEQ ID NO: 90 |
| 552-LN1-E9 | VH = SEQ ID NO: 98 |
| | VL = SEQ ID NO: 105 |
| 552-LN1-F4 | VH = SEQ ID NO: 122 |
| | VL = SEQ ID NO: 124 |
| 552-LN2-E6 | VH = SEQ ID NO: 112 |
| | VL = SEQ ID NO: 118 |
| 552-LN2-F8 | VH = SEQ ID NO: 127 |
| | VL = SEQ ID NO: 133 |

Example 2: Anti-BCMA Antibody Production and Purification 2.1 Cloning VH and VL into Expression Vectors:

DNA sequence encoding the heavy or light chain variable regions of the anti-BCMA antibody clones were subcloned in frame into the pcDNA3.4 vector (InvivoGen, USA)

eukaryotic expression vectors encoding the constant regions of human IgG1 (G1m1 allotype; SEQ ID NO:254), and the constant region of human kappa light chain (SEQ ID NO:262) or human lambda light chain 1 (SEQ ID NO:263), for the production of human-mouse chimeric antibodies.

| Antibody | Name | Heavy chain | Light chain |
|---|---|---|---|
| [1] | 538-SP5-B10 hIgG1 | SEQ ID NO: 302 | SEQ ID NO: 303 |
| [2] | 539-SP1-C8 hIgG1 | SEQ ID NO: 304 | SEQ ID NO: 305 |
| [3] | 539-SP2-H3 hIgG1 | SEQ ID NO: 306 | SEQ ID NO: 307 |
| [4] | 539-SP5-D7 hIgG1 | SEQ ID NO: 308 | SEQ ID NO: 309 |
| [5] | 539-SP7-F4 hIgG1 | SEQ ID NO: 310 | SEQ ID NO: 311 |
| [6] | 552-LN1-E9 hIgG1 | SEQ ID NO: 312 | SEQ ID NO: 313 |
| [7] | 552-LN1-F4 hIgG1 | SEQ ID NO: 314 | SEQ ID NO: 315 |
| [8] | 552-LN2-E6 hIgG1 | SEQ ID NO: 316 | SEQ ID NO: 317 |
| [9] | 552-LN2-F8 hIgG1 | SEQ ID NO: 318 | SEQ ID NO: 319 |

2.2 Expression of Antibodies in Mammalian Cells

Antibodies were expressed using the HD 293F cell expression system.

1) One day before transfection, the cells were seeded at an appropriate density in Corning® Erlenmeyer Flasks.

2) On the day of transfection, expression vector DNA and the transfection reagent were mixed at an optimal ratio and then added to cell culture flasks HD 293F cells in suspension culture.

3) Cell culture supernatant was collected on day 6 post-transfection and used for subsequent purification of the expressed antibodies.

2.3 Antibody Purification 2.3.1 Purification from HD 293F Cells

1) Cell culture broth was centrifuged and filtered.

2) Filtered cell culture supernatant was loaded onto an affinity purification column at an appropriate flowrate.

3) After washing and elution with appropriate buffers, the eluted fractions were pooled and buffer exchanged to final formulation buffer.

4) The purified protein was analysed by SDS-PAGE for evaluation of molecular weight and purity.

5) The concentration of the expressed antibody was determined by measuring absorbance at 280 nm using a NanoDrop spectrophotometer.

2.3.2 Purification from B Cell Hybridomas Supernatants 1-2 ml of hybridoma culture supernatant was incubated with 100 µl of MabSelect™ SuRe™ resin (GE Lifesciences) overnight at 4° C. or for 2 hours at room temperature. Tubes were centrifuged at 8,000 rpm for 5 min, and the supernatants discarded. Resins were washed 3 times with a phosphate buffer 10 mM, pH 7.2, and bound IgGs were eluted using a sodium citrate buffer 50 mM, pH 3.5. Eluted IgGs were neutralised using 45 mM Tris pH 9.5 (final concentration), and buffer exchanged to PBS using 30kD Protein Concentrator (Thermofisher). Antibody concentration was determined by measuring absorbance at 280 nm using a NanoDrop spectrophotometer.

Example 3: Characterisation of the Anti-BCMA Antibodies 3.1 ELISAs for Evaluating Antibody Specificity and Affinity ELISAs were performed in order to determine the binding specificity of the anti-BCMA antibodies produced from the hybridomas.

The antibodies produced from the hybridomas were analysed for binding to recombinant human, mouse and cynomolgus macaque BCMA, as well as cynomolgus macaque BCMA (single point). All proteins were obtained from Acro Biosystems (human BCMA: Cat #BCA-H522y; cyno BCMA: Cat #BCA-C52H7; mouse BCMA: Cat #BCA-M52H3).

ELISAs were performed according to standard protocols. Briefly, wells of 384-well plates (Nunc, Denmark) were coated with 1 µg/ml of His-tagged human, mouse or cynomolgus macaque BCMA in phosphate-buffered saline (PBS) for 16 h at 4° C. After blocking for 1 h 30 min with 1% BSA in 1×PBS at room temperature, cell culture supernatant containing the anti-BCMA antibodies, or IgG antibodies purified from the cell culture supernatant of B cell hybridomas serially diluted to obtain an 11 point dilution series dilution factor of 3, highest concentration=10 µg/ml) and added to the plate. After 1 h incubation at room temperature, plates were washed three times with 1×PBS containing 0.05% Tween 20, and were then incubated with a HRP-conjugated anti-mouse Fc antibody (Invitrogen, Cat #A24512) at a 1:7000 dilution in PBS for 1 h at room temperature. After three further washes with 1×PBS containing 0.05% Tween 20, plates were developed with colorimetric detection substrate 3,3', 5,5'-tetramethylbenzidine (Turbo-TMB; Pierce, USA). The reaction was stopped with 2M $H_2SO_4$, and OD was measured at 450 nM using a BioTek PowerWave HT.

The results obtained using cell culture supernatant containing the anti-BCMA antibodies are shown in the table below. ELISA absorbance values indicative of binding to the relevant proteins are shown in bold. Antibodies produced by all nine hybridomas were found to be cross-reactive for binding to both human and cynomolgus macaque BCMA. Antibodies produced by hybridoma clones 538-SP5-B10, 539-SP1-C8, 539-SP2-H3 and 539-SP7-F4 were additionally found to display binding to mouse BCMA.

| | ELISA values | | |
|---|---|---|---|
| Clone | Human BCMA | Mouse BCMA | Cyno BCMA |
| 538-SP5-B10 | 0.812 | 0.247 | 2.444 |
| 539-SP1-C8 | 0.686 | 0.339 | 2.038 |
| 539-SP2-H3 | 0.813 | 0.542 | 0.669 |
| 539-SP5-D7 | 0.817 | 0.025 | 0.252 |
| 539-SP7-F4 | 0.893 | 0.318 | 2.35 |
| 552-LN1-E9 | 0.836 | 0.017 | 2.074 |
| 552-LN1-F4 | 0.845 | 0.006 | 1.887 |
| 552-LN2-E6 | 0.832 | 0.002 | 0.729 |
| 552-LN2-F8 | 0.884 | 0.001 | 1.834 |

In further experiments, IgG antibodies purified from the cell culture supernatant of B cell hybridomas were analysed for binding to recombinant human and mouse BCMA at different concentrations by ELISA, as described above. Binding was compared to known anti-BCMA antibody J6M0 (described e.g. in WO 2012/163805 A1, which is hereby incorporated by reference in its entirety). Dose-response curves were fitted and EC50 values for binding to the relevant target proteins were derived from the dose-response curves, where possible.

The results are shown in FIGS. 1A, 1B, 2A and 2B, and in the table below.

| | EC50 (µg/ml) | |
|---|---|---|
| Clone | Human BCMA | Mouse BCMA |
| 538-SP5-B10 | 0.0358 | 20.96 |
| 539-SP2-H3 | 0.1516 | — |
| 539-SP1-C8 | 0.0299 | 9.191 |

-continued

| | EC50 (µg/ml) | |
| --- | --- | --- |
| Clone | Human BCMA | Mouse BCMA |
| 539-SP5-D7 | 0.0335 | — |
| 539-SP7-F4 | 0.0182 | 14.56 |
| 552-LN1-E9 | 0.071 | — |
| 552-LN2-E6 | 0.0505 | — |
| 552-LN1-F4 | 0.037 | — |
| 552-LN2-F8 | 0.0585 | — |
| J6M0 | 0.0126 | — |

In further experiments, purified antibodies produced in human IgG1 format (see Example 2.1 above) were analysed by ELISA for binding to recombinant human, cynomolgus macaque and mouse BCMA at different concentrations.

Briefly, wells of 384-well plates (Nunc, Denmark) were coated with 1 µg/ml of His-tagged human, mouse or cynomolgus macaque BCMA in phosphate-buffered saline (PBS) for 16 h at 4° C. After blocking for 1 h 30 min with 1% BSA in 1×PBS at room temperature, cell culture supernatant containing the anti-BCMA antibodies was serially diluted to obtain an 11 point dilution series (dilution factor of 3, highest concentration=10 µg/ml) and added to the plate. After 1 h incubation at room temperature, plates were washed three times with 1×PBS containing 0.05% Tween 20, and were then incubated with a HRP-conjugated goat anti-Human IgG antibody (Abcam, Cat #ab97225) at a 1:7000 dilution in PBS for 1 h at room temperature. After three further washes with 1×PBS containing 0.05% Tween 20, plates were developed with colorimetric detection substrate 3,3', 5,5'-tetramethylbenzidine (Turbo-TMB; Pierce, USA). The reaction was stopped with 2M $H_2SO_4$, and OD was measured at 450 nM using a BioTek PowerWave HT. An isotype-matched IgG1 negative control antibody (Invitrogen, Cat. #31154) was included in the experiment as a negative control.

The results are shown in FIGS. 3A, 3B, 4A, 4B, 5A and 5B.

In a further experiment performed essentially as described above, binding of the following antibodies to human BCMA was analysed using a 12 point, half-log dilution series: [1], [2] and [6] of Example 2.1, J6M0-hIgG1, and human IgG Isotype control (Invitrogen Cat. #31154). EC50 (nM) values for binding to human BCMA were determined.

Figure 20:
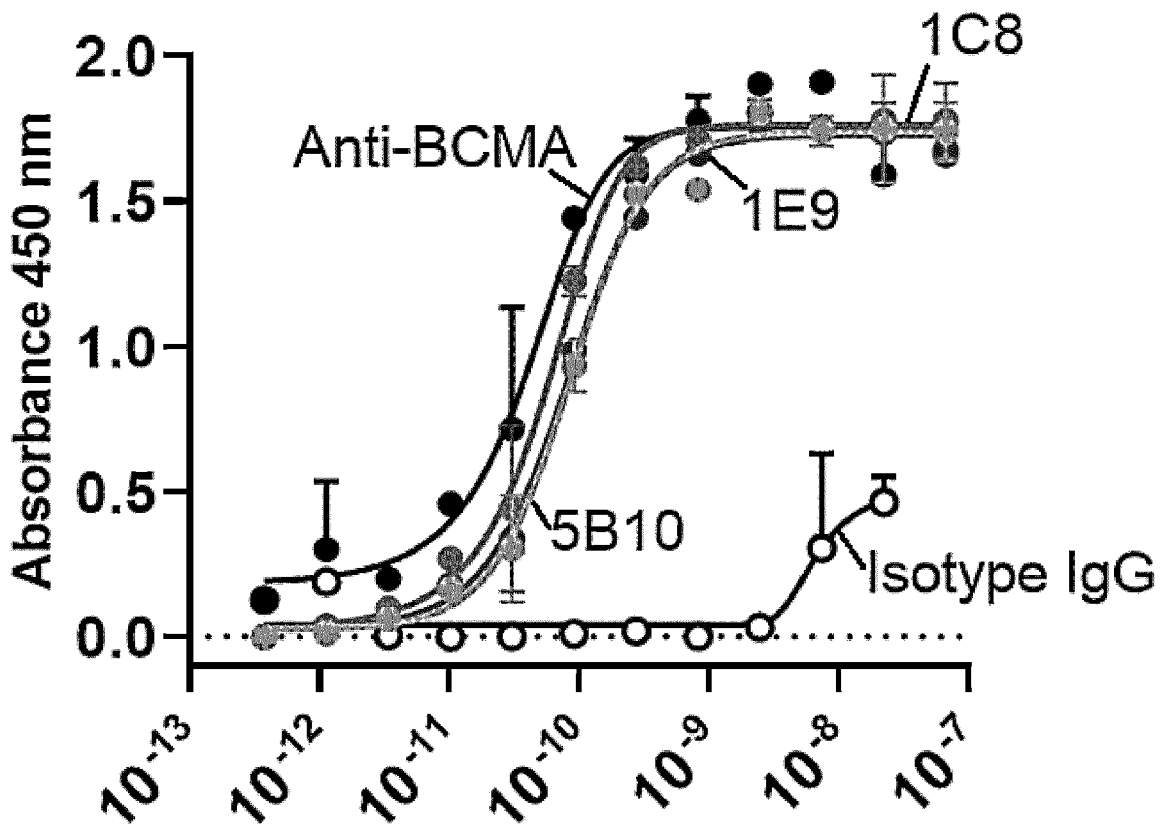
FIG. 20. Graph and table showing binding of anti-BCMA antibodies to human BCMA, as determined by ELISA. Results for the analysis of binding of 552-LN1-E9 (1E9), 538-SP5-B10 (5B10), 539-SP1-C8 (1C8), J6M0 (anti-BCMA), and isotype-matched IgG control (Isotype IgG) are shown.

The results are shown in FIG. 20.

In further experiments, purified antibodies produced in human IgG1 format (see Example 2.1 above) were analysed by ELISA for binding to recombinant his-tagged human TACI (Sinobiological—cat #11937-H08H) at different concentrations. ELISAs were performed essentially as described immediately above, except that wells of 384-well plates were coated with 1 µg/ml of His-tagged human TACI in phosphate-buffered saline (PBS) for 16 h at 4° C.

Figure 6A:
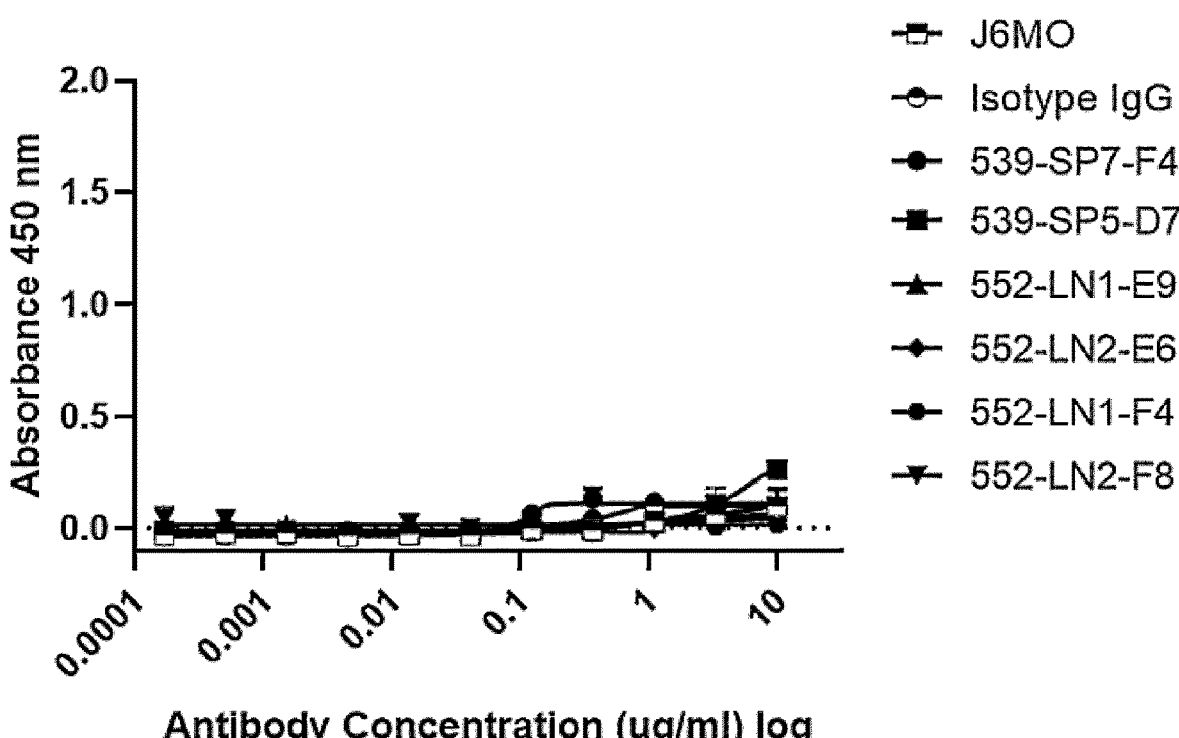
FIGS. 6A and 6B. Graphs showing binding of anti-BCMA antibodies to human TACT, as determined by ELISA. (6A) shows results for 539-SP7-F4, 539-SP5-D7, 552-LN1-E9, 552-LN2-E6, 552-LN1-F4, 552 LN2-F8, J6M0, and iso-type-matched IgG control. (6B) shows results for 539-SP2-H3, 538-SP5-B10, 539-SP1-C8, J6M0, and isotype-matched IgG control.
Figure 6B:
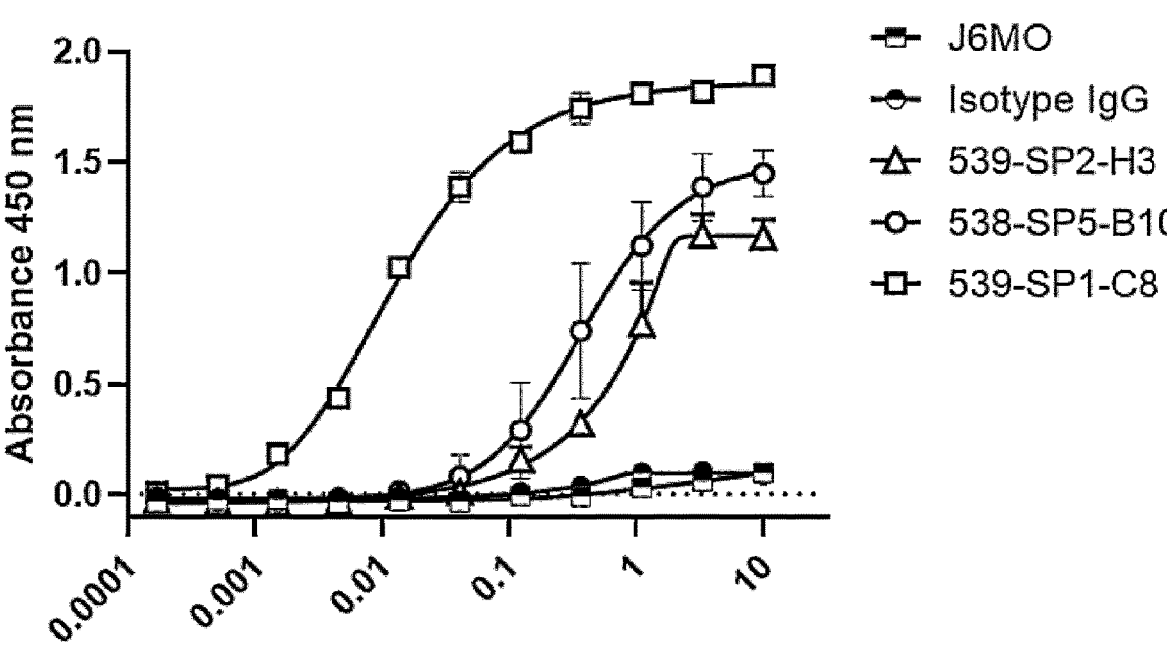

The results are shown in FIGS. 6A and 6B. Antibodies [1], [2] and [3] displayed binding to human TACI. In a further experiment performed essentially as described above, binding of the following antibodies to human TACI was analysed using a 12 point, half-log dilution series: [1], [2] and [6] of Example 2.1, J6M0-hIgG1, and human IgG Isotype control (Invitrogen Cat. #31154). EC50 (nM) values for binding to human TACI were determined.

Figure 21:
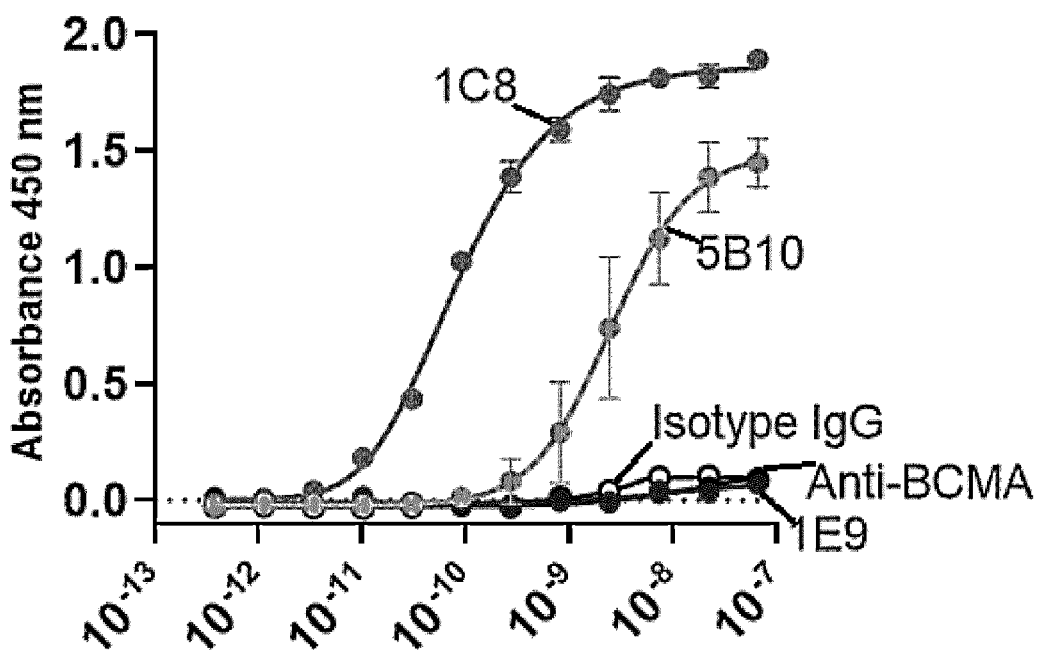
FIG. 21. Graph and table showing binding of anti-BCMA antibodies to human TACT, as determined by ELISA. Results for the analysis of binding of 552-LN1-E9 (1E9), 538-SP5-B10 (5B10), 539-SP1-C8 (1C8), J6M0 (anti-BCMA), and isotype-matched IgG control (Isotype IgG) are shown.

The results are shown in FIG. 21. Antibodies [1] and [2] displayed binding to human TACT.

3.2 Analysis of Cell Surface Antigen-Binding by Flow Cytometry

HEK 293T cells transfected with cDNA encoding human BCMA and stably expressing human BCMA, or non-transfected HEK 293T cells, were incubated at 4° C. for 1 hr with cell culture supernatant of the B cell hybridomas, or anti-BCMA antibody J6M0 (positive control). The cells were washed three times with PBS and resuspended in PE-conjugated goat anti-mouse IgG (Biolegend, Cat #405307) diluted 1:400 in PBS, for 1 h at 4° C.

The human BCMA-expressing and non-transfected HEK 293T cells were separately incubated at 4° C. for 1 h with 20 µg/ml APO-labelled anti-human BCMA antibody clone REA315 (Miltenyi Biotec, Germany), and PE-labelled anti-human BCMA clone 19F2 (Biolegend Inc.) as further positive controls.

Cells were washed again and resuspended in 200 µL of FACS flow buffer (PBS with 5 mM EDTA, containing DAPI) for flow cytometric analysis using MACSQuant™ X (Miltenyi Biotec, Germany). After acquisition, all raw data were analysed using Flowlogic software. Cells were gated using forward and side scatter profile and further gated for negative staining by DAPI (DAPI staining solution, Miltenyi Biotec) to include live cells only. This population constitutes the parent population from which the percentage of positive cells was determined after staining by anti-BCMA antibody clones. The gating for BCMA positive cells was determined using non transfected cells as a reference.

Figure 7A:
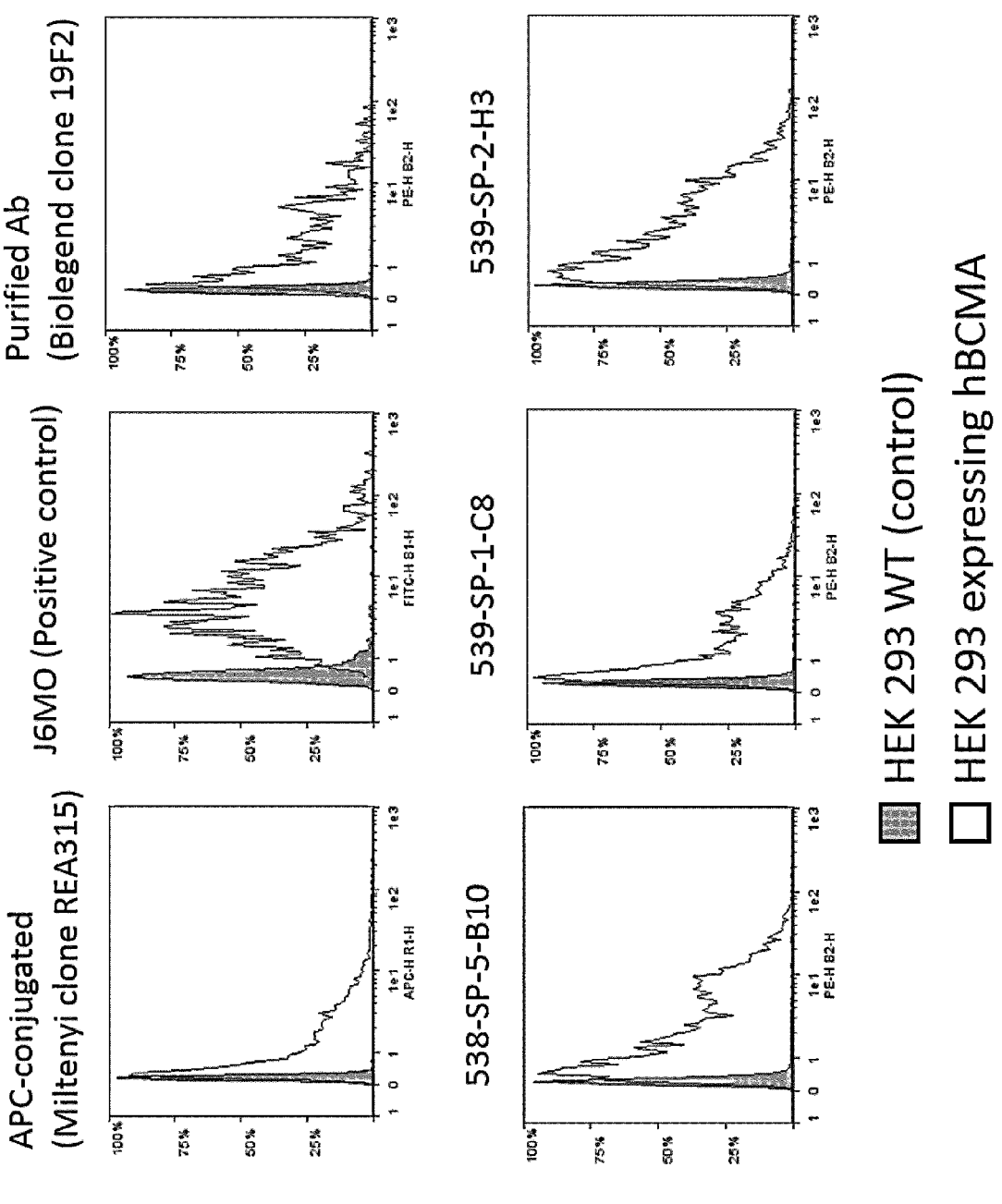
FIGS. 7A and 7B. Histograms showing binding of anti-BCMA antibodies to HEK293T cells stably expressing human BCMA, or wildtype non-transfected HEK293T cells, as determined by flow cytometry. (7A) shows results for REA315, J6M0, 19F2, 538-SP5-B10, 539-SP1-C8 and 539-SP2-H3. (7B) shows results for 539-SP5-D7, 539-SP7-F4, 552-LN1-E9, 552-LN1-F4, 552-LN2-E6 and 552-LN2-F8.
Figure 7B:
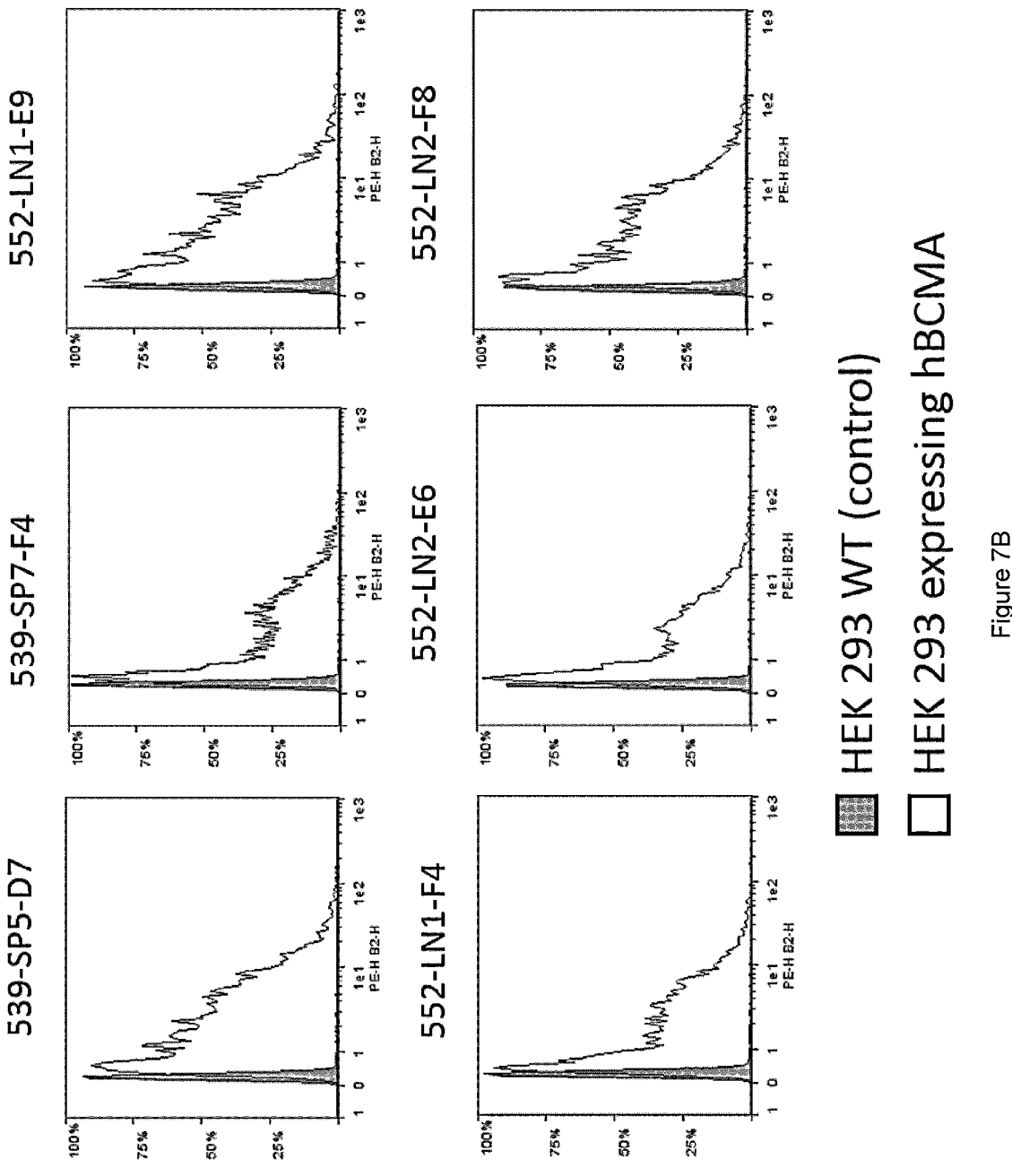
Figure 8A:
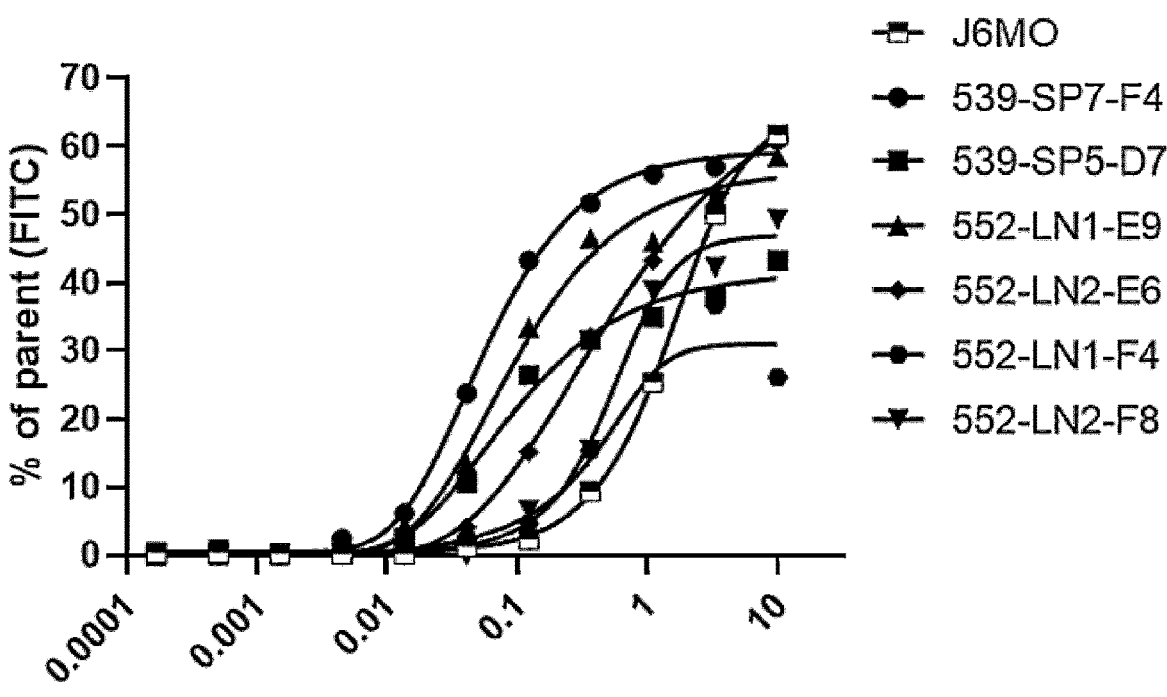
FIGS. 8A to 8D. Graphs showing binding of anti-BCMA antibodies to cells expressing human BCMA, as determined by flow cytometry. (8A) shows binding of 539-SP7-F4, 539-SP5-D7, 552-LN1-E9, 552-LN2-E6, 552-LN1-F4, 552-LN2-F8 and J6M0 to HEK293 cells engineered to stably express human BCMA. (8B) shows binding of 539-SP2-H3, 538-SP5-B10, 539-SP1-C8 and J6M0 to HEK293 cells engineered to stably express human BCMA. (8C) shows binding of 539-SP7-F4, 539-SP5-D7, 552-LN1-E9, 552-LN2-E6, 552-LN1-F4, 552-LN2-F8 and J6M0 to wildtype HEK293 cells. (8D) shows binding of 539-SP2-H3, 538-SP5-B10, 539-SP1-C8 and J6M0 to wildtype HEK293 cells.
Figure 8B:
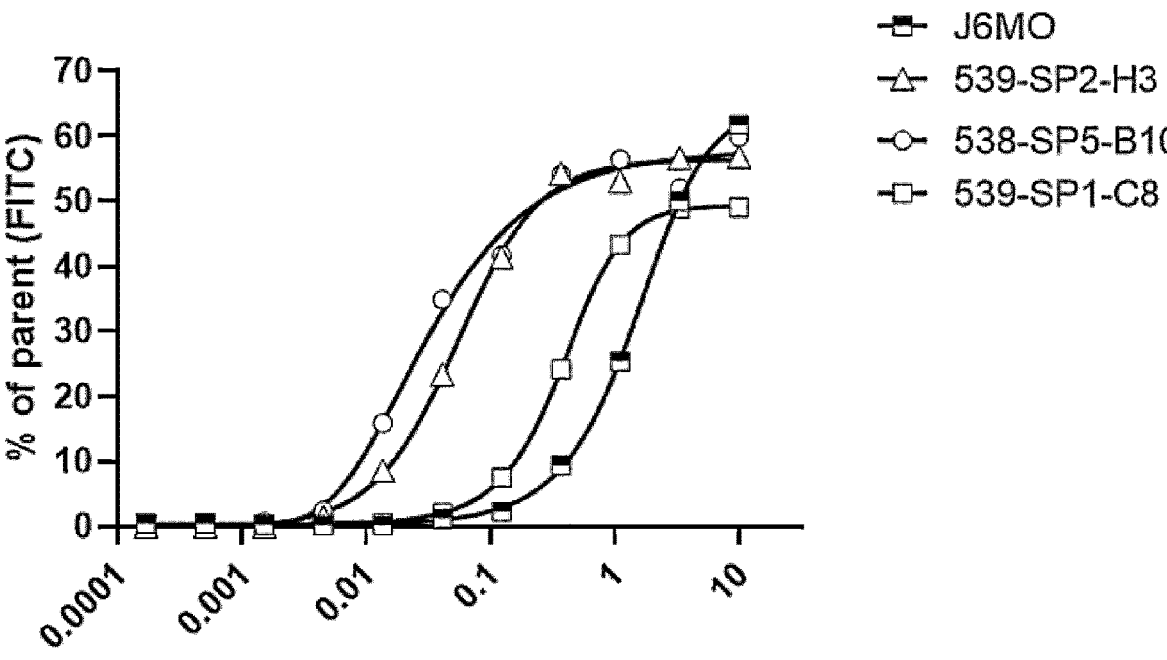
Figure 8C:
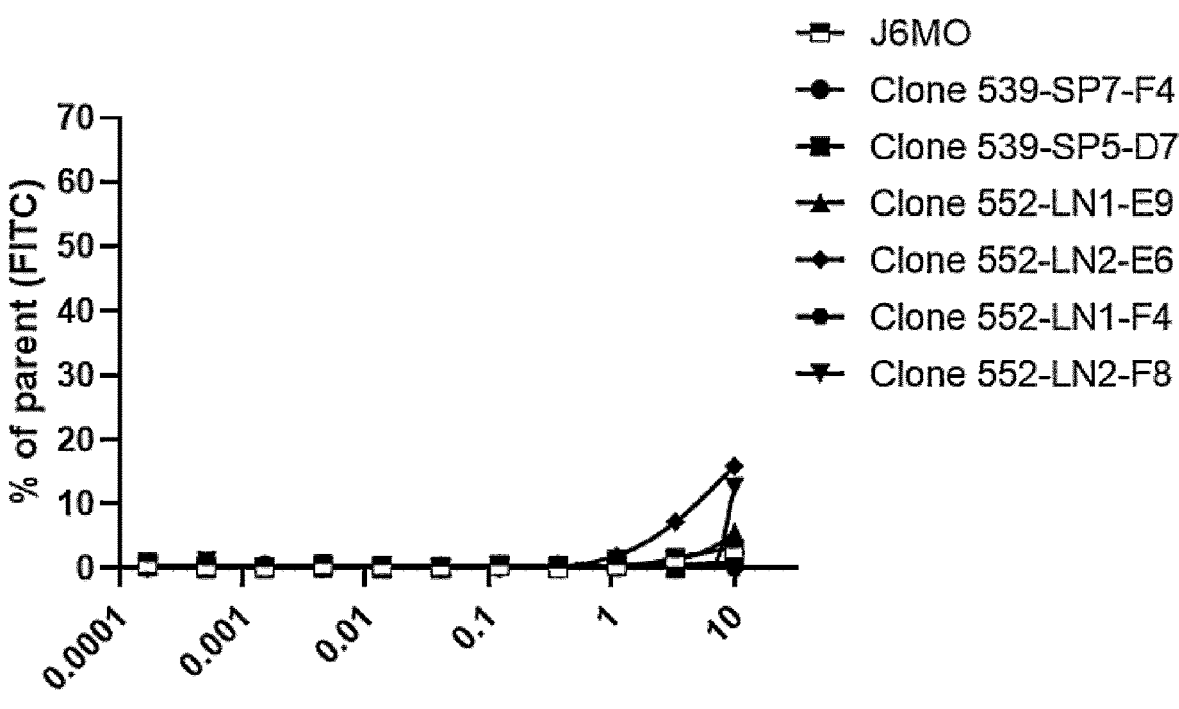
Figure 8D:
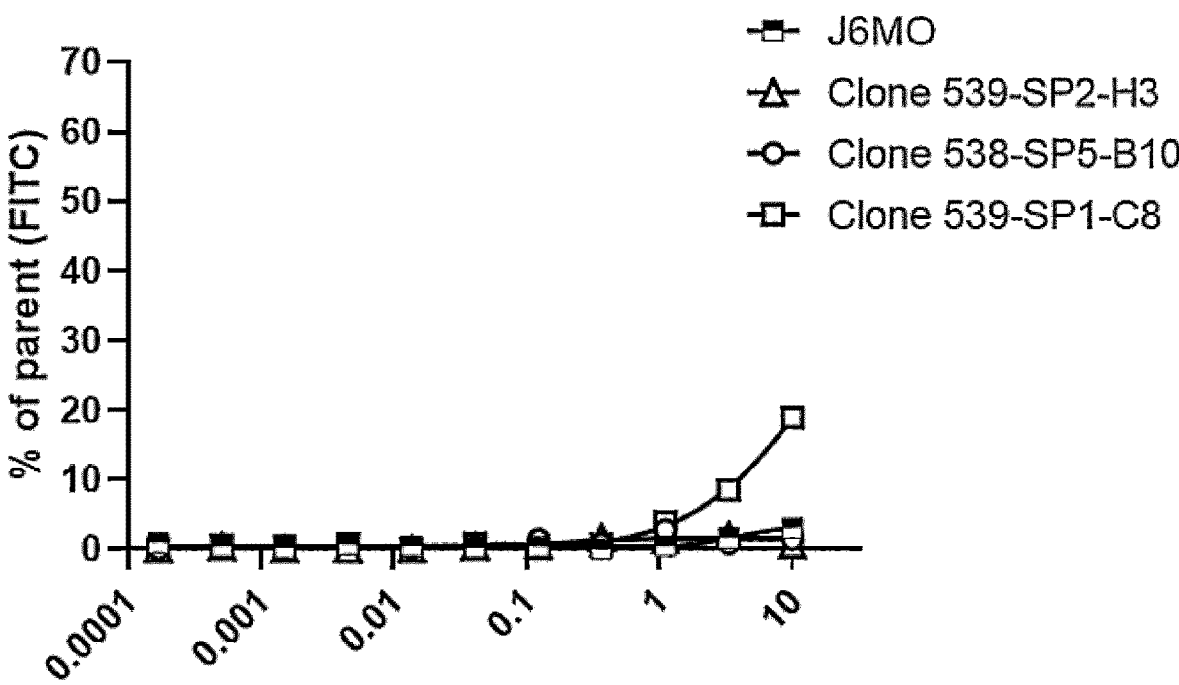
Figure 9A:
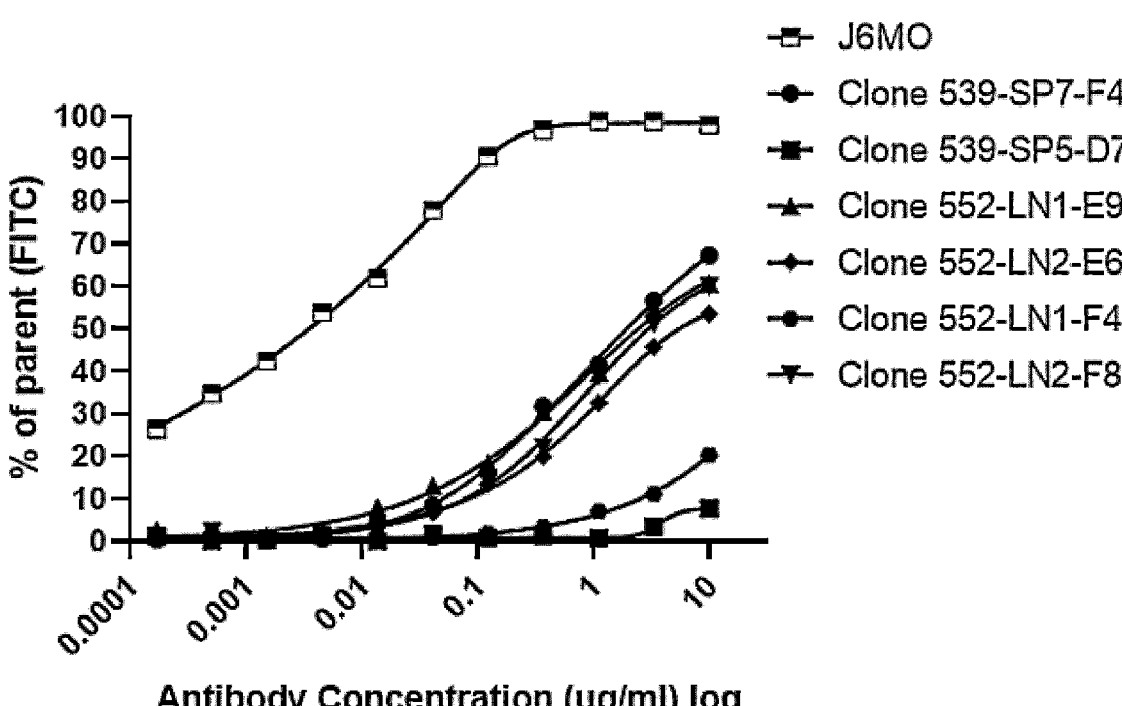
FIGS. 9A to 9F. Graphs showing binding of anti-BCMA antibodies to cells expressing cynomolgous macaque or mouse BCMA, as determined by flow cytometry. (9A) shows binding of 539-SP7-F4, 539-SP5-D7, 552-LN1-E9, 552-LN2-E6, 552-LN1-F4, 552-LN2-F8 and J6M0 to CHOK1 cells engineered to transiently express cynomolgous macaque BCMA. (9B) shows binding of 539-SP2-H3, 538-SP5-B10, 539-SP1-C8 and J6M0 to CHOK1 cells engineered to transiently express cynomolgous macaque BCMA. (9C) shows binding of 539-SP7-F4, 539-SP5-D7, 552-LN1-E9, 552-LN2-E6, 552-LN1-F4, 552-LN2-F8 and J6M0 to CHOK1 cells engineered to transiently express mouse BCMA. (9D) shows binding of 539-SP2-H3, 538-SP5-B10, 539-SP1-C8 and J6M0 to CHOK1 cells engineered to transiently express mouse BCMA. (9E) shows binding of 539-SP7-F4, 539-SP5-D7, 552-LN1-E9, 552-LN2-E6, 552-LN1-F4, 552-LN2-F8 and J6M0 to wildtype CHOK1 cells. (9F) shows binding of 539-SP2-H3, 538-SP5-B10, 539-SP1-C8 and J6M0 to wildtype CHOK1 cells.
Figure 9B:
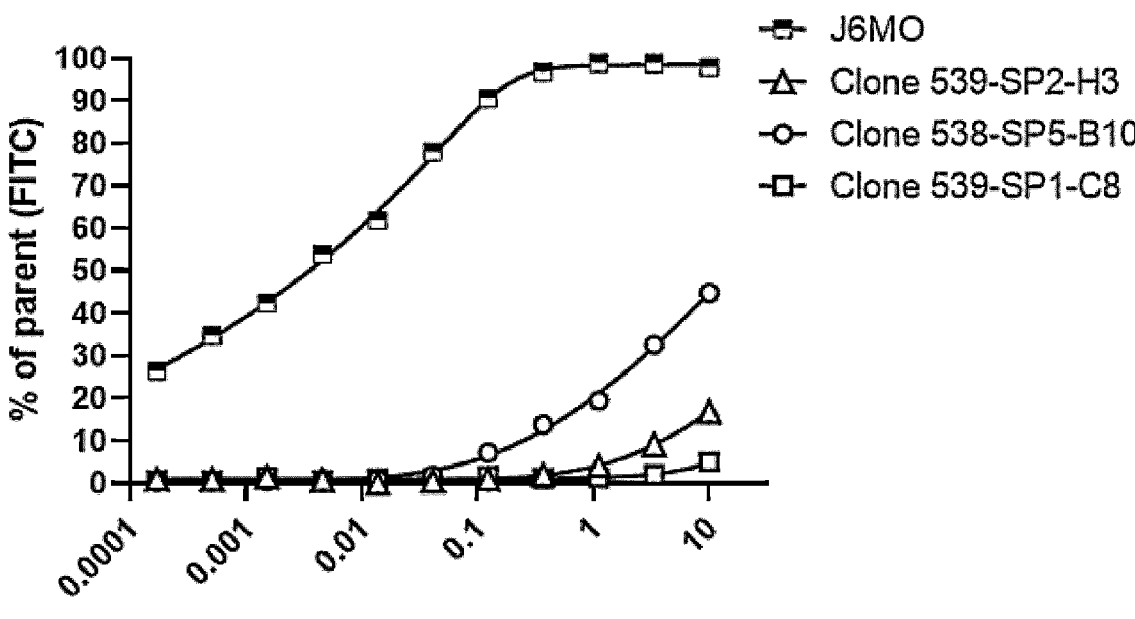
Figure 9C:
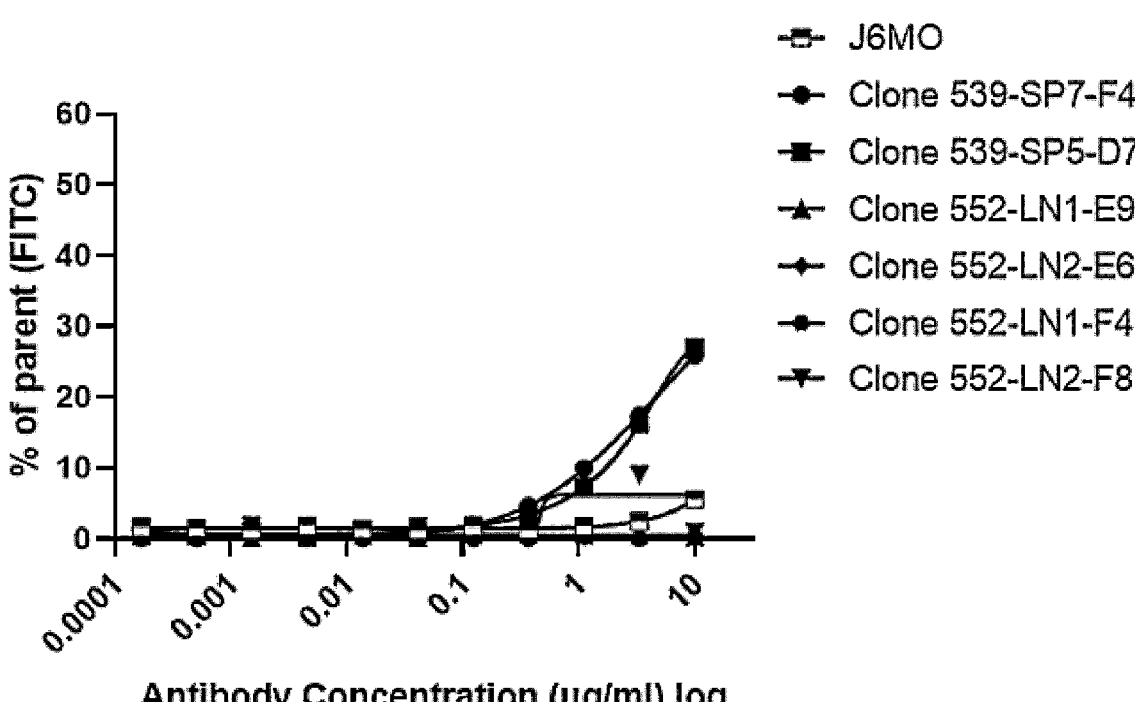
Figure 9D:
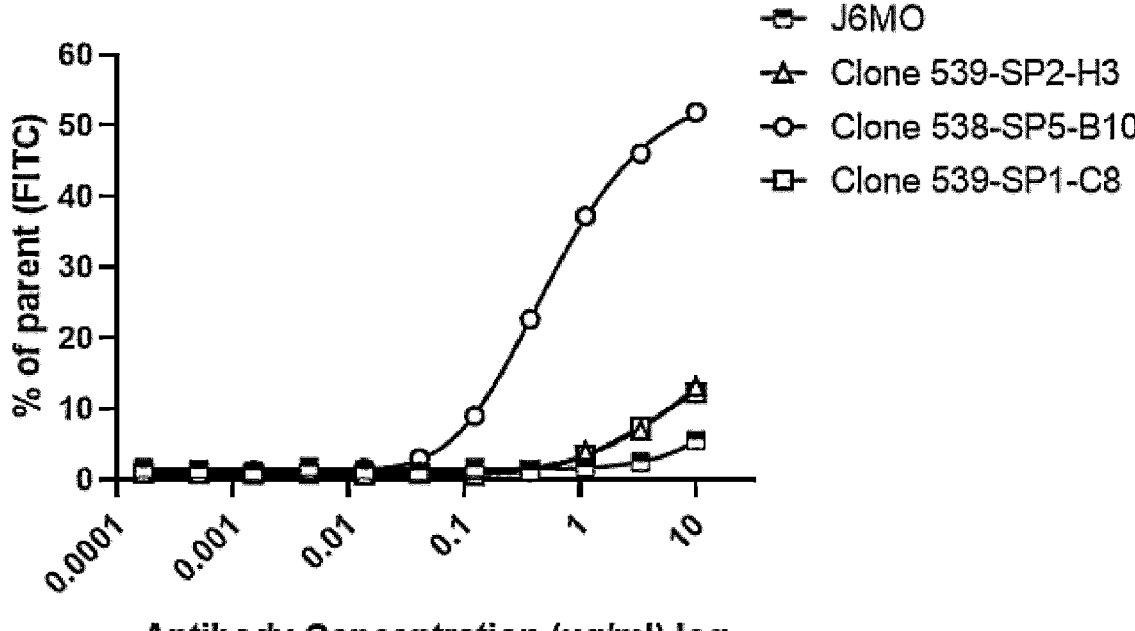
Figure 9E:
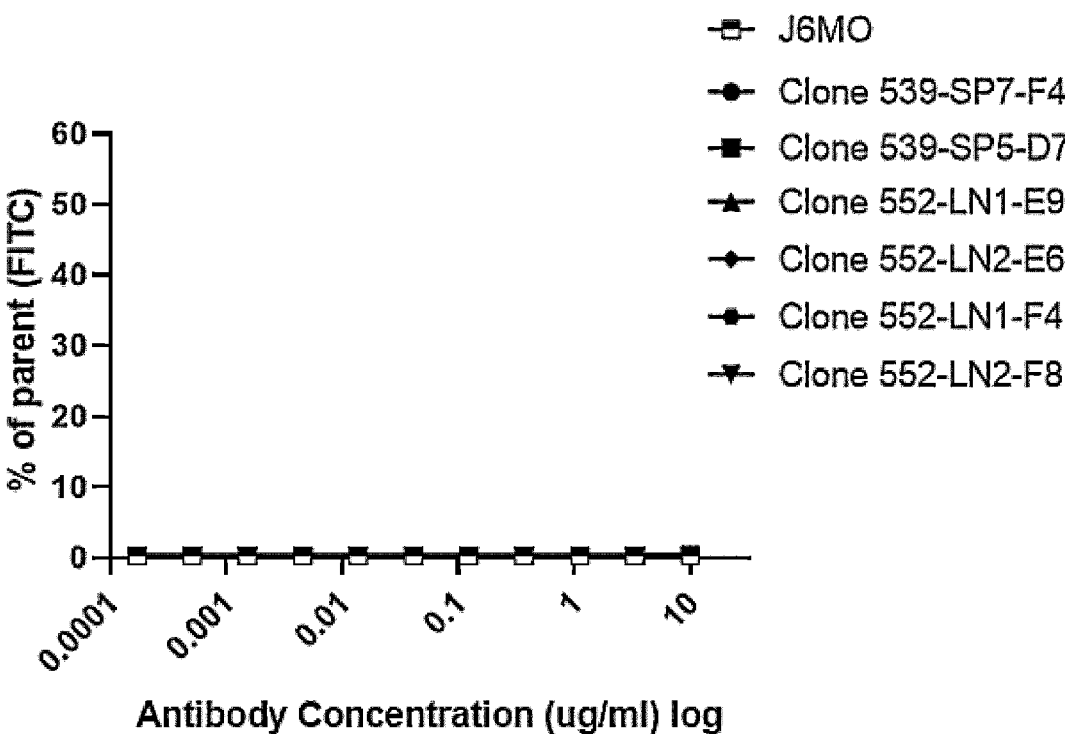
Figure 9F:
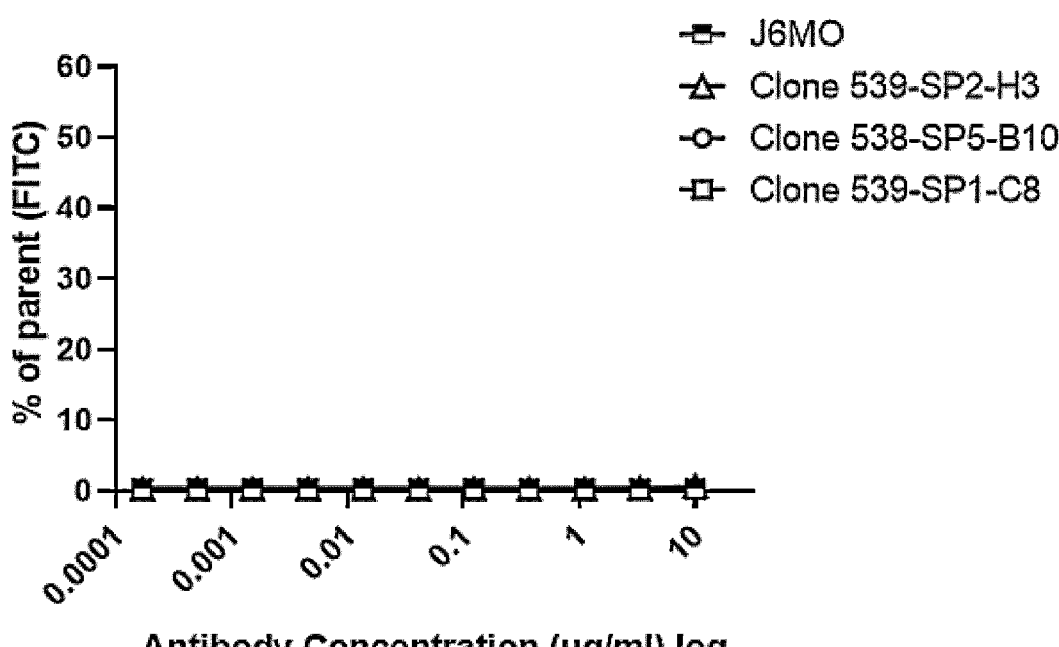

The results are shown in FIGS. 7A and 7B, and in the table below.

| | % Parent | |
| --- | --- | --- |
| Clone | Non-transfected HEK293 cells | Human BCMA-expressing HEK293 cells |
| 538-SP5-B10 | 1.17 | 70.8 |
| 539-SP1-C8 | 0.46 | 56.52 |
| 539-SP2-H3 | 1.09 | 74.26 |
| 539-SP5-D7 | 0.27 | 76.16 |
| 539-SP7-F4 | 0.38 | 63.76 |
| 552-LN1-E9 | 0.49 | 75.36 |
| 552-LN1-F4 | 0.4 | 66.36 |
| 552-LN2-E6 | 0.14 | 60.78 |
| 552-LN2-F8 | 0.24 | 73.84 |

In further experiments, purified antibodies produced in human IgG1 format (see Example 2.1 above) and J6M0 were analysed for their ability to bind to HEK 293T cells engineered to express human BCMA, or non-transfected HEK 293T cells. Briefly, 50,000 cells were added to wells of 96-well polypropylene plates, and were incubated with a dilution series to obtain an 11 point dilution series (dilution factor of 3, highest concentration=10 µg/ml) of the different antibodies for 1 h at 4° C. The cells were washed three times with PBS and resuspended in FITC-conjugated anti-human IgG (ThermoFisher, Cat. #A11013) diluted 1:400 in PBS, for 1 h at 4° C. Cells were washed three times with PBS and resuspended in 200 µL of FACS flow buffer (PBS with 5 mM EDTA, containing DAPI) for flow cytometric analysis using MACSQuant™ X (Miltenyi Biotec, Germany). The data were processed and analysed as described above.

The results are shown in FIGS. 8A to 8D.

In further experiments performed essentially as described immediately above, binding of the following antibodies to human BCMA-expressing HEK 293T cells was analysed using a 12 point, half-log dilution series: [1], [2] and [6] of Example 2.1, J6M0-hIgG1, and human IgG Isotype control (Invitrogen Cat. #31154). EC50 (nM) values for binding to human BCMA-expressing HEK 293T cells were determined.

Figure 22:
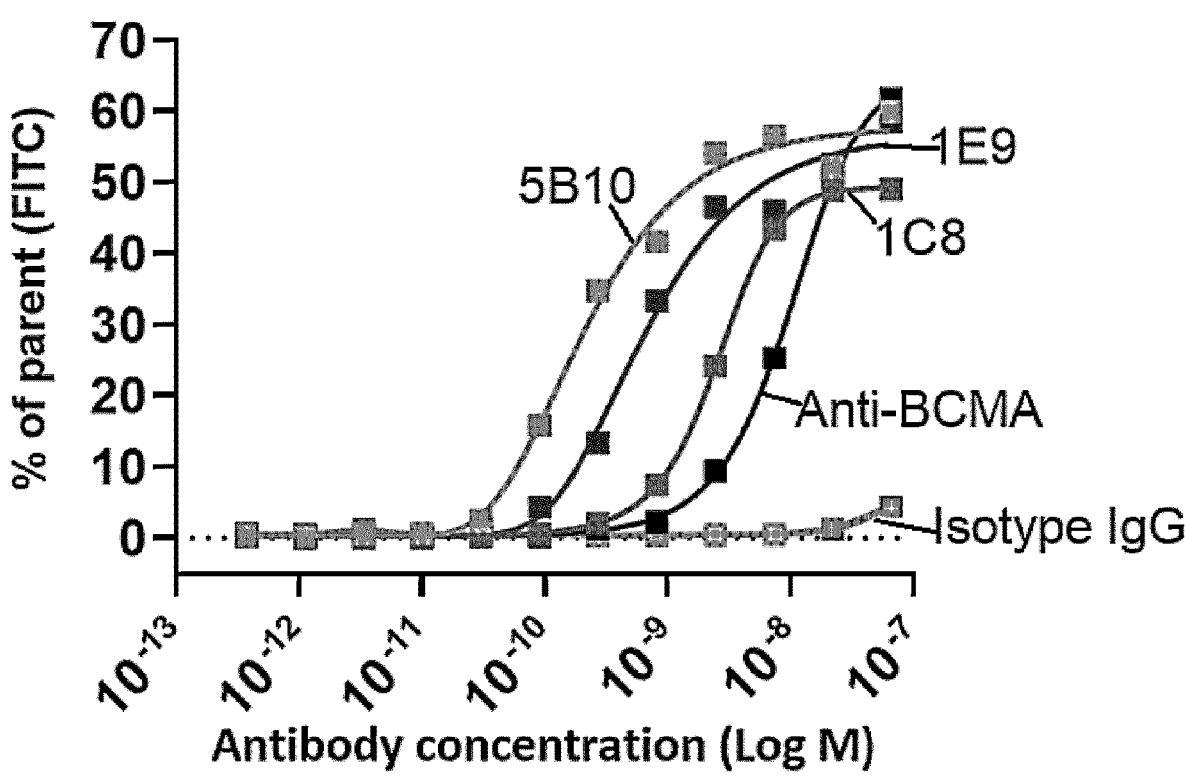
FIG. 22. Graph and table showing binding of anti-BCMA antibodies to HEK 293 cells engineered to express human BCMA as determined by flow cytometry. Results for the analysis of binding of 552-LN1-E9 (1E9), 538-SP5-B10 (5B10), 539-SP1-C8 (1C8), J6M0 (anti-BCMA), and isotype-matched IgG control (Isotype IgG) are shown.

The results are shown in FIG. 22.

In further experiments, purified antibodies produced in human IgG1 format (see Example 2.1 above) and J6M0 were analysed by flow cytometry for their ability to bind to CHOK1 cells engineered to express cynomolgous macaque BCMA or mouse BCMA, or non-transfected CHOK1 cells, as described immediately above.

The results are shown in FIGS. 9A to 9F.

In further experiments, purified antibodies produced in human IgG1 format (see Example 2.1 above) and J6M0 were analysed by flow cytometry for their ability to bind to CHOK1 and HEK 293 cells engineered to express human TACI as described immediately above.

Figure 10A:
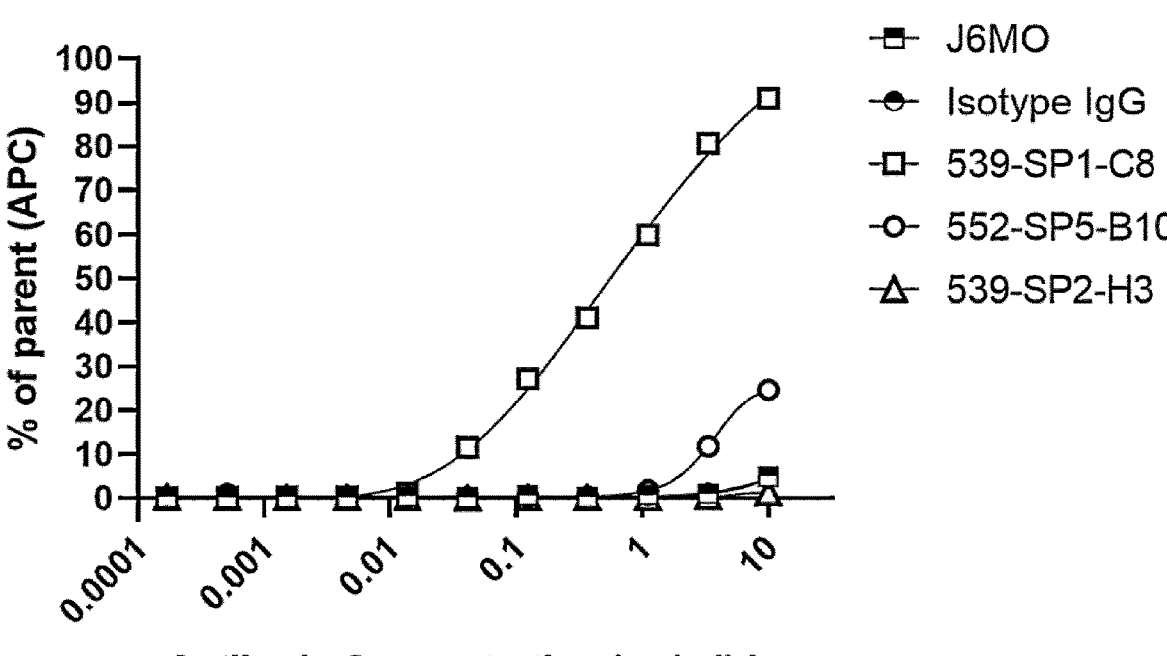
FIGS. 10A and 10B. Graphs showing binding of anti-BCMA antibodies to CHOK1 and HEK 293 cells engineered to express human TACI as determined by flow cytometry. (10A) shows binding of 539-SP2-H3, 538-SP5-B10, 539-SP1-C8, IgG isotype control and J6M0 to HEK 293 cells engineered to transiently express human TACT. (10B) shows binding of 539-SP2-H3, 538-SP5-B10, 539-SP1-C8, IgG isotype control and J6M0 to CHO cells engineered to transiently express human TACI.
Figure 10B:
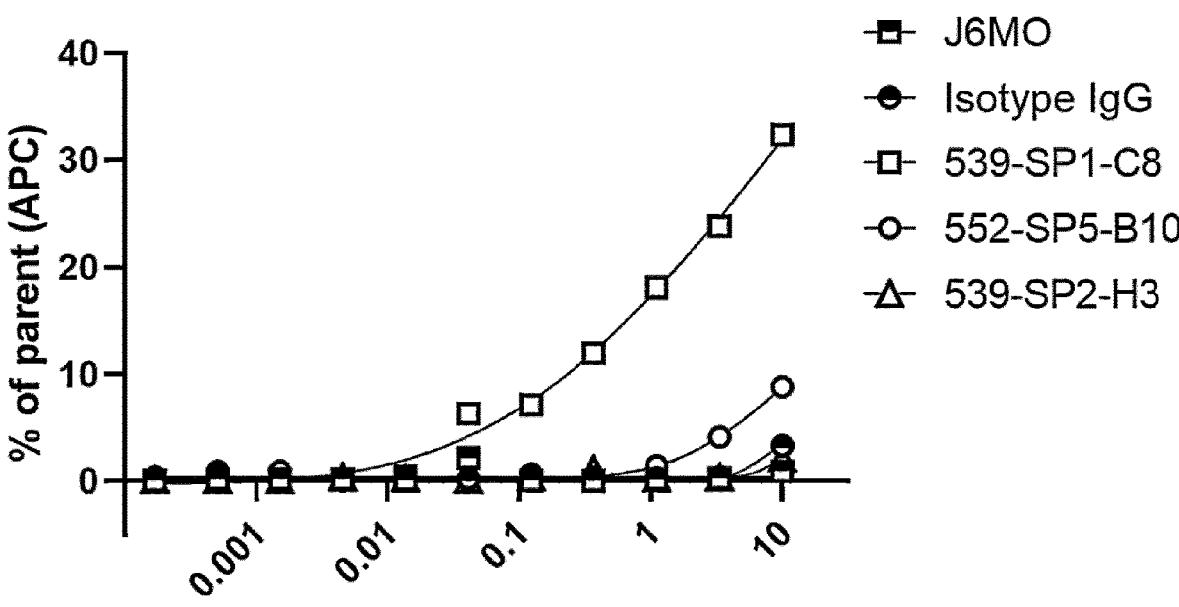
Figure 11A:
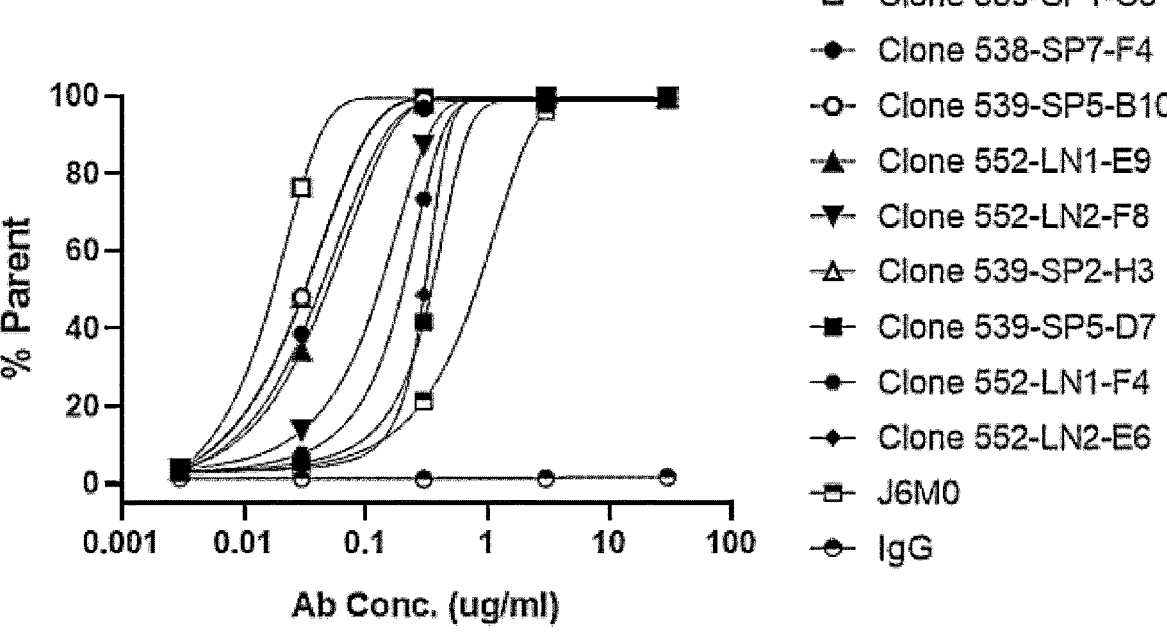
FIGS. 11A to 11F. Graphs showing binding of anti-BCMA antibodies to cells of cancer cell lines, as determined by flow cytometry. (11A) shows binding of 539-SP1-C8, 539-SP7-F4, 538-SP5-B10, 552-LN1-E9, 552-LN2-F8, 539-SP2-H3, 539-SP5-D7, 552-LN1-F4, 552-LN2-E6, J6M0 and isotype-matched IgG control to H929 cells. (11B) shows binding of 539-SP7-F4, 538-SP5-B10, 539-SP1-C8, 552-LN1-E9, 552-LN2-F8, J6M0 and isotype-matched IgG control to HCT116 cells. (11C) shows binding of 539-SP2-H3, 539-SP5-D7, 552-LN1-F4, 552-LN2-E6, J6M0 and isotype-matched IgG control to HCT116 cells. (11D) shows binding of 539-SP7-F4, 538-SP5-B10, 539-SP1-C8, 552-LN1-E9, 552-LN2-F8, J6M0 and isotype-matched IgG control to NCI-H460 cells. (11E) shows binding of 539-SP2-H3, 539-SP5-D7, 552 LN1-F4, 552-LN2-E6, J6M0 and isotype-matched IgG control to NCI-H460 cells. (11F) shows binding of 539-SP7-F4, 538-SP5-B10, 539-SP1-C8, 552-LN1-E9, 552-LN2-F8, 539-SP2-H3, 539-SP5-D7, 552-LN1-F4, 552-LN2-E6, J6M0 and isotype-matched IgG control to A549 cells.
Figure 11B:
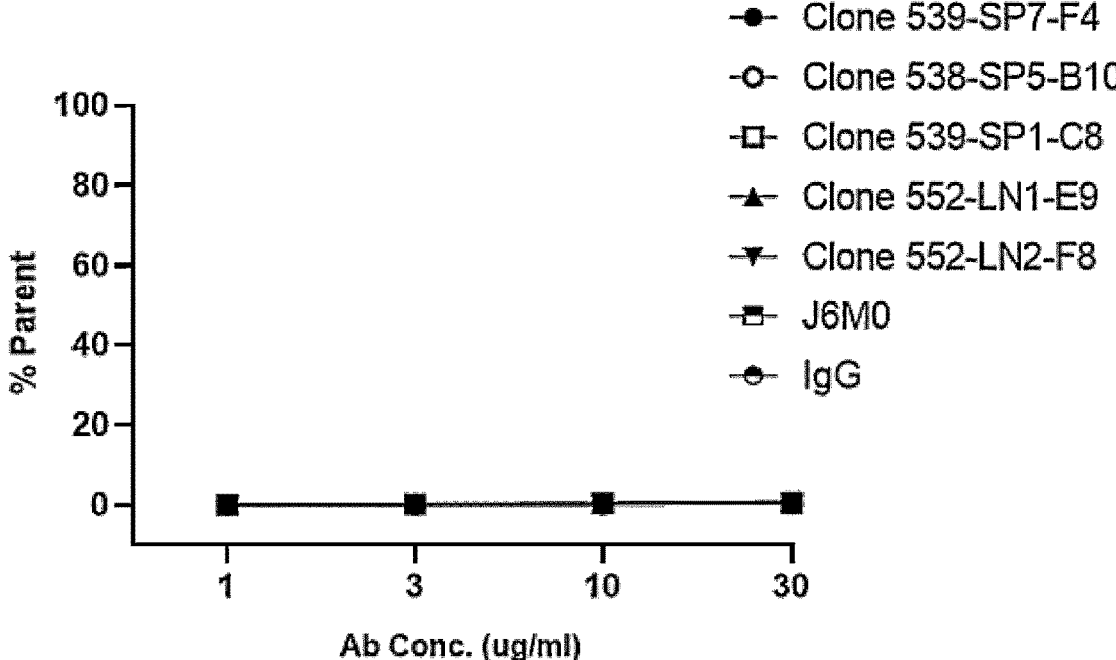
Figure 11C:
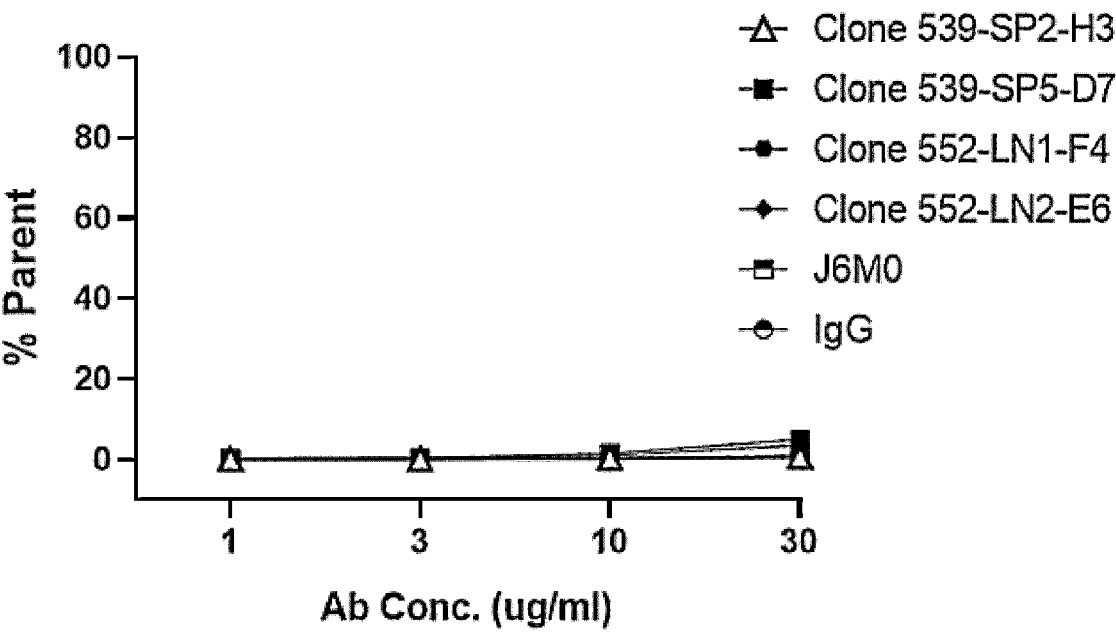
Figure 11D:
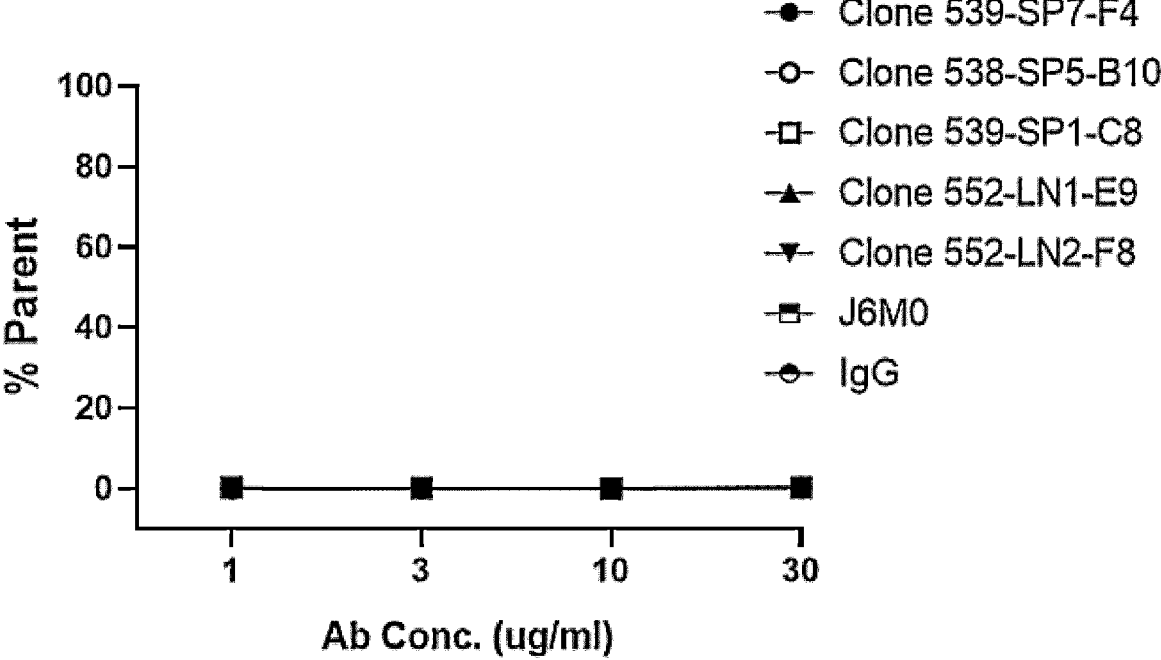
Figure 11E:
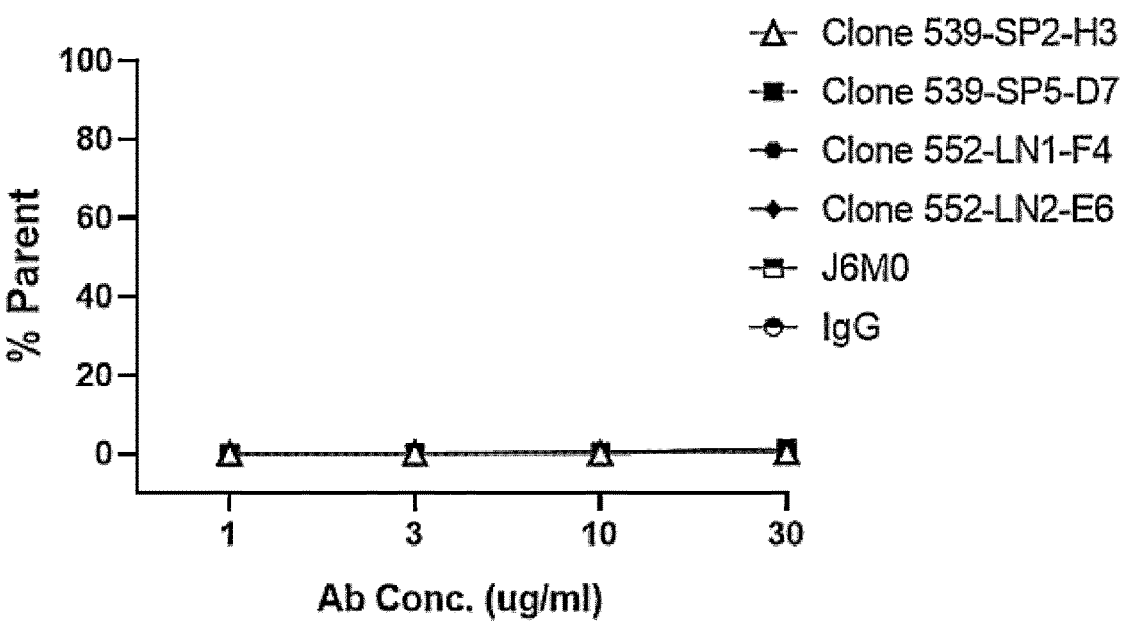
Figure 11F:
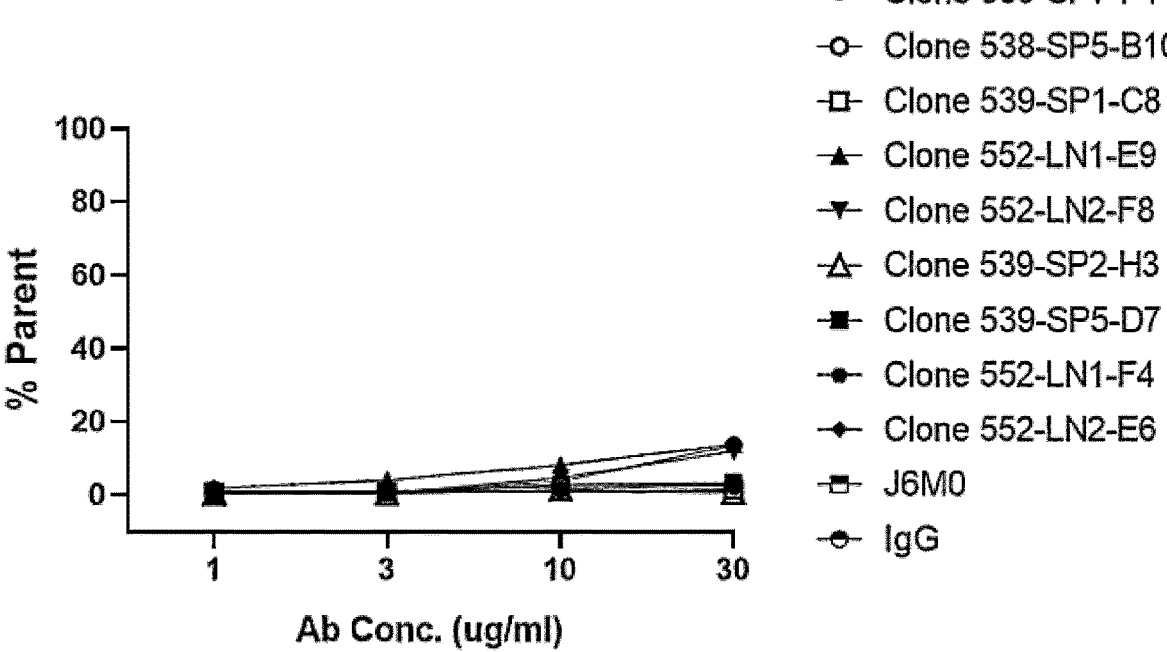

The results are shown in FIGS. 10A and 10B.

In further experiments performed essentially as described immediately above, binding of the following antibodies to human TACI-expressing HEK 293T cells was analysed using a 12 point, half-log dilution series: [1] and [2] of Example 2.1, J6M0-hIgG1, and human IgG Isotype control (Invitrogen Cat. #31154). EC50 (nM) values for binding to human TACI-expressing HEK 293T cells were determined.

Figure 23:
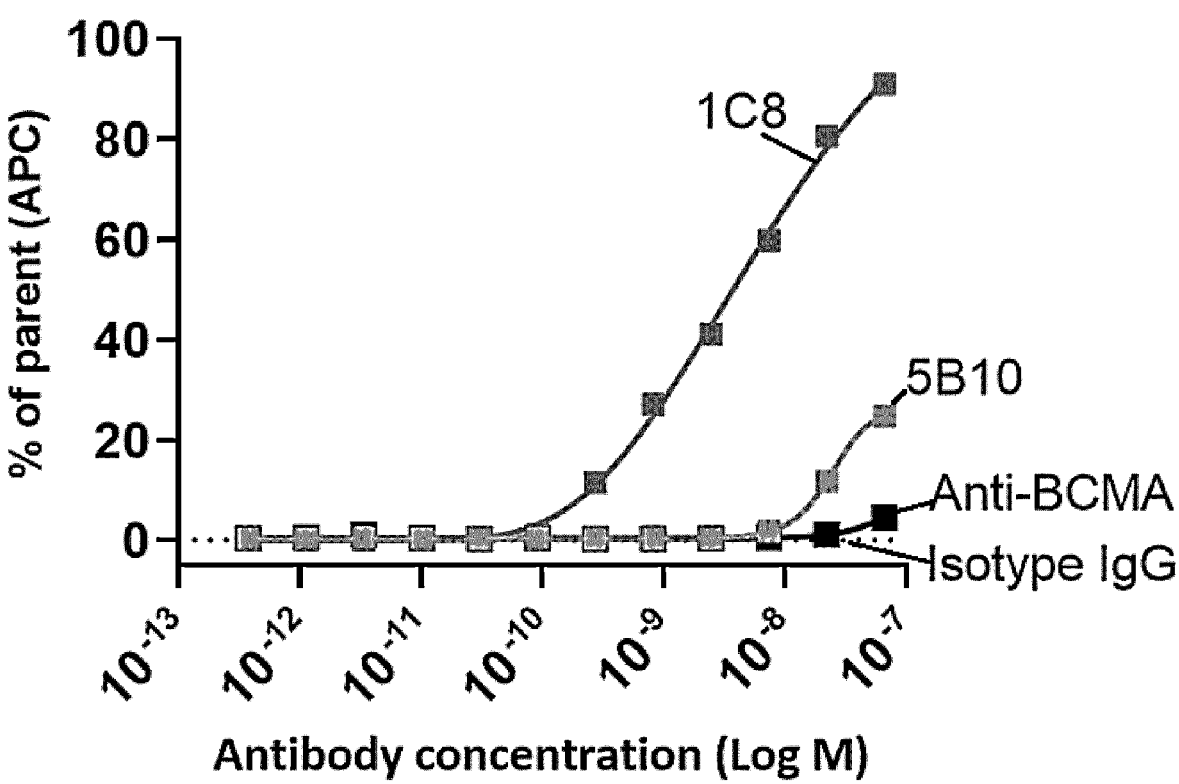
FIG. 23. Graph and table showing binding of anti-BCMA antibodies to HEK 293 cells engineered to express human TACI as determined by flow cytometry. Results for the analysis of binding of 538-SP5-B10 (5B10), 539-SP1-C8 (1C8), J6M0 (anti-BCMA), and isotype-matched IgG control (Isotype IgG) are shown.

The results are shown in FIG. 23.

In further experiments, purified antibodies produced in human IgG1 format and J6M0 were analysed by flow cytometry for their ability to bind to cells of the following human cancer cell lines: H929, HCT116, NCI-H460 and A549. H929 cells express BCMA, whereas HCT116, NCI-H460 and A549 cells do not express BCMA.

Briefly, 50,000 cells were added to wells of 96-well polypropylene plates, and were incubated with a dilution series (5 point dilution series, dilution factor of 10, highest concentration=30 µg/ml) of the different antibodies for 1 hour at 4° C. The cells were washed three times with PBS and resuspended in FITC-conjugated anti-human IgG (ThermoFisher, Cat. #A11013) diluted 1:400 in PBS, for 1 h at 4° C. Cells were washed three times with PBS and resuspended in 200 µL of FACS flow buffer (PBS with 5 mM EDTA, containing DAPI) for flow cytometric analysis using MACSQuant™ X (Miltenyi Biotec, Germany). An isotype-matched IgG1 negative control antibody (Invitrogen, Cat. #31154) was included in the experiment as a negative control. The data were processed and analysed as described above.

The results are shown in FIGS. 11A to 11F.

In a further experiment performed essentially as described above, binding of the following antibodies to H929 cells or HCT116 cells was analysed using a 11 point, half-log dilution series (at concentrations ranging from 10 µg/ml to 0.0001 µg/ml): [1] and [2] of Example 2.1, J6M0-hIgG1, and human IgG Isotype control (Invitrogen Cat. #31154).

Figure 15A:
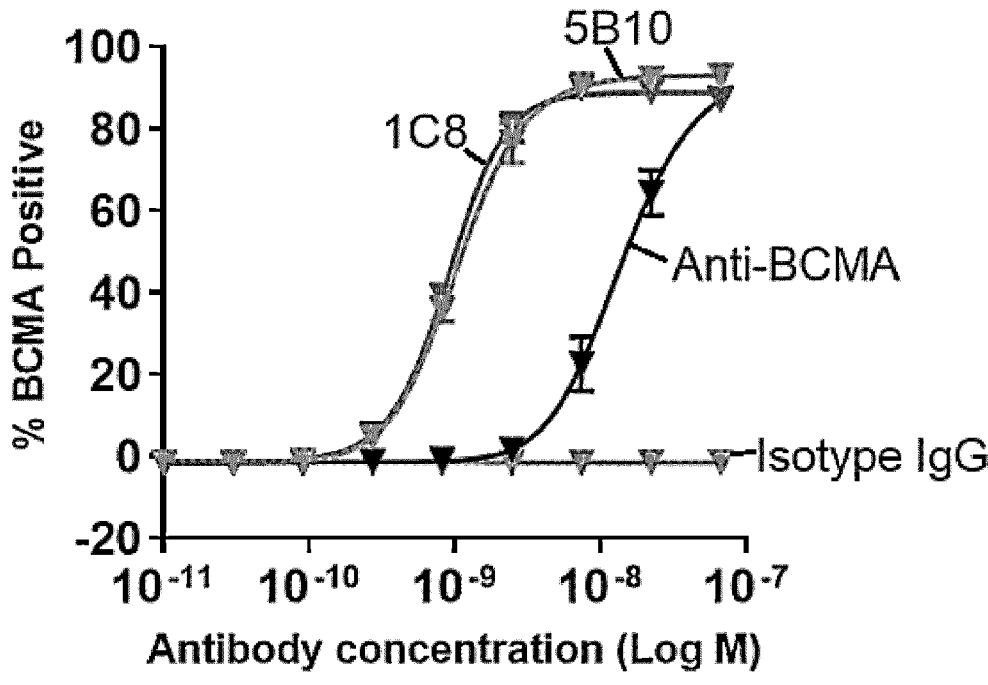
FIGS. 15A and 15B. Graphs showing binding of anti-BCMA antibodies to H929 cells and HCT116 cells, as determined by flow cytometry. (15A and 15B) show binding of 539-SP1-C8 (1C8), 538-SP5-B10 (5B10), J6M0 (anti-BCMA) and isotype-matched IgG control (Isotype IgG) to (15A) H929 cells and (15B) HCT116 cells.
Figure 15B:
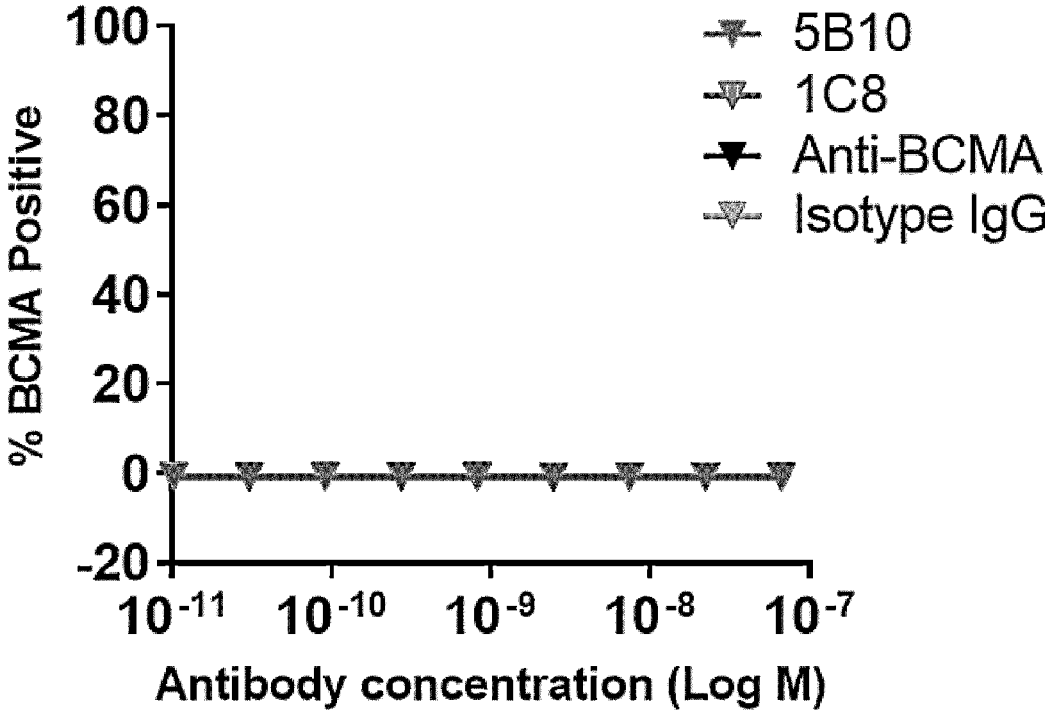

The results are shown in FIGS. 15A and 15B.

3.3 Analysis of Ability to Block BCMA-APRIL Interaction

To determine the ability of BCMA clones to inhibit APRIL binding the following ELISA was performed. Plates were first coated with APRIL-Fc (1 µg/ml) in PBS buffer for 16 h at 4° C. After blocking for 1 h with 1% BSA in Tris buffered saline (TBS) at room temperature, anti-BCMA antibodies were added to wells in a 6 point, 10-fold dilution series, to final concentrations of 10 µg/ml, 1 µg/ml, 100 ng/ml, 10 ng/ml, 1 ng/ml and 0.1 ng/ml (15 µl/well).

After 15 min incubation, His-tagged human BCMA protein was added to wells at final concentration of 1 ug/ml (15 µl/well) and incubated at RT for 1 h. Plates were then washed three times with TBS containing 0.05% Tween 20

(TBS-T), and then incubated with a HRP-conjugated anti-His antibody (Life Technologies, Inc., USA) for 1 h at room temperature. After washing, plates were developed with colorimetric detection substrate Turbo-TMB (Pierce, USA). The reaction was stopped with 2M H2504, and OD was measured at 450 nM.

Figure 12A:
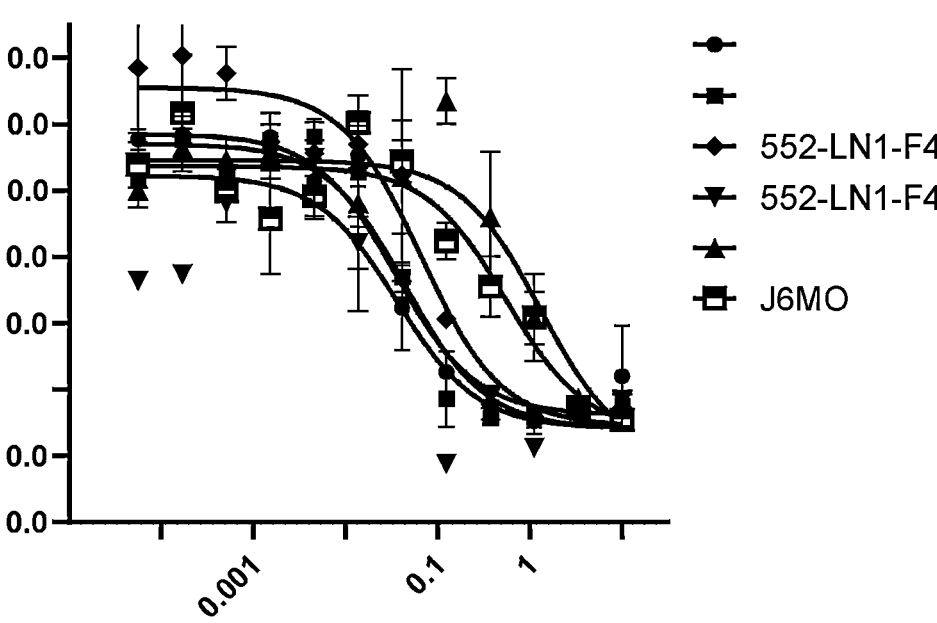
FIGS. 12A and 12B. Graphs showing inhibition of interaction between human BCMA and human APRIL by anti-BCMA antibodies, as determined by ELISA. (12A) shows results for 538-SP5-B10, 539-SP2-H3, 539-SP1-C8, 539-SP5-D7, 539-SP7-F4 and J6M0. (12B) shows results for 552-LN1-E9, 552 LN2-E6, 552-LN1-F4, 552-LN2-F8 and J6M0.
Figure 12B:
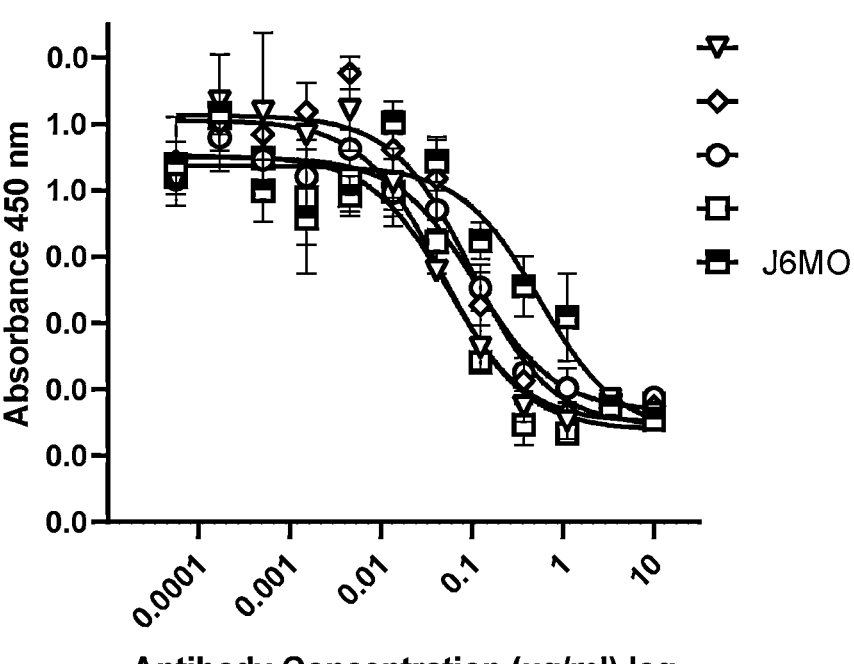

The results are shown in FIGS. 12A and 12B. Several of the anti-BCMA binding antibodies were found to be potent inhibitors of BCMA-APRIL interaction.

In a further experiment performed essentially as described above, anti-BCMA antibodies were added to wells in a 10 point, half-log dilution series (at concentrations ranging from 30 µg/ml to 0.005 µg/ml). The following antibodies were analysed in the experiment: [1] and [2] of Example 2.1, J6M0-hIgG1, and human IgG Isotype control (Invitrogen Cat. #31154). Percentage inhibition of APRIL binding was calculated using the following formula: % APRIL binding inhibition=100−[(background-subtracted signal obtained using the antibody)/(maximal background-subtracted APRIL signal obtained in the absence of antibody)×100]. 1050 (nM) values for inhibition of BCMA:APRIL interaction were determined.

Figures 16A, 16B:
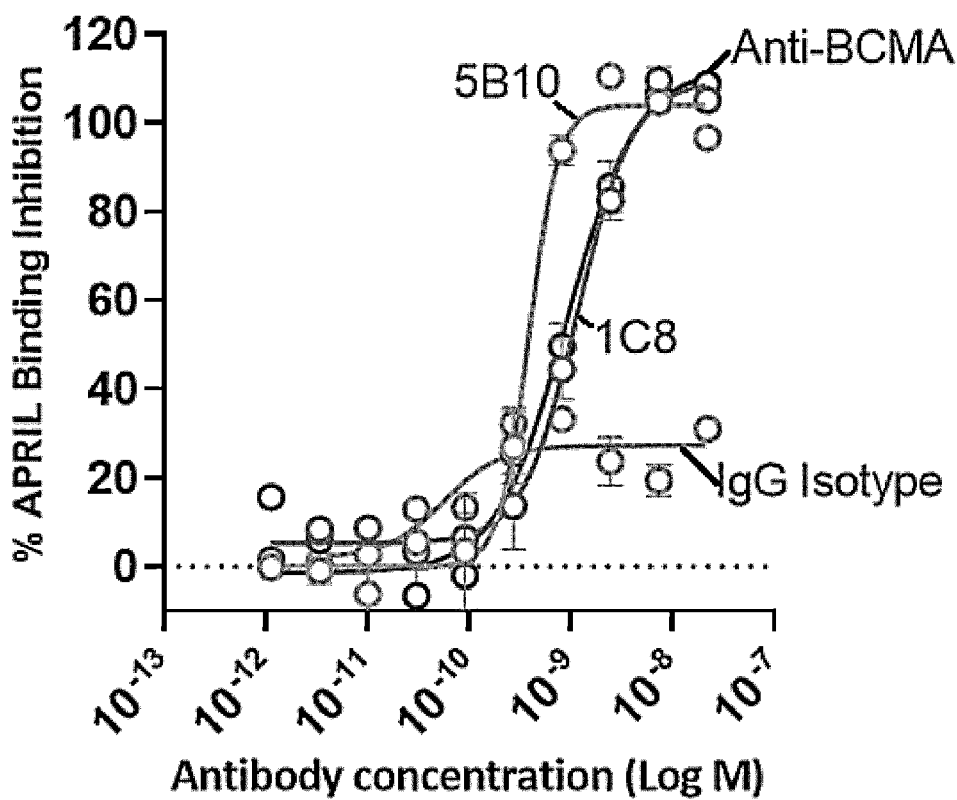
FIGS. 16A and 16B. (16A) Graph and (16B) table showing inhibition of interaction between human BCMA and human APRIL by anti-BCMA antibodies 539-SP1-C8 (1C8), 538-SP5-B10 (5B10), J6M0 (anti-BCMA) and isotype-matched IgG control (IgG Isotype), as determined by ELISA.

The results are shown in FIGS. 16A and 16B.

3.4 Analysis of Affinity of Binding to BCMA by Biolayer Interferometry

Binding of the purified antibodies provided in human IgG1 format (see Example 2.1 above) to human, cynomolgous macaque and mouse BCMA was analysed by Biolayer Interferometry (BLI). Ultra LEAF IgG1 Isotype Control QA16A12 (BioLegend, Cat #403502) and J6M0 were included in the experiments as negative and positive controls, respectively.

BLI experiments were performed using a Pall ForteBio Octet Red384 system, using HIS1K Anti-Penta Hisbiosensor tips (Bio Forte Lot No. 2003494) for capturing antigens.

Biosensors were first hydrated for at least 10 min in assay buffer (phosphate buffered saline), followed by buffer baseline for 60 s and loading of His-tagged human BCMA (Acro Biosystems, BCA-H522y; at a concentration of 2000 nM), His-tagged cynomolgous macaque BCMA (Acro Biosystems, BCA-C52H7; at a concentration of 500 nM) or His-tagged mouse BCMA (Acro Biosystems, BCA-M52H3; at a concentration of 2000 nM) onto the biosensor tips for 120 s. The tips were then washed briefly for 60 s with the assay buffer to remove unbound BCMA for obtaining a second buffer baseline. The association phase of the IgGs (at concentrations ranging from 1000 nM to 31.3 nM) with the antigens was set up at 120 s which was followed by a dissociation phase (assay buffer alone) for 120 s. All runs were measured at room temperature at a stirring speed of 1000 rpm and HIS1K Anti-Penta His biosensors were regenerated using 10 mM of glycine (pH 2.7) after the assay (40 s). Binding affinity between the antibodies and BCMA immobilized on the HIS1K Anti-Penta His sensors was determined by analysing the binding kinetic curves. All sensorgrams were reference subtracted and globally fitted into a 1:1 model which analysed the binding curves at different concentrations of antigens and generated kinetic constants (KD/Ka/Kd) for the globally fitted data. All the binding curves were subjected to step correction which corrects the misalignment between association and dissociation steps, and only curves with $R^2$ values greater than 0.9 were used for the determination of $K_D$ values.

The results are shown in FIG. 13. All of antibodies [1] to [9] were shown to bind to human BCMA with sub-picomolar affinity (i.e. $K_D < 1 \times 10^{-12}$ M). Antibodies [1], [2] and [4] to [9] were shown to bind to cynomolgous macaque BCMA with affinity in the nanomolar range (affinities ranging from 14.7 nM to 167 nM). Antibodies [1] to [5] displayed binding to mouse BCMA, with antibodies [1], [2] and [4] displaying affinities in the nanomolar range (affinities ranging from 4.86 nM to 47.5 nM).

3.5 Analysis of Affinity of Binding to Human BCMA in the Presence of Human APRIL by Biolayer Interferometry Binding of the purified antibodies provided in human IgG1 format (see Example 2.1 above) to human BCMA in the presence of human APRIL was analysed by BLI. Human IgG Isotype Control (Invitrogen, Cat #31154) and J6M0 were included in the experiments as negative and positive controls, respectively.

Biosensors were hydrated for at least 10 min in assay buffer (phosphate buffered saline), followed by buffer baseline for 60 s and loading of His-tagged human BCMA onto the biosensor tips (Acro Biosystems, BCA-H522y) at a concentration of 3000 nM, for 120 s. The tips were then washed briefly for 60 s with the assay buffer to remove unbound BCMA for obtaining a second buffer baseline. Human APRIL (Acro Biosystems, APL-H5244) was then applied at a concentration of 3000 nM for 120 s. Tips were then washed again for 60 s with assay buffer to remove unbound proteins. The association phase of the IgGs (at concentrations ranging from 1000 nM to 31.3 nM) with the antigens was set up at 120 s which was followed by a dissociation phase (assay buffer alone) for 120 s. All runs were measured at room temperature at a stirring speed of 1000 rpm and HIS1K Anti-Penta His biosensors were regenerated using 10 mM of glycine (pH 2.7) after the assay (40 s). Binding affinity between the antibodies and BCMA immobilized on the HIS1K Anti-Penta His sensors was determined by analysing the binding kinetic curves. All sensorgrams were reference subtracted and globally fitted into a 1:1 model which analysed the binding curves at different concentrations of antigens and generated kinetic constants (KD/Ka/Kd) for the globally fitted data. All the binding curves were subjected to step correction which corrects the misalignment between association and dissociation steps, and only curves with $R^2$ values greater than 0.9 were used for the determination of $K_D$ values.

The results are shown in FIG. 14. Antibodies [6], [7], [8] and [9] were found to display binding to BCMA despite prior incubation of BCMA with APRIL.

Taken together with the results of Example 3.3, these data suggest that 552-LN1-E9, 552-LN1-F4, 552-LN2-E6 and 552-LN2-F8 are allosteric inhibitors of binding of APRIL to BCMA, or are competitive inhibitors of binding of APRIL to BCMA that bind to BCMA with such high affinity that they are able to displace APRIL from BCMA:APRIL polypeptide complexes.

Example 4: Humanised Anti-BCMA Antibodies 4.1 Humanised Anti-BCMA Antibodies Humanised versions of clones 538-SP5-B10, 539-SP1-C8, 552-LN1-E9, 552-LN2-F8 were designed.

| Parental clone | Humanised antibody | VH/VL sequences |
|---|---|---|
| 552-LN1-E9 | 1E9-4H | VH = SEQ ID NO: 338 |
| | | VL = SEQ ID NO: 341 |
| | 1E9-QE | VH = SEQ ID NO: 346 |
| | | VL = SEQ ID NO: 349 |

-continued

| Parental clone | Humanised antibody | VH/VL sequences |
|---|---|---|
| 552-LN2-F8 | 2F8-2Q | VH = SEQ ID NO: 353 |
| | | VL = SEQ ID NO: 357 |
| | 2F8-5U | VH = SEQ ID NO: 361 |
| | | VL = SEQ ID NO: 365 |
| 538-SP5-B10 | 5B10-4Y | VH = SEQ ID NO: 367 |
| | | VL = SEQ ID NO: 370 |
| | 5B10-5I | VH = SEQ ID NO: 372 |
| | | VL = SEQ ID NO: 376 |
| 539-SP1-C8 | 1C8-6A | VH = SEQ ID NO: 380 |
| | | VL = SEQ ID NO: 383 |
| | 1C8-EH | VH = SEQ ID NO: 387 |
| | | VL = SEQ ID NO: 391 |

The humanised anti-BCMA antibodies were produced and purified in human IgG1 format, as described in Example 2.

| Antibody | Name | Heavy chain | Light chain |
|---|---|---|---|
| [10] | 1E9-4H hIgG1 | SEQ ID NO: 424 | SEQ ID NO: 425 |
| [11] | 1E9-QE hIgG1 | SEQ ID NO: 426 | SEQ ID NO: 427 |
| [12] | 2F8-2Q hIgG1 | SEQ ID NO: 428 | SEQ ID NO: 429 |
| [13] | 2F8-5U hIgG1 | SEQ ID NO: 430 | SEQ ID NO: 431 |
| [14] | 5B10-4Y hIgG1 | SEQ ID NO: 432 | SEQ ID NO: 433 |
| [15] | 5B10-5I hIgG1 | SEQ ID NO: 434 | SEQ ID NO: 435 |
| [16] | 1C8-6A hIgG1 | SEQ ID NO: 436 | SEQ ID NO: 437 |
| [17] | 1C8-EH hIgG1 | SEQ ID NO: 438 | SEQ ID NO: 439 |

4.2 Characterisation of the Humanised Anti-BCMA Antibodies

ELISAs are performed as described in Example 3.1 in order to determine the binding specificity of humanised anti-BCMA antibodies [10] to [17] of Example 4.1.

The humanised anti-BCMA antibodies are found to bind to human BCMA with high affinity, and to retain the binding specificity for mouse BCMA, cynomolgous macaque BCMA and/or human TACI displayed by the parental clone from which they are derived.

In further experiments, humanised anti-BCMA antibodies [10] to [17] of Example 4.1 are analysed for their ability to bind to cells expressing human BCMA, mouse BCMA, cynomolgous macaque BCMA or human TACI by flow cytometry, as described in Example 3.2.

The humanised anti-BCMA antibodies are found to bind to cells expressing human BCMA, and to retain the ability to bind to cells expressing mouse BCMA, cynomolgous macaque BCMA or human TACI displayed by the parental clone from which they are derived.

In further experiments, humanised anti-BCMA antibodies [10] to [17] of Example 4.1 are analysed by flow cytometry for their ability to bind to cells of human cancer cell lines, as described in Example 3.2.

The humanised anti-BCMA antibodies are found to bind to cancer cells expressing human BCMA.

In further experiments, humanised anti-BCMA antibodies [10] to [17] of Example 4.1 are analysed in order to determine their ability to inhibit interaction between BCMA and APRIL, as described in Example 3.3.

The humanised anti-BCMA antibodies are found to retain the ability to inhibit interaction between BCMA and APRIL displayed by the parental clone from which they are derived.

In further experiments, humanised anti-BCMA antibodies [10] to [17] of Example 4.1 are analysed in order to determine with which they bind to human BCMA, mouse BCMA and cynomolgous macaque BCMA, as described in Example 3.4.

The humanised anti-BCMA antibodies are found to bind to human BCMA with sub-picomolar affinity, and to display high-affinity binding to cynomolgous macaque BCMA. Antibodies [14] to [17] are also found to display high-affinity binding to mouse BCMA.

In further experiments, humanised anti-BCMA antibodies [10] to [17] of Example 4.1 are analysed in order to determine their ability to bind to BCMA in the presence of APRIL, as described in Example 3.5.

The humanised anti-BCMA antibodies are found to retain the ability to bind to BCMA following prior incubation with APRIL displayed by the parental clone from which they are derived.

Example 5: Anti-CD47 Antibody Clones

The anti-CD47 antibody clones employed in the exemplary molecules of the present disclosure are described in WO 2019/086573 A1, which is incorporated by reference in its entirety. In particular, Examples 1 to 7 and FIGS. 1 to 13 of WO 2019/086573 A1 are specifically incorporated by reference.

Example 1 of WO 2019/086573 A1 describes the production of hybridomas production antibodies specific for human CD47.

Example 2 of WO 2019/086573 A1 describes the production of human-mouse chimeric antibodies comprising mouse heavy and light chain antibody variable domains, and human heavy and light chain antibody constant regions.

Figure 2A:
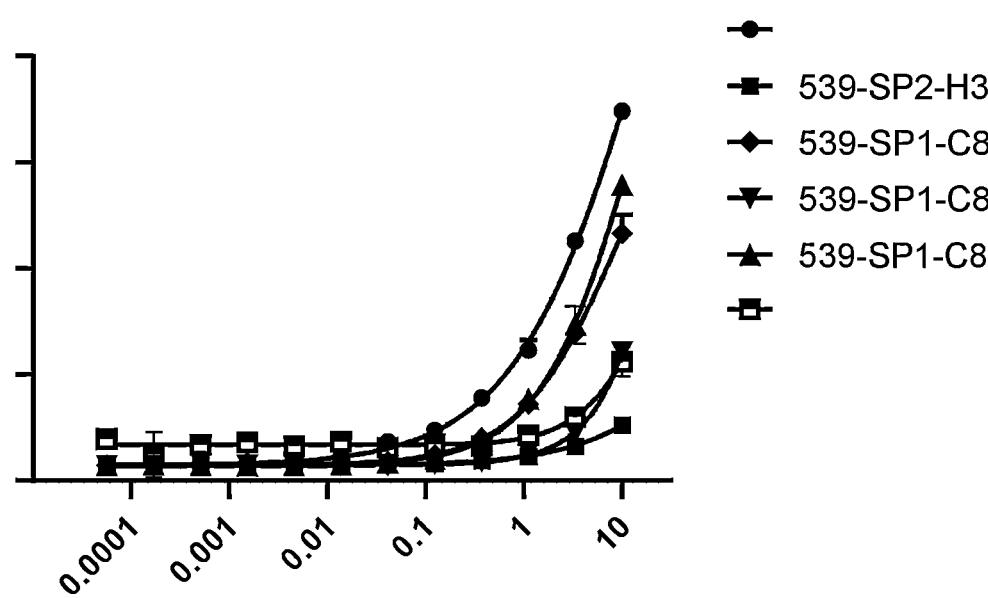
FIGS. 2A and 2B. Graphs showing binding of anti-BCMA antibodies to mouse BCMA, as determined by ELISA. (2A) shows results for 538-SP5-B10, 539-SP2-H3, 539-SP1-C8, 539-SP5-D7, 539-SP7-F4 and J6M0. (2B) shows results for 552-LN1-E9, 552-LN1-F4, 552-LN2-E6, 552-LN2-F8 and J6M0.
Figure 2B:
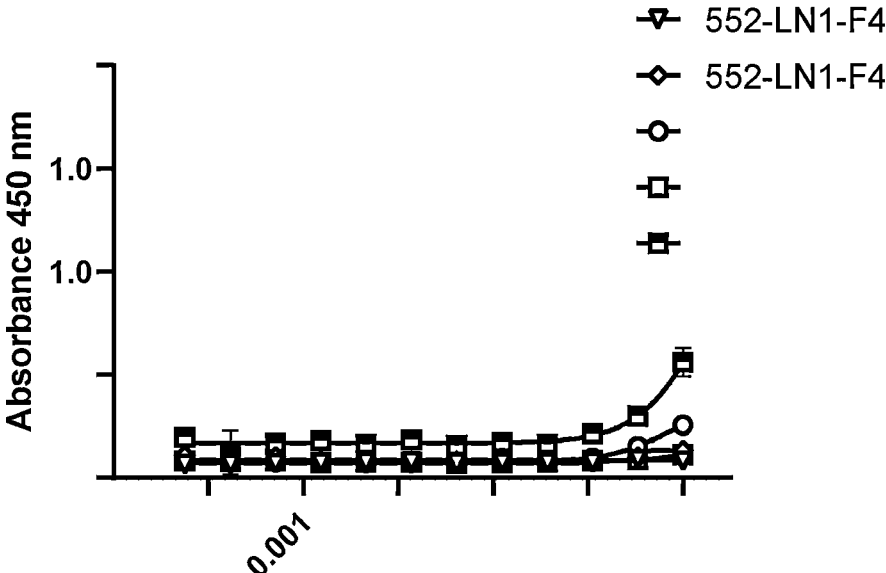
Figure 3A:
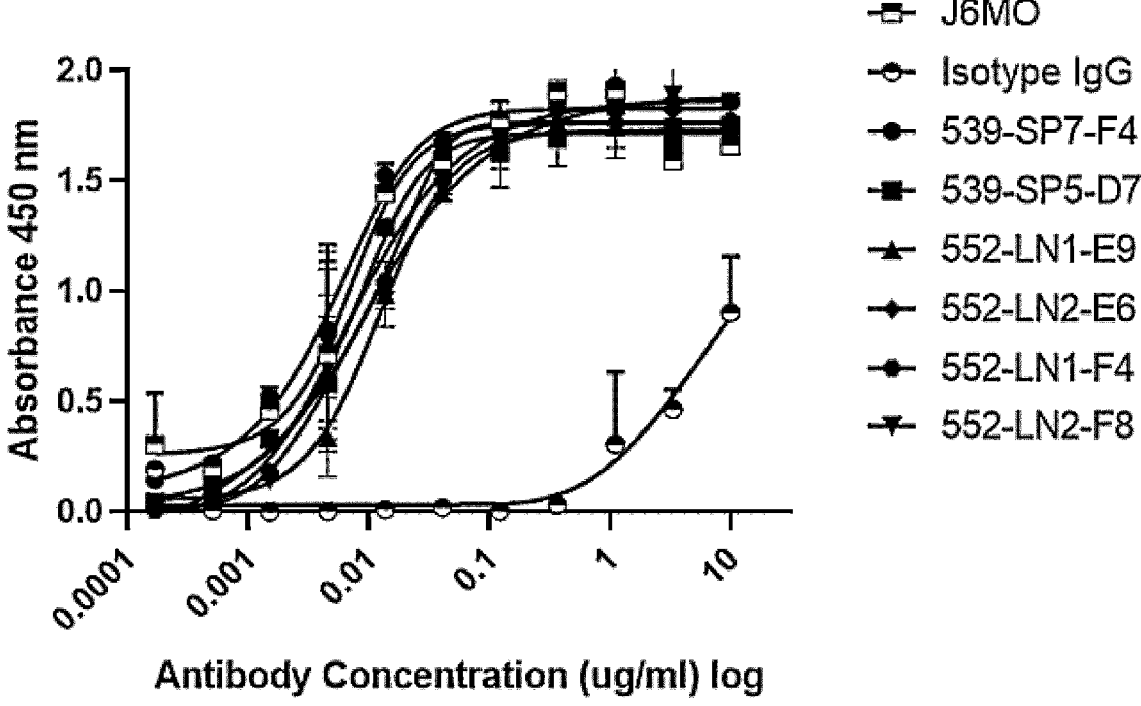
FIGS. 3A and 3B. Graphs showing binding of anti-BCMA antibodies to human BCMA, as determined by ELISA. (3A) shows results for 539-SP7-F4, 539-SP5-D7, 552-LN1-E9, 552-LN2-E6, 552 LN1-F4, 552-LN2-F8, J6M0, and iso-type-matched IgG control. (3B) shows results for 539-SP2-H3, 538-SP5-B10, 539-SP1-C8, J6M0, and isotype-matched IgG control.
Figure 3B:
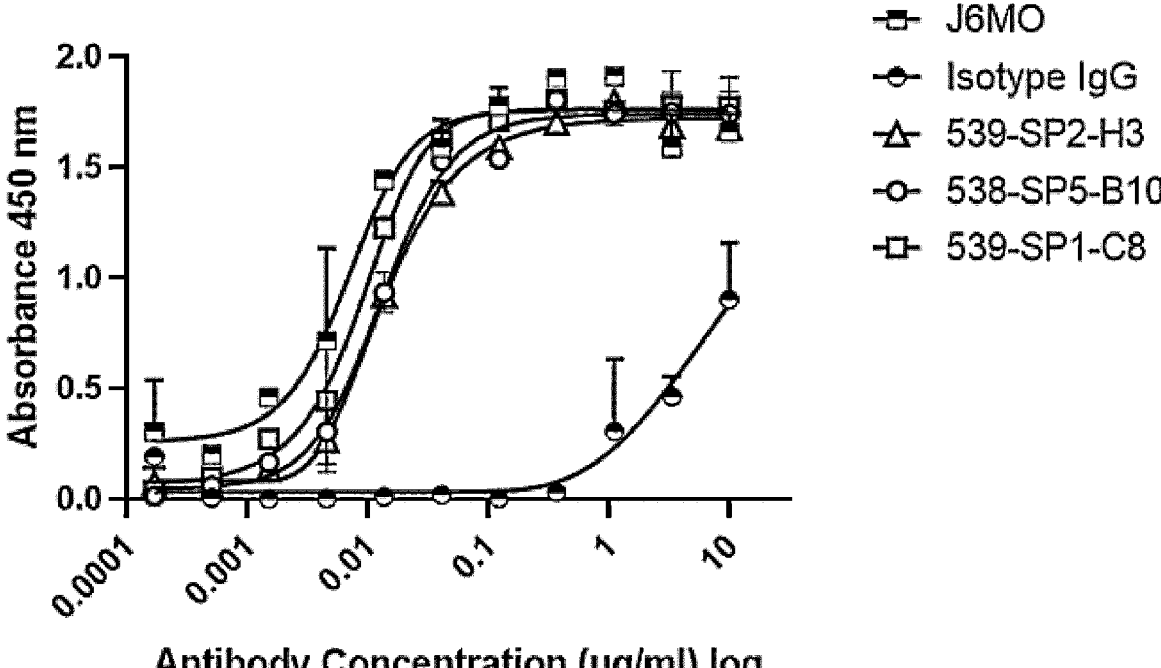
Figure 4A:
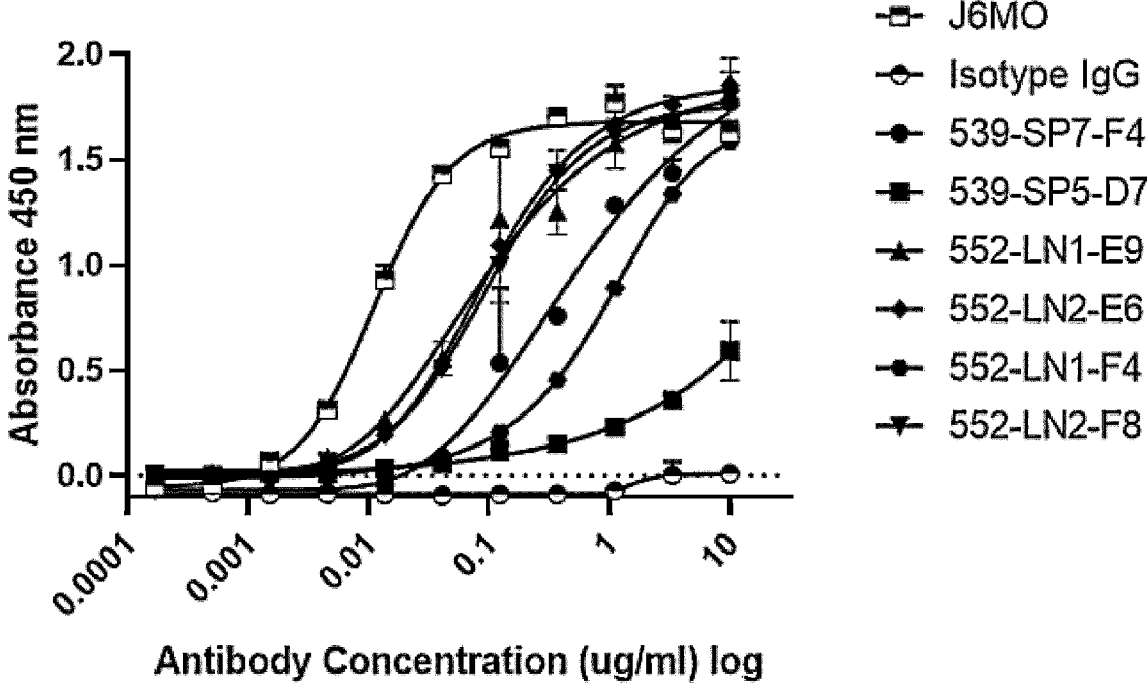
FIGS. 4A and 4B. Graphs showing binding of anti-BCMA antibodies to cynomolgous macaque BCMA, as determined by ELISA. (4A) shows results for 539-SP7-F4, 539-SP5-D7, 552-LN1-E9, 552 LN2-E6, 552-LN1-F4, 552-LN2-F8, J6M0, and isotype-matched IgG control. (4B) shows results for 539-SP2-H3, 538-SP5-B10, 539-SP1-C8, J6M0, and isotype-matched IgG control.
Figure 4B:
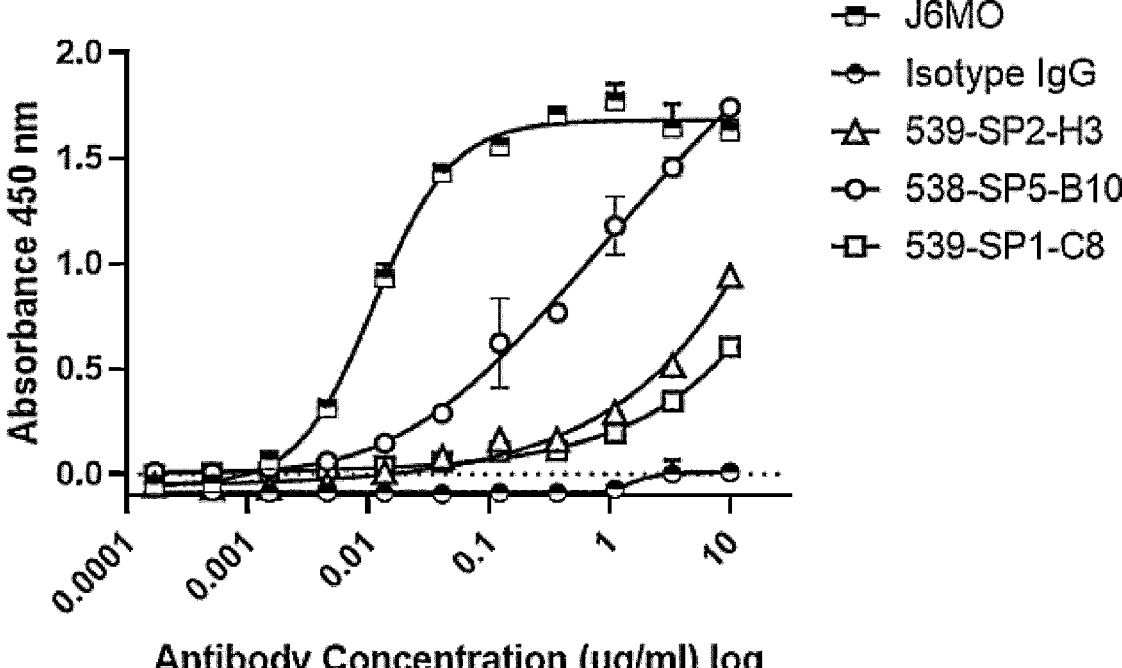
Figure 5A:
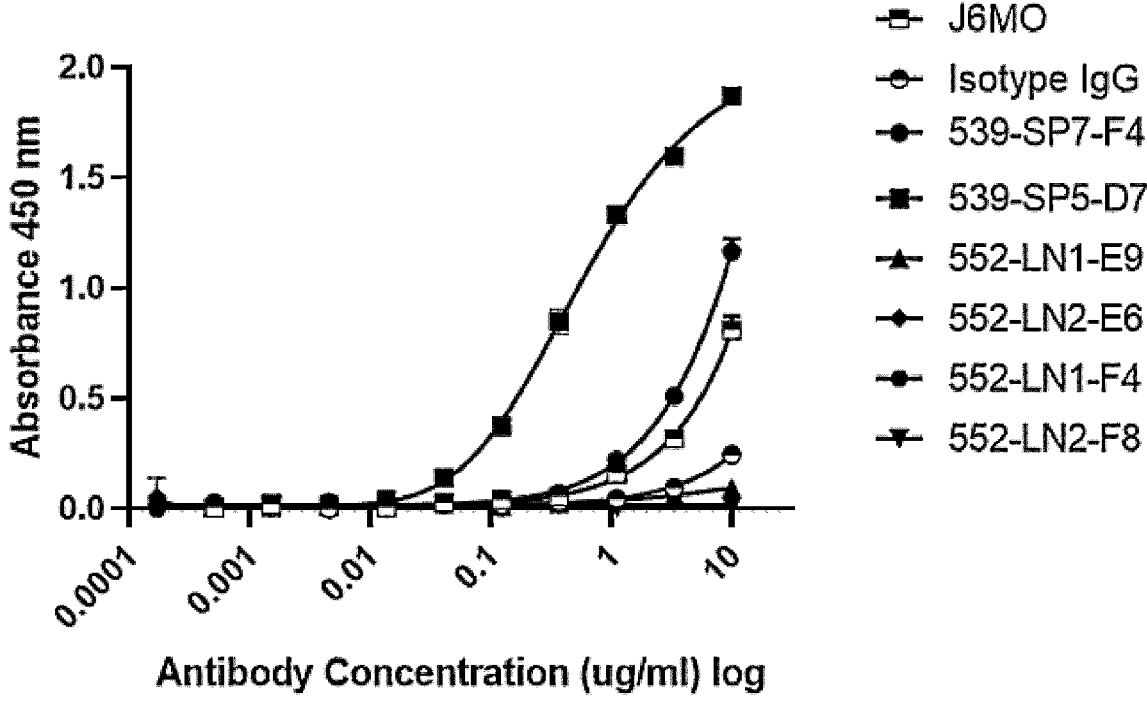
FIGS. 5A and 5B. Graphs showing binding of anti-BCMA antibodies to mouse BCMA, as determined by ELISA. (5A) shows results for 539-SP7-F4, 539-SP5-D7, 552-LN1-E9, 552-LN2-E6, 552 LN1-F4, 552-LN2-F8, J6M0, and iso-type-matched IgG control. (5B) shows results for 539-SP2-H3, 538-SP5-B10, 539-SP1-C8, J6M0, and isotype-matched IgG control.
Figure 5B:
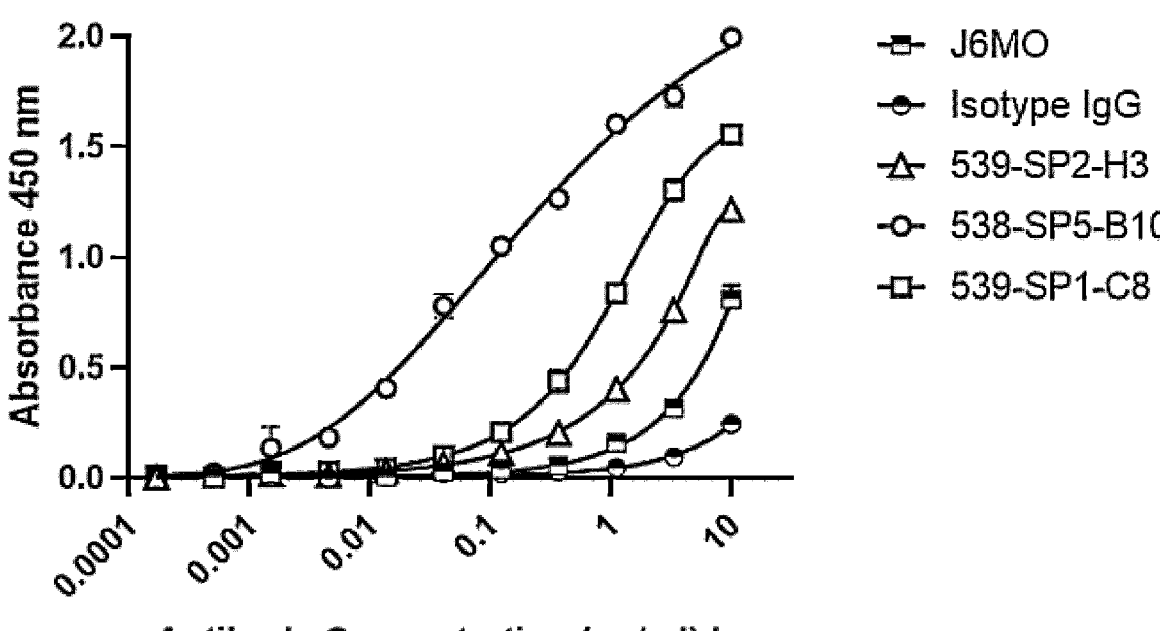

Example 3.1 of WO 2019/086573 A1 describes the analysis of affinity of binding to human CD47 by the anti-CD47 antibodies, and the results are shown in FIGS. 2A, 3B and 8 of WO 2019/086573 A1. Example 3.2 of WO 2019/086573 A1 describes analysis of binding to cells expressing human CD47 for the anti-CD47 antibodies by flow cytometry, and the results are shown in FIGS. 3A and 3B and in the table on page 81 of WO 2019/086573 A1. Example 3.3 of WO 2019/086573 A1 describes the results of analysis of binding to human CD47 and rhesus macaque CD47 for the anti-CD47 antibodies by ELISA, and the results are shown in FIG. 5 of WO 2019/086573 A1.

Example 4.1 of WO 2019/086573 A1 describes analysis of the ability of the anti-CD47 antibodies to block interaction between human CD47 and human SIRPα as determined by competition ELISA, and the results are shown in FIG. 4 of WO 2019/086573 A1. Example 4.2 of WO 2019/086573 A1 describes analysis of the ability of the anti-CD47 antibodies to promote phagocytosis of Raji and HL-60 cells by macrophages, and the results are shown in FIGS. 7A to 7C of WO 2019/086573 A1.

Example 5 of WO 2019/086573 A1 describes humanised anti-CD47 antibodies derived from clone 1-1-A1 described in WO 2019/086573 A1.

Example 6.1 of WO 2019/086573 A1 describes the analysis of binding to human CD47 and human VISTA by the humanised anti-CD47 antibodies described in Example 5 of WO 2019/086573 A1. The results are shown in FIGS. 9 and 10, and in the table on page 87 of WO 2019/086573 A1. Example 6.2 of WO 2019/086573 A1 describes the analysis of affinity of binding to human CD47 by the humanised anti-CD47 antibodies, and the results are shown in FIGS. 11A to 11H, and in the table on page 88 of WO 2019/086573 A1.

Example 7.1 of WO 2019/086573 A1 describes analysis of the ability of the humanised anti-CD47 antibodies described in Example 5 of WO 2019/086573 to block interaction between human CD47 and human SIRPα as determined by competition ELISA, and the results are shown in FIG. 12 and in the table on page 89 of WO 2019/086573 A1. Example 7.1 of WO 2019/086573 A1 describes analysis of the hemagglutinating capacity of the humanised anti-CD47 antibodies, and the results are shown in FIG. 13 of WO 2019/086573 A1.

Example 6: Bispecific BCMA– and CD47-Binding Antibodies

Bispecific BCMA– and CD47-expressing antibodies are produced in $KiH_{s\text{-}s}$ format.

Briefly, bispecific antibodies are expressed and purified as described in Example 2 from cells transfected with vectors encoding the following combinations of polypeptides:

| Antibody | Name | Polypeptides |
|---|---|---|
| [18] | 538-SP5-B10 Fab/11A1H5 scFv hIgG1 | SEQ ID NO: 320 + SEQ ID NO: 303 + SEQ ID NO: 329 |
| [19] | 539-SP1-C8 Fab/11A1H5 scFv hIgG1 | SEQ ID NO: 321 + SEQ ID NO: 305 + SEQ ID NO: 329 |
| [20] | 539-SP2-H3 Fab/11A1H5 scFv hIgG1 | SEQ ID NO: 322 + SEQ ID NO: 307 + SEQ ID NO: 329 |
| [21] | 539-SP5-D7 Fab/11A1H5 scFv hIgG1 | SEQ ID NO: 323 + SEQ ID NO: 309 + SEQ ID NO: 329 |
| [22] | 539-SP7-F4 Fab/11A1H5 scFv hIgG1 | SEQ ID NO: 324 + SEQ ID NO: 311 + SEQ ID NO: 329 |
| [23] | 552-LN1-E9 Fab/11A1H5 scFv hIgG1 | SEQ ID NO: 325 + SEQ ID NO: 313 + SEQ ID NO: 329 |
| [24] | 552-LN1-F4 Fab/11A1H5 scFv hIgG1 | SEQ ID NO: 326 + SEQ ID NO: 315 + SEQ ID NO: 329 |
| [25] | 552-LN2-E6 Fab/11A1H5 scFv hIgG1 | SEQ ID NO: 327 + SEQ ID NO: 317 + SEQ ID NO: 329 |
| [26] | 552-LN2-F8 Fab/11A1H5 scFv hIgG1 | SEQ ID NO: 328 + SEQ ID NO: 319 + SEQ ID NO: 329 |
| [27] | 1E9-4H Fab/11A1H5 scFv hIgG1 | SEQ ID NO: 440 + SEQ ID NO: 425 + SEQ ID NO: 329 |
| [28] | 1E9-QE Fab/11A1H5 scFv hIgG1 | SEQ ID NO: 441 + SEQ ID NO: 427 + SEQ ID NO: 329 |
| [29] | 2F8-2Q Fab/11A1H5 scFv hIgG1 | SEQ ID NO: 442 + SEQ ID NO: 429 + SEQ ID NO: 329 |
| [30] | 2F8-5U Fab/11A1H5 scFv hIgG1 | SEQ ID NO: 443 + SEQ ID NO: 431 + SEQ ID NO: 329 |
| [31] | 5B10-4Y Fab/11A1H5 scFv hIgG1 | SEQ ID NO: 444 + SEQ ID NO: 433 + SEQ ID NO: 329 |
| [32] | 5B10-51 Fab/11A1H5 scFv hIgG1 | SEQ ID NO: 445 + SEQ ID NO: 435 + SEQ ID NO: 329 |
| [33] | 1C8-6A Fab/11A1H5 scFv hIgG1 | SEQ ID NO: 446 + SEQ ID NO: 437 + SEQ ID NO: 329 |
| [34] | 1C8-EH Fab/11A1H5 scFv hIgG1 | SEQ ID NO: 447 + SEQ ID NO: 439 + SEQ ID NO: 329 |
| [35] | 1C8-402 Fab/11A1H5 scFv hIgG1 | SEQ ID NO: 520 + SEQ ID NO: 505 + SEQ ID NO: 329 |
| [36] | 1C8-403 Fab/11A1H5 scFv hIgG1 | SEQ ID NO: 520 + SEQ ID NO: 506 + SEQ ID NO: 329 |
| [37] | 1C8-507 Fab/11A1H5 scFv hIgG1 | SEQ ID NO: 521 + SEQ ID NO: 508 + SEQ ID NO: 329 |
| [38] | 1C8-610 Fab/11A1H5 scFv hIgG1 | SEQ ID NO: 522 + SEQ ID NO: 510 + SEQ ID NO: 329 |
| [39] | 1C8-6A3 Fab/11A1H5 scFv hIgG1 | SEQ ID NO: 523 + SEQ ID NO: 512 + SEQ ID NO: 329 |
| [40] | 1C8-25 Fab/11A1H5 scFv hIgG1 | SEQ ID NO: 524 + SEQ ID NO: 514 + SEQ ID NO: 329 |
| [41] | 1C8-27 Fab/11A1H5 scFv hIgG1 | SEQ ID NO: 524 + SEQ ID NO: 515 + SEQ ID NO: 329 |

222

The resulting bispecific antigen-binding molecules comprise a BCMA-specific Fab, and a CD47-specific scFv, in human IgG1 format.

Example 7: Characterisation of the Bispecific BCMA– and CD47-Binding Antibodies

7.1 ELISAs for Evaluating Antibody Specificity and Affinity

ELISAs are performed in order to confirm the ability of the bispecific antibodies of Example 6 to bind to human BCMA and human CD47.

ELISAs are performed as described in Example 3.1 above, for the analysis of binding of the bispecific antibodies to His-tagged human BCMA or His-tagged human CD47.

The bispecific antibodies are shown to bind to human BCMA and human CD47.

The ability of the bispecific antibodies to simultaneously bind to BCMA and CD47 is investigated.

Briefly, wells of 96-well plates (Nunc, Denmark) are coated with 6 µg/ml of untagged human CD47 protein in PBS, for 16 hrs at 4° C. After blocking for 1 h 30 min with 1% BSA in 1×PBS at room temperature, his-tagged human BCMA (6 µg/ml) is added to the wells, along with 10 µg/ml of the bispecific anti-BCMA, anti-CD47 antibodies, and the plates are incubated at room temperature for 1 h. Plates are then washed three times with 1×PBS containing 0.05% Tween 20, and incubated with a HRP-conjugated anti-His antibody (Life Technologies, Inc., USA) at a 1:5000 dilution, for 1 h at room temperature. After washing, plates are developed with colorimetric detection substrate 3,3', 5,5'-tetramethylbenzidine (Turbo-TMB; Pierce, USA). The reaction is stopped after 3 min with 2M H2504, and OD is measured at 450 nM using a BioTek PowerWave HT.

The bispecific antibodies are shown to be able to bind simultaneously to human BCMA and human CD47.

7.2 Analysis of Cell Surface Antigen-Binding by Flow Cytometry

The bispecific antibodies of Example 6 are analysed for their ability to bind to cells expressing human BCMA, cells expressing human CD47, or cells expressing both human BCMA and human CD47. Experiments are performed as described in Example 3.2 above, for the analysis of binding of the bispecific antibodies to HEK293T CD47 knockout cells engineered by transfection to express BCMA, CD47-expressing HEK293T cells, or HEK293T engineered by transfection to express both BCMA and CD47, or non-transfected HEK 293T cells (negative control).

The bispecific antibodies are shown to bind to cells expressing human BCMA and cells expressing human CD47, and cells expressing human BCMA and human CD47.

7.3 Analysis of Affinity for BCMA and CD47 by Biolayer Interferometry

The bispecific antibodies of Example 6 are analysed in order to determine their affinity for binding to human BCMA and human CD47.

Experiments are performed as described in Example 3.4 above, using His-tagged human BCMA or His-tagged human CD47.

The bispecific antibodies are shown to bind to human BCMA and human CD47 with high affinity.

7.4 Analysis of Ability to Block BCMA-APRIL Interaction

The bispecific antibodies of Example 6 are analysed for their ability to inhibit interaction between BCMA and APRIL as described in Example 3.3 above.

Certain of the bispecific antibodies are shown to inhibit interaction between BCMA and APRIL.

7.5 Analysis of Ability to Block CD47-SIRPα Interaction

The bispecific antibodies of Example 6 are analysed for their ability to inhibit interaction between CD47 and SIRPα.

Briefly, 96-well plates (Nunc, Denmark) are coated with 1 µg/ml of untagged human CD47 protein (Sinobiological Inc, China) in 1×PBS for 16 h at 4° C. After blocking for 1 h with 1% BSA in TBS at room temperature, 1 µg/ml of His-tagged human SIRPα fusion protein (Sinobiological Inc, China) is added either in the absence of antibody, or in the presence of increasing concentrations of the bispecific anti-BCMA, anti-CD47 antibodies at room temperature for 1 h. Plates are subsequently washed three times with TBS-T and incubated with a HRP-conjugated anti-his secondary antibody (Thermo Scientific, USA) for 1 h at room temperature. After washing, plates are developed with colorimetric detection substrate Turbo-TMB (Pierce, USA). The reaction is stopped with 2M H2504, and OD is measured at 450 nM. Percent inhibition of CD47-SIRPα interaction is calculated relative to the signal in the absence of SIRPα (100%).

The bispecific antibodies are shown to inhibit interaction between CD47 and SIRPα.

7.6 In Vitro Phagocytosis Assay

The bispecific antibodies of Example 6 are analysed for their effects in an in vitro assay of phagocytosis of HL-60 or Raji cells by human macrophages.

Briefly, HL-60 or Raji cells are cultured in RPMI-1640 supplemented with 10% fetal bovine serum (FBS) and 1% Pen/Strep at 37° C. in a 5% $CO_2$ incubator. HL-60 or Raji cells are harvested and CFSE-labelled using CellTrace CFSE Cell Proliferation Kit (Thermo Scientific, USA), in accordance with the manufacturer's instructions. The labelled cells are then incubated with human peripheral blood-derived macrophages (Stemcell Technologies, Canada) in the presence of 20 µg/ml of the bispecific anti-BCMA, anti-CD47 antibodies, for 2 h at 37° C. Cells are washed thrice with 1×PBS to remove all the non-phagocytosed labelled cells, and resuspended in 200 µL of FACS flow buffer (PBS with 5 mM EDTA) for flow cytometric analysis using MACSQuant™ 10 (Miltenyi Biotec, Germany). After acquisition, all raw data are analysed using Flowlogic software. Cells are gated using forward and side scatter profile and percentage of the engulfed HL-60/Raji cells is calculated.

The bispecific antibodies are shown to potently promote phagocytosis of Raji cells and HL-60 cells by macrophages.

In further experiments, bispecific antibody [19] of Example 6 was investigated for its ability to potentiate phagocytosis of H929 cells, which express BCMA.

PBMCs were isolated from fresh blood of 3 donors using SepMate™ Tubes with Histopaque®-1077 (Sigma, 10771-500ML). Monocytes were isolated from the PBMCs using Classical Monocyte Isolation Kit (Miltenyi, #130-117-337). Monocytes were differentiated to M0 macrophages by culture for 5 days in the presence of 80 ng/ml M-CSF. On day 5, M0 macrophages were harvested and seeded in 96-well flat bottom plates (30,000 cells/well) and allowed to attach overnight.

H929 cells (target) were stained with 2.5 µM of CFSE, and the stained cells were treated with anti-CD47 IgG1 (Invitrogen, Catalog #16047981), J6M0-hIgG1, 11A1H5-hIgG1, UltraLEAF human IgG1 isotype (BioLegend, Catalog #403502), bispecific J6M0 Fab/11A1H5 scFv hIgG1 or bispecific antibody [19] of Example 6 (referred to in FIG. 24 as '1C8P×1-1A1H5') at the following concentrations: 10 ug/ml, 3.3 ug/ml, 1.1 ug/ml, 0.37 ug/ml, 0.123 ug/ml, 0.04 ug/ml, 0.013 ug/ml and 0 ug/ml, for 1 h.

Macrophages were then co-cultured with the antibody-treated, CFSE-labelled H929 target cells (15,000 macrophages/well; giving a macrophage-to-H929 cell ratio of 2:1) for 4 h at 5% $CO_2$, 37° C.

The macrophages were harvested using accutase, washed thrice with 1×PBS to remove all the non-phagocytosed labelled cells and stained with an APC-conjugated anti-CD14 antibody. Cells are washed thrice with 1×PBS, and resuspended in 200 μL of FACS flow buffer (PBS+5 mM EDTA) for flow cytometric analysis using MACSQuant™ 10 (Miltenyi Biotec, Germany). After acquisition, all raw data are analysed using Flowlogic software. Phagocytosis was evaluated by determining the percentage of CD14+ cells that were CFSE+. Dose-response curves were fitted and EC50 values for phagocytosis were derived from the dose-response curves, where possible.

Figure 24:
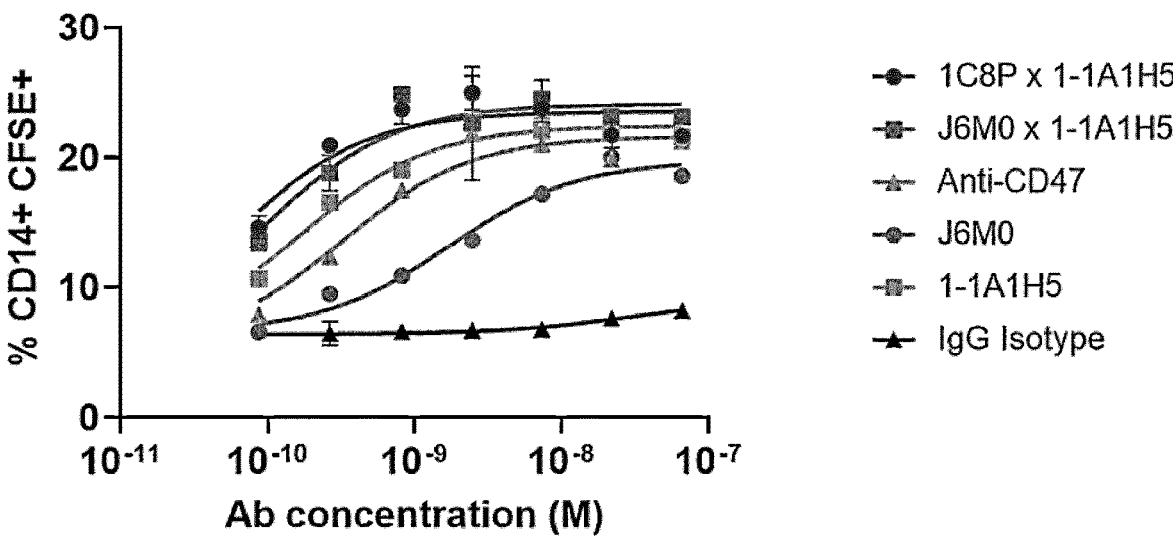
FIG. 24. Graph showing the ability of bispecific anti-BCMA/TACI, anti-CD47 antibodies to increase phagocytosis of BCMA-expressing cells by macrophages. CFSE-labelled H929 cells were incubated with the indicated antibodies, and then co-cultured with macrophages derived from PBMCs of three different donors. Macrophages that had phagocytosed the CFSE-labelled cells were identified by flow cytometry as CD14+, CSFE+ cells.
Figure 25A:
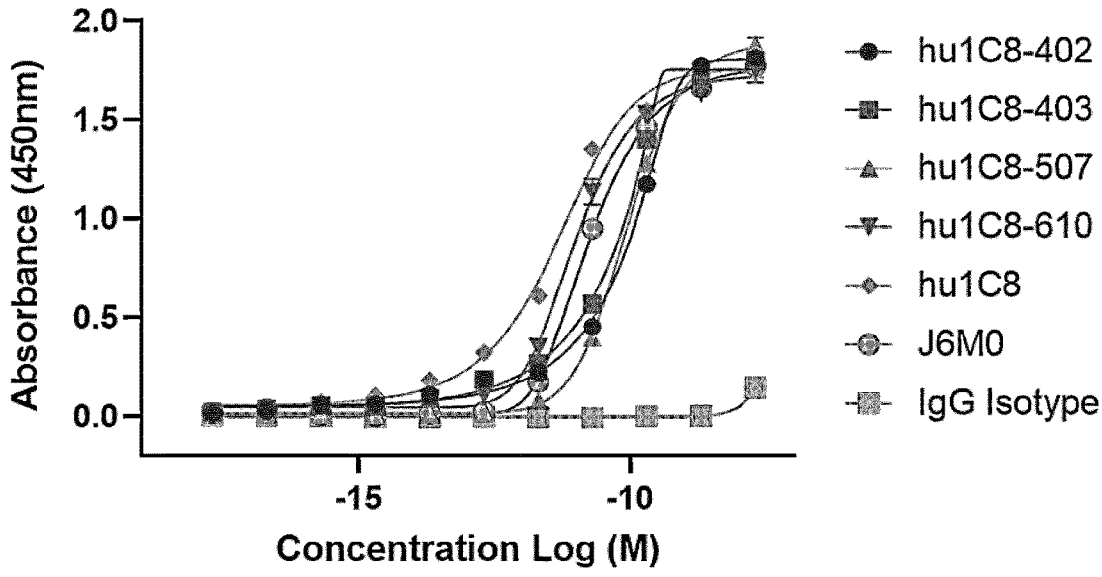
FIGS. 25A to 25F. Graphs and table showing binding of anti-BCMA/TACI antibodies to (25A) human BCMA, (25B) human TACT, (25C) cynomolgous macaque BCMA, (25D) cynomolgous macaque TACT, and (25F) human HER3, as determined by ELISA. (25E) EC50 values for binding to human BCMA, human TACT, cynomolgous macaque BCMA and cynomolgous macaque TACI are shown. NA=not assessed.
Figure 25B:
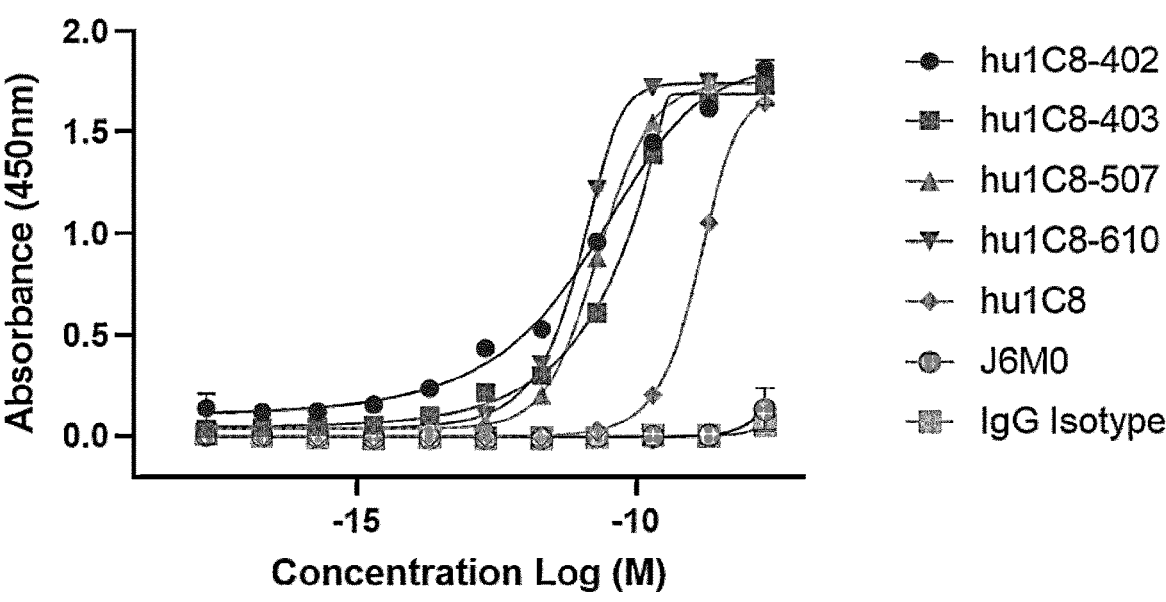
Figure 25C:
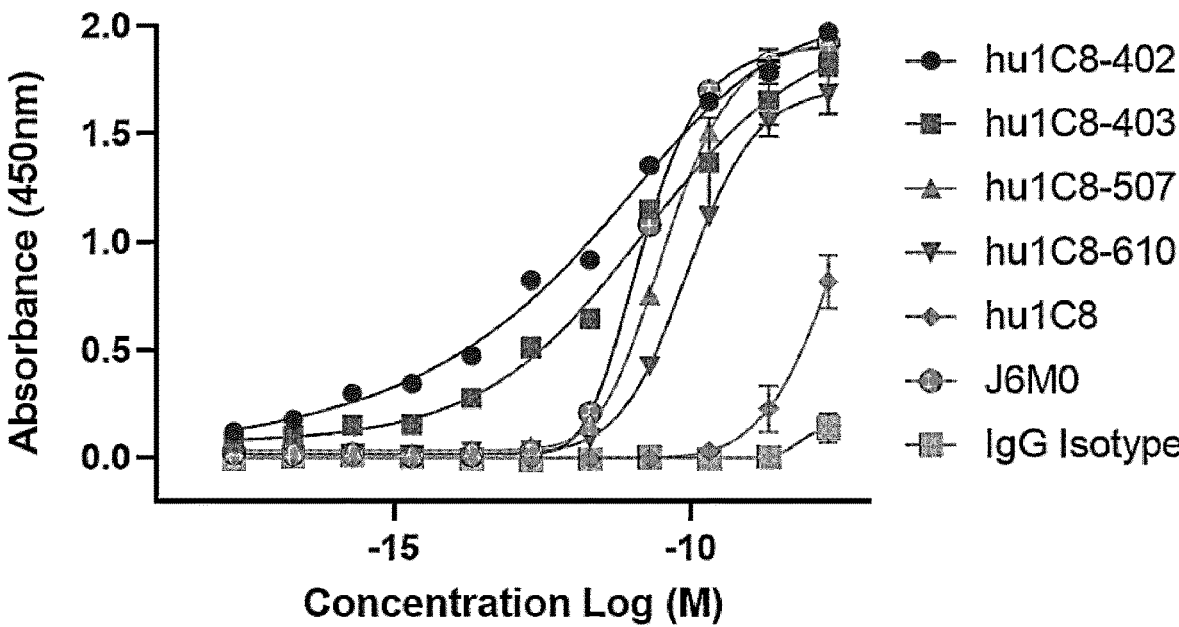
Figures 25D, 25E:
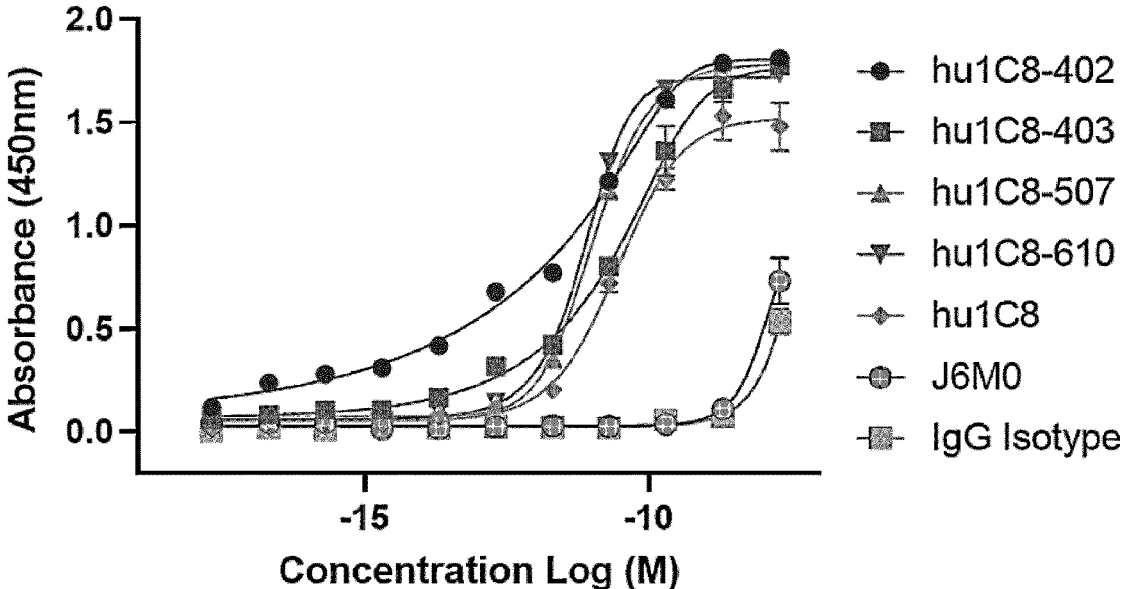
Figure 25F:
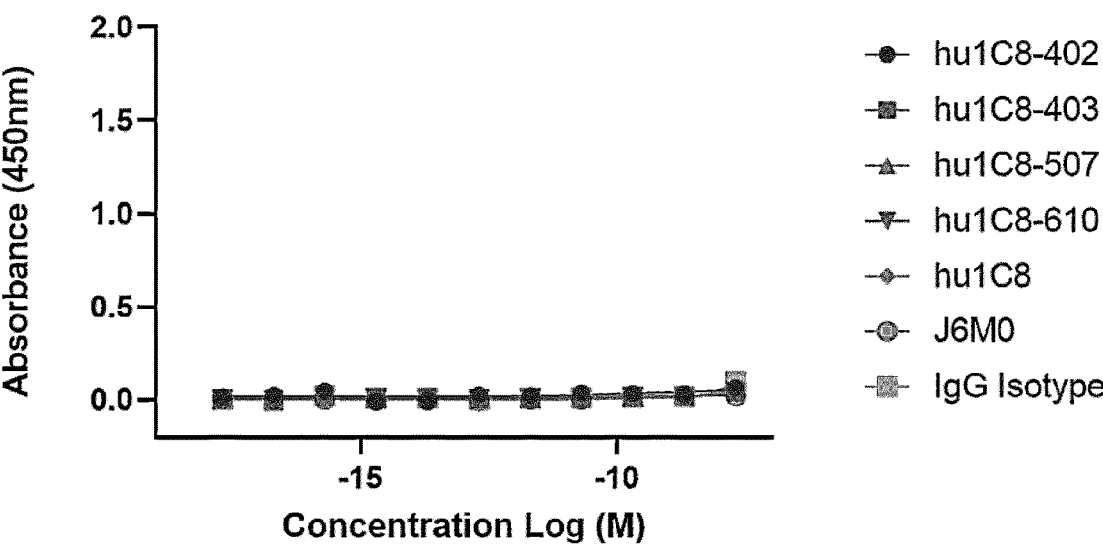

The results of the experiment are shown in FIG. 24. Bispecific antibody [19] was found to strongly promote phagocytosis of H929 cells.

7.7 In Vitro Hemagglutination Assay

The bispecific antibodies of Example 6 are analysed for their hemagglutinating capacity.

Briefly, human RBCs are prepared by extensively washing blood with 1×PBS and centrifuging at 1500 rpm for 5 min, until a clear supernatant is observed. For the assay, 1% human RBCs are incubated for 1 h at RT in presence or absence of increasing concentrations of the bispecific anti-BCMA, anti-CD47 antibodies in wells of round-bottom 96 well plates. Presence of hemagglutination was assessed by the presence of non-settled RBCs, appearing as a haze compared to a punctuated red dot of non-hemagglutinated RBCs. An anti-red blood cell antibody (AbCam, cat. no. ab34858) condition is included as a positive control for hemagglutination, and an isotype control antibody condition is included as a negative control.

The bispecific antibodies are found not to induce significant hemagglutination at moderate to high concentrations of the antibody.

7.8 Analysis of Preferential Binding to Cells Expressing BCMA and CD47, Over Cells Expressing BCMA Only or CD47 Only The bispecific antibodies of Example 6 are analysed in order to determine whether they bind preferentially to cells expressing both BCMA and CD47, over cells expressing BCMA only or CD47 only.

Briefly, HEK293T CD47 knockout cells engineered by transfection to express BCMA, CD47-expressing HEK293T cells, or HEK293T engineered by transfection to express both BCMA and CD47 are CFSE-labelled using CellTrace CFSE Cell Proliferation Kit (Thermo Scientific, USA) in accordance with the manufacturer's instructions.

The following cells are then mixed in a 1:1 ratio:
a) CFSE-labelled, BCMA and CD47-expressing cells+ unlabelled BCMA-expressing cells
b) CFSE-labelled, BCMA and CD47-expressing cells+ unlabelled CD47-expressing cells
c) CFSE-labelled, BCMA-expressing cells+unlabelled BCMA and CD47-expressing cells
d) CFSE-labelled, CD47-expressing cells+unlabelled BCMA and CD47-expressing cells The cell mixtures are then incubated with the bispecific anti-BCMA, anti-CD47 antibodies at a concentration of 10 μg/ml for 1 h 30 min at 4° C. The cells are then stained with APC-conjugated anti-human Fc secondary antibody for 30 min at 4° C. Cells are washed thrice with PBS and resuspended in 200 μL of FACSflow buffer (PBS with 5 mM EDTA for flow cytometric analysis using MACSQuant™ 10

(Miltenyi Biotec, Germany). After acquisition, all raw data are analysed using Flowlogic software. Cells are gated using forward and side scatter profile and the percentage of the double positive cells (CFSE+/APC+) was calculated.

The bispecific antibodies are found to bind to cells expressing both BCMA and CD47 to a greater extent than cells expressing BCMA only, or cells expressing CD47 only.

7.9 Analysis of Therapeutic Efficacy In Vivo

The bispecific antibodies of Example 6 are analysed for their therapeutic efficacy for the treatment of cancer in vivo.

NOD SLID mice approximately 6-8 weeks old are housed under specific pathogen-free conditions and are treated in compliance with the Institutional Animal Care and Use Committee (IACUC) guidelines.

$6×10^6$ Raji cells, U-266/70, U-266/84 cells, RPMI-8226 cells or MM.1 S cells are mixed with an equal volume of Matrigel (Corning, USA) prior to implantation. Cells are implanted subcutaneously into the right flanks of mice. 3 days post-implantation bispecific anti-BCMA, anti-CD47 antibodies are administered intraperitoneally at a dose of 10 mg/kg. Mice are treated twice weekly for four weeks. The untreated control group receives vehicle treatment at the same dose interval. Tumor volume is measured 3 times a week using a digital caliper and calculated using the formula [L×W2/2]. Study end point is reached once the tumors of the control arm measures >1.5 cm in length. Mouse survival is also monitored.

Administration of bispecific antibodies is found to delay disease onset, increase survival, and to cause a dramatic reduction in tumor growth as compared to the untreated control group. Tumor incidence in the bispecific antibody-treated group is also lower than in the untreated control group, suggesting that the bispecific antibodies are also useful for the prevention of disease onset.

Example 8: Characterisation of the Regions of BCMA and TACI Bound by Cross-Reactive Clones As explained at Example 3.1, some of the antibody clones described herein display binding to both BCMA and TACI.

Human BCMA and human TACI share only 21% amino acid sequence identity, and so it is very challenging to produce monoclonal antibodies which bind specifically to both BCMA and TACI (i.e. cross-reactive antibodies).

However, using an artificial intelligence-powered proprietary platform integrating sequence similarity and structural homology between the molecules, the inventors identified a candidate, conserved three-dimensional epitope formed by regions of BCMA and TACI to be targeted, which might provide for the production of antibodies cross-reactive for BCMA and TACI.

Having successfully raised antibodies which bind specifically to both BCMA and TACI, the inventors investigated whether the region identified by their modelling studies was important for binding of those antibodies to the molecules.

The following cDNA constructs were prepared:
'BCMA Mut' construct encoding human BCMA comprising the substitutions Y13A, D15A, L17G and L18G and relative to SEQ ID NO:1 (SEQ ID NO:450); and
'TACI Mut' construct encoding human TACI comprising the substitutions Y39A, D41A, L43G and L44G and relative to SEQ ID NO:330 (SEQ ID NO:451).

HEK293T cells were transfected with expression vectors encoding BCMA Mut, TACI Mut, wildtype human BCMA or wildtype human TACI. 24 hours later, the cells were harvested and binding of antibodies to cells expressing the different proteins was analysed by flow cytometry, essentially as described in Example 3.2. The BCMA- or TACI-binding antibodies characterised in the experiment were [1] and [2] of Example 2.1, J6M0 (as a positive control for binding to BCMA) and anti-huTACI (APC) (Biolegend, #311912; as a positive control for binding to TACI).

Figure 17A:
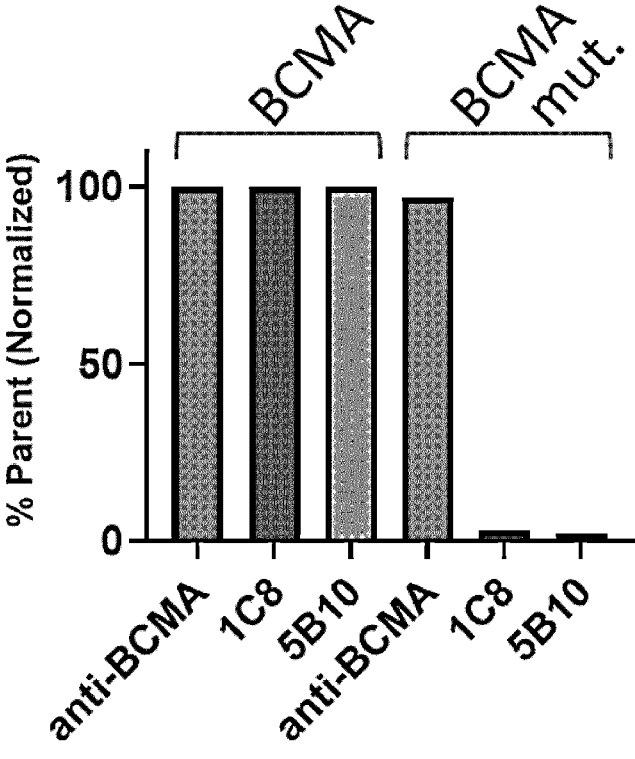
FIGS. 17A and 17B. Bar charts showing binding of antibodies 539-SP1-C8 (1C8), 538-SP5-B10 (5B10), J6M0 (anti-BCMA) and anti-huTACI antibody (anti-TACI) to HEK293 cells expressing (17A) BCMA or BCMA Mut, and (17B) TACI or TACI Mut, as determined by flow cytometry.
Figure 17B:
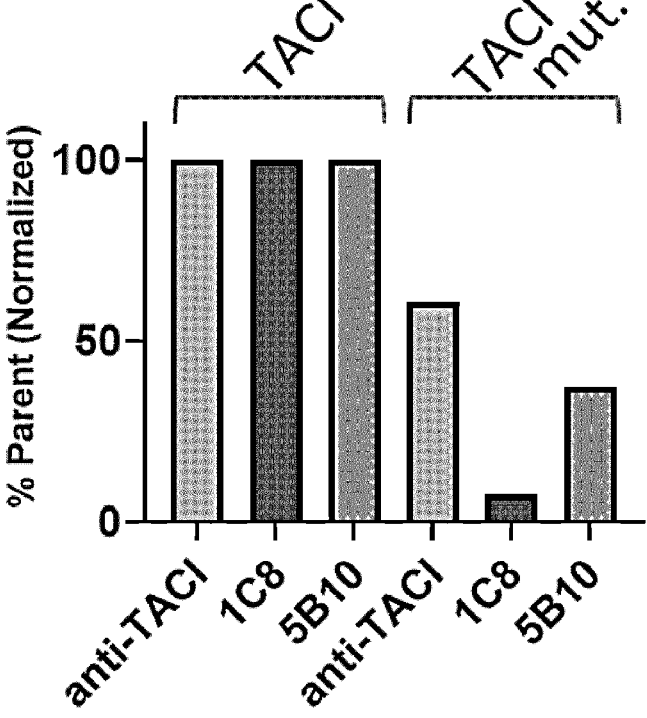
Figure 18A:
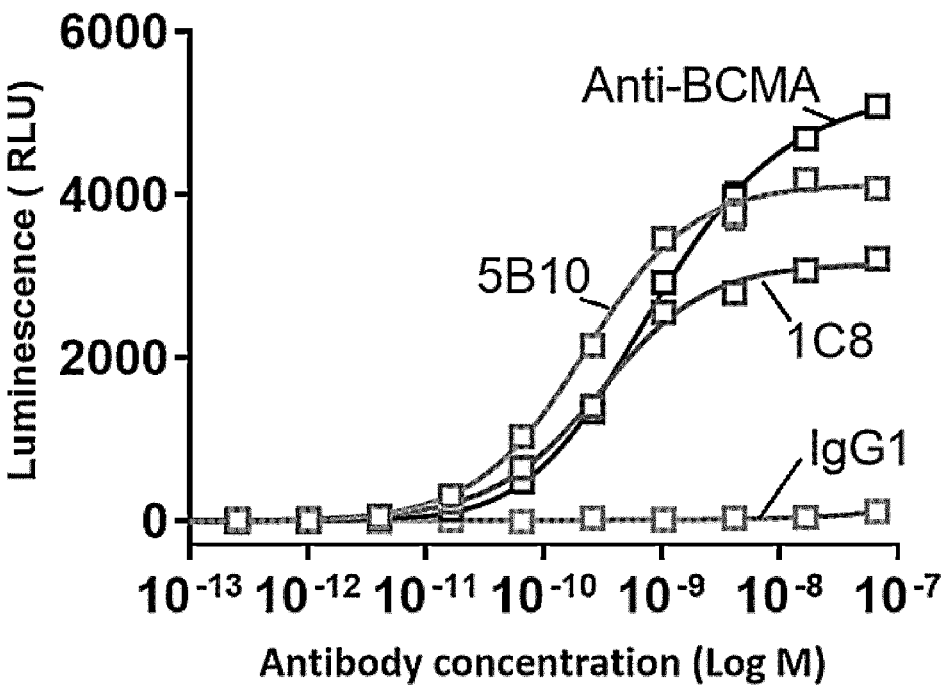
FIGS. 18A to 18D. Graphs and table showing induction of ADCC against cells expressing (18A) human BCMA, (18B) human TACT, or (18C) human BCMA and human TACT, by antibodies 539-SP1-C8 (1C8), 538-SP5-B10 (5B10), J6M0 (anti-BCMA) or isotype-matched IgG control (IgG1), as determined using the Jurkat-Lucia® cell ADCC reporter assay described in Example 9. (18D) summarises the EC50 values determined for induction of ADCC against cells expressing the indicated molecules.
Figure 18B:
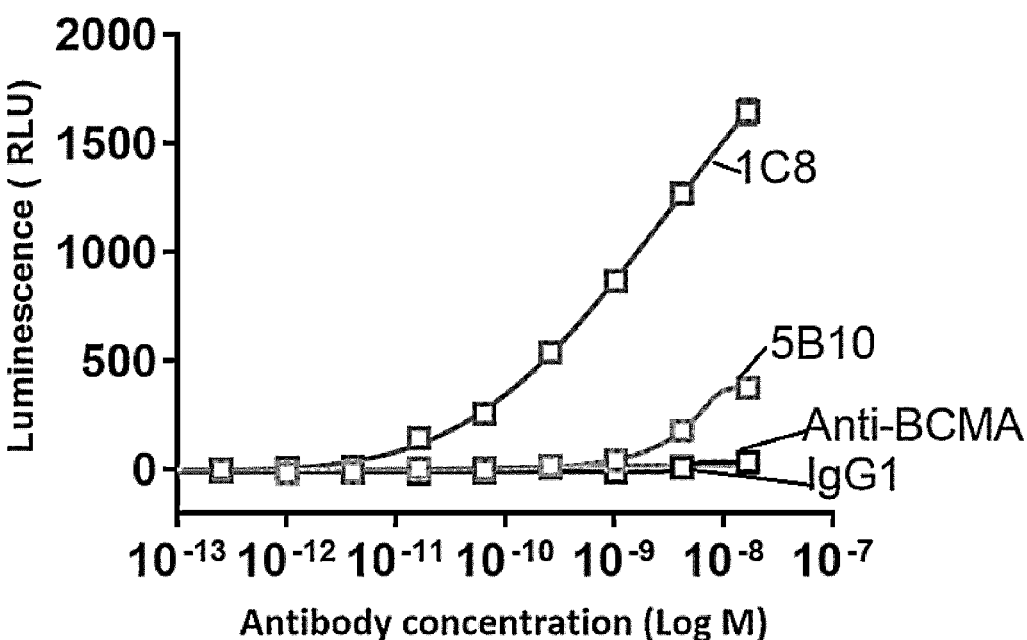
Figures 18C, 18D:
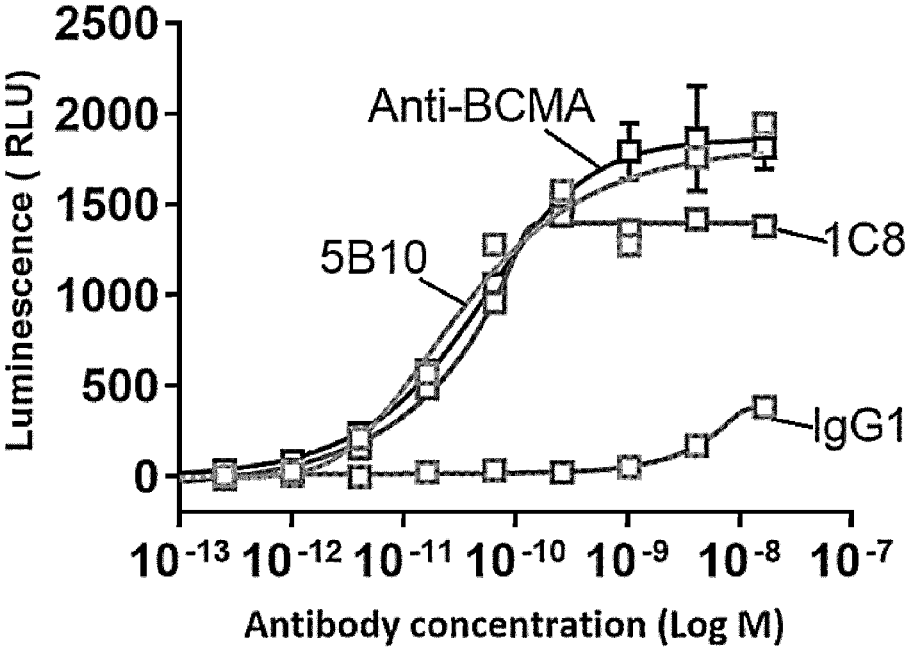

The results of the analysis are shown in FIGS. 17A and 17B.

FIG. 17A shows that introduction of the substitutions Y13A, D15A, L17G and L18G into the amino acid sequence of BCMA completely disrupted binding of 538-SP5-B10 and 539-SP1-C8 to BCMA, indicating that this region of BCMA is important for binding of the antibodies to BCMA. By contrast, binding of J6M0 was unaffected, indicating that J6M0 binds to a distinct epitope of BCMA to the epitope bound by 538-SP5-B10 and 539-SP1-C8.

FIG. 17B shows that introduction of the substitutions Y13A, D15A, L17G and L18G into the amino acid sequence of TACI significantly reduced binding of 538-SP5-B10 and 539-SP1-C8 to TACI, indicating that this region of TACI is important for binding of the antibodies to TACI. Binding of anti-huTACI (Biolegend, #311912) was also reduced by introduction of the mutations, but to a lesser extent.

The results implicate the regions shown in SEQ ID NOs:448 and 449 as being important for the binding of 538-SP5-B10 and 539-SP1-C8 to BCMA and TACI, respectively.

In further experiments, humanised anti-BCMA antibodies [10] to [17] of Example 4.1 are analysed in order to determine their ability to bind to BCMA Mut and TACI Mut. The humanised anti-BCMA antibodies are found to retain the ability to bind to BCMA Mut and TACI Mut displayed by the parental clone from which they are derived.

Example 9: Analysis of Induction of ADCC Against Cells Expressing BCMA and/or TACI The inventors investigated the ability of different antibodies to direct antibody-dependent cell-mediated cytotoxicity (ADCC) against cells expressing BCMA, TACI, or both BCMA and TACI.

HEK293T cells were transfected with expression vectors encoding human BCMA, human TACI, or both human BCMA and human TACI proteins. The BCMA- and/or TACI-expressing target cells were subsequently harvested, seeded in cells of a 96 well plate at $1\times10^5$ cells/well, and incubated for 1 h at 37° C., 5% $CO_2$ in the presence of the following antibodies, in an 11 point, 4-fold dilution series (at concentrations from 10 μg/ml to 0.0000095 μg/ml): [1] and [2] of Example 2.1, J6M0-hIgG1, and human IgG Isotype control (Biolegend Cat. #403501). Subsequently, $2\times10^5$ Jurkat Lucia NFAT CD16 effector cells (Invivogen Cat. No. jktl-nfat-cd16) were added to each well, and the co-cultures of target and effector cells were incubated overnight at 37° C., 5% $CO_2$. Cell culture supernatants from the co-cultures were collected, and 10 μl was transferred to wells of 384 well white, opaque plates. 25 μl of QUANTI-Luc luminescence substrate (Invivogen Cat. #rep-glc1) was added, and luminescence was measured using Victor Nivo (Perkin Elmer).

The results are shown in FIGS. 18A to 18D. [2] of Example 2.1 was found to potently induce ADCC against cells expressing human BCMA, human TACI, or cells expressing both human BCMA and human TACI.

In further experiments, humanised anti-BCMA antibodies [10] to [17] of Example 4.1 are analysed in order to determine their ability to direct ADCC against cells transiently expressing BCMA, TACI, or cells expressing both BCMA and TACI. The humanised anti-BCMA antibodies are found to retain the ability to elicit ADCC against BCMA- and/or TACI-expressing target cells displayed by the parental clone from which they are derived.

Example 10: Bispecific BCMA- and CD3-Binding Antibodies

Bispecific BCMA- and CD3-binding antibodies are produced in KiH$_{s-s}$ format.

The CD3-binding domain is based on the well-characterised CD3ε-binding antibody clone OKT3, having the heavy and light chain variable region sequences shown respectively in SEQ ID NOs:452 and 453. Briefly, bispecific antibodies are expressed and purified essentially as described in Example 2 from cells transfected with vectors encoding the following combinations of polypeptides:

| Antibody | Name | Polypeptides |
|---|---|---|
| [42] | 538-SP5-B10 Fab/OKT3 scFv hIgG1 | SEQ ID NO: 320 + SEQ ID NO: 303 + SEQ ID NO: 454 |
| [43] | 539-SP1-C8 Fab/OKT3 scFv hIgG1 | SEQ ID NO: 321 + SEQ ID NO: 305 + SEQ ID NO: 454 |
| [44] | 539-SP2-H3 Fab/OKT3 scFv hIgG1 | SEQ ID NO: 322 + SEQ ID NO: 307 + SEQ ID NO: 454 |
| [45] | 539-SP5-D7 Fab/OKT3 scFv hIgG1 | SEQ ID NO: 323 + SEQ ID NO: 309 + SEQ ID NO: 454 |
| [46] | 539-SP7-F4 Fab/OKT3 scFv hIgG1 | SEQ ID NO: 324 + SEQ ID NO: 311 + SEQ ID NO: 454 |
| [47] | 552-LN1-E9 Fab/OKT3 scFv hIgG1 | SEQ ID NO: 325 + SEQ ID NO: 313 + SEQ ID NO: 454 |
| [48] | 552-LN1-F4 Fab/OKT3 scFv hIgG1 | SEQ ID NO: 326 + SEQ ID NO: 315 + SEQ ID NO: 454 |
| [49] | 552-LN2-E6 Fab/OKT3 scFv hIgG1 | SEQ ID NO: 327 + SEQ ID NO: 317 + SEQ ID NO: 454 |
| [50] | 552-LN2-F8 Fab/OKT3 scFv hIgG1 | SEQ ID NO: 328 + SEQ ID NO: 319 + SEQ ID NO: 454 |
| [51] | 1E9-4H Fab/OKT3 scFv hIgG1 | SEQ ID NO: 440 + SEQ ID NO: 425 + SEQ ID NO: 454 |
| [52] | 1E9-QE Fab/OKT3 scFv hIgG1 | SEQ ID NO: 441 + SEQ ID NO: 427 + SEQ ID NO: 454 |
| [53] | 2F8-2Q Fab/OKT3 scFv hIgG1 | SEQ ID NO: 442 + SEQ ID NO: 429 + SEQ ID NO: 454 |
| [54] | 2F8-5U Fab/OKT3 scFv hIgG1 | SEQ ID NO: 443 + SEQ ID NO: 431 + SEQ ID NO: 454 |
| [55] | 5B10-4Y Fab/OKT3 scFv hIgG1 | SEQ ID NO: 444 + SEQ ID NO: 433 + SEQ ID NO: 454 |
| [56] | 5B10-5I Fab/OKT3 scFv hIgG1 | SEQ ID NO: 445 + SEQ ID NO: 435 + SEQ ID NO: 454 |
| [57] | 1C8-6A Fab/OKT3 scFv hIgG1 | SEQ ID NO: 446 + SEQ ID NO: 437 + SEQ ID NO: 454 |
| [58] | 1C8-EH Fab/OKT3 scFv hIgG1 | SEQ ID NO: 447 + SEQ ID NO: 439 + SEQ ID NO: 454 |
| [59] | 1C8-402 Fab/OKT3 scFv hIgG1 | SEQ ID NO: 520 + SEQ ID NO: 505 + SEQ ID NO: 454 |
| [60] | 1C8-403 Fab/OKT3 scFv hIgG1 | SEQ ID NO: 520 + SEQ ID NO: 506 + SEQ ID NO: 454 |
| [61] | 1C8-507 Fab/OKT3 scFv hIgG1 | SEQ ID NO: 521 + SEQ ID NO: 508 + SEQ ID NO: 454 |
| [62] | 1C8-610 Fab/OKT3 scFv hIgG1 | SEQ ID NO: 522 + SEQ ID NO: 510 + SEQ ID NO: 454 |
| [63] | 1C8-6A3 Fab/OKT3 scFv hIgG1 | SEQ ID NO: 523 + SEQ ID NO: 512 + SEQ ID NO: 454 |
| [64] | 1C8-25 Fab/OKT3 scFv hIgG1 | SEQ ID NO: 524 + SEQ ID NO: 514 + SEQ ID NO: 454 |
| [65] | 1C8-27 Fab/OKT3 scFv hIgG1 | SEQ ID NO: 524 + SEQ ID NO: 515 + SEQ ID NO: 454 |
| [66] | 538-SP5-B10 Fab/SP34 scFv hIgG1 | SEQ ID NO: 320 + SEQ ID NO: 303 + SEQ ID NO: 553 |

-continued

| Antibody | Name | Polypeptides |
|---|---|---|
| [67] | 539-SP1-C8 Fab/SP34 scFv hIgG1 | SEQ ID NO: 321 + SEQ ID NO: 305 + SEQ ID NO: 553 |
| [68] | 539-SP2-H3 Fab/SP34 scFv hIgG1 | SEQ ID NO: 322 + SEQ ID NO: 307 + SEQ ID NO: 553 |
| [69] | 539-SP5-D7 Fab/SP34 scFv hIgG1 | SEQ ID NO: 323 + SEQ ID NO: 309 + SEQ ID NO: 553 |
| [70] | 539-SP7-F4 Fab/SP34 scFv hIgG1 | SEQ ID NO: 324 + SEQ ID NO: 311 + SEQ ID NO: 553 |
| [71] | 552-LN1-E9 Fab/SP34 scFv hIgG1 | SEQ ID NO: 325 + SEQ ID NO: 313 + SEQ ID NO: 553 |
| [72] | 552-LN1-F4 Fab/SP34 scFv hIgG1 | SEQ ID NO: 326 + SEQ ID NO: 315 + SEQ ID NO: 553 |
| [73] | 552-LN2-E6 Fab/SP34 scFv hIgG1 | SEQ ID NO: 327 + SEQ ID NO: 317 + SEQ ID NO: 553 |
| [74] | 552-LN2-F8 Fab/SP34 scFv hIgG1 | SEQ ID NO: 328 + SEQ ID NO: 319 + SEQ ID NO: 553 |
| [75] | 1E9-4H Fab/SP34 scFv hIgG1 | SEQ ID NO: 440 + SEQ ID NO: 425 + SEQ ID NO: 553 |
| [76] | 1E9-QE Fab/SP34 scFv hIgG1 | SEQ ID NO: 441 + SEQ ID NO: 427 + SEQ ID NO: 553 |
| [77] | 2F8-2Q Fab/SP34 scFv hIgG1 | SEQ ID NO: 442 + SEQ ID NO: 429 + SEQ ID NO: 553 |
| [78] | 2F8-5U Fab/SP34 scFv hIgG1 | SEQ ID NO: 443 + SEQ ID NO: 431 + SEQ ID NO: 553 |
| [79] | 5B10-4Y Fab/SP34 scFv hIgG1 | SEQ ID NO: 444 + SEQ ID NO: 433 + SEQ ID NO: 553 |
| [80] | 5B10-5I Fab/SP34 scFv hIgG1 | SEQ ID NO: 445 + SEQ ID NO: 435 + SEQ ID NO: 553 |
| [81] | 1C8-6A Fab/SP34 scFv hIgG1 | SEQ ID NO: 446 + SEQ ID NO: 437 + SEQ ID NO: 553 |
| [82] | 1C8-EH Fab/SP34 scFv hIgG1 | SEQ ID NO: 447 + SEQ ID NO: 439 + SEQ ID NO: 553 |
| [83] | 1C8-402 Fab/SP34 scFv hIgG1 | SEQ ID NO: 520 + SEQ ID NO: 505 + SEQ ID NO: 553 |
| [84] | 1C8-403 Fab/SP34 scFv hIgG1 | SEQ ID NO: 520 + SEQ ID NO: 506 + SEQ ID NO: 553 |
| [85] | 1C8-507 Fab/SP34 scFv hIgG1 | SEQ ID NO: 521 + SEQ ID NO: 508 + SEQ ID NO: 553 |
| [86] | 1C8-610 Fab/SP34 scFv hIgG1 | SEQ ID NO: 522 + SEQ ID NO: 510 + SEQ ID NO: 553 |
| [87] | 1C8-6A3 Fab/SP34 scFv hIgG1 | SEQ ID NO: 523 + SEQ ID NO: 512 + SEQ ID NO: 553 |
| [88] | 1C8-25 Fab/SP34 scFv hIgG1 | SEQ ID NO: 524 + SEQ ID NO: 514 + SEQ ID NO: 553 |
| [89] | 1C8-27 Fab/SP34 scFv hIgG1 | SEQ ID NO: 524 + SEQ ID NO: 515 + SEQ ID NO: 553 |

The resulting bispecific antigen-binding molecules comprise a BCMA-specific Fab, and a CD3-specific scFv, in human IgG1 format.

Example 11: Analysis of Induction of T Cell-Mediated Killing of Cells Expressing BCMA and/or TACI The inventors investigated the ability of different BCMAxCD3 bispecific antibodies to potentiate T cell-mediated killing of cancer cells expressing BCMA and TACT.

Briefly, populations of T cells were isolated from human PBMCs collected from two different donors using the Pan T Cell Isolation Kit (Miltenyi Biotec). The isolated T cells were cultured overnight in cell culture medium comprising RPMI supplemented with 2% heat-inactivated human AB serum, and 20 IU/ml IL-2 (Peprotech).

H929 cells (BCMA++, TACI+) or SK-MEL-1 (BCMA−, TACI−) cells were labelled with 0.5 mM CellTrace CFSE for 8 min at 37° C. $1\times10^4$ CFSE-labelled H929 or SK-MEL-1 cells were subsequently transferred to wells of U-bottom 96 well plates. $5\times10^4$ T cells were then added to the wells (except for wells which were to serve as 'spontaneous lysis' controls), and serial dilutions of the following antibodies were added to the co-cultures: [42], [43] or [47] of Example 10; the BCMAxCD3 bispecific antibody from BPS Bioscience (Cat. #100689; as a positive control); and human IgG Isotype control (Biolegend Cat. #403502; as a negative control). The cells were co-cultured in the presence of the antibodies at 37° C., 5% $CO_2$ for 48 h, and then pelleted by centrifugation, and resuspended in PBS with 5 mM EDTA, containing DAPI at a 1:200 dilution. In order to obtain maximal lysis control readings, CFSE-labelled H929 or SK-MEL-1 cells were incubated with 1% triton-X-100 for 10 min at room temperature. The percentage of DAPI+ cells within the CFSE+ population was determined by flow cytometry. The percentage of cytotoxicity was calculated as follows: % cytotoxicity=(sample lysis−spontaneous lysis)/(maximal lysis−spontaneous lysis)×100.

Figure 19A:
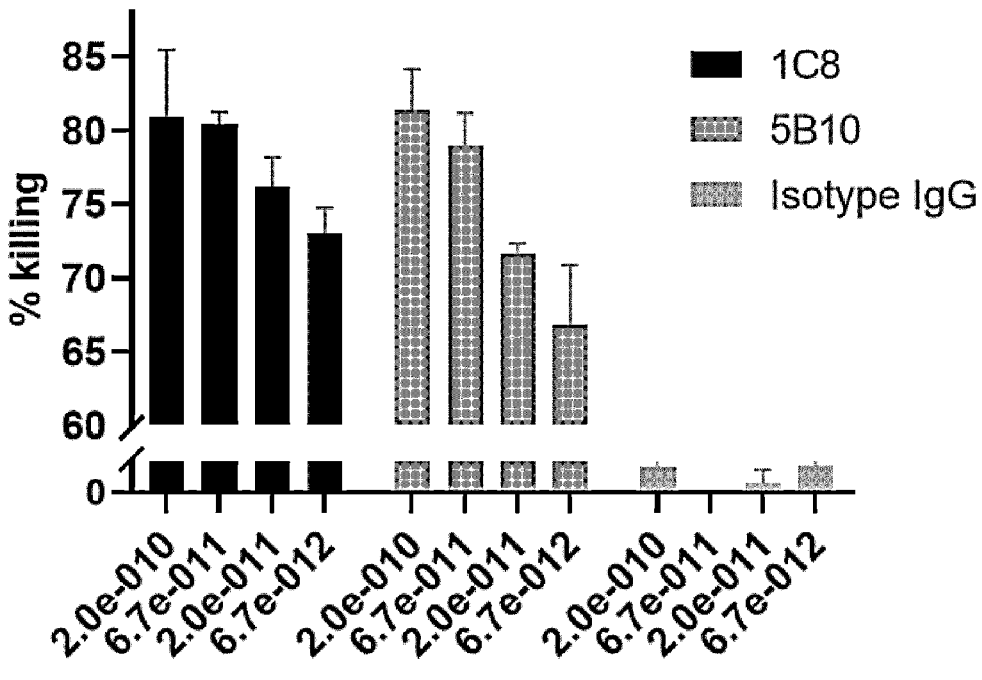
FIGS. 19A and 19B. Bar chart showing induction T cell-mediated killing of (19A) H929 cells, and (19B) SK-MEL-1 cells by bispecific anti-BCMA x anti-CD3 antibodies comprising a BCMA-binding arm based on 539-SP1-C8 (1C8), 538-SP5-B10 (5B10), or 552-LN1-E9 (1E9), the bispecific anti-BCMA x anti-CD3 antibody from BPS Bioscience (Cat. #100689), or isotype-matched IgG control (IgG), as determined using the assay described in Example 10.
Figure 19A:
Figure 19B:
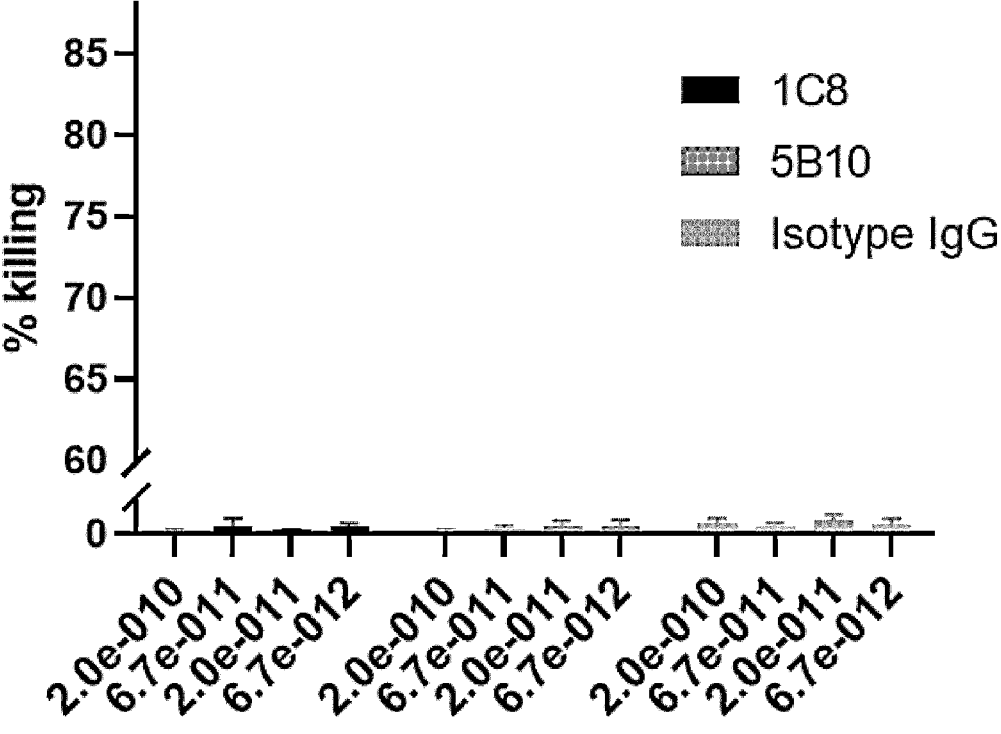

The results are shown in FIGS. 19A and 19B. The bispecific BCMAxCD3 molecules were found to induce T cell-mediated lysis of H929 cells (which express BCMA and TACI), but not SK-MEL-1 cells (which are BCMA and TACI-negative).

In further experiments, bispecific anti-BCMA x anti-CD3 antibodies prepared using the humanised VH and VL region sequences for 552-LN1-E9, 552-LN2-F8, 538-SP5-B10 and 539-SP1-C8 described at Example 10 are analysed in order to determine their ability to direct T cell-mediated effector activity against H929 and SK-MEL-1 cells. The bispecific anti-BCMA x anti-CD3 antibodies prepared using the humanised anti-BCMA antibody sequences are found to retain the ability to potentiate T cell-mediated killing of cancer cells expressing BCMA and TACI displayed by bispecific molecules having a BCMA-binding moiety based on their parental clone.

Example 12: Antigen-Binding Molecules Cross-Reactive for BCMA and TACI—Conclusions The inventors have successfully immuno-engineered a B cell response to an AI-predicted, three-dimensional epitope conserved between BCMA and TACI, yielding antibodies capable of:

(i) binding to both BCMA and TACI, and cells expressing these target antigens, with high affinity and specificity;

(ii) inducing ADCC against BCMA− and/or TACI-expressing cells; and (iii) being employed as a BCMA− and/or TACI-binding arm in T cell engager molecules which are able to induce T cell-mediated killing of cells expressing BCMA and/or TACT.

Such BCMA− and/or TACI-binding molecules have the potential to extend anti-BCMA based therapy in the treatment of cancers such as multiple myeloma, providing a 'second string to the bow' that can overcome the resistance caused by BCMA antigen loss.

Example 13: Further Humanised Anti-BCMA Antibodies

13.1 Further Humanised Anti-BCMA Antibodies

Further Humanised versions of clone 539-SP1-C8 were designed.

| Parental clone | Humanised antibody | VH/VL sequences |
|---|---|---|
| 539-SP1-C8 | 1C8-402 | VH = SEQ ID NO: 455<br>VL = SEQ ID NO: 459 |
| | 1C8-403 | VH = SEQ ID NO: 455<br>VL = SEQ ID NO: 463 |
| | 1C8-507 | VH = SEQ ID NO: 465<br>VL = SEQ ID NO: 468 |
| | 1C8-610 | VH = SEQ ID NO: 471<br>VL = SEQ ID NO: 4740 |
| | 1C8-6A3 | VH = SEQ ID NO: 477<br>VL = SEQ ID NO: 478 |
| | 1C8-25 | VH = SEQ ID NO: 479<br>VL = SEQ ID NO: 483 |
| | 1C8-27 | VH = SEQ ID NO: 479<br>VL = SEQ ID NO: 487 |

The humanised anti-BCMA antibodies were produced and purified in human IgG1 format, as described in Example 2.

| Antibody | Name | Heavy chain | Light chain |
|---|---|---|---|
| [90] | 1C8-402 hIgG1 | SEQ ID NO: 504 | SEQ ID NO: 505 |
| [91] | 1C8-403 hIgG1 | SEQ ID NO: 504 | SEQ ID NO: 506 |
| [92] | 1C8-507 hIgG1 | SEQ ID NO: 507 | SEQ ID NO: 508 |
| [93] | 1C8-610 hIgG1 | SEQ ID NO: 509 | SEQ ID NO: 510 |
| [94] | 1C8-6A3 hIgG1 | SEQ ID NO: 511 | SEQ ID NO: 512 |
| [95] | 1C8-25 hIgG1 | SEQ ID NO: 513 | SEQ ID NO: 514 |
| [96] | 1C8-27 hIgG1 | SEQ ID NO: 513 | SEQ ID NO: 515 |

13.2 Characterisation of the Further Humanised Anti-BCMA Antibodies

ELISAs were performed in order to determine the binding specificity of humanised anti-BCMA antibodies [90] to [96] of Example 13.1 (referred to respectively as hu1C8-402, hu1C8-403, hu1C8-507, hu1C8-610, hu1C8, 1C8p-27 and 1C8-p25 in FIGS. 25 to 27).

His-tagged target antigen proteins were obtained from Sino Biological and Acro Biosystems: Human BCMA-His (Sino Biological, 10620-H08H), Human TACI-His (Sino Biological, 11937-H08H), Cyno BCMA-His (Acro Biosystems, BCA-C52H7), Cyno TACI-His (Sino Biological, 90976-C08H), Human HERS-His (Sino Biological, 10201-H08H). Human IgG Isotype control antibody (ThermoFisher Scientific Catalog #31154), and anti-BCMA antibody J6M0 were included in the experiments as a control conditions.

ELISAs were performed according to standard protocols. Briefly, wells of 384-well plates (Nunc, Denmark) were coated with 1 µg/ml of His-tagged target antigen in phosphate-buffered saline (PBS) for 16 h at 4° C. Plates were washed three times with 1×PBS containing 0.05% Tween 20, and subsequently blocked for 1 h with 1% BSA in 1×PBS at room temperature. Plates were washed with 1×PBS containing 0.05% Tween 20, and subsequently the purified antibodies were applied to wells in an 11 point, 10-fold dilution series (highest concentration=3 µg/ml), and incubated at room temperature for 2 h. Plates were then washed three times with 1×PBS containing 0.05% Tween 20, and subsequently incubated with a HRP-conjugated anti-human IgG1 antibody at a 1:7000 dilution in PBS for 1 h at room temperature. After three further washes with 1×PBS containing 0.05% Tween 20, plates were developed with colorimetric detection substrate 3,3', 5,5'-tetramethylbenzidine (ThermoFisher Scientific Catalog #34022). The reaction was stopped with 2M H2SO4, and OD was measured at 450 nM using a BioTek PowerWave HT.

Dose-response curves were fitted and EC50 values for binding to the relevant target proteins were derived from the dose-response curves, where possible.

The results are shown in FIGS. 25A to 25F. Antibodies [90] to [94] were found to bind to human BCMA, human TACI, cynomolgus macaque BCMA and cynomolgus macaque TACI with high affinity, and did not bind to human HER3.

In further experiments, antibodies [90] to [94] of Example 13.1 were analysed for their ability to bind to human cells expressing BCMA and/or TACI, by flow cytometry.

H929 Cells (BCMA+):

80,000 cells were added to wells of 96-well polypropylene plates, and blocked with Human TruStain FcX (BioLegend Cat #22302) for 10 min at room temperature. The purified antibodies were applied to wells in an 10 point, 3-fold dilution series (highest concentration=30 µg/ml) in FACS buffer (PBS+0.5% BSA+2 mM EDTA), and incubated at 4° C. for 1 h. The cells were washed three times with FACS buffer and resuspended in FITC-conjugated anti-human IgG (LifeTech, Cat. #H10120) diluted 1:500 in FACS buffer, for 45 min at 4° C. Cells were washed three times with FACS buffer, and resuspended in 200 µL of FACS buffer containing DAPI (1:200 dilution) for flow cytometric analysis using MACSQuant™ X (Miltenyi Biotec, Germany).

RPM 8226 Cells (BCMA+, TACI+):

Cells were blocked with Human TruStain FcX (BioLegend Cat #22302) for 10 min at room temperature. Cells were stained with DAPI resuspension in FACS buffer containing DAPI (1:200 dilution), and subsequently washed twice with FACS buffer. Cells were then fixed using fixative solution (Invitrogen Catalog #FB002) for 15 min at room temperature. Cells were subsequently washed with 1×PBS, and then 80,000 cells were added to wells of 96-well polypropylene plates. The purified antibodies were applied to wells in an 10 point, 3-fold dilution series (highest concentration=30 µg/ml) in FACS buffer (PBS+0.5% BSA+2 mM EDTA), and incubated at 4° C. for 1 h. The cells were washed three times with FACS buffer and resuspended in FITC-conjugated anti-human IgG (LifeTech, Cat. #H10120) diluted 1:500 in FACS buffer, for 45 min at 4° C. Cells were washed three times with FACS buffer, and resuspended in 200 µL of FACS buffer for flow cytometric analysis using MACSQuant™ X (Miltenyi Biotec, Germany).

After acquisition, all raw data were analysed using Flowlogic software. Cells were gated using forward and side scatter profile and further gated for negative staining by DAPI (DAPI staining solution, Miltenyi Biotec) to include live cells only. This population constitutes the parent population from which the percentage of positive cells was determined.

Figure 26A:
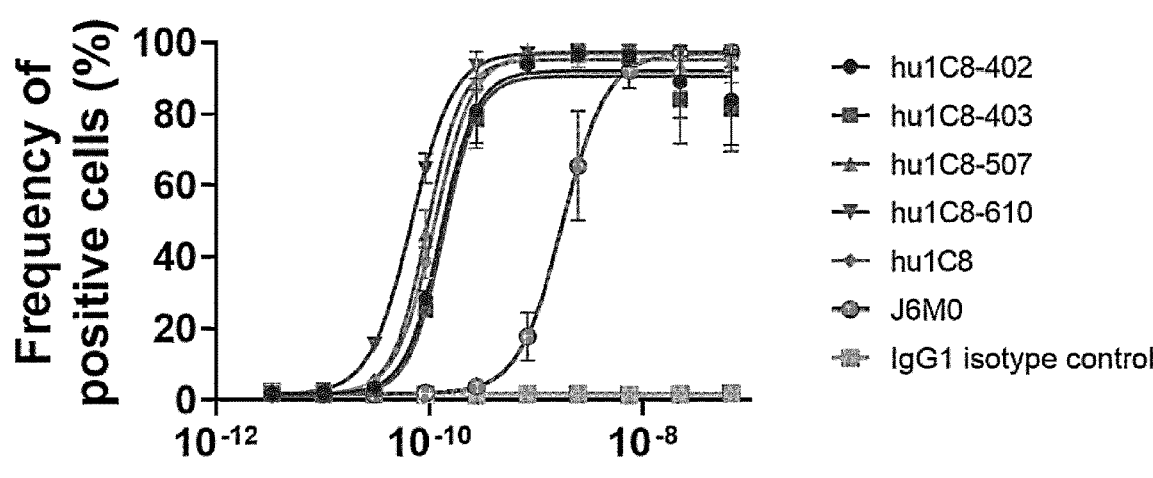
Figure 26B:
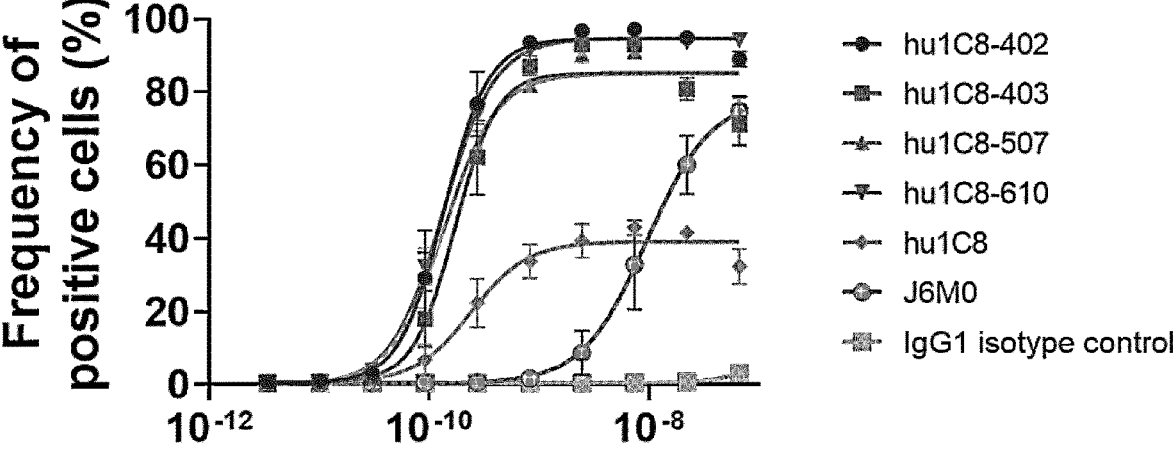

The results are shown in FIGS. 26A and 26B. Antibodies [90] to [94] were found to bind to cells expressing human BCMA and/or human TACI.

In further experiments, antibodies [90] to [96] of Example 13.1 were analysed by Biolayer Interferometry in order to determine the kinetics of binding to human BCMA, cynomolgous macaque BCMA, and human TACI.

BLI experiments were performed using a CaptureGATOR (ProbeLife) system, using HFC biosensor (Lot No. 2010024 T7) for capturing antigens.

Biosensors were hydrated in Q buffer (PBS (10 mM PH7.4)+0.02% Tween 20+0.2% BSA), followed by buffer baseline for 60 s and loading of the different antibodies at a concentration of 30 nM onto the biosensor tips for 120 s. The tips were then washed briefly for 60 s with Q buffer to remove unbound antigen for obtaining a second buffer baseline (60 s). The association phase was established by applying His-tagged human BCMA (Acro Biosystems, BCA-H522y), His-tagged cynomolgous macaque BCMA (Acro Biosystems, BCA-C52H7), His-tagged human TACI (Sino Biological, 11937-H08H) or His-tagged cynomolgous macaque TACI (Sino Biological, 90976-C08H) at concentrations ranging from 300 nM to 37.5 nM, diluted in Q buffer, for 120 s. The association phase was followed by a dissociation phase (Q buffer alone) for 180 s. All runs were performed at room temperature. Biosensors were regenerated using regeneration buffer (deionised water+10 mM glycine+150 nM NaCl (pH 2.0)) after the assay (50 s). Binding affinity between the antibodies and immobilized antigens was determined by analysing the binding kinetic curves. All sensorgrams were reference subtracted and globally fitted into a 1:1 model which analysed the binding curves at different concentrations of antigens and generated kinetic constants (KD/Ka/Kd) for the globally fitted data. All the binding curves were subjected to step correction which corrects the misalignment between association and dissociation steps, and only curves with $R^2$ values greater than 0.9 were used for the determination of $K_D$ values.

The results are shown in FIG. 27. The antibodies were found to bind to human and cynomolgous BCMA and TACI with high affinity.

Example 14: Analysis of the Epitope of BCMA to which 539-SP1-C8 and Humanised, 1C8-Derived Antibodies Bind The inventors investigated the region of BCMA to which 539-SP1-C8 humanised, 1C8-derived antibodies bind by hydrogen-deuterium exchange mass spectrometry (HDXMS) analysis.

Epitope mapping by HDXMS was conducted using His-tagged human BCMA (residues 1-54, Acro Biosystems, Cat. #BCA-H522y) and the antibody formed by polypeptides having the amino acid sequences of SEQ ID NO:516+SEQ ID NO:505, which is 1C8-402 in human IgG1 format, comprising the Fc-silencing L243A/L235A ('LALA') substitutions in the CH2 region (referred to herein as '1C8-402 hIgG1 (LALA)').

In order to form BCMA:1C8-402 hIgG1 (LALA) complexes, BCMA and 1C8-402 hIgG1 (LALA) were mixed in 1:1 molar ratio. The mixed antigen-antibody complexes were incubated for 15 min at 25° C. prior to deuterium labelling.

For deuterium labelling, free BCMA and BCMA:1C8-402 hIgG1 (LALA) complexes were diluted in deuterated PBS with a final deuterium oxide (D2O) concentration at 90%. Labelling reactions were carried out at 25° C. for 1 min, 5 min, 10 min and 100 min time points.

Samples were then subjected to pepsin proteolytic cleavage followed by separation on an ACQUITY C18 column (1.0×100 mm) by nanoACQUITY UPLC (Waters, Milford, MA) and detection by Synapt G2-Si mass spectrometer (Waters, Manchester, UK), operated in HDMSE mode. Peptide identification and deuterium uptake monitoring were respectively performed using Protein Lynx Global Server 3.0.1 and DynamX 3.0 (Waters). Deuterium uptake for the peptides were calculated as differences in masses of the centroids of deuterated and undeuterated samples (Wales et al., Methods Mol Biology (2013) 1007: 263-288) and reported as an average of triplicate measurements (Masson et al., Nat Methods (2019) 16: 595-602).

Figure 28:
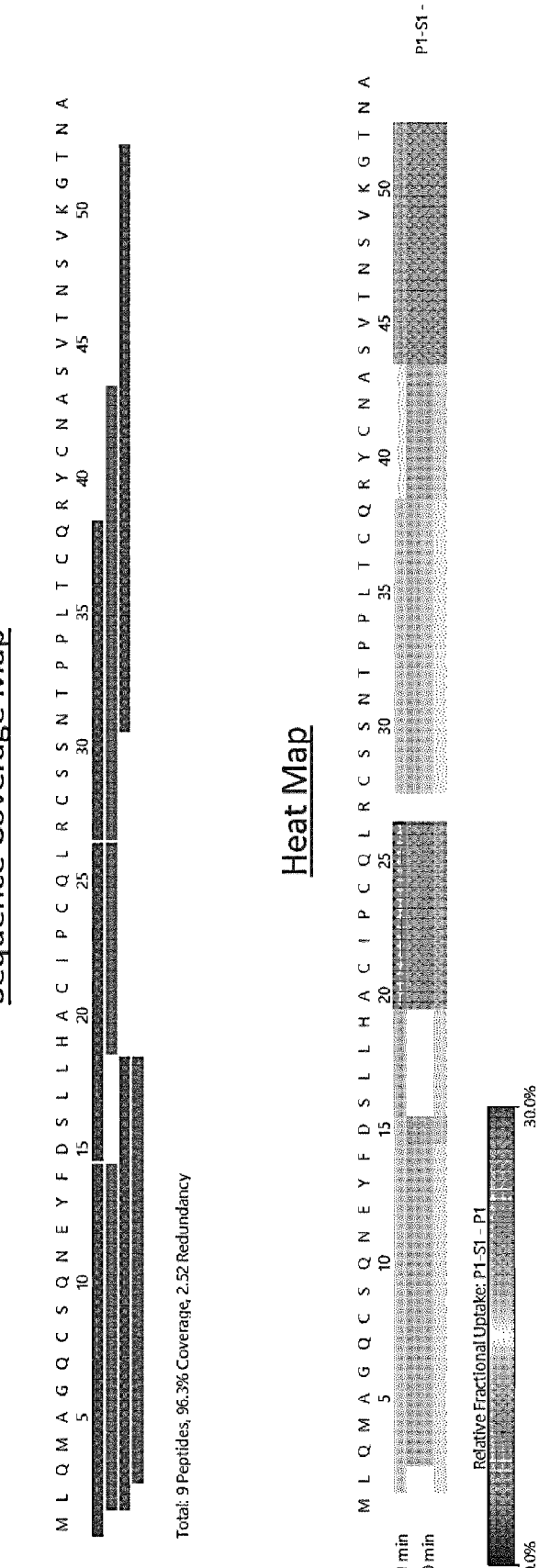
FIG. 28. Schematics showing the results of analysis of binding of anti-BMCA/TACI antibody 1C8 402 to human BCMA, as determined by hydrogen-deuterium exchange mass spectrometry (HDXMS) analysis. Sequence coverage map showing the regions of BCMA covered by the 9 peptides employed in the analysis, and heat map showing relative fractional uptake of deuterium by BCMA alone (P1) and BCMA:1C8-402 hIgG1 (LALA) complexes (P1-S1).

The results of the HDXMS analysis of interaction between BCMA and 1C8-402 hIgG1 (LALA) are shown in FIG. 28. Comparison of deuterium exchange between 1C8-402 hIgG1 (LALA) bound BCMA and free BCMA showed a significant decrease in deuterium uptake at 2 peptides spanning residues 2-18 of BCMA (SEQ ID NO:557) and residues 19-26 of BCMA (SEQ ID NO:556) of BCMA, indicating that these regions were protected against deuterium exchange via protein-protein interaction. The reduction in deuterium exchange observed at an early timepoint (1 min) for residues 19-26 (SEQ ID NO:556) suggested that this is the primary epitope. Large-magnitude reduction of deuterium exchange at later timepoints (5 and 10 min) observed for residues 2-18 (SEQ ID NO:557) may represent a weaker binding or a secondary binding event subsequent to, or co-operative with, binding of the primary epitope. This secondary binding was likely to happen at the residues 15-18 (SEQ ID NO:558) as no difference in deuterium uptake was observed for overlapping peptide covering residues 2-14. Taken together, the HDXMS data indicate that the residues 15-26 of BCMA (SEQ ID NO:555) form the BCMA epitope of 1C8-402 hIgG1 (LALA). Mapping of these identified peptides to the BCMA structure confirmed that the determined epitope overlapped with the predicted target region.

701

The invention claimed is:

1. An antigen-binding molecule, optionally isolated, which binds to B-cell maturation antigen (BCMA), wherein the antigen-binding molecule comprises:
  (a)
    (i) a heavy chain variable (VH) region incorporating the following CDRs:
      HC-CDR1 having the amino acid sequence of SEQ ID NO:99
      HC-CDR2 having the amino acid sequence of SEQ ID NO:100
      HC-CDR3 having the amino acid sequence of SEQ ID NO: 101; and
    (ii) a light chain variable (VL) region incorporating the following CDRs:
      LC-CDR1 having the amino acid sequence of SEQ ID NO: 106
      LC-CDR2 having the amino acid sequence of SEQ ID NO: 107
      LC-CDR3 having the amino acid sequence of SEQ ID NO: 108; or
  (b)
    (i) a heavy chain variable (VH) region incorporating the following CDRs:
      HC-CDR1 having the amino acid sequence of SEQ NO: 99
      HC-CDR2 having the amino acid sequence of SEQ NO: 347
      HC-CDR3 having the amino acid sequence of SEQ NO: 101; and
    (ii) a light chain variable (VL) region incorporating the following CDRs:
      LC-CDR1 having the amino acid sequence of SEQ NO: 106
      LC-CDR2 having the amino acid sequence of SEQ NO: 107
      LC-CDR3 having the amino acid sequence of SEQ NO: 108.

2. The antigen-binding molecule according to claim 1, wherein the antigen-binding molecule comprises:
  (i) a VH region comprising an amino acid sequence having at least 70% sequence identity to the amino acid sequence of SEQ ID NO:338; and
    a VL region comprising an amino acid sequence having at least 70% sequence identity to the amino acid sequence of SEQ ID NO:341;
  or
  (ii) a VH region comprising an amino acid sequence having at least 70% sequence identity to the amino acid sequence of SEQ ID NO:346; and
    a VL region comprising an amino acid sequence having at least 70% sequence identity to the amino acid sequence of SEQ ID NO:349;
  or
  (iii) a VH region comprising an amino acid sequence having at least 70% sequence identity to the amino acid sequence of SEQ ID NO:98; and
    a VL region comprising an amino acid sequence having at least 70% sequence identity to the amino acid sequence of SEQ ID NO: 105.

3. The antigen-binding molecule according to claim 1, wherein the antigen-binding molecule binds to human BCMA and mouse BCMA.

4. The antigen-binding molecule according to claim 1, wherein the antigen-binding molecule is a multispecific antigen-binding molecule, and wherein the multispecific

702 antigen-binding molecule further comprises an antigen-binding domain which binds to an antigen other than BCMA.

5. The multispecific antigen-binding molecule according to claim 4, wherein the antigen other than BCMA is CD47.

6. The multispecific antigen-binding molecule according to claim 4, wherein the multispecific antigen-binding molecule comprises an antigen-binding domain which binds to CD47 and inhibits interaction between CD47 and SIRPα; optionally wherein the multispecific antigen-binding molecule is capable of increasing phagocytosis of BCMA-expressing cells and/or CD47-expressing cells.

7. The multispecific antigen-binding molecule according to claim 4, wherein the antigen other than BCMA is a CD3 polypeptide.

8. An antigen-binding molecule, optionally isolated, which binds to B-cell maturation antigen (BCMA), wherein the antigen-binding molecule comprises:
  (a)
    (i) a heavy chain variable (VH) region incorporating the following CDRs:
      HC-CDR1 having the amino acid sequence of SEQ ID NO: 128
      HC-CDR2 having the amino acid sequence of SEQ ID NO:347
      HC-CDR3 having the amino acid sequence of SEQ ID NO: 129; and
    (ii) a light chain variable (VL) region incorporating the following CDRs:
      LC-CDR1 having the amino acid sequence of SEQ ID NO: 125
      LC-CDR2 having the amino acid sequence of SEQ ID NO: 120
      LC-CDR3 having the amino acid sequence of SEQ ID NO: 108; or
  (b)
    (i) a heavy chain variable (VH) region incorporating the following CDRs:
      HC-CDR1 having the amino acid sequence of SEQ NO: 128
      HC-CDR2 having the amino acid sequence of SEQ NO: 100
      HC-CDR3 having the amino acid sequence of SEQ NO: 129; and
    (ii) a light chain variable (VL) region incorporating the following CDRs:
      LC-CDR1 having the amino acid sequence of SEQ NO: 125
      LC-CDR2 having the amino acid sequence of SEQ NO: 120
      LC-CDR3 having the amino acid sequence of SEQ NO: 108.

9. The antigen-binding molecule according to claim 8, wherein the antigen-binding molecule comprises:
  a VH region comprising an amino acid sequence having at least 70% sequence identity to the amino acid sequence of SEQ ID NO:353; and
    a VL region comprising an amino acid sequence having at least 70% sequence identity to the amino acid sequence of SEQ ID NO:357;
  or
  (ii) a VH region comprising an amino acid sequence having at least 70% sequence identity to the amino acid sequence of SEQ ID NO:361; and
    a VL region comprising an amino acid sequence having at least 70% sequence identity to the amino acid sequence of SEQ ID NO:365;

or (iii) a VH region comprising an amino acid sequence having at least 70% sequence identity to the amino acid sequence of SEQ ID NO: 127; and a VL region comprising an amino acid sequence having at least 70% sequence identity to the amino acid sequence of SEQ ID NO:133.

10. The antigen-binding molecule according to claim 8, wherein the antigen-binding molecule binds to human BCMA and mouse BCMA.

11. The antigen-binding molecule according to claim 8, wherein the antigen-binding molecule is a multispecific antigen-binding molecule, and wherein the multispecific antigen-binding molecule further comprises an antigen-binding domain which binds to an antigen other than BCMA.

12. The multispecific antigen-binding molecule according to claim 11, wherein the antigen other than BCMA is CD47.

13. The multispecific antigen-binding molecule according to claim 11, wherein the multispecific antigen-binding molecule comprises an antigen-binding domain which binds to CD47 and inhibits interaction between CD47 and SIRPα.

14. The multispecific antigen-binding molecule according to claim 13, wherein the multispecific antigen-binding molecule is capable of increasing phagocytosis of BCMA-expressing cells and/or CD47-expressing cells.

15. The multispecific antigen-binding molecule according to claim 11, wherein the antigen other than BCMA is a CD3 polypeptide.

16. A nucleic acid, or a plurality of nucleic acids, optionally isolated, encoding an antigen-binding molecule which binds to B-cell maturation antigen (BCMA), wherein the antigen-binding molecule comprises:

(a)

(i) a heavy chain variable (VH) region incorporating the following CDRs:

HC-CDR1 having the amino acid sequence of SEQ ID NO:99

HC-CDR2 having the amino acid sequence of SEQ ID NO: 100

HC-CDR3 having the amino acid sequence of SEQ ID NO: 101; and (ii) a light chain variable (VL) region incorporating the following CDRs:

LC-CDR1 having the amino acid sequence of SEQ ID NO: 106

LC-CDR2 having the amino acid sequence of SEQ ID NO: 107

LC-CDR3 having the amino acid sequence of SEQ ID NO: 108; or (b)

(i) a heavy chain variable (VH) region incorporating the following CDRs:

HC-CDR1 having the amino acid sequence of SEQ NO: 99

HC-CDR2 having the amino acid sequence of SEQ NO: 347

HC-CDR3 having the amino acid sequence of SEQ NO: 101; and (ii) a light chain variable (VL) region incorporating the following CDRs:

LC-CDR1 having the amino acid sequence of SEQ NO: 106

LC-CDR2 having the amino acid sequence of SEQ NO: 107

LC-CDR3 having the amino acid sequence of SEQ NO: 108.

17. A method of treating cancer comprising administering to a subject in need thereof a therapeutically effective amount of an antigen-binding molecule according to claim 1.

18. The method according to claim 17, wherein the cancer is selected from: a hematologic malignancy, a myeloid hematologic malignancy, a lymphoblastic hematologic malignancy, a B cell malignancy, multiple myeloma (MM), myelodysplastic syndrome (MDS), acute myeloid leukemia (AML), chronic myeloid leukemia (CML), acute lymphoblastic leukemia (ALL), lymphocytic leukemia, lymphoma, B cell lymphoma, Hodgkin's lymphoma (HL), non-Hodgkin's lymphoma (NHL), follicular lymphoma (FL), mantle cell lymphoma (MCL), Burkitt lymphoma, bladder cancer, brain cancer, glioblastoma, ovarian cancer, breast cancer, colon cancer, liver cancer, hepatocellular carcinoma, prostate cancer, lung cancer, non-small cell lung cancer (NSCLC), skin cancer, and melanoma.

* * * * *

```
                        SEQUENCE LISTING

<160> NUMBER OF SEQ ID NOS: 558

<210> SEQ ID NO 1
<211> LENGTH: 184
<212> TYPE: PRT
<213> ORGANISM: Homo sapiens

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45
```

-continued

```
Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180

<210> SEQ ID NO 2
<211> LENGTH: 135
<212> TYPE: PRT
<213> ORGANISM: Homo sapiens

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Arg Ser Gly Leu Leu
                35                  40                  45

Gly Met Ala Asn Ile Asp Leu Glu Lys Ser Arg Thr Gly Asp Glu Ile
    50                  55                  60

Ile Leu Pro Arg Gly Leu Glu Tyr Thr Val Glu Glu Cys Thr Cys Glu
65                  70                  75                  80

Asp Cys Ile Lys Ser Lys Pro Lys Val Asp Ser Asp His Cys Phe Pro
                85                  90                  95

Leu Pro Ala Met Glu Glu Gly Ala Thr Ile Leu Val Thr Thr Lys Thr
                100                 105                 110

Asn Asp Tyr Cys Lys Ser Leu Pro Ala Ala Leu Ser Ala Thr Glu Ile
        115                 120                 125

Glu Lys Ser Ile Ser Ala Arg
    130                 135

<210> SEQ ID NO 3
<211> LENGTH: 54
<212> TYPE: PRT
<213> ORGANISM: Homo sapiens

<400> SEQUENCE: 3

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
        35                  40                  45
```

-continued

```
Val Lys Gly Thr Asn Ala
    50

<210> SEQ ID NO 4
<211> LENGTH: 35
<212> TYPE: PRT
<213> ORGANISM: Homo sapiens

<400> SEQUENCE: 4

Gln Cys Ser Gln Asn Glu Tyr Phe Asp Ser Leu Leu His Ala Cys Ile
1               5                   10                  15

Pro Cys Gln Leu Arg Cys Ser Ser Asn Thr Pro Pro Leu Thr Cys Gln
            20                  25                  30

Arg Tyr Cys
        35

<210> SEQ ID NO 5
<211> LENGTH: 23
<212> TYPE: PRT
<213> ORGANISM: Homo sapiens

<400> SEQUENCE: 5

Ile Leu Trp Thr Cys Leu Gly Leu Ser Leu Ile Ile Ser Leu Ala Val
1               5                   10                  15

Phe Val Leu Met Phe Leu Leu
            20

<210> SEQ ID NO 6
<211> LENGTH: 107
<212> TYPE: PRT
<213> ORGANISM: Homo sapiens

<400> SEQUENCE: 6

Arg Lys Ile Asn Ser Glu Pro Leu Lys Asp Glu Phe Lys Asn Thr Gly
1               5                   10                  15

Ser Gly Leu Leu Gly Met Ala Asn Ile Asp Leu Glu Lys Ser Arg Thr
            20                  25                  30

Gly Asp Glu Ile Ile Leu Pro Arg Gly Leu Glu Tyr Thr Val Glu Glu
        35                  40                  45

Cys Thr Cys Glu Asp Cys Ile Lys Ser Lys Pro Lys Val Asp Ser Asp
    50                  55                  60

His Cys Phe Pro Leu Pro Ala Met Glu Glu Gly Ala Thr Ile Leu Val
65                  70                  75                  80

Thr Thr Lys Thr Asn Asp Tyr Cys Lys Ser Leu Pro Ala Ala Leu Ser
                85                  90                  95

Ala Thr Glu Ile Glu Lys Ser Ile Ser Ala Arg
            100                 105

<210> SEQ ID NO 7
<211> LENGTH: 25
<212> TYPE: PRT
<213> ORGANISM: Homo sapiens

<400> SEQUENCE: 7

Leu Glu Tyr Thr Val Glu Glu Cys Thr Cys Glu Asp Cys Ile Lys Ser
1               5                   10                  15

Lys Pro Lys Val Asp Ser Asp His Cys
            20                  25

<210> SEQ ID NO 8
```

<211> LENGTH: 183
<212> TYPE: PRT
<213> ORGANISM: Cynomorium macaque

<400> SEQUENCE: 8

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
            35                  40                  45

Lys Gly Met Asn Ala Ile Leu Trp Thr Cys Leu Gly Leu Ser Leu Ile
        50                  55                  60

Ile Ser Leu Ala Val Phe Val Leu Thr Phe Leu Leu Arg Lys Met Ser
65                  70                  75                  80

Ser Glu Pro Leu Lys Asp Glu Phe Lys Asn Thr Gly Ser Gly Leu Leu
                85                  90                  95

Gly Met Ala Asn Ile Asp Leu Glu Lys Gly Arg Thr Gly Asp Glu Ile
            100                 105                 110

Val Leu Pro Arg Gly Leu Glu Tyr Thr Val Glu Glu Cys Thr Cys Glu
            115                 120                 125

Asp Cys Ile Lys Asn Lys Pro Lys Val Asp Ser Asp His Cys Phe Pro
        130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
                180

<210> SEQ ID NO 9
<211> LENGTH: 53
<212> TYPE: PRT
<213> ORGANISM: Cynomorium macaque

<400> SEQUENCE: 9

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
            35                  40                  45

Lys Gly Met Asn Ala
    50

<210> SEQ ID NO 10
<211> LENGTH: 34
<212> TYPE: PRT
<213> ORGANISM: Cynomorium macaque

<400> SEQUENCE: 10

Gln Cys Ser Gln Asn Glu Tyr Phe Asp Ser Leu Leu His Asp Cys Lys
1               5                   10                  15

Pro Cys Gln Leu Arg Cys Ser Ser Thr Pro Pro Leu Thr Cys Gln Arg
            20                  25                  30

Tyr Cys

-continued

<210> SEQ ID NO 11
<211> LENGTH: 23
<212> TYPE: PRT
<213> ORGANISM: Cynomorium macaque

<400> SEQUENCE: 11

Ile Leu Trp Thr Cys Leu Gly Leu Ser Leu Ile Ile Ser Leu Ala Val
1               5                   10                  15

Phe Val Leu Thr Phe Leu Leu
            20

<210> SEQ ID NO 12
<211> LENGTH: 107
<212> TYPE: PRT
<213> ORGANISM: Cynomorium macaque

<400> SEQUENCE: 12

Arg Lys Met Ser Ser Glu Pro Leu Lys Asp Glu Phe Lys Asn Thr Gly
1               5                   10                  15

Ser Gly Leu Leu Gly Met Ala Asn Ile Asp Leu Glu Lys Gly Arg Thr
                20                  25                  30

Gly Asp Glu Ile Val Leu Pro Arg Gly Leu Glu Tyr Thr Val Glu Glu
            35                  40                  45

Cys Thr Cys Glu Asp Cys Ile Lys Asn Lys Pro Lys Val Asp Ser Asp
        50                  55                  60

His Cys Phe Pro Leu Pro Ala Met Glu Glu Gly Ala Thr Ile Leu Val
65                  70                  75                  80

Thr Thr Lys Thr Asn Asp Tyr Cys Asn Ser Leu Ser Ala Ala Leu Ser
                85                  90                  95

Val Thr Glu Ile Glu Lys Ser Ile Ser Ala Arg
            100                 105

<210> SEQ ID NO 13
<211> LENGTH: 25
<212> TYPE: PRT
<213> ORGANISM: Cynomorium macaque

<400> SEQUENCE: 13

Leu Glu Tyr Thr Val Glu Glu Cys Thr Cys Glu Asp Cys Ile Lys Asn
1               5                   10                  15

Lys Pro Lys Val Asp Ser Asp His Cys
            20                  25

<210> SEQ ID NO 14
<211> LENGTH: 185
<212> TYPE: PRT
<213> ORGANISM: Mus musculus

<400> SEQUENCE: 14

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
                20                  25                  30

Gln Pro Tyr Cys Asp Pro Ser Val Thr Ser Ser Val Lys Gly Thr Tyr
            35                  40                  45

Thr Val Leu Trp Ile Phe Leu Gly Leu Thr Leu Val Leu Ser Leu Ala
        50                  55                  60

Leu Phe Thr Ile Ser Phe Leu Leu Arg Lys Met Asn Pro Glu Ala Leu
65                  70                  75                  80

-continued

```
Lys Asp Glu Pro Gln Ser Pro Gly Gln Leu Asp Gly Ser Ala Gln Leu
                    85               90              95

Asp Lys Ala Asp Thr Glu Leu Thr Arg Ile Arg Ala Gly Asp Asp Arg
                100             105             110

Ile Phe Pro Arg Ser Leu Glu Tyr Thr Val Glu Glu Cys Thr Cys Glu
                115             120             125

Asp Cys Val Lys Ser Lys Pro Lys Gly Asp Ser Asp His Phe Phe Pro
        130             135             140

Leu Pro Ala Met Glu Glu Gly Ala Thr Ile Leu Val Thr Thr Lys Thr
145             150             155             160

Gly Asp Tyr Gly Lys Ser Ser Val Pro Thr Ala Leu Gln Ser Val Met
                165             170             175

Gly Met Glu Lys Pro Thr His Thr Arg
                180             185

<210> SEQ ID NO 15
<211> LENGTH: 180
<212> TYPE: PRT
<213> ORGANISM: Mus musculus

<400> SEQUENCE: 15

Met Ala Gln Gln Cys Phe His Ser Glu Tyr Phe Asp Ser Leu Leu His
1               5               10              15

Ala Cys Lys Pro Cys His Leu Arg Cys Ser Asn Pro Pro Ala Thr Cys
                20              25              30

Gln Pro Tyr Cys Asp Pro Ser Val Thr Ser Ser Val Lys Gly Thr Tyr
            35              40              45

Thr Val Leu Trp Ile Phe Leu Gly Leu Thr Leu Val Leu Ser Leu Ala
        50              55              60

Leu Phe Thr Ile Ser Phe Leu Leu Arg Lys Met Asn Pro Glu Ala Leu
65              70              75              80

Lys Asp Glu Pro Gln Ser Gly Ser Ala Gln Leu Asp Lys Ala Asp Thr
                85              90              95

Glu Leu Thr Arg Ile Arg Ala Gly Asp Asp Arg Ile Phe Pro Arg Ser
                100             105             110

Leu Glu Tyr Thr Val Glu Glu Cys Thr Cys Glu Asp Cys Val Lys Ser
            115             120             125

Lys Pro Lys Gly Asp Ser Asp His Phe Phe Pro Leu Pro Ala Met Glu
        130             135             140

Glu Gly Ala Thr Ile Leu Val Thr Thr Lys Thr Gly Asp Tyr Gly Lys
145             150             155             160

Ser Ser Val Pro Thr Ala Leu Gln Ser Val Met Gly Met Glu Lys Pro
                165             170             175

Thr His Thr Arg
            180

<210> SEQ ID NO 16
<211> LENGTH: 49
<212> TYPE: PRT
<213> ORGANISM: Mus musculus

<400> SEQUENCE: 16

Met Ala Gln Gln Cys Phe His Ser Glu Tyr Phe Asp Ser Leu Leu His
1               5               10              15

Ala Cys Lys Pro Cys His Leu Arg Cys Ser Asn Pro Pro Ala Thr Cys
                20              25              30
```

```
Gln Pro Tyr Cys Asp Pro Ser Val Thr Ser Ser Val Lys Gly Thr Tyr
        35              40              45

Thr

<210> SEQ ID NO 17
<211> LENGTH: 33
<212> TYPE: PRT
<213> ORGANISM: Cynomorium macaque

<400> SEQUENCE: 17

Gln Cys Phe His Ser Glu Tyr Phe Asp Ser Leu Leu His Ala Cys Lys
1               5               10              15

Pro Cys His Leu Arg Cys Ser Asn Pro Pro Ala Thr Cys Gln Pro Tyr
        20              25              30

Cys

<210> SEQ ID NO 18
<211> LENGTH: 21
<212> TYPE: PRT
<213> ORGANISM: Mus musculus

<400> SEQUENCE: 18

Val Leu Trp Ile Phe Leu Gly Leu Thr Leu Val Leu Ser Leu Ala Leu
1               5               10              15

Phe Thr Ile Ser Phe
            20

<210> SEQ ID NO 19
<211> LENGTH: 115
<212> TYPE: PRT
<213> ORGANISM: Mus musculus

<400> SEQUENCE: 19

Leu Leu Arg Lys Met Asn Pro Glu Ala Leu Lys Asp Glu Pro Gln Ser
1               5               10              15

Pro Gly Gln Leu Asp Gly Ser Ala Gln Leu Asp Lys Ala Asp Thr Glu
        20              25              30

Leu Thr Arg Ile Arg Ala Gly Asp Asp Arg Ile Phe Pro Arg Ser Leu
        35              40              45

Glu Tyr Thr Val Glu Glu Cys Thr Cys Glu Asp Cys Val Lys Ser Lys
    50              55              60

Pro Lys Gly Asp Ser Asp His Phe Phe Pro Leu Pro Ala Met Glu Glu
65              70              75              80

Gly Ala Thr Ile Leu Val Thr Thr Lys Thr Gly Asp Tyr Gly Lys Ser
                85              90              95

Ser Val Pro Thr Ala Leu Gln Ser Val Met Gly Met Glu Lys Pro Thr
            100             105             110

His Thr Arg
        115

<210> SEQ ID NO 20
<211> LENGTH: 110
<212> TYPE: PRT
<213> ORGANISM: Mus musculus

<400> SEQUENCE: 20

Leu Leu Arg Lys Met Asn Pro Glu Ala Leu Lys Asp Glu Pro Gln Ser
1               5               10              15

Gly Ser Ala Gln Leu Asp Lys Ala Asp Thr Glu Leu Thr Arg Ile Arg
```

-continued

```
                    20              25              30

Ala Gly Asp Asp Arg Ile Phe Pro Arg Ser Leu Glu Tyr Thr Val Glu
        35              40              45

Glu Cys Thr Cys Glu Asp Cys Val Lys Ser Lys Pro Lys Gly Asp Ser
    50              55              60

Asp His Phe Phe Pro Leu Pro Ala Met Glu Glu Gly Ala Thr Ile Leu
65              70              75              80

Val Thr Thr Lys Thr Gly Asp Tyr Gly Lys Ser Ser Val Pro Thr Ala
            85              90              95

Leu Gln Ser Val Met Gly Met Glu Lys Pro Thr His Thr Arg
            100             105             110

<210> SEQ ID NO 21
<211> LENGTH: 25
<212> TYPE: PRT
<213> ORGANISM: Mus musculus

<400> SEQUENCE: 21

Leu Glu Tyr Thr Val Glu Glu Cys Thr Cys Glu Asp Cys Val Lys Ser
1               5               10              15

Lys Pro Lys Gly Asp Ser Asp His Phe
            20              25

<210> SEQ ID NO 22
<211> LENGTH: 119
<212> TYPE: PRT
<213> ORGANISM: Artificial Sequence
<220> FEATURE:
<223> OTHER INFORMATION: synthetic construct

<400> SEQUENCE: 22

Glu Val Gln Leu Gln Gln Ser Gly Pro Glu Leu Val Lys Pro Gly Ala
1               5               10              15

Ser Val Lys Met Ser Cys Lys Ala Ser Gly Tyr Thr Phe Thr Ser Tyr
            20              25              30

Val Met His Trp Val Lys Gln Lys Pro Gly Arg Gly Leu Glu Trp Ile
        35              40              45

Ala Tyr Ile Leu Pro Phe Asn Asp Val Thr Lys Tyr Asn Glu Lys Phe
    50              55              60

Lys Gly Lys Ala Thr Leu Thr Ser Asp Lys Ser Ser Asn Thr Ala Tyr
65              70              75              80

Met Glu Leu Ser Ser Leu Thr Ser Glu Asp Ser Ala Val Tyr Tyr Cys
            85              90              95

Ala Arg Trp Glu Trp Asp Asp Gly Tyr Phe Asp Tyr Trp Gly Gln Gly
            100             105             110

Thr Thr Leu Thr Val Ser Ser
        115

<210> SEQ ID NO 23
<211> LENGTH: 8
<212> TYPE: PRT
<213> ORGANISM: Artificial Sequence
<220> FEATURE:
<223> OTHER INFORMATION: synthetic construct

<400> SEQUENCE: 23

Gly Tyr Thr Phe Thr Ser Tyr Val
1               5
```

<210> SEQ ID NO 24
<211> LENGTH: 8
<212> TYPE: PRT
<213> ORGANISM: Artificial Sequence
<220> FEATURE:
<223> OTHER INFORMATION: synthetic construct

<400> SEQUENCE: 24

Ile Leu Pro Phe Asn Asp Val Thr
1               5

<210> SEQ ID NO 25
<211> LENGTH: 12
<212> TYPE: PRT
<213> ORGANISM: Artificial Sequence
<220> FEATURE:
<223> OTHER INFORMATION: synthetic construct

<400> SEQUENCE: 25

Ala Arg Trp Glu Trp Asp Asp Gly Tyr Phe Asp Tyr
1               5                   10

<210> SEQ ID NO 26
<211> LENGTH: 25
<212> TYPE: PRT
<213> ORGANISM: Artificial Sequence
<220> FEATURE:
<223> OTHER INFORMATION: synthetic construct

<400> SEQUENCE: 26

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 27
<211> LENGTH: 17
<212> TYPE: PRT
<213> ORGANISM: Artificial Sequence
<220> FEATURE:
<223> OTHER INFORMATION: synthetic construct

<400> SEQUENCE: 27

Met His Trp Val Lys Gln Lys Pro Gly Arg Gly Leu Glu Trp Ile Ala
1               5                   10                  15

Tyr

<210> SEQ ID NO 28
<211> LENGTH: 38
<212> TYPE: PRT
<213> ORGANISM: Artificial Sequence
<220> FEATURE:
<223> OTHER INFORMATION: synthetic construct

<400> SEQUENCE: 28

Lys Tyr Asn Glu Lys Phe Lys Gly Lys Ala Thr Leu Thr Ser Asp Lys
1               5                   10                  15

Ser Ser Asn Thr Ala Tyr Met Glu Leu Ser Ser Leu Thr Ser Glu Asp
            20                  25                  30

Ser Ala Val Tyr Tyr Cys
        35

<210> SEQ ID NO 29
<211> LENGTH: 11
<212> TYPE: PRT

-continued

```
<213> ORGANISM: Artificial Sequence
<220> FEATURE:
<223> OTHER INFORMATION: synthetic construct

<400> SEQUENCE: 29

Trp Gly Gln Gly Thr Thr Leu Thr Val Ser Ser
1               5                   10

<210> SEQ ID NO 30
<211> LENGTH: 112
<212> TYPE: PRT
<213> ORGANISM: Artificial Sequence
<220> FEATURE:
<223> OTHER INFORMATION: synthetic construct

<400> SEQUENCE: 30

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Ser His Val Pro Phe Thr Phe Gly Ala Gly Thr Lys Leu Glu Leu Lys
            100                 105                 110

<210> SEQ ID NO 31
<211> LENGTH: 11
<212> TYPE: PRT
<213> ORGANISM: Artificial Sequence
<220> FEATURE:
<223> OTHER INFORMATION: synthetic construct

<400> SEQUENCE: 31

Gln Ser Leu Glu Asn Ser Asn Gly Asn Thr Tyr
1               5                   10

<210> SEQ ID NO 32
<211> LENGTH: 3
<212> TYPE: PRT
<213> ORGANISM: Artificial Sequence
<220> FEATURE:
<223> OTHER INFORMATION: synthetic construct

<400> SEQUENCE: 32

Arg Val Ser
1

<210> SEQ ID NO 33
<211> LENGTH: 9
<212> TYPE: PRT
<213> ORGANISM: Artificial Sequence
<220> FEATURE:
<223> OTHER INFORMATION: synthetic construct

<400> SEQUENCE: 33

Leu Gln Val Ser His Val Pro Phe Thr
1               5
```

-continued

```
<210> SEQ ID NO 34
<211> LENGTH: 26
<212> TYPE: PRT
<213> ORGANISM: Artificial Sequence
<220> FEATURE:
<223> OTHER INFORMATION: synthetic construct

<400> SEQUENCE: 34

Asp Ala Val Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 35
<211> LENGTH: 17
<212> TYPE: PRT
<213> ORGANISM: Artificial Sequence
<220> FEATURE:
<223> OTHER INFORMATION: synthetic construct

<400> SEQUENCE: 35

Leu Asn Trp Tyr Leu Gln Lys Pro Gly Gln Ser Pro Gln Leu Leu Ile
1               5                   10                  15

Tyr

<210> SEQ ID NO 36
<211> LENGTH: 36
<212> TYPE: PRT
<213> ORGANISM: Artificial Sequence
<220> FEATURE:
<223> OTHER INFORMATION: synthetic construct

<400> SEQUENCE: 36

Asn Arg Phe Ser Gly Val Leu Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 37
<211> LENGTH: 10
<212> TYPE: PRT
<213> ORGANISM: Artificial Sequence
<220> FEATURE:
<223> OTHER INFORMATION: synthetic construct

<400> SEQUENCE: 37

Phe Gly Ala Gly Thr Lys Leu Glu Leu Lys
1               5                   10

<210> SEQ ID NO 38
<211> LENGTH: 121
<212> TYPE: PRT
<213> ORGANISM: Artificial Sequence
<220> FEATURE:
<223> OTHER INFORMATION: synthetic construct

<400> SEQUENCE: 38

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

```
Val Ile His Trp Val Lys Gln Lys Pro Gly Gln Gly Leu Glu Trp Ile
    35                  40                  45

Gly Tyr Val Leu Pro Tyr Asn Asp Val Ile Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Arg Trp Gly Asp Phe Asp Glu Gly Ile Trp Phe Pro Tyr Trp Gly
            100                 105                 110

Gln Gly Thr Leu Val Thr Val Ser Ala
        115                 120

<210> SEQ ID NO 39
<211> LENGTH: 8
<212> TYPE: PRT
<213> ORGANISM: Artificial Sequence
<220> FEATURE:
<223> OTHER INFORMATION: synthetic construct

<400> SEQUENCE: 39

Val Leu Pro Tyr Asn Asp Val Ile
1               5

<210> SEQ ID NO 40
<211> LENGTH: 14
<212> TYPE: PRT
<213> ORGANISM: Artificial Sequence
<220> FEATURE:
<223> OTHER INFORMATION: synthetic construct

<400> SEQUENCE: 40

Ala Arg Trp Gly Asp Phe Asp Glu Gly Ile Trp Phe Pro Tyr
1               5                   10

<210> SEQ ID NO 41
<211> LENGTH: 17
<212> TYPE: PRT
<213> ORGANISM: Artificial Sequence
<220> FEATURE:
<223> OTHER INFORMATION: synthetic construct

<400> SEQUENCE: 41

Ile His Trp Val Lys Gln Lys Pro Gly Gln Gly Leu Glu Trp Ile Gly
1               5                   10                  15

Tyr

<210> SEQ ID NO 42
<211> LENGTH: 38
<212> TYPE: PRT
<213> ORGANISM: Artificial Sequence
<220> FEATURE:
<223> OTHER INFORMATION: synthetic construct

<400> SEQUENCE: 42

Lys Tyr Asn Glu Lys Phe Lys Gly Lys Ala Thr Leu Thr Ser Asp Lys
1               5                   10                  15

Ser Ser Ser Thr Ala Tyr Met Asp Leu Ser Ser Leu Thr Ser Glu Asp
            20                  25                  30

Ser Ala Val Tyr Tyr Cys
        35
```

-continued

```
<210> SEQ ID NO 43
<211> LENGTH: 11
<212> TYPE: PRT
<213> ORGANISM: Artificial Sequence
<220> FEATURE:
<223> OTHER INFORMATION: synthetic construct

<400> SEQUENCE: 43

Trp Gly Gln Gly Thr Leu Val Thr Val Ser Ala
1               5                   10

<210> SEQ ID NO 44
<211> LENGTH: 112
<212> TYPE: PRT
<213> ORGANISM: Artificial Sequence
<220> FEATURE:
<223> OTHER INFORMATION: synthetic construct

<400> SEQUENCE: 44

Asp Val Leu Met Thr Gln Thr Pro Leu Ser Leu Pro Val Ser Leu Gly
1               5                   10                  15

Asp His Ala Ser Val Ser Cys Arg Ser Ser Gln Ser Ile Val His Thr
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 45
<211> LENGTH: 11
<212> TYPE: PRT
<213> ORGANISM: Artificial Sequence
<220> FEATURE:
<223> OTHER INFORMATION: synthetic construct

<400> SEQUENCE: 45

Gln Ser Ile Val His Thr Asp Gly Asn Thr Tyr
1               5                   10

<210> SEQ ID NO 46
<211> LENGTH: 3
<212> TYPE: PRT
<213> ORGANISM: Artificial Sequence
<220> FEATURE:
<223> OTHER INFORMATION: synthetic construct

<400> SEQUENCE: 46

Lys Val Ser
1

<210> SEQ ID NO 47
<211> LENGTH: 9
<212> TYPE: PRT
<213> ORGANISM: Artificial Sequence
<220> FEATURE:
<223> OTHER INFORMATION: synthetic construct

<400> SEQUENCE: 47
```

```
Phe Gln Gly Ser His Val Pro Trp Thr
1               5

<210> SEQ ID NO 48
<211> LENGTH: 26
<212> TYPE: PRT
<213> ORGANISM: Artificial Sequence
<220> FEATURE:
<223> OTHER INFORMATION: synthetic construct

<400> SEQUENCE: 48

Asp Val Leu Met Thr Gln Thr Pro Leu Ser Leu Pro Val Ser Leu Gly
1               5                   10                  15

Asp His Ala Ser Val Ser Cys Arg Ser Ser
            20                  25

<210> SEQ ID NO 49
<211> LENGTH: 17
<212> TYPE: PRT
<213> ORGANISM: Artificial Sequence
<220> FEATURE:
<223> OTHER INFORMATION: synthetic construct

<400> SEQUENCE: 49

Leu Glu Trp Tyr Leu Gln Lys Pro Gly Gln Ser Pro Lys Leu Leu Ile
1               5                   10                  15

Tyr

<210> SEQ ID NO 50
<211> LENGTH: 36
<212> TYPE: PRT
<213> ORGANISM: Artificial Sequence
<220> FEATURE:
<223> OTHER INFORMATION: synthetic construct

<400> SEQUENCE: 50

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 51
<211> LENGTH: 10
<212> TYPE: PRT
<213> ORGANISM: Artificial Sequence
<220> FEATURE:
<223> OTHER INFORMATION: synthetic construct

<400> SEQUENCE: 51

Phe Gly Gly Gly Thr Lys Leu Glu Ile Lys
1               5                   10

<210> SEQ ID NO 52
<211> LENGTH: 118
<212> TYPE: PRT
<213> ORGANISM: Artificial Sequence
<220> FEATURE:
<223> OTHER INFORMATION: synthetic construct

<400> SEQUENCE: 52

Glu Val Gln Leu Gln Gln Ser Gly Pro Glu Leu Val Lys Pro Gly Ser
1               5                   10                  15
```

-continued

```
Ser Val Lys Met Ser Cys Lys Ala Ser Gly Tyr Thr Phe Thr Asn Tyr
          20                  25                  30

Val Met His Trp Val Lys Gln Lys Pro Gly Gln Gly Leu Glu Trp Ile
          35                  40                  45

Gly Tyr Ile Leu Pro Tyr Asn Asp Gly Thr Lys Tyr Asn Glu Lys Phe
          50                  55                  60

Lys Gly Lys Ala Thr Leu Thr Ser Asp Lys Ser Ser Ser Thr Ala Tyr
65                  70                  75                  80

Met Glu Phe Ser Val Leu Thr Ser Glu Asp Ser Ala Val Tyr Tyr Cys
                  85                  90                  95

Ala Arg Tyr Asp Tyr Glu Gly Ser Phe Asp Tyr Trp Gly Gln Gly Thr
          100                 105                 110

Ala Leu Thr Val Ser Ser
          115

<210> SEQ ID NO 53
<211> LENGTH: 8
<212> TYPE: PRT
<213> ORGANISM: Artificial Sequence
<220> FEATURE:
<223> OTHER INFORMATION: synthetic construct

<400> SEQUENCE: 53

Gly Tyr Thr Phe Thr Asn Tyr Val
1               5

<210> SEQ ID NO 54
<211> LENGTH: 8
<212> TYPE: PRT
<213> ORGANISM: Artificial Sequence
<220> FEATURE:
<223> OTHER INFORMATION: synthetic construct

<400> SEQUENCE: 54

Ile Leu Pro Tyr Asn Asp Gly Thr
1               5

<210> SEQ ID NO 55
<211> LENGTH: 11
<212> TYPE: PRT
<213> ORGANISM: Artificial Sequence
<220> FEATURE:
<223> OTHER INFORMATION: synthetic construct

<400> SEQUENCE: 55

Ala Arg Tyr Asp Tyr Glu Gly Ser Phe Asp Tyr
1               5                   10

<210> SEQ ID NO 56
<211> LENGTH: 25
<212> TYPE: PRT
<213> ORGANISM: Artificial Sequence
<220> FEATURE:
<223> OTHER INFORMATION: synthetic construct

<400> SEQUENCE: 56

Glu Val Gln Leu Gln Gln Ser Gly Pro Glu Leu Val Lys Pro Gly Ser
1               5                   10                  15

Ser Val Lys Met Ser Cys Lys Ala Ser
          20                  25

<210> SEQ ID NO 57
<211> LENGTH: 17
```

```
<212> TYPE: PRT
<213> ORGANISM: Artificial Sequence
<220> FEATURE:
<223> OTHER INFORMATION: synthetic construct

<400> SEQUENCE: 57

Met His Trp Val Lys Gln Lys Pro Gly Gln Gly Leu Glu Trp Ile Gly
1               5                   10                  15

Tyr

<210> SEQ ID NO 58
<211> LENGTH: 38
<212> TYPE: PRT
<213> ORGANISM: Artificial Sequence
<220> FEATURE:
<223> OTHER INFORMATION: synthetic construct

<400> SEQUENCE: 58

Lys Tyr Asn Glu Lys Phe Lys Gly Lys Ala Thr Leu Thr Ser Asp Lys
1               5                   10                  15

Ser Ser Ser Thr Ala Tyr Met Glu Phe Ser Val Leu Thr Ser Glu Asp
            20                  25                  30

Ser Ala Val Tyr Tyr Cys
        35

<210> SEQ ID NO 59
<211> LENGTH: 11
<212> TYPE: PRT
<213> ORGANISM: Artificial Sequence
<220> FEATURE:
<223> OTHER INFORMATION: synthetic construct

<400> SEQUENCE: 59

Trp Gly Gln Gly Thr Ala Leu Thr Val Ser Ser
1               5                   10

<210> SEQ ID NO 60
<211> LENGTH: 107
<212> TYPE: PRT
<213> ORGANISM: Artificial Sequence
<220> FEATURE:
<223> OTHER INFORMATION: synthetic construct

<400> SEQUENCE: 60

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Met
            35                  40                  45

Cys Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly Asn Thr Phe Pro Pro
                85                  90                  95

Thr Phe Gly Gly Gly Thr Lys Leu Glu Ile Lys
            100                 105

<210> SEQ ID NO 61
<211> LENGTH: 6
<212> TYPE: PRT
```

-continued

```
<213> ORGANISM: Artificial Sequence
<220> FEATURE:
<223> OTHER INFORMATION: synthetic construct

<400> SEQUENCE: 61

Gln Asp Ile Ser Asn Tyr
1               5

<210> SEQ ID NO 62
<211> LENGTH: 3
<212> TYPE: PRT
<213> ORGANISM: Artificial Sequence
<220> FEATURE:
<223> OTHER INFORMATION: synthetic construct

<400> SEQUENCE: 62

Tyr Thr Ser
1

<210> SEQ ID NO 63
<211> LENGTH: 9
<212> TYPE: PRT
<213> ORGANISM: Artificial Sequence
<220> FEATURE:
<223> OTHER INFORMATION: synthetic construct

<400> SEQUENCE: 63

Gln Gln Gly Asn Thr Phe Pro Pro Thr
1               5

<210> SEQ ID NO 64
<211> LENGTH: 26
<212> TYPE: PRT
<213> ORGANISM: Artificial Sequence
<220> FEATURE:
<223> OTHER INFORMATION: synthetic construct

<400> SEQUENCE: 64

Asp Ile Gln Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 65
<211> LENGTH: 17
<212> TYPE: PRT
<213> ORGANISM: Artificial Sequence
<220> FEATURE:
<223> OTHER INFORMATION: synthetic construct

<400> SEQUENCE: 65

Leu Asn Trp Tyr Gln Gln Lys Pro Asp Gly Thr Val Lys Leu Leu Met
1               5                   10                  15

Cys

<210> SEQ ID NO 66
<211> LENGTH: 36
<212> TYPE: PRT
<213> ORGANISM: Artificial Sequence
<220> FEATURE:
<223> OTHER INFORMATION: synthetic construct

<400> SEQUENCE: 66

Arg Leu His Ser Gly Val Pro Ser Arg Phe Ser Gly Ser Gly Ser Gly
1               5                   10                  15
```

```
Thr Asp Phe Ser Leu Thr Ile Ser Asn Leu Glu Gln Glu Asp Ile Ala
            20                  25                  30

Thr Tyr Phe Cys
        35

<210> SEQ ID NO 67
<211> LENGTH: 123
<212> TYPE: PRT
<213> ORGANISM: Artificial Sequence
<220> FEATURE:
<223> OTHER INFORMATION: synthetic construct

<400> SEQUENCE: 67

Glu Val Met Leu Val Asp Ser Gly Gly Asn Leu Val Lys Pro Gly Gly
1               5                   10                  15

Ser Leu Lys Leu Ser Cys Ala Ala Ser Gly Phe Thr Phe Ser Asn Tyr
            20                  25                  30

Val Ile Ser Trp Val Arg Gln Thr Pro Glu Lys Arg Leu Glu Trp Val
        35                  40                  45

Ala Thr Ile Ser Thr Val Gly Thr Asn Thr Tyr Tyr Pro Asp Ser Val
        50                  55                  60

Arg Gly Arg Phe Thr Ile Ser Arg Asp Asn Ala Glu Asn Thr Leu Tyr
65                  70                  75                  80

Leu Gln Met Ser Ser Leu Arg Ser Glu Asp Thr Ala Ile Tyr Tyr Cys
                85                  90                  95

Ser Arg His Lys Tyr Gly Tyr Asp Asp Pro Ser Tyr Ala Met Asp Tyr
            100                 105                 110

Trp Gly Gln Gly Thr Ser Val Thr Val Ser Ser
        115                 120

<210> SEQ ID NO 68
<211> LENGTH: 8
<212> TYPE: PRT
<213> ORGANISM: Artificial Sequence
<220> FEATURE:
<223> OTHER INFORMATION: synthetic construct

<400> SEQUENCE: 68

Gly Phe Thr Phe Ser Asn Tyr Val
1               5

<210> SEQ ID NO 69
<211> LENGTH: 8
<212> TYPE: PRT
<213> ORGANISM: Artificial Sequence
<220> FEATURE:
<223> OTHER INFORMATION: synthetic construct

<400> SEQUENCE: 69

Ile Ser Thr Val Gly Thr Asn Thr
1               5

<210> SEQ ID NO 70
<211> LENGTH: 16
<212> TYPE: PRT
<213> ORGANISM: Artificial Sequence
<220> FEATURE:
<223> OTHER INFORMATION: synthetic construct

<400> SEQUENCE: 70

Ser Arg His Lys Tyr Gly Tyr Asp Asp Pro Ser Tyr Ala Met Asp Tyr
1               5                   10                  15
```

-continued

```
<210> SEQ ID NO 71
<211> LENGTH: 25
<212> TYPE: PRT
<213> ORGANISM: Artificial Sequence
<220> FEATURE:
<223> OTHER INFORMATION: synthetic construct

<400> SEQUENCE: 71

Glu Val Met Leu Val Asp Ser Gly Gly Asn Leu Val Lys Pro Gly Gly
1               5                   10                  15

Ser Leu Lys Leu Ser Cys Ala Ala Ser
            20                  25

<210> SEQ ID NO 72
<211> LENGTH: 17
<212> TYPE: PRT
<213> ORGANISM: Artificial Sequence
<220> FEATURE:
<223> OTHER INFORMATION: synthetic construct

<400> SEQUENCE: 72

Ile Ser Trp Val Arg Gln Thr Pro Glu Lys Arg Leu Glu Trp Val Ala
1               5                   10                  15

Thr

<210> SEQ ID NO 73
<211> LENGTH: 38
<212> TYPE: PRT
<213> ORGANISM: Artificial Sequence
<220> FEATURE:
<223> OTHER INFORMATION: synthetic construct

<400> SEQUENCE: 73

Tyr Tyr Pro Asp Ser Val Arg Gly Arg Phe Thr Ile Ser Arg Asp Asn
1               5                   10                  15

Ala Glu Asn Thr Leu Tyr Leu Gln Met Ser Ser Leu Arg Ser Glu Asp
            20                  25                  30

Thr Ala Ile Tyr Tyr Cys
        35

<210> SEQ ID NO 74
<211> LENGTH: 11
<212> TYPE: PRT
<213> ORGANISM: Artificial Sequence
<220> FEATURE:
<223> OTHER INFORMATION: synthetic construct

<400> SEQUENCE: 74

Trp Gly Gln Gly Thr Ser Val Thr Val Ser Ser
1               5                   10

<210> SEQ ID NO 75
<211> LENGTH: 115
<212> TYPE: PRT
<213> ORGANISM: Artificial Sequence
<220> FEATURE:
<223> OTHER INFORMATION: synthetic construct

<400> SEQUENCE: 75

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
            20                  25                  30
```

-continued

```
Ile Glu Trp Tyr Gln Gln Gln Pro Leu Lys Pro Pro Lys Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Ala Glu Asp Glu Ala Ile Tyr Ile Cys Gly Val Gly Asp
                85                  90                  95

Thr Val Lys Glu Gln Phe Val Tyr Val Phe Gly Gly Gly Thr Lys Val
                100                 105                 110

Thr Val Leu
        115

<210> SEQ ID NO 76
<211> LENGTH: 7
<212> TYPE: PRT
<213> ORGANISM: Artificial Sequence
<220> FEATURE:
<223> OTHER INFORMATION: synthetic construct

<400> SEQUENCE: 76

Ser Gln His Ser Thr Tyr Thr
1               5

<210> SEQ ID NO 77
<211> LENGTH: 7
<212> TYPE: PRT
<213> ORGANISM: Artificial Sequence
<220> FEATURE:
<223> OTHER INFORMATION: synthetic construct

<400> SEQUENCE: 77

Leu Lys Lys Asp Gly Ser His
1               5

<210> SEQ ID NO 78
<211> LENGTH: 13
<212> TYPE: PRT
<213> ORGANISM: Artificial Sequence
<220> FEATURE:
<223> OTHER INFORMATION: synthetic construct

<400> SEQUENCE: 78

Gly Val Gly Asp Thr Val Lys Glu Gln Phe Val Tyr Val
1               5                   10

<210> SEQ ID NO 79
<211> LENGTH: 25
<212> TYPE: PRT
<213> ORGANISM: Artificial Sequence
<220> FEATURE:
<223> OTHER INFORMATION: synthetic construct

<400> SEQUENCE: 79

Gln Leu Val Leu Thr Gln Ser Ser Ser Ala Ser Phe Ser Leu Gly Ala
1               5                   10                  15

Ser Ala Lys Leu Thr Cys Thr Leu Ser
                20                  25

<210> SEQ ID NO 80
<211> LENGTH: 17
<212> TYPE: PRT
<213> ORGANISM: Artificial Sequence
<220> FEATURE:
```

-continued

<223> OTHER INFORMATION: synthetic construct

<400> SEQUENCE: 80

Ile Glu Trp Tyr Gln Gln Gln Pro Leu Lys Pro Pro Lys Tyr Val Met
1               5                   10                  15

Glu

<210> SEQ ID NO 81
<211> LENGTH: 36
<212> TYPE: PRT
<213> ORGANISM: Artificial Sequence
<220> FEATURE:
<223> OTHER INFORMATION: synthetic construct

<400> SEQUENCE: 81

Ser Thr Gly Asp Gly Ile Pro Asp Arg Phe Ser Gly Ser Ser Ser Gly
1               5                   10                  15

Ala Asp Arg Tyr Leu Ser Ile Ser Asn Ile Gln Ala Glu Asp Glu Ala
            20                  25                  30

Ile Tyr Ile Cys
        35

<210> SEQ ID NO 82
<211> LENGTH: 10
<212> TYPE: PRT
<213> ORGANISM: Artificial Sequence
<220> FEATURE:
<223> OTHER INFORMATION: synthetic construct

<400> SEQUENCE: 82

Phe Gly Gly Gly Thr Lys Val Thr Val Leu
1               5                   10

<210> SEQ ID NO 83
<211> LENGTH: 115
<212> TYPE: PRT
<213> ORGANISM: Artificial Sequence
<220> FEATURE:
<223> OTHER INFORMATION: synthetic construct

<400> SEQUENCE: 83

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Asp Ser Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Phe Ser Leu Thr Ser Glu Asp Ser Thr Val Tyr Tyr Cys
                85                  90                  95

Ala Ala Gly Glu Glu Phe Ala Tyr Trp Gly Gln Gly Thr Leu Val Thr
            100                 105                 110

Val Ser Ala
        115

<210> SEQ ID NO 84
<211> LENGTH: 8
<212> TYPE: PRT

-continued

```
<213> ORGANISM: Artificial Sequence
<220> FEATURE:
<223> OTHER INFORMATION: synthetic construct

<400> SEQUENCE: 84

Gly Tyr Ser Phe Thr Gly Tyr Ile
1               5

<210> SEQ ID NO 85
<211> LENGTH: 8
<212> TYPE: PRT
<213> ORGANISM: Artificial Sequence
<220> FEATURE:
<223> OTHER INFORMATION: synthetic construct

<400> SEQUENCE: 85

Ile Asn Pro Tyr Asn Gly Asp Ser
1               5

<210> SEQ ID NO 86
<211> LENGTH: 8
<212> TYPE: PRT
<213> ORGANISM: Artificial Sequence
<220> FEATURE:
<223> OTHER INFORMATION: synthetic construct

<400> SEQUENCE: 86

Ala Ala Gly Glu Glu Phe Ala Tyr
1               5

<210> SEQ ID NO 87
<211> LENGTH: 25
<212> TYPE: PRT
<213> ORGANISM: Artificial Sequence
<220> FEATURE:
<223> OTHER INFORMATION: synthetic construct

<400> SEQUENCE: 87

Glu Val Gln Leu Gln Gln Ser Gly Pro Glu Leu Val Lys Pro Gly Ala
1               5                   10                  15

Ser Met Lys Ile Ser Cys Lys Ala Ser
            20                  25

<210> SEQ ID NO 88
<211> LENGTH: 17
<212> TYPE: PRT
<213> ORGANISM: Artificial Sequence
<220> FEATURE:
<223> OTHER INFORMATION: synthetic construct

<400> SEQUENCE: 88

Met Asn Trp Val Lys Gln Ser His Gly Lys Asn Leu Glu Trp Ile Gly
1               5                   10                  15

Leu

<210> SEQ ID NO 89
<211> LENGTH: 38
<212> TYPE: PRT
<213> ORGANISM: Artificial Sequence
<220> FEATURE:
<223> OTHER INFORMATION: synthetic construct

<400> SEQUENCE: 89

Ile Tyr Asn Gln Lys Phe Lys Gly Lys Ala Thr Leu Thr Val Asp Lys
1               5                   10                  15
```

-continued

```
Ser Ser Ser Thr Ala Tyr Met Glu Leu Phe Ser Leu Thr Ser Glu Asp
        20                  25                  30

Ser Thr Val Tyr Tyr Cys
        35

<210> SEQ ID NO 90
<211> LENGTH: 107
<212> TYPE: PRT
<213> ORGANISM: Artificial Sequence
<220> FEATURE:
<223> OTHER INFORMATION: synthetic construct

<400> SEQUENCE: 90

Asp Ile Gln Met Thr Gln Thr Ser Ser Ser Leu Ser Ala Ser Leu Gly
1               5                   10                  15

Asp Arg Val Thr Ile Ser Cys Arg Ala Ser Gln Asp Ile Ser Ile Tyr
        20                  25                  30

Leu Asn Trp Phe Gln Gln Lys Pro Asp Gly Thr Val Lys Leu Leu Ile
        35                  40                  45

Tyr Phe Thr Ser Arg Leu His Pro Gly Val Pro Ser Arg Phe Ser Ala
    50                  55                  60

Ser Gly Ser Gly Thr Asp Tyr Ser Leu Thr Ile Ser His Leu Glu His
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Val Glu Leu Lys
            100                 105

<210> SEQ ID NO 91
<211> LENGTH: 6
<212> TYPE: PRT
<213> ORGANISM: Artificial Sequence
<220> FEATURE:
<223> OTHER INFORMATION: synthetic construct

<400> SEQUENCE: 91

Gln Asp Ile Ser Ile Tyr
1               5

<210> SEQ ID NO 92
<211> LENGTH: 3
<212> TYPE: PRT
<213> ORGANISM: Artificial Sequence
<220> FEATURE:
<223> OTHER INFORMATION: synthetic construct

<400> SEQUENCE: 92

Phe Thr Ser
1

<210> SEQ ID NO 93
<211> LENGTH: 9
<212> TYPE: PRT
<213> ORGANISM: Artificial Sequence
<220> FEATURE:
<223> OTHER INFORMATION: synthetic construct

<400> SEQUENCE: 93

Gln Gln Gly Asn Thr Leu Pro Arg Thr
1               5

<210> SEQ ID NO 94
<211> LENGTH: 26
```

-continued

```
<212> TYPE: PRT
<213> ORGANISM: Artificial Sequence
<220> FEATURE:
<223> OTHER INFORMATION: synthetic construct

<400> SEQUENCE: 94

Asp Ile Gln Met Thr Gln Thr Ser Ser Ser Leu Ser Ala Ser Leu Gly
1               5                   10                  15

Asp Arg Val Thr Ile Ser Cys Arg Ala Ser
            20                  25

<210> SEQ ID NO 95
<211> LENGTH: 17
<212> TYPE: PRT
<213> ORGANISM: Artificial Sequence
<220> FEATURE:
<223> OTHER INFORMATION: synthetic construct

<400> SEQUENCE: 95

Leu Asn Trp Phe Gln Gln Lys Pro Asp Gly Thr Val Lys Leu Leu Ile
1               5                   10                  15

Tyr

<210> SEQ ID NO 96
<211> LENGTH: 36
<212> TYPE: PRT
<213> ORGANISM: Artificial Sequence
<220> FEATURE:
<223> OTHER INFORMATION: synthetic construct

<400> SEQUENCE: 96

Arg Leu His Pro Gly Val Pro Ser Arg Phe Ser Ala Ser Gly Ser Gly
1               5                   10                  15

Thr Asp Tyr Ser Leu Thr Ile Ser His Leu Glu His Glu Asp Ile Ala
            20                  25                  30

Thr Tyr Phe Cys
        35

<210> SEQ ID NO 97
<211> LENGTH: 10
<212> TYPE: PRT
<213> ORGANISM: Artificial Sequence
<220> FEATURE:
<223> OTHER INFORMATION: synthetic construct

<400> SEQUENCE: 97

Phe Gly Gly Gly Thr Lys Val Glu Leu Lys
1               5                   10

<210> SEQ ID NO 98
<211> LENGTH: 117
<212> TYPE: PRT
<213> ORGANISM: Artificial Sequence
<220> FEATURE:
<223> OTHER INFORMATION: synthetic construct

<400> SEQUENCE: 98

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Tyr Trp Val Lys Gln Ala Pro Gly Lys Gly Leu Lys Trp Met
        35                  40                  45
```

-continued

```
Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Asn Thr Leu Lys Asn Glu Asp Thr Ala Thr Tyr Phe Cys
                85                  90                  95

Ser Ile Ser Tyr Tyr Tyr Ala Met Asp Tyr Trp Gly Gln Gly Thr Ser
                100                 105                 110

Val Thr Val Ser Ser
        115

<210> SEQ ID NO 99
<211> LENGTH: 8
<212> TYPE: PRT
<213> ORGANISM: Artificial Sequence
<220> FEATURE:
<223> OTHER INFORMATION: synthetic construct

<400> SEQUENCE: 99

Gly Tyr Thr Phe Thr Asp Tyr Ser
1               5

<210> SEQ ID NO 100
<211> LENGTH: 8
<212> TYPE: PRT
<213> ORGANISM: Artificial Sequence
<220> FEATURE:
<223> OTHER INFORMATION: synthetic construct

<400> SEQUENCE: 100

Ile Asn Thr Glu Thr Gly Glu Pro
1               5

<210> SEQ ID NO 101
<211> LENGTH: 10
<212> TYPE: PRT
<213> ORGANISM: Artificial Sequence
<220> FEATURE:
<223> OTHER INFORMATION: synthetic construct

<400> SEQUENCE: 101

Ser Ile Ser Tyr Tyr Tyr Ala Met Asp Tyr
1               5                   10

<210> SEQ ID NO 102
<211> LENGTH: 25
<212> TYPE: PRT
<213> ORGANISM: Artificial Sequence
<220> FEATURE:
<223> OTHER INFORMATION: synthetic construct

<400> SEQUENCE: 102

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 103
<211> LENGTH: 17
<212> TYPE: PRT
<213> ORGANISM: Artificial Sequence
<220> FEATURE:
<223> OTHER INFORMATION: synthetic construct

<400> SEQUENCE: 103
```

-continued

Ile Tyr Trp Val Lys Gln Ala Pro Gly Lys Gly Leu Lys Trp Met Gly
1               5                   10                  15

Trp

<210> SEQ ID NO 104
<211> LENGTH: 38
<212> TYPE: PRT
<213> ORGANISM: Artificial Sequence
<220> FEATURE:
<223> OTHER INFORMATION: synthetic construct

<400> SEQUENCE: 104

Thr Tyr Ala Asp Asp Phe Lys Gly Arg Phe Ala Phe Ser Leu Glu Thr
1               5                   10                  15

Ser Ala Ser Ser Ala Tyr Leu Gln Ile Asn Thr Leu Lys Asn Glu Asp
            20                  25                  30

Thr Ala Thr Tyr Phe Cys
            35

<210> SEQ ID NO 105
<211> LENGTH: 111
<212> TYPE: PRT
<213> ORGANISM: Artificial Sequence
<220> FEATURE:
<223> OTHER INFORMATION: synthetic construct

<400> SEQUENCE: 105

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Phe Leu His Trp Tyr Gln Gln Lys Pro Gly Gln Pro Pro
            35                  40                  45

Lys Leu Leu Ile Tyr Phe Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
            85                  90                  95

Glu Leu Pro Arg Thr Phe Gly Gly Gly Thr Lys Leu Glu Ile Lys
            100                 105                 110

<210> SEQ ID NO 106
<211> LENGTH: 10
<212> TYPE: PRT
<213> ORGANISM: Artificial Sequence
<220> FEATURE:
<223> OTHER INFORMATION: synthetic construct

<400> SEQUENCE: 106

Lys Ser Val Ser Thr Ser Gly Tyr Ser Phe
1               5                   10

<210> SEQ ID NO 107
<211> LENGTH: 3
<212> TYPE: PRT
<213> ORGANISM: Artificial Sequence
<220> FEATURE:
<223> OTHER INFORMATION: synthetic construct

<400> SEQUENCE: 107

Phe Ala Ser
1

<210> SEQ ID NO 108
<211> LENGTH: 9
<212> TYPE: PRT
<213> ORGANISM: Artificial Sequence
<220> FEATURE:
<223> OTHER INFORMATION: synthetic construct

<400> SEQUENCE: 108

Gln His Ser Arg Glu Leu Pro Arg Thr
1               5

<210> SEQ ID NO 109
<211> LENGTH: 26
<212> TYPE: PRT
<213> ORGANISM: Artificial Sequence
<220> FEATURE:
<223> OTHER INFORMATION: synthetic construct

<400> SEQUENCE: 109

Asp Ile Val Leu Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 110
<211> LENGTH: 17
<212> TYPE: PRT
<213> ORGANISM: Artificial Sequence
<220> FEATURE:
<223> OTHER INFORMATION: synthetic construct

<400> SEQUENCE: 110

Leu His Trp Tyr Gln Gln Lys Pro Gly Gln Pro Pro Lys Leu Leu Ile
1               5                   10                  15

Tyr

<210> SEQ ID NO 111
<211> LENGTH: 36
<212> TYPE: PRT
<213> ORGANISM: Artificial Sequence
<220> FEATURE:
<223> OTHER INFORMATION: synthetic construct

<400> SEQUENCE: 111

Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
            20                  25                  30

Thr Tyr Tyr Cys
        35

<210> SEQ ID NO 112
<211> LENGTH: 117
<212> TYPE: PRT
<213> ORGANISM: Artificial Sequence
<220> FEATURE:
<223> OTHER INFORMATION: synthetic construct

<400> SEQUENCE: 112

Gln Ile Gln Leu Val Gln Ser Gly Pro Glu Leu Lys Lys Pro Gly Glu
1               5                   10                  15

```
Thr Val Lys Ile Ser Cys Met Ala Ser Gly Tyr Thr Phe Thr Asp Tyr
            20                  25                  30

Ser Val Arg Trp Val Lys Gln Ala Pro Gly Lys Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Ser Tyr Tyr Tyr Ala Leu Asp Tyr Trp Gly His Gly Thr Ser
            100                 105                 110

Val Thr Val Ser Ser
        115
```

```
<210> SEQ ID NO 113
<211> LENGTH: 10
<212> TYPE: PRT
<213> ORGANISM: Artificial Sequence
<220> FEATURE:
<223> OTHER INFORMATION: synthetic construct

<400> SEQUENCE: 113

Ala Ile Ser Tyr Tyr Tyr Ala Leu Asp Tyr
1               5                   10
```

```
<210> SEQ ID NO 114
<211> LENGTH: 25
<212> TYPE: PRT
<213> ORGANISM: Artificial Sequence
<220> FEATURE:
<223> OTHER INFORMATION: synthetic construct

<400> SEQUENCE: 114

Gln Ile Gln Leu Val Gln Ser Gly Pro Glu Leu Lys Lys Pro Gly Glu
1               5                   10                  15

Thr Val Lys Ile Ser Cys Met Ala Ser
            20                  25
```

```
<210> SEQ ID NO 115
<211> LENGTH: 17
<212> TYPE: PRT
<213> ORGANISM: Artificial Sequence
<220> FEATURE:
<223> OTHER INFORMATION: synthetic construct

<400> SEQUENCE: 115

Val Arg Trp Val Lys Gln Ala Pro Gly Lys Gly Leu Glu Trp Met Gly
1               5                   10                  15

Trp
```

```
<210> SEQ ID NO 116
<211> LENGTH: 38
<212> TYPE: PRT
<213> ORGANISM: Artificial Sequence
<220> FEATURE:
<223> OTHER INFORMATION: synthetic construct

<400> SEQUENCE: 116

Thr Tyr Ala Asp Asp Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
```

-continued

```
                20              25              30

Thr Ala Thr Tyr Phe Cys
        35

<210> SEQ ID NO 117
<211> LENGTH: 11
<212> TYPE: PRT
<213> ORGANISM: Artificial Sequence
<220> FEATURE:
<223> OTHER INFORMATION: synthetic construct

<400> SEQUENCE: 117

Trp Gly His Gly Thr Ser Val Thr Val Ser Ser
1               5               10

<210> SEQ ID NO 118
<211> LENGTH: 111
<212> TYPE: PRT
<213> ORGANISM: Artificial Sequence
<220> FEATURE:
<223> OTHER INFORMATION: synthetic construct

<400> SEQUENCE: 118

Asp Ile Val Leu Thr Gln Ser Pro Ala Ser Leu Thr Val Ser Leu Gly
1               5                   10                  15

Gln Arg Ala Thr Ile Ser Cys Arg Ala Ser Lys Ser Val Ser Thr Ser
            20                  25                  30

Val Tyr Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys
            100                 105                 110

<210> SEQ ID NO 119
<211> LENGTH: 10
<212> TYPE: PRT
<213> ORGANISM: Artificial Sequence
<220> FEATURE:
<223> OTHER INFORMATION: synthetic construct

<400> SEQUENCE: 119

Lys Ser Val Ser Thr Ser Val Tyr Ser Phe
1               5               10

<210> SEQ ID NO 120
<211> LENGTH: 3
<212> TYPE: PRT
<213> ORGANISM: Artificial Sequence
<220> FEATURE:
<223> OTHER INFORMATION: synthetic construct

<400> SEQUENCE: 120

Leu Ala Ser
1

<210> SEQ ID NO 121
<211> LENGTH: 26
<212> TYPE: PRT
```

-continued

```
<213> ORGANISM: Artificial Sequence
<220> FEATURE:
<223> OTHER INFORMATION: synthetic construct

<400> SEQUENCE: 121

Asp Ile Val Leu Thr Gln Ser Pro Ala Ser Leu Thr Val Ser Leu Gly
1               5                   10                  15

Gln Arg Ala Thr Ile Ser Cys Arg Ala Ser
            20                  25

<210> SEQ ID NO 122
<211> LENGTH: 117
<212> TYPE: PRT
<213> ORGANISM: Artificial Sequence
<220> FEATURE:
<223> OTHER INFORMATION: synthetic construct

<400> SEQUENCE: 122

Gln Ile Gln Leu Val Gln Ser Gly Pro Glu Leu Lys Lys Pro Gly Glu
1               5                   10                  15

Thr Val Lys Ile Ser Cys Met Ala Ser Gly Tyr Thr Phe Thr Asp Tyr
            20                  25                  30

Ser Val Arg Trp Val Lys Gln Ala Pro Gly Lys Gly Leu Glu Trp Met
        35                  40                  45

Gly Trp Ile Asn Thr Glu Thr Gly Glu Pro Thr Tyr Ala His Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asp Glu Asp Thr Ser Thr Tyr Phe Cys
                85                  90                  95

Ala Ile Ser Tyr Tyr Tyr Ala Leu Asp Tyr Trp Gly His Gly Thr Ser
                100                 105                 110

Val Thr Val Ser Ser
        115

<210> SEQ ID NO 123
<211> LENGTH: 38
<212> TYPE: PRT
<213> ORGANISM: Artificial Sequence
<220> FEATURE:
<223> OTHER INFORMATION: synthetic construct

<400> SEQUENCE: 123

Thr Tyr Ala His Asp Phe Lys Gly Arg Phe Ala Phe Ser Leu Glu Thr
1               5                   10                  15

Ser Ala Ser Thr Ala Tyr Leu Gln Ile Asn Asn Leu Lys Asp Glu Asp
            20                  25                  30

Thr Ser Thr Tyr Phe Cys
        35

<210> SEQ ID NO 124
<211> LENGTH: 111
<212> TYPE: PRT
<213> ORGANISM: Artificial Sequence
<220> FEATURE:
<223> OTHER INFORMATION: synthetic construct

<400> SEQUENCE: 124

Asp Ile Val Leu Thr Gln Ser Pro Ala Ser Leu Thr Val Ser Leu Gly
1               5                   10                  15

Gln Arg Ala Thr Ile Ser Cys Arg Ala Ser Lys Ser Val Ser Thr Ser
```

-continued

```
                   20                25                30

Gly Tyr Asn Phe Leu His Trp Tyr Gln Gln Lys Pro Gly Gln Pro Pro
            35                40                45

Lys Leu Leu Ile Tyr Leu Ala Ser Asn Leu Glu Ser Gly Ala Pro Ala
    50                55                60

Arg Phe Ser Gly Ser Gly Ser Gly Thr Asp Phe Thr Leu Asn Ile His
65                70                75                80

Pro Val Glu Glu Glu Asp Ala Ala Thr Tyr Tyr Cys Gln His Ser Arg
                85                90                95

Glu Leu Pro Arg Thr Phe Gly Gly Gly Thr Lys Leu Glu Ile Lys
            100               105               110
```

```
<210> SEQ ID NO 125
<211> LENGTH: 10
<212> TYPE: PRT
<213> ORGANISM: Artificial Sequence
<220> FEATURE:
<223> OTHER INFORMATION: synthetic construct

<400> SEQUENCE: 125

Lys Ser Val Ser Thr Ser Gly Tyr Asn Phe
1               5                10
```

```
<210> SEQ ID NO 126
<211> LENGTH: 36
<212> TYPE: PRT
<213> ORGANISM: Artificial Sequence
<220> FEATURE:
<223> OTHER INFORMATION: synthetic construct

<400> SEQUENCE: 126

Asn Leu Glu Ser Gly Ala Pro Ala Arg Phe Ser Gly Ser Gly Ser Gly
1               5                10                15

Thr Asp Phe Thr Leu Asn Ile His Pro Val Glu Glu Glu Asp Ala Ala
            20                25                30

Thr Tyr Tyr Cys
        35
```

```
<210> SEQ ID NO 127
<211> LENGTH: 117
<212> TYPE: PRT
<213> ORGANISM: Artificial Sequence
<220> FEATURE:
<223> OTHER INFORMATION: synthetic construct

<400> SEQUENCE: 127

Gln Ile Gln Leu Val Gln Ser Gly Pro Glu Leu Lys Lys Pro Gly Glu
1               5                10                15

Thr Val Lys Ile Ser Cys Lys Ala Ser Gly Tyr Thr Phe Thr Asp Tyr
            20                25                30

Thr Met Tyr Trp Val Lys Gln Ala Pro Gly Lys Gly Leu Lys Trp Met
        35                40                45

Gly Trp Ile Asn Thr Glu Thr Gly Glu Pro Thr Tyr Ala Asp Asp Phe
    50                55                60

Lys Gly Arg Phe Val Phe Ser Leu Glu Thr Ser Ala Asn Thr Ala Tyr
65                70                75                80

Leu Gln Ile Asn Asn Leu Lys Asn Glu Asp Thr Ala Thr Tyr Phe Cys
                85                90                95

Ala Ile Ser Tyr Tyr Tyr Gly Met Asp Tyr Trp Gly Gln Gly Thr Ser
            100               105               110
```

Val Thr Val Thr Ser
        115

<210> SEQ ID NO 128
<211> LENGTH: 8
<212> TYPE: PRT
<213> ORGANISM: Artificial Sequence
<220> FEATURE:
<223> OTHER INFORMATION: synthetic construct

<400> SEQUENCE: 128

Gly Tyr Thr Phe Thr Asp Tyr Thr
1               5

<210> SEQ ID NO 129
<211> LENGTH: 10
<212> TYPE: PRT
<213> ORGANISM: Artificial Sequence
<220> FEATURE:
<223> OTHER INFORMATION: synthetic construct

<400> SEQUENCE: 129

Ala Ile Ser Tyr Tyr Tyr Gly Met Asp Tyr
1               5               10

<210> SEQ ID NO 130
<211> LENGTH: 17
<212> TYPE: PRT
<213> ORGANISM: Artificial Sequence
<220> FEATURE:
<223> OTHER INFORMATION: synthetic construct

<400> SEQUENCE: 130

Met Tyr Trp Val Lys Gln Ala Pro Gly Lys Gly Leu Lys Trp Met Gly
1               5               10              15

Trp

<210> SEQ ID NO 131
<211> LENGTH: 38
<212> TYPE: PRT
<213> ORGANISM: Artificial Sequence
<220> FEATURE:
<223> OTHER INFORMATION: synthetic construct

<400> SEQUENCE: 131

Thr Tyr Ala Asp Asp Phe Lys Gly Arg Phe Val Phe Ser Leu Glu Thr
1               5               10              15

Ser Ala Asn Thr Ala Tyr Leu Gln Ile Asn Asn Leu Lys Asn Glu Asp
            20              25              30

Thr Ala Thr Tyr Phe Cys
        35

<210> SEQ ID NO 132
<211> LENGTH: 11
<212> TYPE: PRT
<213> ORGANISM: Artificial Sequence
<220> FEATURE:
<223> OTHER INFORMATION: synthetic construct

<400> SEQUENCE: 132

Trp Gly Gln Gly Thr Ser Val Thr Val Thr Ser
1               5               10

<210> SEQ ID NO 133

```
<211> LENGTH: 111
<212> TYPE: PRT
<213> ORGANISM: Artificial Sequence
<220> FEATURE:
<223> OTHER INFORMATION: synthetic construct

<400> SEQUENCE: 133

Asp Ile Ile Leu Thr Gln Ser Pro Ala Ser Leu Ala Val Ser Leu Gly
1               5                   10                  15

Gln Arg Ala Thr Ile Thr Cys Arg Ala Ser Lys Ser Val Ser Thr Ser
            20                  25                  30

Gly Tyr Asn Phe Val Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys
            100                 105                 110

<210> SEQ ID NO 134
<211> LENGTH: 26
<212> TYPE: PRT
<213> ORGANISM: Artificial Sequence
<220> FEATURE:
<223> OTHER INFORMATION: synthetic construct

<400> SEQUENCE: 134

Asp Ile Ile Leu Thr Gln Ser Pro Ala Ser Leu Ala Val Ser Leu Gly
1               5                   10                  15

Gln Arg Ala Thr Ile Thr Cys Arg Ala Ser
            20                  25

<210> SEQ ID NO 135
<211> LENGTH: 17
<212> TYPE: PRT
<213> ORGANISM: Artificial Sequence
<220> FEATURE:
<223> OTHER INFORMATION: synthetic construct

<400> SEQUENCE: 135

Val Tyr Trp Tyr Gln Gln Lys Pro Gly Gln Pro Pro Lys Leu Leu Ile
1               5                   10                  15

Tyr

<210> SEQ ID NO 136
<211> LENGTH: 121
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: Xaa = A or S
<220> FEATURE:
<221> NAME/KEY: misc_feature
<222> LOCATION: (31)..(31)
<223> OTHER INFORMATION: Xaa = S or N
<220> FEATURE:
<221> NAME/KEY: misc_feature
<222> LOCATION: (34)..(34)
<223> OTHER INFORMATION: Xaa = M or I
```

-continued

```
<220> FEATURE:
<221> NAME/KEY: misc_feature
<222> LOCATION: (43)..(43)
<223> OTHER INFORMATION: Xaa = Q or R
<220> FEATURE:
<221> NAME/KEY: misc_feature
<222> LOCATION: (49)..(49)
<223> OTHER INFORMATION: Xaa = G or A
<220> FEATURE:
<221> NAME/KEY: misc_feature
<222> LOCATION: (51)..(51)
<223> OTHER INFORMATION: Xaa = I or V
<220> FEATURE:
<221> NAME/KEY: misc_feature
<222> LOCATION: (54)..(54)
<223> OTHER INFORMATION: Xaa = Y or F
<220> FEATURE:
<221> NAME/KEY: misc_feature
<222> LOCATION: (57)..(57)
<223> OTHER INFORMATION: Xaa = V or G
<220> FEATURE:
<221> NAME/KEY: misc_feature
<222> LOCATION: (58)..(58)
<223> OTHER INFORMATION: Xaa = T or I
<220> FEATURE:
<221> NAME/KEY: misc_feature
<222> LOCATION: (77)..(77)
<223> OTHER INFORMATION: Xaa = S or N
<220> FEATURE:
<221> NAME/KEY: misc_feature
<222> LOCATION: (82)..(82)
<223> OTHER INFORMATION: Xaa = E or D
<220> FEATURE:
<221> NAME/KEY: misc_feature
<222> LOCATION: (83)..(83)
<223> OTHER INFORMATION: Xaa = L or F
<220> FEATURE:
<221> NAME/KEY: misc_feature
<222> LOCATION: (85)..(85)
<223> OTHER INFORMATION: Xaa = S or V
<220> FEATURE:
<221> NAME/KEY: misc_feature
<222> LOCATION: (99)..(99)
<223> OTHER INFORMATION: Xaa = W or Y
<220> FEATURE:
<221> NAME/KEY: misc_feature
<222> LOCATION: (100)..(100)
<223> OTHER INFORMATION: Xaa = absent or G
<220> FEATURE:
<221> NAME/KEY: misc_feature
<222> LOCATION: (101)..(101)
<223> OTHER INFORMATION: Xaa = D or E
<220> FEATURE:
<221> NAME/KEY: misc_feature
<222> LOCATION: (102)..(102)
<223> OTHER INFORMATION: Xaa = W, F or Y
<220> FEATURE:
<221> NAME/KEY: misc_feature
<222> LOCATION: (103)..(103)
<223> OTHER INFORMATION: Xaa = D or E
<220> FEATURE:
<221> NAME/KEY: misc_feature
<222> LOCATION: (104)..(104)
<223> OTHER INFORMATION: Xaa = D, E or G
<220> FEATURE:
<221> NAME/KEY: misc_feature
<222> LOCATION: (105)..(105)
<223> OTHER INFORMATION: Xaa = G or S
<220> FEATURE:
<221> NAME/KEY: misc_feature
<222> LOCATION: (106)..(106)
<223> OTHER INFORMATION: Xaa = absent or I
<220> FEATURE:
<221> NAME/KEY: misc_feature
<222> LOCATION: (107)..(107)
<223> OTHER INFORMATION: Xaa = Y, W or absent
<220> FEATURE:
<221> NAME/KEY: misc_feature
<222> LOCATION: (109)..(109)
```

```
<223> OTHER INFORMATION: Xaa = D or P
<220> FEATURE:
<221> NAME/KEY: misc_feature
<222> LOCATION: (116)..(116)
<223> OTHER INFORMATION: Xaa = T, L or A
<220> FEATURE:
<221> NAME/KEY: misc_feature
<222> LOCATION: (117)..(117)
<223> OTHER INFORMATION: Xaa = L or V
<220> FEATURE:
<221> NAME/KEY: misc_feature
<222> LOCATION: (121)..(121)
<223> OTHER INFORMATION: Xaa = S or A

<400> SEQUENCE: 136

Glu Val Gln Leu Gln Gln Ser Gly Pro Glu Leu Val Lys Pro Gly Xaa
1               5                   10                  15

Ser Val Lys Met Ser Cys Lys Ala Ser Gly Tyr Thr Phe Thr Xaa Tyr
            20                  25                  30

Val Xaa His Trp Val Lys Gln Lys Pro Gly Xaa Gly Leu Glu Trp Ile
        35                  40                  45

Xaa Tyr Xaa Leu Pro Xaa Asn Asp Xaa Xaa Lys Tyr Asn Glu Lys Phe
    50                  55                  60

Lys Gly Lys Ala Thr Leu Thr Ser Asp Lys Ser Ser Xaa Thr Ala Tyr
65                  70                  75                  80

Met Xaa Xaa Ser Xaa Leu Thr Ser Glu Asp Ser Ala Val Tyr Tyr Cys
            85                  90                  95

Ala Arg Xaa Xaa Xaa Xaa Xaa Xaa Xaa Xaa Xaa Phe Xaa Tyr Trp Gly
            100                 105                 110

Gln Gly Thr Xaa Xaa Thr Val Ser Xaa
        115                 120

<210> SEQ ID NO 137
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = S or N

<400> SEQUENCE: 137

Gly Tyr Thr Phe Thr Xaa Tyr Val
1               5

<210> SEQ ID NO 138
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = I or V
<220> FEATURE:
<221> NAME/KEY: misc_feature
<222> LOCATION: (4)..(4)
<223> OTHER INFORMATION: Xaa = Y or F
<220> FEATURE:
<221> NAME/KEY: misc_feature
<222> LOCATION: (7)..(7)
<223> OTHER INFORMATION: Xaa = V or G
<220> FEATURE:
<221> NAME/KEY: misc_feature
<222> LOCATION: (8)..(8)
```

-continued

```
<223> OTHER INFORMATION: Xaa = T or I

<400> SEQUENCE: 138

Xaa Leu Pro Xaa Asn Asp Xaa Xaa
1               5

<210> SEQ ID NO 139
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa = W or Y
<220> FEATURE:
<221> NAME/KEY: misc_feature
<222> LOCATION: (4)..(4)
<223> OTHER INFORMATION: Xaa = absent or G
<220> FEATURE:
<221> NAME/KEY: misc_feature
<222> LOCATION: (5)..(5)
<223> OTHER INFORMATION: Xaa = D or E
<220> FEATURE:
<221> NAME/KEY: misc_feature
<222> LOCATION: (6)..(6)
<223> OTHER INFORMATION: Xaa = W, F or Y
<220> FEATURE:
<221> NAME/KEY: misc_feature
<222> LOCATION: (7)..(7)
<223> OTHER INFORMATION: Xaa = D or E
<220> FEATURE:
<221> NAME/KEY: misc_feature
<222> LOCATION: (8)..(8)
<223> OTHER INFORMATION: Xaa = D, E or G
<220> FEATURE:
<221> NAME/KEY: misc_feature
<222> LOCATION: (9)..(9)
<223> OTHER INFORMATION: Xaa = G or S
<220> FEATURE:
<221> NAME/KEY: misc_feature
<222> LOCATION: (10)..(10)
<223> OTHER INFORMATION: Xaa = absent or I
<220> FEATURE:
<221> NAME/KEY: misc_feature
<222> LOCATION: (11)..(11)
<223> OTHER INFORMATION: Xaa = Y, W or absent
<220> FEATURE:
<221> NAME/KEY: misc_feature
<222> LOCATION: (13)..(13)
<223> OTHER INFORMATION: Xaa = D or P

<400> SEQUENCE: 139

Ala Arg Xaa Xaa Xaa Xaa Xaa Xaa Xaa Xaa Xaa Phe Xaa Tyr
1               5                   10

<210> SEQ ID NO 140
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: Xaa = A or S

<400> SEQUENCE: 140

Glu Val Gln Leu Gln Gln Ser Gly Pro Glu Leu Val Lys Pro Gly Xaa
1               5                   10                  15

Ser Val Lys Met Ser Cys Lys Ala Ser
            20                  25
```

```
<210> SEQ ID NO 141
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = M or I
<220> FEATURE:
<221> NAME/KEY: misc_feature
<222> LOCATION: (10)..(10)
<223> OTHER INFORMATION: Xaa = Q or R
<220> FEATURE:
<221> NAME/KEY: misc_feature
<222> LOCATION: (16)..(16)
<223> OTHER INFORMATION: Xaa = G or A

<400> SEQUENCE: 141

Xaa His Trp Val Lys Gln Lys Pro Gly Xaa Gly Leu Glu Trp Ile Xaa
1               5                   10                  15

Tyr

<210> SEQ ID NO 142
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: Xaa = S or N
<220> FEATURE:
<221> NAME/KEY: misc_feature
<222> LOCATION: (24)..(24)
<223> OTHER INFORMATION: Xaa = E or D
<220> FEATURE:
<221> NAME/KEY: misc_feature
<222> LOCATION: (25)..(25)
<223> OTHER INFORMATION: Xaa = L or F
<220> FEATURE:
<221> NAME/KEY: misc_feature
<222> LOCATION: (27)..(27)
<223> OTHER INFORMATION: Xaa = S or V

<400> SEQUENCE: 142

Lys Tyr Asn Glu Lys Phe Lys Gly Lys Ala Thr Leu Thr Ser Asp Lys
1               5                   10                  15

Ser Ser Xaa Thr Ala Tyr Met Xaa Xaa Ser Xaa Leu Thr Ser Glu Asp
            20                  25                  30

Ser Ala Val Tyr Tyr Cys
        35

<210> SEQ ID NO 143
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = T, L or A
<220> FEATURE:
<221> NAME/KEY: misc_feature
<222> LOCATION: (7)..(7)
<223> OTHER INFORMATION: Xaa = L or V
<220> FEATURE:
```

```
<221> NAME/KEY: misc_feature
<222> LOCATION: (11)..(11)
<223> OTHER INFORMATION: Xaa = S or A

<400> SEQUENCE: 143

Trp Gly Gln Gly Thr Xaa Xaa Thr Val Ser Xaa
1               5                   10

<210> SEQ ID NO 144
<211> LENGTH: 117
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (23)..(23)
<223> OTHER INFORMATION: Xaa = K or M
<220> FEATURE:
<221> NAME/KEY: misc_feature
<222> LOCATION: (33)..(33)
<223> OTHER INFORMATION: Xaa = S or T
<220> FEATURE:
<221> NAME/KEY: misc_feature
<222> LOCATION: (34)..(34)
<223> OTHER INFORMATION: Xaa = V, I or M
<220> FEATURE:
<221> NAME/KEY: misc_feature
<222> LOCATION: (35)..(35)
<223> OTHER INFORMATION: Xaa = Y or R
<220> FEATURE:
<221> NAME/KEY: misc_feature
<222> LOCATION: (46)..(46)
<223> OTHER INFORMATION: Xaa = K or E
<220> FEATURE:
<221> NAME/KEY: misc_feature
<222> LOCATION: (62)..(62)
<223> OTHER INFORMATION: Xaa = D or H
<220> FEATURE:
<221> NAME/KEY: misc_feature
<222> LOCATION: (69)..(69)
<223> OTHER INFORMATION: Xaa = A or V
<220> FEATURE:
<221> NAME/KEY: misc_feature
<222> LOCATION: (77)..(77)
<223> OTHER INFORMATION: Xaa = S or N
<220> FEATURE:
<221> NAME/KEY: misc_feature
<222> LOCATION: (78)..(78)
<223> OTHER INFORMATION: Xaa = T or S
<220> FEATURE:
<221> NAME/KEY: misc_feature
<222> LOCATION: (85)..(85)
<223> OTHER INFORMATION: Xaa = N or T
<220> FEATURE:
<221> NAME/KEY: misc_feature
<222> LOCATION: (88)..(88)
<223> OTHER INFORMATION: Xaa = N or D
<220> FEATURE:
<221> NAME/KEY: misc_feature
<222> LOCATION: (92)..(92)
<223> OTHER INFORMATION: Xaa = A or S
<220> FEATURE:
<221> NAME/KEY: misc_feature
<222> LOCATION: (97)..(97)
<223> OTHER INFORMATION: Xaa = A or S
<220> FEATURE:
<221> NAME/KEY: misc_feature
<222> LOCATION: (103)..(103)
<223> OTHER INFORMATION: Xaa = A or G
<220> FEATURE:
<221> NAME/KEY: misc_feature
<222> LOCATION: (104)..(104)
<223> OTHER INFORMATION: Xaa = L or M
<220> FEATURE:
<221> NAME/KEY: misc_feature
<222> LOCATION: (109)..(109)
```

```
<223> OTHER INFORMATION: Xaa = Q or H
<220> FEATURE:
<221> NAME/KEY: misc_feature
<222> LOCATION: (116)..(116)
<223> OTHER INFORMATION: Xaa = S or T

<400> SEQUENCE: 144

Gln Ile Gln Leu Val Gln Ser Gly Pro Glu Leu Lys Lys Pro Gly Glu
1               5                   10                  15

Thr Val Lys Ile Ser Cys Xaa Ala Ser Gly Tyr Thr Phe Thr Asp Tyr
            20                  25                  30

Xaa Xaa Xaa Trp Val Lys Gln Ala Pro Gly Lys Gly Leu Xaa Trp Met
        35                  40                  45

Gly Trp Ile Asn Thr Glu Thr Gly Glu Pro Thr Tyr Ala Xaa Asp Phe
    50                  55                  60

Lys Gly Arg Phe Xaa Phe Ser Leu Glu Thr Ser Ala Xaa Xaa Ala Tyr
65                  70                  75                  80

Leu Gln Ile Asn Xaa Leu Lys Xaa Glu Asp Thr Xaa Thr Tyr Phe Cys
                85                  90                  95

Xaa Ile Ser Tyr Tyr Tyr Xaa Xaa Asp Tyr Trp Gly Xaa Gly Thr Ser
            100                 105                 110

Val Thr Val Xaa Ser
        115

<210> SEQ ID NO 145
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: Xaa = S or T

<400> SEQUENCE: 145

Gly Tyr Thr Phe Thr Asp Tyr Xaa
1               5

<210> SEQ ID NO 146
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = A or S
<220> FEATURE:
<221> NAME/KEY: misc_feature
<222> LOCATION: (7)..(7)
<223> OTHER INFORMATION: Xaa = A or G
<220> FEATURE:
<221> NAME/KEY: misc_feature
<222> LOCATION: (8)..(8)
<223> OTHER INFORMATION: Xaa = L or M

<400> SEQUENCE: 146

Xaa Ile Ser Tyr Tyr Tyr Xaa Xaa Asp Tyr
1               5                   10

<210> SEQ ID NO 147
<211> LENGTH: 25
<212> TYPE: PRT
<213> ORGANISM: Artificial Sequence
```

<220> FEATURE:
<223> OTHER INFORMATION: synthetic construct
<220> FEATURE:
<221> NAME/KEY: misc_feature
<222> LOCATION: (23)..(23)
<223> OTHER INFORMATION: Xaa = K or M

<400> SEQUENCE: 147

Gln Ile Gln Leu Val Gln Ser Gly Pro Glu Leu Lys Lys Pro Gly Glu
1               5                   10                  15

Thr Val Lys Ile Ser Cys Xaa Ala Ser
            20                  25

<210> SEQ ID NO 148
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = V, I or M
<220> FEATURE:
<221> NAME/KEY: misc_feature
<222> LOCATION: (2)..(2)
<223> OTHER INFORMATION: Xaa = Y or R
<220> FEATURE:
<221> NAME/KEY: misc_feature
<222> LOCATION: (13)..(13)
<223> OTHER INFORMATION: Xaa = K or E

<400> SEQUENCE: 148

Xaa Xaa Trp Val Lys Gln Ala Pro Gly Lys Gly Leu Xaa Trp Met Gly
1               5                   10                  15

Trp

<210> SEQ ID NO 149
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa = D or H
<220> FEATURE:
<221> NAME/KEY: misc_feature
<222> LOCATION: (11)..(11)
<223> OTHER INFORMATION: Xaa = A or V
<220> FEATURE:
<221> NAME/KEY: misc_feature
<222> LOCATION: (19)..(19)
<223> OTHER INFORMATION: Xaa = S or N
<220> FEATURE:
<221> NAME/KEY: misc_feature
<222> LOCATION: (20)..(20)
<223> OTHER INFORMATION: Xaa = T or S
<220> FEATURE:
<221> NAME/KEY: misc_feature
<222> LOCATION: (27)..(27)
<223> OTHER INFORMATION: Xaa = N or T
<220> FEATURE:
<221> NAME/KEY: misc_feature
<222> LOCATION: (30)..(30)
<223> OTHER INFORMATION: Xaa = N or D
<220> FEATURE:
<221> NAME/KEY: misc_feature
<222> LOCATION: (34)..(34)
<223> OTHER INFORMATION: Xaa = A or S

<400> SEQUENCE: 149

```
Thr Tyr Ala Xaa Asp Phe Lys Gly Arg Phe Xaa Phe Ser Leu Glu Thr
1               5                   10                  15

Ser Ala Xaa Xaa Ala Tyr Leu Gln Ile Asn Xaa Leu Lys Xaa Glu Asp
            20                  25                  30

Thr Xaa Thr Tyr Phe Cys
        35

<210> SEQ ID NO 150
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa = Q or H
<220> FEATURE:
<221> NAME/KEY: misc_feature
<222> LOCATION: (10)..(10)
<223> OTHER INFORMATION: Xaa = S or T

<400> SEQUENCE: 150

Trp Gly Xaa Gly Thr Ser Val Thr Val Xaa Ser
1               5                   10

<210> SEQ ID NO 151
<211> LENGTH: 111
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (12)..(12)
<223> OTHER INFORMATION: Xaa = T or A
<220> FEATURE:
<221> NAME/KEY: misc_feature
<222> LOCATION: (22)..(22)
<223> OTHER INFORMATION: Xaa = S or T
<220> FEATURE:
<221> NAME/KEY: misc_feature
<222> LOCATION: (33)..(33)
<223> OTHER INFORMATION: Xaa = G or V
<220> FEATURE:
<221> NAME/KEY: misc_feature
<222> LOCATION: (35)..(35)
<223> OTHER INFORMATION: Xaa = S or N
<220> FEATURE:
<221> NAME/KEY: misc_feature
<222> LOCATION: (37)..(37)
<223> OTHER INFORMATION: Xaa = L or V
<220> FEATURE:
<221> NAME/KEY: misc_feature
<222> LOCATION: (38)..(38)
<223> OTHER INFORMATION: Xaa = H or Y
<220> FEATURE:
<221> NAME/KEY: misc_feature
<222> LOCATION: (54)..(54)
<223> OTHER INFORMATION: Xaa = L or F
<220> FEATURE:
<221> NAME/KEY: misc_feature
<222> LOCATION: (62)..(62)
<223> OTHER INFORMATION: Xaa = V or A

<400> SEQUENCE: 151

Asp Ile Val Leu Thr Gln Ser Pro Ala Ser Leu Xaa Val Ser Leu Gly
1               5                   10                  15

Gln Arg Ala Thr Ile Xaa Cys Arg Ala Ser Lys Ser Val Ser Thr Ser
            20                  25                  30
```

-continued

```
Xaa Tyr Xaa Phe Xaa Xaa Trp Tyr Gln Gln Lys Pro Gly Gln Pro Pro
        35                  40                  45

Lys Leu Leu Ile Tyr Xaa Ala Ser Asn Leu Glu Ser Gly Xaa Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys
            100                 105                 110

<210> SEQ ID NO 152
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: Xaa = G or V
<220> FEATURE:
<221> NAME/KEY: misc_feature
<222> LOCATION: (9)..(9)
<223> OTHER INFORMATION: Xaa = S or N

<400> SEQUENCE: 152

Lys Ser Val Ser Thr Ser Xaa Tyr Xaa Phe
1               5                   10

<210> SEQ ID NO 153
<211> LENGTH: 3
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = L or F

<400> SEQUENCE: 153

Xaa Ala Ser
1

<210> SEQ ID NO 154
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (12)..(12)
<223> OTHER INFORMATION: Xaa = T or A
<220> FEATURE:
<221> NAME/KEY: misc_feature
<222> LOCATION: (22)..(22)
<223> OTHER INFORMATION: Xaa = S or T

<400> SEQUENCE: 154

Asp Ile Val Leu Thr Gln Ser Pro Ala Ser Leu Xaa Val Ser Leu Gly
1               5                   10                  15

Gln Arg Ala Thr Ile Xaa Cys Arg Ala Ser
            20                  25

<210> SEQ ID NO 155
```

-continued

```
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = L or V
<220> FEATURE:
<221> NAME/KEY: misc_feature
<222> LOCATION: (2)..(2)
<223> OTHER INFORMATION: Xaa = H or Y

<400> SEQUENCE: 155

Xaa Xaa Trp Tyr Gln Gln Lys Pro Gly Gln Pro Pro Lys Leu Leu Ile
1               5                   10                  15

Tyr

<210> SEQ ID NO 156
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = V or A

<400> SEQUENCE: 156

Asn Leu Glu Ser Gly Xaa Pro Ala Arg Phe Ser Gly Ser Gly Ser Gly
1               5                   10                  15

Thr Asp Phe Thr Leu Asn Ile His Pro Val Glu Glu Glu Asp Ala Ala
                20                  25                  30

Thr Tyr Tyr Cys
        35

<210> SEQ ID NO 157
<211> LENGTH: 121
<212> TYPE: PRT
<213> ORGANISM: Artificial Sequence
<220> FEATURE:
<223> OTHER INFORMATION: synthetic construct

<400> SEQUENCE: 157

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
                100                 105                 110

Gln Gly Thr Leu Val Thr Val Ser Ser
        115                 120
```

-continued

```
<210> SEQ ID NO 158
<211> LENGTH: 8
<212> TYPE: PRT
<213> ORGANISM: Artificial Sequence
<220> FEATURE:
<223> OTHER INFORMATION: synthetic construct

<400> SEQUENCE: 158

Gly Gly Thr Phe Ser Asn Tyr Trp
1               5

<210> SEQ ID NO 159
<211> LENGTH: 8
<212> TYPE: PRT
<213> ORGANISM: Artificial Sequence
<220> FEATURE:
<223> OTHER INFORMATION: synthetic construct

<400> SEQUENCE: 159

Thr Tyr Arg Gly His Ser Asp Thr
1               5

<210> SEQ ID NO 160
<211> LENGTH: 14
<212> TYPE: PRT
<213> ORGANISM: Artificial Sequence
<220> FEATURE:
<223> OTHER INFORMATION: synthetic construct

<400> SEQUENCE: 160

Ala Arg Gly Ala Ile Tyr Asp Gly Tyr Asp Val Leu Asp Asn
1               5                   10

<210> SEQ ID NO 161
<211> LENGTH: 25
<212> TYPE: PRT
<213> ORGANISM: Artificial Sequence
<220> FEATURE:
<223> OTHER INFORMATION: synthetic construct

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 162
<211> LENGTH: 17
<212> TYPE: PRT
<213> ORGANISM: Artificial Sequence
<220> FEATURE:
<223> OTHER INFORMATION: synthetic construct

<400> SEQUENCE: 162

Met His Trp Val Arg Gln Ala Pro Gly Gln Gly Leu Glu Trp Met Gly
1               5                   10                  15

Ala

<210> SEQ ID NO 163
<211> LENGTH: 38
<212> TYPE: PRT
<213> ORGANISM: Artificial Sequence
<220> FEATURE:
<223> OTHER INFORMATION: synthetic construct

<400> SEQUENCE: 163
```

-continued

```
Tyr Tyr Asn Gln Lys Phe Lys Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
            35

<210> SEQ ID NO 164
<211> LENGTH: 11
<212> TYPE: PRT
<213> ORGANISM: Artificial Sequence
<220> FEATURE:
<223> OTHER INFORMATION: synthetic construct

<400> SEQUENCE: 164

Trp Gly Gln Gly Thr Leu Val Thr Val Ser Ser
1               5                   10

<210> SEQ ID NO 165
<211> LENGTH: 107
<212> TYPE: PRT
<213> ORGANISM: Artificial Sequence
<220> FEATURE:
<223> OTHER INFORMATION: synthetic construct

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys
            100                 105

<210> SEQ ID NO 166
<211> LENGTH: 9
<212> TYPE: PRT
<213> ORGANISM: Artificial Sequence
<220> FEATURE:
<223> OTHER INFORMATION: synthetic construct

<400> SEQUENCE: 166

Gln Gln Tyr Arg Lys Leu Pro Trp Thr
1               5

<210> SEQ ID NO 167
<211> LENGTH: 26
<212> TYPE: PRT
<213> ORGANISM: Artificial Sequence
<220> FEATURE:
<223> OTHER INFORMATION: synthetic construct

<400> SEQUENCE: 167

Asp Ile Gln Met Thr Gln Ser Pro Ser Ser Leu Ser Ala Ser Val Gly
1               5                   10                  15
```

```
Asp Arg Val Thr Ile Thr Cys Ser Ala Ser
          20                  25

<210> SEQ ID NO 168
<211> LENGTH: 17
<212> TYPE: PRT
<213> ORGANISM: Artificial Sequence
<220> FEATURE:
<223> OTHER INFORMATION: synthetic construct

<400> SEQUENCE: 168

Leu Asn Trp Tyr Gln Gln Lys Pro Gly Lys Ala Pro Lys Leu Leu Ile
1               5                   10                  15

Tyr

<210> SEQ ID NO 169
<211> LENGTH: 36
<212> TYPE: PRT
<213> ORGANISM: Artificial Sequence
<220> FEATURE:
<223> OTHER INFORMATION: synthetic construct

<400> SEQUENCE: 169

Asn Leu His Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
          20                  25                  30

Thr Tyr Tyr Cys
        35

<210> SEQ ID NO 170
<211> LENGTH: 10
<212> TYPE: PRT
<213> ORGANISM: Artificial Sequence
<220> FEATURE:
<223> OTHER INFORMATION: synthetic construct

<400> SEQUENCE: 170

Phe Gly Gln Gly Thr Lys Leu Glu Ile Lys
1               5                   10

<210> SEQ ID NO 171
<211> LENGTH: 323
<212> TYPE: PRT
<213> ORGANISM: Homo sapiens

<400> SEQUENCE: 171

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
          20                  25                  30

Cys Asn Asp Thr Val Val Ile Pro Cys Phe Val Thr Asn Met Glu Ala
          35                  40                  45

Gln Asn Thr Thr Glu Val Tyr Val Lys Trp Lys Phe Lys Gly Arg Asp
     50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
               85                  90                  95

Ser Leu Lys Met Asp Lys Ser Asp Ala Val Ser His Thr Gly Asn Tyr
          100                 105                 110
```

-continued

```
Thr Cys Glu Val Thr Glu Leu Thr Arg Glu Gly Glu Thr Ile Ile Glu
    115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
    275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 172
<211> LENGTH: 292
<212> TYPE: PRT
<213> ORGANISM: Homo sapiens

<400> SEQUENCE: 172

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
    115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160
```

-continued

---

```
Gly Ile Lys Thr Leu Lys Tyr Arg Ser Gly Gly Met Asp Glu Lys Thr
              165             170             175

Ile Ala Leu Leu Val Ala Gly Leu Val Ile Thr Val Ile Val Ile Val
              180             185             190

Gly Ala Ile Leu Phe Val Pro Gly Glu Tyr Ser Leu Lys Asn Ala Thr
              195             200             205

Gly Leu Gly Leu Ile Val Thr Ser Thr Gly Ile Leu Ile Leu Leu His
      210             215             220

Tyr Tyr Val Phe Ser Thr Ala Ile Gly Leu Thr Ser Phe Val Ile Ala
  225             230             235             240

Ile Leu Val Ile Gln Val Ile Ala Tyr Ile Leu Ala Val Val Gly Leu
              245             250             255

Ser Leu Cys Ile Ala Ala Cys Ile Pro Met His Gly Pro Leu Leu Ile
              260             265             270

Ser Gly Leu Ser Ile Leu Ala Leu Ala Gln Leu Leu Gly Leu Val Tyr
              275             280             285

Met Lys Phe Val
      290

<210> SEQ ID NO 173
<211> LENGTH: 305
<212> TYPE: PRT
<213> ORGANISM: Homo sapiens

<400> SEQUENCE: 173

Met Trp Pro Leu Val Ala Ala Leu Leu Leu Gly Ser Ala Cys Cys Gly
1               5               10              15

Ser Ala Gln Leu Leu Phe Asn Lys Thr Lys Ser Val Glu Phe Thr Phe
              20              25              30

Cys Asn Asp Thr Val Val Ile Pro Cys Phe Val Thr Asn Met Glu Ala
              35              40              45

Gln Asn Thr Thr Glu Val Tyr Val Lys Trp Lys Phe Lys Gly Arg Asp
      50              55              60

Ile Tyr Thr Phe Asp Gly Ala Leu Asn Lys Ser Thr Val Pro Thr Asp
65              70              75              80

Phe Ser Ser Ala Lys Ile Glu Val Ser Gln Leu Leu Lys Gly Asp Ala
              85              90              95

Ser Leu Lys Met Asp Lys Ser Asp Ala Val Ser His Thr Gly Asn Tyr
              100             105             110

Thr Cys Glu Val Thr Glu Leu Thr Arg Glu Gly Glu Thr Ile Ile Glu
              115             120             125

Leu Lys Tyr Arg Val Val Ser Trp Phe Ser Pro Asn Glu Asn Ile Leu
      130             135             140

Ile Val Ile Phe Pro Ile Phe Ala Ile Leu Leu Phe Trp Gly Gln Phe
145             150             155             160

Gly Ile Lys Thr Leu Lys Tyr Arg Ser Gly Gly Met Asp Glu Lys Thr
              165             170             175

Ile Ala Leu Leu Val Ala Gly Leu Val Ile Thr Val Ile Val Ile Val
              180             185             190

Gly Ala Ile Leu Phe Val Pro Gly Glu Tyr Ser Leu Lys Asn Ala Thr
              195             200             205

Gly Leu Gly Leu Ile Val Thr Ser Thr Gly Ile Leu Ile Leu Leu His
      210             215             220

Tyr Tyr Val Phe Ser Thr Ala Ile Gly Leu Thr Ser Phe Val Ile Ala
  225             230             235             240
```

-continued

```
Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 174
<211> LENGTH: 311
<212> TYPE: PRT
<213> ORGANISM: Homo sapiens

<400> SEQUENCE: 174

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
            85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
```

```
                290                 295                 300

Ala Val Glu Glu Pro Leu Asn
305                 310

<210> SEQ ID NO 175
<211> LENGTH: 305
<212> TYPE: PRT
<213> ORGANISM: Homo sapiens

<400> SEQUENCE: 175

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
            115                 120                 125

Ile Phe Pro Ile Phe Ala Ile Leu Leu Phe Trp Gly Gln Phe Gly Ile
        130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
                180                 185                 190

Gly Leu Ile Val Thr Ser Thr Gly Ile Leu Ile Leu Leu His Tyr Tyr
            195                 200                 205

Val Phe Ser Thr Ala Ile Gly Leu Thr Ser Phe Val Ile Ala Ile Leu
        210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
            275                 280                 285

Glu Glu Pro Leu Asn Ala Phe Lys Glu Ser Lys Gly Met Met Asn Asp
        290                 295                 300

Glu
305

<210> SEQ ID NO 176
<211> LENGTH: 274
<212> TYPE: PRT
<213> ORGANISM: Homo sapiens
```

-continued

```
<400> SEQUENCE: 176

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
            85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
            165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
        195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
            245                 250                 255

Leu Ser Ile Leu Ala Leu Ala Gln Leu Leu Gly Leu Val Tyr Met Lys
            260                 265                 270

Phe Val

<210> SEQ ID NO 177
<211> LENGTH: 287
<212> TYPE: PRT
<213> ORGANISM: Homo sapiens

<400> SEQUENCE: 177

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
```

-continued

```
                 85              90              95

Glu Val Thr Glu Leu Thr Arg Glu Gly Glu Thr Ile Ile Glu Leu Lys
             100             105             110

Tyr Arg Val Val Ser Trp Phe Ser Pro Asn Glu Asn Ile Leu Ile Val
             115             120             125

Ile Phe Pro Ile Phe Ala Ile Leu Leu Phe Trp Gly Gln Phe Gly Ile
             130             135             140

Lys Thr Leu Lys Tyr Arg Ser Gly Gly Met Asp Glu Lys Thr Ile Ala
145             150             155             160

Leu Leu Val Ala Gly Leu Val Ile Thr Val Ile Val Ile Val Gly Ala
             165             170             175

Ile Leu Phe Val Pro Gly Glu Tyr Ser Leu Lys Asn Ala Thr Gly Leu
             180             185             190

Gly Leu Ile Val Thr Ser Thr Gly Ile Leu Ile Leu Leu His Tyr Tyr
             195             200             205

Val Phe Ser Thr Ala Ile Gly Leu Thr Ser Phe Val Ile Ala Ile Leu
             210             215             220

Val Ile Gln Val Ile Ala Tyr Ile Leu Ala Val Val Gly Leu Ser Leu
225             230             235             240

Cys Ile Ala Ala Cys Ile Pro Met His Gly Pro Leu Leu Ile Ser Gly
             245             250             255

Leu Ser Ile Leu Ala Leu Ala Gln Leu Leu Gly Leu Val Tyr Met Lys
             260             265             270

Phe Val Ala Ser Asn Gln Lys Thr Ile Gln Pro Pro Arg Asn Asn
             275             280             285

<210> SEQ ID NO 178
<211> LENGTH: 293
<212> TYPE: PRT
<213> ORGANISM: Homo sapiens

<400> SEQUENCE: 178

Gln Leu Leu Phe Asn Lys Thr Lys Ser Val Glu Phe Thr Phe Cys Asn
1               5               10              15

Asp Thr Val Val Ile Pro Cys Phe Val Thr Asn Met Glu Ala Gln Asn
             20              25              30

Thr Thr Glu Val Tyr Val Lys Trp Lys Phe Lys Gly Arg Asp Ile Tyr
             35              40              45

Thr Phe Asp Gly Ala Leu Asn Lys Ser Thr Val Pro Thr Asp Phe Ser
     50              55              60

Ser Ala Lys Ile Glu Val Ser Gln Leu Leu Lys Gly Asp Ala Ser Leu
65              70              75              80

Lys Met Asp Lys Ser Asp Ala Val Ser His Thr Gly Asn Tyr Thr Cys
             85              90              95

Glu Val Thr Glu Leu Thr Arg Glu Gly Glu Thr Ile Ile Glu Leu Lys
             100             105             110

Tyr Arg Val Val Ser Trp Phe Ser Pro Asn Glu Asn Ile Leu Ile Val
             115             120             125

Ile Phe Pro Ile Phe Ala Ile Leu Leu Phe Trp Gly Gln Phe Gly Ile
             130             135             140

Lys Thr Leu Lys Tyr Arg Ser Gly Gly Met Asp Glu Lys Thr Ile Ala
145             150             155             160

Leu Leu Val Ala Gly Leu Val Ile Thr Val Ile Val Ile Val Gly Ala
             165             170             175
```

-continued

```
Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
            195                 200                 205

Val Phe Ser Thr Ala Ile Gly Leu Thr Ser Phe Val Ile Ala Ile Leu
            210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
            275                 280                 285

Glu Glu Pro Leu Asn
        290

<210> SEQ ID NO 179
<211> LENGTH: 109
<212> TYPE: PRT
<213> ORGANISM: Artificial Sequence
<220> FEATURE:
<223> OTHER INFORMATION: synthetic construct

<400> SEQUENCE: 179

Gln Leu Leu Phe Asn Lys Thr Lys Ser Val Glu Phe Thr Phe Cys Asn
1                 5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile
            100                 105

<210> SEQ ID NO 180
<211> LENGTH: 123
<212> TYPE: PRT
<213> ORGANISM: Homo sapiens

<400> SEQUENCE: 180

Gln Leu Leu Phe Asn Lys Thr Lys Ser Val Glu Phe Thr Phe Cys Asn
1                 5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
```

-continued

```
                    85                 90                 95
Glu Val Thr Glu Leu Thr Arg Glu Gly Glu Thr Ile Ile Glu Leu Lys
                  100                105                110
Tyr Arg Val Val Ser Trp Phe Ser Pro Asn Glu
              115                120

<210> SEQ ID NO 181
<211> LENGTH: 21
<212> TYPE: PRT
<213> ORGANISM: Homo sapiens

<400> SEQUENCE: 181

Asn Ile Leu Ile Val Ile Phe Pro Ile Phe Ala Ile Leu Leu Phe Trp
1               5                  10                 15
Gly Gln Phe Gly Ile
            20

<210> SEQ ID NO 182
<211> LENGTH: 14
<212> TYPE: PRT
<213> ORGANISM: Homo sapiens

<400> SEQUENCE: 182

Lys Thr Leu Lys Tyr Arg Ser Gly Gly Met Asp Glu Lys Thr
1               5                  10

<210> SEQ ID NO 183
<211> LENGTH: 21
<212> TYPE: PRT
<213> ORGANISM: Homo sapiens

<400> SEQUENCE: 183

Ile Ala Leu Leu Val Ala Gly Leu Val Ile Thr Val Ile Val Ile Val
1               5                  10                 15
Gly Ala Ile Leu Phe
            20

<210> SEQ ID NO 184
<211> LENGTH: 10
<212> TYPE: PRT
<213> ORGANISM: Homo sapiens

<400> SEQUENCE: 184

Val Pro Gly Glu Tyr Ser Leu Lys Asn Ala
1               5                  10

<210> SEQ ID NO 185
<211> LENGTH: 21
<212> TYPE: PRT
<213> ORGANISM: Homo sapiens

<400> SEQUENCE: 185

Thr Gly Leu Gly Leu Ile Val Thr Ser Thr Gly Ile Leu Ile Leu Leu
1               5                  10                 15
His Tyr Tyr Val Phe
            20

<210> SEQ ID NO 186
<211> LENGTH: 7
<212> TYPE: PRT
<213> ORGANISM: Homo sapiens

<400> SEQUENCE: 186
```

-continued

```
Ser Thr Ala Ile Gly Leu Thr
1               5

<210> SEQ ID NO 187
<211> LENGTH: 21
<212> TYPE: PRT
<213> ORGANISM: Homo sapiens

<400> SEQUENCE: 187

Ser Phe Val Ile Ala Ile Leu Val Ile Gln Val Ile Ala Tyr Ile Leu
1               5                   10                  15

Ala Val Val Gly Leu
            20

<210> SEQ ID NO 188
<211> LENGTH: 12
<212> TYPE: PRT
<213> ORGANISM: Homo sapiens

<400> SEQUENCE: 188

Ser Leu Cys Ile Ala Ala Cys Ile Pro Met His Gly
1               5                   10

<210> SEQ ID NO 189
<211> LENGTH: 21
<212> TYPE: PRT
<213> ORGANISM: Homo sapiens

<400> SEQUENCE: 189

Pro Leu Leu Ile Ser Gly Leu Ser Ile Leu Ala Leu Ala Gln Leu Leu
1               5                   10                  15

Gly Leu Val Tyr Met
            20

<210> SEQ ID NO 190
<211> LENGTH: 34
<212> TYPE: PRT
<213> ORGANISM: Homo sapiens

<400> SEQUENCE: 190

Lys Phe Val Ala Ser Asn Gln Lys Thr Ile Gln Pro Pro Arg Lys Ala
1               5                   10                  15

Val Glu Glu Pro Leu Asn Ala Phe Lys Glu Ser Lys Gly Met Met Asn
            20                  25                  30

Asp Glu

<210> SEQ ID NO 191
<211> LENGTH: 10
<212> TYPE: PRT
<213> ORGANISM: Homo sapiens

<400> SEQUENCE: 191

Val Lys Trp Lys Phe Lys Gly Arg Asp Ile
1               5                   10

<210> SEQ ID NO 192
<211> LENGTH: 117
<212> TYPE: PRT
<213> ORGANISM: Artificial Sequence
<220> FEATURE:
<223> OTHER INFORMATION: synthetic construct

<400> SEQUENCE: 192
```

-continued

```
Gln Val Gln Leu Gln Gln Ser Gly Pro Asp Leu Lys Lys Pro Gly Ala
1               5                   10                  15

Ser Val Lys Val Ser Cys Lys Val Ser Gly Tyr Thr Phe Thr Asn Tyr
                20                  25                  30

Val Ile His Trp Val Arg Gln Lys Pro Gly Gln Gly Leu Glu Trp Met
        35                  40                  45

Gly Tyr Ile Asn Pro Tyr Asn Asp Gly Thr Lys Ser Asn Glu Lys Phe
    50                  55                  60

Lys Gly Lys Ala Thr Leu Thr Ser Asp Lys Ser Ser Thr Ser Ala Tyr
65                  70                  75                  80

Met Glu Leu Ser Ser Leu Thr Ser Glu Asp Thr Ala Val Tyr Tyr Cys
                85                  90                  95

Ala Ser Gly Gly Tyr Tyr Thr Met Asp Tyr Trp Gly Gln Gly Thr Ser
            100                 105                 110

Val Thr Val Ser Ser
        115
```

<210> SEQ ID NO 193
<211> LENGTH: 8
<212> TYPE: PRT
<213> ORGANISM: Artificial Sequence
<220> FEATURE:
<223> OTHER INFORMATION: synthetic construct

<400> SEQUENCE: 193

```
Ile Asn Pro Tyr Asn Asp Gly Thr
1               5
```

<210> SEQ ID NO 194
<211> LENGTH: 10
<212> TYPE: PRT
<213> ORGANISM: Artificial Sequence
<220> FEATURE:
<223> OTHER INFORMATION: synthetic construct

<400> SEQUENCE: 194

```
Ala Ser Gly Gly Tyr Tyr Thr Met Asp Tyr
1               5                   10
```

<210> SEQ ID NO 195
<211> LENGTH: 25
<212> TYPE: PRT
<213> ORGANISM: Artificial Sequence
<220> FEATURE:
<223> OTHER INFORMATION: synthetic construct

<400> SEQUENCE: 195

```
Gln Val Gln Leu Gln Gln Ser Gly Pro Asp Leu Lys Lys Pro Gly Ala
1               5                   10                  15

Ser Val Lys Val Ser Cys Lys Val Ser
                20                  25
```

<210> SEQ ID NO 196
<211> LENGTH: 17
<212> TYPE: PRT
<213> ORGANISM: Artificial Sequence
<220> FEATURE:
<223> OTHER INFORMATION: synthetic construct

<400> SEQUENCE: 196

```
Ile His Trp Val Arg Gln Lys Pro Gly Gln Gly Leu Glu Trp Met Gly
1               5                   10                  15
```

-continued

Tyr

<210> SEQ ID NO 197
<211> LENGTH: 38
<212> TYPE: PRT
<213> ORGANISM: Artificial Sequence
<220> FEATURE:
<223> OTHER INFORMATION: synthetic construct

<400> SEQUENCE: 197

Lys Ser Asn Glu Lys Phe Lys Gly Lys Ala Thr Leu Thr Ser Asp Lys
1               5                   10                  15

Ser Ser Thr Ser Ala Tyr Met Glu Leu Ser Ser Leu Thr Ser Glu Asp
            20                  25                  30

Thr Ala Val Tyr Tyr Cys
        35

<210> SEQ ID NO 198
<211> LENGTH: 112
<212> TYPE: PRT
<213> ORGANISM: Artificial Sequence
<220> FEATURE:
<223> OTHER INFORMATION: synthetic construct

<400> SEQUENCE: 198

Asp Val Val Met Thr Gln Thr Pro Leu Ser Leu Pro Val Thr Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
            35                  40                  45

Pro Gln Leu Leu Ile Tyr Lys Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 199
<211> LENGTH: 11
<212> TYPE: PRT
<213> ORGANISM: Artificial Sequence
<220> FEATURE:
<223> OTHER INFORMATION: synthetic construct

<400> SEQUENCE: 199

Gln His Leu Glu Tyr Ser Asn Gly Tyr Ser Tyr
1               5                   10

<210> SEQ ID NO 200
<211> LENGTH: 3
<212> TYPE: PRT
<213> ORGANISM: Artificial Sequence
<220> FEATURE:
<223> OTHER INFORMATION: synthetic construct

<400> SEQUENCE: 200

Lys Ile Ser
1

-continued

<210> SEQ ID NO 201
<211> LENGTH: 9
<212> TYPE: PRT
<213> ORGANISM: Artificial Sequence
<220> FEATURE:
<223> OTHER INFORMATION: synthetic construct

<400> SEQUENCE: 201

Ser Gln Ser Thr His Val Pro Tyr Thr
1               5

<210> SEQ ID NO 202
<211> LENGTH: 26
<212> TYPE: PRT
<213> ORGANISM: Artificial Sequence
<220> FEATURE:
<223> OTHER INFORMATION: synthetic construct

<400> SEQUENCE: 202

Asp Val Val Met Thr Gln Thr Pro Leu Ser Leu Pro Val Thr Leu Gly
1               5                   10                  15

Asp Gln Ala Ser Ile Ser Cys Arg Ser Ser
            20                  25

<210> SEQ ID NO 203
<211> LENGTH: 17
<212> TYPE: PRT
<213> ORGANISM: Artificial Sequence
<220> FEATURE:
<223> OTHER INFORMATION: synthetic construct

<400> SEQUENCE: 203

Leu His Trp Tyr Gln Gln Arg Pro Gly Gln Ser Pro Gln Leu Leu Ile
1               5                   10                  15

Tyr

<210> SEQ ID NO 204
<211> LENGTH: 117
<212> TYPE: PRT
<213> ORGANISM: Artificial Sequence
<220> FEATURE:
<223> OTHER INFORMATION: synthetic construct

<400> SEQUENCE: 204

Glu Val Gln Leu Gln Gln Ser Gly Pro Asp Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Thr Lys Ser Asn Glu Lys Phe
    50                  55                  60

Lys Gly Lys Ala Thr Leu Thr Ser Asp Lys Ser Ser Thr Ser Ala Tyr
65                  70                  75                  80

Met Glu Leu Ser Ser Leu Thr Ser Glu Asp Ser Ala Val Tyr Tyr Cys
                85                  90                  95

Ala Ser Gly Gly Tyr Tyr Thr Met Asp Tyr Trp Gly Gln Gly Thr Ser
            100                 105                 110

Val Thr Val Ser Ser
        115

-continued

```
<210> SEQ ID NO 205
<211> LENGTH: 25
<212> TYPE: PRT
<213> ORGANISM: Artificial Sequence
<220> FEATURE:
<223> OTHER INFORMATION: synthetic construct

<400> SEQUENCE: 205

Glu Val Gln Leu Gln Gln Ser Gly Pro Asp Leu Val Lys Pro Gly Ala
1               5                   10                  15

Ser Val Lys Met Ser Cys Lys Ala Ser
            20                  25

<210> SEQ ID NO 206
<211> LENGTH: 38
<212> TYPE: PRT
<213> ORGANISM: Artificial Sequence
<220> FEATURE:
<223> OTHER INFORMATION: synthetic construct

<400> SEQUENCE: 206

Lys Ser Asn Glu Lys Phe Lys Gly Lys Ala Thr Leu Thr Ser Asp Lys
1               5                   10                  15

Ser Ser Thr Ser Ala Tyr Met Glu Leu Ser Ser Leu Thr Ser Glu Asp
            20                  25                  30

Ser Ala Val Tyr Tyr Cys
        35

<210> SEQ ID NO 207
<211> LENGTH: 112
<212> TYPE: PRT
<213> ORGANISM: Artificial Sequence
<220> FEATURE:
<223> OTHER INFORMATION: synthetic construct

<400> SEQUENCE: 207

Asp Val Val Met Thr Gln Thr Pro Leu Ser Leu Pro Val Ser Leu Gly
1               5                   10                  15

Asp Gln Ala Ser Ile Ser Cys Arg Ser Ser Gln His Leu Glu Tyr Ser
            20                  25                  30

Asn Gly Tyr Ser Tyr Leu His Trp Tyr Leu Gln Lys Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 208
<211> LENGTH: 26
<212> TYPE: PRT
<213> ORGANISM: Artificial Sequence
<220> FEATURE:
<223> OTHER INFORMATION: synthetic construct

<400> SEQUENCE: 208

Asp Val Val Met Thr Gln Thr Pro Leu Ser Leu Pro Val Ser Leu Gly
1               5                   10                  15

Asp Gln Ala Ser Ile Ser Cys Arg Ser Ser
```

```
                        20                   25

<210> SEQ ID NO 209
<211> LENGTH: 17
<212> TYPE: PRT
<213> ORGANISM: Artificial Sequence
<220> FEATURE:
<223> OTHER INFORMATION: synthetic construct

<400> SEQUENCE: 209

Leu His Trp Tyr Leu Gln Lys Pro Gly Gln Ser Pro Gln Leu Leu Ile
1               5                   10                  15

Tyr

<210> SEQ ID NO 210
<211> LENGTH: 36
<212> TYPE: PRT
<213> ORGANISM: Artificial Sequence
<220> FEATURE:
<223> OTHER INFORMATION: synthetic construct

<400> SEQUENCE: 210

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
                20                  25                  30

Val Tyr Phe Cys
        35

<210> SEQ ID NO 211
<211> LENGTH: 117
<212> TYPE: PRT
<213> ORGANISM: Artificial Sequence
<220> FEATURE:
<223> OTHER INFORMATION: synthetic construct

<400> SEQUENCE: 211

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Ile His Trp Val Arg Gln Ala Pro Gly Lys Gly Leu Glu Trp Met
            35                  40                  45

Gly Tyr Ile Asn Pro Tyr Asn Asp Gly Thr Lys Ser Asn Glu Lys Phe
        50                  55                  60

Lys Gly Arg Val Thr Leu Thr Ser Asp Lys Ser Ser Thr Ser Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser
        115

<210> SEQ ID NO 212
<211> LENGTH: 112
<212> TYPE: PRT
<213> ORGANISM: Artificial Sequence
<220> FEATURE:
<223> OTHER INFORMATION: synthetic construct

<400> SEQUENCE: 212
```

-continued

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110
```

```
<210> SEQ ID NO 213
<211> LENGTH: 117
<212> TYPE: PRT
<213> ORGANISM: Artificial Sequence
<220> FEATURE:
<223> OTHER INFORMATION: synthetic construct

<400> SEQUENCE: 213
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Lys Gly Leu Glu Trp Met
        35                  40                  45

Gly Tyr Ile Asn Pro Tyr Asn Asp Gly Thr Lys Ser Asn Glu Lys Phe
    50                  55                  60

Lys Gly Arg Val Thr Leu Thr Ser Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Thr Val Ser Ser
        115
```

```
<210> SEQ ID NO 214
<211> LENGTH: 113
<212> TYPE: PRT
<213> ORGANISM: Artificial Sequence
<220> FEATURE:
<223> OTHER INFORMATION: synthetic construct

<400> SEQUENCE: 214
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Ser Asn Glu Lys Phe
    50                  55                  60

Gln Gly Arg Val Thr Leu Thr Ser Asp Thr Ser Thr Ser Thr Ala Tyr
```

-continued

```
65                   70                   75                   80

Met Glu Leu Ser Ser Leu Arg Ser Glu Asp Thr Ala Val Tyr Tyr Cys
                 85                   90                   95

Ala Ser Gly Gly Tyr Tyr Thr Met Asp Tyr Trp Gly Gln Gly Thr Leu
                100                  105                  110

Val

<210> SEQ ID NO 215
<211> LENGTH: 113
<212> TYPE: PRT
<213> ORGANISM: Artificial Sequence
<220> FEATURE:
<223> OTHER INFORMATION: synthetic construct

<400> SEQUENCE: 215

Gln Val Gln Leu Val Gln Ser Gly Ala Glu Val Lys Lys Pro Gly Ala
1                 5                   10                  15

Ser Val Lys Val Ser Cys Lys Ala Ser Gly Tyr Thr Phe Thr Asn Tyr
                 20                   25                   30

Val Ile His Trp Val Arg Gln Ala Pro Gly Gln Gly Leu Glu Trp Met
          35                   40                   45

Gly Tyr Ile Asn Pro Tyr Asn Asp Gly Thr Lys Tyr Asn Gln Lys Phe
     50                   55                   60

Lys Gly Arg Val Thr Leu Thr Ser Asp Thr Ser Thr Thr Thr Ala Tyr
65                   70                   75                   80

Met Glu Leu Ser Arg Leu Arg Ser Asp Asp Thr Ala Val Tyr Tyr Cys
                 85                   90                   95

Ala Ser Gly Gly Tyr Tyr Thr Met Asp Tyr Trp Gly Gln Gly Thr Leu
                100                  105                  110

Val

<210> SEQ ID NO 216
<211> LENGTH: 117
<212> TYPE: PRT
<213> ORGANISM: Artificial Sequence
<220> FEATURE:
<223> OTHER INFORMATION: synthetic construct

<400> SEQUENCE: 216

Gln Val Gln Leu Val Gln Ser Gly Ala Glu Val Lys Lys Pro Gly Ala
1                 5                   10                  15

Ser Val Lys Val Ser Cys Lys Ala Ser Gly Tyr Thr Phe Thr Gly Tyr
                 20                   25                   30

Val Ile His Trp Val Arg Gln Ala Pro Gly Gln Gly Leu Glu Trp Met
          35                   40                   45

Gly Tyr Ile Asn Pro Tyr Asn Gly Gly Thr Asn Tyr Ala Gln Lys Phe
     50                   55                   60

Lys Gly Arg Val Thr Leu Thr Ser Asp Thr Ser Thr Thr Thr Ala Tyr
65                   70                   75                   80

Met Glu Leu Ser Arg Leu Arg Ser Glu Asp Thr Ala Val Tyr Tyr Cys
                 85                   90                   95

Ala Ser Gly Gly Tyr Tyr Thr Met Asp Tyr Trp Gly Gln Gly Thr Leu
                100                  105                  110

Val Thr Val Ser Ser
         115

<210> SEQ ID NO 217
```

```
<211> LENGTH: 112
<212> TYPE: PRT
<213> ORGANISM: Artificial Sequence
<220> FEATURE:
<223> OTHER INFORMATION: synthetic construct

<400> SEQUENCE: 217

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Gln Gly Tyr Ser Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 218
<211> LENGTH: 112
<212> TYPE: PRT
<213> ORGANISM: Artificial Sequence
<220> FEATURE:
<223> OTHER INFORMATION: synthetic construct

<400> SEQUENCE: 218

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Thr Gly Tyr Ser Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 219
<211> LENGTH: 112
<212> TYPE: PRT
<213> ORGANISM: Artificial Sequence
<220> FEATURE:
<223> OTHER INFORMATION: synthetic construct

<400> SEQUENCE: 219

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45
```

```
Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110
```

```
<210> SEQ ID NO 220
<211> LENGTH: 112
<212> TYPE: PRT
<213> ORGANISM: Artificial Sequence
<220> FEATURE:
<223> OTHER INFORMATION: synthetic construct

<400> SEQUENCE: 220
```

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
                20                  25                  30

Asn Gly Tyr Ser Tyr Leu His Trp Tyr Gln Gln Arg Pro Gly Gln Ser
            35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Val Pro Tyr Thr Phe Gly Gly Gly Thr Lys Val Glu Ile Lys
            100                 105                 110
```

```
<210> SEQ ID NO 221
<211> LENGTH: 8
<212> TYPE: PRT
<213> ORGANISM: Artificial Sequence
<220> FEATURE:
<223> OTHER INFORMATION: synthetic construct

<400> SEQUENCE: 221
```

```
Gly Tyr Thr Phe Thr Gly Tyr Val
1               5
```

```
<210> SEQ ID NO 222
<211> LENGTH: 8
<212> TYPE: PRT
<213> ORGANISM: Artificial Sequence
<220> FEATURE:
<223> OTHER INFORMATION: synthetic construct

<400> SEQUENCE: 222
```

```
Ile Asn Pro Tyr Asn Gly Gly Thr
1               5
```

```
<210> SEQ ID NO 223
<211> LENGTH: 11
<212> TYPE: PRT
<213> ORGANISM: Artificial Sequence
<220> FEATURE:
<223> OTHER INFORMATION: synthetic construct

<400> SEQUENCE: 223
```

```
Gln His Leu Glu Tyr Ser Gln Gly Tyr Ser Tyr
1               5                   10

<210> SEQ ID NO 224
<211> LENGTH: 11
<212> TYPE: PRT
<213> ORGANISM: Artificial Sequence
<220> FEATURE:
<223> OTHER INFORMATION: synthetic construct

<400> SEQUENCE: 224

Gln His Leu Glu Tyr Ser Thr Gly Tyr Ser Tyr
1               5                   10

<210> SEQ ID NO 225
<211> LENGTH: 3
<212> TYPE: PRT
<213> ORGANISM: Artificial Sequence
<220> FEATURE:
<223> OTHER INFORMATION: synthetic construct

<400> SEQUENCE: 225

Lys Val Ser
1

<210> SEQ ID NO 226
<211> LENGTH: 9
<212> TYPE: PRT
<213> ORGANISM: Artificial Sequence
<220> FEATURE:
<223> OTHER INFORMATION: synthetic construct

<400> SEQUENCE: 226

Ser Gln Gly Thr His Val Pro Tyr Thr
1               5

<210> SEQ ID NO 227
<211> LENGTH: 25
<212> TYPE: PRT
<213> ORGANISM: Artificial Sequence
<220> FEATURE:
<223> OTHER INFORMATION: synthetic construct

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 228
<211> LENGTH: 17
<212> TYPE: PRT
<213> ORGANISM: Artificial Sequence
<220> FEATURE:
<223> OTHER INFORMATION: synthetic construct

<400> SEQUENCE: 228

Ile His Trp Val Arg Gln Ala Pro Gly Lys Gly Leu Glu Trp Met Gly
1               5                   10                  15

Tyr

<210> SEQ ID NO 229
<211> LENGTH: 17
<212> TYPE: PRT
<213> ORGANISM: Artificial Sequence
<220> FEATURE:
```

<223> OTHER INFORMATION: synthetic construct

<400> SEQUENCE: 229

Met His Trp Val Arg Gln Ala Pro Gly Gln Gly Leu Glu Trp Met Gly
1               5                   10                  15

Tyr

<210> SEQ ID NO 230
<211> LENGTH: 17
<212> TYPE: PRT
<213> ORGANISM: Artificial Sequence
<220> FEATURE:
<223> OTHER INFORMATION: synthetic construct

<400> SEQUENCE: 230

Ile His Trp Val Arg Gln Ala Pro Gly Gln Gly Leu Glu Trp Met Gly
1               5                   10                  15

Tyr

<210> SEQ ID NO 231
<211> LENGTH: 38
<212> TYPE: PRT
<213> ORGANISM: Artificial Sequence
<220> FEATURE:
<223> OTHER INFORMATION: synthetic construct

<400> SEQUENCE: 231

Lys Ser Asn Glu Lys Phe Lys Gly Arg Val Thr Leu Thr Ser Asp Lys
1               5                   10                  15

Ser Ser Thr Ser Ala Tyr Met Glu Leu Ser Ser Leu Arg Ser Glu Asp
            20                  25                  30

Thr Ala Val Tyr Tyr Cys
        35

<210> SEQ ID NO 232
<211> LENGTH: 38
<212> TYPE: PRT
<213> ORGANISM: Artificial Sequence
<220> FEATURE:
<223> OTHER INFORMATION: synthetic construct

<400> SEQUENCE: 232

Lys Ser Asn Glu Lys Phe Lys Gly Arg Val Thr Leu Thr Ser Asp Thr
1               5                   10                  15

Ser Thr Thr Thr Ala Tyr Met Glu Leu Ser Ser Leu Arg Ser Glu Asp
            20                  25                  30

Thr Ala Val Tyr Tyr Cys
        35

<210> SEQ ID NO 233
<211> LENGTH: 38
<212> TYPE: PRT
<213> ORGANISM: Artificial Sequence
<220> FEATURE:
<223> OTHER INFORMATION: synthetic construct

<400> SEQUENCE: 233

Lys Ser Asn Glu Lys Phe Gln Gly Arg Val Thr Leu Thr Ser Asp Thr
1               5                   10                  15

Ser Thr Ser Thr Ala Tyr Met Glu Leu Ser Ser Leu Arg Ser Glu Asp
            20                  25                  30

Thr Ala Val Tyr Tyr Cys

-continued

35

```
<210> SEQ ID NO 234
<211> LENGTH: 38
<212> TYPE: PRT
<213> ORGANISM: Artificial Sequence
<220> FEATURE:
<223> OTHER INFORMATION: synthetic construct

<400> SEQUENCE: 234

Lys Tyr Asn Gln Lys Phe Lys Gly Arg Val Thr Leu Thr Ser Asp Thr
1               5                   10                  15

Ser Thr Thr Thr Ala Tyr Met Glu Leu Ser Arg Leu Arg Ser Asp Asp
            20                  25                  30

Thr Ala Val Tyr Tyr Cys
        35

<210> SEQ ID NO 235
<211> LENGTH: 38
<212> TYPE: PRT
<213> ORGANISM: Artificial Sequence
<220> FEATURE:
<223> OTHER INFORMATION: synthetic construct

<400> SEQUENCE: 235

Asn Tyr Ala Gln Lys Phe Lys Gly Arg Val Thr Leu Thr Ser Asp Thr
1               5                   10                  15

Ser Thr Thr Thr Ala Tyr Met Glu Leu Ser Arg Leu Arg Ser Glu Asp
            20                  25                  30

Thr Ala Val Tyr Tyr Cys
        35

<210> SEQ ID NO 236
<211> LENGTH: 11
<212> TYPE: PRT
<213> ORGANISM: Artificial Sequence
<220> FEATURE:
<223> OTHER INFORMATION: synthetic construct

<400> SEQUENCE: 236

Trp Gly Gln Gly Thr Leu Val Thr Val Ser Ser
1               5                   10

<210> SEQ ID NO 237
<211> LENGTH: 7
<212> TYPE: PRT
<213> ORGANISM: Artificial Sequence
<220> FEATURE:
<223> OTHER INFORMATION: synthetic construct

<400> SEQUENCE: 237

Trp Gly Gln Gly Thr Leu Val
1               5

<210> SEQ ID NO 238
<211> LENGTH: 26
<212> TYPE: PRT
<213> ORGANISM: Artificial Sequence
<220> FEATURE:
<223> OTHER INFORMATION: synthetic construct

<400> SEQUENCE: 238

Asp Val Val Met Thr Gln Ser Pro Leu Ser Leu Pro Val Thr Leu Gly
1               5                   10                  15
```

Gln Pro Ala Ser Ile Ser Cys Arg Ser Ser
            20                  25

<210> SEQ ID NO 239
<211> LENGTH: 17
<212> TYPE: PRT
<213> ORGANISM: Artificial Sequence
<220> FEATURE:
<223> OTHER INFORMATION: synthetic construct

<400> SEQUENCE: 239

Leu His Trp Tyr Gln Gln Arg Pro Gly Gln Ser Pro Arg Leu Leu Ile
1               5                   10                  15

Tyr

<210> SEQ ID NO 240
<211> LENGTH: 36
<212> TYPE: PRT
<213> ORGANISM: Artificial Sequence
<220> FEATURE:
<223> OTHER INFORMATION: synthetic construct

<400> SEQUENCE: 240

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 241
<211> LENGTH: 36
<212> TYPE: PRT
<213> ORGANISM: Artificial Sequence
<220> FEATURE:
<223> OTHER INFORMATION: synthetic construct

<400> SEQUENCE: 241

Asn Arg Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 242
<211> LENGTH: 10
<212> TYPE: PRT
<213> ORGANISM: Artificial Sequence
<220> FEATURE:
<223> OTHER INFORMATION: synthetic construct

<400> SEQUENCE: 242

Phe Gly Gly Gly Thr Lys Val Glu Ile Lys
1               5                   10

<210> SEQ ID NO 243
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)

-continued

```
<223> OTHER INFORMATION: Xaa = N or G

<400> SEQUENCE: 243

Gly Tyr Thr Phe Thr Xaa Tyr Val
1               5

<210> SEQ ID NO 244
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = D or G

<400> SEQUENCE: 244

Ile Asn Pro Tyr Asn Xaa Gly Thr
1               5

<210> SEQ ID NO 245
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: Xaa = N, Q or T

<400> SEQUENCE: 245

Gln His Leu Glu Tyr Ser Xaa Gly Tyr Ser Tyr
1               5                   10

<210> SEQ ID NO 246
<211> LENGTH: 3
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa = I or V

<400> SEQUENCE: 246

Lys Xaa Ser
1

<210> SEQ ID NO 247
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa = S or G

<400> SEQUENCE: 247

Ser Gln Xaa Thr His Val Pro Tyr Thr
1               5

<210> SEQ ID NO 248
<211> LENGTH: 17
<212> TYPE: PRT
```

-continued

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = I or M
<220> FEATURE:
<221> NAME/KEY: misc_feature
<222> LOCATION: (10)..(10)
<223> OTHER INFORMATION: Xaa = Q or K

<400> SEQUENCE: 248

Xaa His Trp Val Arg Gln Ala Pro Gly Xaa Gly Leu Glu Trp Met Gly
1               5                   10                  15

Tyr

<210> SEQ ID NO 249
<211> LENGTH: 37
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = K or N
<220> FEATURE:
<221> NAME/KEY: misc_feature
<222> LOCATION: (2)..(2)
<223> OTHER INFORMATION: Xaa = S or Y
<220> FEATURE:
<221> NAME/KEY: misc_feature
<222> LOCATION: (3)..(3)
<223> OTHER INFORMATION: Xaa = N or A
<220> FEATURE:
<221> NAME/KEY: misc_feature
<222> LOCATION: (4)..(4)
<223> OTHER INFORMATION: Xaa = E or Q
<220> FEATURE:
<221> NAME/KEY: misc_feature
<222> LOCATION: (7)..(7)
<223> OTHER INFORMATION: Xaa = K or Q
<220> FEATURE:
<221> NAME/KEY: misc_feature
<222> LOCATION: (15)..(15)
<223> OTHER INFORMATION: Xaa = T or K
<220> FEATURE:
<221> NAME/KEY: misc_feature
<222> LOCATION: (17)..(17)
<223> OTHER INFORMATION: Xaa = T or S
<220> FEATURE:
<221> NAME/KEY: misc_feature
<222> LOCATION: (19)..(19)
<223> OTHER INFORMATION: Xaa = T or S
<220> FEATURE:
<221> NAME/KEY: misc_feature
<222> LOCATION: (26)..(26)
<223> OTHER INFORMATION: Xaa = S or R
<220> FEATURE:
<221> NAME/KEY: misc_feature
<222> LOCATION: (30)..(30)
<223> OTHER INFORMATION: Xaa = E or D

<400> SEQUENCE: 249

Xaa Xaa Xaa Xaa Lys Phe Xaa Arg Val Thr Leu Thr Ser Asp Xaa Ser
1               5                   10                  15

Xaa Ser Xaa Ala Tyr Met Glu Leu Ser Xaa Leu Arg Ser Xaa Asp Thr
            20                  25                  30

Ala Val Tyr Tyr Cys
        35
```

-continued

```
<210> SEQ ID NO 250
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: Xaa = T or absent
<220> FEATURE:
<221> NAME/KEY: misc_feature
<222> LOCATION: (9)..(9)
<223> OTHER INFORMATION: Xaa = V or absent
<220> FEATURE:
<221> NAME/KEY: misc_feature
<222> LOCATION: (10)..(10)
<223> OTHER INFORMATION: Xaa = S or absent
<220> FEATURE:
<221> NAME/KEY: misc_feature
<222> LOCATION: (11)..(11)
<223> OTHER INFORMATION: Xaa = S or absent

<400> SEQUENCE: 250

Trp Gly Gln Gly Thr Leu Val Xaa Xaa Xaa Xaa
1               5                   10

<210> SEQ ID NO 251
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa = D or F

<400> SEQUENCE: 251

Asn Arg Xaa Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 252
<211> LENGTH: 117
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (31)..(31)
<223> OTHER INFORMATION: Xaa = N or G
<220> FEATURE:
<221> NAME/KEY: misc_feature
<222> LOCATION: (34)..(34)
<223> OTHER INFORMATION: Xaa = I or M
<220> FEATURE:
<221> NAME/KEY: misc_feature
<222> LOCATION: (43)..(43)
<223> OTHER INFORMATION: Xaa = Q or K
<220> FEATURE:
<221> NAME/KEY: misc_feature
<222> LOCATION: (56)..(56)
<223> OTHER INFORMATION: Xaa = D or G
<220> FEATURE:
<221> NAME/KEY: misc_feature
<222> LOCATION: (59)..(59)
<223> OTHER INFORMATION: Xaa = K or N
<220> FEATURE:
```

-continued

<221> NAME/KEY: misc_feature
<222> LOCATION: (60)..(60)
<223> OTHER INFORMATION: Xaa = S or Y
<220> FEATURE:
<221> NAME/KEY: misc_feature
<222> LOCATION: (61)..(61)
<223> OTHER INFORMATION: Xaa = N or A
<220> FEATURE:
<221> NAME/KEY: misc_feature
<222> LOCATION: (62)..(62)
<223> OTHER INFORMATION: Xaa = E or Q
<220> FEATURE:
<221> NAME/KEY: misc_feature
<222> LOCATION: (65)..(65)
<223> OTHER INFORMATION: Xaa = K or Q
<220> FEATURE:
<221> NAME/KEY: misc_feature
<222> LOCATION: (74)..(74)
<223> OTHER INFORMATION: Xaa = T or K
<220> FEATURE:
<221> NAME/KEY: misc_feature
<222> LOCATION: (76)..(76)
<223> OTHER INFORMATION: Xaa = T or S
<220> FEATURE:
<221> NAME/KEY: misc_feature
<222> LOCATION: (78)..(78)
<223> OTHER INFORMATION: Xaa = T or S
<220> FEATURE:
<221> NAME/KEY: misc_feature
<222> LOCATION: (85)..(85)
<223> OTHER INFORMATION: Xaa = S or R
<220> FEATURE:
<221> NAME/KEY: misc_feature
<222> LOCATION: (89)..(89)
<223> OTHER INFORMATION: Xaa = E or D
<220> FEATURE:
<221> NAME/KEY: misc_feature
<222> LOCATION: (114)..(114)
<223> OTHER INFORMATION: Xaa = T or absent
<220> FEATURE:
<221> NAME/KEY: misc_feature
<222> LOCATION: (115)..(115)
<223> OTHER INFORMATION: Xaa = V or absent
<220> FEATURE:
<221> NAME/KEY: misc_feature
<222> LOCATION: (116)..(116)
<223> OTHER INFORMATION: Xaa = S or absent
<220> FEATURE:
<221> NAME/KEY: misc_feature
<222> LOCATION: (117)..(117)
<223> OTHER INFORMATION: Xaa = S or absent

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Tyr
            20                  25                  30

Val Xaa His Trp Val Arg Gln Ala Pro Gly Xaa Gly Leu Glu Trp Met
        35                  40                  45

Gly Tyr Ile Asn Pro Tyr Asn Xaa Gly Thr Xaa Xaa Xaa Xaa Lys Phe
    50                  55                  60

Xaa Gly Arg Val Thr Leu Thr Ser Asp Xaa Ser Xaa Ser Xaa Ala Tyr
65                  70                  75                  80

Met Glu Leu Ser Xaa Leu Arg Ser Xaa Asp Thr Ala Val Tyr Tyr Cys
                85                  90                  95

Ala Ser Gly Gly Tyr Tyr Thr Met Asp Tyr Trp Gly Gln Gly Thr Leu
            100                 105                 110

Val Xaa Xaa Xaa Xaa
        115

```
<210> SEQ ID NO 253
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (33)..(33)
<223> OTHER INFORMATION: Xaa = N, Q or T
<220> FEATURE:
<221> NAME/KEY: misc_feature
<222> LOCATION: (56)..(56)
<223> OTHER INFORMATION: Xaa = I or V
<220> FEATURE:
<221> NAME/KEY: misc_feature
<222> LOCATION: (60)..(60)
<223> OTHER INFORMATION: Xaa = D or F
<220> FEATURE:
<221> NAME/KEY: misc_feature
<222> LOCATION: (96)..(96)
<223> OTHER INFORMATION: Xaa = S or G

<400> SEQUENCE: 253

Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Xaa Gly Tyr Ser Tyr Leu His Trp Tyr Gln Gln Arg Pro Gly Gln Ser
        35                  40                  45

Pro Arg Leu Leu Ile Tyr Lys Xaa Ser Asn Arg Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Xaa
                85                  90                  95

Thr His Val Pro Tyr Thr Phe Gly Gly Gly Thr Lys Val Glu Ile Lys
            100                 105                 110

<210> SEQ ID NO 254
<211> LENGTH: 330
<212> TYPE: PRT
<213> ORGANISM: Homo sapiens

<400> SEQUENCE: 254

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

-continued

```
        130              135              140

Val Val Val Asp Val Ser His Glu Asp Pro Glu Val Lys Phe Asn Trp
145              150              155              160

Tyr Val Asp Gly Val Glu Val His Asn Ala Lys Thr Lys Pro Arg Glu
                165              170              175

Glu Gln Tyr Asn Ser Thr Tyr Arg Val Val Ser Val Leu Thr Val Leu
            180              185              190

His Gln Asp Trp Leu Asn Gly Lys Glu Tyr Lys Cys Lys Val Ser Asn
        195              200              205

Lys Ala Leu Pro Ala Pro Ile Glu Lys Thr Ile Ser Lys Ala Lys Gly
        210              215              220

Gln Pro Arg Glu Pro Gln Val Tyr Thr Leu Pro Pro Ser Arg Asp Glu
225              230              235              240

Leu Thr Lys Asn Gln Val Ser Leu Thr Cys Leu Val Lys Gly Phe Tyr
                245              250              255

Pro Ser Asp Ile Ala Val Glu Trp Glu Ser Asn Gly Gln Pro Glu Asn
                260              265              270

Asn Tyr Lys Thr Thr Pro Pro Val Leu Asp Ser Asp Gly Ser Phe Phe
            275              280              285

Leu Tyr Ser Lys Leu Thr Val Asp Lys Ser Arg Trp Gln Gln Gly Asn
        290              295              300

Val Phe Ser Cys Ser Val Met His Glu Ala Leu His Asn His Tyr Thr
305              310              315              320

Gln Lys Ser Leu Ser Leu Ser Pro Gly Lys
            325              330
```

```
<210> SEQ ID NO 255
<211> LENGTH: 98
<212> TYPE: PRT
<213> ORGANISM: Artificial Sequence
<220> FEATURE:
<223> OTHER INFORMATION: synthetic construct

<400> SEQUENCE: 255

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val
```

```
<210> SEQ ID NO 256
<211> LENGTH: 12
<212> TYPE: PRT
<213> ORGANISM: Artificial Sequence
<220> FEATURE:
<223> OTHER INFORMATION: synthetic construct

<400> SEQUENCE: 256

Glu Pro Lys Ser Cys Asp Lys Thr His Thr Cys Pro
```

-continued

```
1                 5                 10
```

<210> SEQ ID NO 257
<211> LENGTH: 113
<212> TYPE: PRT
<213> ORGANISM: Artificial Sequence
<220> FEATURE:
<223> OTHER INFORMATION: synthetic construct

<400> SEQUENCE: 257

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 258
<211> LENGTH: 107
<212> TYPE: PRT
<213> ORGANISM: Artificial Sequence
<220> FEATURE:
<223> OTHER INFORMATION: synthetic construct

<400> SEQUENCE: 258

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 259
<211> LENGTH: 330
<212> TYPE: PRT
<213> ORGANISM: Homo sapiens

<400> SEQUENCE: 259

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30
```

-continued

_____

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 260
<211> LENGTH: 98
<212> TYPE: PRT
<213> ORGANISM: Artificial Sequence
<220> FEATURE:
<223> OTHER INFORMATION: synthetic construct

<400> SEQUENCE: 260

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 261
<211> LENGTH: 107
<212> TYPE: PRT
<213> ORGANISM: Artificial Sequence
<220> FEATURE:
<223> OTHER INFORMATION: synthetic construct

<400> SEQUENCE: 261

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 262
<211> LENGTH: 107
<212> TYPE: PRT
<213> ORGANISM: Artificial Sequence
<220> FEATURE:
<223> OTHER INFORMATION: synthetic construct

<400> SEQUENCE: 262

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 263
<211> LENGTH: 106
<212> TYPE: PRT
<213> ORGANISM: Artificial Sequence
<220> FEATURE:
<223> OTHER INFORMATION: synthetic construct -continued

```
<400> SEQUENCE: 263

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 264
<211> LENGTH: 106
<212> TYPE: PRT
<213> ORGANISM: Artificial Sequence
<220> FEATURE:
<223> OTHER INFORMATION: synthetic construct

<400> SEQUENCE: 264

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 265
<211> LENGTH: 106
<212> TYPE: PRT
<213> ORGANISM: Artificial Sequence
<220> FEATURE:
<223> OTHER INFORMATION: synthetic construct

<400> SEQUENCE: 265

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80
```

```
Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 266
<211> LENGTH: 106
<212> TYPE: PRT
<213> ORGANISM: Artificial Sequence
<220> FEATURE:
<223> OTHER INFORMATION: synthetic construct

<400> SEQUENCE: 266

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 267
<211> LENGTH: 106
<212> TYPE: PRT
<213> ORGANISM: Artificial Sequence
<220> FEATURE:
<223> OTHER INFORMATION: synthetic construct

<400> SEQUENCE: 267

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 268
<211> LENGTH: 12
<212> TYPE: PRT
<213> ORGANISM: Artificial Sequence
<220> FEATURE:
<223> OTHER INFORMATION: synthetic construct

<400> SEQUENCE: 268

```
Glu Pro Lys Ser Ser Asp Lys Thr His Thr Cys Pro
```

-continued 1                  5                    10

<210> SEQ ID NO 269
<211> LENGTH: 220
<212> TYPE: PRT
<213> ORGANISM: Artificial Sequence
<220> FEATURE:
<223> OTHER INFORMATION: synthetic construct

<400> SEQUENCE: 269

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Cys Arg
            115                 120                 125

Asp Glu Leu Thr Lys Asn Gln Val Ser Leu Trp Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 270
<211> LENGTH: 220
<212> TYPE: PRT
<213> ORGANISM: Artificial Sequence
<220> FEATURE:
<223> OTHER INFORMATION: synthetic construct

<400> SEQUENCE: 270

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

```
Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
           100                 105                 110

Lys Gly Gln Pro Arg Glu Pro Gln Val Cys Thr Leu Pro Pro Ser Arg
           115                 120                 125

Asp Glu Leu Thr Lys Asn Gln Val Ser Leu Ser Cys Ala Val Lys Gly
       130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
               165                 170                 175

Phe Phe Leu Val Ser Lys Leu Thr Val Asp Lys Ser Arg Trp Gln Gln
           180                 185                 190

Gly Asn Val Phe Ser Cys Ser Val Met His Glu Ala Leu His Asn His
           195                 200                 205

Tyr Thr Gln Lys Ser Leu Ser Leu Ser Pro Gly Lys
       210                 215                 220
```

<210> SEQ ID NO 271
<211> LENGTH: 220
<212> TYPE: PRT
<213> ORGANISM: Artificial Sequence
<220> FEATURE:
<223> OTHER INFORMATION: synthetic construct

<400> SEQUENCE: 271

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
           20                  25                  30

Thr Cys Val Val Val Asp Val Ser His Glu Asp Pro Glu Val Lys Phe
           35                  40                  45

Asn Trp Tyr Val Asp Gly Val Glu Val His Asn Ala Lys Thr Lys Pro
       50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
           100                 105                 110

Lys Gly Gln Pro Arg Glu Pro Gln Val Tyr Thr Leu Pro Pro Ser Arg
           115                 120                 125

Asp Glu Leu Thr Lys Asn Gln Val Ser Leu Thr Cys Leu Val Lys Gly
       130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
               165                 170                 175

Phe Phe Leu Tyr Ser Arg Leu Thr Val Asp Lys Ser Arg Trp Gln Gln
           180                 185                 190

Gly Asn Val Phe Ser Cys Ser Val Met His Glu Ala Leu His Asn His
           195                 200                 205

Tyr Thr Gln Lys Ser Leu Ser Leu Ser Pro Gly Lys
       210                 215                 220
```

-continued

```
<210> SEQ ID NO 272
<211> LENGTH: 232
<212> TYPE: PRT
<213> ORGANISM: Artificial Sequence
<220> FEATURE:
<223> OTHER INFORMATION: synthetic construct

<400> SEQUENCE: 272

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Cys Arg Asp Glu Leu Thr
        130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 273
<211> LENGTH: 232
<212> TYPE: PRT
<213> ORGANISM: Artificial Sequence
<220> FEATURE:
<223> OTHER INFORMATION: synthetic construct

<400> SEQUENCE: 273

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
               100                 105                 110

Leu Pro Ala Pro Ile Glu Lys Thr Ile Ser Lys Ala Lys Gly Gln Pro
               115                 120                 125

Arg Glu Pro Gln Val Cys Thr Leu Pro Pro Ser Arg Asp Glu Leu Thr
       130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
               165                 170                 175

Lys Thr Thr Pro Pro Val Leu Asp Ser Asp Gly Ser Phe Phe Leu Val
               180                 185                 190

Ser Lys Leu Thr Val Asp Lys Ser Arg Trp Gln Gln Gly Asn Val Phe
       195                 200                 205

Ser Cys Ser Val Met His Glu Ala Leu His Asn His Tyr Thr Gln Lys
       210                 215                 220

Ser Leu Ser Leu Ser Pro Gly Lys
225                 230

<210> SEQ ID NO 274
<211> LENGTH: 232
<212> TYPE: PRT
<213> ORGANISM: Artificial Sequence
<220> FEATURE:
<223> OTHER INFORMATION: synthetic construct

<400> SEQUENCE: 274

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
               20                  25                  30

Lys Asp Thr Leu Met Ile Ser Arg Thr Pro Glu Val Thr Cys Val Val
               35                  40                  45

Val Asp Val Ser His Glu Asp Pro Glu Val Lys Phe Asn Trp Tyr Val
       50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
               100                 105                 110

Leu Pro Ala Pro Ile Glu Lys Thr Ile Ser Lys Ala Lys Gly Gln Pro
               115                 120                 125

Arg Glu Pro Gln Val Tyr Thr Leu Pro Pro Ser Arg Asp Glu Leu Thr
       130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
               165                 170                 175

Lys Thr Thr Pro Pro Val Leu Asp Ser Asp Gly Ser Phe Phe Leu Tyr
               180                 185                 190

Ser Arg Leu Thr Val Asp Lys Ser Arg Trp Gln Gln Gly Asn Val Phe
       195                 200                 205
```

-continued

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 275
<211> LENGTH: 220
<212> TYPE: PRT
<213> ORGANISM: Artificial Sequence
<220> FEATURE:
<223> OTHER INFORMATION: synthetic construct

<400> SEQUENCE: 275

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Cys Arg
        115                 120                 125

Glu Glu Met Thr Lys Asn Gln Val Ser Leu Trp Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 276
<211> LENGTH: 220
<212> TYPE: PRT
<213> ORGANISM: Artificial Sequence
<220> FEATURE:
<223> OTHER INFORMATION: synthetic construct

<400> SEQUENCE: 276

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro

```
            50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Cys Thr Leu Pro Pro Ser Arg
                115                 120                 125

Glu Glu Met Thr Lys Asn Gln Val Ser Leu Ser Cys Ala Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Val Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
    210                 215                 220

<210> SEQ ID NO 277
<211> LENGTH: 220
<212> TYPE: PRT
<213> ORGANISM: Artificial Sequence
<220> FEATURE:
<223> OTHER INFORMATION: synthetic construct

<400> SEQUENCE: 277

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Glu Glu Met Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Gln
                180                 185                 190

Gly Asn Val Phe Ser Cys Ser Val Met His Glu Ala Leu His Asn His
```

-continued

```
            195                 200                 205

Tyr Thr Gln Lys Ser Leu Ser Leu Ser Pro Gly Lys
    210                 215                 220

<210> SEQ ID NO 278
<211> LENGTH: 232
<212> TYPE: PRT
<213> ORGANISM: Artificial Sequence
<220> FEATURE:
<223> OTHER INFORMATION: synthetic construct

<400> SEQUENCE: 278

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 279
<211> LENGTH: 232
<212> TYPE: PRT
<213> ORGANISM: Artificial Sequence
<220> FEATURE:
<223> OTHER INFORMATION: synthetic construct

<400> SEQUENCE: 279

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

-continued

```
Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Cys Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

```
<210> SEQ ID NO 280
<211> LENGTH: 232
<212> TYPE: PRT
<213> ORGANISM: Artificial Sequence
<220> FEATURE:
<223> OTHER INFORMATION: synthetic construct

<400> SEQUENCE: 280
```

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

-continued

```
Lys Thr Thr Pro Pro Val Leu Asp Ser Asp Gly Ser Phe Phe Leu Tyr
            180             185             190

Ser Arg Leu Thr Val Asp Lys Ser Arg Trp Gln Gln Gly Asn Val Phe
        195             200             205

Ser Cys Ser Val Met His Glu Ala Leu His Asn His Tyr Thr Gln Lys
        210             215             220

Ser Leu Ser Leu Ser Pro Gly Lys
225             230

<210> SEQ ID NO 281
<211> LENGTH: 250
<212> TYPE: PRT
<213> ORGANISM: Homo sapiens

<400> SEQUENCE: 281

Met Pro Ala Ser Ser Pro Phe Leu Leu Ala Pro Lys Gly Pro Pro Gly
1               5               10              15

Asn Met Gly Gly Pro Val Arg Glu Pro Ala Leu Ser Val Ala Leu Trp
            20              25              30

Leu Ser Trp Gly Ala Ala Leu Gly Ala Val Ala Cys Ala Met Ala Leu
        35              40              45

Leu Thr Gln Gln Thr Glu Leu Gln Ser Leu Arg Arg Glu Val Ser Arg
        50              55              60

Leu Gln Gly Thr Gly Gly Pro Ser Gln Asn Gly Glu Gly Tyr Pro Trp
65              70              75              80

Gln Ser Leu Pro Glu Gln Ser Ser Asp Ala Leu Glu Ala Trp Glu Asn
            85              90              95

Gly Glu Arg Ser Arg Lys Arg Arg Ala Val Leu Thr Gln Lys Gln Lys
            100             105             110

Lys Gln His Ser Val Leu His Leu Val Pro Ile Asn Ala Thr Ser Lys
        115             120             125

Asp Asp Ser Asp Val Thr Glu Val Met Trp Gln Pro Ala Leu Arg Arg
        130             135             140

Gly Arg Gly Leu Gln Ala Gln Gly Tyr Gly Val Arg Ile Gln Asp Ala
145             150             155             160

Gly Val Tyr Leu Leu Tyr Ser Gln Val Leu Phe Gln Asp Val Thr Phe
            165             170             175

Thr Met Gly Gln Val Val Ser Arg Glu Gly Gln Gly Arg Gln Glu Thr
            180             185             190

Leu Phe Arg Cys Ile Arg Ser Met Pro Ser His Pro Asp Arg Ala Tyr
        195             200             205

Asn Ser Cys Tyr Ser Ala Gly Val Phe His Leu His Gln Gly Asp Ile
        210             215             220

Leu Ser Val Ile Ile Pro Arg Ala Arg Ala Lys Leu Asn Leu Ser Pro
225             230             235             240

His Gly Thr Phe Leu Gly Phe Val Lys Leu
            245             250

<210> SEQ ID NO 282
<211> LENGTH: 234
<212> TYPE: PRT
<213> ORGANISM: Homo sapiens

<400> SEQUENCE: 282

Met Pro Ala Ser Ser Pro Phe Leu Leu Ala Pro Lys Gly Pro Pro Gly
1               5               10              15
```

-continued

```
Asn Met Gly Gly Pro Val Arg Glu Pro Ala Leu Ser Val Ala Leu Trp
        20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Asn Asp Ser Asp Val Thr Glu Val Met Trp Gln Pro Ala Leu Arg Arg
            115                 120                 125

Gly Arg Gly Leu Gln Ala Gln Gly Tyr Gly Val Arg Ile Gln Asp Ala
        130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
            180                 185                 190

Asn Ser Cys Tyr Ser Ala Gly Val Phe His Leu His Gln Gly Asp Ile
            195                 200                 205

Leu Ser Val Ile Ile Pro Arg Ala Arg Ala Lys Leu Asn Leu Ser Pro
        210                 215                 220

His Gly Thr Phe Leu Gly Phe Val Lys Leu
225                 230
```

```
<210> SEQ ID NO 283
<211> LENGTH: 247
<212> TYPE: PRT
<213> ORGANISM: Homo sapiens

<400> SEQUENCE: 283
```

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
        20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
            115                 120                 125

Asp Asp Ser Asp Val Thr Glu Val Met Trp Gln Pro Ala Leu Arg Arg
        130                 135                 140

Gly Arg Gly Leu Gln Ala Gln Gly Tyr Gly Val Arg Ile Gln Asp Ala
145                 150                 155                 160
```

```
Gly Val Tyr Leu Leu Tyr Ser Gln Val Leu Phe Gln Asp Val Thr Phe
            165             170             175

Thr Met Gly Gln Val Val Ser Arg Glu Gly Gln Gly Arg Gln Glu Thr
            180             185             190

Leu Phe Arg Cys Ile Arg Ser Met Pro Ser His Pro Asp Arg Ala Tyr
        195             200             205

Asn Ser Cys Tyr Ser Ala Gly Val Phe His Leu His Gln Gly Asp Ile
    210             215             220

Leu Ser Val Ile Ile Pro Arg Ala Arg Ala Lys Leu Asn Leu Ser Pro
225             230             235             240

His Gly Thr Phe Leu Gly Leu
            245

<210> SEQ ID NO 284
<211> LENGTH: 222
<212> TYPE: PRT
<213> ORGANISM: Homo sapiens

<400> SEQUENCE: 284

Met Pro Ala Ser Ser Pro Phe Leu Leu Ala Pro Lys Gly Pro Pro Gly
1               5               10              15

Asn Met Gly Gly Pro Val Arg Glu Pro Ala Leu Ser Val Ala Leu Trp
            20              25              30

Leu Ser Trp Gly Ala Ala Leu Gly Ala Val Ala Cys Ala Met Ala Leu
            35              40              45

Leu Thr Gln Gln Thr Glu Leu Gln Ser Leu Arg Arg Glu Val Ser Arg
    50              55              60

Leu Gln Gly Thr Gly Gly Pro Ser Gln Asn Gly Glu Gly Tyr Pro Trp
65              70              75              80

Gln Ser Leu Pro Glu Gln His Ser Val Leu His Leu Val Pro Ile Asn
            85              90              95

Ala Thr Ser Lys Asp Asp Ser Asp Val Thr Glu Val Met Trp Gln Pro
            100             105             110

Ala Leu Arg Arg Gly Arg Gly Leu Gln Ala Gln Gly Tyr Gly Val Arg
            115             120             125

Ile Gln Asp Ala Gly Val Tyr Leu Leu Tyr Ser Gln Val Leu Phe Gln
    130             135             140

Asp Val Thr Phe Thr Met Gly Gln Val Val Ser Arg Glu Gly Gln Gly
145             150             155             160

Arg Gln Glu Thr Leu Phe Arg Cys Ile Arg Ser Met Pro Ser His Pro
            165             170             175

Asp Arg Ala Tyr Asn Ser Cys Tyr Ser Ala Gly Val Phe His Leu His
            180             185             190

Gln Gly Asp Ile Leu Ser Val Ile Ile Pro Arg Ala Arg Ala Lys Leu
        195             200             205

Asn Leu Ser Pro His Gly Thr Phe Leu Gly Phe Val Lys Leu
    210             215             220

<210> SEQ ID NO 285
<211> LENGTH: 330
<212> TYPE: PRT
<213> ORGANISM: Homo sapiens

<400> SEQUENCE: 285

Met Ala Ala Arg Arg Ser Gln Arg Arg Arg Gly Arg Arg Gly Glu Pro
1               5               10              15
```

```
Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Ser Ser Asp Ala Leu Glu Ala Trp Glu Asn
                165                 170                 175

Gly Glu Arg Ser Arg Lys Arg Arg Ala Val Leu Thr Gln Lys Gln Lys
            180                 185                 190

Lys Gln His Ser Val Leu His Leu Val Pro Ile Asn Ala Thr Ser Lys
            195                 200                 205

Asp Asp Ser Asp Val Thr Glu Val Met Trp Gln Pro Ala Leu Arg Arg
    210                 215                 220

Gly Arg Gly Leu Gln Ala Gln Gly Tyr Gly Val Arg Ile Gln Asp Ala
225                 230                 235                 240

Gly Val Tyr Leu Leu Tyr Ser Gln Val Leu Phe Gln Asp Val Thr Phe
                245                 250                 255

Thr Met Gly Gln Val Val Ser Arg Glu Gly Gln Gly Arg Gln Glu Thr
            260                 265                 270

Leu Phe Arg Cys Ile Arg Ser Met Pro Ser His Pro Asp Arg Ala Tyr
            275                 280                 285

Asn Ser Cys Tyr Ser Ala Gly Val Phe His Leu His Gln Gly Asp Ile
    290                 295                 300

Leu Ser Val Ile Ile Pro Arg Ala Arg Ala Lys Leu Asn Leu Ser Pro
305                 310                 315                 320

His Gly Thr Phe Leu Gly Phe Val Lys Leu
                325                 330
```

```
<210> SEQ ID NO 286
<211> LENGTH: 205
<212> TYPE: PRT
<213> ORGANISM: Homo sapiens

<400> SEQUENCE: 286

Met Gly Gly Pro Val Arg Glu Pro Ala Leu Ser Val Ala Leu Trp Leu
1                   5                   10                  15

Ser Trp Gly Ala Ala Leu Gly Ala Val Ala Cys Ala Met Ala Leu Leu
            20                  25                  30

Thr Gln Gln Thr Glu Leu Gln Ser Leu Arg Arg Glu Val Ser Arg Leu
            35                  40                  45

Gln Gly Thr Gly Gly Pro Ser Gln Asn Gly Glu Gly Tyr Pro Trp Gln
```

-continued

```
        50              55              60

Ser Leu Pro Glu Gln His Ser Val Leu His Leu Val Pro Ile Asn Ala
65                  70                  75                  80

Thr Ser Lys Asp Asp Ser Asp Val Thr Glu Val Met Trp Gln Pro Ala
                85                  90                  95

Leu Arg Arg Gly Arg Gly Leu Gln Ala Gln Gly Tyr Gly Val Arg Ile
                100                 105                 110

Gln Asp Ala Gly Val Tyr Leu Leu Tyr Ser Gln Val Leu Phe Gln Asp
                115                 120                 125

Val Thr Phe Thr Met Gly Gln Val Val Ser Arg Glu Gly Gln Gly Arg
                130                 135                 140

Gln Glu Thr Leu Phe Arg Cys Ile Arg Ser Met Pro Ser His Pro Asp
145                 150                 155                 160

Arg Ala Tyr Asn Ser Cys Tyr Ser Ala Gly Val Phe His Leu His Gln
                165                 170                 175

Gly Asp Ile Leu Ser Val Ile Ile Pro Arg Ala Arg Ala Lys Leu Asn
                180                 185                 190

Leu Ser Pro His Gly Thr Phe Leu Gly Phe Val Lys Leu
                195                 200                 205

<210> SEQ ID NO 287
<211> LENGTH: 146
<212> TYPE: PRT
<213> ORGANISM: Homo sapiens

<400> SEQUENCE: 287

Ala Val Leu Thr Gln Lys Gln Lys Lys Gln His Ser Val Leu His Leu
1               5                   10                  15

Val Pro Ile Asn Ala Thr Ser Lys Asp Asp Ser Asp Val Thr Glu Val
                20                  25                  30

Met Trp Gln Pro Ala Leu Arg Arg Gly Arg Gly Leu Gln Ala Gln Gly
            35                  40                  45

Tyr Gly Val Arg Ile Gln Asp Ala Gly Val Tyr Leu Leu Tyr Ser Gln
        50                  55                  60

Val Leu Phe Gln Asp Val Thr Phe Thr Met Gly Gln Val Val Ser Arg
65                  70                  75                  80

Glu Gly Gln Gly Arg Gln Glu Thr Leu Phe Arg Cys Ile Arg Ser Met
                85                  90                  95

Pro Ser His Pro Asp Arg Ala Tyr Asn Ser Cys Tyr Ser Ala Gly Val
                100                 105                 110

Phe His Leu His Gln Gly Asp Ile Leu Ser Val Ile Ile Pro Arg Ala
                115                 120                 125

Arg Ala Lys Leu Asn Leu Ser Pro His Gly Thr Phe Leu Gly Phe Val
                130                 135                 140

Lys Leu
145

<210> SEQ ID NO 288
<211> LENGTH: 130
<212> TYPE: PRT
<213> ORGANISM: Homo sapiens

<400> SEQUENCE: 288

Ala Val Leu Thr Gln Lys Gln Lys Asn Asp Ser Asp Val Thr Glu Val
1               5                   10                  15

Met Trp Gln Pro Ala Leu Arg Arg Gly Arg Gly Leu Gln Ala Gln Gly
```

-continued

```
            20              25              30

Tyr Gly Val Arg Ile Gln Asp Ala Gly Val Tyr Leu Leu Tyr Ser Gln
        35              40              45

Val Leu Phe Gln Asp Val Thr Phe Thr Met Gly Gln Val Val Ser Arg
    50              55              60

Glu Gly Gln Gly Arg Gln Glu Thr Leu Phe Arg Cys Ile Arg Ser Met
65              70              75              80

Pro Ser His Pro Asp Arg Ala Tyr Asn Ser Cys Tyr Ser Ala Gly Val
            85              90              95

Phe His Leu His Gln Gly Asp Ile Leu Ser Val Ile Ile Pro Arg Ala
            100             105             110

Arg Ala Lys Leu Asn Leu Ser Pro His Gly Thr Phe Leu Gly Phe Val
            115             120             125

Lys Leu
    130
```

<210> SEQ ID NO 289
<211> LENGTH: 143
<212> TYPE: PRT
<213> ORGANISM: Homo sapiens

<400> SEQUENCE: 289

```
Ala Val Leu Thr Gln Lys Gln Lys Gln His Ser Val Leu His Leu
1               5               10              15

Val Pro Ile Asn Ala Thr Ser Lys Asp Asp Ser Asp Val Thr Glu Val
            20              25              30

Met Trp Gln Pro Ala Leu Arg Arg Gly Arg Gly Leu Gln Ala Gln Gly
            35              40              45

Tyr Gly Val Arg Ile Gln Asp Ala Gly Val Tyr Leu Leu Tyr Ser Gln
            50              55              60

Val Leu Phe Gln Asp Val Thr Phe Thr Met Gly Gln Val Val Ser Arg
65              70              75              80

Glu Gly Gln Gly Arg Gln Glu Thr Leu Phe Arg Cys Ile Arg Ser Met
            85              90              95

Pro Ser His Pro Asp Arg Ala Tyr Asn Ser Cys Tyr Ser Ala Gly Val
            100             105             110

Phe His Leu His Gln Gly Asp Ile Leu Ser Val Ile Ile Pro Arg Ala
            115             120             125

Arg Ala Lys Leu Asn Leu Ser Pro His Gly Thr Phe Leu Gly Leu
    130             135             140
```

<210> SEQ ID NO 290
<211> LENGTH: 146
<212> TYPE: PRT
<213> ORGANISM: Homo sapiens

<400> SEQUENCE: 290

```
Ala Val Leu Thr Gln Lys Gln Lys Gln His Ser Val Leu His Leu
1               5               10              15

Val Pro Ile Asn Ala Thr Ser Lys Asp Asp Ser Asp Val Thr Glu Val
            20              25              30

Met Trp Gln Pro Ala Leu Arg Arg Gly Arg Gly Leu Gln Ala Gln Gly
            35              40              45

Tyr Gly Val Arg Ile Gln Asp Ala Gly Val Tyr Leu Leu Tyr Ser Gln
    50              55              60

Val Leu Phe Gln Asp Val Thr Phe Thr Met Gly Gln Val Val Ser Arg
```

-continued

```
65              70              75              80

Glu Gly Gln Gly Arg Gln Glu Thr Leu Phe Arg Cys Ile Arg Ser Met
                85              90              95

Pro Ser His Pro Asp Arg Ala Tyr Asn Ser Cys Tyr Ser Ala Gly Val
            100             105             110

Phe His Leu His Gln Gly Asp Ile Leu Ser Val Ile Ile Pro Arg Ala
        115             120             125

Arg Ala Lys Leu Asn Leu Ser Pro His Gly Thr Phe Leu Gly Phe Val
    130             135             140

Lys Leu
145

<210> SEQ ID NO 291
<211> LENGTH: 285
<212> TYPE: PRT
<213> ORGANISM: Homo sapiens

<400> SEQUENCE: 291

Met Asp Asp Ser Thr Glu Arg Glu Gln Ser Arg Leu Thr Ser Cys Leu
1               5               10              15

Lys Lys Arg Glu Glu Met Lys Leu Lys Glu Cys Val Ser Ile Leu Pro
            20              25              30

Arg Lys Glu Ser Pro Ser Val Arg Ser Ser Lys Asp Gly Lys Leu Leu
        35              40              45

Ala Ala Thr Leu Leu Leu Ala Leu Leu Ser Cys Cys Leu Thr Val Val
    50              55              60

Ser Phe Tyr Gln Val Ala Ala Leu Gln Gly Asp Leu Ala Ser Leu Arg
65              70              75              80

Ala Glu Leu Gln Gly His His Ala Glu Lys Leu Pro Ala Gly Ala Gly
                85              90              95

Ala Pro Lys Ala Gly Leu Glu Glu Ala Pro Ala Val Thr Ala Gly Leu
            100             105             110

Lys Ile Phe Glu Pro Pro Ala Pro Gly Glu Gly Asn Ser Ser Gln Asn
        115             120             125

Ser Arg Asn Lys Arg Ala Val Gln Gly Pro Glu Glu Thr Val Thr Gln
    130             135             140

Asp Cys Leu Gln Leu Ile Ala Asp Ser Glu Thr Pro Thr Ile Gln Lys
145             150             155             160

Gly Ser Tyr Thr Phe Val Pro Trp Leu Leu Ser Phe Lys Arg Gly Ser
            165             170             175

Ala Leu Glu Glu Lys Glu Asn Lys Ile Leu Val Lys Glu Thr Gly Tyr
            180             185             190

Phe Phe Ile Tyr Gly Gln Val Leu Tyr Thr Asp Lys Thr Tyr Ala Met
        195             200             205

Gly His Leu Ile Gln Arg Lys Lys Val His Val Phe Gly Asp Glu Leu
    210             215             220

Ser Leu Val Thr Leu Phe Arg Cys Ile Gln Asn Met Pro Glu Thr Leu
225             230             235             240

Pro Asn Asn Ser Cys Tyr Ser Ala Gly Ile Ala Lys Leu Glu Glu Gly
            245             250             255

Asp Glu Leu Gln Leu Ala Ile Pro Arg Glu Asn Ala Gln Ile Ser Leu
            260             265             270

Asp Gly Asp Val Thr Phe Phe Gly Ala Leu Lys Leu Leu
        275             280             285
```

```
<210> SEQ ID NO 292
<211> LENGTH: 266
<212> TYPE: PRT
<213> ORGANISM: Homo sapiens

<400> SEQUENCE: 292

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
            245                 250                 255

Val Thr Phe Phe Gly Ala Leu Lys Leu Leu
            260                 265

<210> SEQ ID NO 293
<211> LENGTH: 164
<212> TYPE: PRT
<213> ORGANISM: Homo sapiens

<400> SEQUENCE: 293

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60
```

```
Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
        130                 135                 140

Asp Cys Leu Gln Leu Ile Ala Asp Ser Glu Thr Pro Thr Ile Gln Lys
145                 150                 155                 160

Gly Phe Ile Tyr

<210> SEQ ID NO 294
<211> LENGTH: 46
<212> TYPE: PRT
<213> ORGANISM: Homo sapiens

<400> SEQUENCE: 294

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys
        35                  40                  45

<210> SEQ ID NO 295
<211> LENGTH: 21
<212> TYPE: PRT
<213> ORGANISM: Homo sapiens

<400> SEQUENCE: 295

Leu Leu Ala Ala Thr Leu Leu Leu Ala Leu Leu Ser Cys Cys Leu Thr
1               5                   10                  15

Val Val Ser Phe Tyr
            20

<210> SEQ ID NO 296
<211> LENGTH: 218
<212> TYPE: PRT
<213> ORGANISM: Homo sapiens

<400> SEQUENCE: 296

Gln Val Ala Ala Leu Gln Gly Asp Leu Ala Ser Leu Arg Ala Glu Leu
1               5                   10                  15

Gln Gly His His Ala Glu Lys Leu Pro Ala Gly Ala Gly Ala Pro Lys
            20                  25                  30

Ala Gly Leu Glu Glu Ala Pro Ala Val Thr Ala Gly Leu Lys Ile Phe
        35                  40                  45

Glu Pro Pro Ala Pro Gly Glu Gly Asn Ser Ser Gln Asn Ser Arg Asn
    50                  55                  60

Lys Arg Ala Val Gln Gly Pro Glu Glu Thr Val Thr Gln Asp Cys Leu
65                  70                  75                  80

Gln Leu Ile Ala Asp Ser Glu Thr Pro Thr Ile Gln Lys Gly Ser Tyr
                85                  90                  95

Thr Phe Val Pro Trp Leu Leu Ser Phe Lys Arg Gly Ser Ala Leu Glu
            100                 105                 110
```

-continued

---

```
Glu Lys Glu Asn Lys Ile Leu Val Lys Glu Thr Gly Tyr Phe Phe Ile
        115                 120                 125

Tyr Gly Gln Val Leu Tyr Thr Asp Lys Thr Tyr Ala Met Gly His Leu
    130                 135                 140

Ile Gln Arg Lys Lys Val His Val Phe Gly Asp Glu Leu Ser Leu Val
145                 150                 155                 160

Thr Leu Phe Arg Cys Ile Gln Asn Met Pro Glu Thr Leu Pro Asn Asn
                165                 170                 175

Ser Cys Tyr Ser Ala Gly Ile Ala Lys Leu Glu Glu Gly Asp Glu Leu
                180                 185                 190

Gln Leu Ala Ile Pro Arg Glu Asn Ala Gln Ile Ser Leu Asp Gly Asp
        195                 200                 205

Val Thr Phe Phe Gly Ala Leu Lys Leu Leu
    210                 215
```

```
<210> SEQ ID NO 297
<211> LENGTH: 199
<212> TYPE: PRT
<213> ORGANISM: Homo sapiens

<400> SEQUENCE: 297
```

```
Gln Val Ala Ala Leu Gln Gly Asp Leu Ala Ser Leu Arg Ala Glu Leu
1               5                   10                  15

Gln Gly His His Ala Glu Lys Leu Pro Ala Gly Ala Gly Ala Pro Lys
                20                  25                  30

Ala Gly Leu Glu Glu Ala Pro Ala Val Thr Ala Gly Leu Lys Ile Phe
            35                  40                  45

Glu Pro Pro Ala Pro Gly Glu Gly Asn Ser Ser Gln Asn Ser Arg Asn
        50                  55                  60

Lys Arg Ala Val Gln Gly Pro Glu Glu Thr Gly Ser Tyr Thr Phe Val
65                  70                  75                  80

Pro Trp Leu Leu Ser Phe Lys Arg Gly Ser Ala Leu Glu Glu Lys Glu
                85                  90                  95

Asn Lys Ile Leu Val Lys Glu Thr Gly Tyr Phe Phe Ile Tyr Gly Gln
                100                 105                 110

Val Leu Tyr Thr Asp Lys Thr Tyr Ala Met Gly His Leu Ile Gln Arg
        115                 120                 125

Lys Lys Val His Val Phe Gly Asp Glu Leu Ser Leu Val Thr Leu Phe
        130                 135                 140

Arg Cys Ile Gln Asn Met Pro Glu Thr Leu Pro Asn Asn Ser Cys Tyr
145                 150                 155                 160

Ser Ala Gly Ile Ala Lys Leu Glu Glu Gly Asp Glu Leu Gln Leu Ala
                165                 170                 175

Ile Pro Arg Glu Asn Ala Gln Ile Ser Leu Asp Gly Asp Val Thr Phe
                180                 185                 190

Phe Gly Ala Leu Lys Leu Leu
        195
```

```
<210> SEQ ID NO 298
<211> LENGTH: 97
<212> TYPE: PRT
<213> ORGANISM: Homo sapiens

<400> SEQUENCE: 298
```

```
Gln Val Ala Ala Leu Gln Gly Asp Leu Ala Ser Leu Arg Ala Glu Leu
1               5                   10                  15
```

-continued

```
Gln Gly His His Ala Glu Lys Leu Pro Ala Gly Ala Gly Ala Pro Lys
            20                  25                  30

Ala Gly Leu Glu Glu Ala Pro Ala Val Thr Ala Gly Leu Lys Ile Phe
            35                  40                  45

Glu Pro Pro Ala Pro Gly Glu Gly Asn Ser Ser Gln Asn Ser Arg Asn
    50                  55                  60

Lys Arg Ala Val Gln Gly Pro Glu Glu Thr Val Thr Gln Asp Cys Leu
65                  70                  75                  80

Gln Leu Ile Ala Asp Ser Glu Thr Pro Thr Ile Gln Lys Gly Phe Ile
                85                  90                  95

Tyr

<210> SEQ ID NO 299
<211> LENGTH: 152
<212> TYPE: PRT
<213> ORGANISM: Homo sapiens

<400> SEQUENCE: 299

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
                20                  25                  30

Val Pro Trp Leu Leu Ser Phe Lys Arg Gly Ser Ala Leu Glu Glu Lys
            35                  40                  45

Glu Asn Lys Ile Leu Val Lys Glu Thr Gly Tyr Phe Phe Ile Tyr Gly
    50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
                100                 105                 110

Tyr Ser Ala Gly Ile Ala Lys Leu Glu Glu Gly Asp Glu Leu Gln Leu
            115                 120                 125

Ala Ile Pro Arg Glu Asn Ala Gln Ile Ser Leu Asp Gly Asp Val Thr
    130                 135                 140

Phe Phe Gly Ala Leu Lys Leu Leu
145                 150

<210> SEQ ID NO 300
<211> LENGTH: 133
<212> TYPE: PRT
<213> ORGANISM: Homo sapiens

<400> SEQUENCE: 300

Ala Val Gln Gly Pro Glu Glu Thr Gly Ser Tyr Thr Phe Val Pro Trp
1               5                   10                  15

Leu Leu Ser Phe Lys Arg Gly Ser Ala Leu Glu Glu Lys Glu Asn Lys
            20                  25                  30

Ile Leu Val Lys Glu Thr Gly Tyr Phe Phe Ile Tyr Gly Gln Val Leu
            35                  40                  45

Tyr Thr Asp Lys Thr Tyr Ala Met Gly His Leu Ile Gln Arg Lys Lys
    50                  55                  60

Val His Val Phe Gly Asp Glu Leu Ser Leu Val Thr Leu Phe Arg Cys
65                  70                  75                  80
```

```
Ile Gln Asn Met Pro Glu Thr Leu Pro Asn Asn Ser Cys Tyr Ser Ala
            85                  90                  95

Gly Ile Ala Lys Leu Glu Glu Gly Asp Glu Leu Gln Leu Ala Ile Pro
            100                 105                 110

Arg Glu Asn Ala Gln Ile Ser Leu Asp Gly Asp Val Thr Phe Phe Gly
        115                 120                 125

Ala Leu Lys Leu Leu
    130

<210> SEQ ID NO 301
<211> LENGTH: 31
<212> TYPE: PRT
<213> ORGANISM: Homo sapiens

<400> SEQUENCE: 301

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Phe Ile Tyr
            20                  25                  30

<210> SEQ ID NO 302
<211> LENGTH: 449
<212> TYPE: PRT
<213> ORGANISM: Artificial Sequence
<220> FEATURE:
<223> OTHER INFORMATION: synthetic construct

<400> SEQUENCE: 302

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Arg Gly Leu Glu Trp Ile
        35                  40                  45

Ala Tyr Ile Leu Pro Phe Asn Asp Val Thr Lys Tyr Asn Glu Lys Phe
    50                  55                  60

Lys Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
            85                  90                  95

Ala Arg Trp Glu Trp Asp Asp Gly Tyr Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

-continued

```
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 303
<211> LENGTH: 219
<212> TYPE: PRT
<213> ORGANISM: Artificial Sequence
<220> FEATURE:
<223> OTHER INFORMATION: synthetic construct

<400> SEQUENCE: 303

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
                20                  25                  30

Asn Gly Asn Thr Tyr Leu Asn Trp Tyr Leu Gln Lys Pro Gly Gln Ser
                35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Ser His Val Pro Phe Thr Phe Gly Ala Gly Thr Lys Leu Glu Leu Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 304
<211> LENGTH: 448
<212> TYPE: PRT
<213> ORGANISM: Artificial Sequence
<220> FEATURE:
<223> OTHER INFORMATION: synthetic construct

<400> SEQUENCE: 304

Glu Val Gln Leu Gln Gln Ser Gly Pro Glu Leu Val Lys Pro Gly Ser
1               5                   10                  15

Ser Val Lys Met Ser Cys Lys Ala Ser Gly Tyr Thr Phe Thr Asn Tyr
                20                  25                  30

Val Met His Trp Val Lys Gln Lys Pro Gly Gln Gly Leu Glu Trp Ile
            35                  40                  45

Gly Tyr Ile Leu Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Phe Ser Val Leu Thr Ser Glu Asp Ser Ala Val Tyr Tyr Cys
                85                  90                  95

Ala Arg Tyr Asp Tyr Glu Gly Ser Phe Asp Tyr Trp Gly Gln Gly Thr
            100                 105                 110

Ala Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 305
<211> LENGTH: 214
<212> TYPE: PRT
<213> ORGANISM: Artificial Sequence
<220> FEATURE:
<223> OTHER INFORMATION: synthetic construct

<400> SEQUENCE: 305

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Met
            35                  40                  45

Cys Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly Asn Thr Phe Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

-continued

```
Phe Asn Arg Gly Glu Cys
    210

<210> SEQ ID NO 306
<211> LENGTH: 451
<212> TYPE: PRT
<213> ORGANISM: Artificial Sequence
<220> FEATURE:
<223> OTHER INFORMATION: synthetic construct

<400> SEQUENCE: 306

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Val Leu Pro Tyr Asn Asp Val Ile Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Arg Trp Gly Asp Phe Asp Glu Gly Ile Trp Phe Pro Tyr Trp Gly
            100                 105                 110

Gln Gly Thr Leu Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350
```

-continued

```
Tyr Thr Leu Pro Pro Ser Arg Asp Glu Leu Thr Lys Asn Gln Val Ser
        355             360             365

Leu Thr Cys Leu Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro Gly Lys
    450

<210> SEQ ID NO 307
<211> LENGTH: 219
<212> TYPE: PRT
<213> ORGANISM: Artificial Sequence
<220> FEATURE:
<223> OTHER INFORMATION: synthetic construct

<400> SEQUENCE: 307

Asp Val Leu Met Thr Gln Thr Pro Leu Ser Leu Pro Val Ser Leu Gly
1               5               10              15

Asp His Ala Ser Val Ser Cys Arg Ser Ser Gln Ser Ile Val His Thr
            20              25              30

Asp Gly Asn Thr Tyr Leu Glu Trp Tyr Leu Gln Lys Pro Gly Gln Ser
        35              40              45

Pro Lys Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Tyr Cys Phe Gln Gly
            85              90              95

Ser His Val Pro Trp Thr Phe Gly Gly Gly Thr Lys Leu Glu Ile Lys
            100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
        180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215

<210> SEQ ID NO 308
<211> LENGTH: 453
<212> TYPE: PRT
<213> ORGANISM: Artificial Sequence
```

```
<220> FEATURE:
<223> OTHER INFORMATION: synthetic construct

<400> SEQUENCE: 308

Glu Val Met Leu Val Asp Ser Gly Gly Asn Leu Val Lys Pro Gly Gly
1               5                   10                  15

Ser Leu Lys Leu Ser Cys Ala Ala Ser Gly Phe Thr Phe Ser Asn Tyr
            20                  25                  30

Val Ile Ser Trp Val Arg Gln Thr Pro Glu Lys Arg Leu Glu Trp Val
        35                  40                  45

Ala Thr Ile Ser Thr Val Gly Thr Asn Thr Tyr Tyr Pro Asp Ser Val
    50                  55                  60

Arg Gly Arg Phe Thr Ile Ser Arg Asp Asn Ala Glu Asn Thr Leu Tyr
65                  70                  75                  80

Leu Gln Met Ser Ser Leu Arg Ser Glu Asp Thr Ala Ile Tyr Tyr Cys
                85                  90                  95

Ser Arg His Lys Tyr Gly Tyr Asp Asp Pro Ser Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450

<210> SEQ ID NO 309
<211> LENGTH: 221
<212> TYPE: PRT
<213> ORGANISM: Artificial Sequence
<220> FEATURE:
<223> OTHER INFORMATION: synthetic construct

<400> SEQUENCE: 309

Gln Leu Val Leu Thr Gln Ser Ser Ser Ala Ser Phe Ser Leu Gly Ala
1               5               10              15

Ser Ala Lys Leu Thr Cys Thr Leu Ser Ser Gln His Ser Thr Tyr Thr
            20              25              30

Ile Glu Trp Tyr Gln Gln Gln Pro Leu Lys Pro Pro Lys Tyr Val Met
            35              40              45

Glu Leu Lys Lys Asp Gly Ser His Ser Thr Gly Asp Gly Ile Pro Asp
    50              55              60

Arg Phe Ser Gly Ser Ser Ser Gly Ala Asp Arg Tyr Leu Ser Ile Ser
65              70              75              80

Asn Ile Gln Ala Glu Asp Glu Ala Ile Tyr Ile Cys Gly Val Gly Asp
            85              90              95

Thr Val Lys Glu Gln Phe Val Tyr Val Phe Gly Gly Gly Thr Lys Val
            100             105             110

Thr Val Leu Gly Gln Pro Lys Ala Asn Pro Thr Val Thr Leu Phe Pro
            115             120             125

Pro Ser Ser Glu Glu Leu Gln Ala Asn Lys Ala Thr Leu Val Cys Leu
    130             135             140

Ile Ser Asp Phe Tyr Pro Gly Ala Val Thr Val Ala Trp Lys Ala Asp
145             150             155             160

Gly Ser Pro Val Lys Ala Gly Val Glu Thr Thr Lys Pro Ser Lys Gln
            165             170             175

Ser Asn Asn Lys Tyr Ala Ala Ser Ser Tyr Leu Ser Leu Thr Pro Glu
            180             185             190

Gln Trp Lys Ser His Arg Ser Tyr Ser Cys Gln Val Thr His Glu Gly
            195             200             205

Ser Thr Val Glu Lys Thr Val Ala Pro Thr Glu Cys Ser
    210             215             220

<210> SEQ ID NO 310
<211> LENGTH: 445
<212> TYPE: PRT
<213> ORGANISM: Artificial Sequence
<220> FEATURE:
<223> OTHER INFORMATION: synthetic construct

<400> SEQUENCE: 310

Glu Val Gln Leu Gln Gln Ser Gly Pro Glu Leu Val Lys Pro Gly Ala
1               5               10              15

Ser Met Lys Ile Ser Cys Lys Ala Ser Gly Tyr Ser Phe Thr Gly Tyr
```

-continued

```
                20                25                30
Ile Met Asn Trp Val Lys Gln Ser His Gly Lys Asn Leu Glu Trp Ile
        35                40                45
Gly Leu Ile Asn Pro Tyr Asn Gly Asp Ser Ile Tyr Asn Gln Lys Phe
    50                55                60
Lys Gly Lys Ala Thr Leu Thr Val Asp Lys Ser Ser Ser Thr Ala Tyr
65                70                75                80
Met Glu Leu Phe Ser Leu Thr Ser Glu Asp Ser Thr Val Tyr Tyr Cys
                85                90                95
Ala Ala Gly Glu Glu Phe Ala Tyr Trp Gly Gln Gly Thr Leu Val Thr
            100               105               110
Val Ser Ala Ala Ser Thr Lys Gly Pro Ser Val Phe Pro Leu Ala Pro
        115               120               125
Ser Ser Lys Ser Thr Ser Gly Gly Thr Ala Ala Leu Gly Cys Leu Val
        130               135               140
Lys Asp Tyr Phe Pro Glu Pro Val Thr Val Ser Trp Asn Ser Gly Ala
145               150               155               160
Leu Thr Ser Gly Val His Thr Phe Pro Ala Val Leu Gln Ser Ser Gly
            165               170               175
Leu Tyr Ser Leu Ser Ser Val Val Thr Val Pro Ser Ser Ser Leu Gly
        180               185               190
Thr Gln Thr Tyr Ile Cys Asn Val Asn His Lys Pro Ser Asn Thr Lys
        195               200               205
Val Asp Lys Lys Val Glu Pro Lys Ser Cys Asp Lys Thr His Thr Cys
    210               215               220
Pro Pro Cys Pro Ala Pro Glu Leu Leu Gly Gly Pro Ser Val Phe Leu
225               230               235               240
Phe Pro Pro Lys Pro Lys Asp Thr Leu Met Ile Ser Arg Thr Pro Glu
            245               250               255
Val Thr Cys Val Val Val Asp Val Ser His Glu Asp Pro Glu Val Lys
            260               265               270
Phe Asn Trp Tyr Val Asp Gly Val Glu Val His Asn Ala Lys Thr Lys
    275               280               285
Pro Arg Glu Glu Gln Tyr Asn Ser Thr Tyr Arg Val Val Ser Val Leu
    290               295               300
Thr Val Leu His Gln Asp Trp Leu Asn Gly Lys Glu Tyr Lys Cys Lys
305               310               315               320
Val Ser Asn Lys Ala Leu Pro Ala Pro Ile Glu Lys Thr Ile Ser Lys
            325               330               335
Ala Lys Gly Gln Pro Arg Glu Pro Gln Val Tyr Thr Leu Pro Pro Ser
            340               345               350
Arg Asp Glu Leu Thr Lys Asn Gln Val Ser Leu Thr Cys Leu Val Lys
            355               360               365
Gly Phe Tyr Pro Ser Asp Ile Ala Val Glu Trp Glu Ser Asn Gly Gln
    370               375               380
Pro Glu Asn Asn Tyr Lys Thr Thr Pro Pro Val Leu Asp Ser Asp Gly
385               390               395               400
Ser Phe Phe Leu Tyr Ser Lys Leu Thr Val Asp Lys Ser Arg Trp Gln
            405               410               415
Gln Gly Asn Val Phe Ser Cys Ser Val Met His Glu Ala Leu His Asn
            420               425               430
His Tyr Thr Gln Lys Ser Leu Ser Leu Ser Pro Gly Lys
        435               440               445
```

-continued

```
<210> SEQ ID NO 311
<211> LENGTH: 214
<212> TYPE: PRT
<213> ORGANISM: Artificial Sequence
<220> FEATURE:
<223> OTHER INFORMATION: synthetic construct

<400> SEQUENCE: 311

Asp Ile Gln Met Thr Gln Thr Ser Ser Ser Leu Ser Ala Ser Leu Gly
1               5                   10                  15

Asp Arg Val Thr Ile Ser Cys Arg Ala Ser Gln Asp Ile Ser Ile Tyr
                20                  25                  30

Leu Asn Trp Phe Gln Gln Lys Pro Asp Gly Thr Val Lys Leu Leu Ile
            35                  40                  45

Tyr Phe Thr Ser Arg Leu His Pro Gly Val Pro Ser Arg Phe Ser Ala
    50                  55                  60

Ser Gly Ser Gly Thr Asp Tyr Ser Leu Thr Ile Ser His Leu Glu His
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 312
<211> LENGTH: 447
<212> TYPE: PRT
<213> ORGANISM: Artificial Sequence
<220> FEATURE:
<223> OTHER INFORMATION: synthetic construct

<400> SEQUENCE: 312

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile Tyr Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Asn Thr Leu Lys Asn Glu Asp Thr Ala Thr Tyr Phe Cys
```

```
                        85                    90                    95
Ser Ile Ser Tyr Tyr Tyr Ala Met Asp Tyr Trp Gly Gln Gly Thr Ser
            100                   105                   110
Val Thr Val Ser Ser Ala Ser Thr Lys Gly Pro Ser Val Phe Pro Leu
            115                   120                   125
Ala Pro Ser Ser Lys Ser Thr Ser Gly Gly Thr Ala Ala Leu Gly Cys
        130                   135                   140
Leu Val Lys Asp Tyr Phe Pro Glu Pro Val Thr Val Ser Trp Asn Ser
145                   150                   155                   160
Gly Ala Leu Thr Ser Gly Val His Thr Phe Pro Ala Val Leu Gln Ser
            165                   170                   175
Ser Gly Leu Tyr Ser Leu Ser Ser Val Val Thr Val Pro Ser Ser Ser
            180                   185                   190
Leu Gly Thr Gln Thr Tyr Ile Cys Asn Val Asn His Lys Pro Ser Asn
            195                   200                   205
Thr Lys Val Asp Lys Lys Val Glu Pro Lys Ser Cys Asp Lys Thr His
        210                   215                   220
Thr Cys Pro Pro Cys Pro Ala Pro Glu Leu Leu Gly Gly Pro Ser Val
225                   230                   235                   240
Phe Leu Phe Pro Pro Lys Pro Lys Asp Thr Leu Met Ile Ser Arg Thr
            245                   250                   255
Pro Glu Val Thr Cys Val Val Val Asp Val Ser His Glu Asp Pro Glu
            260                   265                   270
Val Lys Phe Asn Trp Tyr Val Asp Gly Val Glu Val His Asn Ala Lys
            275                   280                   285
Thr Lys Pro Arg Glu Glu Gln Tyr Asn Ser Thr Tyr Arg Val Val Ser
        290                   295                   300
Val Leu Thr Val Leu His Gln Asp Trp Leu Asn Gly Lys Glu Tyr Lys
305                   310                   315                   320
Cys Lys Val Ser Asn Lys Ala Leu Pro Ala Pro Ile Glu Lys Thr Ile
            325                   330                   335
Ser Lys Ala Lys Gly Gln Pro Arg Glu Pro Gln Val Tyr Thr Leu Pro
            340                   345                   350
Pro Ser Arg Asp Glu Leu Thr Lys Asn Gln Val Ser Leu Thr Cys Leu
            355                   360                   365
Val Lys Gly Phe Tyr Pro Ser Asp Ile Ala Val Glu Trp Glu Ser Asn
        370                   375                   380
Gly Gln Pro Glu Asn Asn Tyr Lys Thr Thr Pro Pro Val Leu Asp Ser
385                   390                   395                   400
Asp Gly Ser Phe Phe Leu Tyr Ser Lys Leu Thr Val Asp Lys Ser Arg
            405                   410                   415
Trp Gln Gln Gly Asn Val Phe Ser Cys Ser Val Met His Glu Ala Leu
            420                   425                   430
His Asn His Tyr Thr Gln Lys Ser Leu Ser Leu Ser Pro Gly Lys
            435                   440                   445
```

```
<210> SEQ ID NO 313
<211> LENGTH: 218
<212> TYPE: PRT
<213> ORGANISM: Artificial Sequence
<220> FEATURE:
<223> OTHER INFORMATION: synthetic construct

<400> SEQUENCE: 313

Asp Ile Val Leu Thr Gln Ser Pro Ala Ser Leu Ala Val Ser Leu Gly
```

-continued

```
1               5               10              15

Gln Arg Ala Thr Ile Ser Cys Arg Ala Ser Lys Ser Val Ser Thr Ser
            20              25              30

Gly Tyr Ser Phe Leu His Trp Tyr Gln Gln Lys Pro Gly Gln Pro Pro
            35              40              45

Lys Leu Leu Ile Tyr Phe Ala Ser Asn Leu Glu Ser Gly Val Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln His Ser Arg
                85              90              95

Glu Leu Pro Arg Thr Phe Gly Gly Gly Thr Lys Leu Glu Ile Lys Arg
            100             105             110

Thr Val Ala Ala Pro Ser Val Phe Ile Phe Pro Pro Ser Asp Glu Gln
            115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
                165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
            195             200             205

Val Thr Lys Ser Phe Asn Arg Gly Glu Cys
    210             215
```

<210> SEQ ID NO 314
<211> LENGTH: 447
<212> TYPE: PRT
<213> ORGANISM: Artificial Sequence
<220> FEATURE:
<223> OTHER INFORMATION: synthetic construct

<400> SEQUENCE: 314

```
Gln Ile Gln Leu Val Gln Ser Gly Pro Glu Leu Lys Lys Pro Gly Glu
1               5               10              15

Thr Val Lys Ile Ser Cys Met Ala Ser Gly Tyr Thr Phe Thr Asp Tyr
            20              25              30

Ser Val Arg Trp Val Lys Gln Ala Pro Gly Lys Gly Leu Glu Trp Met
            35              40              45

Gly Trp Ile Asn Thr Glu Thr Gly Glu Pro Thr Tyr Ala His Asp Phe
    50              55              60

Lys Gly Arg Phe Ala Phe Ser Leu Glu Thr Ser Ala Ser Thr Ala Tyr
65              70              75              80

Leu Gln Ile Asn Asn Leu Lys Asp Glu Asp Thr Ser Thr Tyr Phe Cys
                85              90              95

Ala Ile Ser Tyr Tyr Tyr Ala Leu Asp Tyr Trp Gly His Gly Thr Ser
            100             105             110

Val Thr Val Ser Ser Ala Ser Thr Lys Gly Pro Ser Val Phe Pro Leu
            115             120             125

Ala Pro Ser Ser Lys Ser Thr Ser Gly Gly Thr Ala Ala Leu Gly Cys
    130             135             140

Leu Val Lys Asp Tyr Phe Pro Glu Pro Val Thr Val Ser Trp Asn Ser
```

-continued

```
145                150                155                160

Gly Ala Leu Thr Ser Gly Val His Thr Phe Pro Ala Val Leu Gln Ser
                165                170                175

Ser Gly Leu Tyr Ser Leu Ser Ser Val Val Thr Val Pro Ser Ser Ser
                180                185                190

Leu Gly Thr Gln Thr Tyr Ile Cys Asn Val Asn His Lys Pro Ser Asn
                195                200                205

Thr Lys Val Asp Lys Lys Val Glu Pro Lys Ser Cys Asp Lys Thr His
        210                215                220

Thr Cys Pro Pro Cys Pro Ala Pro Glu Leu Leu Gly Gly Pro Ser Val
225                230                235                240

Phe Leu Phe Pro Pro Lys Pro Lys Asp Thr Leu Met Ile Ser Arg Thr
                245                250                255

Pro Glu Val Thr Cys Val Val Val Asp Val Ser His Glu Asp Pro Glu
                260                265                270

Val Lys Phe Asn Trp Tyr Val Asp Gly Val Glu Val His Asn Ala Lys
                275                280                285

Thr Lys Pro Arg Glu Glu Gln Tyr Asn Ser Thr Tyr Arg Val Val Ser
        290                295                300

Val Leu Thr Val Leu His Gln Asp Trp Leu Asn Gly Lys Glu Tyr Lys
305                310                315                320

Cys Lys Val Ser Asn Lys Ala Leu Pro Ala Pro Ile Glu Lys Thr Ile
                325                330                335

Ser Lys Ala Lys Gly Gln Pro Arg Glu Pro Gln Val Tyr Thr Leu Pro
                340                345                350

Pro Ser Arg Asp Glu Leu Thr Lys Asn Gln Val Ser Leu Thr Cys Leu
                355                360                365

Val Lys Gly Phe Tyr Pro Ser Asp Ile Ala Val Glu Trp Glu Ser Asn
        370                375                380

Gly Gln Pro Glu Asn Asn Tyr Lys Thr Thr Pro Pro Val Leu Asp Ser
385                390                395                400

Asp Gly Ser Phe Phe Leu Tyr Ser Lys Leu Thr Val Asp Lys Ser Arg
                405                410                415

Trp Gln Gln Gly Asn Val Phe Ser Cys Ser Val Met His Glu Ala Leu
                420                425                430

His Asn His Tyr Thr Gln Lys Ser Leu Ser Leu Ser Pro Gly Lys
        435                440                445

<210> SEQ ID NO 315
<211> LENGTH: 218
<212> TYPE: PRT
<213> ORGANISM: Artificial Sequence
<220> FEATURE:
<223> OTHER INFORMATION: synthetic construct

<400> SEQUENCE: 315

Asp Ile Val Leu Thr Gln Ser Pro Ala Ser Leu Thr Val Ser Leu Gly
1                5                10                15

Gln Arg Ala Thr Ile Ser Cys Arg Ala Ser Lys Ser Val Ser Thr Ser
                20                25                30

Gly Tyr Asn Phe Leu His Trp Tyr Gln Gln Lys Pro Gly Gln Pro Pro
                35                40                45

Lys Leu Leu Ile Tyr Leu Ala Ser Asn Leu Glu Ser Gly Ala Pro Ala
        50                55                60

Arg Phe Ser Gly Ser Gly Ser Gly Thr Asp Phe Thr Leu Asn Ile His
```

-continued

```
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 316
<211> LENGTH: 447
<212> TYPE: PRT
<213> ORGANISM: Artificial Sequence
<220> FEATURE:
<223> OTHER INFORMATION: synthetic construct

<400> SEQUENCE: 316

Gln Ile Gln Leu Val Gln Ser Gly Pro Glu Leu Lys Lys Pro Gly Glu
1               5                   10                  15

Thr Val Lys Ile Ser Cys Met Ala Ser Gly Tyr Thr Phe Thr Asp Tyr
            20                  25                  30

Ser Val Arg Trp Val Lys Gln Ala Pro Gly Lys Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ile Ser Tyr Tyr Tyr Ala Leu Asp Tyr Trp Gly His Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
```

```
            210             215             220
Thr Cys Pro Pro Cys Pro Ala Pro Glu Leu Leu Gly Gly Pro Ser Val
225                 230             235             240

Phe Leu Phe Pro Pro Lys Pro Lys Asp Thr Leu Met Ile Ser Arg Thr
            245             250             255

Pro Glu Val Thr Cys Val Val Val Asp Val Ser His Glu Asp Pro Glu
            260             265             270

Val Lys Phe Asn Trp Tyr Val Asp Gly Val Glu Val His Asn Ala Lys
        275             280             285

Thr Lys Pro Arg Glu Glu Gln Tyr Asn Ser Thr Tyr Arg Val Val Ser
        290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
            325             330             335

Ser Lys Ala Lys Gly Gln Pro Arg Glu Pro Gln Val Tyr Thr Leu Pro
            340             345             350

Pro Ser Arg Asp Glu Leu Thr Lys Asn Gln Val Ser Leu Thr Cys Leu
        355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys
            435             440             445
```

<210> SEQ ID NO 317
<211> LENGTH: 218
<212> TYPE: PRT
<213> ORGANISM: Artificial Sequence
<220> FEATURE:
<223> OTHER INFORMATION: synthetic construct

<400> SEQUENCE: 317

```
Asp Ile Val Leu Thr Gln Ser Pro Ala Ser Leu Thr Val Ser Leu Gly
1               5               10              15

Gln Arg Ala Thr Ile Ser Cys Arg Ala Ser Lys Ser Val Ser Thr Ser
            20              25              30

Val Tyr Ser Phe Leu His Trp Tyr Gln Gln Lys Pro Gly Gln Pro Pro
        35              40              45

Lys Leu Leu Ile Tyr Leu Ala Ser Asn Leu Glu Ser Gly Val Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln His Ser Arg
            85              90              95

Glu Leu Pro Arg Thr Phe Gly Gly Gly Thr Lys Leu Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
```

-continued

```
          130              135              140

Pro Arg Glu Ala Lys Val Gln Trp Lys Val Asp Asn Ala Leu Gln Ser
145              150              155              160

Gly Asn Ser Gln Glu Ser Val Thr Glu Gln Asp Ser Lys Asp Ser Thr
              165              170              175

Tyr Ser Leu Ser Ser Thr Leu Thr Leu Ser Lys Ala Asp Tyr Glu Lys
              180              185              190

His Lys Val Tyr Ala Cys Glu Val Thr His Gln Gly Leu Ser Ser Pro
              195              200              205

Val Thr Lys Ser Phe Asn Arg Gly Glu Cys
      210              215

<210> SEQ ID NO 318
<211> LENGTH: 447
<212> TYPE: PRT
<213> ORGANISM: Artificial Sequence
<220> FEATURE:
<223> OTHER INFORMATION: synthetic construct

<400> SEQUENCE: 318

Gln Ile Gln Leu Val Gln Ser Gly Pro Glu Leu Lys Lys Pro Gly Glu
1               5               10              15

Thr Val Lys Ile Ser Cys Lys Ala Ser Gly Tyr Thr Phe Thr Asp Tyr
              20              25              30

Thr Met Tyr Trp Val Lys Gln Ala Pro Gly Lys Gly Leu Lys Trp Met
              35              40              45

Gly Trp Ile Asn Thr Glu Thr Gly Glu Pro Thr Tyr Ala Asp Asp Phe
      50              55              60

Lys Gly Arg Phe Val Phe Ser Leu Glu Thr Ser Ala Asn Thr Ala Tyr
65              70              75              80

Leu Gln Ile Asn Asn Leu Lys Asn Glu Asp Thr Ala Thr Tyr Phe Cys
              85              90              95

Ala Ile Ser Tyr Tyr Tyr Gly Met Asp Tyr Trp Gly Gln Gly Thr Ser
              100             105             110

Val Thr Val Thr Ser Ala Ser Thr Lys Gly Pro Ser Val Phe Pro Leu
              115             120             125

Ala Pro Ser Ser Lys Ser Thr Ser Gly Gly Thr Ala Ala Leu Gly Cys
      130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
              165             170             175

Ser Gly Leu Tyr Ser Leu Ser Ser Val Val Thr Val Pro Ser Ser Ser
              180             185             190

Leu Gly Thr Gln Thr Tyr Ile Cys Asn Val Asn His Lys Pro Ser Asn
              195             200             205

Thr Lys Val Asp Lys Lys Val Glu Pro Lys Ser Cys Asp Lys Thr His
      210             215             220

Thr Cys Pro Pro Cys Pro Ala Pro Glu Leu Leu Gly Gly Pro Ser Val
225             230             235             240

Phe Leu Phe Pro Pro Lys Pro Lys Asp Thr Leu Met Ile Ser Arg Thr
              245             250             255

Pro Glu Val Thr Cys Val Val Val Asp Val Ser His Glu Asp Pro Glu
              260             265             270

Val Lys Phe Asn Trp Tyr Val Asp Gly Val Glu Val His Asn Ala Lys
```

-continued

```
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 319
<211> LENGTH: 218
<212> TYPE: PRT
<213> ORGANISM: Artificial Sequence
<220> FEATURE:
<223> OTHER INFORMATION: synthetic construct

<400> SEQUENCE: 319

Asp Ile Ile Leu Thr Gln Ser Pro Ala Ser Leu Ala Val Ser Leu Gly
1               5                   10                  15

Gln Arg Ala Thr Ile Thr Cys Arg Ala Ser Lys Ser Val Ser Thr Ser
                20                  25                  30

Gly Tyr Asn Phe Val Tyr Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
```

-continued

```
            195                 200                 205

Val Thr Lys Ser Phe Asn Arg Gly Glu Cys
    210                 215

<210> SEQ ID NO 320
<211> LENGTH: 449
<212> TYPE: PRT
<213> ORGANISM: Artificial Sequence
<220> FEATURE:
<223> OTHER INFORMATION: synthetic construct

<400> SEQUENCE: 320

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Arg Gly Leu Glu Trp Ile
        35                  40                  45

Ala Tyr Ile Leu Pro Phe Asn Asp Val Thr Lys Tyr Asn Glu Lys Phe
    50                  55                  60

Lys Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Glu Trp Asp Asp Gly Tyr Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

-continued

```
                  340              345              350
Leu Pro Pro Cys Arg Asp Glu Leu Thr Lys Asn Gln Val Ser Leu Trp
              355              360              365
Cys Leu Val Lys Gly Phe Tyr Pro Ser Asp Ile Ala Val Glu Trp Glu
          370              375              380
Ser Asn Gly Gln Pro Glu Asn Asn Tyr Lys Thr Thr Pro Pro Val Leu
385              390              395              400
Asp Ser Asp Gly Ser Phe Phe Leu Tyr Ser Lys Leu Thr Val Asp Lys
              405              410              415
Ser Arg Trp Gln Gln Gly Asn Val Phe Ser Cys Ser Val Met His Glu
          420              425              430
Ala Leu His Asn His Tyr Thr Gln Lys Ser Leu Ser Leu Ser Pro Gly
          435              440              445
Lys
```

```
<210> SEQ ID NO 321
<211> LENGTH: 448
<212> TYPE: PRT
<213> ORGANISM: Artificial Sequence
<220> FEATURE:
<223> OTHER INFORMATION: synthetic construct

<400> SEQUENCE: 321

Glu Val Gln Leu Gln Gln Ser Gly Pro Glu Leu Val Lys Pro Gly Ser
1               5               10              15
Ser Val Lys Met Ser Cys Lys Ala Ser Gly Tyr Thr Phe Thr Asn Tyr
              20              25              30
Val Met His Trp Val Lys Gln Lys Pro Gly Gln Gly Leu Glu Trp Ile
          35              40              45
Gly Tyr Ile Leu Pro Tyr Asn Asp Gly Thr Lys Tyr Asn Glu Lys Phe
      50              55              60
Lys Gly Lys Ala Thr Leu Thr Ser Asp Lys Ser Ser Ser Thr Ala Tyr
65              70              75              80
Met Glu Phe Ser Val Leu Thr Ser Glu Asp Ser Ala Val Tyr Tyr Cys
              85              90              95
Ala Arg Tyr Asp Tyr Glu Gly Ser Phe Asp Tyr Trp Gly Gln Gly Thr
              100             105             110
Ala Leu Thr Val Ser Ser Ala Ser Thr Lys Gly Pro Ser Val Phe Pro
          115             120             125
Leu Ala Pro Ser Ser Lys Ser Thr Ser Gly Gly Thr Ala Ala Leu Gly
          130             135             140
Cys Leu Val Lys Asp Tyr Phe Pro Glu Pro Val Thr Val Ser Trp Asn
145             150             155             160
Ser Gly Ala Leu Thr Ser Gly Val His Thr Phe Pro Ala Val Leu Gln
              165             170             175
Ser Ser Gly Leu Tyr Ser Leu Ser Ser Val Val Thr Val Pro Ser Ser
              180             185             190
Ser Leu Gly Thr Gln Thr Tyr Ile Cys Asn Val Asn His Lys Pro Ser
          195             200             205
Asn Thr Lys Val Asp Lys Lys Val Glu Pro Lys Ser Cys Asp Lys Thr
      210             215             220
His Thr Cys Pro Pro Cys Pro Ala Pro Glu Leu Leu Gly Gly Pro Ser
225             230             235             240
Val Phe Leu Phe Pro Pro Lys Pro Lys Asp Thr Leu Met Ile Ser Arg
              245             250             255
```

-continued

```
Thr Pro Glu Val Thr Cys Val Val Val Asp Val Ser His Glu Asp Pro
        260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
        290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Cys Arg Asp Glu Leu Thr Lys Asn Gln Val Ser Leu Trp Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
        435             440             445
```

```
<210> SEQ ID NO 322
<211> LENGTH: 451
<212> TYPE: PRT
<213> ORGANISM: Artificial Sequence
<220> FEATURE:
<223> OTHER INFORMATION: synthetic construct

<400> SEQUENCE: 322
```

```
Glu Val Gln Leu Gln Gln Ser Gly Pro Glu Leu Val Lys Pro Gly Ala
1               5               10              15

Ser Val Lys Met Ser Cys Lys Ala Ser Gly Tyr Thr Phe Thr Ser Tyr
            20              25              30

Val Ile His Trp Val Lys Gln Lys Pro Gly Gln Gly Leu Glu Trp Ile
        35              40              45

Gly Tyr Val Leu Pro Tyr Asn Asp Val Ile Lys Tyr Asn Glu Lys Phe
        50              55              60

Lys Gly Lys Ala Thr Leu Thr Ser Asp Lys Ser Ser Ser Thr Ala Tyr
65              70              75              80

Met Asp Leu Ser Ser Leu Thr Ser Glu Asp Ser Ala Val Tyr Tyr Cys
            85              90              95

Ala Arg Trp Gly Asp Phe Asp Glu Gly Ile Trp Phe Pro Tyr Trp Gly
            100             105             110

Gln Gly Thr Leu Val Thr Val Ser Ala Ala Ser Thr Lys Gly Pro Ser
        115             120             125

Val Phe Pro Leu Ala Pro Ser Ser Lys Ser Thr Ser Gly Gly Thr Ala
        130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175
```

-continued

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
            355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

```
<210> SEQ ID NO 323
<211> LENGTH: 453
<212> TYPE: PRT
<213> ORGANISM: Artificial Sequence
<220> FEATURE:
<223> OTHER INFORMATION: synthetic construct

<400> SEQUENCE: 323

Glu Val Met Leu Val Asp Ser Gly Gly Asn Leu Val Lys Pro Gly Gly
1               5                   10                  15

Ser Leu Lys Leu Ser Cys Ala Ala Ser Gly Phe Thr Phe Ser Asn Tyr
            20                  25                  30

Val Ile Ser Trp Val Arg Gln Thr Pro Glu Lys Arg Leu Glu Trp Val
            35                  40                  45

Ala Thr Ile Ser Thr Val Gly Thr Asn Thr Tyr Tyr Pro Asp Ser Val
    50                  55                  60

Arg Gly Arg Phe Thr Ile Ser Arg Asp Asn Ala Glu Asn Thr Leu Tyr
65                  70                  75                  80
```

-continued

```
Leu Gln Met Ser Ser Leu Arg Ser Glu Asp Thr Ala Ile Tyr Tyr Cys
            85                  90                  95

Ser Arg His Lys Tyr Gly Tyr Asp Asp Pro Ser Tyr Ala Met Asp Tyr
            100                 105                 110

Trp Gly Gln Gly Thr Ser Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450
```

<210> SEQ ID NO 324
<211> LENGTH: 445
<212> TYPE: PRT
<213> ORGANISM: Artificial Sequence
<220> FEATURE:

<223> OTHER INFORMATION: synthetic construct

<400> SEQUENCE: 324

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Asp Ser Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Phe Ser Leu Thr Ser Glu Asp Ser Thr Val Tyr Tyr Cys
                85                  90                  95

Ala Ala Gly Glu Glu Phe Ala Tyr Trp Gly Gln Gly Thr Leu Val Thr
                100                 105                 110

Val Ser Ala Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
                340                 345                 350

Arg Asp Glu Leu Thr Lys Asn Gln Val Ser Leu Trp Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

-continued

```
Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly Lys
        435             440             445

<210> SEQ ID NO 325
<211> LENGTH: 447
<212> TYPE: PRT
<213> ORGANISM: Artificial Sequence
<220> FEATURE:
<223> OTHER INFORMATION: synthetic construct

<400> SEQUENCE: 325

Gln Ile Gln Leu Val Gln Ser Gly Pro Glu Leu Lys Lys Pro Gly Glu
1               5               10              15

Thr Val Lys Ile Ser Cys Lys Ala Ser Gly Tyr Thr Phe Thr Asp Tyr
            20              25              30

Ser Ile Tyr Trp Val Lys Gln Ala Pro Gly Lys Gly Leu Lys Trp Met
        35              40              45

Gly Trp Ile Asn Thr Glu Thr Gly Glu Pro Thr Tyr Ala Asp Asp Phe
    50              55              60

Lys Gly Arg Phe Ala Phe Ser Leu Glu Thr Ser Ala Ser Ser Ala Tyr
65              70              75              80

Leu Gln Ile Asn Thr Leu Lys Asn Glu Asp Thr Ala Thr Tyr Phe Cys
                85              90              95

Ser Ile Ser Tyr Tyr Tyr Ala Met Asp Tyr Trp Gly Gln Gly Thr Ser
            100             105             110

Val Thr Val Ser Ser Ala Ser Thr Lys Gly Pro Ser Val Phe Pro Leu
        115             120             125

Ala Pro Ser Ser Lys Ser Thr Ser Gly Gly Thr Ala Ala Leu Gly Cys
    130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
                165             170             175

Ser Gly Leu Tyr Ser Leu Ser Ser Val Val Thr Val Pro Ser Ser Ser
            180             185             190

Leu Gly Thr Gln Thr Tyr Ile Cys Asn Val Asn His Lys Pro Ser Asn
        195             200             205

Thr Lys Val Asp Lys Lys Val Glu Pro Lys Ser Cys Asp Lys Thr His
    210             215             220

Thr Cys Pro Pro Cys Pro Ala Pro Glu Leu Leu Gly Gly Pro Ser Val
225             230             235             240

Phe Leu Phe Pro Pro Lys Pro Lys Asp Thr Leu Met Ile Ser Arg Thr
                245             250             255

Pro Glu Val Thr Cys Val Val Val Asp Val Ser His Glu Asp Pro Glu
            260             265             270

Val Lys Phe Asn Trp Tyr Val Asp Gly Val Glu Val His Asn Ala Lys
        275             280             285

Thr Lys Pro Arg Glu Glu Gln Tyr Asn Ser Thr Tyr Arg Val Val Ser
    290             295             300

Val Leu Thr Val Leu His Gln Asp Trp Leu Asn Gly Lys Glu Tyr Lys
305             310             315             320
```

-continued

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Cys Arg Asp Glu Leu Thr Lys Asn Gln Val Ser Leu Trp Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445
```

```
<210> SEQ ID NO 326
<211> LENGTH: 447
<212> TYPE: PRT
<213> ORGANISM: Artificial Sequence
<220> FEATURE:
<223> OTHER INFORMATION: synthetic construct

<400> SEQUENCE: 326
```

```
Gln Ile Gln Leu Val Gln Ser Gly Pro Glu Leu Lys Lys Pro Gly Glu
1                   5                   10                  15

Thr Val Lys Ile Ser Cys Met Ala Ser Gly Tyr Thr Phe Thr Asp Tyr
                20                  25                  30

Ser Val Arg Trp Val Lys Gln Ala Pro Gly Lys Gly Leu Glu Trp Met
            35                  40                  45

Gly Trp Ile Asn Thr Glu Thr Gly Glu Pro Thr Tyr Ala His Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asp Glu Asp Thr Ser Thr Tyr Phe Cys
                85                  90                  95

Ala Ile Ser Tyr Tyr Tyr Ala Leu Asp Tyr Trp Gly His Gly Thr Ser
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245             250             255

Pro Glu Val Thr Cys Val Val Val Asp Val Ser His Glu Asp Pro Glu
            260             265             270

Val Lys Phe Asn Trp Tyr Val Asp Gly Val Glu Val His Asn Ala Lys
        275             280             285

Thr Lys Pro Arg Glu Glu Gln Tyr Asn Ser Thr Tyr Arg Val Val Ser
    290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
            325             330             335

Ser Lys Ala Lys Gly Gln Pro Arg Glu Pro Gln Val Tyr Thr Leu Pro
        340             345             350

Pro Cys Arg Asp Glu Leu Thr Lys Asn Gln Val Ser Leu Trp Cys Leu
        355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys
        435             440             445

<210> SEQ ID NO 327
<211> LENGTH: 447
<212> TYPE: PRT
<213> ORGANISM: Artificial Sequence
<220> FEATURE:
<223> OTHER INFORMATION: synthetic construct

<400> SEQUENCE: 327

Gln Ile Gln Leu Val Gln Ser Gly Pro Glu Leu Lys Lys Pro Gly Glu
1               5               10              15

Thr Val Lys Ile Ser Cys Met Ala Ser Gly Tyr Thr Phe Thr Asp Tyr
            20              25              30

Ser Val Arg Trp Val Lys Gln Ala Pro Gly Lys Gly Leu Glu Trp Met
        35              40              45

Gly Trp Ile Asn Thr Glu Thr Gly Glu Pro Thr Tyr Ala Asp Asp Phe
    50              55              60

Lys Gly Arg Phe Ala Phe Ser Leu Glu Thr Ser Ala Ser Thr Ala Tyr
65              70              75              80

Leu Gln Ile Asn Asn Leu Lys Asn Glu Asp Thr Ala Thr Tyr Phe Cys
            85              90              95

Ala Ile Ser Tyr Tyr Tyr Ala Leu Asp Tyr Trp Gly His Gly Thr Ser
            100             105             110

Val Thr Val Ser Ser Ala Ser Thr Lys Gly Pro Ser Val Phe Pro Leu
        115             120             125

Ala Pro Ser Ser Lys Ser Thr Ser Gly Gly Thr Ala Ala Leu Gly Cys
        130             135             140

Leu Val Lys Asp Tyr Phe Pro Glu Pro Val Thr Val Ser Trp Asn Ser
145             150             155             160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 328
<211> LENGTH: 447
<212> TYPE: PRT
<213> ORGANISM: Artificial Sequence
<220> FEATURE:
<223> OTHER INFORMATION: synthetic construct

<400> SEQUENCE: 328

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Thr Met Tyr Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Glu Thr Ser Ala Asn Thr Ala Tyr
65                  70                  75                  80
```

```
Leu Gln Ile Asn Asn Leu Lys Asn Glu Asp Thr Ala Thr Tyr Phe Cys
              85                  90                  95

Ala Ile Ser Tyr Tyr Tyr Gly Met Asp Tyr Trp Gly Gln Gly Thr Ser
             100                 105                 110

Val Thr Val Thr Ser Ala Ser Thr Lys Gly Pro Ser Val Phe Pro Leu
             115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
             165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
             195                 200                 205

Thr Lys Val Asp Lys Lys Val Glu Pro Lys Ser Cys Asp Lys Thr His
             210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
             245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
             275                 280                 285

Thr Lys Pro Arg Glu Glu Gln Tyr Asn Ser Thr Tyr Arg Val Val Ser
             290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
             325                 330                 335

Ser Lys Ala Lys Gly Gln Pro Arg Glu Pro Gln Val Tyr Thr Leu Pro
             340                 345                 350

Pro Cys Arg Asp Glu Leu Thr Lys Asn Gln Val Ser Leu Trp Cys Leu
             355                 360                 365

Val Lys Gly Phe Tyr Pro Ser Asp Ile Ala Val Glu Trp Glu Ser Asn
             370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
             405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
             435                 440                 445
```

```
<210> SEQ ID NO 329
<211> LENGTH: 478
<212> TYPE: PRT
<213> ORGANISM: Artificial Sequence
<220> FEATURE:
<223> OTHER INFORMATION: synthetic construct

<400> SEQUENCE: 329
```

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln His Leu Glu Tyr Ser
            20                  25                  30

Asn Gly Tyr Ser Tyr Leu His Trp Tyr Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Tyr Thr Phe Gly Gly Gly Thr Lys Val Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Gly Tyr Val
145                 150                 155                 160

Ile His Trp Val Arg Gln Ala Pro Gly Gln Gly Leu Glu Trp Met Gly
            165                 170                 175

Tyr Ile Asn Pro Tyr Asn Gly Gly Thr Asn Tyr Ala Gln Lys Phe Lys
            180                 185                 190

Gly Arg Val Thr Leu Thr Ser Asp Thr Ser Thr Thr Thr Ala Tyr Met
            195                 200                 205

Glu Leu Ser Arg Leu Arg Ser Glu Asp Thr Ala Val Tyr Tyr Cys Ala
    210                 215                 220

Ser Gly Gly Tyr Tyr Thr Met Asp Tyr Trp Gly Gln Gly Thr Leu Val
225                 230                 235                 240

Thr Val Ser Ser Gly Gly Arg Pro Lys Ser Ala Asp Lys Thr His Thr
            245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
    275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Cys Thr Leu Pro Pro
    370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
```

-continued

```
                      420                 425                 430

Gly Ser Phe Phe Leu Val Ser Lys Leu Thr Val Asp Lys Ser Arg Trp
        435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys
465                 470                 475

<210> SEQ ID NO 330
<211> LENGTH: 293
<212> TYPE: PRT
<213> ORGANISM: Homo sapiens

<400> SEQUENCE: 330

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
        210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 331
<211> LENGTH: 247
```

```
<212> TYPE: PRT
<213> ORGANISM: Homo sapiens

<400> SEQUENCE: 331

Met Ser Gly Leu Gly Arg Ser Arg Arg Gly Gly Arg Ser Arg Val Asp
1               5                   10                  15

Gln Glu Glu Arg Trp Ser Leu Ser Cys Arg Lys Glu Gln Gly Lys Phe
            20                  25                  30

Tyr Asp His Leu Leu Arg Asp Cys Ile Ser Cys Ala Ser Ile Cys Gly
        35                  40                  45

Gln His Pro Lys Gln Cys Ala Tyr Phe Cys Glu Asn Lys Leu Arg Ser
    50                  55                  60

Pro Val Asn Leu Pro Pro Glu Leu Arg Arg Gln Arg Ser Gly Glu Val
65                  70                  75                  80

Glu Asn Asn Ser Asp Asn Ser Gly Arg Tyr Gln Gly Leu Glu His Arg
                85                  90                  95

Gly Ser Glu Ala Ser Pro Ala Leu Pro Gly Leu Lys Leu Ser Ala Asp
            100                 105                 110

Gln Val Ala Leu Val Tyr Ser Thr Leu Gly Leu Cys Leu Cys Ala Val
        115                 120                 125

Leu Cys Cys Phe Leu Val Ala Val Ala Cys Phe Leu Lys Lys Arg Gly
    130                 135                 140

Asp Pro Cys Ser Cys Gln Pro Arg Ser Arg Pro Arg Gln Ser Pro Ala
145                 150                 155                 160

Lys Ser Ser Gln Asp His Ala Met Glu Ala Gly Ser Pro Val Ser Thr
                165                 170                 175

Ser Pro Glu Pro Val Glu Thr Cys Ser Phe Cys Phe Pro Glu Cys Arg
            180                 185                 190

Ala Pro Thr Gln Glu Ser Ala Val Thr Pro Gly Thr Pro Asp Pro Thr
            195                 200                 205

Cys Ala Gly Arg Trp Gly Cys His Thr Arg Thr Thr Val Leu Gln Pro
    210                 215                 220

Cys Pro His Ile Pro Asp Ser Gly Leu Gly Ile Val Cys Val Pro Ala
225                 230                 235                 240

Gln Glu Gly Gly Pro Gly Ala
                245

<210> SEQ ID NO 332
<211> LENGTH: 176
<212> TYPE: PRT
<213> ORGANISM: Homo sapiens

<400> SEQUENCE: 332

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95
```

```
Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Pro Arg Gly Cys Pro Ala Pro Gly Thr Arg Lys
145                 150                 155                 160

Ser Phe Trp Asp Lys Glu Asn Phe Gln Gly Glu Gly Phe His Leu Gly
                165                 170                 175
```

<210> SEQ ID NO 333
<211> LENGTH: 165
<212> TYPE: PRT
<213> ORGANISM: Homo sapiens

<400> SEQUENCE: 333

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser
                165
```

<210> SEQ ID NO 334
<211> LENGTH: 35
<212> TYPE: PRT
<213> ORGANISM: Homo sapiens

<400> SEQUENCE: 334

```
Ser Cys Pro Glu Glu Gln Tyr Trp Asp Pro Leu Leu Gly Thr Cys Met
1               5                   10                  15

Ser Cys Lys Thr Ile Cys Asn His Gln Ser Gln Arg Thr Cys Ala Ala
                20                  25                  30

Phe Cys Arg
        35
```

<210> SEQ ID NO 335
<211> LENGTH: 35
<212> TYPE: PRT
<213> ORGANISM: Homo sapiens -continued

```
<400> SEQUENCE: 335

Ser Cys Arg Lys Glu Gln Gly Lys Phe Tyr Asp His Leu Leu Arg Asp
1               5                   10                  15

Cys Ile Ser Cys Ala Ser Ile Cys Gly Gln His Pro Lys Gln Cys Ala
            20                  25                  30

Tyr Phe Cys
        35

<210> SEQ ID NO 336
<211> LENGTH: 21
<212> TYPE: PRT
<213> ORGANISM: Homo sapiens

<400> SEQUENCE: 336

Thr Leu Gly Leu Cys Leu Cys Ala Val Leu Cys Cys Phe Leu Val Ala
1               5                   10                  15

Val Ala Cys Phe Leu
            20

<210> SEQ ID NO 337
<211> LENGTH: 107
<212> TYPE: PRT
<213> ORGANISM: Homo sapiens

<400> SEQUENCE: 337

Lys Lys Arg Gly Asp Pro Cys Ser Cys Gln Pro Arg Ser Arg Pro Arg
1               5                   10                  15

Gln Ser Pro Ala Lys Ser Ser Gln Asp His Ala Met Glu Ala Gly Ser
            20                  25                  30

Pro Val Ser Thr Ser Pro Glu Pro Val Glu Thr Cys Ser Phe Cys Phe
        35                  40                  45

Pro Glu Cys Arg Ala Pro Thr Gln Glu Ser Ala Val Thr Pro Gly Thr
    50                  55                  60

Pro Asp Pro Thr Cys Ala Gly Arg Trp Gly Cys His Thr Arg Thr Thr
65                  70                  75                  80

Val Leu Gln Pro Cys Pro His Ile Pro Asp Ser Gly Leu Gly Ile Val
                85                  90                  95

Cys Val Pro Ala Gln Glu Gly Gly Pro Gly Ala
            100                 105

<210> SEQ ID NO 338
<211> LENGTH: 117
<212> TYPE: PRT
<213> ORGANISM: Artificial Sequence
<220> FEATURE:
<223> OTHER INFORMATION: synthetic construct

<400> SEQUENCE: 338

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Tyr Trp Val Arg Gln Ala Pro Gly Gln Gly Leu Glu Trp Met
        35                  40                  45

Gly Trp Ile Asn Thr Glu Thr Gly Glu Pro Asn Tyr Ala Gln Asp Val
    50                  55                  60

Gln Gly Arg Phe Thr Met Thr Leu Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85              90              95

Ser Ile Ser Tyr Tyr Tyr Ala Met Asp Tyr Trp Gly Gln Gly Thr Leu
            100             105             110

Val Thr Val Ser Ser
        115

<210> SEQ ID NO 339
<211> LENGTH: 17
<212> TYPE: PRT
<213> ORGANISM: Artificial Sequence
<220> FEATURE:
<223> OTHER INFORMATION: synthetic construct

<400> SEQUENCE: 339

Ile Tyr Trp Val Arg Gln Ala Pro Gly Gln Gly Leu Glu Trp Met Gly
1               5               10              15

Trp

<210> SEQ ID NO 340
<211> LENGTH: 38
<212> TYPE: PRT
<213> ORGANISM: Artificial Sequence
<220> FEATURE:
<223> OTHER INFORMATION: synthetic construct

<400> SEQUENCE: 340

Asn Tyr Ala Gln Asp Val Gln Gly Arg Phe Thr Met Thr Leu Asp Thr
1               5               10              15

Ser Thr Ser Thr Ala Tyr Met Glu Leu Arg Ser Leu Arg Ser Asp Asp
            20              25              30

Thr Ala Val Tyr Tyr Cys
        35

<210> SEQ ID NO 341
<211> LENGTH: 111
<212> TYPE: PRT
<213> ORGANISM: Artificial Sequence
<220> FEATURE:
<223> OTHER INFORMATION: synthetic construct

<400> SEQUENCE: 341

Asp Ile Val Met Thr Gln Thr Pro Leu Ser Leu Ser Val Thr Pro Gly
1               5               10              15

Gln Pro Ala Ser Ile Ser Cys Lys Ser Ser Lys Ser Val Ser Thr Ser
            20              25              30

Gly Tyr Ser Phe Leu His Trp Tyr Leu Gln Lys Pro Gly Gln Pro Pro
        35              40              45

Gln Leu Leu Ile Tyr Phe Ala Ser Asn Leu Glu Ser Gly Val Pro Asp
    50              55              60

Arg Phe Ser Gly Ser Gly Ser Gly Thr Asp Phe Thr Leu Lys Ile Ser
65              70              75              80

Arg Val Glu Ala Glu Asp Val Gly Val Tyr Tyr Cys Gln His Ser Arg
                85              90              95

Glu Leu Pro Arg Thr Phe Gly Gln Gly Thr Lys Val Glu Ile Lys
            100             105             110

<210> SEQ ID NO 342
<211> LENGTH: 26
<212> TYPE: PRT
<213> ORGANISM: Artificial Sequence
```

<220> FEATURE:
<223> OTHER INFORMATION: synthetic construct

<400> SEQUENCE: 342

Asp Ile Val Met Thr Gln Thr Pro Leu Ser Leu Ser Val Thr Pro Gly
1               5                   10                  15

Gln Pro Ala Ser Ile Ser Cys Lys Ser Ser
            20                  25

<210> SEQ ID NO 343
<211> LENGTH: 16
<212> TYPE: PRT
<213> ORGANISM: Artificial Sequence
<220> FEATURE:
<223> OTHER INFORMATION: synthetic construct

<400> SEQUENCE: 343

Leu His Trp Tyr Leu Gln Lys Pro Gly Gln Pro Pro Gln Leu Leu Ile
1               5                   10                  15

<210> SEQ ID NO 344
<211> LENGTH: 36
<212> TYPE: PRT
<213> ORGANISM: Artificial Sequence
<220> FEATURE:
<223> OTHER INFORMATION: synthetic construct

<400> SEQUENCE: 344

Asn Leu Glu Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 345
<211> LENGTH: 10
<212> TYPE: PRT
<213> ORGANISM: Artificial Sequence
<220> FEATURE:
<223> OTHER INFORMATION: synthetic construct

<400> SEQUENCE: 345

Phe Gly Gln Gly Thr Lys Val Glu Ile Lys
1               5                   10

<210> SEQ ID NO 346
<211> LENGTH: 117
<212> TYPE: PRT
<213> ORGANISM: Artificial Sequence
<220> FEATURE:
<223> OTHER INFORMATION: synthetic construct

<400> SEQUENCE: 346

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Tyr Trp Val Arg Gln Ala Pro Gly Gln Gly Leu Glu Trp Met
        35                  40                  45

Gly Trp Ile Asn Thr Glu Thr Gly Glu Thr Asn Tyr Ala Gln Asp Phe
    50                  55                  60

Gln Gly Arg Val Thr Met Thr Thr Asp Thr Glu Thr Ser Thr Ala Tyr

-continued

```
65              70              75              80

Met Glu Leu Arg Ser Leu Arg Ser Asp Asp Thr Ala Val Tyr Tyr Cys
                85              90              95

Ser Ile Ser Tyr Tyr Tyr Ala Met Asp Tyr Trp Gly Gln Gly Thr Leu
                100             105             110

Val Thr Val Ser Ser
        115

<210> SEQ ID NO 347
<211> LENGTH: 8
<212> TYPE: PRT
<213> ORGANISM: Artificial Sequence
<220> FEATURE:
<223> OTHER INFORMATION: synthetic construct

<400> SEQUENCE: 347

Ile Asn Thr Glu Thr Gly Glu Thr
1               5

<210> SEQ ID NO 348
<211> LENGTH: 38
<212> TYPE: PRT
<213> ORGANISM: Artificial Sequence
<220> FEATURE:
<223> OTHER INFORMATION: synthetic construct

<400> SEQUENCE: 348

Asn Tyr Ala Gln Asp Phe Gln Gly Arg Val Thr Met Thr Thr Asp Thr
1               5               10              15

Glu Thr Ser Thr Ala Tyr Met Glu Leu Arg Ser Leu Arg Ser Asp Asp
                20              25              30

Thr Ala Val Tyr Tyr Cys
        35

<210> SEQ ID NO 349
<211> LENGTH: 111
<212> TYPE: PRT
<213> ORGANISM: Artificial Sequence
<220> FEATURE:
<223> OTHER INFORMATION: synthetic construct

<400> SEQUENCE: 349

Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Ser Val Ser Thr Ser
                20              25              30

Gly Tyr Ser Phe Leu His Trp Tyr Gln Gln Lys Pro Gly Gln Ala Pro
        35              40              45

Arg Leu Leu Ile Tyr Phe Ala Ser Asn Leu Glu Thr Gly Ile Pro Ala
    50              55              60

Arg Phe Ser Gly Ser Gly Ser Gly Thr Asp Phe Thr Leu Thr Ile Ser
65              70              75              80

Arg Leu Glu Pro Glu Asp Phe Ala Val Tyr Tyr Cys Gln His Ser Arg
                85              90              95

Glu Leu Pro Arg Thr Phe Gly Gln Gly Thr Lys Leu Glu Ile Lys
                100             105             110

<210> SEQ ID NO 350
<211> LENGTH: 26
<212> TYPE: PRT
<213> ORGANISM: Artificial Sequence
```

-continued

```
<220> FEATURE:
<223> OTHER INFORMATION: synthetic construct

<400> SEQUENCE: 350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 351
<211> LENGTH: 17
<212> TYPE: PRT
<213> ORGANISM: Artificial Sequence
<220> FEATURE:
<223> OTHER INFORMATION: synthetic construct

<400> SEQUENCE: 351

Leu His Trp Tyr Gln Gln Lys Pro Gly Gln Ala Pro Arg Leu Leu Ile
1               5                   10                  15

Tyr

<210> SEQ ID NO 352
<211> LENGTH: 36
<212> TYPE: PRT
<213> ORGANISM: Artificial Sequence
<220> FEATURE:
<223> OTHER INFORMATION: synthetic construct

<400> SEQUENCE: 352

Asn Leu Glu Thr Gly Ile Pro Ala Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 353
<211> LENGTH: 117
<212> TYPE: PRT
<213> ORGANISM: Artificial Sequence
<220> FEATURE:
<223> OTHER INFORMATION: synthetic construct

<400> SEQUENCE: 353

Glu Val Gln Leu Val Glu Ser Gly Gly Gly Leu Val Gln Pro Gly Glu
1               5                   10                  15

Ser Leu Arg Leu Ser Cys Ala Ala Ser Gly Tyr Thr Phe Thr Asp Tyr
            20                  25                  30

Thr Met Tyr Trp Val Arg Gln Ala Pro Gly Lys Gly Leu Glu Trp Met
        35                  40                  45

Gly Trp Ile Asn Thr Glu Thr Gly Glu Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Tyr Tyr Tyr Gly Met Asp Tyr Trp Gly Gln Gly Thr Leu
            100                 105                 110

Val Thr Val Ser Ser
        115
```

<210> SEQ ID NO 354
<211> LENGTH: 25
<212> TYPE: PRT
<213> ORGANISM: Artificial Sequence
<220> FEATURE:
<223> OTHER INFORMATION: synthetic construct

<400> SEQUENCE: 354

Glu Val Gln Leu Val Glu Ser Gly Gly Gly Leu Val Gln Pro Gly Glu
1               5                   10                  15

Ser Leu Arg Leu Ser Cys Ala Ala Ser
            20                  25

<210> SEQ ID NO 355
<211> LENGTH: 17
<212> TYPE: PRT
<213> ORGANISM: Artificial Sequence
<220> FEATURE:
<223> OTHER INFORMATION: synthetic construct

<400> SEQUENCE: 355

Met Tyr Trp Val Arg Gln Ala Pro Gly Lys Gly Leu Glu Trp Met Gly
1               5                   10                  15

Trp

<210> SEQ ID NO 356
<211> LENGTH: 38
<212> TYPE: PRT
<213> ORGANISM: Artificial Sequence
<220> FEATURE:
<223> OTHER INFORMATION: synthetic construct

<400> SEQUENCE: 356

Asn Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 357
<211> LENGTH: 111
<212> TYPE: PRT
<213> ORGANISM: Artificial Sequence
<220> FEATURE:
<223> OTHER INFORMATION: synthetic construct

<400> SEQUENCE: 357

Asp Ile Gln Met Thr Gln Ser Pro Ser Thr Leu Ser Val Ser Val Gly
1               5                   10                  15

Asp Arg Val Thr Ile Thr Cys Arg Ala Ser Lys Ser Val Ser Thr Ser
            20                  25                  30

Gly Tyr Asn Phe Val Tyr Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Arg
                85                  90                  95

Glu Leu Pro Arg Thr Phe Gly Gln Gly Thr Lys Val Glu Ile Lys

-continued

```
            100              105              110
```

<210> SEQ ID NO 358
<211> LENGTH: 26
<212> TYPE: PRT
<213> ORGANISM: Artificial Sequence
<220> FEATURE:
<223> OTHER INFORMATION: synthetic construct

<400> SEQUENCE: 358

```
Asp Ile Gln Met Thr Gln Ser Pro Ser Thr Leu Ser Val Ser Val Gly
1               5                   10                  15

Asp Arg Val Thr Ile Thr Cys Arg Ala Ser
            20                  25
```

<210> SEQ ID NO 359
<211> LENGTH: 17
<212> TYPE: PRT
<213> ORGANISM: Artificial Sequence
<220> FEATURE:
<223> OTHER INFORMATION: synthetic construct

<400> SEQUENCE: 359

```
Val Tyr Trp Tyr Gln Gln Lys Pro Gly Lys Ala Pro Lys Leu Leu Ile
1               5                   10                  15

Tyr
```

<210> SEQ ID NO 360
<211> LENGTH: 36
<212> TYPE: PRT
<213> ORGANISM: Artificial Sequence
<220> FEATURE:
<223> OTHER INFORMATION: synthetic construct

<400> SEQUENCE: 360

```
Asn Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35
```

<210> SEQ ID NO 361
<211> LENGTH: 117
<212> TYPE: PRT
<213> ORGANISM: Artificial Sequence
<220> FEATURE:
<223> OTHER INFORMATION: synthetic construct

<400> SEQUENCE: 361

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Thr Met Tyr Trp Val Arg Gln Ala Pro Gly Lys Gly Leu Glu Trp Met
        35                  40                  45

Gly Asp Ile Asn Thr Glu Thr Gly Glu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Ile Ser Tyr Tyr Tyr Gly Met Asp Tyr Trp Gly Gln Gly Thr Leu
            100                 105                 110

Val Thr Val Ser Ser
        115

<210> SEQ ID NO 362
<211> LENGTH: 25
<212> TYPE: PRT
<213> ORGANISM: Artificial Sequence
<220> FEATURE:
<223> OTHER INFORMATION: synthetic construct

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 363
<211> LENGTH: 17
<212> TYPE: PRT
<213> ORGANISM: Artificial Sequence
<220> FEATURE:
<223> OTHER INFORMATION: synthetic construct

<400> SEQUENCE: 363

Met Tyr Trp Val Arg Gln Ala Pro Gly Lys Gly Leu Glu Trp Met Gly
1               5                   10                  15

Asp

<210> SEQ ID NO 364
<211> LENGTH: 38
<212> TYPE: PRT
<213> ORGANISM: Artificial Sequence
<220> FEATURE:
<223> OTHER INFORMATION: synthetic construct

<400> SEQUENCE: 364

Thr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 365
<211> LENGTH: 111
<212> TYPE: PRT
<213> ORGANISM: Artificial Sequence
<220> FEATURE:
<223> OTHER INFORMATION: synthetic construct

<400> SEQUENCE: 365

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Asn Phe Val Tyr Trp Tyr Gln Gln Lys Pro Gly Gln Pro Pro
            35                  40                  45

Lys Leu Leu Ile Tyr Leu Ala Ser Asn Leu Glu Ser Gly Val Pro Ser
        50                  55                  60

```
Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Arg
                85                  90                  95

Glu Leu Pro Arg Thr Phe Gly Gln Gly Thr Lys Val Glu Ile Lys
            100             105                 110
```

```
<210> SEQ ID NO 366
<211> LENGTH: 26
<212> TYPE: PRT
<213> ORGANISM: Artificial Sequence
<220> FEATURE:
<223> OTHER INFORMATION: synthetic construct

<400> SEQUENCE: 366

Asp Ile Gln Met Thr Gln Ser Pro Ser Thr Leu Ser Ala Ser Val Gly
1               5                   10                  15

Asp Arg Val Thr Ile Thr Cys Arg Ala Ser
            20                  25
```

```
<210> SEQ ID NO 367
<211> LENGTH: 119
<212> TYPE: PRT
<213> ORGANISM: Artificial Sequence
<220> FEATURE:
<223> OTHER INFORMATION: synthetic construct

<400> SEQUENCE: 367

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Gly Leu Glu Trp Met
            35                  40                  45

Ala Tyr Ile Leu Pro Phe Asn Asp Val Thr Lys Tyr Asn Glu Lys Phe
            50                  55                  60

Lys Gly Arg Val Thr Met Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Glu Trp Asp Asp Gly Tyr Phe Asp Tyr Trp Gly Gln Gly
            100             105                 110

Thr Leu Val Thr Val Ser Ser
            115
```

```
<210> SEQ ID NO 368
<211> LENGTH: 17
<212> TYPE: PRT
<213> ORGANISM: Artificial Sequence
<220> FEATURE:
<223> OTHER INFORMATION: synthetic construct

<400> SEQUENCE: 368

Met His Trp Val Arg Gln Ala Pro Gly Gln Gly Leu Glu Trp Met Ala
1               5                   10                  15

Tyr
```

```
<210> SEQ ID NO 369
<211> LENGTH: 38
<212> TYPE: PRT
<213> ORGANISM: Artificial Sequence
```

-continued

<220> FEATURE:
<223> OTHER INFORMATION: synthetic construct

<400> SEQUENCE: 369

Lys Tyr Asn Glu Lys Phe Lys Gly Arg Val Thr Met Thr Ser Asp Lys
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 370
<211> LENGTH: 112
<212> TYPE: PRT
<213> ORGANISM: Artificial Sequence
<220> FEATURE:
<223> OTHER INFORMATION: synthetic construct

<400> SEQUENCE: 370

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Ser His Val Pro Phe Thr Phe Gly Gln Gly Thr Lys Leu Glu Ile Lys
            100                 105                 110

<210> SEQ ID NO 371
<211> LENGTH: 17
<212> TYPE: PRT
<213> ORGANISM: Artificial Sequence
<220> FEATURE:
<223> OTHER INFORMATION: synthetic construct

<400> SEQUENCE: 371

Leu Asn Trp Tyr Leu Gln Lys Pro Gly Gln Ser Pro Lys Leu Leu Ile
1               5                   10                  15

Tyr

<210> SEQ ID NO 372
<211> LENGTH: 119
<212> TYPE: PRT
<213> ORGANISM: Artificial Sequence
<220> FEATURE:
<223> OTHER INFORMATION: synthetic construct

<400> SEQUENCE: 372

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Arg Gln Ala Pro Gly Gln Gly Leu Glu Trp Ile
        35                  40                  45

```
Ala Tyr Ile Leu Pro Phe Asn Asp Val Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Glu Trp Asp Asp Gly Tyr Phe Asp Tyr Trp Gly Gln Gly
                100                 105                 110

Thr Leu Val Thr Val Ser Ser
        115

<210> SEQ ID NO 373
<211> LENGTH: 25
<212> TYPE: PRT
<213> ORGANISM: Artificial Sequence
<220> FEATURE:
<223> OTHER INFORMATION: synthetic construct

<400> SEQUENCE: 373

Gln Val Gln Leu Val Gln Ser Gly Ala Glu Val Lys Lys Pro Gly Ala
1                   5                   10                  15

Ser Val Lys Met Ser Cys Lys Ala Ser
            20                  25

<210> SEQ ID NO 374
<211> LENGTH: 17
<212> TYPE: PRT
<213> ORGANISM: Artificial Sequence
<220> FEATURE:
<223> OTHER INFORMATION: synthetic construct

<400> SEQUENCE: 374

Met His Trp Val Arg Gln Ala Pro Gly Gln Gly Leu Glu Trp Ile Ala
1                   5                   10                  15

Tyr

<210> SEQ ID NO 375
<211> LENGTH: 38
<212> TYPE: PRT
<213> ORGANISM: Artificial Sequence
<220> FEATURE:
<223> OTHER INFORMATION: synthetic construct

<400> SEQUENCE: 375

Asn Tyr Asn Gln Lys Phe Gln Gly Arg Val Thr Met Thr Arg Asp Thr
1                   5                   10                  15

Ser Ile Ser Thr Ala Tyr Met Glu Leu Ser Arg Leu Arg Ser Asp Asp
            20                  25                  30

Thr Ala Val Tyr Tyr Cys
        35

<210> SEQ ID NO 376
<211> LENGTH: 112
<212> TYPE: PRT
<213> ORGANISM: Artificial Sequence
<220> FEATURE:
<223> OTHER INFORMATION: synthetic construct

<400> SEQUENCE: 376

Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Leu Glu Asn Ser
```

-continued

```
              20                  25                  30

Asn Gly Asn Thr Tyr Leu Asn Trp Tyr Gln Gln Lys Pro Gly Gln Pro
          35                  40                  45

Pro Lys Leu Leu Ile Tyr Arg Val Ser Thr Arg Phe Ser Gly Val Leu
      50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Val
                  85                  90                  95

Ser His Val Pro Phe Thr Phe Gly Gly Gly Thr Lys Val Glu Ile Lys
              100                 105                 110
```

```
<210> SEQ ID NO 377
<211> LENGTH: 26
<212> TYPE: PRT
<213> ORGANISM: Artificial Sequence
<220> FEATURE:
<223> OTHER INFORMATION: synthetic construct

<400> SEQUENCE: 377

Asp Ile Val Met Thr Gln Ser Pro Asp Ser Leu Ala Val Ser Leu Gly
1               5                   10                  15

Glu Arg Ala Thr Ile Asn Cys Lys Ser Ser
              20                  25
```

```
<210> SEQ ID NO 378
<211> LENGTH: 17
<212> TYPE: PRT
<213> ORGANISM: Artificial Sequence
<220> FEATURE:
<223> OTHER INFORMATION: synthetic construct

<400> SEQUENCE: 378

Leu Asn Trp Tyr Gln Gln Lys Pro Gly Gln Pro Pro Lys Leu Leu Ile
1               5                   10                  15

Tyr
```

```
<210> SEQ ID NO 379
<211> LENGTH: 36
<212> TYPE: PRT
<213> ORGANISM: Artificial Sequence
<220> FEATURE:
<223> OTHER INFORMATION: synthetic construct

<400> SEQUENCE: 379

Thr Arg Phe Ser Gly Val Leu Asp Arg Phe Ser Gly Ser Gly Ser Gly
1               5                   10                  15

Thr Asp Phe Thr Leu Thr Ile Ser Ser Leu Gln Ala Glu Asp Val Ala
              20                  25                  30

Val Tyr Tyr Cys
          35
```

```
<210> SEQ ID NO 380
<211> LENGTH: 118
<212> TYPE: PRT
<213> ORGANISM: Artificial Sequence
<220> FEATURE:
<223> OTHER INFORMATION: synthetic construct

<400> SEQUENCE: 380

Gln Val Gln Leu Val Gln Ser Gly Ala Glu Leu Val Lys Pro Gly Ser
1               5                   10                  15
```

```
Ser Val Lys Met Ser Cys Lys Ala Ser Gly Tyr Thr Phe Thr Asn Tyr
            20              25              30

Val Met His Trp Val Arg Gln Ala Pro Gly Gln Gly Leu Glu Trp Met
        35              40              45

Gly Tyr Ile Leu Pro Tyr Asn Asp Gly Thr Asn Tyr Asn Gln Lys Phe
    50              55              60

Gln Gly Arg Val Thr Met Thr Ser Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Tyr Asp Tyr Glu Gly Ser Phe Asp Tyr Trp Gly Gln Gly Thr
            100             105             110

Leu Val Thr Val Ser Ser
        115
```

```
<210> SEQ ID NO 381
<211> LENGTH: 25
<212> TYPE: PRT
<213> ORGANISM: Artificial Sequence
<220> FEATURE:
<223> OTHER INFORMATION: synthetic construct

<400> SEQUENCE: 381

Gln Val Gln Leu Val Gln Ser Gly Ala Glu Leu Val Lys Pro Gly Ser
1               5               10              15

Ser Val Lys Met Ser Cys Lys Ala Ser
            20              25
```

```
<210> SEQ ID NO 382
<211> LENGTH: 38
<212> TYPE: PRT
<213> ORGANISM: Artificial Sequence
<220> FEATURE:
<223> OTHER INFORMATION: synthetic construct

<400> SEQUENCE: 382

Asn Tyr Asn Gln Lys Phe Gln Gly Arg Val Thr Met Thr Ser Asp Lys
1               5               10              15

Ser Thr Ser Thr Ala Tyr Met Glu Leu Ser Ser Leu Arg Ser Glu Asp
            20              25              30

Thr Ala Val Tyr Tyr Cys
        35
```

```
<210> SEQ ID NO 383
<211> LENGTH: 107
<212> TYPE: PRT
<213> ORGANISM: Artificial Sequence
<220> FEATURE:
<223> OTHER INFORMATION: synthetic construct

<400> SEQUENCE: 383

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Ser Asn Tyr
            20              25              30

Leu Asn Trp Tyr Gln Gln Lys Pro Gly Lys Ala Pro Lys Leu Leu Met
        35              40              45

Cys Tyr Thr Ser Arg Leu His Ser Gly Val Pro Ser Arg Phe Ser Gly
    50              55              60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys
            100                 105
```

```
<210> SEQ ID NO 384
<211> LENGTH: 26
<212> TYPE: PRT
<213> ORGANISM: Artificial Sequence
<220> FEATURE:
<223> OTHER INFORMATION: synthetic construct

<400> SEQUENCE: 384

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25
```

```
<210> SEQ ID NO 385
<211> LENGTH: 17
<212> TYPE: PRT
<213> ORGANISM: Artificial Sequence
<220> FEATURE:
<223> OTHER INFORMATION: synthetic construct

<400> SEQUENCE: 385

Leu Asn Trp Tyr Gln Gln Lys Pro Gly Lys Ala Pro Lys Leu Leu Met
1               5                   10                  15

Cys
```

```
<210> SEQ ID NO 386
<211> LENGTH: 36
<212> TYPE: PRT
<213> ORGANISM: Artificial Sequence
<220> FEATURE:
<223> OTHER INFORMATION: synthetic construct

<400> SEQUENCE: 386

Arg Leu His Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

```
<210> SEQ ID NO 387
<211> LENGTH: 118
<212> TYPE: PRT
<213> ORGANISM: Artificial Sequence
<220> FEATURE:
<223> OTHER INFORMATION: synthetic construct

<400> SEQUENCE: 387

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Asn Tyr
            20                  25                  30

Val Met His Trp Val Arg Gln Ala Pro Gly Gln Gly Leu Glu Trp Ile
        35                  40                  45

Ala Tyr Ile Leu Pro Tyr Asn Asp Gly Ala Asn Tyr Asn Glu Lys Val
```

-continued

```
        50              55              60

Lys Gly Arg Phe Thr Ile Ser Arg Asp Asn Ser Lys Asn Thr Leu Tyr
65                  70              75              80

Leu Gln Met Asn Ser Leu Arg Ala Glu Asp Thr Ala Val Tyr Tyr Cys
                85              90              95

Ala Arg Tyr Asp Tyr Glu Gly Ser Phe Asp Tyr Trp Gly Gln Gly Thr
            100             105             110

Leu Val Thr Val Ser Ser
        115

<210> SEQ ID NO 388
<211> LENGTH: 8
<212> TYPE: PRT
<213> ORGANISM: Artificial Sequence
<220> FEATURE:
<223> OTHER INFORMATION: synthetic construct

<400> SEQUENCE: 388

Ile Leu Pro Tyr Asn Asp Gly Ala
1               5

<210> SEQ ID NO 389
<211> LENGTH: 25
<212> TYPE: PRT
<213> ORGANISM: Artificial Sequence
<220> FEATURE:
<223> OTHER INFORMATION: synthetic construct

<400> SEQUENCE: 389

Gln Val Gln Leu Val Glu Ser Gly Gly Gly Val Val Gln Pro Gly Arg
1               5               10              15

Ser Leu Arg Leu Ser Cys Ala Ala Ser
            20              25

<210> SEQ ID NO 390
<211> LENGTH: 38
<212> TYPE: PRT
<213> ORGANISM: Artificial Sequence
<220> FEATURE:
<223> OTHER INFORMATION: synthetic construct

<400> SEQUENCE: 390

Asn Tyr Asn Glu Lys Val Lys Gly Arg Phe Thr Ile Ser Arg Asp Asn
1               5               10              15

Ser Lys Asn Thr Leu Tyr Leu Gln Met Asn Ser Leu Arg Ala Glu Asp
            20              25              30

Thr Ala Val Tyr Tyr Cys
        35

<210> SEQ ID NO 391
<211> LENGTH: 107
<212> TYPE: PRT
<213> ORGANISM: Artificial Sequence
<220> FEATURE:
<223> OTHER INFORMATION: synthetic construct

<400> SEQUENCE: 391

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Ser Asn Tyr
            20              25              30

Leu Asn Trp Tyr Gln Gln Lys Pro Gly Gln Ser Val Lys Leu Leu Ile
```

```
                    35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Phe Pro Pro
                    85                  90                  95

Thr Phe Gly Gly Gly Thr Lys Val Glu Ile Lys
            100                 105

<210> SEQ ID NO 392
<211> LENGTH: 17
<212> TYPE: PRT
<213> ORGANISM: Artificial Sequence
<220> FEATURE:
<223> OTHER INFORMATION: synthetic construct

<400> SEQUENCE: 392

Leu Asn Trp Tyr Gln Gln Lys Pro Gly Gln Ser Val Lys Leu Leu Ile
1                   5                   10                  15

Tyr

<210> SEQ ID NO 393
<211> LENGTH: 117
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (58)..(58)
<223> OTHER INFORMATION: Xaa = P or T
<220> FEATURE:
<221> NAME/KEY: misc_feature
<222> LOCATION: (64)..(64)
<223> OTHER INFORMATION: Xaa = V or F
<220> FEATURE:
<221> NAME/KEY: misc_feature
<222> LOCATION: (68)..(68)
<223> OTHER INFORMATION: Xaa = F or V
<220> FEATURE:
<221> NAME/KEY: misc_feature
<222> LOCATION: (72)..(72)
<223> OTHER INFORMATION: Xaa = L or T
<220> FEATURE:
<221> NAME/KEY: misc_feature
<222> LOCATION: (75)..(75)
<223> OTHER INFORMATION: Xaa = S or E

<400> SEQUENCE: 393

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asp Tyr
                    20                  25                  30

Ser Ile Tyr Trp Val Arg Gln Ala Pro Gly Gln Gly Leu Glu Trp Met
            35                  40                  45

Gly Trp Ile Asn Thr Glu Thr Gly Glu Xaa Asn Tyr Ala Gln Asp Xaa
        50                  55                  60

Gln Gly Arg Xaa Thr Met Thr Xaa Asp Thr Xaa Thr Ser Thr Ala Tyr
65                  70                  75                  80

Met Glu Leu Arg Ser Leu Arg Ser Asp Asp Thr Ala Val Tyr Tyr Cys
                    85                  90                  95

Ser Ile Ser Tyr Tyr Tyr Ala Met Asp Tyr Trp Gly Gln Gly Thr Leu
            100                 105                 110
```

-continued

```
Val Thr Val Ser Ser
        115

<210> SEQ ID NO 394
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: Xaa = P or T

<400> SEQUENCE: 394

Ile Asn Thr Glu Thr Gly Glu Xaa
1               5

<210> SEQ ID NO 395
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = V or F
<220> FEATURE:
<221> NAME/KEY: misc_feature
<222> LOCATION: (10)..(10)
<223> OTHER INFORMATION: Xaa = F or V
<220> FEATURE:
<221> NAME/KEY: misc_feature
<222> LOCATION: (14)..(14)
<223> OTHER INFORMATION: Xaa = L or T
<220> FEATURE:
<221> NAME/KEY: misc_feature
<222> LOCATION: (17)..(17)
<223> OTHER INFORMATION: Xaa = S or E

<400> SEQUENCE: 395

Asn Tyr Ala Gln Asp Xaa Gln Gly Arg Xaa Thr Met Thr Xaa Asp Thr
1               5                   10                  15

Xaa Thr Ser Thr Ala Tyr Met Glu Leu Arg Ser Leu Arg Ser Asp Asp
            20                  25                  30

Thr Ala Val Tyr Tyr Cys
        35

<210> SEQ ID NO 396
<211> LENGTH: 111
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = D or E
<220> FEATURE:
<221> NAME/KEY: misc_feature
<222> LOCATION: (4)..(4)
<223> OTHER INFORMATION: Xaa = M or L
<220> FEATURE:
<221> NAME/KEY: misc_feature
<222> LOCATION: (7)..(7)
<223> OTHER INFORMATION: Xaa = T or S
<220> FEATURE:
<221> NAME/KEY: misc_feature
<222> LOCATION: (9)..(9)
<223> OTHER INFORMATION: Xaa = L or A
```

```
<220> FEATURE:
<221> NAME/KEY: misc_feature
<222> LOCATION: (10)..(10)
<223> OTHER INFORMATION: Xaa = S or T
<220> FEATURE:
<221> NAME/KEY: misc_feature
<222> LOCATION: (13)..(13)
<223> OTHER INFORMATION: Xaa = V or L
<220> FEATURE:
<221> NAME/KEY: misc_feature
<222> LOCATION: (14)..(14)
<223> OTHER INFORMATION: Xaa = T or S
<220> FEATURE:
<221> NAME/KEY: misc_feature
<222> LOCATION: (17)..(17)
<223> OTHER INFORMATION: Xaa = Q or E
<220> FEATURE:
<221> NAME/KEY: misc_feature
<222> LOCATION: (18)..(18)
<223> OTHER INFORMATION: Xaa = P or R
<220> FEATURE:
<221> NAME/KEY: misc_feature
<222> LOCATION: (20)..(20)
<223> OTHER INFORMATION: Xaa = S or T
<220> FEATURE:
<221> NAME/KEY: misc_feature
<222> LOCATION: (21)..(21)
<223> OTHER INFORMATION: Xaa = I or L
<220> FEATURE:
<221> NAME/KEY: misc_feature
<222> LOCATION: (24)..(24)
<223> OTHER INFORMATION: Xaa = K or R
<220> FEATURE:
<221> NAME/KEY: misc_feature
<222> LOCATION: (25)..(25)
<223> OTHER INFORMATION: Xaa = S or A
<220> FEATURE:
<221> NAME/KEY: misc_feature
<222> LOCATION: (41)..(41)
<223> OTHER INFORMATION: Xaa = L or Q
<220> FEATURE:
<221> NAME/KEY: misc_feature
<222> LOCATION: (47)..(47)
<223> OTHER INFORMATION: Xaa = P or A
<220> FEATURE:
<221> NAME/KEY: misc_feature
<222> LOCATION: (49)..(49)
<223> OTHER INFORMATION: Xaa = Q or R
<220> FEATURE:
<221> NAME/KEY: misc_feature
<222> LOCATION: (60)..(60)
<223> OTHER INFORMATION: Xaa = S or T
<220> FEATURE:
<221> NAME/KEY: misc_feature
<222> LOCATION: (62)..(62)
<223> OTHER INFORMATION: Xaa = V or I
<220> FEATURE:
<221> NAME/KEY: misc_feature
<222> LOCATION: (64)..(64)
<223> OTHER INFORMATION: Xaa = D or A
<220> FEATURE:
<221> NAME/KEY: misc_feature
<222> LOCATION: (78)..(78)
<223> OTHER INFORMATION: Xaa = K or T
<220> FEATURE:
<221> NAME/KEY: misc_feature
<222> LOCATION: (82)..(82)
<223> OTHER INFORMATION: Xaa = V or L
<220> FEATURE:
<221> NAME/KEY: misc_feature
<222> LOCATION: (84)..(84)
<223> OTHER INFORMATION: Xaa = A or P
<220> FEATURE:
<221> NAME/KEY: misc_feature
<222> LOCATION: (87)..(87)
<223> OTHER INFORMATION: Xaa = V or F
<220> FEATURE:
<221> NAME/KEY: misc_feature
<222> LOCATION: (88)..(88)
```

-continued

```
<223> OTHER INFORMATION: Xaa = G or A
<220> FEATURE:
<221> NAME/KEY: misc_feature
<222> LOCATION: (108)..(108)
<223> OTHER INFORMATION: Xaa = V or L

<400> SEQUENCE: 396

Xaa Ile Val Xaa Thr Gln Xaa Pro Xaa Xaa Leu Ser Xaa Xaa Pro Gly
1               5                   10                  15

Xaa Xaa Ala Xaa Xaa Ser Cys Xaa Xaa Ser Lys Ser Val Ser Thr Ser
            20                  25                  30

Gly Tyr Ser Phe Leu His Trp Tyr Xaa Gln Lys Pro Gly Gln Xaa Pro
        35                  40                  45

Xaa Leu Leu Ile Tyr Phe Ala Ser Asn Leu Glu Xaa Gly Xaa Pro Xaa
    50                  55                  60

Arg Phe Ser Gly Ser Gly Ser Gly Thr Asp Phe Thr Leu Xaa Ile Ser
65                  70                  75                  80

Arg Xaa Glu Xaa Glu Asp Xaa Xaa Val Tyr Tyr Cys Gln His Ser Arg
            85                  90                  95

Glu Leu Pro Arg Thr Phe Gly Gln Gly Thr Lys Xaa Glu Ile Lys
            100                 105                 110

<210> SEQ ID NO 397
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = D or E
<220> FEATURE:
<221> NAME/KEY: misc_feature
<222> LOCATION: (4)..(4)
<223> OTHER INFORMATION: Xaa = M or L
<220> FEATURE:
<221> NAME/KEY: misc_feature
<222> LOCATION: (7)..(7)
<223> OTHER INFORMATION: Xaa = T or S
<220> FEATURE:
<221> NAME/KEY: misc_feature
<222> LOCATION: (9)..(9)
<223> OTHER INFORMATION: Xaa = L or A
<220> FEATURE:
<221> NAME/KEY: misc_feature
<222> LOCATION: (10)..(10)
<223> OTHER INFORMATION: Xaa = S or T
<220> FEATURE:
<221> NAME/KEY: misc_feature
<222> LOCATION: (13)..(13)
<223> OTHER INFORMATION: Xaa = V or L
<220> FEATURE:
<221> NAME/KEY: misc_feature
<222> LOCATION: (14)..(14)
<223> OTHER INFORMATION: Xaa = T or S
<220> FEATURE:
<221> NAME/KEY: misc_feature
<222> LOCATION: (17)..(17)
<223> OTHER INFORMATION: Xaa = Q or E
<220> FEATURE:
<221> NAME/KEY: misc_feature
<222> LOCATION: (18)..(18)
<223> OTHER INFORMATION: Xaa = P or R
<220> FEATURE:
<221> NAME/KEY: misc_feature
<222> LOCATION: (20)..(20)
<223> OTHER INFORMATION: Xaa = S or T
<220> FEATURE:
<221> NAME/KEY: misc_feature
<222> LOCATION: (21)..(21)
```

```
<223> OTHER INFORMATION: Xaa = I or L
<220> FEATURE:
<221> NAME/KEY: misc_feature
<222> LOCATION: (24)..(24)
<223> OTHER INFORMATION: Xaa = K or R
<220> FEATURE:
<221> NAME/KEY: misc_feature
<222> LOCATION: (25)..(25)
<223> OTHER INFORMATION: Xaa = S or A

<400> SEQUENCE: 397

Xaa Ile Val Xaa Thr Gln Xaa Pro Xaa Xaa Leu Ser Xaa Xaa Pro Gly
1               5                   10                  15

Xaa Xaa Ala Xaa Xaa Ser Cys Xaa Xaa Ser
            20                  25

<210> SEQ ID NO 398
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa = L or Q
<220> FEATURE:
<221> NAME/KEY: misc_feature
<222> LOCATION: (11)..(11)
<223> OTHER INFORMATION: Xaa = P or A
<220> FEATURE:
<221> NAME/KEY: misc_feature
<222> LOCATION: (13)..(13)
<223> OTHER INFORMATION: Xaa = Q or R

<400> SEQUENCE: 398

Leu His Trp Tyr Xaa Gln Lys Pro Gly Gln Xaa Pro Xaa Leu Leu Ile
1               5                   10                  15

Tyr

<210> SEQ ID NO 399
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa = S or T
<220> FEATURE:
<221> NAME/KEY: misc_feature
<222> LOCATION: (6)..(6)
<223> OTHER INFORMATION: Xaa = V or I
<220> FEATURE:
<221> NAME/KEY: misc_feature
<222> LOCATION: (8)..(8)
<223> OTHER INFORMATION: Xaa = D or A
<220> FEATURE:
<221> NAME/KEY: misc_feature
<222> LOCATION: (22)..(22)
<223> OTHER INFORMATION: Xaa = K or T
<220> FEATURE:
<221> NAME/KEY: misc_feature
<222> LOCATION: (26)..(26)
<223> OTHER INFORMATION: Xaa = V or L
<220> FEATURE:
<221> NAME/KEY: misc_feature
<222> LOCATION: (28)..(28)
<223> OTHER INFORMATION: Xaa = A or P
<220> FEATURE:
<221> NAME/KEY: misc_feature
<222> LOCATION: (31)..(31)
```

-continued

```
<223> OTHER INFORMATION: Xaa = V or F
<220> FEATURE:
<221> NAME/KEY: misc_feature
<222> LOCATION: (32)..(32)
<223> OTHER INFORMATION: Xaa = G or A

<400> SEQUENCE: 399

Asn Leu Glu Xaa Gly Xaa Pro Xaa Arg Phe Ser Gly Ser Gly Ser Gly
1               5                   10                  15

Thr Asp Phe Thr Leu Xaa Ile Ser Arg Xaa Glu Xaa Glu Asp Xaa Xaa
                20                  25                  30

Val Tyr Tyr Cys
        35

<210> SEQ ID NO 400
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: Xaa = V or L

<400> SEQUENCE: 400

Phe Gly Gln Gly Thr Lys Xaa Glu Ile Lys
1               5                   10

<210> SEQ ID NO 401
<211> LENGTH: 117
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: Xaa = G or E
<220> FEATURE:
<221> NAME/KEY: misc_feature
<222> LOCATION: (50)..(50)
<223> OTHER INFORMATION: Xaa = D or W
<220> FEATURE:
<221> NAME/KEY: misc_feature
<222> LOCATION: (59)..(59)
<223> OTHER INFORMATION: Xaa = T or N

<400> SEQUENCE: 401

Glu Val Gln Leu Val Glu Ser Gly Gly Gly Leu Val Gln Pro Gly Xaa
1               5                   10                  15

Ser Leu Arg Leu Ser Cys Ala Ala Ser Gly Tyr Thr Phe Thr Asp Tyr
                20                  25                  30

Thr Met Tyr Trp Val Arg Gln Ala Pro Gly Lys Gly Leu Glu Trp Met
        35                  40                  45

Gly Xaa Ile Asn Thr Glu Thr Gly Glu Thr Xaa Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Tyr Tyr Tyr Gly Met Asp Tyr Trp Gly Gln Gly Thr Leu
            100                 105                 110

Val Thr Val Ser Ser
        115
```

-continued

```
<210> SEQ ID NO 402
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: Xaa = G or E

<400> SEQUENCE: 402

Glu Val Gln Leu Val Glu Ser Gly Gly Gly Leu Val Gln Pro Gly Xaa
1               5                   10                  15

Ser Leu Arg Leu Ser Cys Ala Ala Ser
            20                  25

<210> SEQ ID NO 403
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (17)..(17)
<223> OTHER INFORMATION: Xaa = D or W

<400> SEQUENCE: 403

Met Tyr Trp Val Arg Gln Ala Pro Gly Lys Gly Leu Glu Trp Met Gly
1               5                   10                  15

Xaa

<210> SEQ ID NO 404
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = T or N

<400> SEQUENCE: 404

Xaa Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 405
<211> LENGTH: 111
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: Xaa = A or V
<220> FEATURE:
<221> NAME/KEY: misc_feature
<222> LOCATION: (46)..(46)
<223> OTHER INFORMATION: Xaa = Q or K
<220> FEATURE:
```

<221> NAME/KEY: misc_feature
<222> LOCATION: (47)..(47)
<223> OTHER INFORMATION: Xaa = P or A

<400> SEQUENCE: 405

Asp Ile Gln Met Thr Gln Ser Pro Ser Thr Leu Ser Xaa Ser Val Gly
1                5                  10                  15

Asp Arg Val Thr Ile Thr Cys Arg Ala Ser Lys Ser Val Ser Thr Ser
                20                  25                  30

Gly Tyr Asn Phe Val Tyr Trp Tyr Gln Gln Lys Pro Gly Xaa Xaa Pro
            35                  40                  45

Lys Leu Leu Ile Tyr Leu Ala Ser Asn Leu Glu Ser Gly Val Pro Ser
        50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Arg
                85                  90                  95

Glu Leu Pro Arg Thr Phe Gly Gln Gly Thr Lys Val Glu Ile Lys
            100                 105                 110

<210> SEQ ID NO 406
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: Xaa = A or V

<400> SEQUENCE: 406

Asp Ile Gln Met Thr Gln Ser Pro Ser Thr Leu Ser Xaa Ser Val Gly
1                5                  10                  15

Asp Arg Val Thr Ile Thr Cys Arg Ala Ser
                20                  25

<210> SEQ ID NO 407
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (10)..(10)
<223> OTHER INFORMATION: Xaa = Q or K
<220> FEATURE:
<221> NAME/KEY: misc_feature
<222> LOCATION: (11)..(11)
<223> OTHER INFORMATION: Xaa = P or A

<400> SEQUENCE: 407

Val Tyr Trp Tyr Gln Gln Lys Pro Gly Xaa Xaa Pro Lys Leu Leu Ile
1                5                  10                  15

Tyr

<210> SEQ ID NO 408
<211> LENGTH: 119
<212> TYPE: PRT
<213> ORGANISM: Artificial Sequence
<220> FEATURE:
<223> OTHER INFORMATION: synthetic construct
<220> FEATURE:
<221> NAME/KEY: misc_feature

```
<222> LOCATION: (20)..(20)
<223> OTHER INFORMATION: Xaa = V or M
<220> FEATURE:
<221> NAME/KEY: misc_feature
<222> LOCATION: (48)..(48)
<223> OTHER INFORMATION: Xaa = M or I
<220> FEATURE:
<221> NAME/KEY: misc_feature
<222> LOCATION: (59)..(59)
<223> OTHER INFORMATION: Xaa = K or N
<220> FEATURE:
<221> NAME/KEY: misc_feature
<222> LOCATION: (62)..(62)
<223> OTHER INFORMATION: Xaa = E or Q
<220> FEATURE:
<221> NAME/KEY: misc_feature
<222> LOCATION: (65)..(65)
<223> OTHER INFORMATION: Xaa = K or Q
<220> FEATURE:
<221> NAME/KEY: misc_feature
<222> LOCATION: (72)..(72)
<223> OTHER INFORMATION: Xaa = S or R
<220> FEATURE:
<221> NAME/KEY: misc_feature
<222> LOCATION: (74)..(74)
<223> OTHER INFORMATION: Xaa = K or T
<220> FEATURE:
<221> NAME/KEY: misc_feature
<222> LOCATION: (76)..(76)
<223> OTHER INFORMATION: Xaa = T or I
<220> FEATURE:
<221> NAME/KEY: misc_feature
<222> LOCATION: (79)..(79)
<223> OTHER INFORMATION: Xaa = V or A
<220> FEATURE:
<221> NAME/KEY: misc_feature
<222> LOCATION: (85)..(85)
<223> OTHER INFORMATION: Xaa = S or R
<220> FEATURE:
<221> NAME/KEY: misc_feature
<222> LOCATION: (89)..(89)
<223> OTHER INFORMATION: Xaa = E or D

<400> SEQUENCE: 408

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Phe Thr Ser Tyr
            20                  25                  30

Val Met His Val Arg Gln Ala Pro Gly Gln Gly Leu Glu Trp Xaa
        35                  40                  45

Ala Tyr Ile Leu Pro Phe Asn Asp Val Thr Xaa Tyr Asn Xaa Lys Phe
    50                  55                  60

Xaa Gly Arg Val Thr Met Thr Xaa Asp Xaa Ser Xaa Ser Thr Xaa Tyr
65                  70                  75                  80

Met Glu Leu Ser Xaa Leu Arg Ser Xaa Asp Thr Ala Val Tyr Tyr Cys
            85                  90                  95

Ala Arg Trp Glu Trp Asp Asp Gly Tyr Phe Asp Tyr Trp Gly Gln Gly
            100                 105                 110

Thr Leu Val Thr Val Ser Ser
        115

<210> SEQ ID NO 409
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (20)..(20)
```

-continued

<223> OTHER INFORMATION: Xaa = V or M

<400> SEQUENCE: 409

Gln Val Gln Leu Val Gln Ser Gly Ala Glu Val Lys Lys Pro Gly Ala
1               5                   10                  15

Ser Val Lys Xaa Ser Cys Lys Ala Ser
            20                  25

<210> SEQ ID NO 410
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (15)..(15)
<223> OTHER INFORMATION: Xaa = M or I

<400> SEQUENCE: 410

Met His Trp Val Arg Gln Ala Pro Gly Gln Gly Leu Glu Trp Xaa Ala
1               5                   10                  15

Tyr

<210> SEQ ID NO 411
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = K or N
<220> FEATURE:
<221> NAME/KEY: misc_feature
<222> LOCATION: (4)..(4)
<223> OTHER INFORMATION: Xaa = E or Q
<220> FEATURE:
<221> NAME/KEY: misc_feature
<222> LOCATION: (7)..(7)
<223> OTHER INFORMATION: Xaa = K or Q
<220> FEATURE:
<221> NAME/KEY: misc_feature
<222> LOCATION: (14)..(14)
<223> OTHER INFORMATION: Xaa = S or R
<220> FEATURE:
<221> NAME/KEY: misc_feature
<222> LOCATION: (16)..(16)
<223> OTHER INFORMATION: Xaa = K or T
<220> FEATURE:
<221> NAME/KEY: misc_feature
<222> LOCATION: (18)..(18)
<223> OTHER INFORMATION: Xaa = T or I
<220> FEATURE:
<221> NAME/KEY: misc_feature
<222> LOCATION: (21)..(21)
<223> OTHER INFORMATION: Xaa = V or A
<220> FEATURE:
<221> NAME/KEY: misc_feature
<222> LOCATION: (27)..(27)
<223> OTHER INFORMATION: Xaa = S or R
<220> FEATURE:
<221> NAME/KEY: misc_feature
<222> LOCATION: (31)..(31)
<223> OTHER INFORMATION: Xaa = E or D

<400> SEQUENCE: 411

Xaa Tyr Asn Xaa Lys Phe Xaa Gly Arg Val Thr Met Thr Xaa Asp Xaa
1               5                   10                  15

Ser Xaa Ser Thr Xaa Tyr Met Glu Leu Ser Xaa Leu Arg Ser Xaa Asp

-continued

```
                 20              25              30

Thr Ala Val Tyr Tyr Cys
        35

<210> SEQ ID NO 412
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: Xaa = S or T
<220> FEATURE:
<221> NAME/KEY: misc_feature
<222> LOCATION: (9)..(9)
<223> OTHER INFORMATION: Xaa = D or L
<220> FEATURE:
<221> NAME/KEY: misc_feature
<222> LOCATION: (12)..(12)
<223> OTHER INFORMATION: Xaa = A or S
<220> FEATURE:
<221> NAME/KEY: misc_feature
<222> LOCATION: (14)..(14)
<223> OTHER INFORMATION: Xaa = S or T
<220> FEATURE:
<221> NAME/KEY: misc_feature
<222> LOCATION: (15)..(15)
<223> OTHER INFORMATION: Xaa = L or P
<220> FEATURE:
<221> NAME/KEY: misc_feature
<222> LOCATION: (17)..(17)
<223> OTHER INFORMATION: Xaa = E or Q
<220> FEATURE:
<221> NAME/KEY: misc_feature
<222> LOCATION: (18)..(18)
<223> OTHER INFORMATION: Xaa = R or P
<220> FEATURE:
<221> NAME/KEY: misc_feature
<222> LOCATION: (20)..(20)
<223> OTHER INFORMATION: Xaa = T or S
<220> FEATURE:
<221> NAME/KEY: misc_feature
<222> LOCATION: (22)..(22)
<223> OTHER INFORMATION: Xaa = N or S
<220> FEATURE:
<221> NAME/KEY: misc_feature
<222> LOCATION: (42)..(42)
<223> OTHER INFORMATION: Xaa = Q or L
<220> FEATURE:
<221> NAME/KEY: misc_feature
<222> LOCATION: (48)..(48)
<223> OTHER INFORMATION: Xaa = P or S
<220> FEATURE:
<221> NAME/KEY: misc_feature
<222> LOCATION: (58)..(58)
<223> OTHER INFORMATION: Xaa = T or N
<220> FEATURE:
<221> NAME/KEY: misc_feature
<222> LOCATION: (64)..(64)
<223> OTHER INFORMATION: Xaa = L or P
<220> FEATURE:
<221> NAME/KEY: misc_feature
<222> LOCATION: (79)..(79)
<223> OTHER INFORMATION: Xaa = T or K
<220> FEATURE:
<221> NAME/KEY: misc_feature
<222> LOCATION: (82)..(84)
<223> OTHER INFORMATION: Xaa = S or R
<220> FEATURE:
<221> NAME/KEY: misc_feature
<222> LOCATION: (83)..(83)
<223> OTHER INFORMATION: Xaa = L or V
<220> FEATURE:
<221> NAME/KEY: misc_feature
<222> LOCATION: (84)..(84)
```

-continued

```
<223> OTHER INFORMATION: Xaa = Q or E
<220> FEATURE:
<221> NAME/KEY: misc_feature
<222> LOCATION: (89)..(89)
<223> OTHER INFORMATION: Xaa = A or G
<220> FEATURE:
<221> NAME/KEY: misc_feature
<222> LOCATION: (105)..(105)
<223> OTHER INFORMATION: Xaa = G or Q
<220> FEATURE:
<221> NAME/KEY: misc_feature
<222> LOCATION: (109)..(109)
<223> OTHER INFORMATION: Xaa = V or L

<400> SEQUENCE: 412

Asp Ile Val Met Thr Gln Xaa Pro Xaa Ser Leu Xaa Val Xaa Xaa Gly
1               5                   10                  15

Xaa Xaa Ala Xaa Ile Xaa Cys Lys Ser Ser Gln Ser Leu Glu Asn Ser
            20                  25                  30

Asn Gly Asn Thr Tyr Leu Asn Trp Tyr Xaa Gln Lys Pro Gly Gln Xaa
        35                  40                  45

Pro Lys Leu Leu Ile Tyr Arg Val Ser Xaa Arg Phe Ser Gly Val Xaa
    50                  55                  60

Asp Arg Phe Ser Gly Ser Gly Ser Gly Thr Asp Phe Thr Leu Xaa Ile
65                  70                  75                  80

Ser Xaa Xaa Xaa Ala Glu Asp Val Xaa Val Tyr Tyr Cys Leu Gln Val
            85                  90                  95

Ser His Val Pro Phe Thr Phe Gly Xaa Gly Thr Lys Xaa Glu Ile Lys
            100                 105                 110

<210> SEQ ID NO 413
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: Xaa= S or T
<220> FEATURE:
<221> NAME/KEY: misc_feature
<222> LOCATION: (9)..(9)
<223> OTHER INFORMATION: Xaa = D or L
<220> FEATURE:
<221> NAME/KEY: misc_feature
<222> LOCATION: (12)..(12)
<223> OTHER INFORMATION: Xaa = A or S
<220> FEATURE:
<221> NAME/KEY: misc_feature
<222> LOCATION: (14)..(14)
<223> OTHER INFORMATION: Xaa = S or T
<220> FEATURE:
<221> NAME/KEY: misc_feature
<222> LOCATION: (15)..(15)
<223> OTHER INFORMATION: Xaa = L or P
<220> FEATURE:
<221> NAME/KEY: misc_feature
<222> LOCATION: (17)..(17)
<223> OTHER INFORMATION: Xaa = E or Q
<220> FEATURE:
<221> NAME/KEY: misc_feature
<222> LOCATION: (18)..(18)
<223> OTHER INFORMATION: Xaa = R or P
<220> FEATURE:
<221> NAME/KEY: misc_feature
<222> LOCATION: (20)..(20)
<223> OTHER INFORMATION: Xaa = T or S
<220> FEATURE:
<221> NAME/KEY: misc_feature
<222> LOCATION: (22)..(22)
```

-continued

```
<223> OTHER INFORMATION: Xaa = N or S

<400> SEQUENCE: 413

Asp Ile Val Met Thr Gln Xaa Pro Xaa Ser Leu Xaa Val Xaa Xaa Gly
1               5                   10                  15

Xaa Xaa Ala Xaa Ile Xaa Cys Lys Ser Ser
            20                  25

<210> SEQ ID NO 414
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa = Q or L
<220> FEATURE:
<221> NAME/KEY: misc_feature
<222> LOCATION: (11)..(11)
<223> OTHER INFORMATION: Xaa = P or S

<400> SEQUENCE: 414

Leu Asn Trp Tyr Xaa Gln Lys Pro Gly Gln Xaa Pro Lys Leu Leu Ile
1               5                   10                  15

Tyr

<210> SEQ ID NO 415
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = T or N
<220> FEATURE:
<221> NAME/KEY: misc_feature
<222> LOCATION: (7)..(7)
<223> OTHER INFORMATION: Xaa = L or P
<220> FEATURE:
<221> NAME/KEY: misc_feature
<222> LOCATION: (22)..(22)
<223> OTHER INFORMATION: Xaa = T or K
<220> FEATURE:
<221> NAME/KEY: misc_feature
<222> LOCATION: (25)..(25)
<223> OTHER INFORMATION: Xaa = S or R
<220> FEATURE:
<221> NAME/KEY: misc_feature
<222> LOCATION: (26)..(26)
<223> OTHER INFORMATION: Xaa = L or V
<220> FEATURE:
<221> NAME/KEY: misc_feature
<222> LOCATION: (27)..(27)
<223> OTHER INFORMATION: Xaa = Q or E
<220> FEATURE:
<221> NAME/KEY: misc_feature
<222> LOCATION: (32)..(32)
<223> OTHER INFORMATION: Xaa = A or G

<400> SEQUENCE: 415

Xaa Arg Phe Ser Gly Val Xaa Asp Arg Phe Ser Gly Ser Gly Ser Gly
1               5                   10                  15

Thr Asp Phe Thr Leu Xaa Ile Ser Xaa Xaa Xaa Ala Glu Asp Val Xaa
            20                  25                  30

Val Tyr Tyr Cys
        35
```

```
<210> SEQ ID NO 416
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa = G or Q
<220> FEATURE:
<221> NAME/KEY: misc_feature
<222> LOCATION: (7)..(7)
<223> OTHER INFORMATION: Xaa = V or L

<400> SEQUENCE: 416

Phe Gly Xaa Gly Thr Lys Xaa Glu Ile Lys
1               5                   10

<210> SEQ ID NO 417
<211> LENGTH: 118
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = Q or E
<220> FEATURE:
<221> NAME/KEY: misc_feature
<222> LOCATION: (9)..(9)
<223> OTHER INFORMATION: Xaa = A or G
<220> FEATURE:
<221> NAME/KEY: misc_feature
<222> LOCATION: (10)..(10)
<223> OTHER INFORMATION: Xaa = E or G
<220> FEATURE:
<221> NAME/KEY: misc_feature
<222> LOCATION: (11)..(11)
<223> OTHER INFORMATION: Xaa = L or V
<220> FEATURE:
<221> NAME/KEY: misc_feature
<222> LOCATION: (13)..(13)
<223> OTHER INFORMATION: Xaa = K or Q
<220> FEATURE:
<221> NAME/KEY: misc_feature
<222> LOCATION: (16)..(16)
<223> OTHER INFORMATION: Xaa = S or R
<220> FEATURE:
<221> NAME/KEY: misc_feature
<222> LOCATION: (18)..(18)
<223> OTHER INFORMATION: Xaa = V or L
<220> FEATURE:
<221> NAME/KEY: misc_feature
<222> LOCATION: (19)..(19)
<223> OTHER INFORMATION: Xaa = K or R
<220> FEATURE:
<221> NAME/KEY: misc_feature
<222> LOCATION: (20)..(20)
<223> OTHER INFORMATION: Xaa = M or L
<220> FEATURE:
<221> NAME/KEY: misc_feature
<222> LOCATION: (23)..(23)
<223> OTHER INFORMATION: Xaa = K or A
<220> FEATURE:
<221> NAME/KEY: misc_feature
<222> LOCATION: (48)..(48)
<223> OTHER INFORMATION: Xaa = M or I
<220> FEATURE:
<221> NAME/KEY: misc_feature
<222> LOCATION: (49)..(49)
<223> OTHER INFORMATION: Xaa = G or A
<220> FEATURE:
<221> NAME/KEY: misc_feature
```

```
<222> LOCATION: (58)..(58)
<223> OTHER INFORMATION: Xaa = T or A
<220> FEATURE:
<221> NAME/KEY: misc_feature
<222> LOCATION: (62)..(62)
<223> OTHER INFORMATION: Xaa = Q or E
<220> FEATURE:
<221> NAME/KEY: misc_feature
<222> LOCATION: (64)..(64)
<223> OTHER INFORMATION: Xaa = F or V
<220> FEATURE:
<221> NAME/KEY: misc_feature
<222> LOCATION: (65)..(65)
<223> OTHER INFORMATION: Xaa = Q or K
<220> FEATURE:
<221> NAME/KEY: misc_feature
<222> LOCATION: (68)..(68)
<223> OTHER INFORMATION: Xaa = V or F
<220> FEATURE:
<221> NAME/KEY: misc_feature
<222> LOCATION: (70)..(70)
<223> OTHER INFORMATION: Xaa = M or I
<220> FEATURE:
<221> NAME/KEY: misc_feature
<222> LOCATION: (71)..(71)
<223> OTHER INFORMATION: Xaa = T or S
<220> FEATURE:
<221> NAME/KEY: misc_feature
<222> LOCATION: (72)..(72)
<223> OTHER INFORMATION: Xaa = S or R
<220> FEATURE:
<221> NAME/KEY: misc_feature
<222> LOCATION: (74)..(74)
<223> OTHER INFORMATION: Xaa = K or N
<220> FEATURE:
<221> NAME/KEY: misc_feature
<222> LOCATION: (76)..(76)
<223> OTHER INFORMATION: Xaa = T or K
<220> FEATURE:
<221> NAME/KEY: misc_feature
<222> LOCATION: (77)..(77)
<223> OTHER INFORMATION: Xaa = S or N
<220> FEATURE:
<221> NAME/KEY: misc_feature
<222> LOCATION: (79)..(79)
<223> OTHER INFORMATION: Xaa = A or L
<220> FEATURE:
<221> NAME/KEY: misc_feature
<222> LOCATION: (81)..(81)
<223> OTHER INFORMATION: Xaa = M or L
<220> FEATURE:
<221> NAME/KEY: misc_feature
<222> LOCATION: (82)..(82)
<223> OTHER INFORMATION: Xaa = E or Q
<220> FEATURE:
<221> NAME/KEY: misc_feature
<222> LOCATION: (83)..(83)
<223> OTHER INFORMATION: Xaa = L or M
<220> FEATURE:
<221> NAME/KEY: misc_feature
<222> LOCATION: (84)..(84)
<223> OTHER INFORMATION: Xaa = S or N
<220> FEATURE:
<221> NAME/KEY: misc_feature
<222> LOCATION: (88)..(88)
<223> OTHER INFORMATION: Xaa = S or A

<400> SEQUENCE: 417

Gln Val Gln Leu Val Xaa Ser Gly Xaa Xaa Xaa Val Xaa Pro Gly Xaa
1               5                   10                  15

Ser Xaa Xaa Xaa Ser Cys Xaa Ala Ser Gly Tyr Thr Phe Thr Asn Tyr
            20                  25                  30

Val Met His Trp Val Arg Gln Ala Pro Gly Gln Gly Leu Glu Trp Xaa
        35                  40                  45

Xaa Tyr Ile Leu Pro Tyr Asn Asp Gly Xaa Asn Tyr Asn Xaa Lys Xaa
```

```
        50                  55                  60

Xaa Gly Arg Xaa Thr Xaa Xaa Xaa Asp Xaa Ser Xaa Xaa Thr Xaa Tyr
65                  70                  75                  80

Xaa Xaa Xaa Xaa Ser Leu Arg Xaa Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser
        115
```

```
<210> SEQ ID NO 418
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: Xaa = T or A

<400> SEQUENCE: 418

Ile Leu Pro Tyr Asn Asp Gly Xaa
1               5
```

```
<210> SEQ ID NO 419
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = Q or E
<220> FEATURE:
<221> NAME/KEY: misc_feature
<222> LOCATION: (9)..(9)
<223> OTHER INFORMATION: Xaa= A or G
<220> FEATURE:
<221> NAME/KEY: misc_feature
<222> LOCATION: (10)..(10)
<223> OTHER INFORMATION: Xaa = E or G
<220> FEATURE:
<221> NAME/KEY: misc_feature
<222> LOCATION: (11)..(11)
<223> OTHER INFORMATION: Xaa = L or V
<220> FEATURE:
<221> NAME/KEY: misc_feature
<222> LOCATION: (13)..(13)
<223> OTHER INFORMATION: Xaa = K or Q
<220> FEATURE:
<221> NAME/KEY: misc_feature
<222> LOCATION: (16)..(16)
<223> OTHER INFORMATION: Xaa = S or R
<220> FEATURE:
<221> NAME/KEY: misc_feature
<222> LOCATION: (18)..(18)
<223> OTHER INFORMATION: Xaa = V or L
<220> FEATURE:
<221> NAME/KEY: misc_feature
<222> LOCATION: (19)..(19)
<223> OTHER INFORMATION: Xaa = K or R
<220> FEATURE:
<221> NAME/KEY: misc_feature
<222> LOCATION: (20)..(20)
<223> OTHER INFORMATION: Xaa = M or L
<220> FEATURE:
<221> NAME/KEY: misc_feature
<222> LOCATION: (23)..(23)
<223> OTHER INFORMATION: Xaa = K or A
```

```
<400> SEQUENCE: 419

Gln Val Gln Leu Val Xaa Ser Gly Xaa Xaa Xaa Val Xaa Pro Gly Xaa
1               5                   10                  15

Ser Xaa Xaa Xaa Ser Cys Xaa Ala Ser
            20                  25

<210> SEQ ID NO 420
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (15)..(15)
<223> OTHER INFORMATION: Xaa = M or I
<220> FEATURE:
<221> NAME/KEY: misc_feature
<222> LOCATION: (16)..(16)
<223> OTHER INFORMATION: Xaa = G or A

<400> SEQUENCE: 420

Met His Trp Val Arg Gln Ala Pro Gly Gln Gly Leu Glu Trp Xaa Xaa
1               5                   10                  15

Tyr

<210> SEQ ID NO 421
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa = Q or E
<220> FEATURE:
<221> NAME/KEY: misc_feature
<222> LOCATION: (6)..(6)
<223> OTHER INFORMATION: Xaa = F or V
<220> FEATURE:
<221> NAME/KEY: misc_feature
<222> LOCATION: (7)..(7)
<223> OTHER INFORMATION: Xaa = Q or K
<220> FEATURE:
<221> NAME/KEY: misc_feature
<222> LOCATION: (10)..(10)
<223> OTHER INFORMATION: Xaa = V or F
<220> FEATURE:
<221> NAME/KEY: misc_feature
<222> LOCATION: (12)..(12)
<223> OTHER INFORMATION: Xaa = M or I
<220> FEATURE:
<221> NAME/KEY: misc_feature
<222> LOCATION: (13)..(13)
<223> OTHER INFORMATION: Xaa = T or S
<220> FEATURE:
<221> NAME/KEY: misc_feature
<222> LOCATION: (14)..(14)
<223> OTHER INFORMATION: Xaa = S or R
<220> FEATURE:
<221> NAME/KEY: misc_feature
<222> LOCATION: (16)..(16)
<223> OTHER INFORMATION: Xaa = K or N
<220> FEATURE:
<221> NAME/KEY: misc_feature
<222> LOCATION: (18)..(18)
<223> OTHER INFORMATION: Xaa = T or K
<220> FEATURE:
<221> NAME/KEY: misc_feature
<222> LOCATION: (19)..(19)
<223> OTHER INFORMATION: Xaa = S or N
<220> FEATURE:
```

```
<221> NAME/KEY: misc_feature
<222> LOCATION: (21)..(21)
<223> OTHER INFORMATION: Xaa = A or L
<220> FEATURE:
<221> NAME/KEY: misc_feature
<222> LOCATION: (23)..(23)
<223> OTHER INFORMATION: Xaa = M or L
<220> FEATURE:
<221> NAME/KEY: misc_feature
<222> LOCATION: (24)..(24)
<223> OTHER INFORMATION: Xaa = E or Q
<220> FEATURE:
<221> NAME/KEY: misc_feature
<222> LOCATION: (25)..(25)
<223> OTHER INFORMATION: Xaa = L or M
<220> FEATURE:
<221> NAME/KEY: misc_feature
<222> LOCATION: (26)..(26)
<223> OTHER INFORMATION: Xaa = S or N
<220> FEATURE:
<221> NAME/KEY: misc_feature
<222> LOCATION: (30)..(30)
<223> OTHER INFORMATION: Xaa = S or A

<400> SEQUENCE: 421

Asn Tyr Asn Xaa Lys Xaa Xaa Gly Arg Xaa Thr Xaa Xaa Xaa Asp Xaa
1               5                   10                  15

Ser Xaa Xaa Thr Xaa Tyr Xaa Xaa Xaa Ser Leu Arg Xaa Glu Asp
            20                  25                  30

Thr Ala Val Tyr Tyr Cys
        35

<210> SEQ ID NO 422
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (42)..(42)
<223> OTHER INFORMATION: Xaa = K or Q
<220> FEATURE:
<221> NAME/KEY: misc_feature
<222> LOCATION: (43)..(43)
<223> OTHER INFORMATION: Xaa = A or S
<220> FEATURE:
<221> NAME/KEY: misc_feature
<222> LOCATION: (44)..(44)
<223> OTHER INFORMATION: Xaa = P or V
<220> FEATURE:
<221> NAME/KEY: misc_feature
<222> LOCATION: (48)..(48)
<223> OTHER INFORMATION: Xaa = M or I
<220> FEATURE:
<221> NAME/KEY: misc_feature
<222> LOCATION: (49)..(49)
<223> OTHER INFORMATION: Xaa = C or Y

<400> SEQUENCE: 422

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Xaa Xaa Xaa Lys Leu Leu Xaa
            35                  40                  45

Xaa Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys
            100                 105

<210> SEQ ID NO 423
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (10)..(10)
<223> OTHER INFORMATION: Xaa = K or Q
<220> FEATURE:
<221> NAME/KEY: misc_feature
<222> LOCATION: (11)..(11)
<223> OTHER INFORMATION: Xaa = A or S
<220> FEATURE:
<221> NAME/KEY: misc_feature
<222> LOCATION: (12)..(12)
<223> OTHER INFORMATION: Xaa = P or V
<220> FEATURE:
<221> NAME/KEY: misc_feature
<222> LOCATION: (16)..(16)
<223> OTHER INFORMATION: Xaa = M or I
<220> FEATURE:
<221> NAME/KEY: misc_feature
<222> LOCATION: (17)..(17)
<223> OTHER INFORMATION: Xaa = C or Y

<400> SEQUENCE: 423

Leu Asn Trp Tyr Gln Gln Lys Pro Gly Xaa Xaa Xaa Lys Leu Leu Xaa
1               5                   10                  15

Xaa

<210> SEQ ID NO 424
<211> LENGTH: 447
<212> TYPE: PRT
<213> ORGANISM: Artificial Sequence
<220> FEATURE:
<223> OTHER INFORMATION: synthetic construct

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Tyr Trp Val Arg Gln Ala Pro Gly Gln Gly Leu Glu Trp Met
        35                  40                  45

Gly Trp Ile Asn Thr Glu Thr Gly Glu Pro Asn Tyr Ala Gln Asp Val
    50                  55                  60

Gln Gly Arg Phe Thr Met Thr Leu Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Ile Ser Tyr Tyr Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

-continued

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445
```

```
<210> SEQ ID NO 425
<211> LENGTH: 218
<212> TYPE: PRT
<213> ORGANISM: Artificial Sequence
<220> FEATURE:
<223> OTHER INFORMATION: synthetic construct

<400> SEQUENCE: 425

Asp Ile Val Met Thr Gln Thr Pro Leu Ser Leu Ser Val Thr Pro Gly
1                   5                   10                  15

Gln Pro Ala Ser Ile Ser Cys Lys Ser Ser Lys Ser Val Ser Thr Ser
                20                  25                  30

Gly Tyr Ser Phe Leu His Trp Tyr Leu Gln Lys Pro Gly Gln Pro Pro
                35                  40                  45

Gln Leu Leu Ile Tyr Phe Ala Ser Asn Leu Glu Ser Gly Val Pro Asp
        50                  55                  60
```

-continued

```
Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Arg Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

```
<210> SEQ ID NO 426
<211> LENGTH: 447
<212> TYPE: PRT
<213> ORGANISM: Artificial Sequence
<220> FEATURE:
<223> OTHER INFORMATION: synthetic construct

<400> SEQUENCE: 426
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Tyr Trp Val Arg Gln Ala Pro Gly Gln Gly Leu Glu Trp Met
        35                  40                  45

Gly Trp Ile Asn Thr Glu Thr Gly Glu Thr Asn Tyr Ala Gln Asp Phe
    50                  55                  60

Gln Gly Arg Val Thr Met Thr Thr Asp Thr Glu Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Ile Ser Tyr Tyr Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205
```

-continued

```
Thr Lys Val Asp Lys Lys Val Glu Pro Lys Ser Cys Asp Lys Thr His
    210             215                 220

Thr Cys Pro Pro Cys Pro Ala Pro Glu Leu Leu Gly Gly Pro Ser Val
225             230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 427
<211> LENGTH: 218
<212> TYPE: PRT
<213> ORGANISM: Artificial Sequence
<220> FEATURE:
<223> OTHER INFORMATION: synthetic construct

<400> SEQUENCE: 427

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Phe Leu His Trp Tyr Gln Gln Lys Pro Gly Gln Ala Pro
        35                  40                  45

Arg Leu Leu Ile Tyr Phe Ala Ser Asn Leu Glu Thr Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
            85                  90                  95

Glu Leu Pro Arg Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125
```

-continued

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 428
<211> LENGTH: 447
<212> TYPE: PRT
<213> ORGANISM: Artificial Sequence
<220> FEATURE:
<223> OTHER INFORMATION: synthetic construct

<400> SEQUENCE: 428

Glu Val Gln Leu Val Glu Ser Gly Gly Gly Leu Val Gln Pro Gly Glu
1               5                   10                  15

Ser Leu Arg Leu Ser Cys Ala Ala Ser Gly Tyr Thr Phe Thr Asp Tyr
            20                  25                  30

Thr Met Tyr Trp Val Arg Gln Ala Pro Gly Lys Gly Leu Glu Trp Met
        35                  40                  45

Gly Trp Ile Asn Thr Glu Thr Gly Glu Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Tyr Tyr Tyr Gly Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270
```

-continued

```
Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 429
<211> LENGTH: 218
<212> TYPE: PRT
<213> ORGANISM: Artificial Sequence
<220> FEATURE:
<223> OTHER INFORMATION: synthetic construct

<400> SEQUENCE: 429

Asp Ile Gln Met Thr Gln Ser Pro Ser Thr Leu Ser Val Ser Val Gly
1               5                   10                  15

Asp Arg Val Thr Ile Thr Cys Arg Ala Ser Lys Ser Val Ser Thr Ser
                20                  25                  30

Gly Tyr Asn Phe Val Tyr Trp Tyr Gln Gln Lys Pro Gly Lys Ala Pro
            35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Arg
                85                  90                  95

Glu Leu Pro Arg Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

-continued

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 430
<211> LENGTH: 447
<212> TYPE: PRT
<213> ORGANISM: Artificial Sequence
<220> FEATURE:
<223> OTHER INFORMATION: synthetic construct

<400> SEQUENCE: 430

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Thr Met Tyr Trp Val Arg Gln Ala Pro Gly Lys Gly Leu Glu Trp Met
        35                  40                  45

Gly Asp Ile Asn Thr Glu Thr Gly Glu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Tyr Tyr Tyr Gly Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

-continued

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445
```

<210> SEQ ID NO 431
<211> LENGTH: 218
<212> TYPE: PRT
<213> ORGANISM: Artificial Sequence
<220> FEATURE:
<223> OTHER INFORMATION: synthetic construct

<400> SEQUENCE: 431

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Asn Phe Val Tyr Trp Tyr Gln Gln Lys Pro Gly Gln Pro Pro
            35                  40                  45

Lys Leu Leu Ile Tyr Leu Ala Ser Asn Leu Glu Ser Gly Val Pro Ser
            50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Arg
                        85                  90                  95

Glu Leu Pro Arg Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 432
<211> LENGTH: 449
<212> TYPE: PRT
<213> ORGANISM: Artificial Sequence
<220> FEATURE:

<223> OTHER INFORMATION: synthetic construct

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Ala Tyr Ile Leu Pro Phe Asn Asp Val Thr Lys Tyr Asn Glu Lys Phe
    50                  55                  60

Lys Gly Arg Val Thr Met Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Glu Trp Asp Asp Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 433
<211> LENGTH: 219
<212> TYPE: PRT
<213> ORGANISM: Artificial Sequence
<220> FEATURE:
<223> OTHER INFORMATION: synthetic construct

<400> SEQUENCE: 433

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
            85                  90                  95

Ser His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 434
<211> LENGTH: 449
<212> TYPE: PRT
<213> ORGANISM: Artificial Sequence
<220> FEATURE:
<223> OTHER INFORMATION: synthetic construct

<400> SEQUENCE: 434

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

-continued

```
Val Met His Trp Val Arg Gln Ala Pro Gly Gln Gly Leu Glu Trp Ile
    35                  40                  45

Ala Tyr Ile Leu Pro Phe Asn Asp Val Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Glu Trp Asp Asp Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 435
<211> LENGTH: 219
<212> TYPE: PRT
<213> ORGANISM: Artificial Sequence
<220> FEATURE:
<223> OTHER INFORMATION: synthetic construct

<400> SEQUENCE: 435

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Glu Asn Ser
            20                  25                  30

Asn Gly Asn Thr Tyr Leu Asn Trp Tyr Gln Gln Lys Pro Gly Gln Pro
        35                  40                  45

Pro Lys Leu Leu Ile Tyr Arg Val Ser Thr Arg Phe Ser Gly Val Leu
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Leu Gln Val
                85                  90                  95

Ser His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 436
<211> LENGTH: 448
<212> TYPE: PRT
<213> ORGANISM: Artificial Sequence
<220> FEATURE:
<223> OTHER INFORMATION: synthetic construct

<400> SEQUENCE: 436

Gln Val Gln Leu Val Gln Ser Gly Ala Glu Leu Val Lys Pro Gly Ser
1               5                   10                  15

Ser Val Lys Met Ser Cys Lys Ala Ser Gly Tyr Thr Phe Thr Asn Tyr
            20                  25                  30

Val Met His Trp Val Arg Gln Ala Pro Gly Gln Gly Leu Glu Trp Met
        35                  40                  45

Gly Tyr Ile Leu Pro Tyr Asn Asp Gly Thr Asn Tyr Asn Gln Lys Phe
    50                  55                  60

Gln Gly Arg Val Thr Met Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
```

```
                    85              90              95

Ala Arg Tyr Asp Tyr Glu Gly Ser Phe Asp Tyr Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
        130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Lys Val Glu Pro Lys Ser Cys Asp Lys Thr
        210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
        290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445
```

<210> SEQ ID NO 437
<211> LENGTH: 214
<212> TYPE: PRT
<213> ORGANISM: Artificial Sequence
<220> FEATURE:
<223> OTHER INFORMATION: synthetic construct

<400> SEQUENCE: 437

Asp Ile Gln Met Thr Gln Ser Pro Ser Ser Leu Ser Ala Ser Val Gly

-continued

```
1              5               10              15

Asp Arg Val Thr Ile Thr Cys Arg Ala Ser Gln Asp Ile Ser Asn Tyr
            20              25              30

Leu Asn Trp Tyr Gln Gln Lys Pro Gly Lys Ala Pro Lys Leu Leu Met
            35              40              45

Cys Tyr Thr Ser Arg Leu His Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Gly Asn Thr Phe Pro Pro
                85              90              95

Thr Phe Gly Gly Gly Thr Lys Val Glu Ile Lys Arg Thr Val Ala Ala
                100             105             110

Pro Ser Val Phe Ile Phe Pro Pro Ser Asp Glu Gln Leu Lys Ser Gly
                115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210
```

```
<210> SEQ ID NO 438
<211> LENGTH: 448
<212> TYPE: PRT
<213> ORGANISM: Artificial Sequence
<220> FEATURE:
<223> OTHER INFORMATION: synthetic construct

<400> SEQUENCE: 438
```

```
Gln Val Gln Leu Val Glu Ser Gly Gly Gly Val Val Gln Pro Gly Arg
1              5               10              15

Ser Leu Arg Leu Ser Cys Ala Ala Ser Gly Tyr Thr Phe Thr Asn Tyr
            20              25              30

Val Met His Trp Val Arg Gln Ala Pro Gly Gln Gly Leu Glu Trp Ile
            35              40              45

Ala Tyr Ile Leu Pro Tyr Asn Asp Gly Ala Asn Tyr Asn Glu Lys Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Tyr Asp Tyr Glu Gly Ser Phe Asp Tyr Trp Gly Gln Gly Thr
                100             105             110

Leu Val Thr Val Ser Ser Ala Ser Thr Lys Gly Pro Ser Val Phe Pro
                115             120             125

Leu Ala Pro Ser Ser Lys Ser Thr Ser Gly Gly Thr Ala Ala Leu Gly
        130             135             140

Cys Leu Val Lys Asp Tyr Phe Pro Glu Pro Val Thr Val Ser Trp Asn
```

-continued

```
                145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                    245                 250                 255

Thr Pro Glu Val Thr Cys Val Val Val Asp Val Ser His Glu Asp Pro
                    260                 265                 270

Glu Val Lys Phe Asn Trp Tyr Val Asp Gly Val Glu Val His Asn Ala
                    275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                    340                 345                 350

Pro Pro Ser Arg Asp Glu Leu Thr Lys Asn Gln Val Ser Leu Thr Cys
                    355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                    420                 425                 430

Leu His Asn His Tyr Thr Gln Lys Ser Leu Ser Leu Ser Pro Gly Lys
        435                 440                 445
```

```
<210> SEQ ID NO 439
<211> LENGTH: 214
<212> TYPE: PRT
<213> ORGANISM: Artificial Sequence
<220> FEATURE:
<223> OTHER INFORMATION: synthetic construct

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Gln Ser Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
```

-continued

```
65                    70                    75                    80

Glu Asp Phe Ala Thr Tyr Tyr Cys Gln Gln Gly Asn Thr Phe Pro Pro
                85                    90                    95

Thr Phe Gly Gly Gly Thr Lys Val Glu Ile Lys Arg Thr Val Ala Ala
                100                   105                   110

Pro Ser Val Phe Ile Phe Pro Pro Ser Asp Glu Gln Leu Lys Ser Gly
                115                   120                   125

Thr Ala Ser Val Val Cys Leu Leu Asn Asn Phe Tyr Pro Arg Glu Ala
    130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                165                   170                   175

Ser Thr Leu Thr Leu Ser Lys Ala Asp Tyr Glu Lys His Lys Val Tyr
                180                   185                   190

Ala Cys Glu Val Thr His Gln Gly Leu Ser Ser Pro Val Thr Lys Ser
                195                   200                   205

Phe Asn Arg Gly Glu Cys
    210
```

```
<210> SEQ ID NO 440
<211> LENGTH: 447
<212> TYPE: PRT
<213> ORGANISM: Artificial Sequence
<220> FEATURE:
<223> OTHER INFORMATION: synthetic construct

<400> SEQUENCE: 440

Gln Val Gln Leu Val Gln Ser Gly Ala Glu Val Lys Lys Pro Gly Ala
1                   5                     10                    15

Ser Val Lys Val Ser Cys Lys Ala Ser Gly Tyr Thr Phe Thr Asp Tyr
                20                    25                    30

Ser Ile Tyr Trp Val Arg Gln Ala Pro Gly Gln Gly Leu Glu Trp Met
            35                    40                    45

Gly Trp Ile Asn Thr Glu Thr Gly Glu Pro Asn Tyr Ala Gln Asp Val
    50                    55                    60

Gln Gly Arg Phe Thr Met Thr Leu Asp Thr Ser Thr Ser Thr Ala Tyr
65                    70                    75                    80

Met Glu Leu Arg Ser Leu Arg Ser Asp Asp Thr Ala Val Tyr Tyr Cys
                85                    90                    95

Ser Ile Ser Tyr Tyr Tyr Ala Met Asp Tyr Trp Gly Gln Gly Thr Leu
                100                   105                   110

Val Thr Val Ser Ser Ala Ser Thr Lys Gly Pro Ser Val Phe Pro Leu
                115                   120                   125

Ala Pro Ser Ser Lys Ser Thr Ser Gly Gly Thr Ala Ala Leu Gly Cys
    130                   135                   140

Leu Val Lys Asp Tyr Phe Pro Glu Pro Val Thr Val Ser Trp Asn Ser
145                   150                   155                   160

Gly Ala Leu Thr Ser Gly Val His Thr Phe Pro Ala Val Leu Gln Ser
                165                   170                   175

Ser Gly Leu Tyr Ser Leu Ser Ser Val Val Thr Val Pro Ser Ser Ser
                180                   185                   190

Leu Gly Thr Gln Thr Tyr Ile Cys Asn Val Asn His Lys Pro Ser Asn
                195                   200                   205

Thr Lys Val Asp Lys Lys Val Glu Pro Lys Ser Cys Asp Lys Thr His
```

-continued

```
        210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Cys Arg Asp Glu Leu Thr Lys Asn Gln Val Ser Leu Trp Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 441
<211> LENGTH: 447
<212> TYPE: PRT
<213> ORGANISM: Artificial Sequence
<220> FEATURE:
<223> OTHER INFORMATION: synthetic construct

<400> SEQUENCE: 441

Gln Val Gln Leu Val Gln Ser Gly Ala Glu Val Lys Lys Pro Gly Ala
1                 5                   10                  15

Ser Val Lys Val Ser Cys Lys Ala Ser Gly Tyr Thr Phe Thr Asp Tyr
                20                  25                  30

Ser Ile Tyr Trp Val Arg Gln Ala Pro Gly Gln Gly Leu Glu Trp Met
            35                  40                  45

Gly Trp Ile Asn Thr Glu Thr Gly Glu Thr Asn Tyr Ala Gln Asp Phe
        50                  55                  60

Gln Gly Arg Val Thr Met Thr Thr Asp Thr Glu Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Ile Ser Tyr Tyr Tyr Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
```

-continued

```
     130              135              140
Leu Val Lys Asp Tyr Phe Pro Glu Pro Val Thr Val Ser Trp Asn Ser
145              150              155              160

Gly Ala Leu Thr Ser Gly Val His Thr Phe Pro Ala Val Leu Gln Ser
             165              170              175

Ser Gly Leu Tyr Ser Leu Ser Ser Val Val Thr Val Pro Ser Ser Ser
             180              185              190

Leu Gly Thr Gln Thr Tyr Ile Cys Asn Val Asn His Lys Pro Ser Asn
             195              200              205

Thr Lys Val Asp Lys Lys Val Glu Pro Lys Ser Cys Asp Lys Thr His
             210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
             245              250              255

Pro Glu Val Thr Cys Val Val Val Asp Val Ser His Glu Asp Pro Glu
             260              265              270

Val Lys Phe Asn Trp Tyr Val Asp Gly Val Glu Val His Asn Ala Lys
             275              280              285

Thr Lys Pro Arg Glu Glu Gln Tyr Asn Ser Thr Tyr Arg Val Val Ser
             290              295              300

Val Leu Thr Val Leu His Gln Asp Trp Leu Asn Gly Lys Glu Tyr Lys
305              310              315              320

Cys Lys Val Ser Asn Lys Ala Leu Pro Ala Pro Ile Glu Lys Thr Ile
             325              330              335

Ser Lys Ala Lys Gly Gln Pro Arg Glu Pro Gln Val Tyr Thr Leu Pro
             340              345              350

Pro Cys Arg Asp Glu Leu Thr Lys Asn Gln Val Ser Leu Trp Cys Leu
             355              360              365

Val Lys Gly Phe Tyr Pro Ser Asp Ile Ala Val Glu Trp Glu Ser Asn
             370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
             405              410              415

Trp Gln Gln Gly Asn Val Phe Ser Cys Ser Val Met His Glu Ala Leu
             420              425              430

His Asn His Tyr Thr Gln Lys Ser Leu Ser Leu Ser Pro Gly Lys
             435              440              445

<210> SEQ ID NO 442
<211> LENGTH: 447
<212> TYPE: PRT
<213> ORGANISM: Artificial Sequence
<220> FEATURE:
<223> OTHER INFORMATION: synthetic construct

<400> SEQUENCE: 442

Glu Val Gln Leu Val Glu Ser Gly Gly Gly Leu Val Gln Pro Gly Glu
1               5               10              15

Ser Leu Arg Leu Ser Cys Ala Ala Ser Gly Tyr Thr Phe Thr Asp Tyr
             20              25              30

Thr Met Tyr Trp Val Arg Gln Ala Pro Gly Lys Gly Leu Glu Trp Met
             35              40              45

Gly Trp Ile Asn Thr Glu Thr Gly Glu Thr Asn Tyr Ala Asp Ser Val
```

-continued

```
            50               55               60

Lys Gly Arg Phe Thr Ile Ser Arg Asp Asn Ser Lys Asn Thr Leu Tyr
65                  70               75                  80

Leu Gln Met Asn Ser Leu Arg Ala Glu Asp Thr Ala Val Tyr Tyr Cys
                85               90               95

Ala Ile Ser Tyr Tyr Tyr Gly Met Asp Tyr Trp Gly Gln Gly Thr Leu
                100              105              110

Val Thr Val Ser Ser Ala Ser Thr Lys Gly Pro Ser Val Phe Pro Leu
            115              120              125

Ala Pro Ser Ser Lys Ser Thr Ser Gly Gly Thr Ala Ala Leu Gly Cys
        130              135              140

Leu Val Lys Asp Tyr Phe Pro Glu Pro Val Thr Val Ser Trp Asn Ser
145              150              155              160

Gly Ala Leu Thr Ser Gly Val His Thr Phe Pro Ala Val Leu Gln Ser
                165              170              175

Ser Gly Leu Tyr Ser Leu Ser Ser Val Val Thr Val Pro Ser Ser Ser
                180              185              190

Leu Gly Thr Gln Thr Tyr Ile Cys Asn Val Asn His Lys Pro Ser Asn
            195              200              205

Thr Lys Val Asp Lys Lys Val Glu Pro Lys Ser Cys Asp Lys Thr His
        210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
                245              250              255

Pro Glu Val Thr Cys Val Val Val Asp Val Ser His Glu Asp Pro Glu
            260              265              270

Val Lys Phe Asn Trp Tyr Val Asp Gly Val Glu Val His Asn Ala Lys
                275              280              285

Thr Lys Pro Arg Glu Glu Gln Tyr Asn Ser Thr Tyr Arg Val Val Ser
        290              295              300

Val Leu Thr Val Leu His Gln Asp Trp Leu Asn Gly Lys Glu Tyr Lys
305              310              315              320

Cys Lys Val Ser Asn Lys Ala Leu Pro Ala Pro Ile Glu Lys Thr Ile
                325              330              335

Ser Lys Ala Lys Gly Gln Pro Arg Glu Pro Gln Val Tyr Thr Leu Pro
            340              345              350

Pro Cys Arg Asp Glu Leu Thr Lys Asn Gln Val Ser Leu Trp Cys Leu
            355              360              365

Val Lys Gly Phe Tyr Pro Ser Asp Ile Ala Val Glu Trp Glu Ser Asn
        370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
                405              410              415

Trp Gln Gln Gly Asn Val Phe Ser Cys Ser Val Met His Glu Ala Leu
                420              425              430

His Asn His Tyr Thr Gln Lys Ser Leu Ser Leu Ser Pro Gly Lys
            435              440              445
```

```
<210> SEQ ID NO 443
<211> LENGTH: 447
<212> TYPE: PRT
<213> ORGANISM: Artificial Sequence
```

```
<220> FEATURE:
<223> OTHER INFORMATION: synthetic construct

<400> SEQUENCE: 443

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Thr Met Tyr Trp Val Arg Gln Ala Pro Gly Lys Gly Leu Glu Trp Met
        35                  40                  45

Gly Asp Ile Asn Thr Glu Thr Gly Glu Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Ser Tyr Tyr Tyr Gly Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

```
Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 444
<211> LENGTH: 449
<212> TYPE: PRT
<213> ORGANISM: Artificial Sequence
<220> FEATURE:
<223> OTHER INFORMATION: synthetic construct

<400> SEQUENCE: 444

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Ala Tyr Ile Leu Pro Phe Asn Asp Val Thr Lys Tyr Asn Glu Lys Phe
    50                  55                  60

Lys Gly Arg Val Thr Met Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Glu Trp Asp Asp Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

```
<210> SEQ ID NO 445
<211> LENGTH: 449
<212> TYPE: PRT
<213> ORGANISM: Artificial Sequence
<220> FEATURE:
<223> OTHER INFORMATION: synthetic construct

<400> SEQUENCE: 445

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Arg Gln Ala Pro Gly Gln Gly Leu Glu Trp Ile
            35                  40                  45

Ala Tyr Ile Leu Pro Phe Asn Asp Val Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Glu Trp Asp Asp Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230             235             240

Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Cys Arg Asp Glu Leu Thr Lys Asn Gln Val Ser Leu Trp
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys
```

```
<210> SEQ ID NO 446
<211> LENGTH: 448
<212> TYPE: PRT
<213> ORGANISM: Artificial Sequence
<220> FEATURE:
<223> OTHER INFORMATION: synthetic construct

<400> SEQUENCE: 446
```

```
Gln Val Gln Leu Val Gln Ser Gly Ala Glu Leu Val Lys Pro Gly Ser
1               5               10              15

Ser Val Lys Met Ser Cys Lys Ala Ser Gly Tyr Thr Phe Thr Asn Tyr
            20              25              30

Val Met His Trp Val Arg Gln Ala Pro Gly Gln Gly Leu Glu Trp Met
        35              40              45

Gly Tyr Ile Leu Pro Tyr Asn Asp Gly Thr Asn Tyr Asn Gln Lys Phe
    50              55              60

Gln Gly Arg Val Thr Met Thr Ser Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Tyr Asp Tyr Glu Gly Ser Phe Asp Tyr Trp Gly Gln Gly Thr
            100             105             110

Leu Val Thr Val Ser Ser Ala Ser Thr Lys Gly Pro Ser Val Phe Pro
        115             120             125

Leu Ala Pro Ser Ser Lys Ser Thr Ser Gly Gly Thr Ala Ala Leu Gly
```

-continued

```
        130               135               140
Cys Leu Val Lys Asp Tyr Phe Pro Glu Pro Val Thr Val Ser Trp Asn
145               150               155               160

Ser Gly Ala Leu Thr Ser Gly Val His Thr Phe Pro Ala Val Leu Gln
                  165               170               175

Ser Ser Gly Leu Tyr Ser Leu Ser Ser Val Val Thr Val Pro Ser Ser
                  180               185               190

Ser Leu Gly Thr Gln Thr Tyr Ile Cys Asn Val Asn His Lys Pro Ser
                  195               200               205

Asn Thr Lys Val Asp Lys Lys Val Glu Pro Lys Ser Cys Asp Lys Thr
        210               215               220

His Thr Cys Pro Pro Cys Pro Ala Pro Glu Leu Leu Gly Gly Pro Ser
225               230               235               240

Val Phe Leu Phe Pro Pro Lys Pro Lys Asp Thr Leu Met Ile Ser Arg
                  245               250               255

Thr Pro Glu Val Thr Cys Val Val Val Asp Val Ser His Glu Asp Pro
                  260               265               270

Glu Val Lys Phe Asn Trp Tyr Val Asp Gly Val Glu Val His Asn Ala
                  275               280               285

Lys Thr Lys Pro Arg Glu Glu Gln Tyr Asn Ser Thr Tyr Arg Val Val
        290               295               300

Ser Val Leu Thr Val Leu His Gln Asp Trp Leu Asn Gly Lys Glu Tyr
305               310               315               320

Lys Cys Lys Val Ser Asn Lys Ala Leu Pro Ala Pro Ile Glu Lys Thr
                  325               330               335

Ile Ser Lys Ala Lys Gly Gln Pro Arg Glu Pro Gln Val Tyr Thr Leu
                  340               345               350

Pro Pro Cys Arg Asp Glu Leu Thr Lys Asn Gln Val Ser Leu Trp Cys
                  355               360               365

Leu Val Lys Gly Phe Tyr Pro Ser Asp Ile Ala Val Glu Trp Glu Ser
        370               375               380

Asn Gly Gln Pro Glu Asn Asn Tyr Lys Thr Thr Pro Pro Val Leu Asp
385               390               395               400

Ser Asp Gly Ser Phe Phe Leu Tyr Ser Lys Leu Thr Val Asp Lys Ser
                  405               410               415

Arg Trp Gln Gln Gly Asn Val Phe Ser Cys Ser Val Met His Glu Ala
                  420               425               430

Leu His Asn His Tyr Thr Gln Lys Ser Leu Ser Leu Ser Pro Gly Lys
                  435               440               445

<210> SEQ ID NO 447
<211> LENGTH: 448
<212> TYPE: PRT
<213> ORGANISM: Artificial Sequence
<220> FEATURE:
<223> OTHER INFORMATION: synthetic construct

<400> SEQUENCE: 447

Gln Val Gln Leu Val Glu Ser Gly Gly Gly Val Val Gln Pro Gly Arg
1               5               10               15

Ser Leu Arg Leu Ser Cys Ala Ala Ser Gly Tyr Thr Phe Thr Asn Tyr
                  20               25               30

Val Met His Trp Val Arg Gln Ala Pro Gly Gln Gly Leu Glu Trp Ile
        35               40               45

Ala Tyr Ile Leu Pro Tyr Asn Asp Gly Ala Asn Tyr Asn Glu Lys Val
```

-continued

```
        50                 55                 60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 448
<211> LENGTH: 6
<212> TYPE: PRT
<213> ORGANISM: Artificial Sequence
<220> FEATURE:
<223> OTHER INFORMATION: synthetic construct

<400> SEQUENCE: 448

Tyr Phe Asp Ser Leu Leu
1               5

<210> SEQ ID NO 449
<211> LENGTH: 6
<212> TYPE: PRT
<213> ORGANISM: Artificial Sequence
<220> FEATURE:
<223> OTHER INFORMATION: synthetic construct

<400> SEQUENCE: 449

Tyr Trp Asp Pro Leu Leu
1               5

<210> SEQ ID NO 450
<211> LENGTH: 184
<212> TYPE: PRT
<213> ORGANISM: Artificial Sequence
<220> FEATURE:
<223> OTHER INFORMATION: synthetic construct

<400> SEQUENCE: 450

Met Leu Gln Met Ala Gly Gln Cys Ser Gln Asn Glu Ala Phe Ala Ser
1               5                   10                  15

Gly Gly His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
        130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180

<210> SEQ ID NO 451
<211> LENGTH: 293
<212> TYPE: PRT
<213> ORGANISM: Artificial Sequence
<220> FEATURE:
<223> OTHER INFORMATION: synthetic construct

<400> SEQUENCE: 451

Met Ser Gly Leu Gly Arg Ser Arg Arg Gly Gly Arg Ser Arg Val Asp
1               5                   10                  15

```
Gln Glu Glu Arg Phe Pro Gln Gly Leu Trp Thr Gly Val Ala Met Arg
         20                  25                  30

Ser Cys Pro Glu Glu Gln Ala Trp Ala Pro Gly Gly Gly Thr Cys Met
         35                  40                  45

Ser Cys Lys Thr Ile Cys Asn His Gln Ser Gln Arg Thr Cys Ala Ala
     50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
             85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
             165                 170                 175

Cys Phe Leu Val Ala Val Ala Cys Phe Leu Lys Lys Arg Gly Asp Pro
             180                 185                 190

Cys Ser Cys Gln Pro Arg Ser Arg Pro Arg Gln Ser Pro Ala Lys Ser
             195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
             245                 250                 255

Gly Arg Trp Gly Cys His Thr Arg Thr Thr Val Leu Gln Pro Cys Pro
             260                 265                 270

His Ile Pro Asp Ser Gly Leu Gly Ile Val Cys Val Pro Ala Gln Glu
             275                 280                 285

Gly Gly Pro Gly Ala
    290
```

```
<210> SEQ ID NO 452
<211> LENGTH: 119
<212> TYPE: PRT
<213> ORGANISM: Artificial Sequence
<220> FEATURE:
<223> OTHER INFORMATION: synthetic construct

<400> SEQUENCE: 452
```

```
Gln Val Gln Leu Gln Gln Ser Gly Ala Glu Leu Ala Arg Pro Gly Ala
1                   5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Lys Ala Thr Leu Thr Thr Asp Lys Ser Ser Ser Thr Ala Tyr
65                  70                  75                  80
```

-continued

```
Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 453
<211> LENGTH: 106
<212> TYPE: PRT
<213> ORGANISM: Artificial Sequence
<220> FEATURE:
<223> OTHER INFORMATION: synthetic construct

<400> SEQUENCE: 453

Gln Ile Val Leu Thr Gln Ser Pro Ala Ile Met Ser Ala Ser Pro Gly
1               5                  10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 454
<211> LENGTH: 474
<212> TYPE: PRT
<213> ORGANISM: Artificial Sequence
<220> FEATURE:
<223> OTHER INFORMATION: synthetic construct

<400> SEQUENCE: 454

Gln Val Gln Leu Gln Gln Ser Gly Ala Glu Leu Ala Arg Pro Gly Ala
1               5                  10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ser Gly Gly Gly Ser Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
```

-continued

```
145              150              155              160

Ser Ser Ser Val Ser Tyr Met Asn Trp Tyr Gln Gln Lys Ser Gly Thr
                165              170              175

Ser Pro Lys Arg Trp Ile Tyr Asp Thr Ser Lys Leu Ala Ser Gly Val
                180              185              190

Pro Ala His Phe Arg Gly Ser Gly Ser Gly Thr Ser Tyr Ser Leu Thr
                195              200              205

Ile Ser Gly Met Glu Ala Glu Asp Ala Ala Thr Tyr Tyr Cys Gln Gln
    210              215              220

Trp Ser Ser Asn Pro Phe Thr Phe Gly Ser Gly Thr Lys Leu Glu Ile
225              230              235              240

Asn Val Glu Pro Lys Ser Cys Asp Lys Thr His Thr Cys Pro Pro Cys
                245              250              255

Pro Ala Pro Glu Leu Leu Gly Gly Pro Ser Val Phe Leu Phe Pro Pro
                260              265              270

Lys Pro Lys Asp Thr Leu Met Ile Ser Arg Thr Pro Glu Val Thr Cys
                275              280              285

Val Val Val Asp Val Ser His Glu Asp Pro Glu Val Lys Phe Asn Trp
    290              295              300

Tyr Val Asp Gly Val Glu Val His Asn Ala Lys Thr Lys Pro Arg Glu
305              310              315              320

Glu Gln Tyr Asn Ser Thr Tyr Arg Val Val Ser Val Leu Thr Val Leu
                325              330              335

His Gln Asp Trp Leu Asn Gly Lys Glu Tyr Lys Cys Lys Val Ser Asn
                340              345              350

Lys Ala Leu Pro Ala Pro Ile Glu Lys Thr Ile Ser Lys Ala Lys Gly
                355              360              365

Gln Pro Arg Glu Pro Gln Val Cys Thr Leu Pro Pro Ser Arg Asp Glu
    370              375              380

Leu Thr Lys Asn Gln Val Ser Leu Ser Cys Ala Val Lys Gly Phe Tyr
385              390              395              400

Pro Ser Asp Ile Ala Val Glu Trp Glu Ser Asn Gly Gln Pro Glu Asn
                405              410              415

Asn Tyr Lys Thr Thr Pro Pro Val Leu Asp Ser Asp Gly Ser Phe Phe
                420              425              430

Leu Val Ser Lys Leu Thr Val Asp Lys Ser Arg Trp Gln Gln Gly Asn
                435              440              445

Val Phe Ser Cys Ser Val Met His Glu Ala Leu His Asn His Tyr Thr
    450              455              460

Gln Lys Ser Leu Ser Leu Ser Pro Gly Lys
465              470
```

```
<210> SEQ ID NO 455
<211> LENGTH: 118
<212> TYPE: PRT
<213> ORGANISM: Artificial Sequence
<220> FEATURE:
<223> OTHER INFORMATION: synthetic construct

<400> SEQUENCE: 455

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asn Tyr
                20              25              30

Val Met His Trp Val Lys Gln Lys Pro Gly Gln Gly Leu Glu Trp Met
```

-continued

```
            35                  40                  45

Gly Tyr Ile Leu Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Trp Glu Gly Ser Phe Asp Tyr Trp Gly Gln Gly Thr
            100                 105                 110

Leu Val Thr Val Ser Ser
        115

<210> SEQ ID NO 456
<211> LENGTH: 11
<212> TYPE: PRT
<213> ORGANISM: Artificial Sequence
<220> FEATURE:
<223> OTHER INFORMATION: synthetic construct

<400> SEQUENCE: 456

Ala Arg Tyr Asp Trp Glu Gly Ser Phe Asp Tyr
1               5                   10

<210> SEQ ID NO 457
<211> LENGTH: 17
<212> TYPE: PRT
<213> ORGANISM: Artificial Sequence
<220> FEATURE:
<223> OTHER INFORMATION: synthetic construct

<400> SEQUENCE: 457

Met His Trp Val Lys Gln Lys Pro Gly Gln Gly Leu Glu Trp Met Gly
1               5                   10                  15

Tyr

<210> SEQ ID NO 458
<211> LENGTH: 38
<212> TYPE: PRT
<213> ORGANISM: Artificial Sequence
<220> FEATURE:
<223> OTHER INFORMATION: synthetic construct

<400> SEQUENCE: 458

Lys Tyr Ala Gln Lys Phe Gln Gly Lys Val Thr Met Thr Ser Asp Lys
1               5                   10                  15

Ser Thr Ser Thr Val Tyr Met Glu Leu Ser Ser Leu Thr Ser Glu Asp
                20                  25                  30

Thr Ala Val Tyr Tyr Cys
        35

<210> SEQ ID NO 459
<211> LENGTH: 107
<212> TYPE: PRT
<213> ORGANISM: Artificial Sequence
<220> FEATURE:
<223> OTHER INFORMATION: synthetic construct

<400> SEQUENCE: 459

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30
```

```
Leu Ser Trp Tyr Gln Gln Lys Pro Gly Lys Ala Pro Lys Leu Leu Met
        35                  40                  45

Arg Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Leu Phe Pro Pro
                85                  90                  95

Thr Phe Gly Gly Gly Thr Lys Val Glu Ile Lys
            100                 105
```

```
<210> SEQ ID NO 460
<211> LENGTH: 9
<212> TYPE: PRT
<213> ORGANISM: Artificial Sequence
<220> FEATURE:
<223> OTHER INFORMATION: synthetic construct

<400> SEQUENCE: 460

Gln Gln Gly Asn Leu Phe Pro Pro Thr
1               5
```

```
<210> SEQ ID NO 461
<211> LENGTH: 17
<212> TYPE: PRT
<213> ORGANISM: Artificial Sequence
<220> FEATURE:
<223> OTHER INFORMATION: synthetic construct

<400> SEQUENCE: 461

Leu Ser Trp Tyr Gln Gln Lys Pro Gly Lys Ala Pro Lys Leu Leu Met
1               5                   10                  15

Arg
```

```
<210> SEQ ID NO 462
<211> LENGTH: 36
<212> TYPE: PRT
<213> ORGANISM: Artificial Sequence
<220> FEATURE:
<223> OTHER INFORMATION: synthetic construct

<400> SEQUENCE: 462

Arg Leu His Ser Gly Val Pro Ser Arg Phe Ser Gly Ser Gly Ser Gly
1               5                   10                  15

Thr Asp Phe Thr Leu Thr Ile Ser Ser Leu Glu Gln Glu Asp Phe Ala
            20                  25                  30

Thr Tyr Tyr Cys
        35
```

```
<210> SEQ ID NO 463
<211> LENGTH: 107
<212> TYPE: PRT
<213> ORGANISM: Artificial Sequence
<220> FEATURE:
<223> OTHER INFORMATION: synthetic construct

<400> SEQUENCE: 463

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Asp Ile Ser Asn Tyr
            20                  25                  30
```

Leu Asn Trp Tyr Gln Gln Lys Pro Gly Lys Ala Pro Lys Leu Leu Met
        35              40              45

Cys Tyr Thr Ser Arg Leu His Ser Gly Val Pro Ser Arg Phe Ser Gly
        50              55              60

Ser Gly Ser Gly Thr Asp Phe Thr Leu Thr Ile Ser Ser Leu Glu Gln
65              70              75              80

Glu Asp Phe Ala Thr Tyr Tyr Cys Gln Gln Gly Asn Thr Phe Pro Pro
                85              90              95

Thr Phe Gly Gly Gly Thr Lys Val Glu Ile Lys
            100             105

<210> SEQ ID NO 464
<211> LENGTH: 6
<212> TYPE: PRT
<213> ORGANISM: Artificial Sequence
<220> FEATURE:
<223> OTHER INFORMATION: synthetic construct

<400> SEQUENCE: 464

Ser Asp Ile Ser Asn Tyr
1               5

<210> SEQ ID NO 465
<211> LENGTH: 118
<212> TYPE: PRT
<213> ORGANISM: Artificial Sequence
<220> FEATURE:
<223> OTHER INFORMATION: synthetic construct

<400> SEQUENCE: 465

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Arg Asn Tyr
            20              25              30

Val Met His Trp Val Lys Gln Lys Pro Gly Gln Gly Leu Glu Trp Met
        35              40              45

Gly Trp Ile Leu Pro Tyr Asn Asp Gly Thr Lys Tyr Ala Gln Lys Phe
        50              55              60

Gln Gly Lys Val Thr Met Thr Ser Asp Lys Ser Thr Ser Thr Val Tyr
65              70              75              80

Met Glu Leu Ser Ser Leu Thr Ser Glu Asp Thr Ala Val Tyr Tyr Cys
                85              90              95

Ala Arg Tyr Asp Tyr Glu Gly Ser Phe Asp Tyr Trp Gly Gln Gly Thr
            100             105             110

Leu Val Thr Val Ser Ser
        115

<210> SEQ ID NO 466
<211> LENGTH: 8
<212> TYPE: PRT
<213> ORGANISM: Artificial Sequence
<220> FEATURE:
<223> OTHER INFORMATION: synthetic construct

<400> SEQUENCE: 466

Gly Tyr Thr Phe Arg Asn Tyr Val
1               5

<210> SEQ ID NO 467
<211> LENGTH: 17
<212> TYPE: PRT

<213> ORGANISM: Artificial Sequence
<220> FEATURE:
<223> OTHER INFORMATION: synthetic construct

<400> SEQUENCE: 467

Met His Trp Val Lys Gln Lys Pro Gly Gln Gly Leu Glu Trp Met Gly
1               5                   10                  15

Trp

<210> SEQ ID NO 468
<211> LENGTH: 107
<212> TYPE: PRT
<213> ORGANISM: Artificial Sequence
<220> FEATURE:
<223> OTHER INFORMATION: synthetic construct

<400> SEQUENCE: 468

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Met
        35                  40                  45

Arg Tyr Thr Ser Leu Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys
            100                 105

<210> SEQ ID NO 469
<211> LENGTH: 17
<212> TYPE: PRT
<213> ORGANISM: Artificial Sequence
<220> FEATURE:
<223> OTHER INFORMATION: synthetic construct

<400> SEQUENCE: 469

Leu Asn Trp Tyr Gln Gln Lys Pro Gly Lys Ala Pro Lys Leu Leu Met
1               5                   10                  15

Arg

<210> SEQ ID NO 470
<211> LENGTH: 36
<212> TYPE: PRT
<213> ORGANISM: Artificial Sequence
<220> FEATURE:
<223> OTHER INFORMATION: synthetic construct

<400> SEQUENCE: 470

Leu Leu His Ser Gly Val Pro Ser Arg Phe Ser Gly Ser Gly Ser Gly
1               5                   10                  15

Thr Asp Phe Thr Leu Thr Ile Ser Ser Leu Glu Gln Glu Asp Phe Ala
            20                  25                  30

Thr Tyr Tyr Cys
            35

<210> SEQ ID NO 471
<211> LENGTH: 118

<212> TYPE: PRT
<213> ORGANISM: Artificial Sequence
<220> FEATURE:
<223> OTHER INFORMATION: synthetic construct

<400> SEQUENCE: 471

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met Phe Trp Val Lys Gln Lys Pro Gly Gln Gly Leu Glu Trp Met
        35                  40                  45

Gly Tyr Ile Thr Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser
        115

<210> SEQ ID NO 472
<211> LENGTH: 8
<212> TYPE: PRT
<213> ORGANISM: Artificial Sequence
<220> FEATURE:
<223> OTHER INFORMATION: synthetic construct

<400> SEQUENCE: 472

Ile Thr Pro Tyr Asn Asp Gly Thr
1               5

<210> SEQ ID NO 473
<211> LENGTH: 17
<212> TYPE: PRT
<213> ORGANISM: Artificial Sequence
<220> FEATURE:
<223> OTHER INFORMATION: synthetic construct

<400> SEQUENCE: 473

Met Phe Trp Val Lys Gln Lys Pro Gly Gln Gly Leu Glu Trp Met Gly
1               5                   10                  15

Tyr

<210> SEQ ID NO 474
<211> LENGTH: 107
<212> TYPE: PRT
<213> ORGANISM: Artificial Sequence
<220> FEATURE:
<223> OTHER INFORMATION: synthetic construct

<400> SEQUENCE: 474

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Met
        35                  40                  45

Arg Tyr Thr Ser Arg Phe His Ser Gly Val Pro Ser Arg Phe Ser Gly

-continued

```
          50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Thr Phe Pro Pro
                85                  90                  95

Thr Ser Gly Gly Gly Thr Lys Val Glu Ile Lys
            100                 105

<210> SEQ ID NO 475
<211> LENGTH: 36
<212> TYPE: PRT
<213> ORGANISM: Artificial Sequence
<220> FEATURE:
<223> OTHER INFORMATION: synthetic construct

<400> SEQUENCE: 475

Arg Phe His Ser Gly Val Pro Ser Arg Phe Ser Gly Ser Gly Ser Gly
1               5                   10                  15

Thr Asp Phe Thr Leu Thr Ile Ser Ser Leu Glu Gln Glu Asp Phe Ala
                20                  25                  30

Thr Tyr Tyr Cys
        35

<210> SEQ ID NO 476
<211> LENGTH: 10
<212> TYPE: PRT
<213> ORGANISM: Artificial Sequence
<220> FEATURE:
<223> OTHER INFORMATION: synthetic construct

<400> SEQUENCE: 476

Ser Gly Gly Gly Thr Lys Val Glu Ile Lys
1               5                   10

<210> SEQ ID NO 477
<211> LENGTH: 118
<212> TYPE: PRT
<213> ORGANISM: Artificial Sequence
<220> FEATURE:
<223> OTHER INFORMATION: synthetic construct

<400> SEQUENCE: 477

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Lys Gln Lys Pro Gly Gln Gly Leu Glu Trp Met
        35                  40                  45

Gly Tyr Ile Leu Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser
        115

<210> SEQ ID NO 478
```

```
<211> LENGTH: 107
<212> TYPE: PRT
<213> ORGANISM: Artificial Sequence
<220> FEATURE:
<223> OTHER INFORMATION: synthetic construct

<400> SEQUENCE: 478

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Met
        35                  40                  45

Cys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys
            100                 105

<210> SEQ ID NO 479
<211> LENGTH: 118
<212> TYPE: PRT
<213> ORGANISM: Artificial Sequence
<220> FEATURE:
<223> OTHER INFORMATION: synthetic construct

<400> SEQUENCE: 479

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Arg Leu Glu Trp Met
        35                  40                  45

Gly Tyr Ile Leu Pro Tyr Asn Asp Gly Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Trp Glu Gly Ser Phe Asp Tyr Trp Gly Gln Gly Thr
            100                 105                 110

Thr Val Thr Val Ser Ser
        115

<210> SEQ ID NO 480
<211> LENGTH: 17
<212> TYPE: PRT
<213> ORGANISM: Artificial Sequence
<220> FEATURE:
<223> OTHER INFORMATION: synthetic construct

<400> SEQUENCE: 480

Met His Trp Val Arg Gln Ala Pro Gly Gln Arg Leu Glu Trp Met Gly
1               5                   10                  15

Tyr
```

<210> SEQ ID NO 481
<211> LENGTH: 38
<212> TYPE: PRT
<213> ORGANISM: Artificial Sequence
<220> FEATURE:
<223> OTHER INFORMATION: synthetic construct

<400> SEQUENCE: 481

Lys Tyr Ser Gln Lys Phe Gln Gly Arg Val Thr Ile Thr Arg Asp Thr
1               5                   10                  15

Ser Ala Ser Thr Ala Tyr Met Glu Leu Ser Ser Leu Arg Ser Glu Asp
            20                  25                  30

Thr Ala Val Tyr Tyr Cys
        35

<210> SEQ ID NO 482
<211> LENGTH: 11
<212> TYPE: PRT
<213> ORGANISM: Artificial Sequence
<220> FEATURE:
<223> OTHER INFORMATION: synthetic construct

<400> SEQUENCE: 482

Trp Gly Gln Gly Thr Thr Val Thr Val Ser Ser
1               5                   10

<210> SEQ ID NO 483
<211> LENGTH: 107
<212> TYPE: PRT
<213> ORGANISM: Artificial Sequence
<220> FEATURE:
<223> OTHER INFORMATION: synthetic construct

<400> SEQUENCE: 483

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Asn Trp Tyr Gln Gln Lys Pro Gly Lys Ala Val Lys Leu Leu Met
        35                  40                  45

Arg Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Thr Phe Pro Pro
                85                  90                  95

Thr Phe Gly Gly Gly Thr Lys Leu Glu Ile Lys
            100                 105

<210> SEQ ID NO 484
<211> LENGTH: 6
<212> TYPE: PRT
<213> ORGANISM: Artificial Sequence
<220> FEATURE:
<223> OTHER INFORMATION: synthetic construct

<400> SEQUENCE: 484

Gln Asp Ile Gly Asn Tyr
1               5

<210> SEQ ID NO 485
<211> LENGTH: 9
<212> TYPE: PRT

-continued

```
<213> ORGANISM: Artificial Sequence
<220> FEATURE:
<223> OTHER INFORMATION: synthetic construct

<400> SEQUENCE: 485

Gln Gln Gly Phe Thr Phe Pro Pro Thr
1               5

<210> SEQ ID NO 486
<211> LENGTH: 17
<212> TYPE: PRT
<213> ORGANISM: Artificial Sequence
<220> FEATURE:
<223> OTHER INFORMATION: synthetic construct

<400> SEQUENCE: 486

Leu Asn Trp Tyr Gln Gln Lys Pro Gly Lys Ala Val Lys Leu Leu Met
1               5                   10                  15

Arg

<210> SEQ ID NO 487
<211> LENGTH: 107
<212> TYPE: PRT
<213> ORGANISM: Artificial Sequence
<220> FEATURE:
<223> OTHER INFORMATION: synthetic construct

<400> SEQUENCE: 487

Asp Ile Gln Met Thr Gln Ser Pro Ser Ser Leu Ser Ala Ser Val Gly
1               5                   10                  15

Asp Arg Val Thr Ile Thr Cys Ala Ala Ser Gln Asp Ile Ser Asn Tyr
            20                  25                  30

Leu Asn Trp Tyr Gln Gln Lys Pro Gly Lys Ala Val Lys Leu Leu Met
        35                  40                  45

Arg Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Arg Phe Pro Pro
                85                  90                  95

Thr Phe Gly Gly Gly Thr Lys Leu Glu Ile Lys
            100                 105

<210> SEQ ID NO 488
<211> LENGTH: 9
<212> TYPE: PRT
<213> ORGANISM: Artificial Sequence
<220> FEATURE:
<223> OTHER INFORMATION: synthetic construct

<400> SEQUENCE: 488

Gln Gln Gly Asn Arg Phe Pro Pro Thr
1               5

<210> SEQ ID NO 489
<211> LENGTH: 26
<212> TYPE: PRT
<213> ORGANISM: Artificial Sequence
<220> FEATURE:
<223> OTHER INFORMATION: synthetic construct

<400> SEQUENCE: 489

Asp Ile Gln Met Thr Gln Ser Pro Ser Ser Leu Ser Ala Ser Val Gly
```

-continued

```
1               5               10              15

Asp Arg Val Thr Ile Thr Cys Ala Ala Ser
            20              25
```

<210> SEQ ID NO 490
<211> LENGTH: 118
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (30)..(30)
<223> OTHER INFORMATION: Xaa = T or R
<220> FEATURE:
<221> NAME/KEY: MISC_FEATURE
<222> LOCATION: (35)..(35)
<223> OTHER INFORMATION: Xaa = H or F
<220> FEATURE:
<221> NAME/KEY: MISC_FEATURE
<222> LOCATION: (38)..(38)
<223> OTHER INFORMATION: Xaa = K or R
<220> FEATURE:
<221> NAME/KEY: MISC_FEATURE
<222> LOCATION: (40)..(40)
<223> OTHER INFORMATION: Xaa = K or A
<220> FEATURE:
<221> NAME/KEY: MISC_FEATURE
<222> LOCATION: (44)..(44)
<223> OTHER INFORMATION: Xaa = G or R
<220> FEATURE:
<221> NAME/KEY: MISC_FEATURE
<222> LOCATION: (50)..(50)
<223> OTHER INFORMATION: Xaa = Y or W
<220> FEATURE:
<221> NAME/KEY: MISC_FEATURE
<222> LOCATION: (52)..(52)
<223> OTHER INFORMATION: Xaa = L or T
<220> FEATURE:
<221> NAME/KEY: MISC_FEATURE
<222> LOCATION: (61)..(61)
<223> OTHER INFORMATION: Xaa = A or S
<220> FEATURE:
<221> NAME/KEY: MISC_FEATURE
<222> LOCATION: (67)..(67)
<223> OTHER INFORMATION: Xaa = K or R
<220> FEATURE:
<221> NAME/KEY: MISC_FEATURE
<222> LOCATION: (70)..(70)
<223> OTHER INFORMATION: Xaa = M or I
<220> FEATURE:
<221> NAME/KEY: MISC_FEATURE
<222> LOCATION: (72)..(72)
<223> OTHER INFORMATION: Xaa = S or R
<220> FEATURE:
<221> NAME/KEY: MISC_FEATURE
<222> LOCATION: (74)..(74)
<223> OTHER INFORMATION: Xaa = K or T
<220> FEATURE:
<221> NAME/KEY: MISC_FEATURE
<222> LOCATION: (76)..(76)
<223> OTHER INFORMATION: Xaa = T or A
<220> FEATURE:
<221> NAME/KEY: MISC_FEATURE
<222> LOCATION: (79)..(79)
<223> OTHER INFORMATION: Xaa = V or A
<220> FEATURE:
<221> NAME/KEY: MISC_FEATURE
<222> LOCATION: (87)..(87)
<223> OTHER INFORMATION: Xaa = T or R
<220> FEATURE:
<221> NAME/KEY: MISC_FEATURE
<222> LOCATION: (101)..(101)
<223> OTHER INFORMATION: Xaa = Y or W
<220> FEATURE:
<221> NAME/KEY: MISC_FEATURE
<222> LOCATION: (113)..(113)

<223> OTHER INFORMATION: Xaa = L or T

<400> SEQUENCE: 490

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Asn Tyr
                20                  25                  30

Val Met Xaa Trp Val Xaa Gln Xaa Pro Gly Gln Xaa Leu Glu Trp Met
            35                  40                  45

Gly Xaa Ile Xaa Pro Tyr Asn Asp Gly Thr Lys Tyr Xaa Gln Lys Phe
        50                  55                  60

Gln Gly Xaa Val Thr Xaa Thr Xaa Asp Xaa Ser Xaa Ser Thr Xaa Tyr
65                  70                  75                  80

Met Glu Leu Ser Ser Leu Xaa Ser Glu Asp Thr Ala Val Tyr Tyr Cys
                85                  90                  95

Ala Arg Tyr Asp Xaa Glu Gly Ser Phe Asp Tyr Trp Gly Gln Gly Thr
                100                 105                 110

Xaa Val Thr Val Ser Ser
        115

<210> SEQ ID NO 491
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa = T or R

<400> SEQUENCE: 491

Gly Tyr Thr Phe Xaa Asn Tyr Val
1               5

<210> SEQ ID NO 492
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa = L or T

<400> SEQUENCE: 492

Ile Xaa Pro Tyr Asn Asp Gly Thr
1               5

<210> SEQ ID NO 493
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa = Y or W

<400> SEQUENCE: 493

Ala Arg Tyr Asp Xaa Glu Gly Ser Phe Asp Tyr
1               5                   10

```
<210> SEQ ID NO 494
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa = H or F
<220> FEATURE:
<221> NAME/KEY: misc_feature
<222> LOCATION: (5)..(5)
<223> OTHER INFORMATION: Xaa = K or R
<220> FEATURE:
<221> NAME/KEY: misc_feature
<222> LOCATION: (7)..(7)
<223> OTHER INFORMATION: Xaa = K or A
<220> FEATURE:
<221> NAME/KEY: misc_feature
<222> LOCATION: (11)..(11)
<223> OTHER INFORMATION: Xaa = G or R
<220> FEATURE:
<221> NAME/KEY: misc_feature
<222> LOCATION: (17)..(17)
<223> OTHER INFORMATION: Xaa = Y or W

<400> SEQUENCE: 494

Met Xaa Trp Val Xaa Gln Xaa Pro Gly Gln Xaa Leu Glu Trp Met Gly
1               5                   10                  15

Xaa

<210> SEQ ID NO 495
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = A or S
<220> FEATURE:
<221> NAME/KEY: MISC_FEATURE
<222> LOCATION: (9)..(9)
<223> OTHER INFORMATION: Xaa = K or R
<220> FEATURE:
<221> NAME/KEY: MISC_FEATURE
<222> LOCATION: (12)..(12)
<223> OTHER INFORMATION: Xaa = M or I
<220> FEATURE:
<221> NAME/KEY: MISC_FEATURE
<222> LOCATION: (14)..(14)
<223> OTHER INFORMATION: Xaa = S or R
<220> FEATURE:
<221> NAME/KEY: MISC_FEATURE
<222> LOCATION: (16)..(16)
<223> OTHER INFORMATION: Xaa = K or T
<220> FEATURE:
<221> NAME/KEY: MISC_FEATURE
<222> LOCATION: (18)..(18)
<223> OTHER INFORMATION: Xaa = T or A
<220> FEATURE:
<221> NAME/KEY: MISC_FEATURE
<222> LOCATION: (21)..(21)
<223> OTHER INFORMATION: Xaa = V or A
<220> FEATURE:
<221> NAME/KEY: MISC_FEATURE
<222> LOCATION: (29)..(29)
<223> OTHER INFORMATION: Xaa = T or R

<400> SEQUENCE: 495

Lys Tyr Xaa Gln Lys Phe Gln Gly Xaa Val Thr Xaa Thr Xaa Asp Xaa
1               5                   10                  15
```

```
Ser Xaa Ser Thr Xaa Tyr Met Glu Leu Ser Ser Leu Xaa Ser Glu Asp
            20                  25                  30

Thr Ala Val Tyr Tyr Cys
        35

<210> SEQ ID NO 496
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa = L or T

<400> SEQUENCE: 496

Trp Gly Gln Gly Thr Xaa Val Thr Val Ser Ser
1               5                   10

<210> SEQ ID NO 497
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (24)..(24)
<223> OTHER INFORMATION: Xaa = R or A
<220> FEATURE:
<221> NAME/KEY: misc_feature
<222> LOCATION: (27)..(27)
<223> OTHER INFORMATION: Xaa = Q or S
<220> FEATURE:
<221> NAME/KEY: misc_feature
<222> LOCATION: (30)..(30)
<223> OTHER INFORMATION: Xaa = S or G
<220> FEATURE:
<221> NAME/KEY: misc_feature
<222> LOCATION: (34)..(34)
<223> OTHER INFORMATION: Xaa = N or S
<220> FEATURE:
<221> NAME/KEY: misc_feature
<222> LOCATION: (44)..(44)
<223> OTHER INFORMATION: Xaa = P or V
<220> FEATURE:
<221> NAME/KEY: misc_feature
<222> LOCATION: (49)..(49)
<223> OTHER INFORMATION: Xaa = R or C
<220> FEATURE:
<221> NAME/KEY: misc_feature
<222> LOCATION: (53)..(53)
<223> OTHER INFORMATION: Xaa = R or L
<220> FEATURE:
<221> NAME/KEY: misc_feature
<222> LOCATION: (54)..(54)
<223> OTHER INFORMATION: Xaa = L or F
<220> FEATURE:
<221> NAME/KEY: misc_feature
<222> LOCATION: (79)..(79)
<223> OTHER INFORMATION: Xaa = E or Q
<220> FEATURE:
<221> NAME/KEY: misc_feature
<222> LOCATION: (80)..(80)
<223> OTHER INFORMATION: Xaa = Q or P
<220> FEATURE:
<221> NAME/KEY: misc_feature
<222> LOCATION: (92)..(92)
<223> OTHER INFORMATION: Xaa = N or F
<220> FEATURE:
<221> NAME/KEY: misc_feature
<222> LOCATION: (93)..(93)
<223> OTHER INFORMATION: Xaa = T, L or R
```

```
<220> FEATURE:
<221> NAME/KEY: misc_feature
<222> LOCATION: (98)..(98)
<223> OTHER INFORMATION: Xaa = F or S
<220> FEATURE:
<221> NAME/KEY: misc_feature
<222> LOCATION: (104)..(104)
<223> OTHER INFORMATION: Xaa = V or L

<400> SEQUENCE: 497

Asp Ile Gln Met Thr Gln Ser Pro Ser Ser Leu Ser Ala Ser Val Gly
1               5                   10                  15

Asp Arg Val Thr Ile Thr Cys Xaa Ala Ser Xaa Asp Ile Xaa Asn Tyr
            20                  25                  30

Leu Xaa Trp Tyr Gln Gln Lys Pro Gly Lys Ala Xaa Lys Leu Leu Met
        35                  40                  45

Xaa Tyr Thr Ser Xaa Xaa His Ser Gly Val Pro Ser Arg Phe Ser Gly
    50                  55                  60

Ser Gly Ser Gly Thr Asp Phe Thr Leu Thr Ile Ser Ser Leu Xaa Xaa
65                  70                  75                  80

Glu Asp Phe Ala Thr Tyr Tyr Cys Gln Gln Gly Xaa Xaa Phe Pro Pro
                85                  90                  95

Thr Xaa Gly Gly Gly Thr Lys Xaa Glu Ile Lys
        100                 105

<210> SEQ ID NO 498
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = Q or S
<220> FEATURE:
<221> NAME/KEY: misc_feature
<222> LOCATION: (4)..(4)
<223> OTHER INFORMATION: Xaa = S or G

<400> SEQUENCE: 498

Xaa Asp Ile Xaa Asn Tyr
1               5

<210> SEQ ID NO 499
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa = N or F
<220> FEATURE:
<221> NAME/KEY: misc_feature
<222> LOCATION: (5)..(5)
<223> OTHER INFORMATION: Xaa = T, L or R

<400> SEQUENCE: 499

Gln Gln Gly Xaa Xaa Phe Pro Pro Thr
1               5

<210> SEQ ID NO 500
<211> LENGTH: 26
<212> TYPE: PRT
<213> ORGANISM: Artificial Sequence
```

```
<220> FEATURE:
<223> OTHER INFORMATION: synthetic construct
<220> FEATURE:
<221> NAME/KEY: misc_feature
<222> LOCATION: (24)..(24)
<223> OTHER INFORMATION: Xaa = R or A

<400> SEQUENCE: 500

Asp Ile Gln Met Thr Gln Ser Pro Ser Ser Leu Ser Ala Ser Val Gly
1               5                   10                  15

Asp Arg Val Thr Ile Thr Cys Xaa Ala Ser
            20                  25

<210> SEQ ID NO 501
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa = N or S
<220> FEATURE:
<221> NAME/KEY: misc_feature
<222> LOCATION: (12)..(12)
<223> OTHER INFORMATION: Xaa = P or V
<220> FEATURE:
<221> NAME/KEY: misc_feature
<222> LOCATION: (17)..(17)
<223> OTHER INFORMATION: Xaa = R or C

<400> SEQUENCE: 501

Leu Xaa Trp Tyr Gln Gln Lys Pro Gly Lys Ala Xaa Lys Leu Leu Met
1               5                   10                  15

Xaa

<210> SEQ ID NO 502
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = R or L
<220> FEATURE:
<221> NAME/KEY: misc_feature
<222> LOCATION: (2)..(2)
<223> OTHER INFORMATION: Xaa = L or F
<220> FEATURE:
<221> NAME/KEY: misc_feature
<222> LOCATION: (27)..(27)
<223> OTHER INFORMATION: Xaa = E or Q
<220> FEATURE:
<221> NAME/KEY: misc_feature
<222> LOCATION: (28)..(28)
<223> OTHER INFORMATION: Xaa = Q or P

<400> SEQUENCE: 502

Xaa Xaa His Ser Gly Val Pro Ser Arg Phe Ser Gly Ser Gly Ser Gly
1               5                   10                  15

Thr Asp Phe Thr Leu Thr Ile Ser Ser Leu Xaa Xaa Glu Asp Phe Ala
            20                  25                  30

Thr Tyr Tyr Cys
        35

<210> SEQ ID NO 503
```

```
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa = F or S
<220> FEATURE:
<221> NAME/KEY: misc_feature
<222> LOCATION: (7)..(7)
<223> OTHER INFORMATION: Xaa = V or L

<400> SEQUENCE: 503

Xaa Gly Gly Gly Thr Lys Xaa Glu Ile Lys
1               5                   10

<210> SEQ ID NO 504
<211> LENGTH: 448
<212> TYPE: PRT
<213> ORGANISM: Artificial Sequence
<220> FEATURE:
<223> OTHER INFORMATION: synthetic construct

<400> SEQUENCE: 504

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Lys Gln Lys Pro Gly Gln Gly Leu Glu Trp Met
            35                  40                  45

Gly Tyr Ile Leu Pro Tyr Asn Asp Gly Thr Lys Tyr Ala Gln Lys Phe
        50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Trp Glu Gly Ser Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270
```

-continued

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 505
<211> LENGTH: 214
<212> TYPE: PRT
<213> ORGANISM: Artificial Sequence
<220> FEATURE:
<223> OTHER INFORMATION: synthetic construct

<400> SEQUENCE: 505

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ser Trp Tyr Gln Gln Lys Pro Gly Lys Ala Pro Lys Leu Leu Met
        35                  40                  45

Arg Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Leu Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

-continued

Ala Cys Glu Val Thr His Gln Gly Leu Ser Ser Pro Val Thr Lys Ser
        195                 200                 205

Phe Asn Arg Gly Glu Cys
    210

<210> SEQ ID NO 506
<211> LENGTH: 214
<212> TYPE: PRT
<213> ORGANISM: Artificial Sequence
<220> FEATURE:
<223> OTHER INFORMATION: synthetic construct

<400> SEQUENCE: 506

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Asp Ile Ser Asn Tyr
            20                  25                  30

Leu Asn Trp Tyr Gln Gln Lys Pro Gly Lys Ala Pro Lys Leu Leu Met
        35                  40                  45

Cys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 507
<211> LENGTH: 448
<212> TYPE: PRT
<213> ORGANISM: Artificial Sequence
<220> FEATURE:
<223> OTHER INFORMATION: synthetic construct

<400> SEQUENCE: 507

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
            20                  25                  30

Val Met His Trp Val Lys Gln Lys Pro Gly Gln Gly Leu Glu Trp Met
        35                  40                  45

Gly Trp Ile Leu Pro Tyr Asn Asp Gly Thr Lys Tyr Ala Gln Lys Phe

```
            50                  55                  60
Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
               100                 105                 110

Leu Val Thr Val Ser Ser Ala Ser Thr Lys Gly Pro Ser Val Phe Pro
           115                 120                 125

Leu Ala Pro Ser Ser Lys Ser Thr Ser Gly Gly Thr Ala Ala Leu Gly
           130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
               165                 170                 175

Ser Ser Gly Leu Tyr Ser Leu Ser Ser Val Val Thr Val Pro Ser Ser
               180                 185                 190

Ser Leu Gly Thr Gln Thr Tyr Ile Cys Asn Val Asn His Lys Pro Ser
           195                 200                 205

Asn Thr Lys Val Asp Lys Lys Val Glu Pro Lys Ser Cys Asp Lys Thr
       210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
               245                 250                 255

Thr Pro Glu Val Thr Cys Val Val Val Asp Val Ser His Glu Asp Pro
               260                 265                 270

Glu Val Lys Phe Asn Trp Tyr Val Asp Gly Val Glu Val His Asn Ala
               275                 280                 285

Lys Thr Lys Pro Arg Glu Glu Gln Tyr Asn Ser Thr Tyr Arg Val Val
       290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
               325                 330                 335

Ile Ser Lys Ala Lys Gly Gln Pro Arg Glu Pro Gln Val Tyr Thr Leu
           340                 345                 350

Pro Pro Ser Arg Asp Glu Leu Thr Lys Asn Gln Val Ser Leu Thr Cys
           355                 360                 365

Leu Val Lys Gly Phe Tyr Pro Ser Asp Ile Ala Val Glu Trp Glu Ser
       370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
               405                 410                 415

Arg Trp Gln Gln Gly Asn Val Phe Ser Cys Ser Val Met His Glu Ala
               420                 425                 430

Leu His Asn His Tyr Thr Gln Lys Ser Leu Ser Leu Ser Pro Gly Lys
           435                 440                 445
```

<210> SEQ ID NO 508
<211> LENGTH: 214
<212> TYPE: PRT
<213> ORGANISM: Artificial Sequence

```
<220> FEATURE:
<223> OTHER INFORMATION: synthetic construct

<400> SEQUENCE: 508

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Met
        35                  40                  45

Arg Tyr Thr Ser Leu Leu His Ser Gly Val Pro Ser Arg Phe Ser Gly
    50                  55                  60

Ser Gly Ser Gly Thr Asp Phe Thr Leu Thr Ile Ser Ser Leu Glu Gln
65                  70                  75                  80

Glu Asp Phe Ala Thr Tyr Tyr Cys Gln Gln Gly Asn Thr Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 509
<211> LENGTH: 448
<212> TYPE: PRT
<213> ORGANISM: Artificial Sequence
<220> FEATURE:
<223> OTHER INFORMATION: synthetic construct

<400> SEQUENCE: 509

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met Phe Trp Val Lys Gln Lys Pro Gly Gln Gly Leu Glu Trp Met
        35                  40                  45

Gly Tyr Ile Thr Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
```

```
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
    435                 440                 445

<210> SEQ ID NO 510
<211> LENGTH: 214
<212> TYPE: PRT
<213> ORGANISM: Artificial Sequence
<220> FEATURE:
<223> OTHER INFORMATION: synthetic construct

<400> SEQUENCE: 510

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Met
```

```
            35              40              45

Arg Tyr Thr Ser Arg Phe His Ser Gly Val Pro Ser Arg Phe Ser Gly
    50              55              60

Ser Gly Ser Gly Thr Asp Phe Thr Leu Thr Ile Ser Ser Leu Glu Gln
65              70              75              80

Glu Asp Phe Ala Thr Tyr Tyr Cys Gln Gln Gly Asn Thr Phe Pro Pro
            85              90              95

Thr Ser Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210

<210> SEQ ID NO 511
<211> LENGTH: 448
<212> TYPE: PRT
<213> ORGANISM: Artificial Sequence
<220> FEATURE:
<223> OTHER INFORMATION: synthetic construct

<400> SEQUENCE: 511

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asn Tyr
            20              25              30

Val Met His Trp Val Lys Gln Lys Pro Gly Gln Gly Leu Glu Trp Met
            35              40              45

Gly Tyr Ile Leu Pro Tyr Asn Asp Gly Thr Lys Tyr Ala Gln Lys Phe
    50              55              60

Gln Gly Lys Val Thr Met Thr Ser Asp Lys Ser Thr Ser Thr Val Tyr
65              70              75              80

Met Glu Leu Ser Ser Leu Thr Ser Glu Asp Thr Ala Val Tyr Tyr Cys
            85              90              95

Ala Arg Tyr Asp Tyr Glu Gly Ser Phe Asp Tyr Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
```

<pre>
          180             185             190
Ser Leu Gly Thr Gln Thr Tyr Ile Cys Asn Val Asn His Lys Pro Ser
      195             200             205

Asn Thr Lys Val Asp Lys Lys Val Glu Pro Lys Ser Cys Asp Lys Thr
      210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
              245             250             255

Thr Pro Glu Val Thr Cys Val Val Val Asp Val Ser His Glu Asp Pro
              260             265             270

Glu Val Lys Phe Asn Trp Tyr Val Asp Gly Val Glu Val His Asn Ala
      275             280             285

Lys Thr Lys Pro Arg Glu Glu Gln Tyr Asn Ser Thr Tyr Arg Val Val
      290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
              325             330             335

Ile Ser Lys Ala Lys Gly Gln Pro Arg Glu Pro Gln Val Tyr Thr Leu
              340             345             350

Pro Pro Ser Arg Asp Glu Leu Thr Lys Asn Gln Val Ser Leu Thr Cys
              355             360             365

Leu Val Lys Gly Phe Tyr Pro Ser Asp Ile Ala Val Glu Trp Glu Ser
      370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
              405             410             415

Arg Trp Gln Gln Gly Asn Val Phe Ser Cys Ser Val Met His Glu Ala
              420             425             430

Leu His Asn His Tyr Thr Gln Lys Ser Leu Ser Leu Ser Pro Gly Lys
      435             440             445

<210> SEQ ID NO 512
<211> LENGTH: 214
<212> TYPE: PRT
<213> ORGANISM: Artificial Sequence
<220> FEATURE:
<223> OTHER INFORMATION: synthetic construct

<400> SEQUENCE: 512

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Ser Asn Tyr
              20              25              30

Leu Asn Trp Tyr Gln Gln Lys Pro Gly Lys Ala Pro Lys Leu Leu Met
      35              40              45

Cys Tyr Thr Ser Arg Leu His Ser Gly Val Pro Ser Arg Phe Ser Gly
      50              55              60

Ser Gly Ser Gly Thr Asp Phe Thr Leu Thr Ile Ser Ser Leu Glu Gln
65              70              75              80

Glu Asp Phe Ala Thr Tyr Tyr Cys Gln Gln Gly Asn Thr Phe Pro Pro
              85              90              95

Thr Phe Gly Gly Gly Thr Lys Val Glu Ile Lys Arg Thr Val Ala Ala
</pre>

-continued

```
              100               105               110
Pro Ser Val Phe Ile Phe Pro Pro Ser Asp Glu Gln Leu Lys Ser Gly
         115               120               125

Thr Ala Ser Val Val Cys Leu Leu Asn Asn Phe Tyr Pro Arg Glu Ala
    130               135               140

Lys Val Gln Trp Lys Val Asp Asn Ala Leu Gln Ser Gly Asn Ser Gln
145               150               155               160

Glu Ser Val Thr Glu Gln Asp Ser Lys Asp Ser Thr Tyr Ser Leu Ser
              165               170               175

Ser Thr Leu Thr Leu Ser Lys Ala Asp Tyr Glu Lys His Lys Val Tyr
              180               185               190

Ala Cys Glu Val Thr His Gln Gly Leu Ser Ser Pro Val Thr Lys Ser
         195               200               205

Phe Asn Arg Gly Glu Cys
    210

<210> SEQ ID NO 513
<211> LENGTH: 448
<212> TYPE: PRT
<213> ORGANISM: Artificial Sequence
<220> FEATURE:
<223> OTHER INFORMATION: synthetic construct

<400> SEQUENCE: 513

Gln Val Gln Leu Val Gln Ser Gly Ala Glu Val Lys Lys Pro Gly Ala
1               5                10                15

Ser Val Lys Val Ser Cys Lys Ala Ser Gly Tyr Thr Phe Thr Asn Tyr
         20                25                30

Val Met His Trp Val Arg Gln Ala Pro Gly Gln Arg Leu Glu Trp Met
         35                40                45

Gly Tyr Ile Leu Pro Tyr Asn Asp Gly Thr Lys Tyr Ser Gln Lys Phe
    50                55                60

Gln Gly Arg Val Thr Ile Thr Arg Asp Thr Ser Ala Ser Thr Ala Tyr
65                70                75                80

Met Glu Leu Ser Ser Leu Arg Ser Glu Asp Thr Ala Val Tyr Tyr Cys
              85                90                95

Ala Arg Tyr Asp Trp Glu Gly Ser Phe Asp Tyr Trp Gly Gln Gly Thr
         100               105               110

Thr Val Thr Val Ser Ser Ala Ser Thr Lys Gly Pro Ser Val Phe Pro
         115               120               125

Leu Ala Pro Ser Ser Lys Ser Thr Ser Gly Gly Thr Ala Ala Leu Gly
    130               135               140

Cys Leu Val Lys Asp Tyr Phe Pro Glu Pro Val Thr Val Ser Trp Asn
145               150               155               160

Ser Gly Ala Leu Thr Ser Gly Val His Thr Phe Pro Ala Val Leu Gln
              165               170               175

Ser Ser Gly Leu Tyr Ser Leu Ser Ser Val Val Thr Val Pro Ser Ser
              180               185               190

Ser Leu Gly Thr Gln Thr Tyr Ile Cys Asn Val Asn His Lys Pro Ser
         195               200               205

Asn Thr Lys Val Asp Lys Lys Val Glu Pro Lys Ser Cys Asp Lys Thr
    210               215               220

His Thr Cys Pro Pro Cys Pro Ala Pro Glu Leu Leu Gly Gly Pro Ser
225               230               235               240

Val Phe Leu Phe Pro Pro Lys Pro Lys Asp Thr Leu Met Ile Ser Arg
```

-continued

```
                    245                250                 255

Thr Pro Glu Val Thr Cys Val Val Val Asp Val Ser His Glu Asp Pro
                260                265                 270

Glu Val Lys Phe Asn Trp Tyr Val Asp Gly Val Glu Val His Asn Ala
                275                280                 285

Lys Thr Lys Pro Arg Glu Glu Gln Tyr Asn Ser Thr Tyr Arg Val Val
                290                295                 300

Ser Val Leu Thr Val Leu His Gln Asp Trp Leu Asn Gly Lys Glu Tyr
305                310                315                 320

Lys Cys Lys Val Ser Asn Lys Ala Leu Pro Ala Pro Ile Glu Lys Thr
                325                330                 335

Ile Ser Lys Ala Lys Gly Gln Pro Arg Glu Pro Gln Val Tyr Thr Leu
                340                345                 350

Pro Pro Ser Arg Asp Glu Leu Thr Lys Asn Gln Val Ser Leu Thr Cys
                355                360                 365

Leu Val Lys Gly Phe Tyr Pro Ser Asp Ile Ala Val Glu Trp Glu Ser
                370                375                 380

Asn Gly Gln Pro Glu Asn Asn Tyr Lys Thr Thr Pro Pro Val Leu Asp
385                390                395                 400

Ser Asp Gly Ser Phe Phe Leu Tyr Ser Lys Leu Thr Val Asp Lys Ser
                405                410                 415

Arg Trp Gln Gln Gly Asn Val Phe Ser Cys Ser Val Met His Glu Ala
                420                425                 430

Leu His Asn His Tyr Thr Gln Lys Ser Leu Ser Leu Ser Pro Gly Lys
                435                440                 445
```

```
<210> SEQ ID NO 514
<211> LENGTH: 214
<212> TYPE: PRT
<213> ORGANISM: Artificial Sequence
<220> FEATURE:
<223> OTHER INFORMATION: synthetic construct

<400> SEQUENCE: 514

Asp Ile Gln Met Thr Gln Ser Pro Ser Ser Leu Ser Ala Ser Val Gly
1                5                10                 15

Asp Arg Val Thr Ile Thr Cys Arg Ala Ser Gln Asp Ile Gly Asn Tyr
                20                25                 30

Leu Asn Trp Tyr Gln Gln Lys Pro Gly Lys Ala Val Lys Leu Leu Met
                35                40                 45

Arg Tyr Thr Ser Arg Leu His Ser Gly Val Pro Ser Arg Phe Ser Gly
                50                55                 60

Ser Gly Ser Gly Thr Asp Phe Thr Leu Thr Ile Ser Ser Leu Gln Pro
65                70                75                 80

Glu Asp Phe Ala Thr Tyr Tyr Cys Gln Gln Gly Phe Thr Phe Pro Pro
                85                90                 95

Thr Phe Gly Gly Gly Thr Lys Leu Glu Ile Lys Arg Thr Val Ala Ala
                100                105                 110

Pro Ser Val Phe Ile Phe Pro Pro Ser Asp Glu Gln Leu Lys Ser Gly
                115                120                 125

Thr Ala Ser Val Val Cys Leu Leu Asn Asn Phe Tyr Pro Arg Glu Ala
                130                135                 140

Lys Val Gln Trp Lys Val Asp Asn Ala Leu Gln Ser Gly Asn Ser Gln
145                150                155                 160

Glu Ser Val Thr Glu Gln Asp Ser Lys Asp Ser Thr Tyr Ser Leu Ser
```

-continued

```
                    165               170               175
Ser Thr Leu Thr Leu Ser Lys Ala Asp Tyr Glu Lys His Lys Val Tyr
            180               185               190

Ala Cys Glu Val Thr His Gln Gly Leu Ser Ser Pro Val Thr Lys Ser
        195               200               205

Phe Asn Arg Gly Glu Cys
    210

<210> SEQ ID NO 515
<211> LENGTH: 214
<212> TYPE: PRT
<213> ORGANISM: Artificial Sequence
<220> FEATURE:
<223> OTHER INFORMATION: synthetic construct

<400> SEQUENCE: 515

Asp Ile Gln Met Thr Gln Ser Pro Ser Ser Leu Ser Ala Ser Val Gly
1               5               10               15

Asp Arg Val Thr Ile Thr Cys Ala Ala Ser Gln Asp Ile Ser Asn Tyr
            20               25               30

Leu Asn Trp Tyr Gln Gln Lys Pro Gly Lys Ala Val Lys Leu Leu Met
        35               40               45

Arg Tyr Thr Ser Arg Leu His Ser Gly Val Pro Ser Arg Phe Ser Gly
    50               55               60

Ser Gly Ser Gly Thr Asp Phe Thr Leu Thr Ile Ser Ser Leu Gln Pro
65               70               75               80

Glu Asp Phe Ala Thr Tyr Tyr Cys Gln Gln Gly Asn Arg Phe Pro Pro
                85               90               95

Thr Phe Gly Gly Gly Thr Lys Leu Glu Ile Lys Arg Thr Val Ala Ala
            100               105               110

Pro Ser Val Phe Ile Phe Pro Pro Ser Asp Glu Gln Leu Lys Ser Gly
        115               120               125

Thr Ala Ser Val Val Cys Leu Leu Asn Asn Phe Tyr Pro Arg Glu Ala
    130               135               140

Lys Val Gln Trp Lys Val Asp Asn Ala Leu Gln Ser Gly Asn Ser Gln
145               150               155               160

Glu Ser Val Thr Glu Gln Asp Ser Lys Asp Ser Thr Tyr Ser Leu Ser
            165               170               175

Ser Thr Leu Thr Leu Ser Lys Ala Asp Tyr Glu Lys His Lys Val Tyr
            180               185               190

Ala Cys Glu Val Thr His Gln Gly Leu Ser Ser Pro Val Thr Lys Ser
        195               200               205

Phe Asn Arg Gly Glu Cys
    210

<210> SEQ ID NO 516
<211> LENGTH: 448
<212> TYPE: PRT
<213> ORGANISM: Artificial Sequence
<220> FEATURE:
<223> OTHER INFORMATION: synthetic construct

<400> SEQUENCE: 516

Gln Val Gln Leu Val Gln Ser Gly Ala Glu Val Lys Lys Pro Gly Ala
1               5               10               15

Ser Val Lys Val Ser Cys Lys Ala Ser Gly Tyr Thr Phe Thr Asn Tyr
            20               25               30
```

-continued

```
Val Met His Trp Val Lys Gln Lys Pro Gly Gln Gly Leu Glu Trp Met
    35                  40                  45

Gly Tyr Ile Leu Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Trp Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445
```

<210> SEQ ID NO 517
<211> LENGTH: 330
<212> TYPE: PRT
<213> ORGANISM: Homo sapiens

<400> SEQUENCE: 517

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 518
<211> LENGTH: 113
<212> TYPE: PRT
<213> ORGANISM: Artificial Sequence
<220> FEATURE:
<223> OTHER INFORMATION: synthetic construct

<400> SEQUENCE: 518

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
        100                 105                 110

Lys
```

```
<210> SEQ ID NO 519
<211> LENGTH: 330
<212> TYPE: PRT
<213> ORGANISM: Homo sapiens

<400> SEQUENCE: 519
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

```
<210> SEQ ID NO 520
<211> LENGTH: 448
<212> TYPE: PRT
<213> ORGANISM: Artificial Sequence
<220> FEATURE:
<223> OTHER INFORMATION: synthetic construct

<400> SEQUENCE: 520
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Lys Gln Lys Pro Gly Gln Gly Leu Glu Trp Met
            35                  40                  45

Gly Tyr Ile Leu Pro Tyr Asn Asp Gly Thr Lys Tyr Ala Gln Lys Phe
            50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Trp Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Cys Arg Asp Glu Leu Thr Lys Asn Gln Val Ser Leu Trp Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 521
<211> LENGTH: 448
<212> TYPE: PRT
<213> ORGANISM: Artificial Sequence
<220> FEATURE:
<223> OTHER INFORMATION: synthetic construct

<400> SEQUENCE: 521

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
                20                  25                  30

Val Met His Trp Val Lys Gln Lys Pro Gly Gln Gly Leu Glu Trp Met
            35                  40                  45

Gly Trp Ile Leu Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205
```

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 522
<211> LENGTH: 448
<212> TYPE: PRT
<213> ORGANISM: Artificial Sequence
<220> FEATURE:
<223> OTHER INFORMATION: synthetic construct

<400> SEQUENCE: 522
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met Phe Trp Val Lys Gln Lys Pro Gly Gln Gly Leu Glu Trp Met
        35                  40                  45

Gly Tyr Ile Thr Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65              70                  75                  80

Met Glu Leu Ser Ser Leu Thr Ser Glu Asp Thr Ala Val Tyr Tyr Cys
            85                  90                  95

Ala Arg Tyr Asp Tyr Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

-continued

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Cys Arg Asp Glu Leu Thr Lys Asn Gln Val Ser Leu Trp Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 523
<211> LENGTH: 448
<212> TYPE: PRT
<213> ORGANISM: Artificial Sequence
<220> FEATURE:
<223> OTHER INFORMATION: synthetic construct

<400> SEQUENCE: 523

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Lys Gln Lys Pro Gly Gln Gly Leu Glu Trp Met
    35                  40                  45
```

Gly Tyr Ile Leu Pro Tyr Asn Asp Gly Thr Lys Tyr Ala Gln Lys Phe
    50                  55                  60

Gln Gly Lys Val Thr Met Thr Ser Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Tyr Asp Tyr Glu Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 524
<211> LENGTH: 448

```
<212> TYPE: PRT
<213> ORGANISM: Artificial Sequence
<220> FEATURE:
<223> OTHER INFORMATION: synthetic construct

<400> SEQUENCE: 524

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Arg Gln Ala Pro Gly Gln Arg Leu Glu Trp Met
            35                  40                  45

Gly Tyr Ile Leu Pro Tyr Asn Asp Gly Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Trp Glu Gly Ser Phe Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
        370                 375                 380
```

-continued

```
Asn Gly Gln Pro Glu Asn Asn Tyr Lys Thr Thr Pro Pro Val Leu Asp
385             390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 525
<211> LENGTH: 8
<212> TYPE: PRT
<213> ORGANISM: Artificial Sequence
<220> FEATURE:
<223> OTHER INFORMATION: synthetic construct

<400> SEQUENCE: 525

Gly Tyr Thr Phe Thr Arg Tyr Thr
1               5

<210> SEQ ID NO 526
<211> LENGTH: 8
<212> TYPE: PRT
<213> ORGANISM: Artificial Sequence
<220> FEATURE:
<223> OTHER INFORMATION: synthetic construct

<400> SEQUENCE: 526

Ile Asn Pro Ser Arg Gly Tyr Thr
1               5

<210> SEQ ID NO 527
<211> LENGTH: 12
<212> TYPE: PRT
<213> ORGANISM: Artificial Sequence
<220> FEATURE:
<223> OTHER INFORMATION: synthetic construct

<400> SEQUENCE: 527

Ala Arg Tyr Tyr Asp Asp His Tyr Cys Leu Asp Tyr
1               5                   10

<210> SEQ ID NO 528
<211> LENGTH: 25
<212> TYPE: PRT
<213> ORGANISM: Artificial Sequence
<220> FEATURE:
<223> OTHER INFORMATION: synthetic construct

<400> SEQUENCE: 528

Gln Val Gln Leu Gln Gln Ser Gly Ala Glu Leu Ala Arg Pro Gly Ala
1               5                   10                  15

Ser Val Lys Met Ser Cys Lys Ala Ser
            20                  25

<210> SEQ ID NO 529
<211> LENGTH: 17
<212> TYPE: PRT
<213> ORGANISM: Artificial Sequence
<220> FEATURE:
<223> OTHER INFORMATION: synthetic construct

<400> SEQUENCE: 529

Met His Trp Val Lys Gln Arg Pro Gly Gln Gly Leu Glu Trp Ile Gly
1               5                   10                  15
```

-continued

Tyr

<210> SEQ ID NO 530
<211> LENGTH: 38
<212> TYPE: PRT
<213> ORGANISM: Artificial Sequence
<220> FEATURE:
<223> OTHER INFORMATION: synthetic construct

<400> SEQUENCE: 530

Asn Tyr Asn Gln Lys Phe Lys Asp Lys Ala Thr Leu Thr Thr Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 531
<211> LENGTH: 5
<212> TYPE: PRT
<213> ORGANISM: Artificial Sequence
<220> FEATURE:
<223> OTHER INFORMATION: synthetic construct

<400> SEQUENCE: 531

Ser Ser Val Ser Tyr
1               5

<210> SEQ ID NO 532
<211> LENGTH: 3
<212> TYPE: PRT
<213> ORGANISM: Artificial Sequence
<220> FEATURE:
<223> OTHER INFORMATION: synthetic construct

<400> SEQUENCE: 532

Asp Thr Ser
1

<210> SEQ ID NO 533
<211> LENGTH: 9
<212> TYPE: PRT
<213> ORGANISM: Artificial Sequence
<220> FEATURE:
<223> OTHER INFORMATION: synthetic construct

<400> SEQUENCE: 533

Gln Gln Trp Ser Ser Asn Pro Phe Thr
1               5

<210> SEQ ID NO 534
<211> LENGTH: 26
<212> TYPE: PRT
<213> ORGANISM: Artificial Sequence
<220> FEATURE:
<223> OTHER INFORMATION: synthetic construct

<400> SEQUENCE: 534

Gln Ile Val Leu Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 535

<211> LENGTH: 17
<212> TYPE: PRT
<213> ORGANISM: Artificial Sequence
<220> FEATURE:
<223> OTHER INFORMATION: synthetic construct

<400> SEQUENCE: 535

Met Asn Trp Tyr Gln Gln Lys Ser Gly Thr Ser Pro Lys Arg Trp Ile
1               5                   10                  15

Tyr

<210> SEQ ID NO 536
<211> LENGTH: 36
<212> TYPE: PRT
<213> ORGANISM: Artificial Sequence
<220> FEATURE:
<223> OTHER INFORMATION: synthetic construct

<400> SEQUENCE: 536

Lys Leu Ala Ser Gly Val Pro Ala His Phe Arg Gly Ser Gly Ser Gly
1               5                   10                  15

Thr Ser Tyr Ser Leu Thr Ile Ser Gly Met Glu Ala Glu Asp Ala Ala
            20                  25                  30

Thr Tyr Tyr Cys
        35

<210> SEQ ID NO 537
<211> LENGTH: 10
<212> TYPE: PRT
<213> ORGANISM: Artificial Sequence
<220> FEATURE:
<223> OTHER INFORMATION: synthetic construct

<400> SEQUENCE: 537

Phe Gly Ser Gly Thr Lys Leu Glu Ile Asn
1               5                   10

<210> SEQ ID NO 538
<211> LENGTH: 125
<212> TYPE: PRT
<213> ORGANISM: Artificial Sequence
<220> FEATURE:
<223> OTHER INFORMATION: synthetic construct

<400> SEQUENCE: 538

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

-continued

```
<210> SEQ ID NO 539
<211> LENGTH: 8
<212> TYPE: PRT
<213> ORGANISM: Artificial Sequence
<220> FEATURE:
<223> OTHER INFORMATION: synthetic construct

<400> SEQUENCE: 539

Gly Phe Thr Phe Asn Thr Tyr Ala
1               5

<210> SEQ ID NO 540
<211> LENGTH: 10
<212> TYPE: PRT
<213> ORGANISM: Artificial Sequence
<220> FEATURE:
<223> OTHER INFORMATION: synthetic construct

<400> SEQUENCE: 540

Ile Arg Ser Lys Tyr Asn Asn Tyr Ala Thr
1               5                   10

<210> SEQ ID NO 541
<211> LENGTH: 16
<212> TYPE: PRT
<213> ORGANISM: Artificial Sequence
<220> FEATURE:
<223> OTHER INFORMATION: synthetic construct

<400> SEQUENCE: 541

Val Arg His Gly Asn Phe Gly Asn Ser Tyr Val Ser Trp Phe Ala Tyr
1               5                   10                  15

<210> SEQ ID NO 542
<211> LENGTH: 25
<212> TYPE: PRT
<213> ORGANISM: Artificial Sequence
<220> FEATURE:
<223> OTHER INFORMATION: synthetic construct

<400> SEQUENCE: 542

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 543
<211> LENGTH: 17
<212> TYPE: PRT
<213> ORGANISM: Artificial Sequence
<220> FEATURE:
<223> OTHER INFORMATION: synthetic construct

<400> SEQUENCE: 543

Met Asn Trp Val Arg Gln Ala Pro Gly Lys Gly Leu Glu Trp Val Ala
1               5                   10                  15

Arg

<210> SEQ ID NO 544
<211> LENGTH: 38
<212> TYPE: PRT
<213> ORGANISM: Artificial Sequence
<220> FEATURE:
<223> OTHER INFORMATION: synthetic construct

<400> SEQUENCE: 544
```

```
Tyr Tyr Ala Asp Ser Val Lys Asp Arg Phe Thr Ile Ser Arg Asp Asp
1               5                   10                  15

Ser Gln Ser Ile Leu Tyr Leu Gln Met Asn Asn Leu Lys Thr Glu Asp
            20                  25                  30

Thr Ala Met Tyr Tyr Cys
        35

<210> SEQ ID NO 545
<211> LENGTH: 109
<212> TYPE: PRT
<213> ORGANISM: Artificial Sequence
<220> FEATURE:
<223> OTHER INFORMATION: synthetic construct

<400> SEQUENCE: 545

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 546
<211> LENGTH: 9
<212> TYPE: PRT
<213> ORGANISM: Artificial Sequence
<220> FEATURE:
<223> OTHER INFORMATION: synthetic construct

<400> SEQUENCE: 546

Thr Gly Ala Val Thr Thr Ser Asn Tyr
1               5

<210> SEQ ID NO 547
<211> LENGTH: 3
<212> TYPE: PRT
<213> ORGANISM: Artificial Sequence
<220> FEATURE:
<223> OTHER INFORMATION: synthetic construct

<400> SEQUENCE: 547

Gly Thr Asn
1

<210> SEQ ID NO 548
<211> LENGTH: 9
<212> TYPE: PRT
<213> ORGANISM: Artificial Sequence
<220> FEATURE:
<223> OTHER INFORMATION: synthetic construct

<400> SEQUENCE: 548

Ala Leu Trp Tyr Ser Asn Leu Trp Val
1               5
```

```
<210> SEQ ID NO 549
<211> LENGTH: 25
<212> TYPE: PRT
<213> ORGANISM: Artificial Sequence
<220> FEATURE:
<223> OTHER INFORMATION: synthetic construct

<400> SEQUENCE: 549

Gln Ala Val Val Thr Gln Glu Ser Ala Leu Thr Thr Ser Pro Gly Glu
1               5                   10                  15

Thr Val Thr Leu Thr Cys Arg Ser Ser
            20                  25

<210> SEQ ID NO 550
<211> LENGTH: 17
<212> TYPE: PRT
<213> ORGANISM: Artificial Sequence
<220> FEATURE:
<223> OTHER INFORMATION: synthetic construct

<400> SEQUENCE: 550

Ala Asn Trp Val Gln Glu Lys Pro Asp His Leu Phe Thr Gly Leu Ile
1               5                   10                  15

Gly

<210> SEQ ID NO 551
<211> LENGTH: 36
<212> TYPE: PRT
<213> ORGANISM: Artificial Sequence
<220> FEATURE:
<223> OTHER INFORMATION: synthetic construct

<400> SEQUENCE: 551

Lys Arg Ala Pro Gly Val Pro Ala Arg Phe Ser Gly Ser Leu Ile Gly
1               5                   10                  15

Asp Lys Ala Ala Leu Thr Ile Thr Gly Ala Gln Thr Glu Asp Glu Ala
            20                  25                  30

Ile Tyr Phe Cys
        35

<210> SEQ ID NO 552
<211> LENGTH: 10
<212> TYPE: PRT
<213> ORGANISM: Artificial Sequence
<220> FEATURE:
<223> OTHER INFORMATION: synthetic construct

<400> SEQUENCE: 552

Phe Gly Gly Gly Thr Lys Leu Thr Val Leu
1               5                   10

<210> SEQ ID NO 553
<211> LENGTH: 483
<212> TYPE: PRT
<213> ORGANISM: Artificial Sequence
<220> FEATURE:
<223> OTHER INFORMATION: synthetic construct

<400> SEQUENCE: 553

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30
```

-continued

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala Ser Gly Gly
                115                 120                 125

Gly Gly Ser Gly Gly Gly Gly Ser Gly Gly Gly Gly Ser Gln Ala Val
        130                 135                 140

Val Thr Gln Glu Ser Ala Leu Thr Thr Ser Pro Gly Glu Thr Val Thr
145                 150                 155                 160

Leu Thr Cys Arg Ser Ser Thr Gly Ala Val Thr Thr Ser Asn Tyr Ala
                165                 170                 175

Asn Trp Val Gln Glu Lys Pro Asp His Leu Phe Thr Gly Leu Ile Gly
                180                 185                 190

Gly Thr Asn Lys Arg Ala Pro Gly Val Pro Ala Arg Phe Ser Gly Ser
                195                 200                 205

Leu Ile Gly Asp Lys Ala Ala Leu Thr Ile Thr Gly Ala Gln Thr Glu
        210                 215                 220

Asp Glu Ala Ile Tyr Phe Cys Ala Leu Trp Tyr Ser Asn Leu Trp Val
225                 230                 235                 240

Phe Gly Gly Gly Thr Lys Leu Thr Val Leu Val Glu Pro Lys Ser Cys
                245                 250                 255

Asp Lys Thr His Thr Cys Pro Pro Cys Pro Ala Pro Glu Leu Leu Gly
                260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
        370                 375                 380

Cys Thr Leu Pro Pro Ser Arg Asp Glu Leu Thr Lys Asn Gln Val Ser
385                 390                 395                 400

Leu Ser Cys Ala Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Val Ser Lys Leu Thr Val
        435                 440                 445
```

-continued

```
Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 554
<211> LENGTH: 25
<212> TYPE: PRT
<213> ORGANISM: Artificial Sequence
<220> FEATURE:
<223> OTHER INFORMATION: synthetic construct

<400> SEQUENCE: 554

Leu Gln Met Ala Gly Gln Cys Ser Gln Asn Glu Tyr Phe Asp Ser Leu
1               5                   10                  15

Leu His Ala Cys Ile Pro Cys Gln Leu
            20                  25

<210> SEQ ID NO 555
<211> LENGTH: 12
<212> TYPE: PRT
<213> ORGANISM: Artificial Sequence
<220> FEATURE:
<223> OTHER INFORMATION: synthetic construct

<400> SEQUENCE: 555

Asp Ser Leu Leu His Ala Cys Ile Pro Cys Gln Leu
1               5                   10

<210> SEQ ID NO 556
<211> LENGTH: 8
<212> TYPE: PRT
<213> ORGANISM: Artificial Sequence
<220> FEATURE:
<223> OTHER INFORMATION: synthetic construct

<400> SEQUENCE: 556

His Ala Cys Ile Pro Cys Gln Leu
1               5

<210> SEQ ID NO 557
<211> LENGTH: 17
<212> TYPE: PRT
<213> ORGANISM: Artificial Sequence
<220> FEATURE:
<223> OTHER INFORMATION: synthetic construct

<400> SEQUENCE: 557

Leu Gln Met Ala Gly Gln Cys Ser Gln Asn Glu Tyr Phe Asp Ser Leu
1               5                   10                  15

Leu

<210> SEQ ID NO 558
<211> LENGTH: 4
<212> TYPE: PRT
<213> ORGANISM: Artificial Sequence
<220> FEATURE:
<223> OTHER INFORMATION: synthetic construct

<400> SEQUENCE: 558

Asp Ser Leu Leu
1
```